(12) United States Patent
Carter et al.

(10) Patent No.: US 7,601,844 B2
(45) Date of Patent: Oct. 13, 2009

(54) PIPERIDINYL DERIVATIVES AS MODULATORS OF CHEMOKINE RECEPTOR ACTIVITY

(75) Inventors: Percy H. Carter, Princeton, NJ (US); Cullen L. Cavallaro, Robbinsville, NJ (US); John V. Duncia, Newtown, PA (US); Daniel S. Gardner, Furlong, PA (US); John Hynes, Washington Crossing, PA (US); Rui-Qin Liu, Belle Mead, NJ (US); Joseph B. Santella, Springfield, PA (US); Dharmpal S. Dodd, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/625,874

(22) Filed: Jan. 23, 2007

(65) Prior Publication Data

US 2007/0208056 A1  Sep. 6, 2007

Related U.S. Application Data

(60) Provisional application No. 60/762,801, filed on Jan. 27, 2006.

(51) Int. Cl.
C07D 211/60 (2006.01)
A61K 31/445 (2006.01)
(52) U.S. Cl. ............................ 546/228; 514/317
(58) Field of Classification Search .......... 546/228; 514/317
See application file for complete search history.

(56) References Cited

U.S. PATENT DOCUMENTS

| 5,492,920 | A  | * | 2/1996  | Chen et al. ............. 514/323 |
| 5,847,148 | A  |   | 12/1998 | Jacobsen et al. |
| 6,194,448 | B1 | * | 2/2001  | Biediger et al. ......... 514/438 |
| 6,344,449 | B1 |   | 2/2002  | Rudolf et al. |
| 6,391,865 | B1 |   | 5/2002  | Baroudy et al. |
| 6,638,950 | B2 | * | 10/2003 | Duncia et al. ........... 514/326 |
| 6,846,836 | B2 | * | 1/2005  | Hamann et al. ......... 514/317 |
| 2003/0162764 | A1 | | 8/2003 | Castelhano et al. |
| 2003/0229067 | A1 | | 12/2003 | Castelhano et al. |
| 2004/0006067 | A1 | | 1/2004 | Fotsch et al. |
| 2007/0123509 | A1 | * | 5/2007 | Cezanne et al. ........ 514/212.08 |
| 2007/0179148 | A1 | * | 8/2007 | Carter et al. ............ 514/252.13 |

FOREIGN PATENT DOCUMENTS

| DE | 4243858 | 6/1994 |
| EP | 0838460 | 4/1998 |
| JP | 2001-354657 | 12/2000 |
| WO | WO 92/15304 | 9/1992 |
| WO | WO 94/25437 | 11/1994 |
| WO | WO 95/34311 | 12/1995 |
| WO | WO 97/38665 | 10/1997 |
| WO | WO 98/17625 | 4/1998 |
| WO | WO 99/08697 | 2/1999 |
| WO | WO 99/08699 | 2/1999 |
| WO | WO 00/74679 | 12/2000 |
| WO | WO 02/059117 | 8/2002 |
| WO | WO 02/070511 | 9/2002 |
| WO | WO 02/092582 | 11/2002 |
| WO | WO 03/007949 | 1/2003 |
| WO | WO 03/009847 | 2/2003 |
| WO | WO 03/022835 | 3/2003 |
| WO | WO 03/092688 | 11/2003 |
| WO | WO 2004/037796 | 5/2004 |
| WO | WO 2004/076418 | 9/2004 |
| WO | WO 2004/113323 | 12/2004 |
| WO | WO 2005/003127 | 1/2005 |
| WO | WO 2005/056015 | 6/2005 |
| WO | WO 2005/084672 | 9/2005 |
| WO | WO 2005/118579 | 12/2005 |
| WO | WO 2006/013073 | 2/2006 |

OTHER PUBLICATIONS

F.Z. Dorwald "Side Reactions in Organic Synthesis: A Guide to Successful Synthesis Design" 2005, Wiley-VCH Verlag GmbH & Co. KGaA, Wienheim.*

Baraldi, P. et al., "Synthesis and biological activity of N-arylpiperazine-modified analogues of KN-62, a potent anagonist of the purinergic P2X$_7$ receptor", J. Med. Chem., vol. 46, pp. 1318-1320 (2003).

Carson, K. et al., "CCR1 Antagonists", Annual Reports in Medicinal Chemistry, vol. 39, pp. 149-158 (2004).

Lang, L. et al., (Database Beilstein, Beilstein Institute for Organic Chemistry, BRN#: 8854794), J. Labelled Compd. Radiopharm., vol. 44, pp. S21-S23 (2001).

Oshiro, Y. et al., "Novel cerebroprotective agents with central nervous system stimulating activity. 2. Synthesis and pharmacology of the 1-(acylamino)-7-hydroxyindan derivatives", J. Med. Chem., vol. 34, No. 7, pp. 2014-2023 (1991).

Pessoa-Mahana, H. et al., "Synthesis of 4-arylpiperazine derivatives of moclobemide: Potential antidepressants with a dual mode of action", Synthetic Communications, vol. 34, No. 14, pp. 2513-2521 (2004).

(Continued)

Primary Examiner—Rita J Desai
Assistant Examiner—John Mabry
(74) Attorney, Agent, or Firm—Elliott Korsen; Terence J. Bogie

(57) ABSTRACT

The present application describes substituted piperidinyl modulators of MIP-1α or CCR-1 or stereoisomers or pharmaceutically acceptable salts thereof. In addition, methods of treating and preventing inflammatory diseases such as asthma and allergic diseases, as well as autoimmune pathologies such as rheumatoid arthritis and transplant rejection using said modulators are disclosed.

8 Claims, No Drawings

OTHER PUBLICATIONS

Richardson, T. et al., "Synthesis and structure-activity relationships of novel arylpiperazines as potent and selective agonists of the melanocortin subtype-4 receptor", J. Med. Chem., vol. 47, pp. 744-755 (2004).

Tiwari, M., (Database Beilstein, Beilstein Institute for Organic Chemistry BRN#: 943608, 944316), J. Indian Chem. Soc., vol. 53, pp. 310-311 (1976).

* cited by examiner

PIPERIDINYL DERIVATIVES AS MODULATORS OF CHEMOKINE RECEPTOR ACTIVITY

RELATED APPLICATION

This application claims the benefit of U.S. Provisional Application No. 60/762,801, filed on Jan. 27, 2006, incorporated herein by reference in its entirety.

FIELD OF THE INVENTION

This invention relates generally to modulators of chemokine receptor activity, pharmaceutical compositions containing the same, and methods of using the same as agents for treatment and prevention of inflammatory diseases, allergic and autoimmune diseases, and in particular, rheumatoid arthritis and transplant rejection.

BACKGROUND OF THE INVENTION

Chemokines are chemotactic cytokines, of molecular weight 6-15 kDa, that are released by a wide variety of cells to attract and activate, among other cell types, macrophages, T and B lymphocytes, eosinophils, basophils and neutrophils (reviewed in: Luster, *New Eng. J. Med.* 1998, 338, 436-445 and Rollins, *Blood* 1997, 90, 909-928). There are two major classes of chemokines, CXC and CC, depending on whether the first two cysteines in the amino acid sequence are separated by a single amino acid (CXC) or are adjacent (CC). The CXC chemokines, such as interleukin-8 (IL-8), neutrophil-activating protein-2 (NAP-2) and melanoma growth stimulatory activity protein (MGSA) are chemotactic primarily for neutrophils and T lymphocytes, whereas the CC chemokines, such as RANTES, MIP-1α, MIP-1β, the monocyte chemotactic proteins (MCP-1, MCP-2, MCP-3, MCP-4, and MCP-5) and the eotaxins (-1 and -2) are chemotactic for, among other cell types, macrophages, T lymphocytes, eosinophils, dendritic cells, and basophils. There also exist the chemokines lymphotactin-1, lymphotactin-2 (both C chemokines), and fractalkine (a $CX_3C$ chemokine) that do not fall into either of the major chemokine subfamilies.

The chemokines bind to specific cell-surface receptors belonging to the family of G-protein-coupled seven-transmembrane-domain proteins (reviewed in: Horuk, *Trends Pharm. Sci.* 1994, 15, 159-165) which are termed "chemokine receptors." On binding their cognate ligands, chemokine receptors transduce an intracellular signal though the associated trimeric G proteins, resulting in, among other responses, a rapid increase in intracellular calcium concentration, changes in cell shape, increased expression of cellular adhesion molecules, degranulation, and promotion of cell migration. There are at least ten human chemokine receptors that bind or respond to CC chemokines with the following characteristic patterns (reviewed in Zlotnik and Oshie *Immunity* 2000, 12, 121): CCR-1 (or "CKR-1" or "CC-CKR-1") [MIP-1α, MCP-3, MCP-4, RANTES] (Ben-Barruch, et al., *Cell* 1993, 72, 415-425, and Luster, *New Eng. J. Med.* 1998, 338, 436-445); CCR-2A and CCR-2B (or "CKR-2A"/"CKR-2B" or "CC-CKR-2A"/"CC-CKR-2B") [MCP-1, MCP-2, MCP-3, MCP-4, MCP-5] (Charo, et al., *Proc. Natl. Acad. Sci. USA* 1994, 91, 2752-2756, and Luster, *New Eng. J. Med.* 1998, 338, 436-445); CCR-3 (or "CKR-3" or "CC-CKR-3") [eotaxin-1, eotaxin-2, RANTES, MCP-3, MCP-4] (Combadiere, et al., *J. Biol. Chem.* 1995, 270, 16491-16494, and Luster, *New Eng. J. Med.* 1998, 338, 436-445); CCR-4 (or "CKR-4" or "CC-CKR-4") [TARC, MDC] (Power, et al., *J. Biol. Chem.* 1995, 270, 19495-19500, and Luster, *New Eng. J. Med.* 1998, 338, 436-445); CCR-5 (or "CKR-5" OR "CC-CKR-5") [MIP-1α, RANTES, MIP-11] (Sanson, et al., *Biochemistry* 1996, 35, 3362-3367); CCR-6 (or "CKR-6" or "CC-CKR-6") [LARC] (Baba, et al., *J. Biol. Chem.* 1997, 272, 14893-14898); CCR-7 (or "CKR-7" or "CC-CKR-7") [ELC] (Yoshie et al., *J. Leukoc. Biol.* 1997, 62, 634-644); CCR-8 (or "CKR-8" or "CC-CKR-8") [1-309] (Napolitano et al., *J. Immunol.*, 1996, 157, 2759-2763); CCR-10 (or "CKR-10" or "CC-CKR-10") [MCP-1, MCP-3] (Bonini, et al., *DNA and Cell Biol.* 1997, 16, 1249-1256); and CCR-11 [MCP-1, MCP-2, and MCP-4] (Schweickert, et al., *J. Biol. Chem.* 2000, 275, 90550).

In addition to the mammalian chemokine receptors, mammalian cytomegaloviruses, herpesviruses and poxviruses have been shown to express, in infected cells, proteins with the binding properties of chemokine receptors (reviewed in: Wells and Schwartz, *Curr. Opin. Biotech.* 1997, 8, 741-748). Human CC chemokines, such as RANTES and MCP-3, can cause rapid mobilization of calcium via these virally encoded receptors. Receptor expression may be permissive for infection by allowing for the subversion of normal immune system surveillance and response to infection. Additionally, human chemokine receptors, such as CXCR4, CCR2, CCR3, CCR5 and CCR8, can act as co-receptors for the infection of mammalian cells by microbes as with, for example, the human immunodeficiency viruses (HIV).

The chemokines and their cognate receptors have been implicated as being important mediators of inflammatory, infectious, and immunoregulatory disorders and diseases, including asthma and allergic diseases, as well as autoimmune pathologies such as rheumatoid arthritis and atherosclerosis (reviewed in: P. H. Carter, *Current Opinion in Chemical Biology* 2002, 6, 510; Trivedi, et al, *Ann. Reports Med. Chem.* 2000, 35, 191; Saunders and Tarby, *Drug Disc. Today* 1999, 4, 80; Premack and Schall, *Nature Medicine* 1996, 2, 1174). For example, the chemokine macrophage inflammatory protein-1 (MIP-1α) and its receptor CC Chemokine Receptor 1 (CCR-1) play a pivotal role in attracting leukocytes to sites of inflammation and in subsequently activating these cells. When the chemokine MIP-1α binds to CCR-1, it induces a rapid increase in intracellular calcium concentration, increased expression of cellular adhesion molecules, cellular degranulation, and the promotion of leukocyte migration.

In addition, demonstration of the chemotactic properties of MIP-1α in humans has been provided experimentally. Human subjects, when injected intradermally with MIP-1α, experienced a rapid and significant influx of leukocytes to the site of injection (Brummet, M. E. *J. Immun.* 2000, 164, 3392-3401).

Demonstration of the importance of the MIP-1α/CCR-1 interaction has been provided by experiments with genetically modified mice. MIP-1α –/– mice had normal numbers of leukocytes, but were unable to recruit monocytes into sites of viral inflammation after immune challenge (Cook, D., et al., *Science.* 1995, 269, 1583-1585). Recently, MIP-1α –/– mice were shown to be resistant to collagen antibody induced arthritis (Chintalacharuvu, S. R. *Immun. Lett.* 2005, 202-204). Likewise, CCR-1–/– mice were unable to recruit neutrophils when challenged with MIP-1α in vivo; moreover, the peripheral blood neutrophils of CCR-1 null mice did not migrate in response to MIP-1α (Gao, B. et al. *J. Exp. Med.* 1997, 185, 1959-1968), thereby demonstrating the specificity of the MIP-1α/CCR-1 interaction. The viability and generally normal health of the MIP-1α –/– and CCR-1 –/– animals is noteworthy, in that disruption of the MIP-1α/CCR-1 interaction does not induce physiological crisis. Taken together, these data lead one to the conclusion that molecules that block the actions of MIP-1α would be useful in treating a number of inflammatory and autoimmune disorders. This hypothesis has now been validated in a number of different animal disease models, as described below.

It is known that MIP-1α is elevated in the synovial fluid and blood of patients with rheumatoid arthritis (Alisa Koch, et al., *J. Clin. Invest.* 1994, 93, 921-928). Moreover, several studies have demonstrated the potential therapeutic value of antagonism of the MIP-1α/CCR1 interaction in treating rheumatoid arthritis (Pease, J. E. & Horuk, R. *Expert Opin. Invest. Drugs* 2005, 14, 785-796).

An antibody to MIP-1α was shown to ameliorate experimental autoimmune encepahlomytis (EAE), a model of multiple sclerosis, in mice (Karpus, W. J., et al., *J. Immun.* 1995, 5003-5010). Likewise, inflammatory disease symptoms could be controlled via direct administration of antibodies for MIP-1α to mice with collagen-induced arthritis (Lukacs, N. W., et al., *J. Clin. Invest.* 1995, 95, 2868-2876).

It should also be noted that CCR-1 is also the receptor for the chemokines RANTES, MCP-3, HCC-1, Lkn-1/HCC-2, HCC-4, and MPIF-1 (Carter, P. H. *Curr. Opin Chem. Bio.* 2002, 6, 510-525). Since it is presumed that the new compounds of the present invention described herein antagonize MIP-1α by binding to the CCR-1 receptor, it may be that these compounds are also effective antagonists of the actions of the aforementioned ligand that are mediated by CCR-1. Accordingly, when reference is made herein to "antagonism of MIP-1α," it is to be assumed that this is equivalent to "antagonism of chemokine stimulation of CCR-1."

For example, demonstration of the chemotactic properties of RANTES in humans has been provided experimentally. Human subjects, when injected intradermally with RANTES, experienced an influx of eosinophils to the site of injection (Beck, L. A. et al. *J. Immun.* 1997, 159, 2962-2972). Likewise, a RANTES antibody has demonstrated the ability to ameliorate the symptoms of disease in the rat Adjuvant induced arthritis (AIA) model (Barnes, D. A. et al. *J. Clin Invest.* 1998, 101, 2910-2919). Similar results were obtained when using a peptide derived antagonist of the RANTES/CCR-1 interaction in both the rat AIA (Shahrara, S. et al. *Arthritis & Rheum.* 2005, 52, 1907-1919) and the mouse CIA (Plater-Zyberk, C. et al. *Imm. Lett.* 1997, 57, 117-120) disease models of joint inflammation.

Recently, a number of groups have described the development of small molecule antagonists of MIP-1α (reviewed in: Carson, K. G., et al, *Ann. Reports Med. Chem.* 2004, 39, 149-158).

SUMMARY OF THE INVENTION

Accordingly, the present invention provides novel antagonists or partial agonists/antagonists of MIP-1α or CCR-1 receptor activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating rheumatoid arthritis and transplant rejection, comprising administering to a host in need of such treatment a therapeutically effective amount of at least one of the compounds of the present invention or a pharmaceutically acceptable salt or prodrug form thereof.

The present invention provides a method for treating inflammatory diseases, comprising administering to a host in need of such treatment a therapeutically effective amount of at least one of the compounds of the present invention or a pharmaceutically acceptable salt or prodrug form thereof.

The present invention provides novel cyclic derivatives for use in therapy.

The present invention provides the use of novel cyclic derivatives for the manufacture of a medicament for the treatment of inflammatory diseases. These and other features of the invention, which will become apparent during the following detailed description, have been achieved by the inventors' discovery that the substituted piperidinyl derivatives of the present invention are effective modulators of MIP-1α and chemokine activity.

DETAILED DESCRIPTION OF THE PRESENT INVENTION

In one embodiment, the present invention provides novel compounds of formula (I):

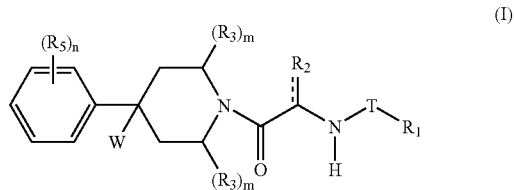

or stereoisomers or prodrugs or pharmaceutically acceptable salt forms thereof, wherein:

the dashed line represents an optional double bond;

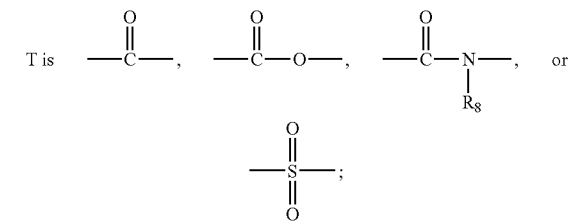

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$$H_2$, —C(=O)$NR_9R_9$, —$NR_9R_9$, —S(O)$_2$$NR_9R_9$, —$NR_9$S(O)$_2$($CF_2$)$_r$$CF_3$, —C(=O)$NR_9$S(O)$_2$$R_6$, —S(O)$_2$$NR_9$C(=O)$OR_6$, —S(O)$_2$$NR_9$C(=O)$NR_9R_9$, —C(=O)$NR_9$S(O)$_2$($CF_2$)$_r$$CF_3$, —C(=O)($CR_8R_8$)$_r$$R_{10}$, —$NR_9$C(=O)H, —$NR_9$C(=O)($CR_8R_8$)$_r$$R_{10}$, —OC(=O)($CR_8R_8$)$_r$$R_{10}$, —C(=$NR_{14}$)$NR_9R_9$, —NHC(=$NR_{14}$)$NR_{14}R_{14}$, —S(=O)($CR_8R_8$)$_r$$R_{10}$, —S(O)$_2$($CR_8R_8$)$_r$$R_{10}$, —$NR_9$C(=O)$OR_8$, —$NR_9$S(O)$_2$$R_8$, —S(O)$_2$$NR_9$C(O)$R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_r$$CF_3$, —O$(CR_8R_8)_rR_{10}$, —OH, —SH, —S$(CR_8R_8)_rR_{10}$, —S(O)$_3$H, —P(O)$_3H_2$, —C(=O)$NR_9R_9$, —$NR_9R_9$, —S(O)$_2NR_9R_9$, —$NR_9$S(O)$_2(CF_2)_rCF_3$, —C(=O)$NR_9$S(O)$_2R_6$, —S(O)$_2NR_9$C(=O)$OR_6$, —S(O)$_2NR_9$C(=O)$NR_9R_9$, —C(=O)$NR_9$S(O)$_2(CF_2)_rCF_3$, —C(=O)$(CR_8R_8)_rR_{10}$, —$NR_9$C(=O)H, —$NR_9$C(=O)$(CR_8R_8)_rR_{10}$, —OC(=O)$(CR_8R_8)_rR_{10}$, —C(=$NR_{14}$)$NR_9R_9$, —NHC(=$NR_{14}$)$NR_{14}R_{14}$, —S(=O)$(CR_8R_8)_rR_{10}$, —S(O)$_2(CR_8R_8)_rR_{10}$, —$NR_9$C(=O)$OR_8$, —$NR_9$S(O$_2$)$R_8$, aryloxy or arylalkyl;

$R_2$ is alkyl, cycloalkyl, cycloalkylalkyl, or alkenyl, wherein the alkyl may be optionally substituted with —OH;

$R_3$, at each occurrence, is alkyl; or any two $R_3$'s attached to the same carbon atom may form a 3- to 6-membered ring;

W is hydrogen, F, —OH, —CN, —$NH_2$;

$R_5$ is halo, —CN or —Oalkyl; or

W and one $R_5$ are taken together with the carbon atoms to which each is attached to form a 3- to 6-membered oxygen containing ring wherein said ring may be optionally substituted with one or more $R_5$'s;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_r$$CF_3$, —O$(CR_8R_8)_rR_{14}$, —OH, —SH, —S$(CR_8R_8)_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}$S(O)$_2(CF_2)_rCF_3$, —C(=O)$NR_{14}$S(O)$_2R_6$, —S(O)$_2NR_{14}$C(=O)$OR_6$, —S(O)$_2NR_{14}$C(=O)$NR_{14}R_{14}$, —C(=O)$NR_{14}$S(O)$_2(CF_2)_rCF_3$, —C(=O)$(CR_8R_8)_rR_{14}$, —$NR_{14}$C(=O)H, —$NR_{14}$C(=O)$(CR_8R_8)_rR_{14}$, —OC(=O)$(CR_8R_8)_rR_{14}$, —C(=$NR_{14}$)$NR_{14}R_{14}$, —NHC(=$NR_{14}$)$NR_{14}R_{14}$, —S(=O)$(CR_8R_8)_rR_{14}$, —S(O)$_2(CR_8R_8)_rR_{14}$, —$NR_{14}$C(=O)$OR_8$, —$NR_{14}$S(O$_2$)$R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_r$$CF_3$, —O$(CR_8R_8)_rR_{14}$, —OH, —SH, —S$(CR_8R_8)_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}$S(O)$_2(CF_2)_rCF_3$, —C(=O)$NR_{14}$S(O)$_2R_6$, —S(O)$_2NR_{14}$C(=O)$NR_{14}R_{14}$, —S(O)$_2NR_{14}$C(=O)$NR_{14}R_{14}$, —C(=O)$NR_{14}$S(O)$_2(CF_2)_rCF_3$, —C(=O)$(CR_8R_8)_rR_{14}$, —$NR_{14}$C(=O)H, —$NR_{14}$C(=O)$(CR_8R_8)_rR_{14}$, —OC(=O)$(CR_3R_8)_rR_{14}$, —C(=$NR_{14}$)$NR_{14}R_{14}$, —NHC(=$NR_{14}$)$NR_{14}R_{14}$, —S(=O)$(CR_8R_8)_rR_{14}$, —S(O)$_2(CR_8R_8)_rR_{14}$, —$NR_{14}$C(=O)$OR_8$, —$NR_{14}$S(O$_2$)$R_8$, aryloxy or arylalkyl;

$R_{14}$, at each occurrence, is independently selected from hydrogen, alkyl, cycloalkyl or phenyl;

m, at each occurrence, is 0-2;

n is 1-3; and r is 0-5.

In another embodiment, compounds of Formula (I) are those compounds having the formula (Ia):

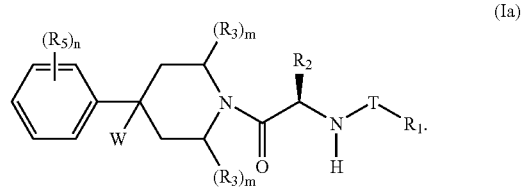

(Ia)

In another embodiment, compounds of the present invention are those in which:

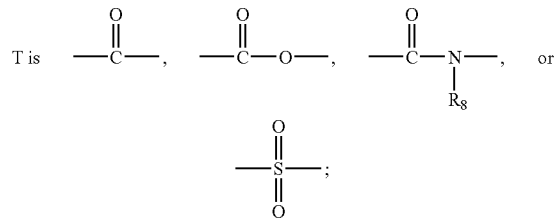

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_r$$CF_3$, —O$(CR_8R_8)_rR_{10}$, —OH, —SH, —S$(CR_8R_8)_rR_{10}$, —S(O)$_3$H, —P(O)$_3H_2$, —C(=O)$NR_9R_9$, —$NR_9R_9$, —S(O)$_2NR_9R_9$, —$NR_9$S(O)$_2(CF_2)_rCF_3$, —C(=O)$NR_9$S(O)$_2R_6$, —S(O)$_2NR_9$C(=O)$OR_6$, —S(O)$_2NR_9$C(=O)$NR_9R_9$, —C(=O)$NR_9$S(O)$_2(CF_2)_rCF_3$, —C(=O)$(CR_8R_8)_rR_{10}$, —$NR_9$C(=O)H, —$NR_9$C(=O)$(CR_8R_8)_rR_{10}$, —OC(=O)$(CR_8R_8)_rR_{10}$, —C(=$NR_{14}$)$NR_9R_9$, —NHC(=$NR_{14}$)$NR_{14}R_{14}$, —S(=O)$(CR_8R_8)_rR_{10}$, —S(O)$_2(CR_8R_8)_rR_{10}$, —$NR_9$C(=O)$OR_8$, —$NR_9$S(O$_2$)$R_8$, —S(O)$_2NR_9$C(O)$R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, aryloxy or arylalkyl;

R$_2$ is alkyl, cycloalkyl, cycloalkylalkyl, or alkenyl, wherein the alkyl may be optionally substituted with —OH;

R$_3$, at each occurrence, is alkyl; or any two R$_3$'s attached to the same carbon atom may form a 3- to 6-membered ring;

W is hydrogen, F, —OH, —NH$_2$;

R$_5$ is halo, —CN or —Oalkyl;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

R$_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

R$_{14}$, at each occurrence, is independently selected from hydrogen, alkyl, cycloalkyl or phenyl;

m, at each occurrence, is 0-2;

n is 1-2; and r is 0-4.

In yet another embodiment, compounds of the present invention are those in which:

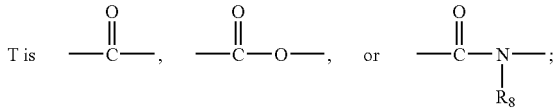

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, Alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, aryloxy or arylalkyl;

R$_2$ is alkyl, cycloalkyl, or cycloalkylalkyl, wherein the alkyl may be optionally substituted with —OH;

R$_3$, at each occurrence, is alkyl; or any two R$_3$'s attached to the same carbon atom may form a 3- to 6-membered ring;

W is hydrogen, F, —OH, —NH$_2$;

R$_5$ is halo or —CN;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r R_{14}$, —O($CF_2$)$_r$ $CF_3$, —O($CR_8R_8$)$_r R_{14}$, —OH, —SH, —S($CR_8R_8$)$_r R_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}$S(O)$_2$($CF_2$)$_r$ $CF_3$, —C(=O)$NR_{14}$S(O)$_2R_6$, —S(O)$_2NR_{14}$C(=O) $OR_6$, —S(O)$_2NR_{14}$C(=O)$NR_{14}R_{14}$, —C(=O)$NR_{14}$S (O)$_2$($CF_2$)$_r CF_3$, —C(=O)($CR_8R_8$)$_r R_{14}$, —$NR_{14}$C (=O)H, —$NR_{14}$C(=O)($CR_8R_8$)$_r R_{14}$, —OC(=O) ($CR_8R_8$)$_r R_{14}$, —C(=$NR_{14}$)$NR_{14}R_{14}$, —NHC (=$NR_{14}$)$NR_{14}R_{14}$, —S(=O)($CR_8R_8$)$_r R_{14}$, —S(O)$_2$ ($CR_8R_8$)$_r R_{14}$, —$NR_{14}$C(=O)$OR_8$, —$NR_{14}$S(O)$_2R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r R_{14}$, —O($CF_2$)$_r$ $CF_3$, —O($CR_8R_8$)$_r R_{14}$, —OH, —SH, —S($CR_8R_8$)$_r R_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}$S(O)$_2$($CF_2$)$_r$ $CF_3$, —C(=O)$NR_{14}$S(O)$_2R_6$, —S(O)$_2NR_{14}$C(=O) $OR_6$, —S(O)$_2NR_{14}$C(=O)$NR_{14}R_{14}$, —C(=O)$NR_{14}$S (O)$_2$($CF_2$)$_r CF_3$, —C(=O)($CR_8R_8$)$_r R_{14}$, —$NR_{14}$C (=O)H, —$NR_{14}$C(=O)($CR_8R_8$)$_r R_{14}$, —OC(=O) ($CR_8R_8$)$_r R_{14}$, —C(=$NR_{14}$)$NR_{14}R_{14}$, —NHC (=$NR_{14}$)$NR_{14}R_{14}$, —S(=O)($CR_8R_8$)$_r R_{14}$, —S(O)$_2$ ($CR_8R_8$)$_r R_{14}$, —$NR_{14}$C(=O)$OR_8$, —$NR_{14}$S(O)$_2R_8$, aryloxy or arylalkyl;

$R_{14}$, at each occurrence, is independently selected from hydrogen, alkyl, cycloalkyl or phenyl;

m, at each occurrence, is 0-2;

n is 1-2; and r is 0-3.

In still yet another embodiment, compounds of the present invention are those in which:

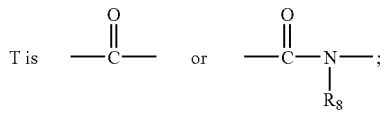

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r R_{10}$, —O($CF_2$)$_r$ $CF_3$, —O($CR_8R_8$)$_r R_{10}$, —OH, —SH, —S($CR_8R_8$)$_r R_{10}$, —S(O)$_3$H, —P(O)$_3H_2$, —C(=O)$NR_9R_9$, —$NR_9R_9$, —S(O)$_2NR_9R_9$, —$NR_9$S(O)$_2$($CF_2$)$_r CF_3$, —C(=O) $NR_9$S(O)$_2R_6$, —S(O)$_2NR_9$C(=O)$OR_6$, —S(O)$_2NR_9$C (=O)$NR_9R_9$, —C(=O)$NR_9$S(O)$_2$($CF_2$)$_r CF_3$, —C(=O)($CR_8R_8$)$_r R_{10}$, —$NR_9$C(=O)H, —$NR_9$C (=O)($CR_8R_8$)$_r R_{10}$, —OC(=O)($CR_8R_8$)$_r R_{10}$, —C(=$NR_{14}$)$NR_9R_9$, —NHC(=$NR_{14}$)$NR_{14}R_{14}$, —S(=O)($CR_8R_8$)$_r R_{10}$, —S(O)$_2$($CR_8R_8$)$_r R_{10}$, —$NR_9$C (=O)$OR_8$, —$NR_9$S(O$_2$)$R_8$, —S(O)$_2NR_9$C(O)$R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r R_{10}$, —O($CF_2$)$_r$ $CF_3$, —O($CR_8R_8$)$_r R_{10}$, —OH, —SH, —S($CR_8R_8$)$_r R_{10}$, —S(O)$_3$H, —P(O)$_3H_2$, —C(=O)$NR_9R_9$, —$NR_9R_9$, —S(O)$_2NR_9R_9$, —$NR_9$S(O)$_2$($CF_2$)$_r CF_3$, —C(=O) $NR_9$S(O)$_2R_6$, —S(O)$_2NR_9$C(=O)$OR_6$, —S(O)$_2NR_9$C (=O)$NR_9R_9$, —C(=O)$NR_9$S(O)$_2$($CF_2$)$_r CF_3$, —C(=O)($CR_8R_8$)$_r R_{10}$, —$NR_9$C(=O)H, —$NR_9$C (=O)($CR_8R_8$)$_r R_{10}$, —OC(=O)($CR_8R_8$)$_r R_{10}$, —C(=$NR_{14}$)$NR_9R_9$, —NHC(=$NR_{14}$)$NR_{14}R_{14}$, —S(=O)($CR_8R_8$)$_r R_{10}$, —S(O)$_2$($CR_8R_8$)$_r R_{10}$, —$NR_9$C (=O)$OR_8$, —$NR_9$S(O$_2$)$R_9$, aryloxy or arylalkyl;

$R_2$ is alkyl or cycloalkyl, wherein the alkyl may be optionally substituted with —OH;

$R_3$, at each occurrence, is alkyl; or any two $R_3$'s attached to the same carbon atom may form a 3- to 6-membered ring;

W is hydrogen, F, —OH, —$NH_2$;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r R_{14}$, —O($CF_2$)$_r$ $CF_3$, —O($CR_8R_8$)$_r R_{14}$, —OH, —SH, —S($CR_8R_8$)$_r R_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}$S(O)$_2$($CF_2$)$_r$ $CF_3$, —C(=O)$NR_{14}$S(O)$_2R_6$, —S(O)$_2NR_{14}$C(=O) $OR_6$, —S(O)$_2NR_{14}$C(=O)$NR_{14}R_{14}$, —C(=O)$NR_{14}$S (O)$_2$($CF_2$)$_r CF_3$, —C(=O)($CR_8R_8$)$_r R_{14}$, —$NR_{14}$C (=O)H, —$NR_{14}$C(=O)($CR_8R_8$)$_r R_{14}$, —OC(=O) ($CR_8R_8$)$_r R_{14}$, —C(=$NR_{14}$)$NR_{14}R_{14}$, —NHC (=$NR_{14}$)$NR_{14}R_{14}$, —S(=O)($CR_8R_8$)$_r R_{14}$, —S(O)$_2$ ($CR_8R_8$)$_r R_{14}$, —$NR_{14}$C(=O)$OR_8$, —$NR_{14}$S(O)$_2R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_rR_{14}$, —O($CF_2$)$_r$ $CF_3$, —O($CR_8R_8$)$_rR_{14}$, —OH, —SH, —S($CR_8R_8$)$_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2(CF_2)_r$ $CF_3$, —C(=O)$NR_{14}S(O)_2R_6$, —S(O)$_2NR_{14}C$(=O) $OR_6$, —S(O)$_2NR_{14}C$(=O)$NR_{14}R_{14}$, —C(=O)$NR_{14}S$ (O)$_2(CF_2)_rCF_3$, —C(=O)($CR_8R_8$)$_rR_{14}$, —$NR_{14}C$ (=O)H, —$NR_{14}C$(=O)($CR_8R_8$)$_rR_{14}$, —OC(=O) ($CR_8R_8$)$_rR_{14}$, —C(=$NR_{14}$)$NR_{14}R_{14}$, —NHC (=$NR_{14}$)$NR_{14}R_{14}$, —S(=O)($CR_8R_8$)$_rR_{14}$, —S(O)$_2$ ($CR_8R_8$)$_rR_{14}$, —$NR_{14}C$(=O)$OR_8$, —$NR_{14}S(O_2)R_8$, aryloxy or arylalkyl;

$R_{14}$, at each occurrence, is independently selected from hydrogen, alkyl, cycloalkyl or phenyl;

m, at each occurrence, is 0-2;

n is 1-2; and r is 0-2.

In yet another embodiment, compounds of the present invention are those in which:

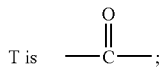

T is $R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_rR_{10}$, —O($CF_2$)$_r$ $CF_3$, —O($CR_8R_8$)$_rR_{10}$, —OH, —SH, —S($CR_8R_8$)$_rR_{10}$, —S(O)$_3$H, —P(O)$_3H_2$, —C(=O)$NR_9R_9$, —$NR_9R_9$, —S(O)$_2NR_9R_9$, —$NR_9S(O)_2(CF_2)_rCF_3$, —C(=O) $NR_9S(O)_2R_6$, —S(O)$_2NR_9C$(=O)$OR_6$, —S(O)$_2NR_9C$ (=O)$NR_9R_9$, —C(=O)$NR_9S(O)_2(CF_2)_rCF_3$, —C(=O)($CR_8R_8$)$_rR_{10}$, —$NR_9C$(=O)H, —$NR_9C$ (=O)($CR_8R_8$)$_rR_{10}$, —OC(=O)($CR_8R_8$)$_rR_{10}$, —C(=$NR_{14}$)$NR_9R_9$, —NHC(=$NR_{14}$)$NR_{14}R_{14}$, —S(=O)($CR_8R_8$)$_rR_{10}$, —S(O)$_2$($CR_8R_8$)$_rR_{10}$, —$NR_9C$ (=O)$OR_8$, —$NR_9S(O_2)R_8$, —S(O)$_2NR_9C(O)R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_rR_{10}$, —O($CF_2$)$_r$ $CF_3$, —O($CR_8R_8$)$_rR_{10}$, —OH, —SH, —S($CR_8R_8$)$_rR_{10}$, —S(O)$_3$H, —P(O)$_3H_2$, —C(=O)$NR_9R_9$, —$NR_9R_9$, —S(O)$_2NR_9R_9$, —$NR_9S(O)_2(CF_2)_rCF_3$, —C(=O) $NR_9S(O)_2R_6$, —S(O)$_2NR_9C$(=O)$OR_6$, —S(O)$_2NR_9C$ (=O)$NR_9R_9$, —C(=O)$NR_9S(O)_2(CF_2)_rCF_3$, —C(=O)($CR_8R_8$)$_rR_{10}$, —$NR_9C$(=O)H, —$NR_9C$ (=O)($CR_8R_8$)$_rR_{10}$, —OC(=O)($CR_8R_8$)$_rR_{10}$, —C(=$NR_{14}$)$NR_9R_9$, —NHC(=$NR_{14}$)$NR_{14}R_{14}$, —S(=O)($CR_8R_8$)$_rR_{10}$, —S(O)$_2$($CR_8R_8$)$_rR_{10}$, —$NR_9C$ (=O)$OR_8$, —$NR_9S(O_2)R_8$, aryloxy or arylalkyl;

$R_2$ is alkyl or cycloalkyl, wherein the alkyl may be optionally substituted with —OH;

$R_3$, at each occurrence, is alkyl;

W is hydrogen, —OH or —$NH_2$;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_rR_{14}$, —O($CF_2$)$_r$ $CF_3$, —O($CR_8R_8$)$_rR_{14}$, —OH, —SH, —S($CR_8R_8$)$_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2(CF_2)_r$ $CF_3$, —C(=O)$NR_{14}S(O)_2R_6$, —S(O)$_2NR_{14}C$(=O) $OR_6$, —S(O)$_2NR_{14}C$(=O)$NR_{14}R_{14}$, —C(=O)$NR_{14}S$ (O)$_2(CF_2)_rCF_3$, —C(=O)($CR_8R_8$)$_rR_{14}$, —$NR_{14}C$ (=O)H, —$NR_{14}C$(=O)($CR_8R_8$)$_rR_{14}$, —OC(=O) ($CR_8R_8$)$_rR_{14}$, —C(=$NR_{14}$)$NR_{14}R_{14}$, —NHC (=$NR_{14}$)$NR_{14}R_{14}$, —S(=O)($CR_8R_8$)$_rR_{14}$, —S(O)$_2$ ($CR_8R_8$)$_rR_{14}$, —$NR_{14}C$(=O)$OR_8$, —$NR_{14}S(O_2)R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_rR_{14}$, —O($CF_2$)$_r$ $CF_3$, —O($CR_8R_8$)$_rR_{14}$, —OH, —SH, —S($CR_8R_8$)$_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2(CF_2)_r$ $CF_3$, —C(=O)$NR_{14}S(O)_2R_6$, —S(O)$_2NR_{14}C$(=O) $OR_6$, —S(O)$_2NR_{14}C$(=O)$NR_{14}R_{14}$, —C(=O)$NR_{14}S$ (O)$_2(CF_2)_rCF_3$, —C(=O)($CR_8R_8$)$_rR_{14}$, —$NR_{14}C$ (=O)H, —$NR_{14}C$(=O)($CR_8R_8$)$_rR_{14}$, —OC(=O) ($CR_8R_8$)$_rR_{14}$, —C(=$NR_{14}$)$NR_{14}R_{14}$, —NHC (=$NR_{14}$)$NR_{14}R_{14}$, —S(=O)($CR_8R_8$)$_rR_{14}$, —S(O)$_2$ ($CR_8R_8$)$_rR_{14}$, —$NR_{14}C$(=O)$OR_8$, —$NR_{14}S(O_2)R_8$, aryloxy or arylalkyl;

$R_{14}$, at each occurrence, is independently selected from hydrogen, alkyl, cycloalkyl or phenyl;

m, at each occurrence, is 0-2;

n is 1-2; and r is 0-2.

In another embodiment, compounds of the present invention are those in which:

T is 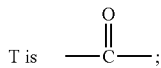

R₁ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH₂, —CN, —NO₂, —C(=O)OH, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —S(O)₃H, —P(O)₃H₂, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —C(=NR₁₄)NR₉R₉, —NHC(=NR₁₄)NR₁₄R₁₄, —S(=O)(CR₈R₈)ᵣR₁₀, —S(O)₂(CR₈R₈)ᵣR₁₀, —NR₉C(=O)OR₈, —NR₉S(O₂)R₈, —S(O)₂NR₉C(O)R₆, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH₂, —CN, —NO₂, —C(=O)OH, —C(=O)O(CR₈R₈)ᵣR₁₀, —O(CF₂)ᵣCF₃, —O(CR₈R₈)ᵣR₁₀, —OH, —SH, —S(CR₈R₈)ᵣR₁₀, —S(O)₃H, —P(O)₃H₂, —C(=O)NR₉R₉, —NR₉R₉, —S(O)₂NR₉R₉, —NR₉S(O)₂(CF₂)ᵣCF₃, —C(=O)NR₉S(O)₂R₆, —S(O)₂NR₉C(=O)OR₆, —S(O)₂NR₉C(=O)NR₉R₉, —C(=O)NR₉S(O)₂(CF₂)ᵣCF₃, —C(=O)(CR₈R₈)ᵣR₁₀, —NR₉C(=O)H, —NR₉C(=O)(CR₈R₈)ᵣR₁₀, —OC(=O)(CR₈R₈)ᵣR₁₀, —C(=NR₁₄)NR₉R₉, —NHC(=NR₁₄)NR₁₄R₁₄, —S(=O)(CR₈R₈)ᵣR₁₀, —S(O)₂(CR₈R₈)ᵣR₁₀, —NR₉C(=O)OR₈, —NR₉S(O₂)R₈, aryloxy or arylalkyl;

R₂ is alkyl or cycloalkyl;

R₃, at each occurrence, is alkyl;

W is hydrogen or —OH;

R₅ is halo;

R₆, at each occurrence, is independently alkyl, cycloalkyl, cycloalkylalkyl, aryl, arylalkyl, heteroaryl or heteroarylalkyl;

R₈, at each occurrence, is independently hydrogen or alkyl;

R₉, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH₂, —CN, —NO₂, —C(=O)OH, —C(=O)O(CR₈R₈)ᵣR₁₄, —O(CF₂)ᵣCF₃, —O(CR₈R₈)ᵣR₁₄, —OH, —SH, —S(CR₈R₈)ᵣR₁₄, —S(O)₃H, —P(O)₃H₂, —C(=O)NR₁₄R₁₄, —NR₁₄R₁₄, —S(O)₂NR₁₄R₁₄, —NR₁₄S(O)₂(CF₂)ᵣCF₃, —C(=O)NR₁₄S(O)₂R₆, —S(O)₂NR₁₄C(=O)OR₆, —S(O)₂NR₁₄C(=O)NR₁₄R₁₄, —C(=O)NR₁₄S(O)₂(CF₂)ᵣCF₃, —C(=O)(CR₈R₈)ᵣR₁₄, —NR₁₄C(=O)H, —NR₁₄C(=O)(CR₈R₈)ᵣR₁₄, —OC(=O)(CR₈R₈)ᵣR₁₄, —C(=NR₁₄)NR₁₄R₁₄, —NHC(=NR₁₄)NR₁₄R₁₄, —S(=O)(CR₈R₈)ᵣR₁₄, —S(O)₂(CR₈R₈)ᵣR₁₄, —NR₁₄C(=O)OR₈, —NR₁₄S(O₂)R₈, aryloxy or arylalkyl;

R₁₀, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH₂, —CN, —NO₂, —C(=O)OH, —C(=O)O(CR₈R₈)ᵣR₁₄, —O(CF₂)ᵣCF₃, —O(CR₈R₈)ᵣR₁₄, —OH, —SH, —S(CR₈R₈)ᵣR₁₄, —S(O)₃H, —P(O)₃H₂, —C(=O)NR₁₄R₁₄, —NR₁₄R₁₄, —S(O)₂NR₁₄R₁₄, —NR₁₄S(O)₂(CF₂)ᵣCF₃, —C(=O)NR₁₄S(O)₂R₆, —S(O)₂NR₁₄C(=O)OR₆, —S(O)₂NR₁₄C(=O)NR₁₄R₁₄, —C(=O)NR₁₄S(O)₂(CF₂)ᵣCF₃, —C(=O)(CR₈R₈)ᵣR₁₄, —NR₁₄C(=O)H, —NR₁₄C(=O)(CR₈R₈)ᵣR₁₄, —OC(=O)(CR₈R₈)ᵣR₁₄, —C(=NR₁₄)NR₁₄R₁₄, —NHC(=NR₁₄)NR₁₄R₁₄, —S(=O)(CR₈R₈)ᵣR₁₄, —S(O)₂(CR₈R₈)ᵣR₁₄, —NR₁₄C(=O)OR₈, —NR₁₄S(O₂)R₈, aryloxy or arylalkyl;

R₁₄, at each occurrence, is independently selected from hydrogen, alkyl, cycloalkyl or phenyl;

m, at each occurrence, is 0-2;

n is 1-2; and r is 0-2.

In one embodiment, the present invention provides novel compounds of formula (Ib):

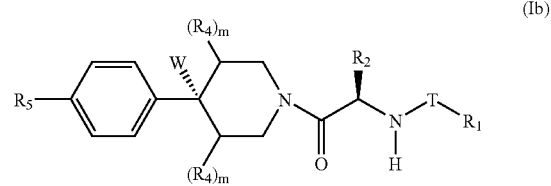

(Ib)

or stereoisomers or prodrugs or pharmaceutically acceptable salt forms thereof, wherein:

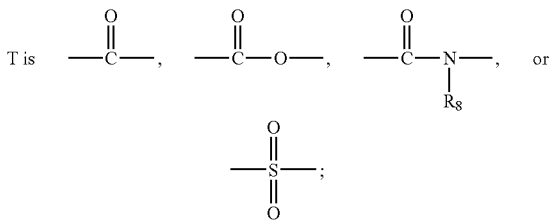

R₁ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH₂, —CN, —NO₂, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, aryloxy or arylalkyl;

R$_2$ is alkyl, cycloalkyl, cycloalkylalkyl, arylalkyl, —CH$_2$CH$_2$CH$_2$NHC(=NR$_{14}$)NR$_{14}$R$_{14}$, —CH$_2$CH$_2$S(CR$_8$R$_8$)$_r$R$_{10}$ or —CH$_2$CH$_2$CN, wherein the alkyl and arylalkyl may be optionally substituted with —OH;

R$_4$, at each occurrence, is F, —OH or alkyl; or any two alkyl R$_4$'s attached to the same carbon atom may form a 3- to 6-membered ring, which optionally may contain 1-4 heteroatoms selected from N, O, and S;

W is hydrogen, F, —OH, —CN, —NH$_2$;

R$_5$ is halo, —CN or —Oalkyl;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_3$R$_8$)$_r$R$_{14}$, —S(O)$_2$(CR$_3$R$_8$)$_r$R$_{14}$, —NR$_{14}$C(=O)OR$_8$, —NR$_{14}$S(O$_2$)R$_8$, aryloxy or arylalkyl;

R$_{14}$, at each occurrence, is independently selected from hydrogen, alkyl, cycloalkyl or phenyl;

m, at each occurrence, is 0-2; and r is 0-5.

In another embodiment, compounds of Formula (Ib) are those compounds having the formula (Ib'):

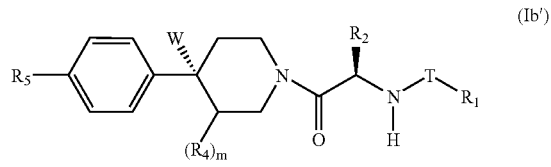

in which W is hydrogen or OH and m is 1 or 2.

In another embodiment, compounds of the present invention are those in which:

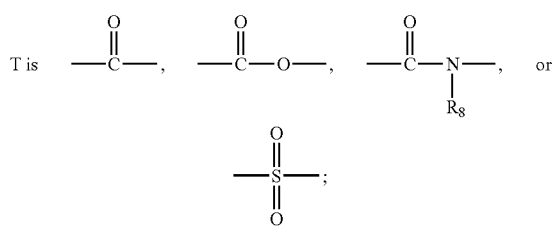

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C (=O)NR$_9$R$_9$, —C(=O)NR$_9$S(O)$_2$(CF$_2$)$_r$ CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, aryloxy or arylalkyl;

R$_2$ is alkyl, cycloalkyl, cycloalkylalkyl, —CH$_2$CH$_2$CH$_2$—NHC(=NH)NH$_2$, —CH$_2$CH$_2$SCH$_3$, —CH$_2$CH$_2$CN,

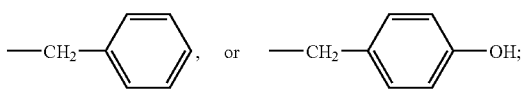

wherein the alkyl may be optionally substituted with —OH;

R$_4$, at each occurrence, is —OH or alkyl; or any two alkyl R$_4$'s attached to the same carbon atom may form a 3- to 6-membered ring, which optionally may contain 1-4 heteroatoms selected from N, O, and S;

R$_5$ is halo, —CN or —Oalkyl;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{14}$, at each occurrence, is independently selected from hydrogen, alkyl, cycloalkyl or phenyl; and r is 0-4.

In yet another embodiment, compounds of the present invention are those in which:

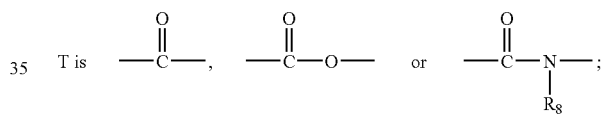

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)

$-NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_8$, $-NR_9S(O_2)R_8$, aryloxy or arylalkyl;

$R_2$ is alkyl, cycloalkyl, cycloalkylalkyl, $-CH_2CH_2SCH_3$, $-CH_2CH_2CN$,

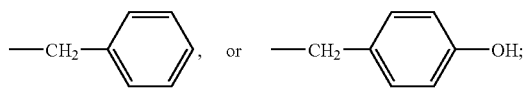

wherein the alkyl may be optionally substituted with $-OH$;

$R_4$, at each occurrence, is $-OH$ or alkyl; or any two alkyl $R_4$'s attached to the same carbon atom may form a 3- to 6-membered ring, which optionally may contain 1-4 heteroatoms selected from N, O, and S;

$R_5$ is halo or $-CN$;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-C(=NR_{14})NR_{14}R_{14}$, $-NHC(=NR_{14})NR_{14}R_{14}$, $-S(=O)(CR_8R_8)_rR_{14}$, $-S(O)_2(CR_8R_8)_rR_{14}$, $-NR_{14}C(=O)OR_8$, $-NR_{14}S(O_2)R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-C(=NR_{14})NR_{14}R_{14}$, $-NHC(=NR_{14})NR_{14}R_{14}$, $-S(=O)(CR_8R_8)_rR_{14}$, $-S(O)_2(CR_8R_8)_rR_{14}$, $-NR_{14}C(=O)OR_8$, $-NR_{14}S(O_2)R_8$, aryloxy or arylalkyl;

$R_{14}$, at each occurrence, is independently selected from hydrogen, alkyl, cycloalkyl or phenyl; and r is 0-3.

In still yet another embodiment, compounds of the present invention are those in which:

T is 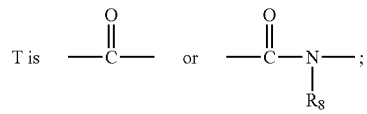

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_8$, $-NR_9S(O_2)R_8$, $-S(O)_2NR_9C(O)R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_8$, $-NR_9S(O_2)R_9$, aryloxy or arylalkyl;

$R_2$ is alkyl, cycloalkyl, cycloalkylalkyl,

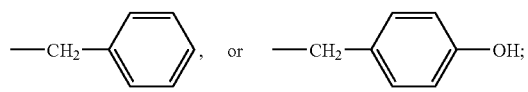

wherein the alkyl may be optionally substituted with $-OH$;

$R_4$, at each occurrence, is alkyl; or any two alkyl $R_4$'s attached to the same carbon atom may form a 3- to 6-membered ring, which optionally may contain 1-4 heteroatoms selected from N, O, and S;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{14}$, at each occurrence, is independently selected from hydrogen, alkyl, cycloalkyl or phenyl; and r is 0-2.

In still yet another embodiment, compounds of the present invention are those in which:

T is $-\overset{\overset{\displaystyle O}{\|}}{C}-$;

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_9$, aryloxy or arylalkyl;

$R_2$ is alkyl, cycloalkyl, or cycloalkylalkyl, wherein the alkyl may be optionally substituted with —OH;

$R_4$, at each occurrence, is alkyl;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_{88}$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_r$$CF_3$, —O$(CR_8R_8)_rR_{14}$, —OH, —SH, —S$(CR_8R_8)_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2(CF_2)_r$$CF_3$, —C(=O)$NR_{14}S(O)_2R_6$, —S(O)$_2NR_{14}$C(=O)$OR_6$, —S(O)$_2NR_{14}$C(=O)$NR_{14}R_{14}$, —C(=O)$NR_{14}$S(O)$_2(CF_2)_rCF_3$, —C(=O)$(CR_8R_8)_rR_{14}$, —$NR_{14}$C(=O)H, —$NR_{14}$C(=O)$(CR_8R_8)_rR_{14}$, —OC(=O)$(CR_8R_8)_rR_{14}$, —C(=$NR_{14}$)$NR_{14}R_{14}$, —NHC(=$NR_{14}$)$NR_{14}R_{14}$, —S(=O)$(CR_8R_8)_rR_{14}$, —S(O)$_2$$(CR_8R_8)_rR_{14}$, —$NR_{14}$C(=O)$OR_8$, —$NR_{14}$S(O$_2$)$R_8$, aryloxy or arylalkyl;

$R_{14}$, at each occurrence, is independently selected from hydrogen, alkyl, cycloalkyl or phenyl; and r is 0-2.

In another embodiment, compounds of the present invention are those in which:

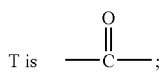

T is —C(=O)—;

$R_1$ is alkyl, cycloalkyl, aryl, heterocyclyl or heteroaryl, all of which may be optionally substituted with 0-5 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_r$$CF_3$, —O$(CR_8R_8)_rR_{10}$, —OH, —SH, —S$(CR_8R_8)_rR_{10}$, —S(O)$_3$H, —P(O)$_3H_2$, —C(=O)$NR_9R_9$, —$NR_9R_9$, —S(O)$_2NR_9R_9$, —$NR_9S(O)_2(CF_2)_rCF_3$, —C(=O)$NR_9S(O)_2R_6$, —S(O)$_2NR_9$C(=O)$OR_6$, —S(O)$_2NR_9$C(=O)$NR_9R_9$, —C(=O)$NR_9S(O)_2(CF_2)_rCF_3$, —C(=O)$(CR_8R_8)_rR_{10}$, —$NR_9$C(=O)H, —$NR_9$C(=O)$(CR_8R_8)_rR_{10}$, —OC(=O)$(CR_8R_8)_rR_{10}$, —C(=$NR_{14}$)$NR_9R_9$, —NHC(=$NR_{14}$)$NR_{14}R_{14}$, —S(=O)$(CR_8R_8)_rR_{10}$, —S(O)$_2(CR_8R_8)_rR_{10}$, —$NR_9$C(=O)$OR_8$, —$NR_9S(O_2)R_8$, —S(O)$_2NR_9C(O)R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{10}$, —O$(CF_2)_r$$CF_3$, —O$(CR_8R_8)_rR_{10}$, —OH, —SH, —S$(CR_8R_8)_rR_{10}$, —S(O)$_3$H, —P(O)$_3H_2$, —C(=O)$NR_9R_9$, —$NR_9R_9$, —S(O)$_2NR_9R_9$, —$NR_9S(O)_2(CF_2)_rCF_3$, —C(=O)$NR_9S(O)_2R_6$, —S(O)$_2NR_9$C(=O)$OR_6$, —S(O)$_2NR_9$C(=O)$NR_9R_9$, —C(=O)$(CR_8R_8)_rR_{10}$, —$NR_9$C(=O)H, —$NR_9$C(=O)$(CR_8R_8)_rR_{10}$, —OC(=O)$(CR_8R_8)_rR_{10}$, —C(=$NR_{14}$)$NR_9R_9$, —NHC(=$NR_{14}$)$NR_{14}R_{14}$, —S(=O)$(CR_8R_8)_rR_{10}$, —S(O)$_2(CR_8R_8)_rR_{10}$, —$NR_9$C(=O)$OR_8$, —$NR_9S(O_2)R_8$, aryloxy or arylalkyl;

$R_2$ is alkyl or cycloalkyl;

$R_4$, at each occurrence, is alkyl;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_r$$CF_3$, —O$(CR_8R_8)_rR_{14}$, —OH, —SH, —S$(CR_8R_8)_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2(CF_2)_rCF_3$, —C(=O)$NR_{14}S(O)_2R_6$, —S(O)$_2NR_{14}$C(=O)$OR_6$, —S(O)$_2NR_{14}$C(=O)$NR_{14}R_{14}$, —C(=O)$NR_{14}$S(O)$_2(CF_2)_rCF_3$, —C(=O)$(CR_8R_8)_rR_{14}$, —$NR_{14}$C(=O)H, —$NR_{14}$C(=O)$(CR_8R_8)_rR_{14}$, —OC(=O)$(CR_8R_8)_rR_{14}$, —C(=$NR_{14}$)$NR_{14}R_{14}$, —NHC(=$NR_{14}$)$NR_{14}R_{14}$, —S(=O)$(CR_8R_8)_rR_{14}$, —S(O)$_2(CR_8R_8)_rR_{14}$, —$NR_{14}$C(=O)$OR_8$, —$NR_{14}S(O_2)R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O$(CR_8R_8)_rR_{14}$, —O$(CF_2)_r$$CF_3$, —O$(CR_8R_8)_rR_{14}$, —OH, —SH, —S$(CR_8R_8)_rR_{14}$, —S(O)$_3$H, —P(O)$_3H_2$, —C(=O)$NR_{14}R_{14}$, —$NR_{14}R_{14}$, —S(O)$_2NR_{14}R_{14}$, —$NR_{14}S(O)_2(CF_2)_r$$CF_3$, —C(=O)$NR_{14}S(O)_2R_6$, —S(O)$_2NR_{14}$C(=O)$OR_6$, —S(O)$_2NR_{14}$C(=O)$NR_{14}R_{14}$, —C(=O)$NR_{14}$S(O)$_2(CF_2)_rCF_3$, —C(=O)$(CR_8R_8)_rR_{14}$, —$NR_{14}$C(=O)H, —$NR_{14}$C(=O)$(CR_8R_8)_rR_{14}$, —OC(=O)$(CR_8R_8)_rR_{14}$, —C(=$NR_{14}$)$NR_{14}R_{14}$, —NHC(=$NR_{14}$)$NR_{14}R_{14}$, —S(=O)$(CR_8R_8)_rR_{14}$, —S(O)$_2(CR_8R_8)_rR_{14}$, —$NR_{14}$C(=O)$OR_8$, —$NR_{14}S(O_2)R_8$, aryloxy or arylalkyl;

$R_{14}$, at each occurrence, is independently selected from hydrogen, alkyl, cycloalkyl or phenyl; and r is 0-2.

In another embodiment, compounds of the present invention are those in which $R_2$ is isopropyl, sec-butyl or cyclopropyl; $R_4$ is methyl; $R_5$ is Cl, F or Br; and $R_1$ is alkyl, cycloalkyl, aryl or heteroaryl, all of which may be optionally substituted with 0-5 $R_{1a}$.

In still another embodiment, compounds of the present invention are those in which:

T is 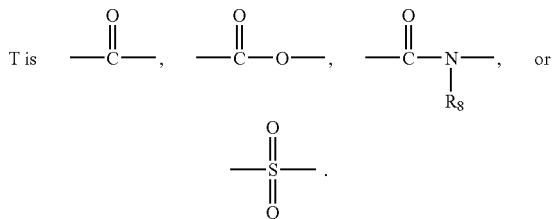

In one embodiment, the present invention provides novel compounds of formula (Ic):

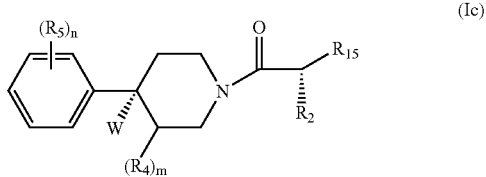

(Ic)

or stereoisomers or prodrugs or pharmaceutically acceptable salt forms thereof, wherein:

$R_{15}$ is —$NHR_1$, heteroaryl or aryl, wherein the heteroaryl and aryl may be optionally substituted with 0-3 $R_{1a}$;

$R_1$ is aryl or heteroaryl, both of which may be optionally substituted with 0-3 $R_{1a}$, provided that when $R_1$ is phenyl, $R_{1a}$ cannot be ortho-methoxy;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_9$, aryloxy or arylalkyl;

$R_2$ is alkyl, cycloalkyl or cycloalkylalkyl, wherein the alkyl may be optionally substituted with —OH;

$R_4$, at each occurrence, is F, —OH or alkyl; or any two alkyl $R_4$'s attached to the same carbon atom may form a 3- to 6-membered ring, which optionally may contain 1-4 heteroatoms selected from N, O, and S;

W is hydrogen, F, —OH or —$NH_2$;

$R_5$ is halo, —CN or —Oalkyl;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{14}$, at each occurrence, is independently selected from hydrogen, alkyl, cycloalkyl or phenyl;

m, at each occurrence, is 0-2;

n is 1-3; and r is 0-5.

In another embodiment, compounds of Formula (Ic) are those compounds having the formula (Id):

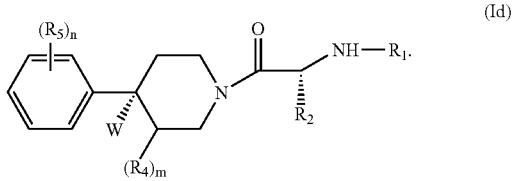

(Id)

In yet another embodiment, compounds of the present invention are those in which:

$R_{15}$ is —$NHR_1$, heteroaryl or aryl, wherein the heteroaryl and aryl may be optionally substituted with 0-3 $R_{1a}$;

$R_1$ is aryl or heteroaryl, both of which may be optionally substituted with 0-3 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$H$_2$, —C(=O)$NR_9R_8$, —$NR_9R_9$, —S(O)$_2NR_9R_9$, —$NR_9$S(O)$_2$($CF_2$)$_r$$CF_3$, —C(=O)$NR_9$S(O)$_2R_6$, —S(O)$_2NR_9$C(=O)$OR_6$, —S(O)$_2NR_9$C(=O)$NR_9R_9$, —C(=O)$NR_9$S(O)$_2$($CF_2$)$_r$$CF_3$, —C(=O)($CR_8R_8$)$_r$$R_{10}$, —$NR_9$C(=O)H, —$NR_9$C(=O)($CR_8R_8$)$_r$$R_{10}$, —OC(=O)($CR_8R_8$)$_r$$R_{10}$, —C(=$NR_{14}$)$NR_9R_9$, —NHC(=$NR_{14}$)$NR_{14}R_{14}$, —S(=O)($CR_8R_8$)$_r$$R_{10}$, —S(O)$_2$($CR_8R_8$)$_r$$R_{10}$, —$NR_9$C(=O)$OR_8$, —$NR_9$S(O)$_2R_8$, —S(O)$_2NR_9$C(O)$R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$H$_2$, —C(=O)$NR_9R_9$, —$NR_9R_9$, —S(O)$_2NR_9R_9$, —$NR_9$S(O)$_2$($CF_2$)$_r$$CF_3$, —C(=O)$NR_9$S(O)$_2R_6$, —S(O)$_2NR_9$C(=O)$OR_6$, —S(O)$_2NR_9$C(=O)$NR_9R_9$, —C(=O)$NR_9$S(O)$_2$($CF_2$)$_r$$CF_3$, —C(=O)($CR_8R_8$)$_r$$R_{10}$, —$NR_9$C(=O)H, —$NR_9$C(=O)($CR_8R_8$)$_r$$R_{10}$, —OC(=O)($CR_8R_8$)$_r$$R_{10}$, —C(=$NR_{14}$)$NR_9R_9$, —NHC(=$NR_{14}$)$NR_{14}R_{14}$, —S(=O)($CR_8R_8$)$_r$$R_{10}$, —S(O)$_2$($CR_8R_8$)$_r$$R_{10}$, —$NR_9$C(=O)$OR_8$, —$NR_9$S(O)$_2R_8$, aryloxy or arylalkyl;

$R_2$ is alkyl or cycloalkyl, wherein the alkyl may be optionally substituted with —OH;

$R_4$, at each occurrence, is F, —OH or alkyl; or any two alkyl $R_4$'s attached to the same carbon atom may form a 3- to 6-membered ring, which optionally may contain 1-4 heteroatoms selected from N, O, and S;

W is hydrogen, F, or —OH;

$R_5$ is halo, —CN or —Oalkyl;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$H$_2$, —C(=O)$NR_{14}R_{14}$, —$NR_{14}R_{14}$, —S(O)$_2NR_{14}R_{14}$, —$NR_{14}$S(O)$_2$($CF_2$)$_r$$CF_3$, —C(=O)$NR_{14}$S(O)$_2R_6$, —S(O)$_2NR_{14}$C(=O)$OR_6$, —S(O)$_2NR_{14}$C(=O)$NR_{14}R_{14}$, —C(=O)$NR_{14}$S(O)$_2$($CF_2$)$_r$$CF_3$, —C(=O)($CR_8R_8$)$_r$$R_{14}$, —$NR_{14}$C(=O)H, —$NR_{14}$C(=O)($CR_8R_8$)$_r$$R_{14}$, —OC(=O)($CR_8R_8$)$_r$$R_{14}$, —C(=$NR_{14}$)$NR_{14}R_{14}$, —NHC(=$NR_{14}$)$NR_{14}R_{14}$, —S(=O)($CR_8R_8$)$_r$$R_{14}$, —S(O)$_2$($CR_8R_8$)$_r$$R_{14}$, —$NR_{14}$C(=O)$OR_8$, —$NR_{14}$S(O)$_2R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{14}$, —O($CF_2$)$_r$$CF_3$, —O($CR_8R_8$)$_r$$R_{14}$, —OH, —SH, —S($CR_8R_8$)$_r$$R_{14}$, —S(O)$_3$H, —P(O)$_3$H$_2$, —C(=O)$NR_{14}R_{14}$, —$NR_{14}R_{14}$, —S(O)$_2NR_{14}R_{14}$, —$NR_{14}$S(O)$_2$($CF_2$)$_r$$CF_3$, —C(=O)$NR_{14}$S(O)$_2R_6$, —S(O)$_2NR_{14}$C(=O)$OR_6$, —S(O)$_2NR_{14}$C(=O)$NR_{14}R_{14}$, —C(=O)$NR_{14}$S(O)$_2$($CF_2$)$_r$$CF_3$, —C(=O)($CR_8R_8$)$_r$$R_{14}$, —$NR_{14}$C(=O)H, —$NR_{14}$C(=O)($CR_8R_8$)$_r$$R_{14}$, —OC(=O)($CR_8R_8$)$_r$$R_{14}$, —C(=$NR_{14}$)$NR_{14}R_{14}$, —NHC(=$NR_{14}$)$NR_{14}R_{14}$, —S(=O)($CR_8R_8$)$_r$$R_{14}$, —S(O)$_2$($CR_8R_8$)$_r$$R_{14}$, —$NR_{14}$C(=O)$OR_8$, —$NR_{14}$S(O)$_2R_8$, aryloxy or arylalkyl;

$R_{14}$, at each occurrence, is independently selected from hydrogen, alkyl, cycloalkyl or phenyl;

m, at each occurrence, is 0-2;

n is 1-2; and r is 0-4.

In still yet another embodiment, compounds of the present invention are those in which:

$R_{15}$ is —$NHR_1$, heteroaryl or aryl, wherein the heteroaryl and aryl may be optionally substituted with 0-3 $R_{1a}$;

$R_1$ is aryl or heteroaryl, which may be optionally substituted with 0-3 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —$NH_2$, —CN, —$NO_2$, —C(=O)OH, —C(=O)O($CR_8R_8$)$_r$$R_{10}$, —O($CF_2$)$_r$$CF_3$, —O($CR_8R_8$)$_r$$R_{10}$, —OH, —SH, —S($CR_8R_8$)$_r$$R_{10}$, —S(O)$_3$H, —P(O)$_3$H$_2$, —C(=O)$NR_9R_9$, —$NR_9R_9$, —S(O)$_2NR_9R_9$, —$NR_9$S(O)$_2$($CF_2$)$_r$$CF_3$, —C(=O)$NR_9$S(O)$_2R_6$, —S(O)$_2NR_9$C(=O)$OR_6$, —S(O)$_2NR_9$C(=O)$NR_9R_9$, —C(=O)$NR_9$S(O)$_2$($CF_2$)$_r$$CF_3$, —C(=O)($CR_8R_8$)$_r$$R_{10}$, —$NR_9$C(=O)H, —$NR_9$C(=O)($CR_8R_8$)$_r$$R_{10}$, —OC(=O)($CR_8R_8$)$_r$$R_{10}$, —C(=$NR_{14}$)$NR_9R_9$, —NHC(=$NR_{14}$)$NR_{14}R_{14}$, —S(=O)($CR_8R_8$)$_r$$R_{10}$, —S(O)$_2$($CR_8R_8$)$_r$$R_{10}$, —$NR_9$C $-C(=O)OR_8$, $-NR_9S(O)_2R_8$, $-S(O)_2NR_9C(O)R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_8$, $-NR_9S(O_2)R_9$, aryloxy or arylalkyl;

$R_2$ is alkyl or cycloalkyl, wherein the alkyl may be optionally substituted with $-OH$;

$R_4$, at each occurrence, is OH or alkyl; or any two alkyl $R_4$'s attached to the same carbon atom may form a 3- to 6-membered ring, which optionally may contain 1-4 heteroatoms selected from N, O, and S;

W is hydrogen or $-OH$;

$R_5$ is halo or $-CN$;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-C(=NR_{14})NR_{14}R_{14}$, $-NHC(=NR_{14})NR_{14}R_{14}$, $-S(=O)(CR_8R_8)_rR_{14}$, $-S(O)_2(CR_8R_8)_rR_{14}$, $-NR_{14}C(=O)OR_8$, $-NR_{14}S(O_2)R_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{14}$, $-O(CF_2)_rCF_3$, $-O(CR_8R_8)_rR_{14}$, $-OH$, $-SH$, $-S(CR_8R_8)_rR_{14}$, $-S(O)_3H$, $-P(O)_3H_2$, $-C(=O)NR_{14}R_{14}$, $-NR_{14}R_{14}$, $-S(O)_2NR_{14}R_{14}$, $-NR_{14}S(O)_2(CF_2)_rCF_3$, $-C(=O)NR_{14}S(O)_2R_6$, $-S(O)_2NR_{14}C(=O)OR_6$, $-S(O)_2NR_{14}C(=O)NR_{14}R_{14}$, $-C(=O)NR_{14}S(O)_2(CF_2)_rCF_3$, $-C(=O)(CR_8R_8)_rR_{14}$, $-NR_{14}C(=O)H$, $-NR_{14}C(=O)(CR_8R_8)_rR_{14}$, $-OC(=O)(CR_8R_8)_rR_{14}$, $-C(=NR_{14})NR_{14}R_{14}$, $-NHC(=NR_{14})NR_{14}R_{14}$, $-S(=O)(CR_8R_8)_rR_{14}$, $-S(O)_2(CR_8R_8)_rR_{14}$, $-NR_{14}C(=O)OR_8$, $-NR_{14}S(O_2)R_8$, aryloxy or arylalkyl;

$R_{14}$, at each occurrence, is independently selected from hydrogen, alkyl, cycloalkyl or phenyl;

m, at each occurrence, is 0-2;

n is 1-2; and r is 0-3.

In yet another embodiment, compounds of the present invention are those in which:

$R_{15}$ is $-NHR_1$, heteroaryl or aryl, wherein the heteroaryl and aryl may be optionally substituted with 0-3 $R_{1a}$;

$R_1$ is aryl or heteroaryl, which may be optionally substituted with 0-3 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_8$, $-NR_9S(O_2)R_8$, $-S(O)_2NR_9C(O)R_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, $-NH_2$, $-CN$, $-NO_2$, $-C(=O)OH$, $-C(=O)O(CR_8R_8)_rR_{10}$, $-O(CF_2)_rCF_3$, $-O(CR_8R_8)_rR_{10}$, $-OH$, $-SH$, $-S(CR_8R_8)_rR_{10}$, $-S(O)_3H$, $-P(O)_3H_2$, $-C(=O)NR_9R_9$, $-NR_9R_9$, $-S(O)_2NR_9R_9$, $-NR_9S(O)_2(CF_2)_rCF_3$, $-C(=O)NR_9S(O)_2R_6$, $-S(O)_2NR_9C(=O)OR_6$, $-S(O)_2NR_9C(=O)NR_9R_9$, $-C(=O)NR_9S(O)_2(CF_2)_rCF_3$, $-C(=O)(CR_8R_8)_rR_{10}$, $-NR_9C(=O)H$, $-NR_9C(=O)(CR_8R_8)_rR_{10}$, $-OC(=O)(CR_8R_8)_rR_{10}$, $-C(=NR_{14})NR_9R_9$, $-NHC(=NR_{14})NR_{14}R_{14}$, $-S(=O)(CR_8R_8)_rR_{10}$, $-S(O)_2(CR_8R_8)_rR_{10}$, $-NR_9C(=O)OR_8$, $-NR_9S(O_2)R_9$, aryloxy or arylalkyl;

$R_2$ is alkyl or cycloalkyl, wherein the alkyl may be optionally substituted with $-OH$;

$R_4$, at each occurrence, is alkyl; or any two $R_4$'s attached to the same carbon atom may form a 3- to 6-membered ring, which optionally may contain 1-4 heteroatoms selected from N, O, and S;

W is hydrogen or $-OH$;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{14}$, at each occurrence, is independently selected from hydrogen, alkyl, cycloalkyl or phenyl;

m, at each occurrence, is 0-2;

n is 1-2; and r is 0-2.

In one embodiment, compounds of the present invention are those in which:

$R_{15}$ is —NHR$_1$ or heteroaryl, wherein the heteroaryl may be optionally substituted with 0-3 $R_{1a}$;

$R_1$ is aryl or heteroaryl, which may be optionally substituted with 0-3 $R_{1a}$;

$R_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 $R_{1b}$;

$R_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, aryloxy or arylalkyl;

$R_2$ is alkyl or cycloalkyl, wherein the alkyl may be optionally substituted with —OH;

$R_4$, at each occurrence, is alkyl;

W is hydrogen or —OH;

$R_5$ is halo;

$R_6$, at each occurrence, is independently alkyl, cycloalkyl, cycloalkylalkyl, aryl, arylalkyl, heteroaryl or heteroarylalkyl;

$R_8$, at each occurrence, is independently hydrogen or alkyl;

$R_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 $R_{9a}$, and the heteroaryl, heteroarylalkyl, heterocyclyl or heterocyclylalkyl contain 1-4 heteroatoms selected from N, O, and S;

$R_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_{88}$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

$R_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 $R_{10a}$, and the heterocyclyl and heterocyclylalkyl contain 1-4 heteroatoms selected from N, O, and S;

$R_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

R$_{14}$, at each occurrence, is independently selected from hydrogen, alkyl, cycloalkyl or phenyl;

m, at each occurrence, is 0-2;

n is 1-2; and r is 0-2.

In another embodiment, compounds of the present invention are those in which:

R$_{15}$ is —NHR$_1$;

R$_1$ is aryl or heteroaryl, which may be optionally substituted with 0-3 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O)$_2$R$_8$, aryloxy or arylalkyl;

R$_2$ is alkyl or cycloalkyl;

R$_4$, at each occurrence, is alkyl;

W is hydrogen or —OH;

R$_5$ is halo;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

R$_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O)$_2$R$_8$, aryloxy or arylalkyl;

R$_{14}$, at each occurrence, is independently selected from hydrogen, alkyl, cycloalkyl or phenyl;

m, at each occurrence, is 0-2;

n is 1-2; and r is 0-2.

In one embodiment, the present invention provides novel compounds of formula (Ie):

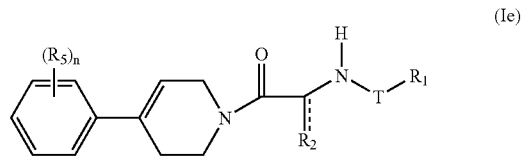

or stereoisomers or prodrugs or pharmaceutically acceptable salt forms thereof, wherein:

the dashed line represents an optional double bond;

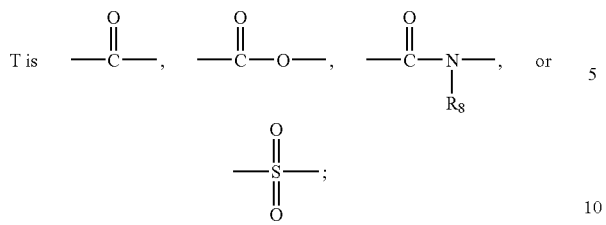

T is

R$_1$ is alkyl, cycloalkyl, aryl, heterocyclyl or heteroaryl, all of which may be optionally substituted with 0-5 R$_{1a}$;

R$_{1a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, —S(O)$_2$NR$_9$C(O)R$_6$, aryloxy or arylalkyl, wherein the aryl, cycloalkyl, cycloalkylalkyl, heteroaryl, heteroarylalkyl, heterocyclyl heterocyclylalkyl, aryloxy and arylalkyl may be optionally substituted with 0-3 R$_{1b}$;

R$_{1b}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{10}$, —O(CF$_2$)$_r$CF$_3$, —O(CR$_8$R$_8$)$_r$R$_{10}$, —OH, —SH, —S(CR$_8$R$_8$)$_r$R$_{10}$, —S(O)$_3$H, —P(O)$_3$H$_2$, —C(=O)NR$_9$R$_9$, —NR$_9$R$_9$, —S(O)$_2$NR$_9$R$_9$, —NR$_9$S(O)$_2$(CF$_2$)$_r$CF$_3$, —C(=O)NR$_9$S(O)$_2$R$_6$, —S(O)$_2$NR$_9$C(=O)OR$_6$, —S(O)$_2$NR$_9$C(=O)NR$_9$R$_9$, —C(=O)NR$_9$S(O)$_2$(CF$_2$)$_r$CF$_3$, —C(=O)(CR$_8$R$_8$)$_r$R$_{10}$, —NR$_9$C(=O)H, —NR$_9$C(=O)(CR$_8$R$_8$)$_r$R$_{10}$, —OC(=O)(CR$_8$R$_8$)$_r$R$_{10}$, —C(=NR$_{14}$)NR$_9$R$_9$, —NHC(=NR$_{14}$)NR$_{14}$R$_{14}$, —S(=O)(CR$_8$R$_8$)$_r$R$_{10}$, —S(O)$_2$(CR$_8$R$_8$)$_r$R$_{10}$, —NR$_9$C(=O)OR$_8$, —NR$_9$S(O$_2$)R$_8$, aryloxy or arylalkyl;

R$_2$ is alkyl, cycloalkyl, cycloalkylalkyl, or alkenyl, wherein the alkyl may be optionally substituted with —OH;

R$_5$ is halo, —CN or —Oalkyl;

R$_6$, at each occurrence, is independently alkyl, cycloalkyl, cycloalkylalkyl, aryl, arylalkyl, heteroaryl or heteroarylalkyl;

R$_8$, at each occurrence, is independently hydrogen or alkyl;

R$_9$, at each occurrence, is independently hydrogen, alkyl, cycloalkyl, aryl, arylalkyl, heteroaryl, heteroarylalkyl, heterocyclyl or heterocyclylalkyl, wherein the aryl, arylalkyl, heteroaryl, heteroarylalkyl, heterocyclyl or heterocyclylalkyl may be optionally substituted with 0-5 R$_{9a}$, and the heteroaryl, heteroarylalkyl, heterocyclyl or heterocyclylalkyl contain 1-4 heteroatoms selected from N, O, and S;

R$_{9a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{10}$, at each occurrence, is independently selected from alkyl, aryl, arylalkyl, heterocyclyl or heterocyclylalkyl, wherein the alkyl, aryl, arylalkyl, heterocyclyl or heterocyclylalkyl may be optionally substituted with 0-3 R$_{10a}$, and the heterocyclyl and heterocyclylalkyl contain 1-4 heteroatoms selected from N, O, and S;

R$_{10a}$, at each occurrence, is independently selected from alkyl, haloalkyl, aryl, alkenyl, alkynyl, cycloalkyl, cycloalkylalkyl, heteroaryl, heteroarylalkyl, heterocyclyl heterocyclylalkyl, halo, —NH$_2$, —CN, —NO$_2$, —C(=O)OH, —C(=O)O(CR$_8$R$_8$)$_r$R$_{14}$, —O(CF$_2$)$_r$CF$_3$, —O(CR$_8$R$_8$)$_r$R$_{14}$, —OH, —SH, —S(CR$_8$R$_8$)$_r$R$_{14}$, —S(O)$_3$H, —P(O)$_3$H$_2$, —C(=O)NR$_{14}$R$_{14}$, —NR$_{14}$R$_{14}$, —S(O)$_2$NR$_{14}$R$_{14}$, —NR$_{14}$S(O)$_2$(CF$_2$)$_r$CF$_3$, —C(=O)NR$_{14}$S(O)$_2$R$_6$, —S(O)$_2$NR$_{14}$C(=O)OR$_6$, —S(O)$_2$NR$_{14}$C(=O)NR$_{14}$R$_{14}$, —C(=O)NR$_{14}$S(O)$_2$(CF$_2$)$_r$CF$_3$, —C(=O)(CR$_8$R$_8$)$_r$R$_{14}$, —NR$_{14}$C(=O)H, —NR$_{14}$C(=O)(CR$_8$R$_8$)$_r$R$_{14}$, —OC(=O)(CR$_8$R$_8$)$_r$R$_{14}$, —C(=NR$_{14}$)NR$_{14}$R$_{14}$, —NHC(=NR$_{14}$)NR$_{14}$R$_{14}$, —S(=O)(CR$_8$R$_8$)$_r$R$_{14}$, —S(O)$_2$(CR$_8$R$_8$)$_r$R$_{14}$, —NR$_{14}$C(=O)OR$_8$, —NR$_{14}$S(O$_2$)R$_8$, aryloxy or arylalkyl;

R$_{14}$, at each occurrence, is independently selected from hydrogen, alkyl, cycloalkyl or phenyl;

m, at each occurrence, is 0-2;

n is 1-3; and r is 0-5.

In one embodiment, compounds of the present invention are selected from the compounds exemplified in the examples.

In one embodiment, compounds of the present invention are selected from the group consisting of:

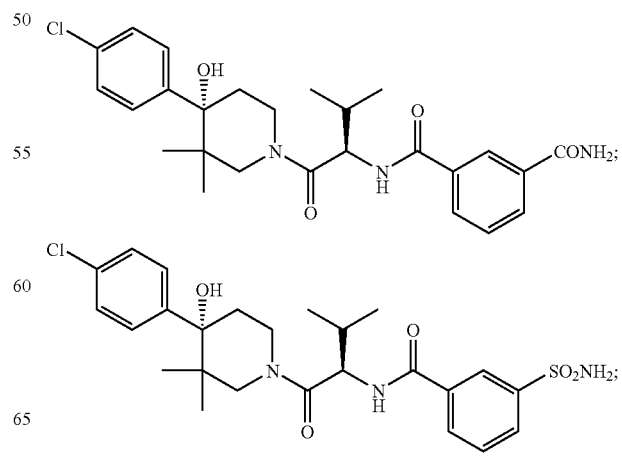

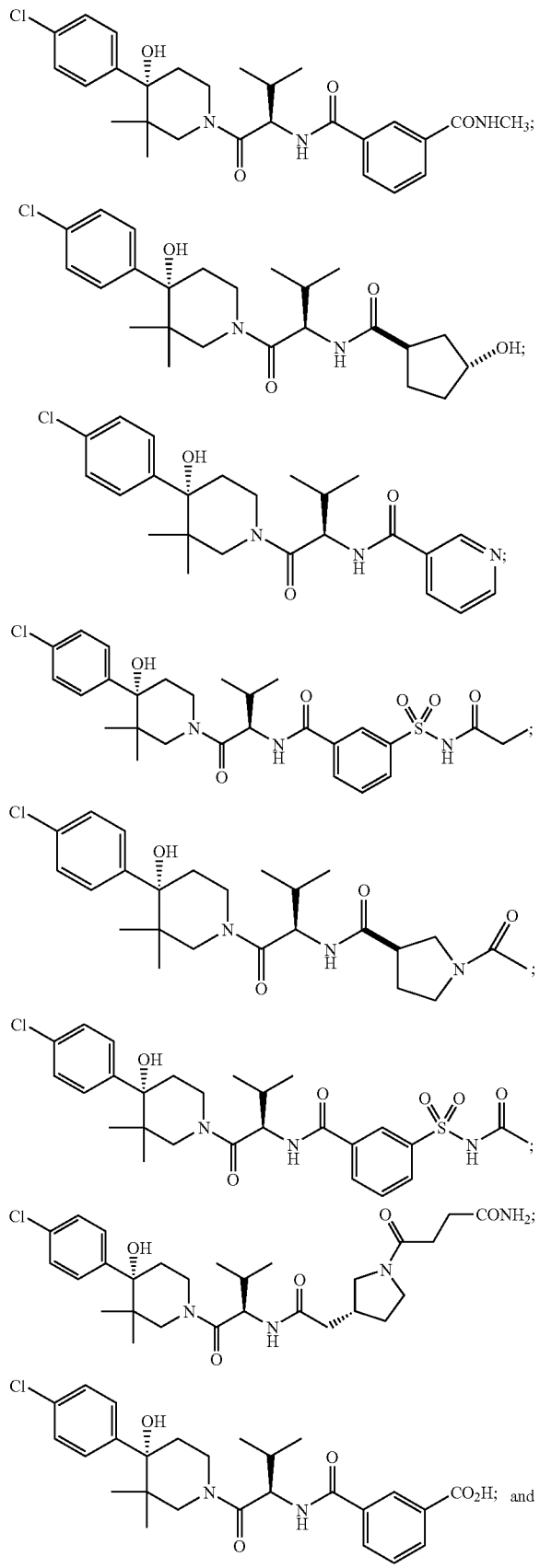

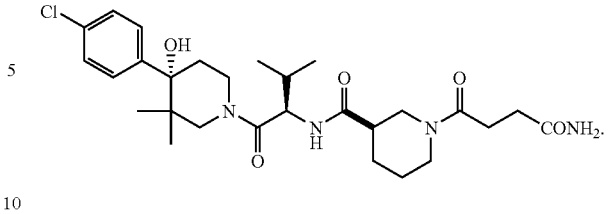

In another embodiment, the present invention is directed to a pharmaceutical composition, comprising a pharmaceutically acceptable carrier and a therapeutically effective amount of a compound of the present invention.

In another embodiment, the present invention is directed to a method for modulation of chemokine or chemokine receptor activity comprising administering to a patient in need thereof a therapeutically effective amount of a compound of the present invention.

In another embodiment, the present invention is directed to a method for modulation of CCR-1 receptor activity comprising administering to a patient in need thereof a therapeutically effective amount of a compound of the present invention.

In another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a compound of the present invention.

In another embodiment, the present invention is directed to a method for treating disorders, comprising administering to a patient in need thereof a therapeutically effective amount of a compound of the present invention, said wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artheroscle-rosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a method for treating inflammatory diseases, comprising administering to a patient in need thereof a therapeutically effective amount of a compound of the present invention.

In another embodiment, the present invention is directed to a method for treating inflammatory bowel disease, comprising administering to a patient in need thereof a therapeutically effective amount of a compound of the present invention.

In another embodiment, the present invention is directed to a method for treating Crohn's disease, comprising administering to a patient in need thereof a therapeutically effective amount of a compound of the present invention.

In another embodiment, the present invention is directed to a method for treating psoriasis, comprising administering to a patient in need thereof a therapeutically effective amount of a compound of the present invention.

In another embodiment, the present invention is directed to a method for treating systemic lupus erythematosus, comprising administering to a patient in need thereof a therapeutically effective amount of a compound of the present invention.

In another embodiment, the present invention is directed to a method for treating multiple sclerosis, comprising administering to a patient in need thereof a therapeutically effective amount of a compound of the present invention.

In another embodiment, the present invention is directed to a method for treating rheumatoid arthritis, comprising administering to a patient in need thereof a therapeutically effective amount of a compound of the present invention.

In another embodiment, the present invention is directed to a method for treating psoriatic arthritis, comprising administering to a patient in need thereof a therapeutically effective amount of a compound of the present invention.

In another embodiment, the present invention is directed to a method for treating multiple myeloma, comprising administering to a patient in need thereof a therapeutically effective amount of a compound of the present invention.

In another embodiment, the present invention is directed to a method for treating allergies, for example, skin and mast cell degranulation in eye conjunctiva, comprising administering to a patient in need thereof a therapeutically effective amount of a compound of the present invention.

In another embodiment, the present invention is directed to a method for treating hepatocellular carcinoma, comprising administering to a patient in need thereof a therapeutically effective amount of a compound of the present invention.

In another embodiment, the present invention is directed to a method for treating osteoporosis, comprising administering to a patient in need thereof a therapeutically effective amount of a compound of the present invention.

In another embodiment, the present invention is directed to a method for treating renal fibrosis, comprising administering to a patient in need thereof a therapeutically effective amount of a compound of the present invention.

In another embodiment, the present invention is directed to a method for treating inflammatory diseases, for example, inflammatory diseases which are at least partially mediated by CCR-1, comprising administering to a patient in need thereof a therapeutically effective amount of a compound of the present invention.

In another embodiment, the present invention is directed to a method for modulation of CCR1 activity comprising administering to a patient in need thereof a therapeutically effective amount of a compound of the present invention.

In another embodiment, the present invention is directed the use of a compound of the present invention in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In another embodiment, the present invention is directed to a compound of the present invention for use in therapy.

In another embodiment, the present invention is directed to a pharmaceutical composition comprising a compound of the present invention and one or more active ingredients.

In another embodiment, the present invention is directed to a method for modulation of chemokine or chemokine receptor activity comprising administering to a patient in need thereof a therapeutically effective amount of a pharmaceutical composition comprised of a compound of the present invention and one or more active ingredients.

In another embodiment, the present invention is directed to a method for modulation of CCR-1 receptor activity comprising administering to a patient in need thereof a therapeutically effective amount of a pharmaceutical composition comprised of a compound of the present invention and one or more active ingredients.

In yet another embodiment, the present invention is directed to a method for modulation of MIP-1α, MCP-3, MCP-4, RANTES activity, preferably modulation of MIP-1α activity, that is mediated by the CCR-1 receptor comprising administering to a patient in need thereof a therapeutically effective amount of a pharmaceutical composition comprised of a compound of the present invention and one or more active ingredients.

In another embodiment, the present invention is directed to a method for treating a disorder, comprising administering to a patient in need thereof a therapeutically effective amount of a pharmaceutical composition comprised of a compound of the present invention and one or more active ingredients, wherein said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In yet another embodiment, the present invention, is directed to a method for treating inflammatory diseases, preferably, inflammatory diseases which are at least partially mediated by CCR-1, comprising administering to a patient in need thereof a therapeutically effective amount of a pharmaceutical composition comprised of a compound of present invention and one or more active ingredients.

In another embodiment, the present invention is directed to a method for modulation of CCR-1 activity comprising administering to a patient in need thereof a therapeutically effective amount of a pharmaceutical composition comprised of a compound of the present invention and one or more active ingredients.

In another embodiment, the present invention is directed to the use of a pharmaceutical composition comprised of a compound of the present invention and one or more active ingredients in the preparation of a medicament for the treatment of a disorder, said disorder is selected from osteoarthritis, aneurysm, fever, cardiovascular effects, Crohn's disease, congestive heart failure, autoimmune diseases, HIV-infection, HIV-associated dementia, psoriasis, idiopathic pulmonary fibrosis, transplant arteriosclerosis, physically- or chemically-induced brain trauma, inflammatory bowel disease, alveolitis, colitis, systemic lupus erythematosus, nephrotoxic serum nephritis, glomerularnephritis, asthma, multiple sclerosis, artherosclerosis, rheumatoid arthritis, restinosis, organ transplantation, psoriatic arthritis, multiple myeloma, allergies, for example, skin and mast cell degranulation in eye conjunctiva, hepatocellular carcinoma, osteoporosis, renal fibrosis and cancer, preferably, Crohn's disease, psoriasis, inflammatory bowel disease, systemic lupus erythematosus, multiple sclerosis, rheumatoid arthritis, multiple myeloma, allergies, for example, skin and mast cell degranulation in eye conjunctiva, hepatocellular carcinoma, osteoporosis and renal fibrosis.

In still yet another embodiment, the present invention is directed to the use of a pharmaceutical composition comprised of a compound of the present invention and one or more active ingredients in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of The present invention may display superior activity compared with the other. Thus, all of the stereochemistries are considered to be a part of the present invention. When required, separation of the racemic material can be achieved by HPLC using a chiral column or by a resolution using a resolving agent such as camphonic chloride as in Steven D. Young, et al, *Antimicrobial Agents and Chemotherapy*, 1995, 2602-2605.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R_4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl)

and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

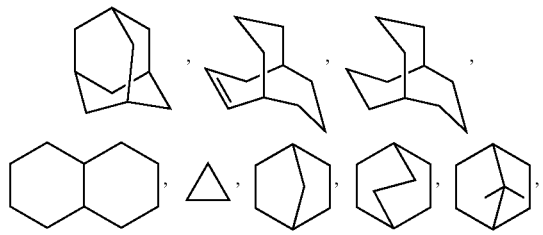

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings for example

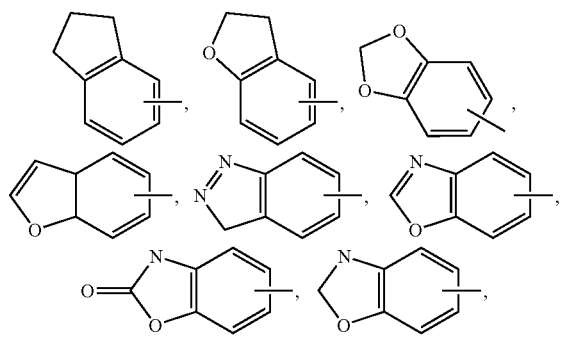

-continued

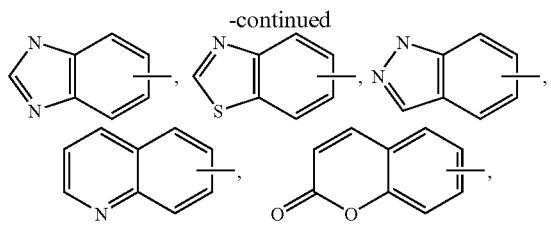

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heterocycles include, but are not limited to, 1H-indazole, 2-pyrrolidonyl, 2H,6H-1,5,2-dithiazinyl, 2H-pyrrolyl, 1H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl. Also included are fused ring and spiro compounds containing, for example, the above heterocycles.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term "heterocyclylalkyl" or "heterocyclyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —NO$_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Any compound that can be converted in vivo to provide the bioactive agent (i.e., the compound of formula I, Ia, Ib, Ib', Ic, Id or Ie) is a prodrug within the scope and spirit of the invention.

The term "prodrugs" as employed herein includes esters and carbonates formed by reacting one or more hydroxyls of compounds of the present invention with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31, (Academic Press, 1996);
b) *Design of prodrugs*, edited by H. Bundgaard, (Elsevier, 1985);
c) *A Textbook of Drug Design and Development*, P. Krogsgaard-Larson and H. Bundgaard, eds. Ch. 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

Said references are incorporated herein by reference.

In addition, compounds of the present invention are, subsequent to their preparation, preferably isolated and purified to obtain a composition containing an amount by weight equal to or greater than 99% of the compound ("substantially pure" compound), which is then used or formulated as described herein. Such "substantially pure" compounds of the present invention are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of the present invention can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit MIP-1α or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

Chemokine receptor antagonists of the present invention can be prepared from the protected amino acid derivative 1.1 by coupling with a piperidine 1.2 under standard amide bond forming conditions to yield 1.3 as shown in Scheme 1. Deprotection of the nitrogen can provide an amine 1.4 which can be reacted further with derivatizing reagents to provide (I & Ia). Additionally, protected amino acid derivatives, such as 1.5, can be reacted with a substituted piperidine 1.6, and further transformed to compounds of the invention Ib and Ib' using a similar sequence as in the preparation of I.

SCHEME 1

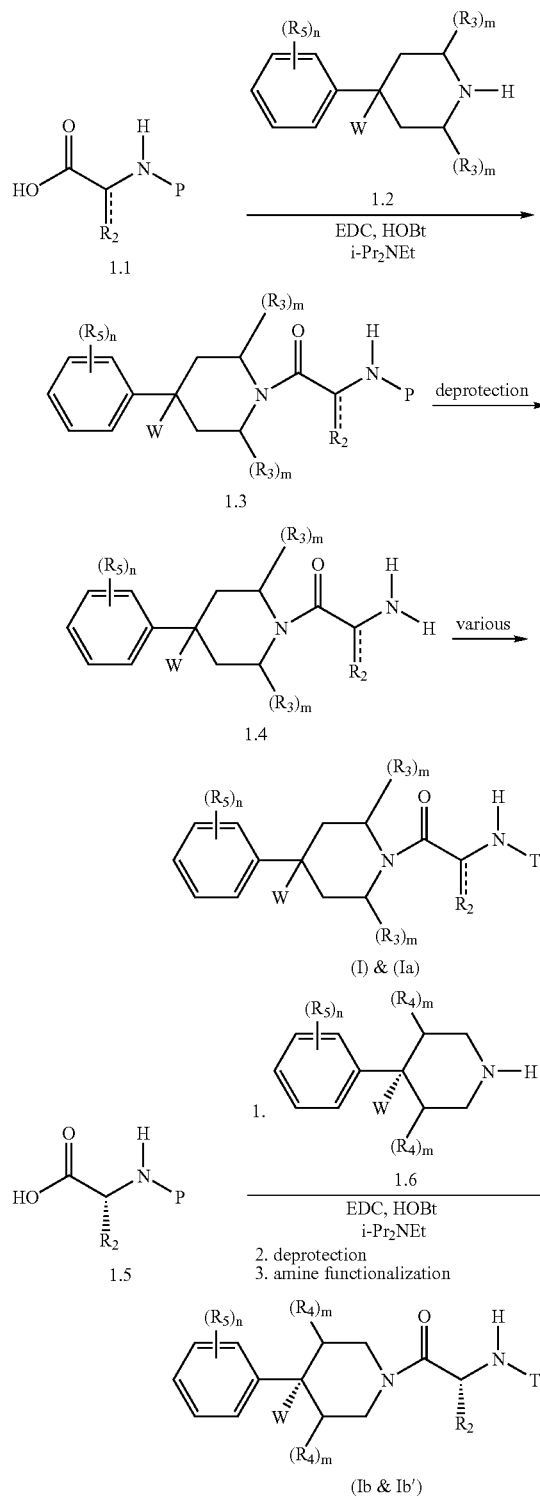

SCHEME 2

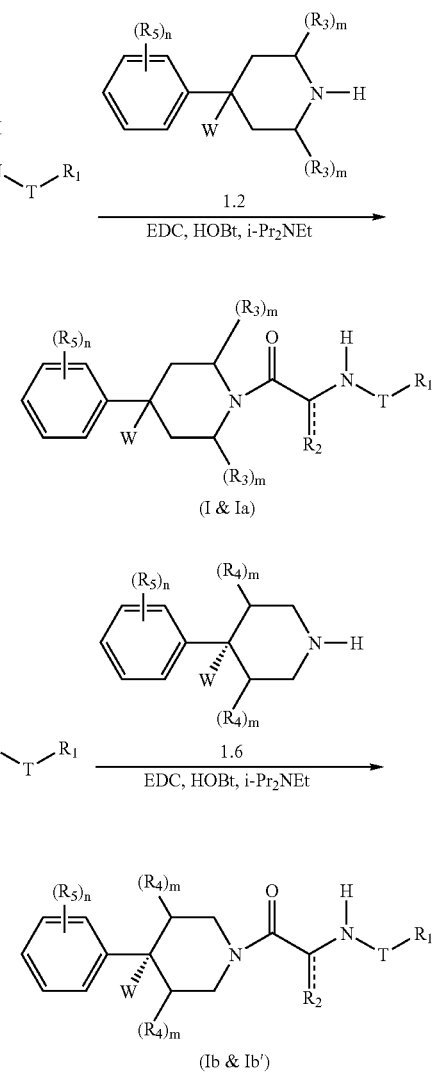

Alternatively, compounds of the present invention can be synthesized as shown in Scheme 2. Coupling of the functionalized amino acid derivative 2.1 with piperidine 1.2 or 1.6 under standard amide bond forming conditions can provide compound I and Ia, (A) or Ib and Ib' (B).

Hydroxypiperidine and dihydropiperidine analogs can be prepared according to the methods outlined in Scheme 3. The functionalized acid 2.1 can be coupled to the hydroxy piperidine 3.1 to furnish 3.2, which in itself can be used as a chemokine inhibitor. Elimination of the hydroxyl group under acidic conditions can yield dihydropiperidines of the present invention.

SCHEME 3

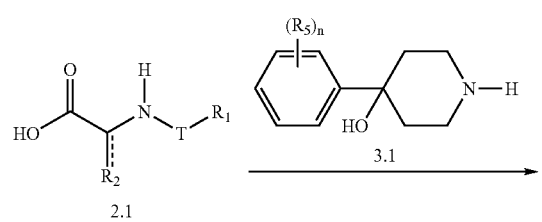

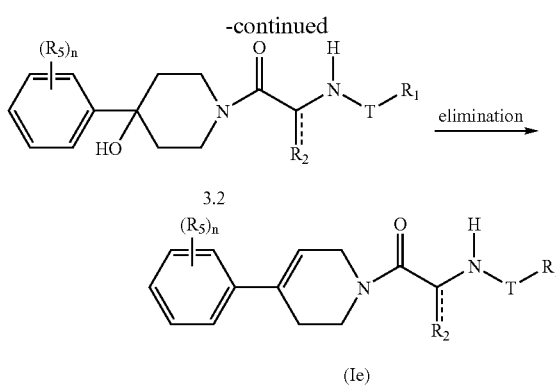

A resin supported synthesis can also be employed using the reactions outlined in Scheme 4. Coupling of an amine ester to a properly functionalized resin can give 4.1 which upon amine functionalization can form 4.2. Standard saponification can yield the pendant acid derivatized resin 4.3. Amide bond formation with amine 1.2 or 3.1 can furnish analogs 4.4 and 4.5, respectively. Removal from the resin using acid can furnish the dihydropiperidine (Ie) from hydroxypiperidine 4.5 and the piperidine (I & Ia) from 4.4.

SCHEME 4

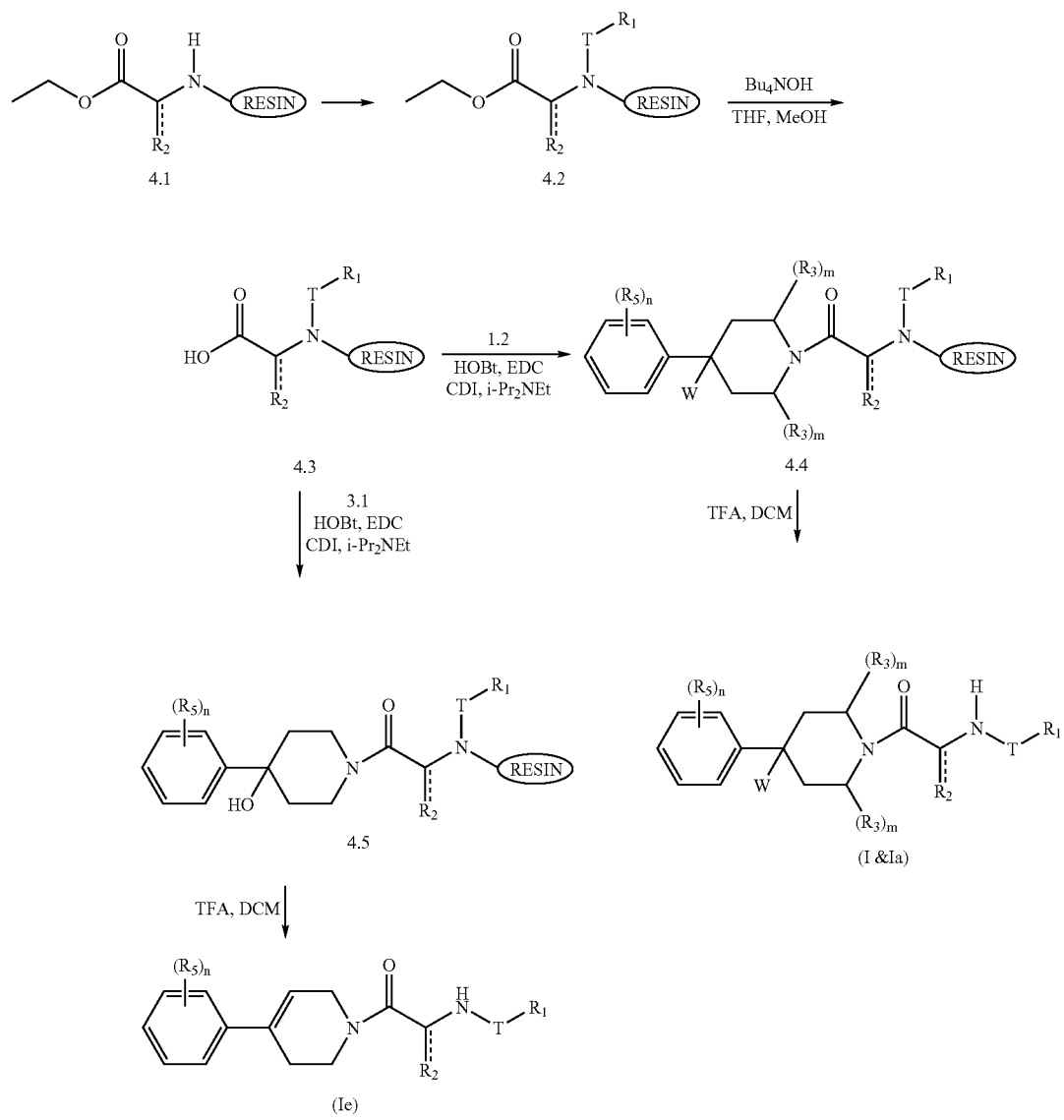

Compounds of the invention can also be prepared according to the methods outlined in Scheme 5. An appropriately functionalized amine 1.4 can be reacted with an isothiocyanate followed by alkylation in the presence of a base with iodomethane to furnish 5.1. Compound 5.1 can be further reacted with, for example a hydrazine or a hydroxylamine derivative, to furnish the substituted triazole or the oxadiazole of the present invention.

Alternatively, compounds of the present invention can be synthesized as shown in Schemes 7a and 7b. Reacting a properly functionalized analog of compounds of the present invention under a variety of conditions known to those skilled in the art can provide additional compounds of the present

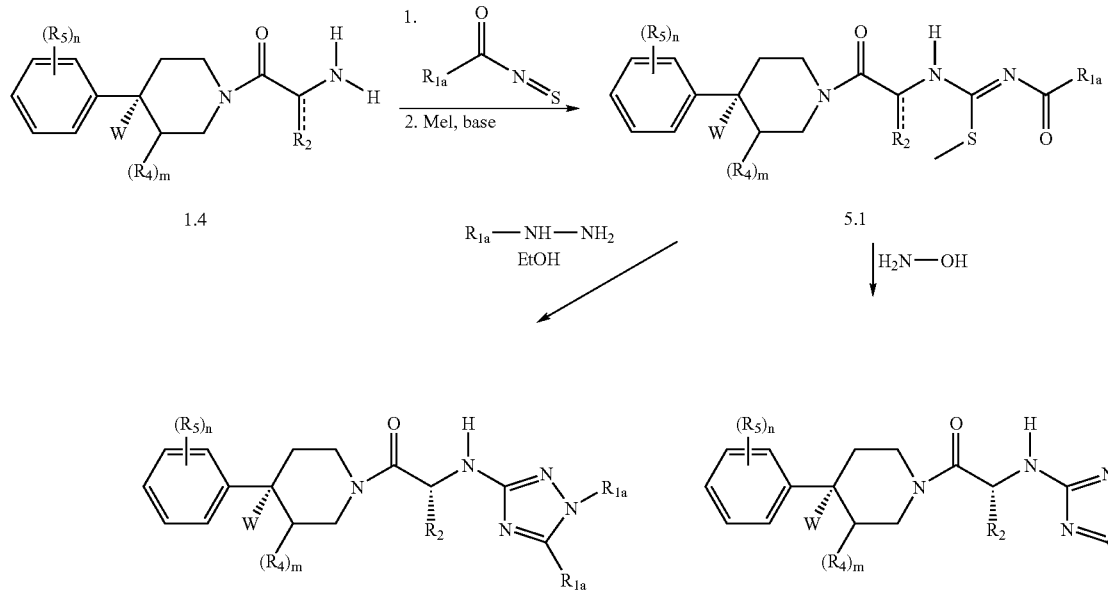

Furthermore, compounds of the present invention can be prepared by reaction compound 6.1 with an appropriate acid containing a displaceable leaving group, such as bromine to give compound 6.2. Compound 6.2 can be reacted with an amine in an appropriate solvent to furnish compounds of the present invention.

invention. It is to be assumed that the examples shown in Schemes 7a and 7b are merely representative of a variety of transformations and interconversions of functionality that are possible with the knowledge of one skilled in the art of organic synthesis.

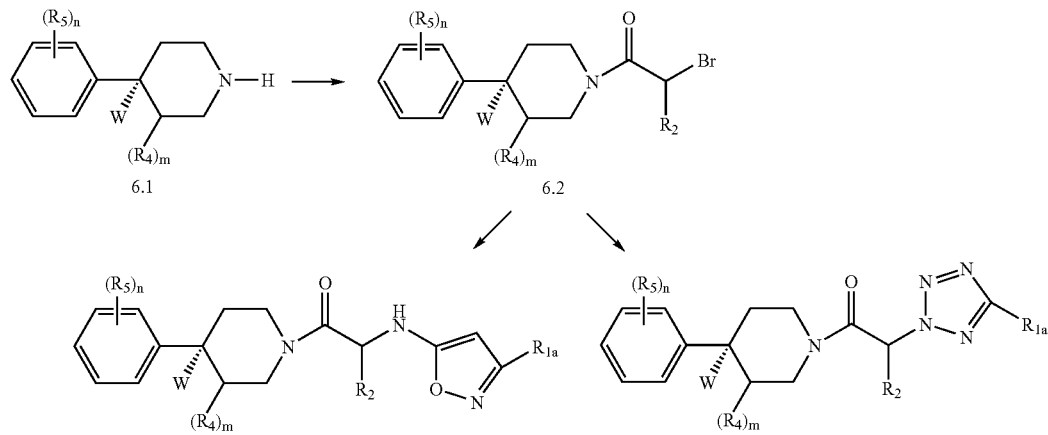

SCHEME 7a
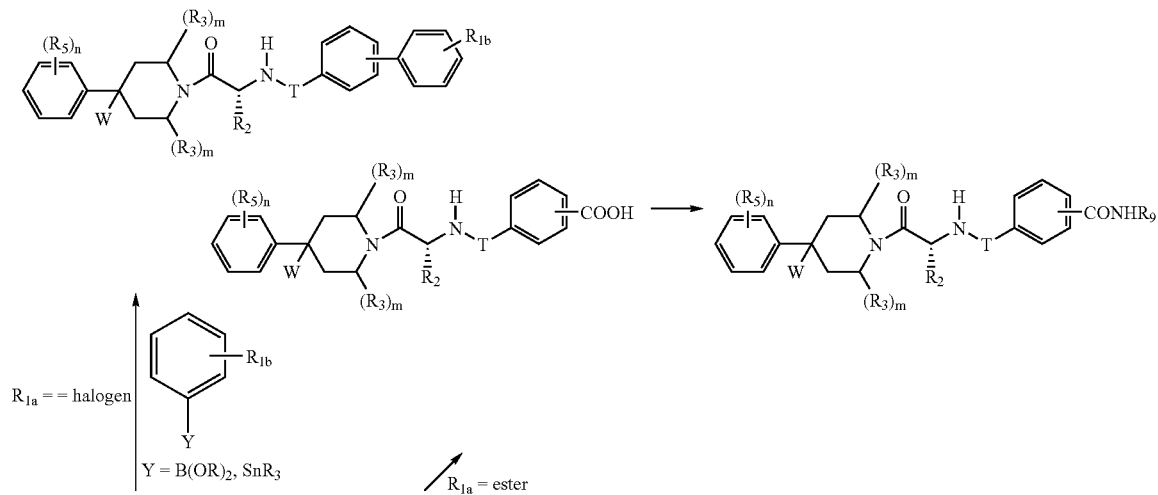
SCHEME 7b
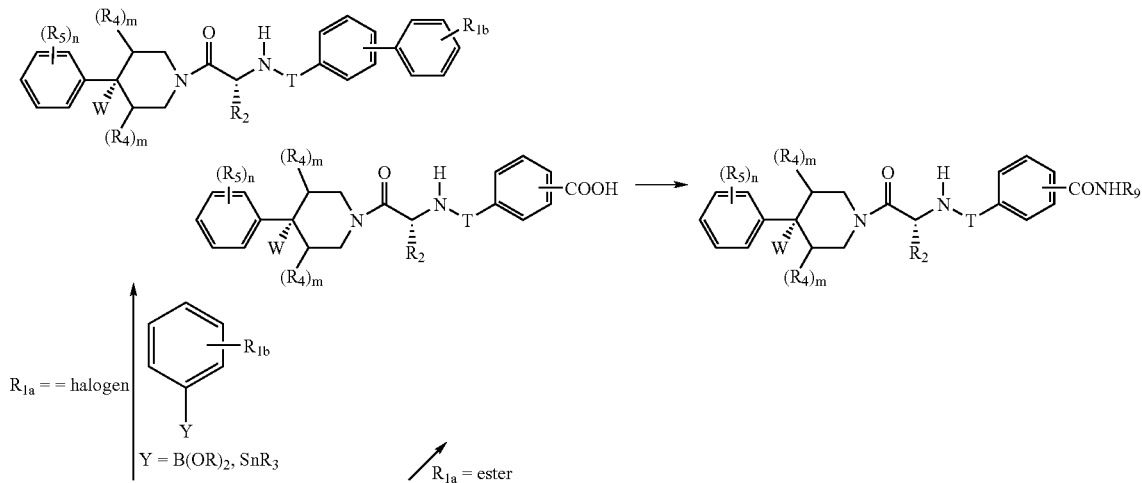

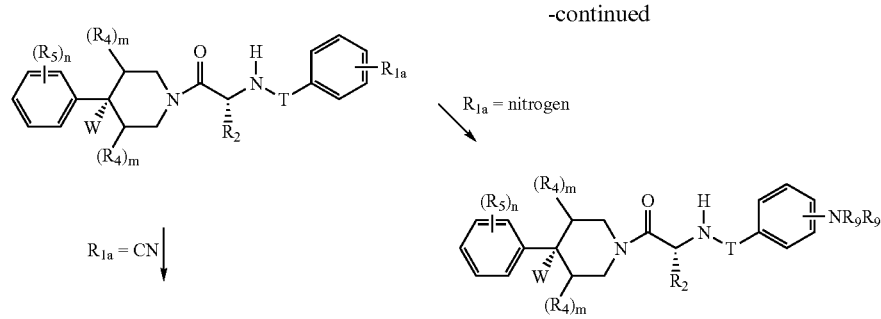

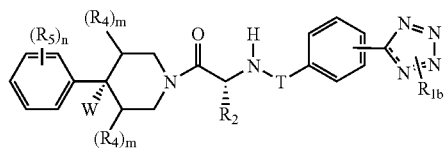

Additional compounds of the present invention can be prepared according to the methods in Scheme 8. Compound 8.1 can be reacted with an aryl halide or heteroaryl halide to give the appropriately substituted amine. Furthermore, compound 8.1 could be reacted with an anhydride to provide the amide or reacted with a haloacetyl halide, such as chloroacetyl chloride, followed by a nucleophile, such as pyrazole to give the substituted amide.

Additional compounds of the present invention can also be prepared according to the methods outlined in Scheme 9. An amino acid, such as D-valine (9.1), can be reacted with an aryl halide, such as -iodobenzene to give the N-aryl amino acid 9.2. This amino acid can then be reacted with an appropriately substituted piperidine, such as 9.3 to provide compounds of the invention of the general formula (Id).

SCHEME 8

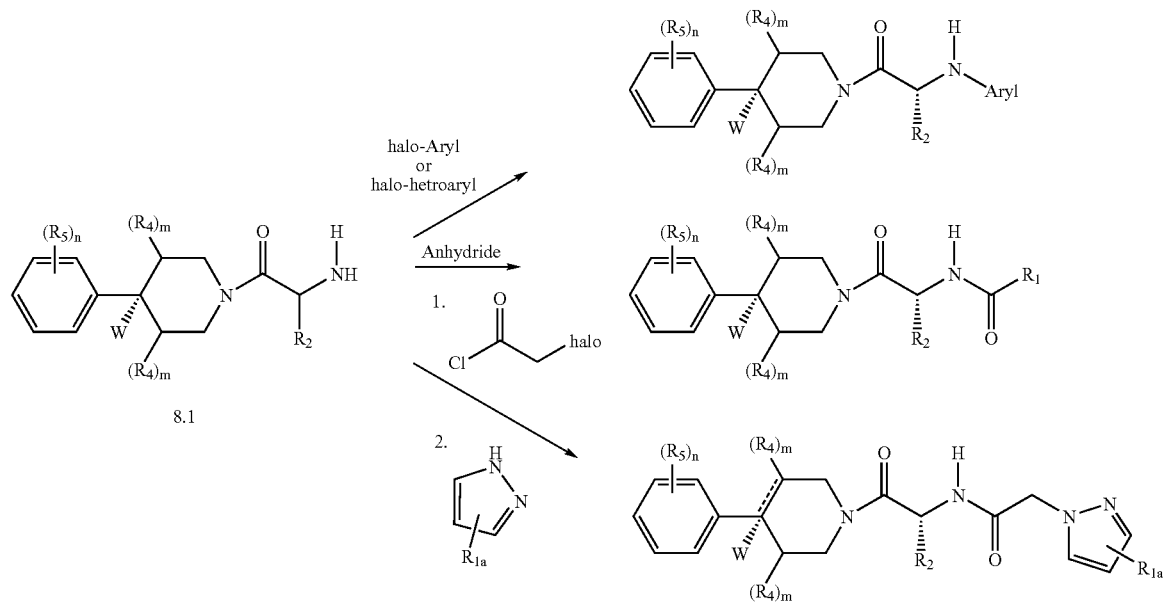

SCHEME 9

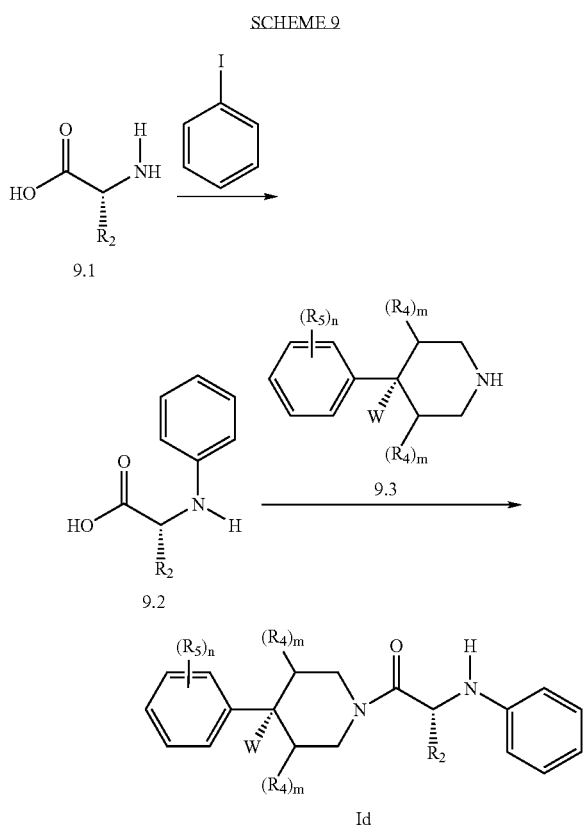

Other features of the invention will become apparent in the course of the following descriptions of exemplary embodiments that are given for illustration of the invention and are not intended to be limiting thereof.

EXAMPLES

Abbreviations used in the Examples are defined as follows: "1×" for once, "2×" for twice, "3×" for thrice, "Boc" for tert-butyloxycarbonyl, "° C." for degrees Celsius, "Cbz" for benzyloxycarbonyl, "DCM" for dichloromethane, "DMF" for N,N-dimethylformamide, "DIEA" for N,N-diisopropylethylamine, "EDC" for N-(3-dimethylaminopropyl)-N-ethylcarbodiimide hydrochloride, "eq" for equivalent or equivalents, "g" for gram or grams, "HOBt" for 1-hydroxybenzotriazole, "LC" for liquid chromatography, "mg" for milligram or milligrams, "mL" for milliliter or milliliters, "μL" for microliter or microliters, "h" for hour or hours, "M" for molar, "MeOH" for methanol, "min" for minute or minutes, "MS" for mass spectroscopy, "rt." for room temperature, "TFA" for trifluoroacetic acid, "THF" for tetrahydrofuran, and "v/v" for volume to volume ratio. "D", "L", "R" and "S" are stereochemical designations familiar to those skilled in the art. Chemical names were derived using ChemDraw Ultra, version 8.0.8. When this program failed to provide a name for the exact structure in question, an appropriate name was assigned using the same methodology utilized by the program.

Intermediates

Preparation A: (R)-2-Amino-1-(4-(4-chlorophenyl)piperidin-1-yl)butan-1-one hydrochloride

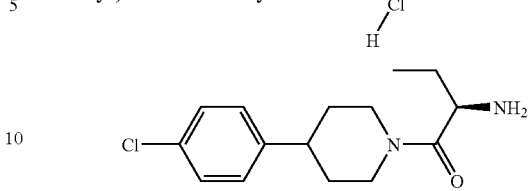

Step 1: (R)-Tert-butyl 1-(4-(4-chlorophenyl)piperidin-1-yl)-1-oxobutan-2-ylcarbamate

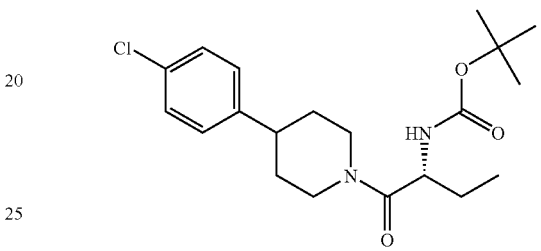

N-Boc-D-2-aminobutanoic acid was dissolved in 2 mL of chloroform. DIEA (0.65 mL), HOBt (0.19 g) and 4-(4-chlorophenyl)piperidine hydrochloride (0.32 g) were added and the solution was stirred at rt for 15 minutes. After this time, EDC (0.26 g) was added and the resulting solution was allowed to stir overnight. At the conclusion of this period, the resulting solution was diluted with chloroform and washed with 5% v/v HCl/water. The organic fraction was extracted with a saturated aqueous solution of sodium bicarbonate. The combined organic fractions were dried over solid magnesium sulfate, filtered, and concentrated by rotary evaporation to give (R)-tert-butyl 1-(4-(4-chlorophenyl)piperidin-1-yl)-1-oxobutan-2-ylcarbamate. MS found: $(M+Na)^+=403$.

Step 2: (R)-2-amino-1-(4-(4-chlorophenyl)piperidin-1-yl)butan-1-one hydrochloride A 4M solution of HCl in dioxane (8 mL) was added to (R)-tert-butyl 1-(4-(4-chlorophenyl)piperidin-1-yl)-1-oxobutan-2-ylcarbamate (0.46 g) and the resulting solution was allowed to stir at rt. for 1.5 h. After this time, the solvent was removed by rotary evaporation to provide an oil. The oil was dried overnight in vacuo to provide (R)-2-amino-1-(4-(4-chlorophenyl)piperidin-1-yl)butan-1-one hydrochloride. MS found: $(M+H)^+=281$.

Preparation B: 2-Amino-1-(4-(4-chlorophenyl)piperidin-1-yl)-3-methylbutan-1-one hydrochloride

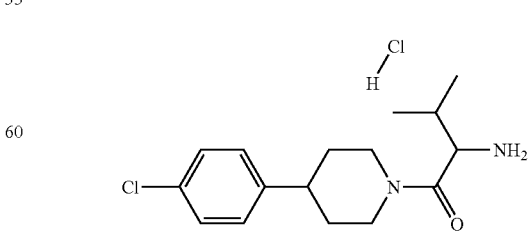

2-Amino-1-(4-(4-chlorophenyl)piperidin-1-yl)-3-methylbutan-1-one hydrochloride was prepared in a similar manner as described in Preparation A with the exception that N-Boc-DL-valine was substituted for N-Boc-D-2-aminobutanoic acid in Step 1. MS found: (M+H)$^+$=295.

Preparation C: (R)-2-Amino-1-(4-(4-chlorophenyl)piperidin-1-yl)-3-methylbutan-1-one hydrochloride

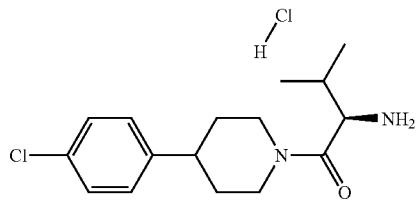

(R)-2-Amino-1-(4-(4-chlorophenyl)piperidin-1-yl)-3-methylbutan-1-one hydrochloride was prepared in a similar manner as described in Preparation A with the exception that N-Boc-D-valine was substituted for N-Boc-D-2-aminobutanoic acid in Step 1. MS found: (M+H)$^+$=295.

Preparation D: (2R,3R)-2-Amino-1-(4-(4-chlorophenyl)piperidin-1-yl)-3-methylpentan-1-one hydrochloride

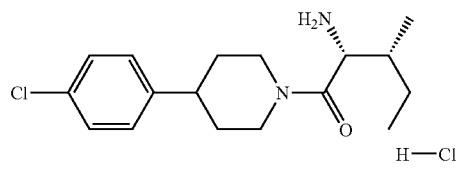

(2R,3R)-2-Amino-1-(4-(4-chlorophenyl)piperidin-1-yl)-3-methylpentan-1-one hydrochloride was prepared in a similar manner as described in Preparation A with the exception that N-Boc-D-isoleucine was substituted for N-Boc-D-2-aminobutanoic acid in Step 1. MS found: (M+H)$^+$=309.

Preparation E: (R)-2-Amino-1-(4-(4-chlorophenyl)piperidin-1-yl)-2-cyclohexylethanone hydrochloride

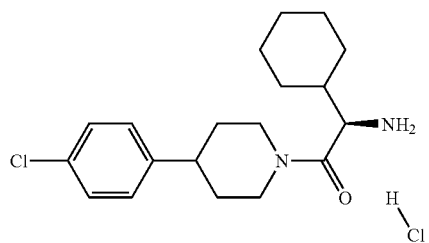

(R)-2-Amino-1-(4-(4-chlorophenyl)piperidin-1-yl)-2-cyclohexylethanone hydrochloride was prepared in a similar manner as described in Preparation A with the exception that N-Boc-D-cyclohexylglycine was substituted for N-Boc-D-2-aminobutanoic acid in Step 1. MS found: (M+H)$^+$=335.

Preparation F: 2-Amino-1-(4-(4-chlorophenyl)piperidin-1-yl)pentan-1-one hydrochloride

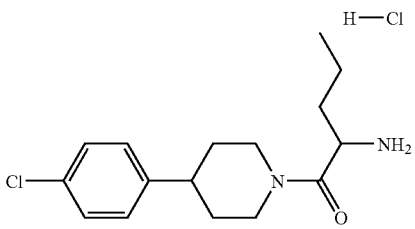

2-Amino-1-(4-(4-chlorophenyl)piperidin-1-yl)pentan-1-one hydrochloride was prepared in a similar manner as described in Preparation A with the exception that N-Boc-DL-norvaline was substituted for N-Boc-D-2-aminobutanoic acid in Step 1. MS found: (M+H)$^+$=295.

Preparation G: 2-Amino-1-(4-(4-chlorophenyl)piperidin-1-yl)-4-methylpentan-1-one hydrochloride

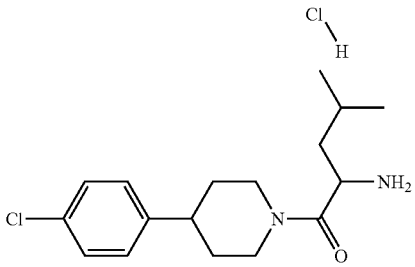

2-Amino-1-(4-(4-chlorophenyl)piperidin-1-yl)-4-methylpentan-1-one hydrochloride was prepared in a similar manner as described in Preparation A with the exception that N-Boc-DL-leucine was substituted for N-Boc-D-2-aminobutanoic acid in Step 1. MS found: (M+H)$^+$=309.

Preparation H: 2-Amino-1-(4-(4-chlorophenyl)piperidin-1-yl)-3,3-dimethylbutan-1-one hydrochloride

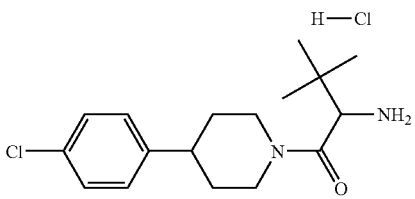

2-Amino-1-(4-(4-chlorophenyl)piperidin-1-yl)-3,3-dimethylbutan-1-one hydrochloride was prepared in a similar manner as described in Preparation A with the exception that N-Boc-DL-α-tert-butylglycine was substituted for N-Boc-D-2-aminobutanoic acid in Step 1. MS found: (M+H)$^+$=309.

Preparation I: (2R,3S)-2-Amino-1-(4-(4-chlorophenyl)piperidin-1-yl)-3-methylpentan-1-one hydrochloride

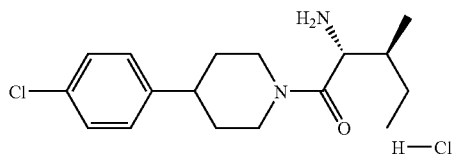

(2R,3S)-2-Amino-1-(4-(4-chlorophenyl)piperidin-1-yl)-3-methylpentan-1-one hydrochloride was prepared in a similar manner as described in Preparation A with the exception that N-Boc-D-allo-isoleucine was substituted for N-Boc-D-2-aminobutanoic acid in Step 1. MS found: (M+H)=309.3.

Preparation J: (R)-2-Amino-1-(4-(4-chlorophenyl)piperidin-1-yl)-2-cyclopropylethaone hydrochloride

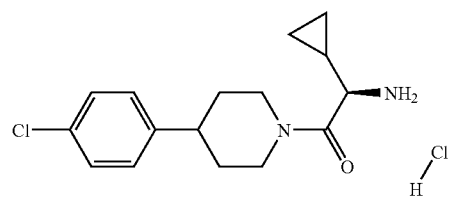

(R)-2-Amino-1-(4-(4-chlorophenyl)piperidin-1-yl)-2-cyclopropylethaone hydrochloride was prepared in a similar manner as described in Preparation A with the exception that N-Boc-D-cyclopropyl glycine was substituted for N-Boc-D-2-aminobutanoic acid in Step 1. MS found: (M+H)$^+$=293.2.

Preparation K: (R)-2-Amino-1-(4-(4-fluorophenyl)piperidin-1-yl)-3-methylbutan-1-one hydrochloride

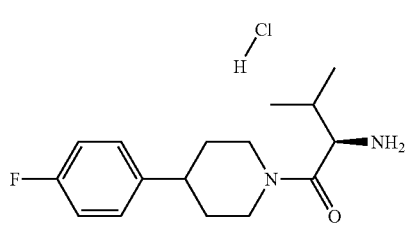

(R)-2-Amino-1-(4-(4-fluorophenyl)piperidin-1-yl)-3-methylbutan-1-one hydrochloride was prepared in a similar manner as described in Preparation C starting from 4-fluorophenyl piperidine hydrochloride. MS found: (M+H)$^+$=279.3.

Example 1

(R)—N-(1-(4-(4-Chlorophenyl)piperidin-1-yl)-1-oxobutan-2-yl)benzamide

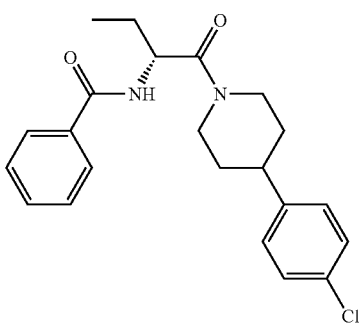

A reaction vessel was charged with HOBt (8 mg), benzoic acid (7 mg) and EDC (11 mg) in DMF (0.6 mL), and the resulting solution was allowed to agitate at rt. for 15 min. After this time, a solution of (R)-2-amino-1-(4-(4-chlorophenyl)piperidin-1-yl)butan-1-one hydrochloride (14 mg) in DIEA (38 µL) and DMF (187 µL) was added. Upon completion of addition, the reaction mixture was shaken overnight at rt. At the conclusion of this period, the resulting solution was diluted with MeOH and purified by preparative LC-MS to provide Example 1. MS found: (M+H)$^+$=386.

Examples 2 to 8

Examples 2 to 8, as described in Table 1, were prepared in a similar manner as described for the preparation of Example 1. In the synthesis of Examples 2 to 8, the appropriate acid needed to produce the product listed was used in place of the benzoic acid used in Example 1. The data in the "MS" column represents the values observed for the (M+H)$^+$ ions in MS experiments.

TABLE 1

| Example | Structure | | MS | Chemical Name |
|---|---|---|---|---|
| 2 | 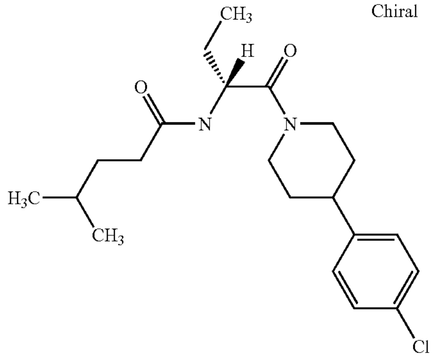 | Chiral | 380 | (R)-N-(1-(4-(4-chlorophenyl)piperidin-1-yl)-1-oxobutan-2-yl)-4-methylpentanamide |
| 3 | 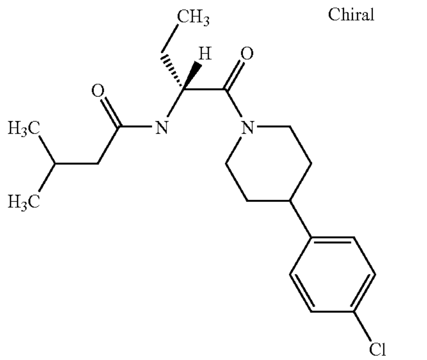 | Chiral | 366 | (R)-N-(1-(4-(4-chlorophenyl)piperidin-1-yl)-1-oxobutan-2-yl)-3-methylbutanamide |
| 4 | 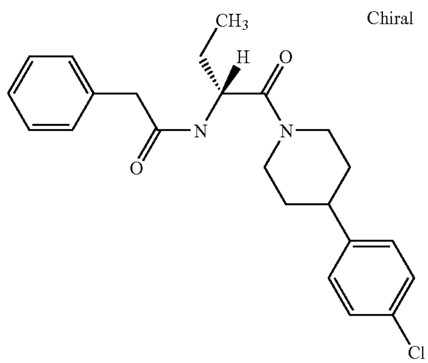 | Chiral | 400 | (R)-N-(1-(4-(4-chlorophenyl)piperidin-1-yl)-1-oxobutan-2-yl)-2-phenylacetamide |
| 5 | 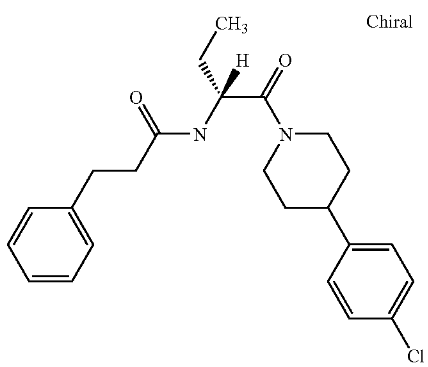 | Chiral | 414 | (R)-N-(1-(4-(4-chlorophenyl)piperidin-1-yl)-1-oxobutan-2-yl)-3-phenylpropanamide |

TABLE 1-continued

| Example | Structure | MS | Chemical Name |
|---|---|---|---|
| 6 | Chiral | 462 | (R)-N-(1-(4-(4-chlorophenyl)piperidin-1-yl)-1-oxobutan-2-yl)-3-phenylbenzamide |
| 7 | Chiral | 462 | (R)-N-(1-(4-(4-chlorophenyl)piperidin-1-yl)-1-oxobutan-2-yl)-2-phenylbenzamide |
| 8 | Chiral | 443 | (R)-N-(1-(4-(4-chlorophenyl)piperidin-1-yl)-1-oxobutan-2-yl)benzo[d]thiazole-2-carboxamide |

Example 9

N-(1-(4-(4-chlorophenyl)piperidin-1-yl)-3-methyl-1-oxobutan-2-yl)-2-phenylacetamide

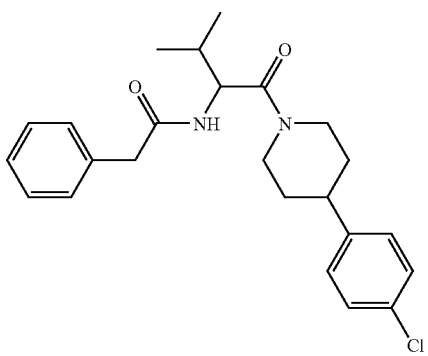

A reaction tube was charged with HOBt (10 mg), phenylacetic acid (12 mg) and EDC (14 mg) in DMF (0.7 mL). The resulting mixture was agitated at rt. for 15 min, and then a solution of 2-amino-1-(4-(4-chlorophenyl)piperidin-1-yl)-3-methylbutan-1-one hydrochloride (20 mg) in DIEA (50 µL) and DMF (250 µL) was added and the resulting mixture was shaken overnight at rt. At the conclusion of this period, the resulting solution was diluted with MeOH and purified by preparative LC-MS to provide Example 9. MS found: $(M+H)^+=414$.

Examples 10 to 74

Examples 10 to 74, as described in Table 2, were prepared in a similar manner as described for the preparation of Example 9. In the synthesis of the Examples 10 to 74, the appropriate acid needed to produce the product listed was used in place of the phenylacetic acid used in Example 9. The data in the "MS" column represents the values observed for the $(M+H)^+$ ions in MS experiments.

TABLE 2

| Example | Structure | MS | Chemical Name |
|---|---|---|---|
| 10 | 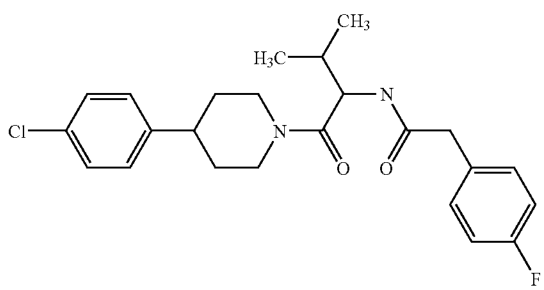 | 432 | N-(1-(4-(4-chlorophenyl)piperidin-1-yl)-3-methyl-1-oxobutan-2-yl)-2-(4-fluorophenyl)acetamide |
| 11 | 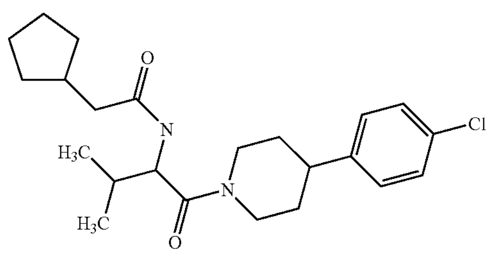 | 406 | N-(1-(4-(4-chlorophenyl)piperidin-1-yl)-3-methyl-1-oxobutan-2-yl)-2-cyclopentylacetamide |
| 12 | 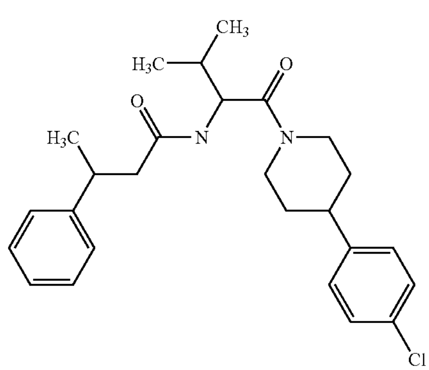 | 442 | N-(1-(4-(4-chlorophenyl)piperidin-1-yl)-3-methyl-1-oxobutan-2-yl)-3-phenylbutanamide |

TABLE 2-continued

| Example | Structure | MS | Chemical Name |
|---|---|---|---|
| 13 | 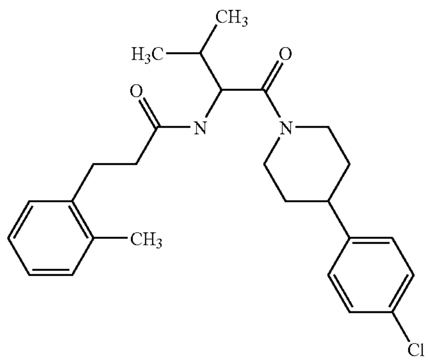 | 442 | N-(1-(4-(4-chlorophenyl)piperidin-1-yl)-3-methyl-1-oxobutan-2-yl)-3-o-tolylpropanamide |
| 14 | 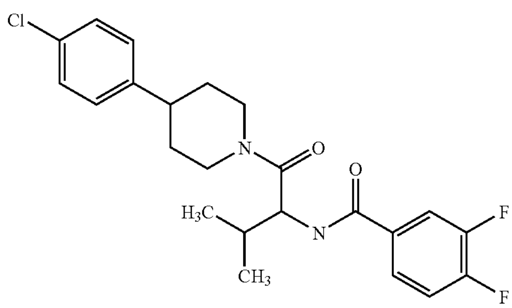 | 436 | N-(1-(4-(4-chlorophenyl)piperidin-1-yl)-3-methyl-1-oxobutan-2-yl)-3,4-difluorobenzamide |
| 15 | 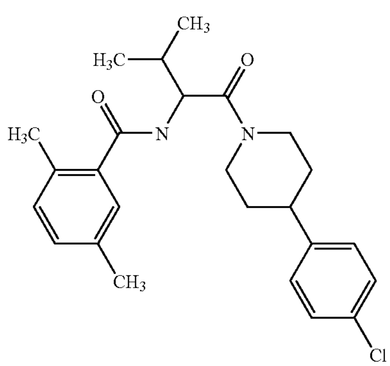 | 428 | N-(1-(4-(4-chlorophenyl)piperidin-1-yl)-3-methyl-1-oxobutan-2-yl)-2,5-dimethylbenzamide |
| 16 | 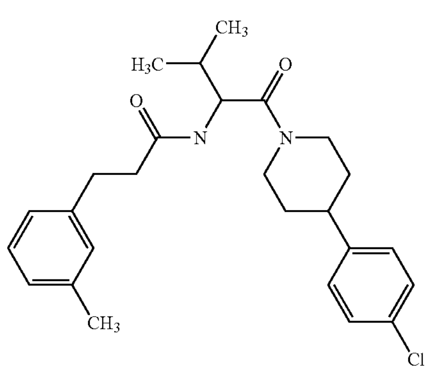 | 442 | N-(1-(4-(4-chlorophenyl)piperidin-1-yl)-3-methyl-1-oxobutan-2-yl)-3-m-tolylpropanamide |

TABLE 2-continued

| Example | Structure | MS | Chemical Name |
|---|---|---|---|
| 17 | 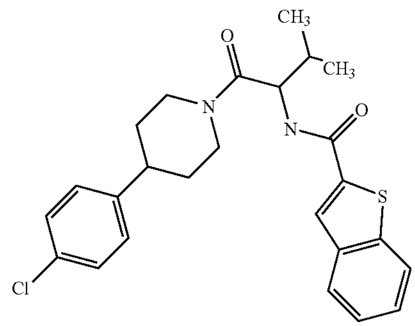 | 456 | N-(1-(4-(4-chlorophenyl)piperidin-1-yl)-3-methyl-1-oxobutan-2-yl)benzo[b]thiophene-2-carboxamide |
| 18 | 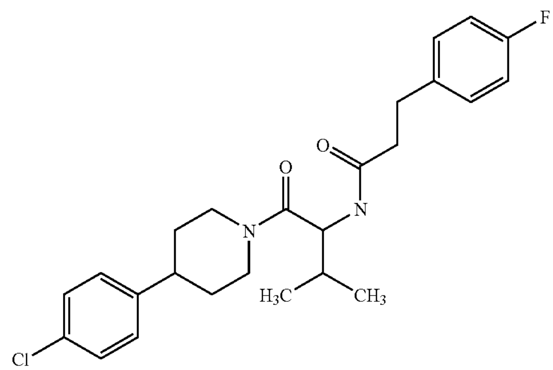 | 446 | N-(1-(4-(4-chlorophenyl)piperidin-1-yl)-3-methyl-1-oxobutan-2-yl)-3-(4-fluorophenyl)propanamide |
| 19 | 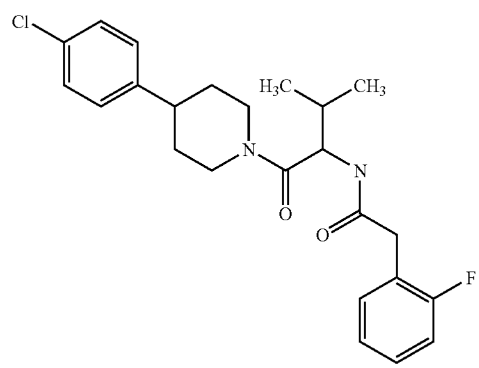 | 432 | N-(1-(4-(4-chlorophenyl)piperidin-1-yl)-3-methyl-1-oxobutan-2-yl)-2-(2-fluorophenyl)acetamide |
| 20 | 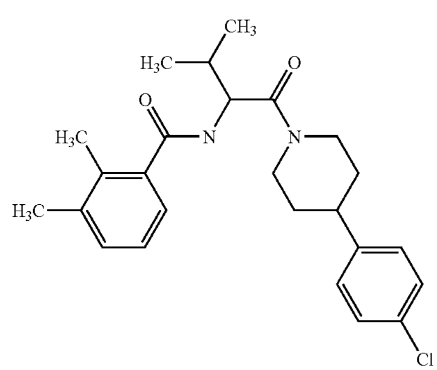 | 428 | N-(1-(4-(4-chlorophenyl)piperidin-1-yl)-3-methyl-1-oxobutan-2-yl)-2,3-dimethylbenzamide |

TABLE 2-continued

| Example | Structure | MS | Chemical Name |
|---------|-----------|-----|---------------|
| 21 | 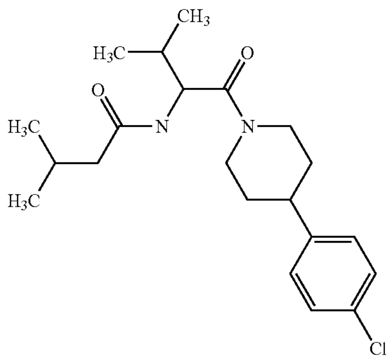 | 380 | N-(1-(4-(4-chlorophenyl)piperidin-1-yl)-3-methyl-1-oxobutan-2-yl)-3-methylbutanamide |
| 22 | 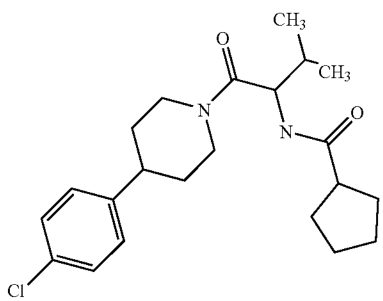 | 392 | N-(1-(4-(4-chlorophenyl)piperidin-1-yl)-3-methyl-1-oxobutan-2-yl)cyclopentanecarboxamide |
| 23 | 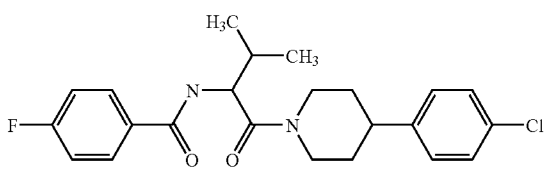 | 418 | N-(1-(4-(4-chlorophenyl)piperidin-1-yl)-3-methyl-1-oxobutan-2-yl)-4-fluorobenzamide |
| 24 | 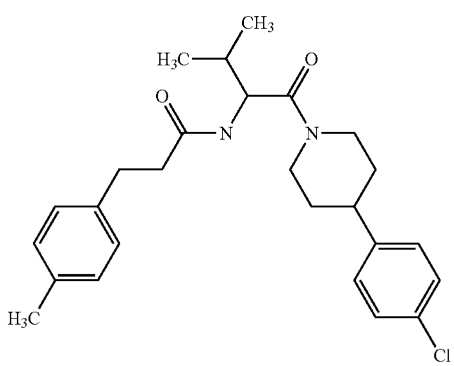 | 442 | N-(1-(4-(4-chlorophenyl)piperidin-1-yl)-3-methyl-1-oxobutan-2-yl)-3-p-tolylpropanamide |
| 25 | 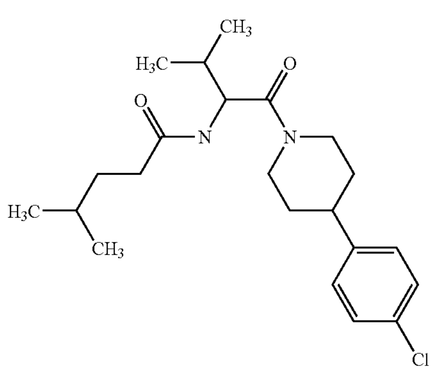 | 394 | N-(1-(4-(4-chlorophenyl)piperidin-1-yl)-3-methyl-1-oxobutan-2-yl)-4-methylpentanamide |

TABLE 2-continued
| Example | Structure | MS | Chemical Name |
|---|---|---|---|
| 26 | 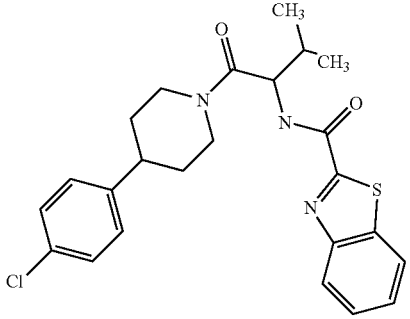 | 457 | N-(1-(4-(4-chlorophenyl)piperidin-1-yl)-3-methyl-1-oxobutan-2-yl)benzo[d]thiazole-2-carboxamide |
| 27 | 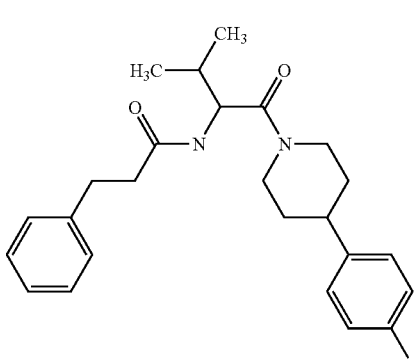 | 428 | N-(1-(4-(4-chlorophenyl)piperidin-1-yl)-3-methyl-1-oxobutan-2-yl)-3-phenylpropanamide |
| 28 | 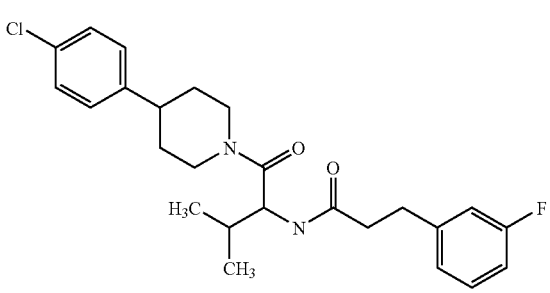 | 446 | N-(1-(4-(4-chlorophenyl)piperidin-1-yl)-3-methyl-1-oxobutan-2-yl)-3-(3-fluorophenyl)propanamide |
| 29 | 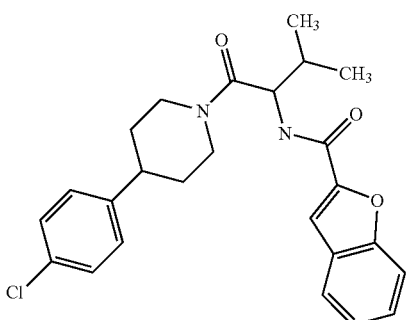 | 440 | N-(1-(4-(4-chlorophenyl)piperidin-1-yl)-3-methyl-1-oxobutan-2-yl)benzofuran-2-carboxamide |

TABLE 2-continued

| Example | Structure | MS | Chemical Name |
| --- | --- | --- | --- |
| 30 | 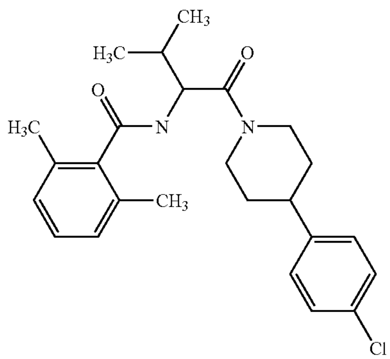 | 428 | N-(1-(4-(4-chlorophenyl)piperidin-1-yl)-3-methyl-1-oxobutan-2-yl)-2,6-dimethylbenzamide |
| 31 | 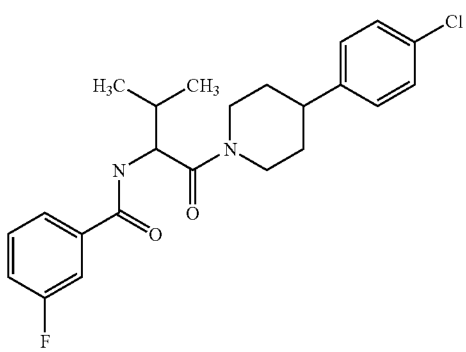 | 418 | N-(1-(4-(4-chlorophenyl)piperidin-1-yl)-3-methyl-1-oxobutan-2-yl)-3-fluorobenzamide |
| 32 | 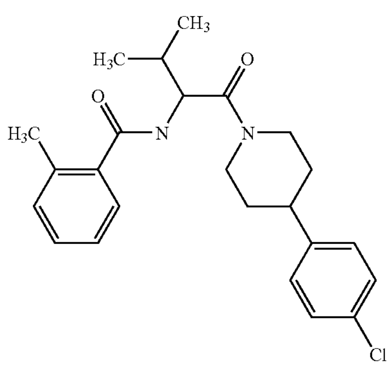 | 414 | N-(1-(4-(4-chlorophenyl)piperidin-1-yl)-3-methyl-1-oxobutan-2-yl)-2-methylbenzamide |
| 33 | 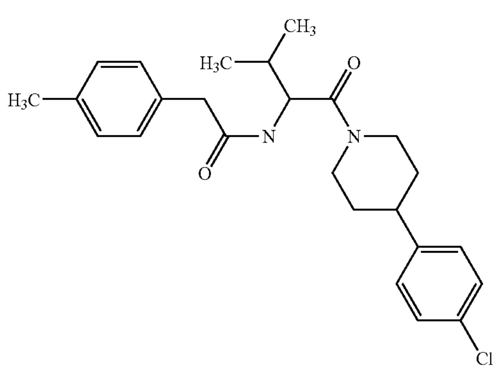 | 428 | N-(1-(4-(4-chlorophenyl)piperidin-1-yl)-3-methyl-1-oxobutan-2-yl)-2-p-tolylacetamide |

TABLE 2-continued

| Example | Structure | MS | Chemical Name |
|---|---|---|---|
| 34 | 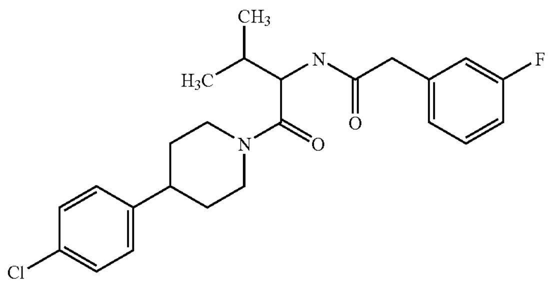 | 432 | N-(1-(4-(4-chlorophenyl)piperidin-1-yl)-3-methyl-1-oxobutan-2-yl)-2-(3-fluorophenyl)acetamide |
| 35 | 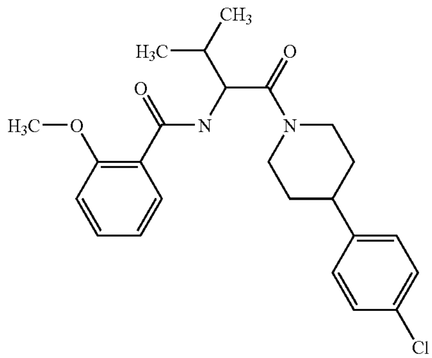 | 430 | N-(1-(4-(4-chlorophenyl)piperidin-1-yl)-3-methyl-1-oxobutan-2-yl)-2-methoxybenzamide |
| 36 | 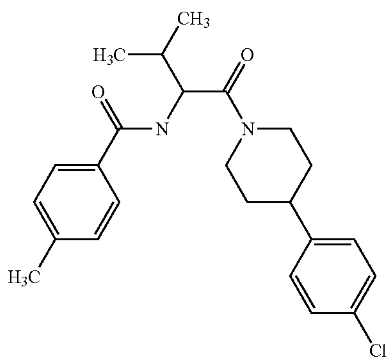 | 414 | N-(1-(4-(4-chlorophenyl)piperidin-1-yl)-3-methyl-1-oxobutan-2-yl)-4-methylbenzamide |
| 37 | 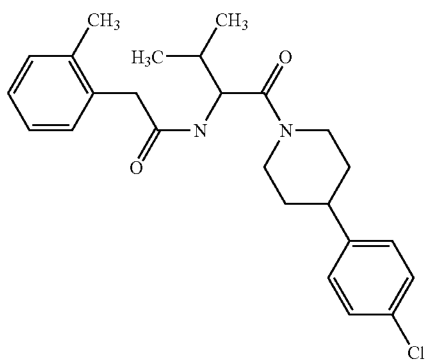 | 428 | N-(1-(4-(4-chlorophenyl)piperidin-1-yl)-3-methyl-1-oxobutan-2-yl)-2-o-tolylacetamide |

TABLE 2-continued

| Example | Structure | MS | Chemical Name |
|---|---|---|---|
| 38 | 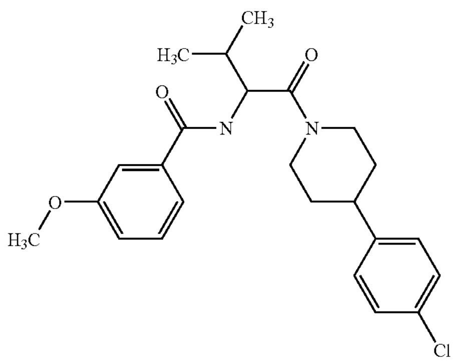 | 430 | N-(1-(4-(4-chlorophenyl)piperidin-1-yl)-3-methyl-1-oxobutan-2-yl)-3-methoxybenzamide |
| 39 | 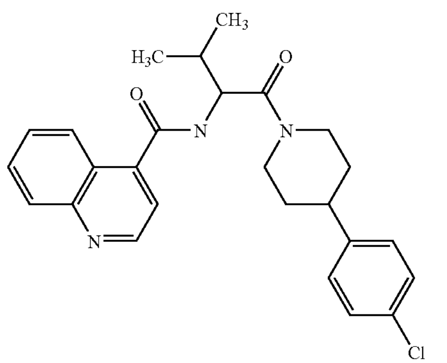 | 451 | N-(1-(4-(4-chlorophenyl)piperidin-1-yl)-3-methyl-1-oxobutan-2-yl)quinoline-4-carboxamide |
| 40 | 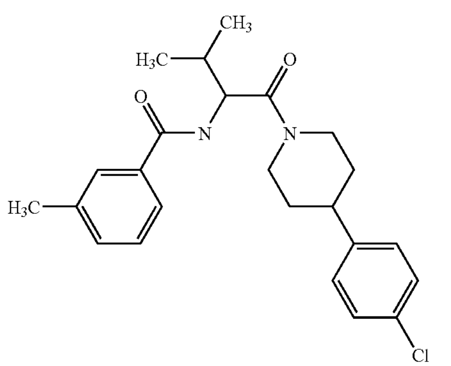 | 414 | N-(1-(4-(4-chlorophenyl)piperidin-1-yl)-3-methyl-1-oxobutan-2-yl)-3-methylbenzamide |
| 41 | 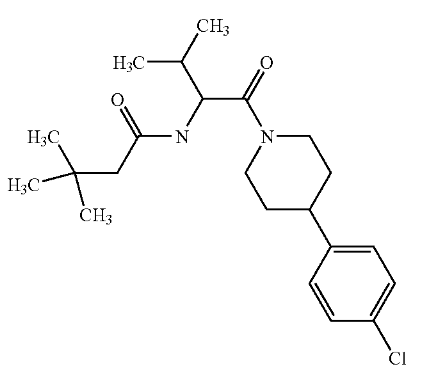 | 394 | N-(1-(4-(4-chlorophenyl)piperidin-1-yl)-3-methyl-1-oxobutan-2-yl)-3,3-dimethylbutanamide |

TABLE 2-continued

| Example | Structure | MS | Chemical Name |
|---------|-----------|-----|---------------|
| 42 | 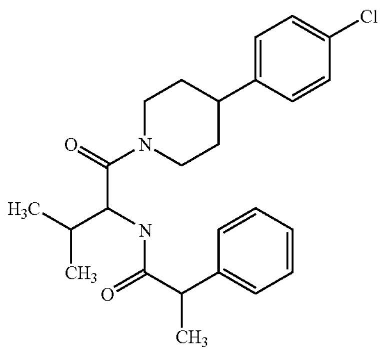 | 428 | N-(1-(4-(4-chlorophenyl)piperidin-1-yl)-3-methyl-1-oxobutan-2-yl)-2-phenylpropanamide |
| 43 | 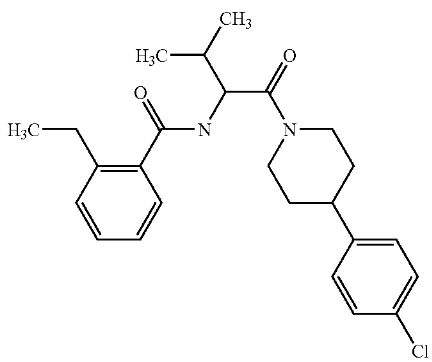 | 428 | N-(1-(4-(4-chlorophenyl)piperidin-1-yl)-3-methyl-1-oxobutan-2-yl)-2-ethylbenzamide |
| 44 | 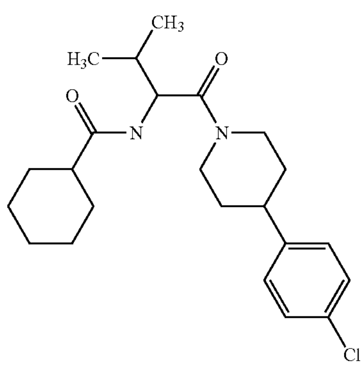 | 406 | N-(1-(4-(4-chlorophenyl)piperidin-1-yl)-3-methyl-1-oxobutan-2-yl)cyclohexanecarboxamide |
| 45 | 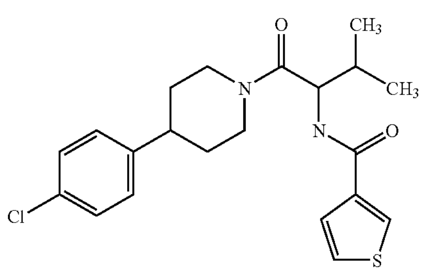 | 406 | N-(1-(4-(4-chlorophenyl)piperidin-1-yl)-3-methyl-1-oxobutan-2-yl)thiophene-3-carboxamide |

TABLE 2-continued

| Example | Structure | MS | Chemical Name |
|---|---|---|---|
| 46 | 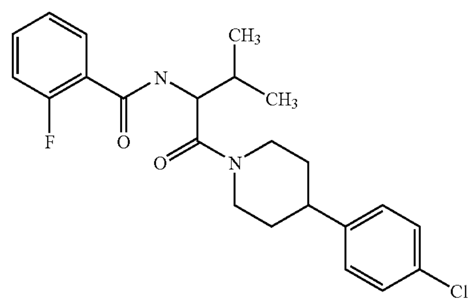 | 418 | N-(1-(4-(4-chlorophenyl)piperidin-1-yl)-3-methyl-1-oxobutan-2-yl)-2-fluorobenzamide |
| 47 | 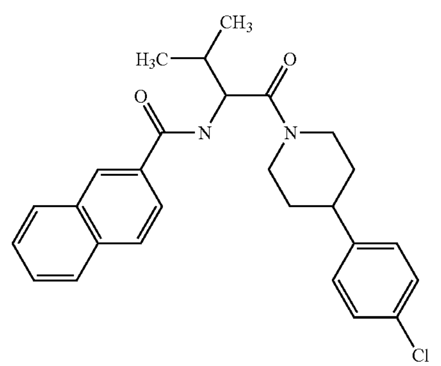 | 450 | N-(1-(4-(4-chlorophenyl)piperidin-1-yl)-3-methyl-1-oxobutan-2-yl)-2-naphthamide |
| 48 | 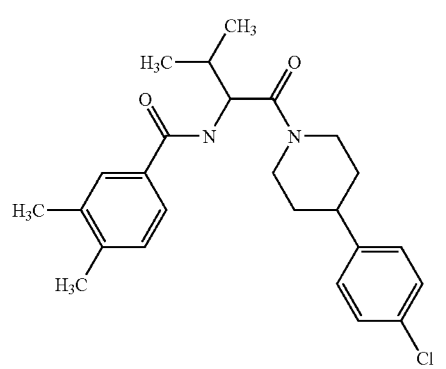 | 428 | N-(1-(4-(4-chlorophenyl)piperidin-1-yl)-3-methyl-1-oxobutan-2-yl)-3,4-dimethylbenzamide |
| 49 | 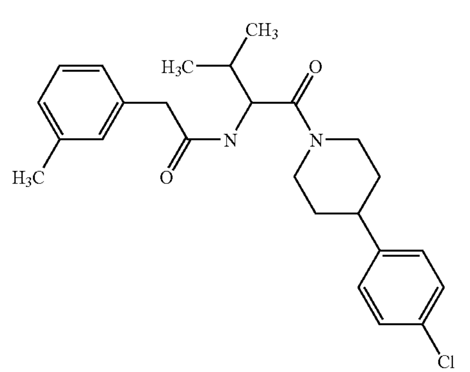 | 428 | N-(1-(4-(4-chlorophenyl)piperidin-1-yl)-3-methyl-1-oxobutan-2-yl)-2-m-tolylacetamide |

TABLE 2-continued

| Example | Structure | MS | Chemical Name |
|---|---|---|---|
| 50 | 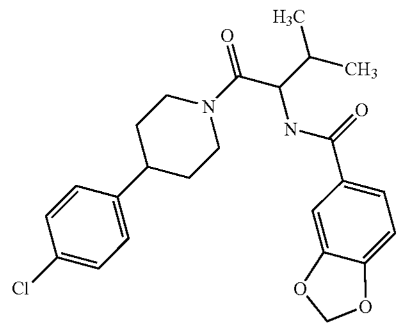 | 444 | N-(1-(4-(4-chlorophenyl)piperidin-1-yl)-3-methyl-1-oxobutan-2-yl)benzo[d][1,3]dioxole-5-carboxamide |
| 51 | 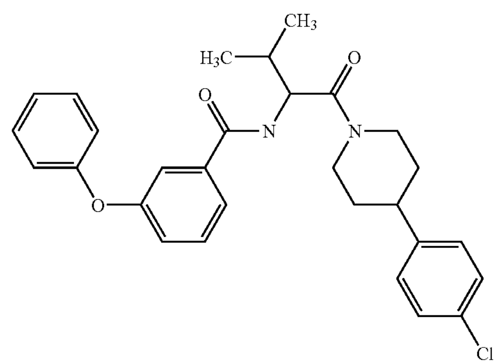 | 492 | N-(1-(4-(4-chlorophenyl)piperidin-1-yl)-3-methyl-1-oxobutan-2-yl)-3-phenoxybenzamide |
| 52 | 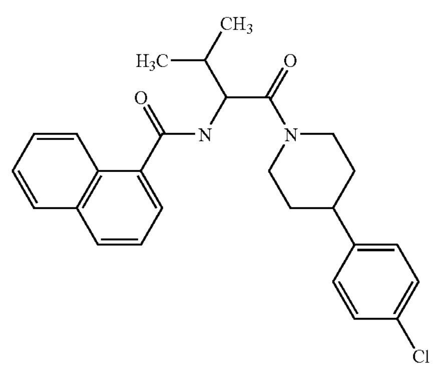 | 450 | N-(1-(4-(4-chlorophenyl)piperidin-1-yl)-3-methyl-1-oxobutan-2-yl)-1-naphthamide |
| 53 | 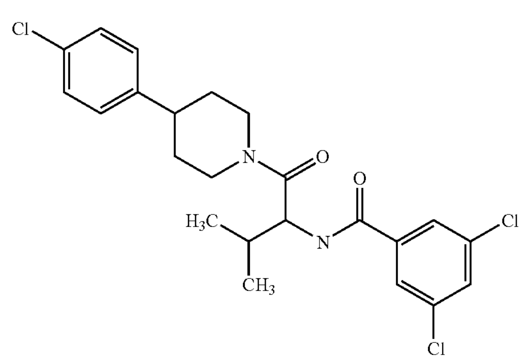 | 469 | 3,5-dichloro-N-(1-(4-(4-chlorophenyl)piperidin-1-yl)-3-methyl-1-oxobutan-2-yl)benzamide |

TABLE 2-continued

| Example | Structure | MS | Chemical Name |
|---------|-----------|-----|---------------|
| 54 | 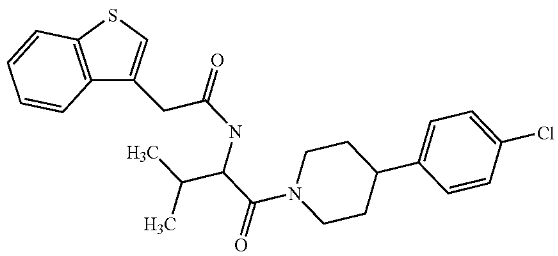 | 470 | 2-(benzo[b]thiophen-3-yl)-N-(1-(4-(4-chlorophenyl)piperidin-1-yl)-3-methyl-1-oxobutan-2-yl)acetamide |
| 55 | 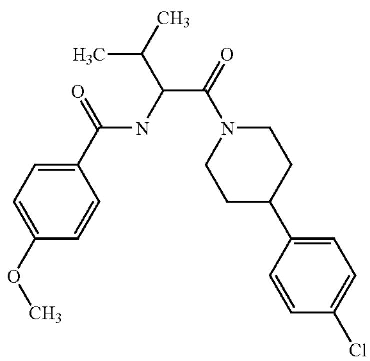 | 430 | N-(1-(4-(4-chlorophenyl)piperidin-1-yl)-3-methyl-1-oxobutan-2-yl)-4-methoxybenzamide |
| 56 | 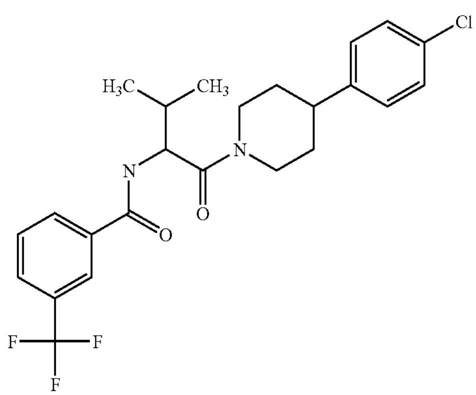 | 468 | N-(1-(4-(4-chlorophenyl)piperidin-1-yl)-3-methyl-1-oxobutan-2-yl)-3-(trifluoromethyl)benzamide |
| 57 | 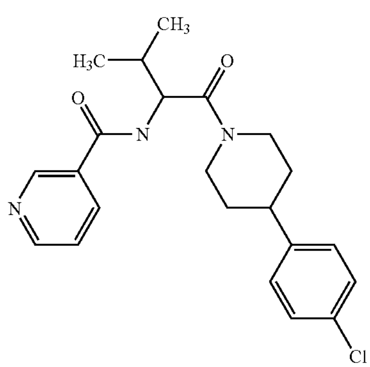 | 401 | N-(1-(4-(4-chlorophenyl)piperidin-1-yl)-3-methyl-1-oxobutan-2-yl)nicotinamide |

TABLE 2-continued

| Example | Structure | MS | Chemical Name |
|---|---|---|---|
| 58 | 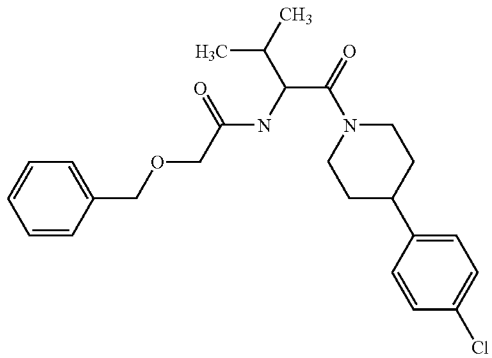 | 444 | 2-(benzyloxy)-N-(1-(4-(4-chlorophenyl)piperidin-1-yl)-3-methyl-1-oxobutan-2-yl)acetamide |
| 59 | 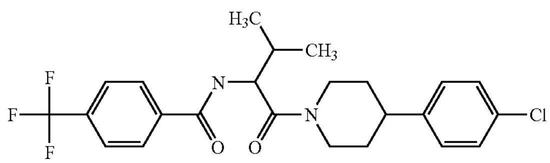 | 468 | N-(1-(4-(4-chlorophenyl)piperidin-1-yl)-3-methyl-1-oxobutan-2-yl)-4-(trifluoromethyl)benzamide |
| 60 | 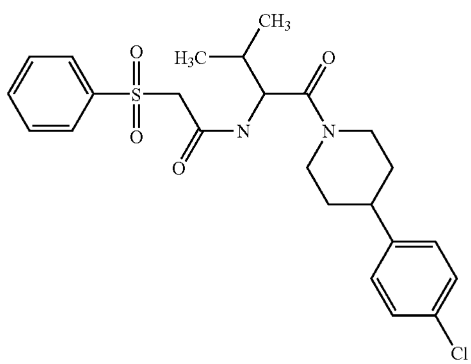 | 478 | N-(1-(4-(4-chlorophenyl)piperidin-1-yl)-3-methyl-1-oxobutan-2-yl)-3-(phenylsulfonyl)propanamide |
| 61 | 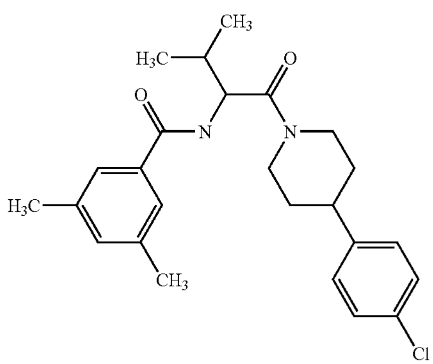 | 428 | N-(1-(4-(4-chlorophenyl)piperidin-1-yl)-3-methyl-1-oxobutan-2-yl)-3,5-dimethylbenzamide |

TABLE 2-continued

| Example | Structure | MS | Chemical Name |
|---|---|---|---|
| 62 | 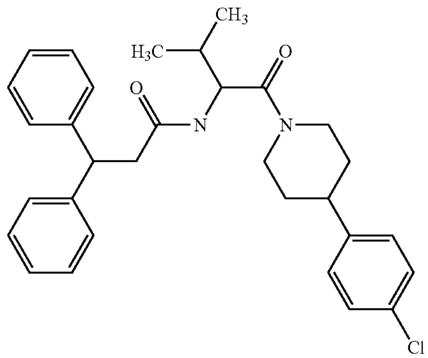 | 504 | N-(1-(4-(4-chlorophenyl)piperidin-1-yl)-3-methyl-1-oxobutan-2-yl)-3,3-diphenylpropanamide |
| 63 | 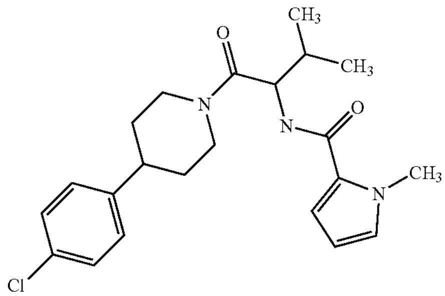 | 403 | N-(1-(4-(4-chlorophenyl)piperidin-1-yl)-3-methyl-1-oxobutan-2-yl)-1-methyl-1H-pyrrole-2-carboxamide |
| 64 | 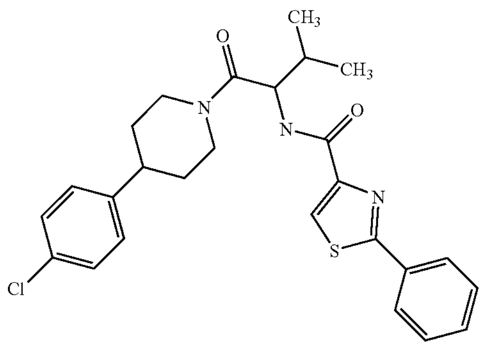 | 483 | N-(1-(4-(4-chlorophenyl)piperidin-1-yl)-3-methyl-1-oxobutan-2-yl)-2-phenylthiazole-4-carboxamide |
| 65 | 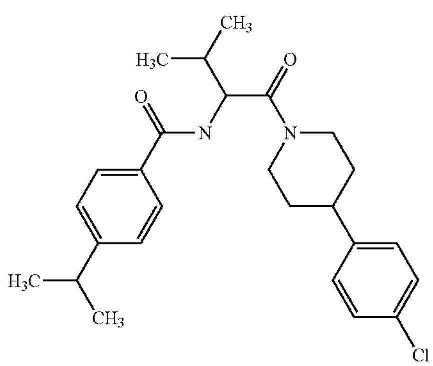 | 442 | N-(1-(4-(4-chlorophenyl)piperidin-1-yl)-3-methyl-1-oxobutan-2-yl)-4-isopropylbenzamide |
| 66 | 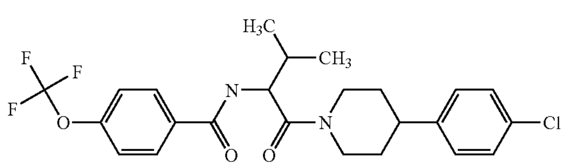 | 484 | N-(1-(4-(4-chlorophenyl)piperidin-1-yl)-3-methyl-1-oxobutan-2-yl)-4-(trifluoromethoxy)benzamide |

TABLE 2-continued

| Example | Structure | MS | Chemical Name |
|---|---|---|---|
| 67 | 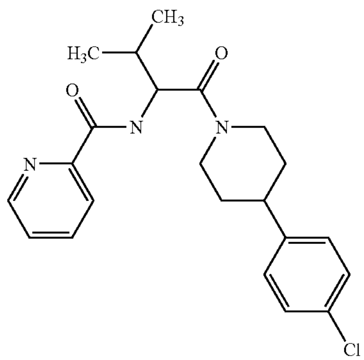 | 401 | N-(1-(4-(4-chlorophenyl)piperidin-1-yl)-3-methyl-1-oxobutan-2-yl)picolinamide |
| 68 | 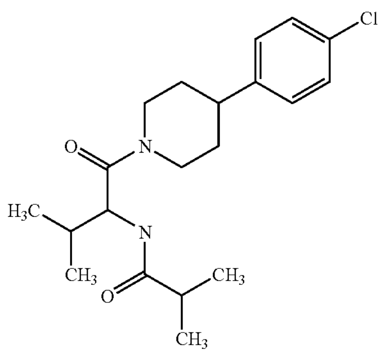 | 366 | N-(1-(4-(4-chlorophenyl)piperidin-1-yl)-3-methyl-1-oxobutan-2-yl)isobutyramide |
| 69 | 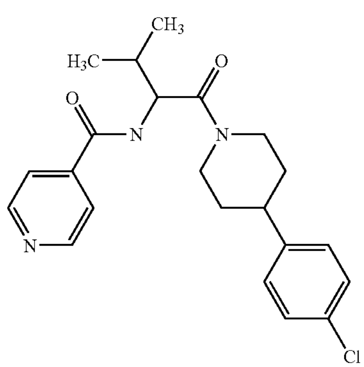 | 401 | N-(1-(4-(4-chlorophenyl)piperidin-1-yl)-3-methyl-1-oxobutan-2-yl)isonicotinamide |
| 70 | 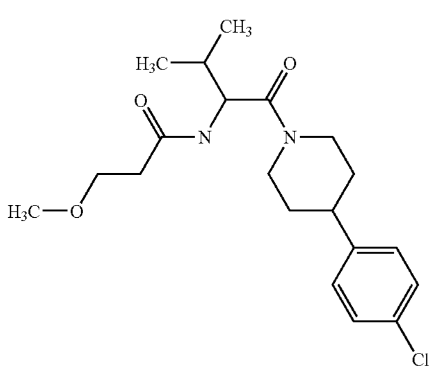 | 382 | N-(1-(4-(4-chlorophenyl)piperidin-1-yl)-3-methyl-1-oxobutan-2-yl)-3-methoxypropanamide |

TABLE 2-continued

| Example | Structure | MS | Chemical Name |
|---|---|---|---|
| 71 | 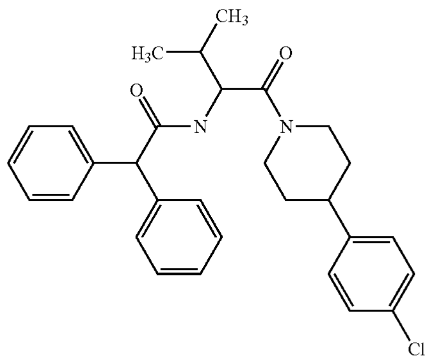 | 490 | N-(1-(4-(4-chlorophenyl)piperidin-1-yl)-3-methyl-1-oxobutan-2-yl)-2,2-diphenylacetamide |
| 72 | 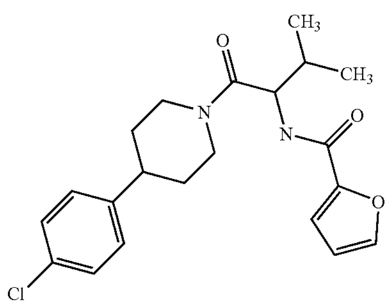 | 390 | N-(1-(4-(4-chlorophenyl)piperidin-1-yl)-3-methyl-1-oxobutan-2-yl)furan-2-carboxamide |
| 73 | 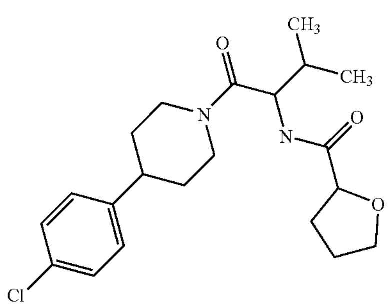 | 394 | N-(1-(4-(4-chlorophenyl)piperidin-1-yl)-3-methyl-1-oxobutan-2-yl)-tetrahydrofuran-2-carboxamide |
| 74 | 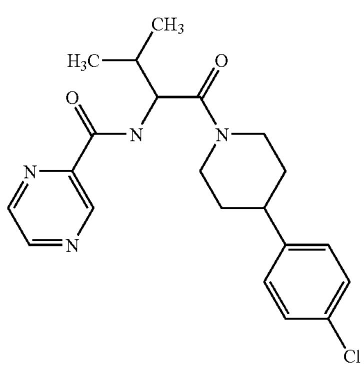 | 402 | N-(1-(4-(4-chlorophenyl)piperidin-1-yl)-3-methyl-1-oxobutan-2-yl)pyrazine-2-carboxamide |

Example 75

(R)—N-(1-(4-(4-Chlorophenyl)piperidin-1-yl)-3-methyl-1-oxobutan-2-yl)benzamide

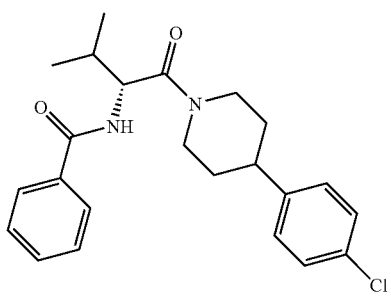

(R)-2-Amino-1-(4-(4-chlorophenyl)piperidin-1-yl)-3-methylbutan-1-one hydrochloride (41 mg) was added to DMF (1 mL). The resulting mixture was stirred until homogeneous and then HOBt (19 mg), DIEA (65 μL), benzoic acid (17 mg) and EDC (26 mg) were added. The resulting solution was allowed to stir overnight at rt. After this time, the solution was diluted with MeOH and purified by preparative LC-MS to provide Example 75. MS found: $(M+Na)^+=421$.

Examples 76 to 148

Examples 76 to 148, as described in Table 3, were prepared in a similar manner as described for the preparation of Example 75. In the synthesis of Examples 76 to 148, the appropriate acid needed to produce the product listed was used in place of the benzoic acid used in Example 75. In Examples # 139, 140, 143, 144 and 149, the acids were obtained from their corresponding commercially available esters after standard saponification (NaOH, THF). The data in the "MS" column represents the values observed for the $(M+H)^+$ ions in MS experiments.

TABLE 3

| Example | Structure | MS | Chemical Name |
|---------|-----------|----|----|
| 76 | Chiral | 394 | (R)-N-(1-(4-(4-chlorophenyl)piperidin-1-yl)-3-methyl-1-oxobutan-2-yl)-4-methylpentanamide |
| 77 | Chiral | 418 | (R)-N-(1-(4-(4-chlorophenyl)piperidin-1-yl)-3-methyl-1-oxobutan-2-yl)-4-fluorobenzamide |
| 78 | Chiral | 392 | (R)-N-(1-(4-(4-chlorophenyl)piperidin-1-yl)-3-methyl-1-oxobutan-2-yl)cyclopentanecarboxamide |

TABLE 3-continued

| Example | Structure | MS | Chemical Name |
|---|---|---|---|
| 79 | 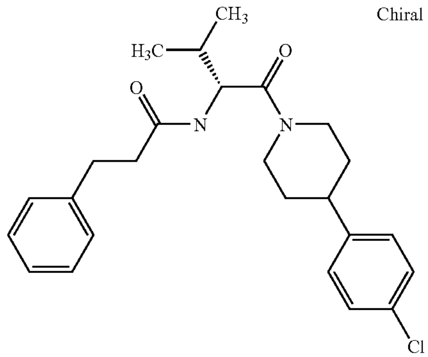 | 428 | (R)-N-(1-(4-(4-chlorophenyl)piperidin-methyl-1-oxobutan-2-yl)-3-phenylpropanamide |
| 80 | 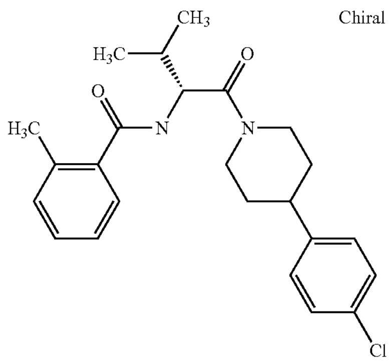 | 414 | (R)-N-(1-(4-(4-chlorophenyl)piperidin-1-yl)-3-methyl-1-oxobutan-2-yl)-2-methylbenzamide |
| 81 | 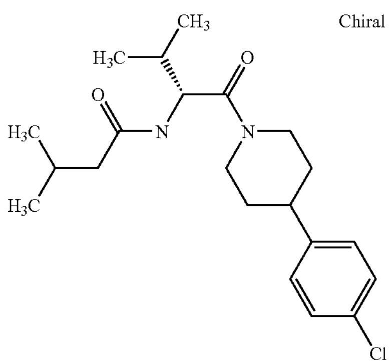 | 380 | (R)-N-(1-(4-(4-chlorophenyl)piperidin-1-yl)-3-methyl-1-oxobutan-2-yl)-3-methylbutanamide |
| 82 | 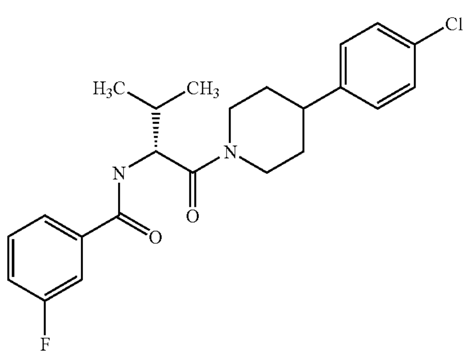 | 418 | (R)-N-(1-(4-(4-chlorophenyl)piperidin-1-yl)-3-methyl-1-oxobutan-2-yl)-3-fluorobenzamide |

TABLE 3-continued

| Example | Structure | MS | Chemical Name |
|---|---|---|---|
| 83 | Chiral | 456 | (R)-N-(1-(4-(4-chlorophenyl)piperidin-1-yl)-3-methyl-1-oxobutan-2-yl)benzo[b]thiophene-2-carboxamide |
| 84 | Chiral | 414 | (R)-N-(1-(4-(4-chlorophenyl)piperidin-1-yl)-3-methyl-1-oxobutan-2-yl)-4-methylbenzamide |
| 85 | Chiral | 414 | (R)-N-(1-(4-(4-chlorophenyl)piperidin-1-yl)-3-methyl-1-oxobutan-2-yl)-2-phenylacetamide |
| 86 | Chiral | 420 | (R)-N-(1-(4-(4-chlorophenyl)piperidin-1-yl)-3-methyl-1-oxobutan-2-yl)-2-cyclohexylacetamide |

TABLE 3-continued

| Example | Structure | MS | Chemical Name |
|---|---|---|---|
| 87 | Chiral | 432 | (R)-N-(1-(4-(4-chlorophenyl)piperidin-1-yl)-3-methyl-1-oxobutan-2-yl)-2-(2-fluorophenyl)acetamide |
| 88 | Chiral | 436 | (R)-N-(1-(4-(4-chlorophenyl)piperidin-1-yl)-3-methyl-1-oxobutan-2-yl)-3,4-difluorobenzamide |
| 89 | Chiral | 446 | (R)-N-(1-(4-(4-chlorophenyl)piperidin-1-yl)-3-methyl-1-oxobutan-2-yl)-3-(2-fluorophenyl)propanamide |
| 90 | Chiral | 457 | (R)-N-(1-(4-(4-chlorophenyl)piperidin-1-yl)-3-methyl-1-oxobutan-2-yl)benzo[d]thiazole-2-carboxamide |
| 91 | Chiral | 442 | (R)-N-(1-(4-(4-chlorophenyl)piperidin-1-yl)-3-methyl-1-oxobutan-2-yl)-3-o-tolylpropanamide |

TABLE 3-continued

| Example | Structure | MS | Chemical Name |
|---|---|---|---|
| 92 | Chiral | 406 | (R)-N-(1-(4-(4-chlorophenyl)piperidin-1-yl)-3-methyl-1-oxobutan-2-yl)-2-cyclopentylacetamide |
| 93 | Chiral | 434 | N-((R)-1-(4-(4-chlorophenyl)piperidin-1-yl)-3-methyl-1-oxobutan-2-yl)-4,4,4-trifluoro-3-methylbutanamide |
| 94 | Chiral | 442 | (R)-N-(1-(4-(4-chlorophenyl)piperidin-1-yl)-3-methyl-1-oxobutan-2-yl)-3-m-tolylpropanamide |
| 95 | Chiral | 404 | N-((R)-1-(4-(4-chlorophenyl)piperidin-1-yl)-3-methyl-1-oxobutan-2-yl)-2-(cyclopent-2-enyl)acetamide |
| 96 | Chiral | 432 | (R)-N-(1-(4-(4-chlorophenyl)piperidin-1-yl)-3-methyl-1-oxobutan-2-yl)-5-fluoro-2-methylbenzamide |

TABLE 3-continued

| Example | Structure | MS | Chemical Name |
|---|---|---|---|
| 97 | Chiral | 442 | (R)-N-((R)-1-(4-(4-chlorophenyl)piperidin-1-yl)-3-methyl-1-oxobutan-2-yl)-3-phenylbutanamide |
| 98 | Chiral | 432 | (R)-N-(1-(4-(4-chlorophenyl)piperidin-1-yl)-3-methyl-1-oxobutan-2-yl)-2-(3-fluorophenyl)acetamide |
| 99 | Chiral | 448 | (R)-2-(3-chlorophenyl)-N-(1-(4-(4-chlorophenyl)piperidin-1-yl)-3-methyl-1-oxobutan-2-yl)acetamide |
| 100 | Chiral | 378 | (R)-N-(1-(4-(4-chlorophenyl)piperidin-1-yl)-3-methyl-1-oxobutan-2-yl)-2-cyclopropylacetamide |
| 101 | Chiral | 442 | N-((R)-1-(4-(4-chlorophenyl)piperidin-1-yl)-3-methyl-1-oxobutan-2-yl)-3-phenylbutanamide |

TABLE 3-continued

| Example | Structure | MS | Chemical Name |
|---|---|---|---|
| 102 | 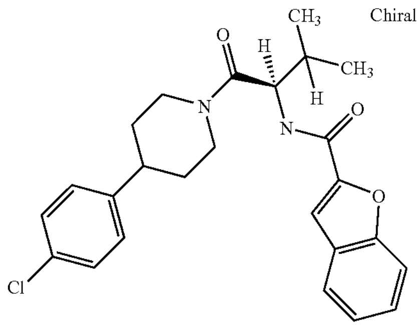 | 440 | (R)-N-(1-(4-(4-chlorophenyl)piperidin-1-yl)-3-methyl-1-oxobutan-2-yl)benzofuran-2-carboxamide |
| 103 | 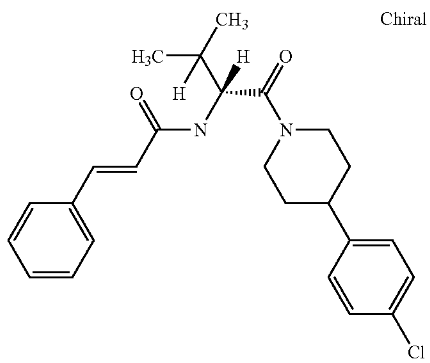 | 426 | (R)-N-(1-(4-(4-chlorophenyl)piperidin-1-yl)-3-methyl-1-oxobutan-2-yl)cinnamamide |
| 104 | 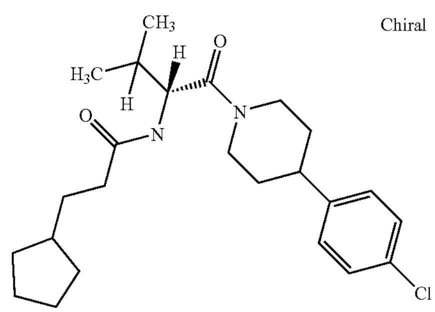 | 420 | (R)-N-(1-(4-(4-chlorophenyl)piperidin-1-yl)-3-methyl-1-oxobutan-2-yl)-3-cyclopentylpropanamide |
| 105 | 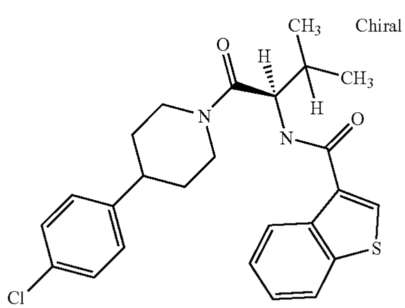 | 456 | (R)-N-(1-(4-(4-chlorophenyl)piperidin-1-yl)-3-methyl-1-oxobutan-2-yl)benzo[b]thiophene-3-carboxamide |

TABLE 3-continued

| Example | Structure | MS | Chemical Name |
|---------|-----------|----|----|
| 106 | Chiral | 482 | (R)-N-(1-(4-(4-chlorophenyl)piperidin-1-yl)-3-methyl-1-oxobutan-2-yl)-2-(2-(trifluoromethyl)phenyl)acetamide |
| 107 | Chiral | 444 | (R)-N-(1-(4-(4-chlorophenyl)piperidin-1-yl)-3-methyl-1-oxobutan-2-yl)-2-(o-tolyloxy)acetamide |
| 108 | Chiral | 482 | (R)-N-(1-(4-(4-chlorophenyl)piperidin-1-yl)-3-methyl-1-oxobutan-2-yl)-2-(4-(trifluoromethyl)phenyl)acetamide |
| 109 | Chiral | 470 | (R)-N-(1-(4-(4-chlorophenyl)piperidin-1-yl)-3-methyl-1-oxobutan-2-yl)-3-methylbenzo[b]thiophene-2-carboxamide |

TABLE 3-continued
| Example | Structure | MS | Chemical Name |
|---|---|---|---|
| 110 | 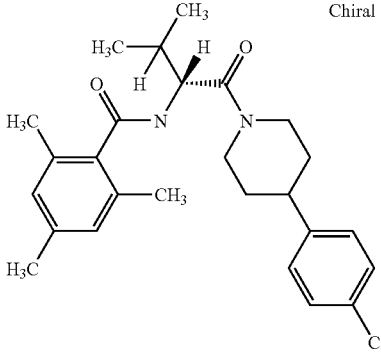 Chiral | 442 | (R)-N-(1-(4-(4-chlorophenyl)piperidin-1-yl)-3-methyl-1-oxobutan-2-yl)-2,4,6-trimethylbenzamide |
| 111 | 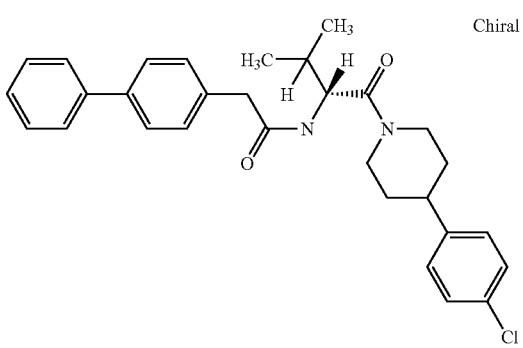 Chiral | 490 | (R)-N-(1-(4-(4-chlorophenyl)piperidin-1-yl)-3-methyl-1-oxobutan-2-yl)-2-(4-(phenyl)phenyl)acetamide |
| 112 | 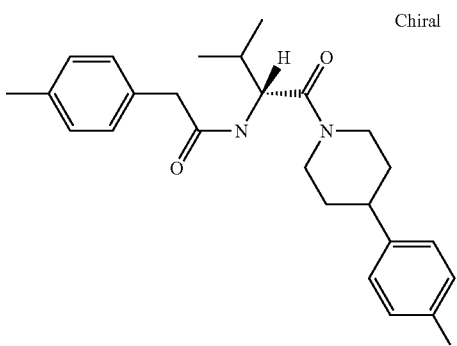 Chiral | 427.1 | |
| 113 | 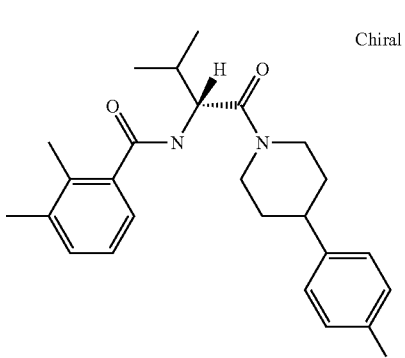 Chiral | 427.1 | |

TABLE 3-continued
| Example | Structure | MS | Chemical Name |
|---------|-----------|-----|---------------|
| 114 | 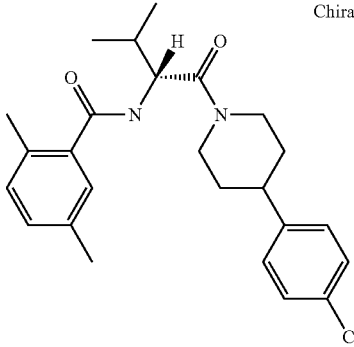 Chiral | 427.1 | |
| 115 | 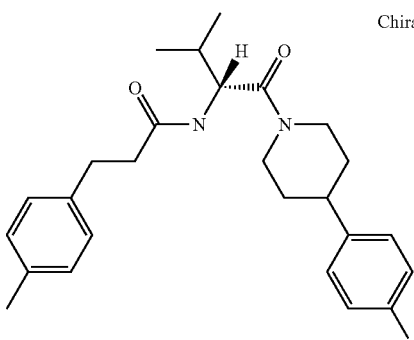 Chiral | 441.1 | |
| 116 | 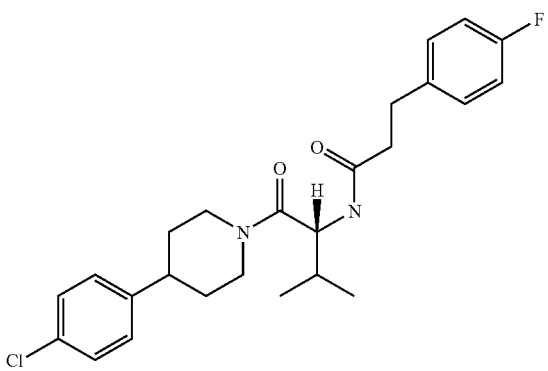 Chiral | 445.1 | |
| 117 | 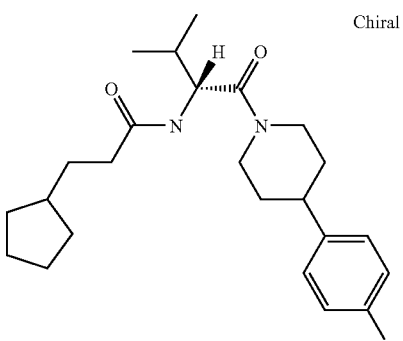 Chiral | 419.1 | |

TABLE 3-continued

| Example | Structure | MS | Chemical Name |
|---------|-----------|-----|---------------|
| 118 | Chiral | 447.1 | |
| 119 | Chiral | 441.1 | |
| 120 | Chiral | 441.1 | |
| 121 | Chiral | 439.1 | |

TABLE 3-continued
| Example | Structure | MS | Chemical Name |
|---|---|---|---|
| 122 | 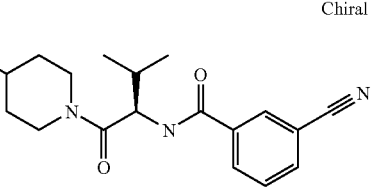 Chiral | 424.3 | |
| 123 | 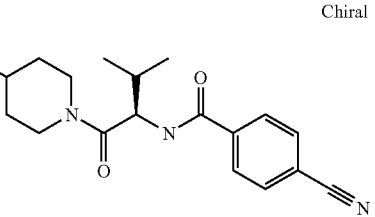 Chiral | 424.3 | |
| 124 | 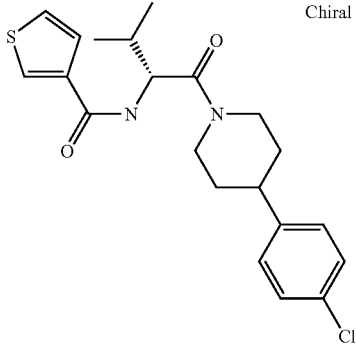 Chiral | 405.3 | |
| 125 | 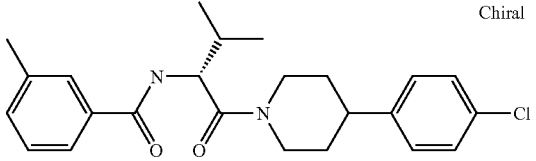 Chiral | 413.3 | |
| 126 | 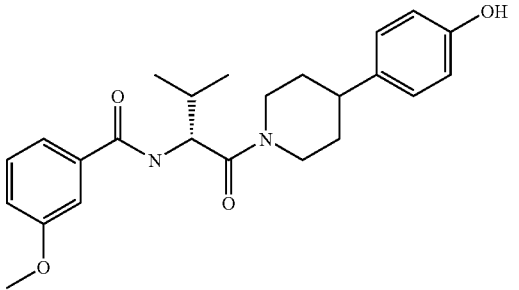 Chiral | 429.3 | |
| 127 | 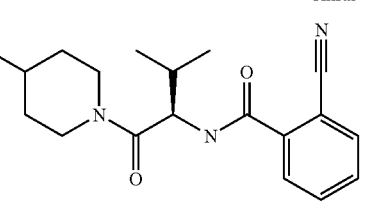 Chiral | 424.4 | |

TABLE 3-continued
| Example | Structure | MS | Chemical Name |
|---|---|---|---|
| 128 | 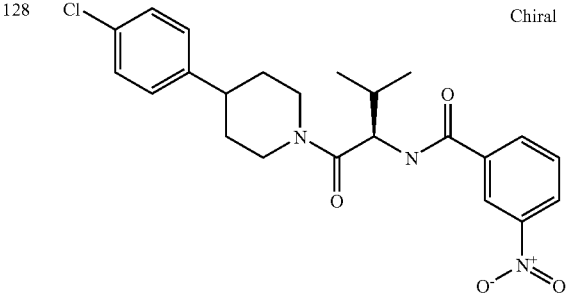 Chiral | 444.3 | (R)-N-(1-(4-(4-chlorophenyl)piperidin-1-yl)-3-methyl-1-oxobutan-2-yl)-3-nitrobenzamide |
| 129 | 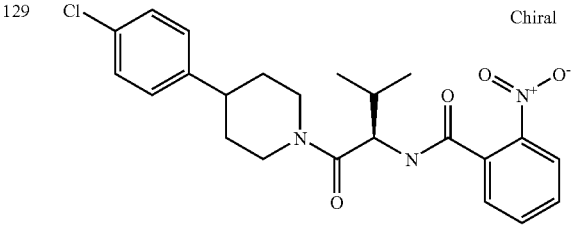 Chiral | 444.3 | (R)-N-(1-(4-(4-chlorophenyl)piperidin-1-yl)-3-methyl-1-oxobutan-2-yl)-2-nitrobenzamide |
| 130 | 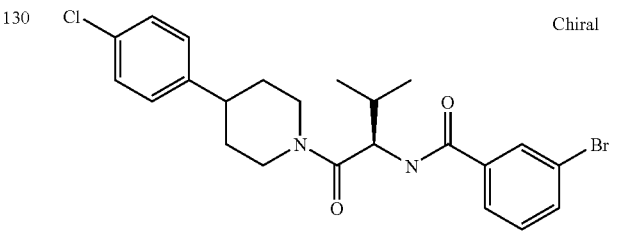 Chiral | 479.25 (M + H) | |
| 131 | 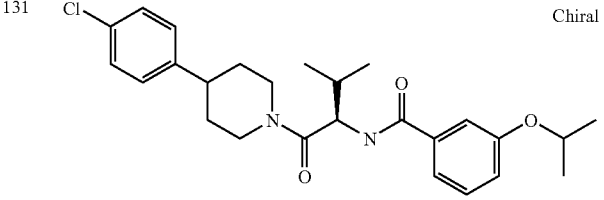 Chiral | 457.4 | |
| 132 | 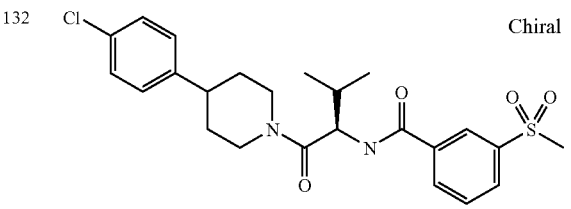 Chiral | 477.3 | |
| 133 | 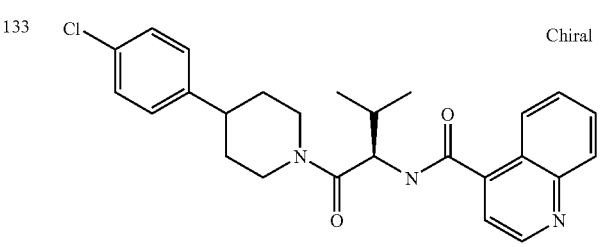 Chiral | 450.4 | |

TABLE 3-continued
| Example | Structure | MS | Chemical Name |
|---|---|---|---|
| 134 | 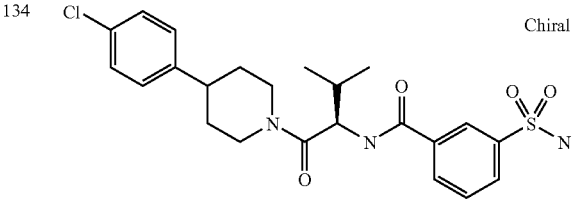 | 478.3 | |
| 135 | 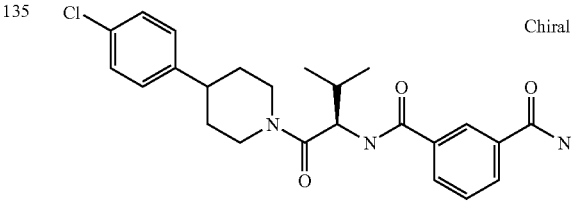 | 442.3 | |
| 136 | 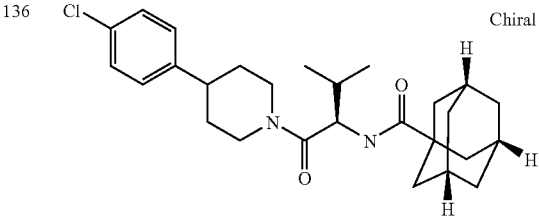 | 457.3 | |
| 137 | 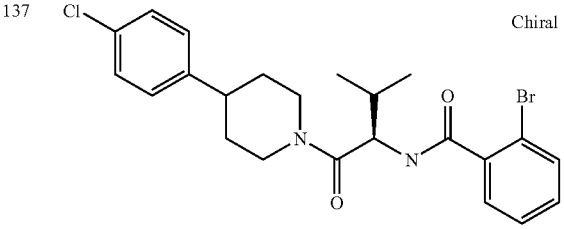 | 501.2 (M + Na) | |
| 138 | 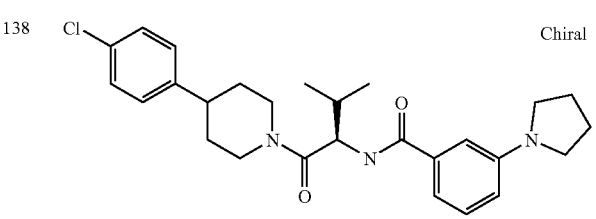 | 468.4 | |
| 139 | 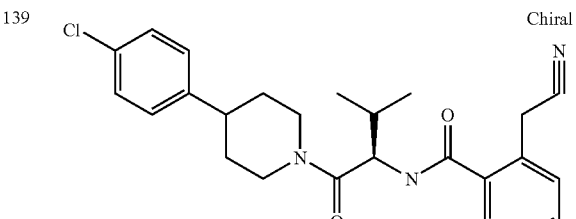 | 438.4 | |

TABLE 3-continued
| Example | Structure | MS | Chemical Name |
|---|---|---|---|
| 140 | 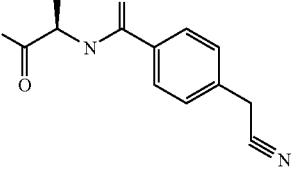 Chiral | 438.4 | |
| 141 | 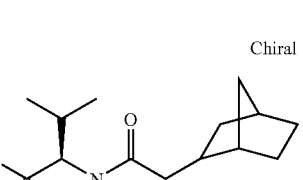 Chiral | 431.4 | |
| 142 | 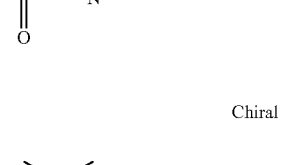 Chiral | 439.4 | |
| 143 | 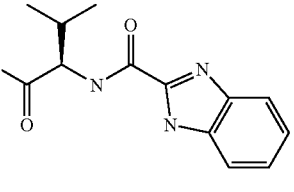 Chiral | 438.3 | |
| 144 | 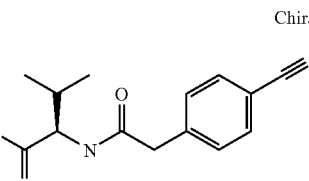 Chiral | 439.3 | |
| 145 | 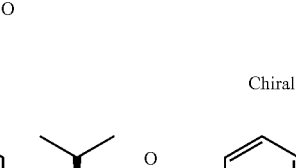 Chiral | 431.3 | |

TABLE 3-continued

| Example | Structure | MS | Chemical Name |
|---|---|---|---|
| 146 | Chiral | 471.3 | |
| 147 | Chiral | 420.4 (M − boc) | |
| 148 | Chiral | 438.3 | |

Example 149

(R)—N-(1-(4-(4-Bromophenyl)piperidin-1-yl)-3-methyl-1-oxobutan-2-yl)benzamide

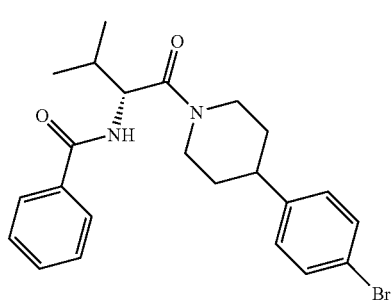

Step 1: (R)-2-Amino-1-(4-(4-bromophenyl)piperidin-1-yl)-3-methylbutan-1-one hydrochloride (R)-2-Amino-1-(4-(4-bromophenyl)piperidin-1-yl)-3-methylbutan-1-one hydrochloride was prepared in a similar manner as described in Preparation A with the exception that 4-bromophenyl piperidine was substituted for 4-chlorophenyl piperidine hydrochloride in Step 1.

Step 2: Example 149

Example 149 was prepared in a similar manner as described for the preparation of Example 75. MS found: (M+Na)$^+$=443.2.

Example 150

N-((2R,3R)-1-(4-(4-Chlorophenyl)piperidin-1-yl)-3-methyl-1-oxopentan-2-yl)benzamide

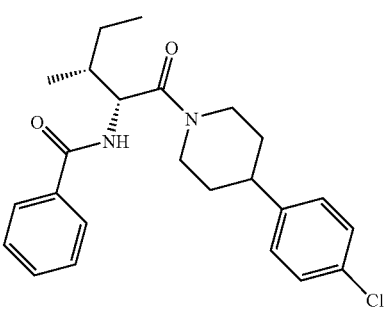

A reaction tube was charged with HOBt (8 mg), benzoic acid (7 mg) and EDC (11 mg) in DMF (0.6 mL) and then agitated at rt. for 15 min. After this time, a solution of (2R)-2-amino-1-(4-(4-chlorophenyl)piperidin-1-yl)-3-methyl-pentan-1-one hydrochloride (16 mg) in DIEA (38 μL) and DMF (187 μL) was added. Upon completion of addition, the reaction mixture was shaken overnight at rt. At the conclusion of this period, the resulting solution was diluted with MeOH and purified by preparative LC-MS to provide Example 150. MS found: $(M+H)^+=414$.

Examples 151 to 177

Examples 151 to 177, as described in Table 4, were prepared in a similar manner as described for the preparation of Example 150. In the synthesis of Examples 151 to 177, the appropriate acid needed to produce the product listed was used in place of the benzoic acid used in Example 150. The data in the "MS" column represents the values observed for the $(M+H)^+$ ions in MS experiments.

TABLE 4

| Example | Structure | MS | Chemical Name |
| --- | --- | --- | --- |
| 151 | 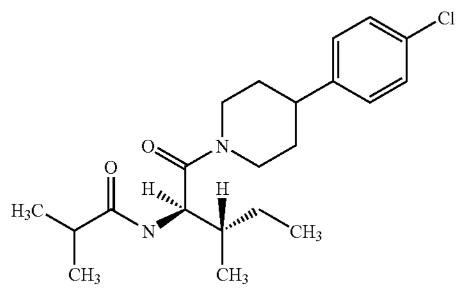 | 380 | N-((2R)-1-(4-(4-chlorophenyl)piperidin-1-yl)-3-methyl-1-oxopentan-2-yl)isobutyramide |
| 152 | 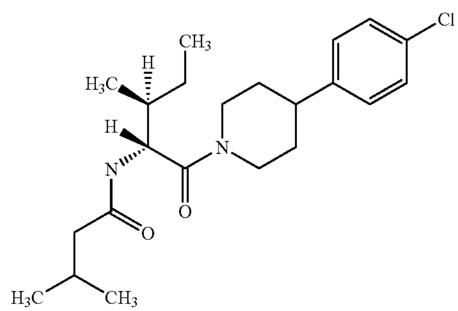 | 394 | N-((2R)-1-(4-(4-chlorophenyl)piperidin-1-yl)-3-methyl-1-oxopentan-2-yl)-3-methylbutanamide |
| 153 | 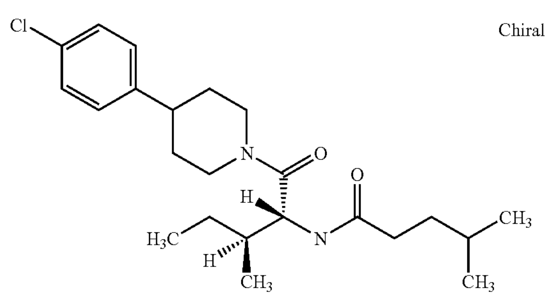 | 408 | N-((2R)-1-(4-(4-chlorophenyl)piperidin-1-yl)-3-methyl-1-oxopentan-2-yl)-4-methylpentanamide |

TABLE 4-continued

| Example | Structure | MS | Chemical Name |
| --- | --- | --- | --- |
| 154 | Chiral | 428 | N-((2R)-1-(4-(4-chlorophenyl)piperidin-1-yl)-3-methyl-1-oxopentan-2-yl)-2-phenylacetamide |
| 155 | Chiral | 442 | N-((2R)-1-(4-(4-chlorophenyl)piperidin-1-yl)-3-methyl-1-oxopentan-2-yl)-3-phenylpropanamide |
| 156 | Chiral | 490 | N-((2R)-1-(4-(4-chlorophenyl)piperidin-1-yl)-3-methyl-1-oxopentan-2-yl)-2-phenylbenzamide |
| 157 | Chiral | 490 | N-((2R)-1-(4-(4-chlorophenyl)piperidin-1-yl)-3-methyl-1-oxopentan-2-yl)-3-phenylbenzamide |
| 158 | Chiral | 471 | N-((2R)-1-(4-(4-chlorophenyl)piperidin-1-yl)-3-methyl-1-oxopentan-2-yl)benzo[d]thiazole-2-carboxamide |

TABLE 4-continued

| Example | Structure | MS | Chemical Name |
|---|---|---|---|
| 159 | Chiral | 391.6 | |
| 160 | Chiral | 405.6 | |
| 161 | Chiral | 414.5 | |
| 162 | Chiral | 419.6 | |
| 163 | Chiral | 427.5 | |

TABLE 4-continued

| Example | Structure | MS | Chemical Name |
|---|---|---|---|
| 164 | 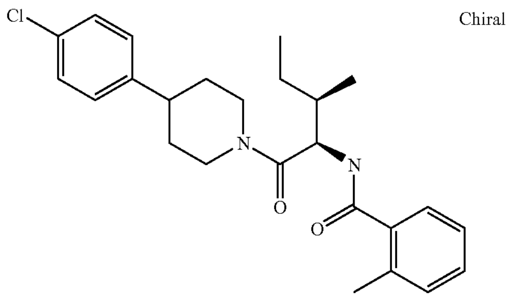 | 427.5 | |
| 165 | 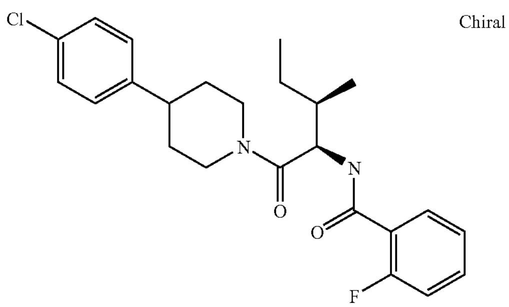 | 431.5 | |
| 166 | 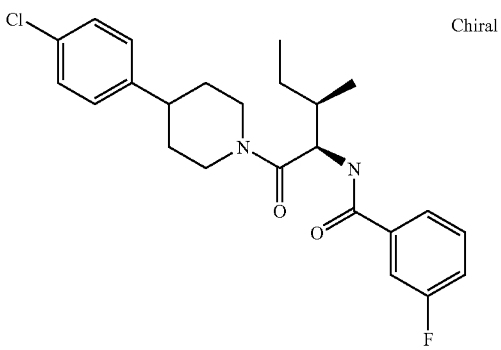 | 431.5 | |
| 167 | 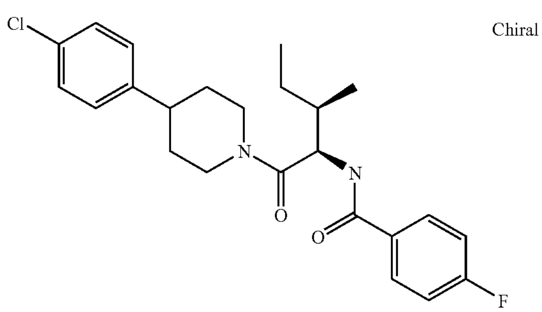 | 431.5 | |
| 168 | 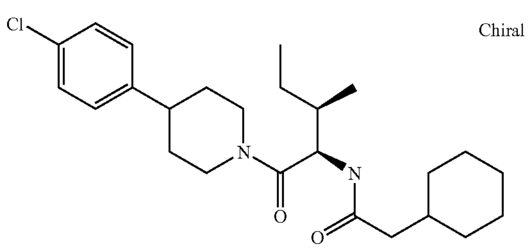 | 433.6 | |

All structures labeled Chiral.

TABLE 4-continued

| Example | Structure | MS | Chemical Name |
|---|---|---|---|
| 169 | Chiral | 445.5 | |
| 170 | Chiral | 445.5 | |
| 171 | Chiral | 445.5 | |
| 172 | Chiral | 447.5 | |
| 173 | Chiral | 449.5 | |

TABLE 4-continued

| Example | Structure | MS | Chemical Name |
|---------|-----------|------|---------------|
| 174 | Chiral | 449.5 | |
| 175 | Chiral | 456.5 | |
| 176 | Chiral | 464.5 | |
| 177 | Chiral | 465.5 | |

Example 178

(R)—N-(2-(4-(4-Chlorophenyl)piperidin-1-yl)-1-cyclohexyl-2-oxoethyl)benzamide

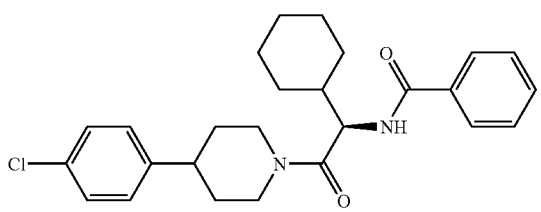

A reaction tube was charged with HOBt (8 mg), benzoic acid (7 mg) and EDC (11 mg) in DMF (0.6 mL) and then allowed to agitate at rt. for 15 min. After this time, a solution of (R)-2-amino-1-(4-(4-chlorophenyl)piperidin-1-yl)-2-cyclohexylethanone hydrochloride (16 mg) in DIEA (38 µL) and DMF (187 µL) was added. Upon completion of addition, the reaction mixture and was shaken overnight at rt. At the conclusion of this period, the resulting solution was diluted with MeOH and purified by preparative LC-MS to provide Example 178. MS found: (M+H)$^+$=440.

Example 179

(R)—N-(2-(4-(4-Chlorophenyl)piperidin-1-yl)-1-cyclohexyl-2-oxoethyl)-4-methylpentanamide

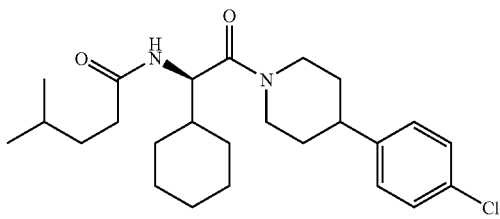

Example 179 was prepared, substituting 4-methylpentanoic acid for benzoic acid, in a similar manner as described for the preparation of Example 178. MS found: (M+H)$^+$=434.

Example 180

N-(1-(4-(4-chlorophenyl)piperidin-1-yl)-1-oxopentan-2-yl)benzamide

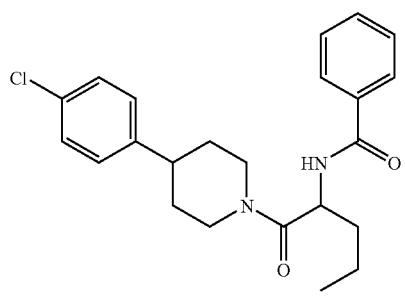

A reaction tube was charged with HOBt (13 mg), benzoic acid (9 mg) and EDC (18 mg) in DMF (0.75 mL) and then agitated at rt. for 15 min. A solution of 2-amino-1-(4-(4-chlorophenyl)piperidin-1-yl)pentan-1-one hydrochloride (20 mg) in DIEA (65 µL) and DMF (185 µL) was added to the reaction tube, and the resulting mixture was shaken overnight at rt. After this time, the resulting solution was diluted with MeOH and purified by preparative LC-MS to provide Example 180. MS found: (M+H)$^+$=400.

Examples 181 to 186

Examples 181 to 186, as described in Table 5, were prepared in a similar manner as described for the preparation of Example 180. In the synthesis of Examples 181 to 186, the appropriate acid needed to produce the product listed was used in place of the benzoic acid used in Example 180. The data in the "MS" column represents the values observed for the (M+H)$^+$ ions in MS experiments.

TABLE 5

| Example | Structure | MS | Chemical Name |
| --- | --- | --- | --- |
| 181 | 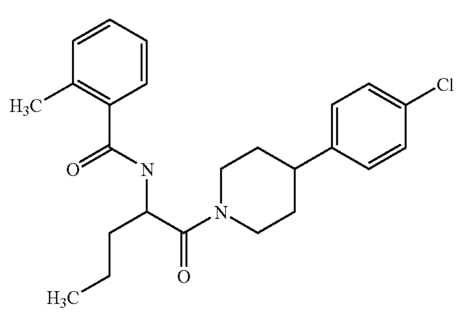 | 414 | N-(1-(4-(4-chlorophenyl)piperidin-1-yl)-1-oxopentan-2-yl)-2-methylbenzamide |

TABLE 5-continued

| Example | Structure | MS | Chemical Name |
|---------|-----------|-----|---------------|
| 182 | 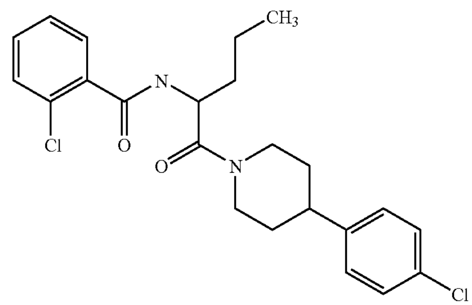 | 434 | 2-chloro-N-(1-(4-(4-chlorophenyl)piperidin-1-yl)-1-oxopentan-2-yl)benzamide |
| 183 | 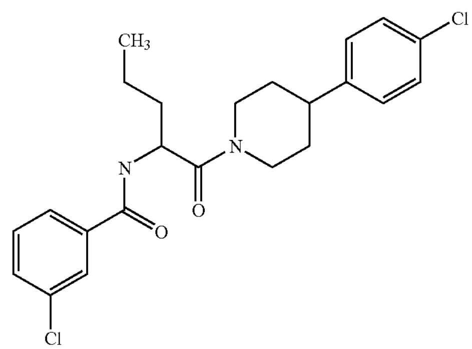 | 434 | 3-chloro-N-(1-(4-(4-chlorophenyl)piperidin-1-yl)-1-oxopentan-2-yl)benzamide |
| 184 | 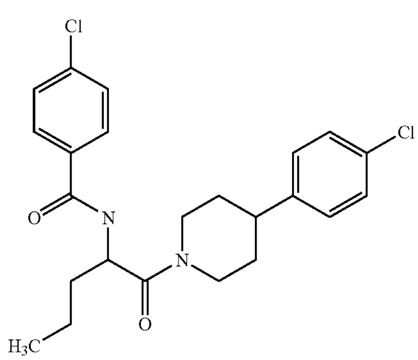 | 434 | 4-chloro-N-(1-(4-(4-chlorophenyl)piperidin-1-yl)-1-oxopentan-2-yl)benzamide |

TABLE 5-continued

| Example | Structure | MS | Chemical Name |
|---|---|---|---|
| 185 | 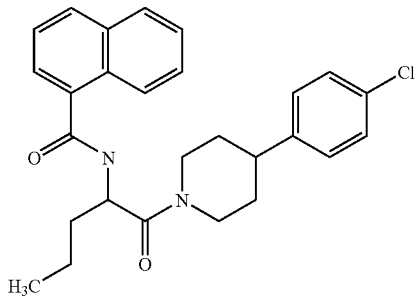 | 450 | N-(1-(4-(4-chlorophenyl)piperidin-1-yl)-1-oxopentan-2-yl)-1-naphthamide |
| 186 | 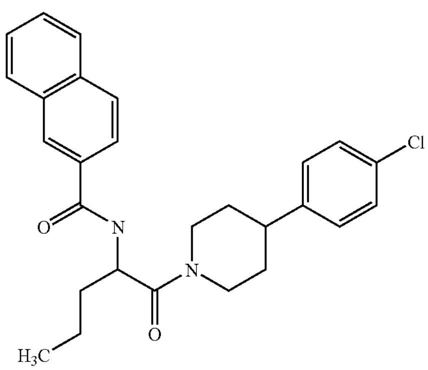 | 450 | N-(1-(4-(4-chlorophenyl)piperidin-1-yl)-1-oxopentan-2-yl)-2-naphthamide |

Example 187

N-(1-(4-(4-Chlorophenyl)piperidin-1-yl)-4-methyl-1-oxopentan-2-yl)benzamide

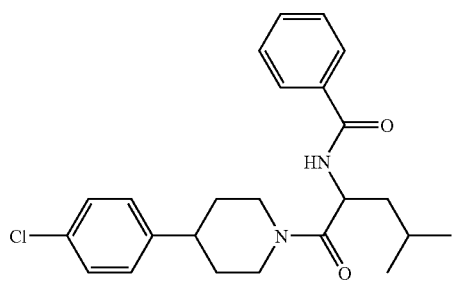

A reaction tube was charged with HOBt (13 mg), benzoic acid (9 mg) and EDC (18 mg) in DMF (0.75 mL) and then agitated for 15 min. After this time, a solution of 2-amino-1-(4-(4-chlorophenyl)piperidin-1-yl)-4-methylpentan-1-one hydrochloride (21 mg) in DIEA (65 µL) and DMF (185 µL) was added to the reaction tube. After the reaction mixture was shaken overnight at rt., the resulting solution was diluted with MeOH and purified by preparative LC-MS to provide Example 187.

MS found: (M+H)$^+$=414.

Examples 188 to 192

Examples 188 to 192, as described in Table 6, were prepared in a similar manner as described for the preparation of Example 187. In the synthesis of Examples 188 to 192, the appropriate acid needed to produce the product listed was used in place of the benzoic acid used in Example 187. The data in the "MS" column represents the values observed for the (M+H)$^+$ ions in MS experiments.

TABLE 6

| Example | Structure | MS | Chemical Name |
|---------|-----------|-----|---------------|
| 188 | 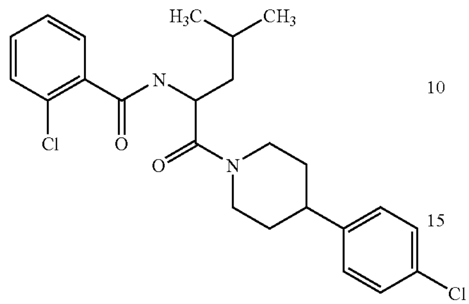 | 448 | 2-chloro-N-(1-(4-(4-chlorophenyl)piperidin-1-yl)-4-methyl-1-oxopentan-2-yl)benzamide |
| 189 | 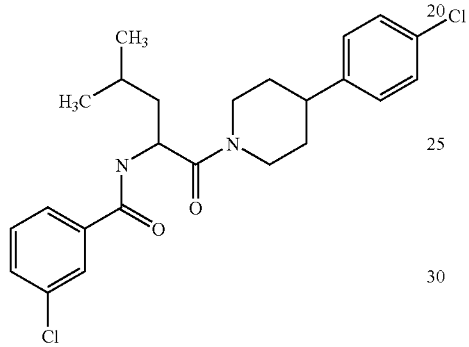 | 448 | 3-chloro-N-(1-(4-(4-chlorophenyl)piperidin-1-yl)-4-methyl-1-oxopentan-2-yl)benzamide |
| 190 | 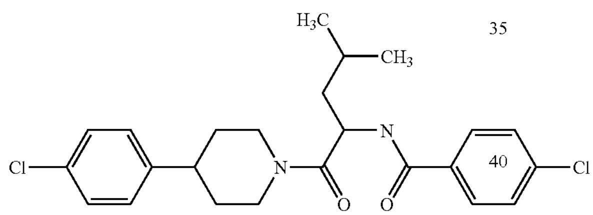 | 448 | 4-chloro-N-(1-(4-(4-chlorophenyl)piperidin-1-yl)-4-methyl-1-oxopentan-2-yl)benzamide |
| 191 | 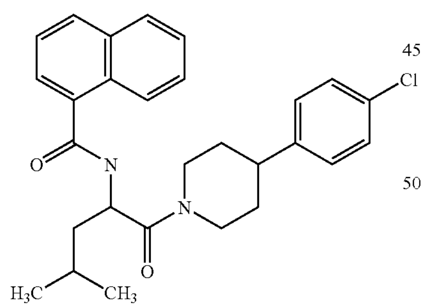 | 464 | N-(1-(4-(4-chlorophenyl)piperidin-1-yl)-4-methyl-1-oxopentan-2-yl)-1-naphthamide |
| 192 | 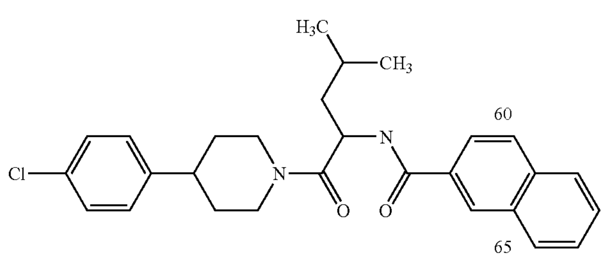 | 464 | N-(1-(4-(4-chlorophenyl)piperidin-1-yl)-4-methyl-1-oxopentan-2-yl)-2-naphthamide |

Example 193

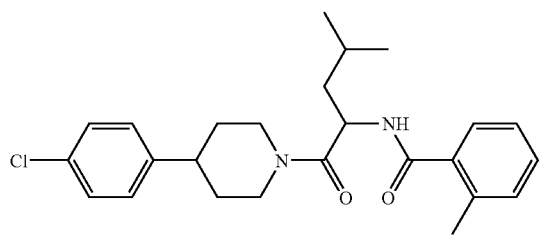

Example 193 was prepared in a similar manner as described for the preparation of Example 187. In the synthesis of Example 193, the appropriate acid needed to produce the product was used in place of the benzoic acid used in Example 187. MS found: (M+H)$^+$=428.

Example 194

N-(1-(4-(4-chlorophenyl)piperidin-1-yl)-3,3-dimethyl-1-oxobutan-2-yl)benzamide

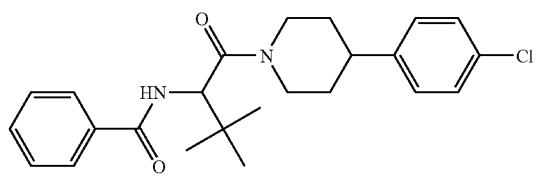

A reaction tube was charged with HOBt (13 mg), benzoic acid (9 mg) and EDC (18 mg) in DMF (0.75 mL) and then agitated for 15 min. After this time, a solution of 2-amino-1-(4-(4-chlorophenyl)piperidin-1-yl)-3,3-dimethylbutan-1-one hydrochloride (21 mg) in DIEA (65 μL) and DMF (185 μL) was added to the tube and the reaction mixture was shaken overnight at rt. At the conclusion of this period, the resulting solution was diluted with MeOH and purified by preparative LC-MS to provide Example 194. MS found: (M+H)$^+$=414.

Examples 195 to 199

Examples 195 to 199, as described in Table 7, were prepared in a similar manner as described for the preparation of Example 194. In the synthesis of Examples 195 to 199, the appropriate acid needed to produce the product listed was used in place of the benzoic acid used in Example 194. The data in the "MS" column represents the values observed for the (M+H)$^+$ ions in MS experiments.

TABLE 7

| Example | Structure | MS | Chemical Name |
|---|---|---|---|
| 195 | 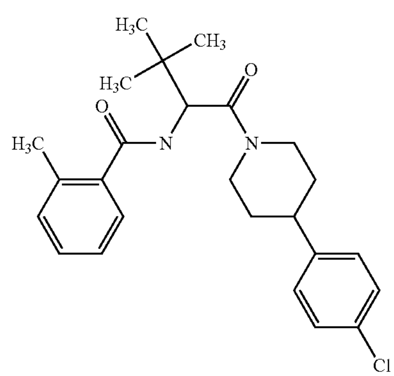 | 428 | N-(1-(4-(4-chlorophenyl)piperidin-1-yl)-3,3-dimethyl-1-oxobutan-2-yl)-2-methylbenzamide |
| 196 | 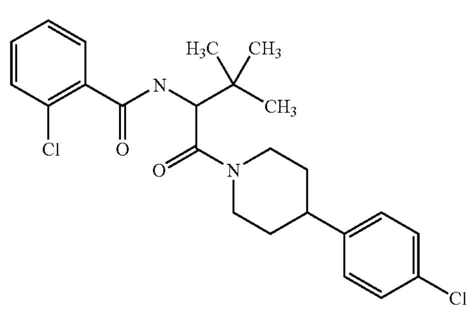 | 448 | 2-chloro-N-(1-(4-(4-chlorophenyl)piperidin-1-yl)-3,3-dimethyl-1-oxobutan-2-yl)benzamide |

TABLE 7-continued
| Example | Structure | MS | Chemical Name |
|---------|-----------|-----|---------------|
| 197 | 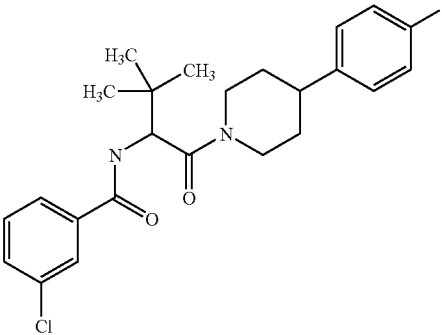 | 448 | 3-chloro-N-(1-(4-(4-chlorophenyl)piperidin-1-yl)-3,3-dimethyl-1-oxobutan-2-yl)benzamide |
| 198 | 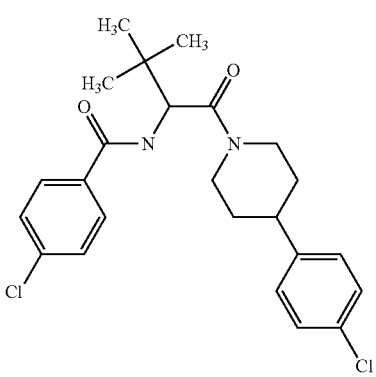 | 448 | 4-chloro-N-(1-(4-(4-chlorophenyl)piperidin-1-yl)-3,3-dimethyl-1-oxobutan-2-yl)benzamide |
| 199 | 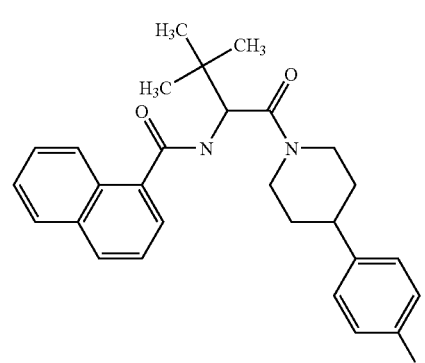 | 464 | N-(1-(4-(4-chlorophenyl)piperidin-1-yl)-3,3-dimethyl-1-oxobutan-2-yl)-1-naphthamide |

Example 200

N-(1-(4-(4-Chlorophenyl)piperidin-1-yl)-3-methyl-1-oxobutan-2-yl)(phenyl)methanesulfonamide

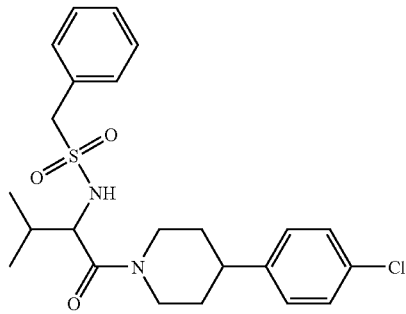

A reaction tube was charged with benzylsulfonyl chloride (14 mg), DIEA (50 µL) and 2-amino-1-(4-(4-chlorophenyl)piperidin-1-yl)-3-methylbutan-1-one hydrochloride (20 mg) in DCM (0.3 mL). The reaction mixture was shaken overnight at rt. At the conclusion of this period, the resulting solution was diluted with MeOH and purified by preparative LC-MS to provide Example 200. MS found: (M+H)$^+$=450.

Example 201

(R)-1-(1-(4-(4-Chlorophenyl)piperidin-1-yl)-3-methyl-1-oxobutan-2-yl)-3-phenylurea

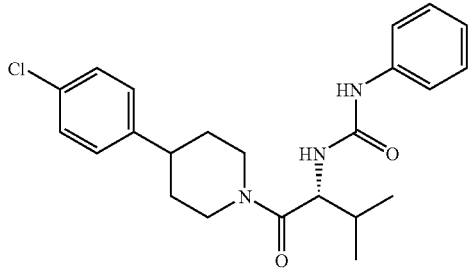

A reaction tube was charged with phenyl isocyanate (12 mg), (R)-2-amino-1-(4-(4-chlorophenyl)piperidin-1-yl)-3-methylbutan-1-one hydrochloride (17 mg) and 1,4-dioxane (0.75 mL). The reaction mixture was shaken overnight at rt. After this time, the resulting solution was diluted with MeOH and purified by preparative LC-MS to provide Example 201. MS found: (M+H)$^+$=429.

Examples 202 to 206

Examples 202 to 206, as described in Table 8, were prepared in a similar manner as described for the preparation of Example 201. In the synthesis of Examples 202 to 206, the appropriate isocyanate needed to produce the product listed was used in place of the isocyanate used in Example 201. The data in the "MS" column represents the values observed for the (M+H)$^+$ ions in MS experiments.

TABLE 8

| Example | Structure | | MS | Chemical Name |
|---|---|---|---|---|
| 202 | (structure shown) | Chiral | 407 | (R)-1-(1-(4-(4-chlorophenyl)piperidin-1-yl)-3-methyl-1-oxobutan-2-yl)-3-cyclopentylurea |
| 203 | (structure shown) | Chiral | 433 | (R)-1-(1-(4-(4-chlorophenyl)piperidin-1-yl)-3-methyl-1-oxobutan-2-yl)-3-(2-fluorophenyl)urea |

TABLE 8-continued

| Example | Structure | MS | Chemical Name |
|---|---|---|---|
| 204 | 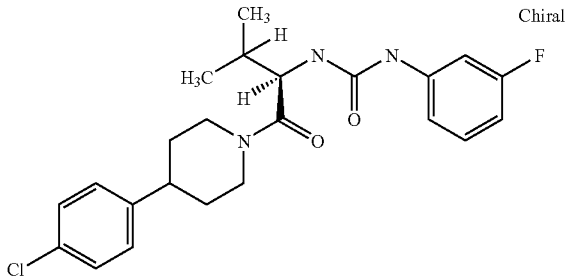 | Chiral 433 | (R)-1-(1-(4-(4-chlorophenyl)piperidin-1-yl)-3-methyl-1-oxobutan-2-yl)-3-(3-fluorophenyl)urea |
| 205 | 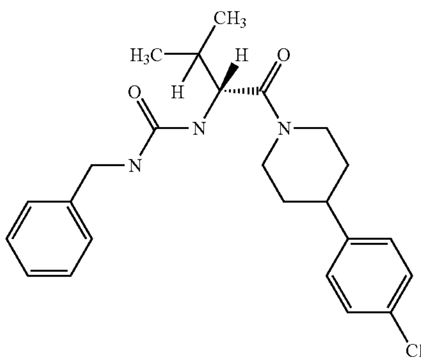 | Chiral 415 | (R)-1-benzyl-3-(1-(4-(4-chlorophenyl)piperidin-1-yl)-3-methyl-1-oxobutan-2-yl)urea |
| 206 | 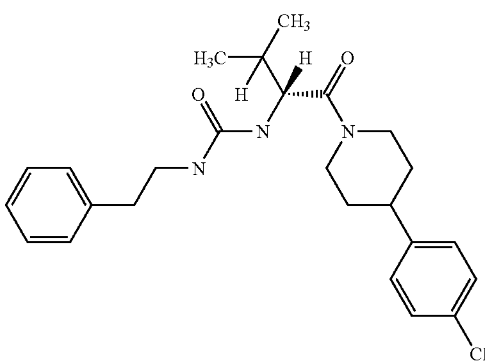 | Chiral 443 | (R)-1-(1-(4-(4-chlorophenyl)piperidin-1-yl)-3-methyl-1-oxobutan-2-yl)-3-phenethylurea |

Example 207

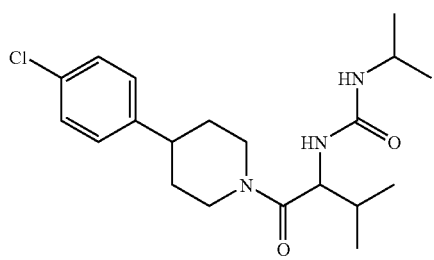

Example 207 was prepared in a similar manner as described for the preparation of Example 201. In the synthesis of Examples 207, the appropriate isocyanate needed to produce the product was used in place of the isocyanate used in Example 201. MS found: (M+H)$^+$=380.6.

Example 208

N-(1-(4-(4-Chlorophenyl)piperidin-1-yl)-3-methyl-1-oxobutan-2-yl)benzamide

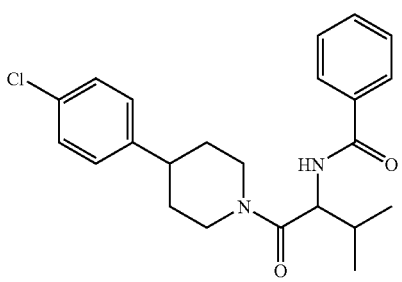

A reaction vessel was charged with benzoyl-DL-valine (24 mg), HOBt (16 mg), DIEA (57 µL), 4-(4-chlorophenyl)piperidine hydrochloride (28 mg) and EDC (23 mg) in DMF (1.5 mL) and then agitated at rt. for 16 h. At the conclusion of this period, the resulting solution was diluted with MeOH and purified by preparative LC-MS to provide Example 208. MS found: (M+H)$^+$=399.

Example 209

N-(1-(4-(4-Chlorophenyl)-4-hydroxypiperidin-1-yl)-3-methyl-1-oxobutan-2-yl)benzamide

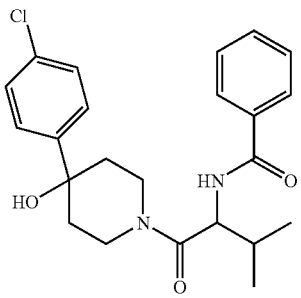

Example 209 was prepared in a similar manner as described for the preparation of Example 208 with the exception that 4-(4-chlorophenyl)-4-hydroxypiperidine was substituted for 4-(4-chlorophenyl)piperidine hydrochloride. MS found: (M+H)$^+$=415.

Example 210

N-(1-(4-(4-Bromophenyl)-4-hydroxypiperidin-1-yl)-3-methyl-1-oxobutan-2-yl)benzamide

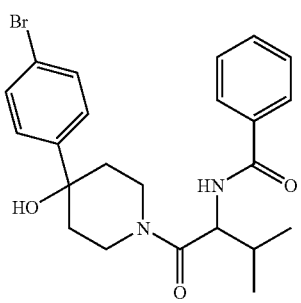

Example 210 was prepared in a similar manner as described for the preparation of Example 208 with exception that 4-(4-bromophenyl)-4-hydroxypiperidine was substituted for 4-(4-chlorophenyl)piperidine hydrochloride. MS found: (M+H)$^+$=460.

Example 211

N-(1-(4-(4-Chlorophenyl)-5,6-dihydropyridin-1(2H)-yl)-3-methyl-1-oxobutan-2-yl)benzamide

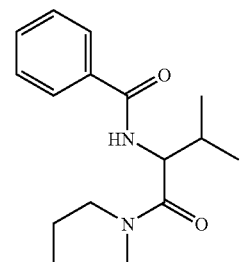

Example 211 was prepared in a similar manner as described for the preparation of Example 208 with the exception that 4-(4-chlorophenyl)-1,2,3,6-tetrahydropyridine hydrochloride was substituted for 4-(4-chlorophenyl)piperidine hydrochloride. MS found: (M+H)$^+$=398.

Example 212

N-(1-(4-(4-Fluorophenyl)piperidin-1-yl)-3-methyl-1-oxobutan-2-yl)benzamide

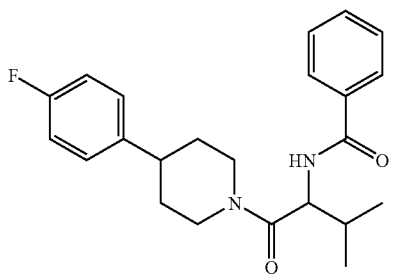

Example 212 was prepared in a similar manner as described for the preparation of Example 208 with the exception that 4-(4-fluorophenyl)piperidine hydrochloride was substituted for 4-(4-chlorophenyl)piperidine hydrochloride, to provide the title compound. MS found: (M+H)$^+$=383.

Example 213

Benzyl 1-(4-(4-chlorophenyl)-4-hydroxypiperidin-1-yl)-3-methyl-1-oxobutan-2-ylcarbamate

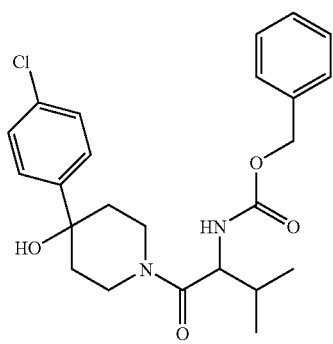

Example 213 was prepared in a similar manner as described for the preparation of Example 208 with the exceptions that Cbz-DL-valine and 4-(4-chlorophenyl)-4-hydroxypiperidine were substituted for benzoyl-DL-valine and 4-(4-chlorophenyl)piperidine hydrochloride, respectively. MS found: (M+H)$^+$=446.

Example 214

(R)-Benzyl 1-(4-(4-chlorophenyl)-4-hydroxypiperidin-1-yl)-1-oxobutan-2-ylcarbamate

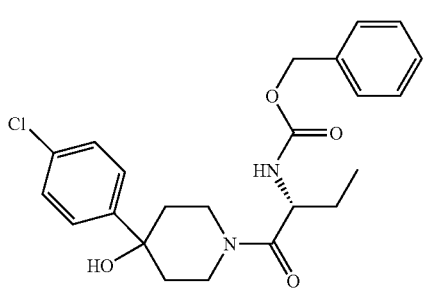

Example 214 was prepared in a similar manner as described for the preparation of Example 208 with the exceptions that Cbz-D-2-aminobutyric acid and 4-(4-chlorophenyl)-4-hydroxypiperidine were substituted for benzoyl-DL-valine and 4-(4-chlorophenyl)piperidine hydrochloride, respectively. MS found: (M+H)$^+$=431.

Example 215

N-(1-(4-(4-Chlorophenyl)-4-hydroxypiperidin-1-yl)-4-methyl-1-oxopentan-2-yl)benzamide

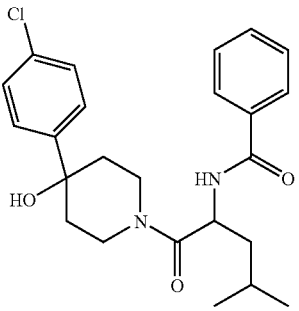

Example 215 was prepared in a similar manner as described for the preparation of Example 208 with the exceptions that benzoyl-DL-leucine and 4-(4-chlorophenyl)-4-hydroxypiperidine were substituted for benzoyl-DL-valine and 4-(4-chlorophenyl)piperidine hydrochloride, respectively. MS found: (M+H)$^+$=430.

Example 216

N-(1-(4-(4-Chlorophenyl)-4-hydroxypiperidin-1-yl)-1-oxopentan-2-yl)benzamide

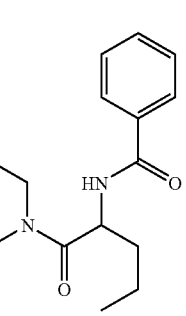

Example 216 was prepared in a similar manner as described for the preparation of Example 208 with the exceptions that benzoyl-2-aminopentanoic acid and 4-(4-chlorophenyl)-4-hydroxypiperidine were substituted for benzoyl-DL-valine and 4-(4-chlorophenyl)piperidine hydrochloride, respectively. MS found: (M+H)$^+$=415.

Example 217

N-(1-(4-(4-Chlorophenyl)-4-hydroxypiperidin-1-yl)-4-(methylthio)-1-oxobutan-2-yl)benzamide

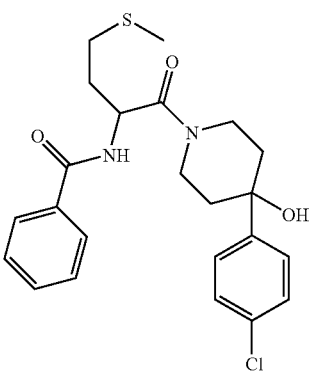

Example 217 was prepared in a similar manner as described for the preparation of Example 208 with the exceptions that benzoyl-DL-methionine and 4-(4-chlorophenyl)-4-hydroxypiperidine were substituted for benzoyl-DL-valine and 4-(4-chlorophenyl)piperidine hydrochloride, respectively. MS found: $(M+H)^+=448$.

Example 218

Benzyl 1-(4-(4-chlorophenyl)-4-hydroxypiperidin-1-yl)-1-oxohexan-2-ylcarbamate

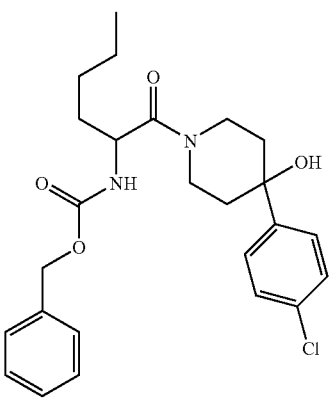

Example 218 was prepared in a similar manner as described for the preparation of Example 208 with the exceptions that Cbz-2-aminohexanoic acid and 4-(4-chlorophenyl)-4-hydroxypiperidine were substituted for benzoyl-DL-valine and 4-(4-chlorophenyl)piperidine hydrochloride, respectively. MS found: $(M+H)^+=460$.

Example 219

(R)-Benzyl 2-(4-(4-chlorophenyl)-4-hydroxypiperidin-1-yl)-1-cyclohexyl-2-oxoethylcarbamate

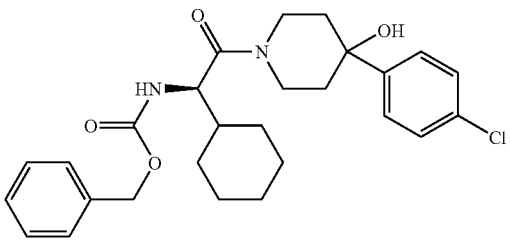

Example 219 was prepared in a similar manner as described for the preparation of Example 208 with the exceptions that Cbz-D-cyclohexylglycine and 4-(4-chlorophenyl)-4-hydroxypiperidine were substituted for benzoyl-DL-valine and 4-(4-chlorophenyl)piperidine hydrochloride, respectively. MS found: $(M+H)^+=486$.

Example 220

N-(1-(4-(4-Fluorophenyl)-4-hydroxypiperidin-1-yl)-3-methyl-1-oxobutan-2-yl)benzamide

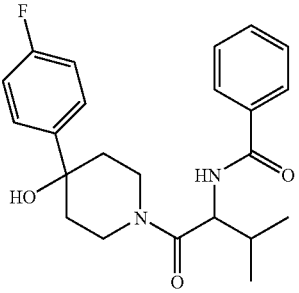

Example 220 was prepared in a similar manner as described for the preparation of Example 208 with the exception that 4-(4-fluorophenyl)-4-hydroxypiperidine was substituted for 4-(4-chlorophenyl)piperidine hydrochloride, to provide the title compound. MS found: $(M+H)^+=399$.

Example 221

3-Chloro-N-(1-(4-(4-chlorophenyl)piperidin-1-yl)-1-oxopropan-2-yl)benzamide

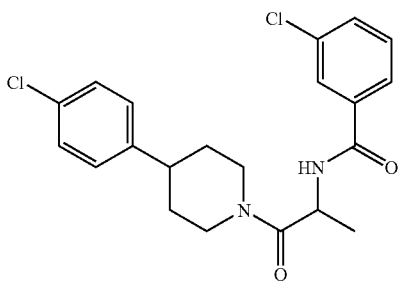

Step 1: Alanine Ester Derivatized Resin

A 250 mL peptide vessel was charged with polystyrene resin functionalized with a 4-formyl-3-methoxyphenyl linker (1.1 mmol/g, 4.7 g) and DMF (50 mL). To this suspension was added DIEA (4.5 mL), DL-alanine ethyl ester hydrochloride (2.0 g), acetic acid (4.3 mL) and sodium triacetoxyborohydride (2.2 g). Following 16 h of shaking at rt. the resin was filtered and washed with solvents as follows: DMF (1×50 mL); 6:3:1 THF/water/acetic acid (2×50 mL); DMF (2×50 mL); THF (2×50 mL); and DCM (2×50 mL) to provide an alanine ester derivatized resin.

Step 2: A Set of Microkans

The alanine ester derivatized resin of Step 1 was loaded into an Irori microkans (20 mg per microkan). A set of 60 microkans were suspended in DMF (200 mL) and then charged with 3-chlorobenzoic acid (3.95 g), HOBt (3.41 g), DIEA (8.8 mL), and N,N'-diisopropylcarbodiimide (3.95 mL). The resulting mixture was shaken at rt for 16 h. After this time, the solvents were removed by filtration and the microkans were washed with DMF (4×200 mL), THF (4×200 mL), and DCM (4×200 mL) to provide a set of microkans.

Step 3: 2-(3-Chlorobenzamido)propanoic acid resin

A set of 180 microkans of Step 2 were added to a mixture of THF (150 mL), 40% tetra-N-butylammonium hydroxide/water (50 mL), and methanol (30 mL). The resulting mixture was shaken at 40° C. for 40 h and then allowed to cool to rt. Once at the prescribed temperature, the solvents were removed by filtration, and the microkans were washed with 8:1:1 THF/water/acetic acid (2×200 mL), THF (3×200 mL), and DCM (3×200 mL). The reaction mixture was checked for completion by treating a small sample of the ethyl 2-(3-chlorobenzamido)propanoate resin with 40% v/v TFA/DCM. Said treatment indicated that the reaction was completed and that the desired product, namely, 2-(3-chlorobenzamido)propanoic acid resin, had been provided. MS found: (M+Na)$^+$=250.

Step 4: Microkans Containing resin-bound 3-chloro-N-(1-(4-(4-chlorophenyl)piperidin-1-yl)-1-oxopropan-2-yl)benzamide A set of 30 microkans of Step 3 was suspended in DMF (80 mL) and treated with HOBt (0.57 g), DIEA (1.57 mL), N,N'-diisopropylcarbodiimide (0.66 mL) and 4-(4-chlorophenyl)piperidine hydrochloride (1.39 g). The resulting microkans were shaken at rt. For 16 h, After this time, the microkans were isolated by filtration and washed with DMF (4×100 mL), THF (3×100 mL), and DCM (3×100 mL) to provide microkans containing resin-bound 3-chloro-N-(1-(4-(4-chlorophenyl)piperidin-1-yl)-1-oxopropan-2-yl)benzamide.

Step 5: Example 221

The microkans containing resin-bound 3-chloro-N-(1-(4-(4-chlorophenyl)piperidin-1-yl)-1-oxopropan-2-yl)benzamide produce in Step 4 were opened and the loose resin was suspended in 30% v/v TFA/DCM. The resulting suspension was stirred at rt. For 1 h. Upon completion of this period, the resin was removed by filtration and the filtrate was concentrated in vacuo to provide an oil. The oil was dissolved in methanol (2 mL) and purified by preparative LC-MS to provide Example 221. MS found: (M+Na)$^+$=427.

Example 222

3-Chloro-N-(1-(4-(4-chlorophenyl)-5,6-dihydropyridin-1(2H)-yl)-1-oxopropan-2-yl)benzamide

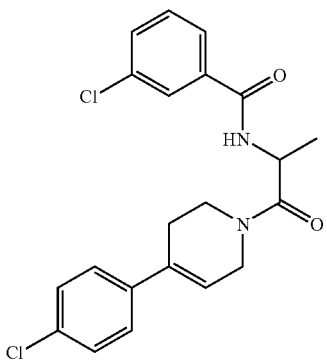

Example 222 was prepared in a similar manner as described for the preparation of Example 221 with the exception that 4-(4-chlorophenyl)-4-hydroxypiperidine was substitute for 4-(4-chlorophenyl)piperidine hydrochloride in Step 4. Example 222 was provided via elimination during Step 5. MS found: (M+H)$^+$=405.

Example 223

4-Chloro-N-(1-(4-(4-chlorophenyl)piperidin-1-yl)-1-oxobutan-2-yl)benzamide

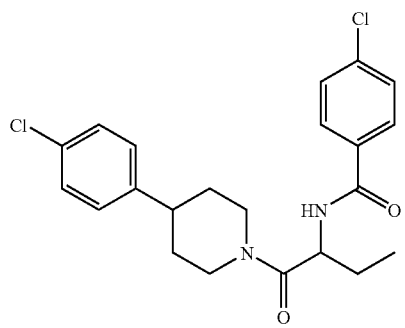

Example 223 was prepared in a similar manner as described for the preparation of Example 221 with the exceptions that 2-aminobutyric acid methyl ester hydrochloride was substituted for DL-alanine ethyl ester hydrochloride in Step 1 and 4-chlorobenzoic acid was substituted for 3-chlorobenzoic acid in Step 2. MS found: (M+H)$^+$=419.

Example 224

4-Chloro-N-(1-(4-(4-chlorophenyl)-5,6-dihydropyridin-1(2H)-yl)-1-oxobutan-2-yl)benzamide

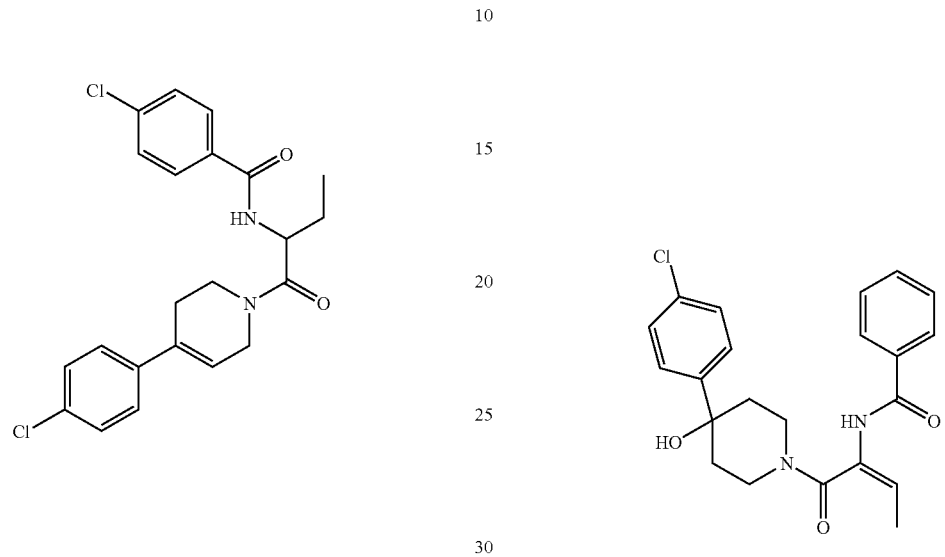

Example 224 was prepared in a similar manner as described for the preparation of Example 221 with the exceptions that 2-aminobutyric acid methyl ester hydrochloride was substituted for DL-alanine ethyl ester hydrochloride in Step 1, 4-chlorobenzoic acid was substituted for 3-chlorobenzoic acid in Step 2, and 4-(4-chlorophenyl)-4-hydroxypiperidine was substituted for 4-(4-chlorophenyl)piperidine hydrochloride in Step 4. Example 224 was provided by elimination during Step 5. MS found: $(M+H)^+=417$.

Example 225

3-Chloro-N-(1-(4-(4-chlorophenyl)piperidin-1-yl)-1-oxobutan-2-yl)benzamide

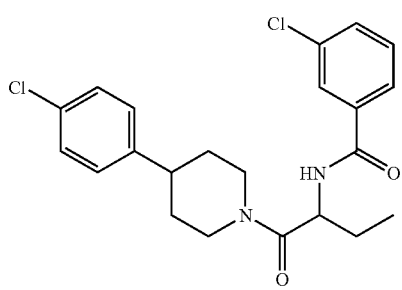

Example 225 was prepared in a similar manner as described for the preparation of Example 221 with the exception that 2-aminobutyric acid methyl ester hydrochloride was substituted for DL-alanine ethyl ester hydrochloride in Step 1. MS found: $(M+H)^+=419$.

Example 226

N-(1-(4-(4-chlorophenyl)-4-hydroxypiperidin-1-yl)-1-oxobut-2-en-2-yl)benzamide

A reaction vessel was charged with N-benzoyl-L-threonine (56 mg), HOBt (42 mg), DIEA (130 μL), 4-(4-chlorophenyl)-4-hydroxypiperidine (66 mg), EDC (60 mg), DMF (1 mL) and 1,2-dichloroethane (1 mL). The reaction mixture was stirred for 16 h at rt and then diluted with methanol (0.5 mL). Upon completion of dilution, the reaction mixture was purified by preparative LC-MS to provide Example 226. MS found: $(M+H)^+=399$.

Examples 227 to 252

Examples 227 to 252, as described in Table 9, were prepared in a similar manner as described for the preparation of Example 150 substituting (2R,3S)-2-amino-1-(4-(4-chlorophenyl)piperidin-1-yl)-3-methylpentan-1-one hydrochloride for (2R)-2-amino-1-(4-(4-chlorophenyl)piperidin-1-yl)-3-methylpentan-1-one hydrochloride. In the synthesis of Examples 227 to 252, the appropriate acid needed to produce the product listed was used in place of the benzoic acid used in Example 150.

TABLE 9

| Example | Structure | MS |
|---|---|---|
| 227 | (Chiral) | 391.6 |
| 228 | (Chiral) | 393.6 |
| 229 | (Chiral) | 405.6 |
| 230 | (Chiral) | 407.6 |
| 231 | (Chiral) | 414.5 |

TABLE 9-continued
| Example | Structure | | MS |
|---|---|---|---|
| 232 | 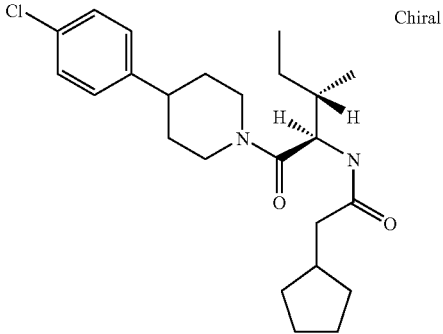 | Chiral | 419.6 |
| 233 | 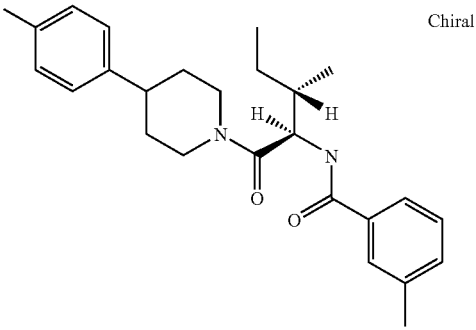 | Chiral | 427.5 |
| 234 | 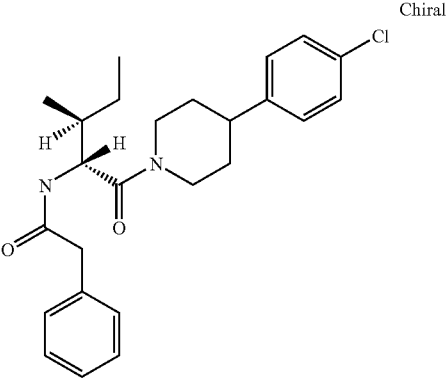 | Chiral | 427.5 |
| 235 | 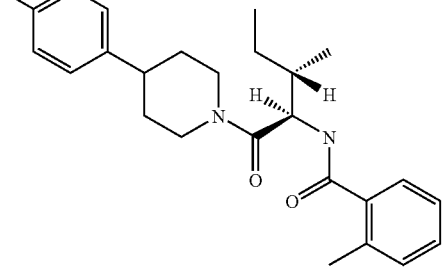 | Chiral | 427.5 |

TABLE 9-continued

| Example | Structure | | MS |
|---|---|---|---|
| 236 | 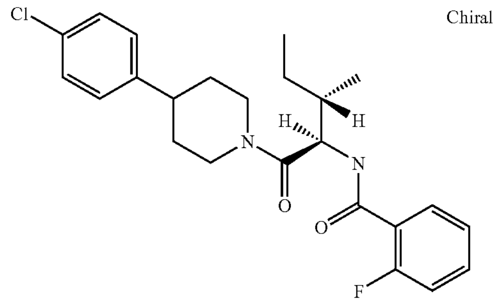 | Chiral | 431.5 |
| 237 | 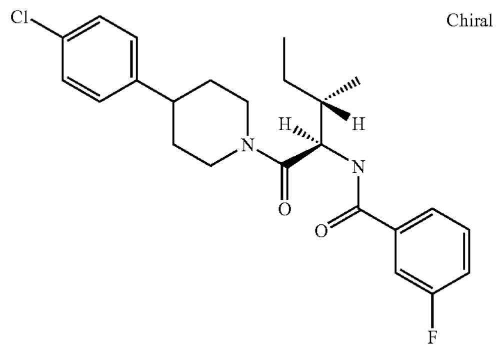 | Chiral | 431.5 |
| 238 | 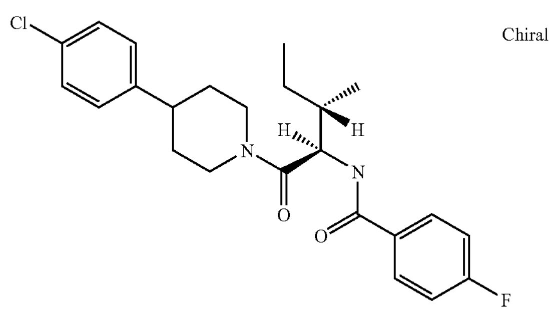 | Chiral | 431.5 |
| 239 | 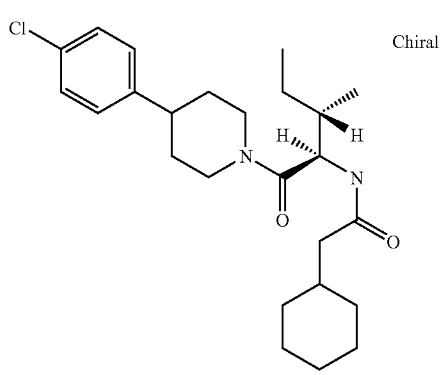 | Chiral | 433.6 |

TABLE 9-continued
| Example | Structure | MS |
|---------|-----------|-----|
| 240 | 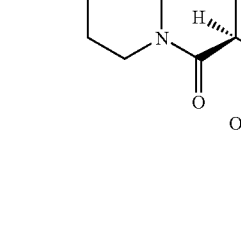 | 445.5 |
| 241 | 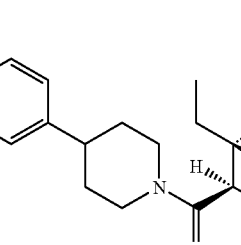 | 445.5 |
| 242 | 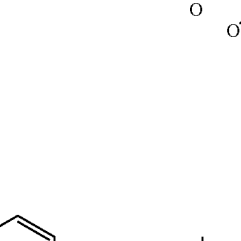 | 445.5 |
| 243 | 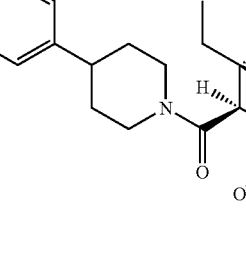 | 447.5 |

TABLE 9-continued

| Example | Structure | MS |
|---|---|---|
| 244 | (Chiral) | 449.5 |
| 245 | (Chiral) | 449.5 |
| 246 | (Chiral) | 456.5 |
| 247 | (Chiral) | 463.5 |

TABLE 9-continued
| Example | Structure | MS |
|---------|-----------|-----|
| 248 | 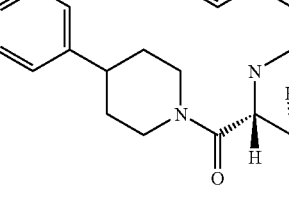 | 464.5 Chiral |
| 249 | 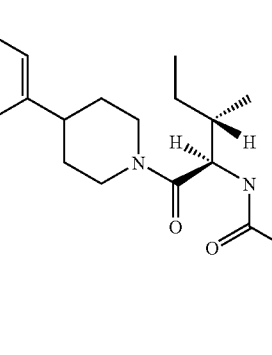 | 465.5 Chiral |
| 250 | 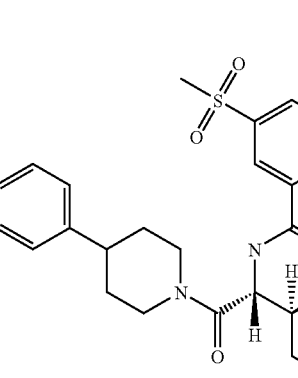 | 491.5 Chiral |
| 251 | 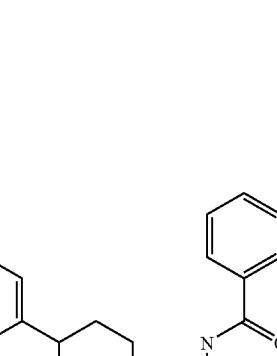 | 505.5 Chiral |

TABLE 9-continued

| Example | Structure | MS |
|---|---|---|
| 252 | [4-(4-chlorophenyl)piperidin-1-yl with isobutyl side chain and N-benzoyl amide] Chiral | 413.4 |

Examples 253 to 271

Examples 253 to 271, as described in Table 10, were prepared in a similar manner as described for the preparation of Example 75 using (R)-2-amino-1-(4-(4-fluorophenyl)piperidin-1-yl)-3-methylbutan-1-one hydrochloride instead of (R)-2-amino-1-(4-(4-chlorophenyl)piperidin-1-yl)-3-methylbutan-1-one hydrochloride. In the synthesis of Examples 253 to 271, the appropriate acid needed to produce the product listed was used in place of the benzoic acid used in Example 75.

TABLE 10

| Example | Structure | MS (M + H) |
|---|---|---|
| 253 | Chiral | 363.2 |
| 254 | Chiral | 375.2 |
| 255 | Chiral | 377.2 |

TABLE 10-continued

| Example | Structure | | MS (M + H) |
|---|---|---|---|
| 256 | (structure) | Chiral | 389.2 |
| 257 | (structure) | Chiral | 397.4 |
| 258 | (structure) | Chiral | 397.2 |
| 259 | (structure) | Chiral | 397.2 |
| 260 | (structure) | Chiral | 401.1 |

TABLE 10-continued
| Example | Structure | | MS (M + H) |
|---|---|---|---|
| 261 | 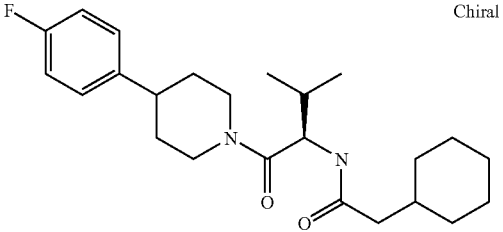 | Chiral | 403.2 |
| 262 | 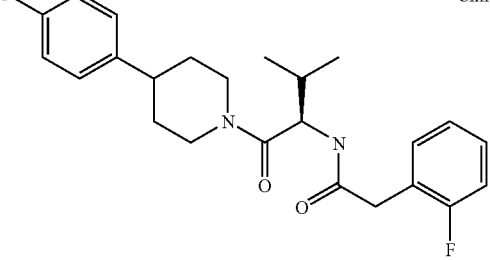 | Chiral | 415.4 |
| 263 | 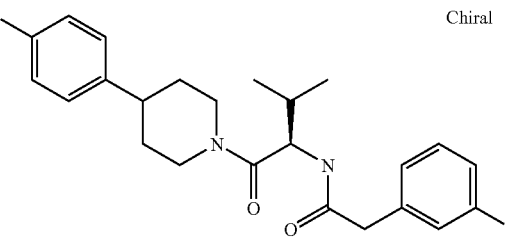 | Chiral | 415.6 |
| 264 | 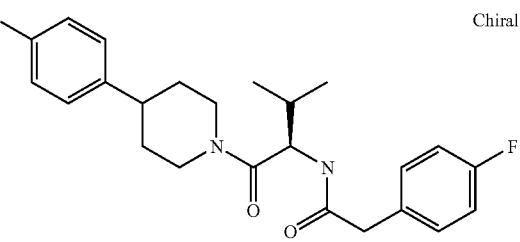 | Chiral | 415.3 |
| 265 | 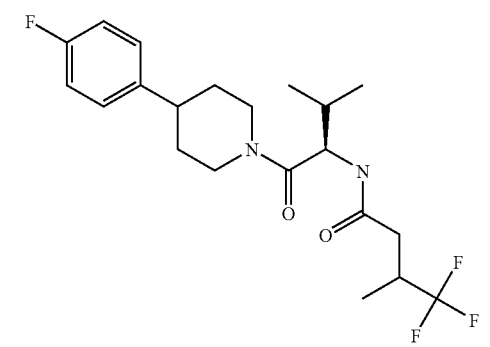 | | 417.3 |

TABLE 10-continued
| Example | Structure | | MS (M + H) |
|---|---|---|---|
| 266 | 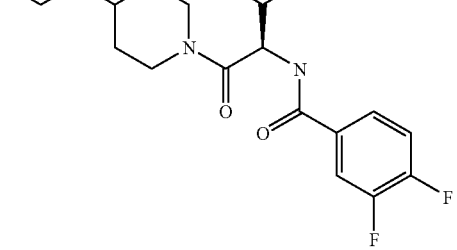 | Chiral | 419.1 |
| 267 | 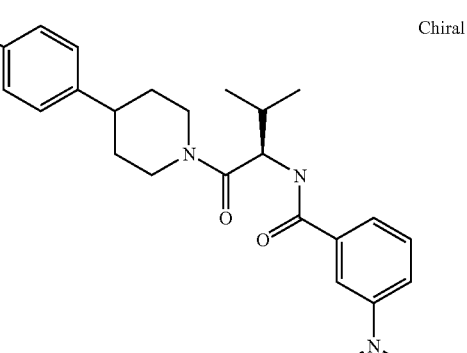 | Chiral | 426.2 |
| 268 | 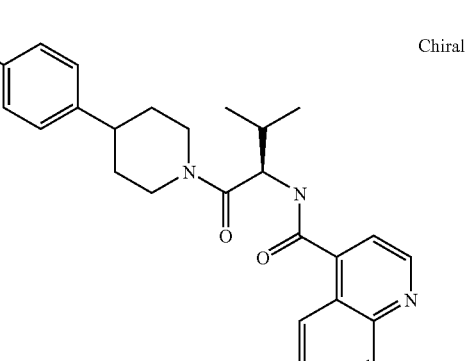 | Chiral | 434.0 |
| 269 | 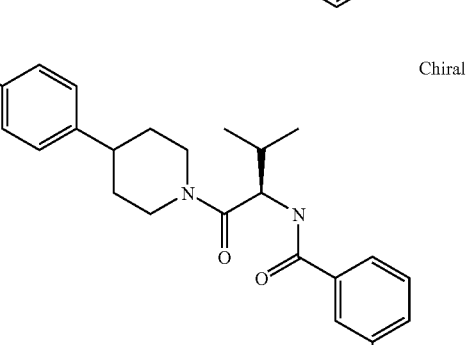 | Chiral | 461.1 |

TABLE 10-continued

| Example | Structure | | MS (M + H) |
|---|---|---|---|
| 270 | 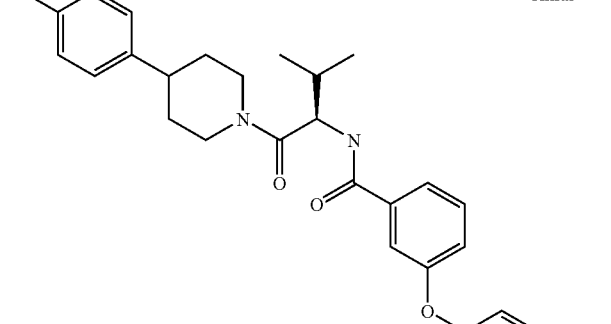 | Chiral | 475.1 |
| 271 | 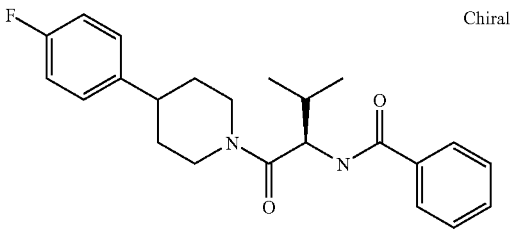 | Chiral | 383.4 |

Examples 272 to 275

Examples 272 to 275, as described in Table 11, were prepared in a similar manner as described for the preparation of Example 201. In the synthesis of Examples 272 to 275, the appropriate chloroformate needed to produce the product listed was used in place of the isocyanate used in Example 201. The data in the "MS" column represents the values observed for the $(M+H)^+$ ions in MS experiments.

TABLE 11

| Example | Structure | MS |
|---|---|---|
| 272 | 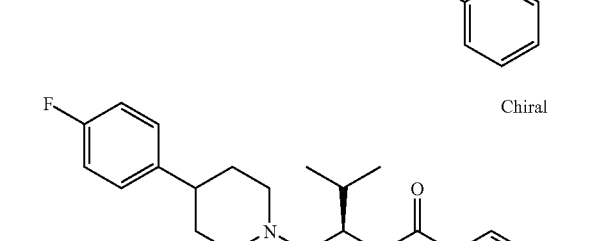 | 395.60 |

TABLE 11-continued

| Example | Structure | MS |
|---|---|---|
| 273 | 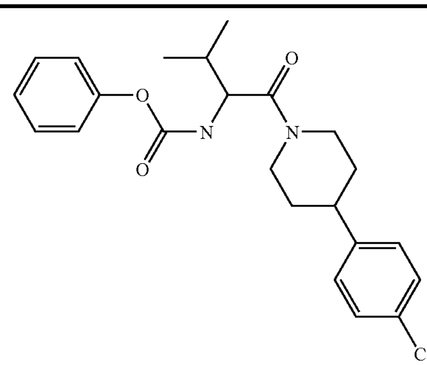 | 415.50 |
| 274 | 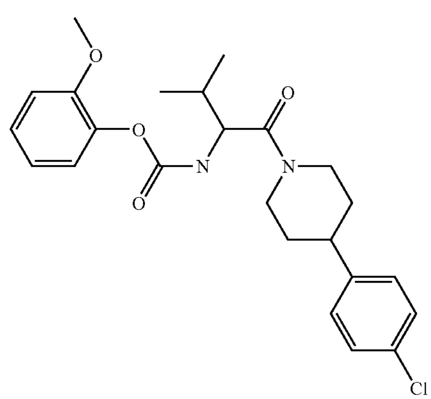 | 445.50 |

TABLE 11-continued

| Example | Structure | MS |
|---|---|---|
| 275 | 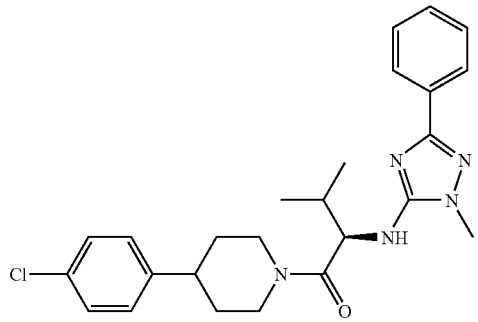 | 429.50 |

Example 276

(R)-1-(4-(4-chlorophenyl)piperidin-1-yl)-3-methyl-
2-(1-methyl-3-phenyl-1H-1,2,4-triazol-5-ylamino)
butan-1-one

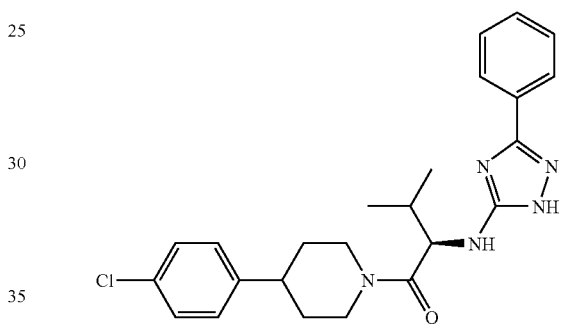

Step 1: (R)—N-(1-(4-(4-chlorophenyl)piperidin-1-yl)-3-methyl-1-oxobutan-2-ylcarbamothioyl)benzamide

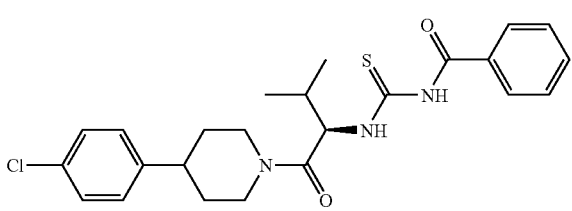

To a solution of (R)-2-Amino-1-(4-(4-chlorophenyl)piperidin-1-yl)-3-methylbutan-1-one hydrochloride (250 mg, 0.75 mmol) in DCM (2 mL) was added DIEA (175 µL, 1 mmol) followed by the dropwise addition of benzoylisothiocyanate (106 µL, 0.78 mmol). The reaction was stirred for 2 h at rt., acidified with 1 N aqueous HCl solution to pH 3 and then extracted with Et₂O (3×10 mL). The extracts were combined, washed sequentially with sat. aqueous NaHCO₃ solution (1×10 mL) and sat. aqueous NaCl solution (1×10 mL), dried (MgSO₄), and the solvent removed to give (R)—N-(1-(4-(4-chlorophenyl)piperidin-1-yl)-3-methyl-1-oxobutan-2-ylcarbamothioyl)benzamide (m/z, 458, M+1) as an oil (300 mg) in greater than 90% HPLC purity.

Step 2: (R,Z)-methyl N'-benzoyl-N-(1-(4-(4-chlorophenyl)piperidin-1-yl)-3-methyl-1-oxobutan-2-yl)carbamimidothioate

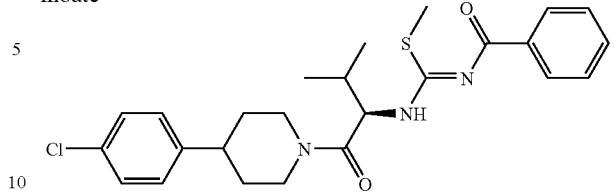

To a solution of (R)—N-(1-(4-(4-chlorophenyl)piperidin-1-yl)-3-methyl-1-oxobutan-2-ylcarbamothioyl)benzamide (300 mg, crude) in CH₃CN (2 mL) was added K₂CO₃ (275 mg, 2 mmol) followed by MeI (75 µL, 2 mmol). The reaction was stirred for 4 h at rt., diluted with Et₂O (10 mL) and the solids were filtered through a plug of celite. The filtrate was condensed in vacuo to give (R,Z)-methyl N'-benzoyl-N-(1-(4-(4-chlorophenyl)piperidin-1-yl)-3-methyl-1-oxobutan-2-yl)carbamimidothioate (300 mg, m/z 473, M+1) as a foam, which was used in subsequent steps without purification.

Step 3: (R)-1-(4-(4-chlorophenyl)piperidin-1-yl)-3-methyl-2-(3-phenyl-1H-1,2,4-triazol-5-ylamino)butan-1-one

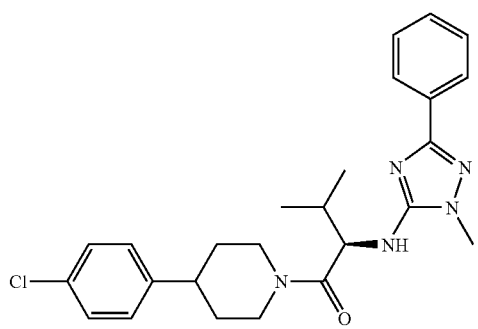

(R,Z)-Methyl N'-benzoyl-N-(1-(4-(4-chlorophenyl)piperidin-1-yl)-3-methyl-1-oxobutan-2-yl)carbamimidothioate (47 mg, 0.1 mmol) was dissolved in THF (0.5 mL) and treated with anhydrous hydrazine (10 µL, 0.3 mmol). The reaction was stirred at rt. overnight. After this time, the THF was removed in vacuo and the resulting residue was dissolved in methanol and then purified by preparative HPLC to give (R)-1-(4-(4-chlorophenyl)piperidin-1-yl)-3-methyl-2-(3-phenyl-1H-1,2,4-triazol-5-ylamino)butan-1-one (20 mg, 45%). MS found: 438 (M+H).

Step 4: (R)-1-(4-(4-chlorophenyl)piperidin-1-yl)-3-methyl-2-(1-methyl-3-phenyl-1H-1,2,4-triazol-5-ylamino)butan-1-one (R)-1-(4-(4-Chlorophenyl)piperidin-1-yl)-3-methyl-2-(3-phenyl-1H-1,2,4-triazol-5-ylamino)butan-1-one (40 mg, 0.09 mmol) was dissolved in THF (0.5 mL) and then treated with MeNHNH$_2$ (10 µL, excess). The reaction was stirred at rt. overnight. After this time, the THF was removed in vacuo and the remains were taken up in MeOH and then purified by preparative HPLC to give (R)-1-(4-(4-chlorophenyl)piperidin-1-yl)-3-methyl-2-(1-methyl-3-phenyl-1H-1,2,4-triazol-5-ylamino)butan-1-one (18 mg, 47%) as a 90/10 mixture of N$_1$—CH$_3$/N$_2$—CH$_3$ isomers. MS found: 452 (M+H).

Example 277

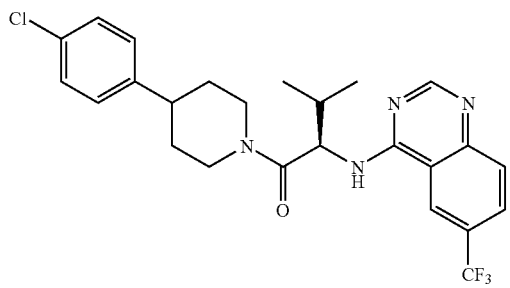

To a solution of 2-amino-1-(4-(4-chlorophenyl)piperidin-1-yl)-3-methylbutan-1-one hydrochloride in ethanol was added TEA (4 eq) and 4-chloro-6-(trifluoromethyl)quinazoline (1.1 eq, see WO 05/021500). Upon completion of addition, the reaction mixture was heated at 100° C. for 30 min. After this time, the reaction mixture was concentrated and purified directly on silica gel (25% EtOAc/hexane to 50% EtOAc/hexane) to give Example 280 in 50% yield. MS found: 491.4, (M+H).

Example 278

1-(4-(4-chlorophenyl)piperidin-1-yl)-3-methyl-2-(5-phenyl-2H-tetrazol-2-yl)butan-1-one

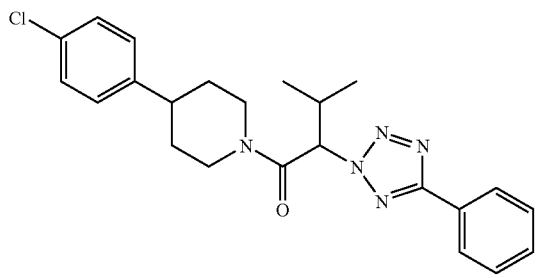

Step 1: 2-bromo-1-(4-(4-chlorophenyl)piperidin-1-yl)-3-methylbutan-1-one

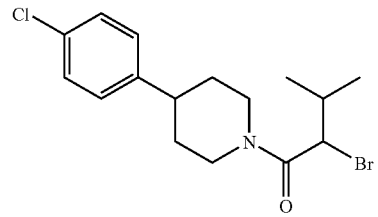

A mixture of 2-bromo-3-methylbutanoic acid (14) (400 mg, 2.2 mmol), 4-(4-chlorophenyl)-piperidine hydrochloride (500 mg, 2.2 mmol), HOBt (300 mg, 2.2 mmol) and EDCI (425 mg, 2.2 mmol) was suspended in DMF (10 mL). DIEA (1.4 mL, 8 mmol) was added and the reaction was stirred overnight. After this time, the reaction was diluted with Et$_2$O (100 mL) and washed sequentially with H$_2$O (2×40 mL); aqueous 1N HCl (2×20 mL); aqueous sat. NaHCO$_3$ (1×20 mL) solution and aqueous sat. NaCl (1×20 mL) solution. The Et$_2$O layer was dried (MgSO$_4$), and the solvents were removed to give 2-bromo-1-(4-(4-chlorophenyl)piperidin-1-yl)-3-methylbutan-1-one (600 mg, 85%) as an impure oil, which was used without purification. MS found: 360 (M+H).

Step 2: 1-(4-(4-chlorophenyl)piperidin-1-yl)-3-methyl-2-(5-phenyl-2H-tetrazol-2-yl)butan-1-one A mixture of 2-bromo-1-(4-(4-chlorophenyl)piperidin-1-yl)-3-methylbutan-1-one (40 mg, 0.11 mmol), K$_2$CO$_3$ (50 mg, 0.36 mmol) and 5-phenyl-2H-tetrazole (15 mg, 0.1 mmol) in CH$_3$CN (1 mL) was heated at 170° C. for 30 min in a microwave reactor. After this time, the reaction was filtered through a plug of celite, diluted with MeOH and purified directly by preparative HPLC to give 1-(4-(4-chlorophenyl)piperidin-1-yl)-3-methyl-2-(5-phenyl-2H-tetrazol-2-yl)butan-1-one (9 mg, 21%) as a solid. MS found: 424 (M+H).

Example 279

1-(4-(4-Chlorophenyl)piperidin-1-yl)-3-methyl-2-(5-phenyl-1,3,4-oxadiazol-2-ylamino)butan-1-one

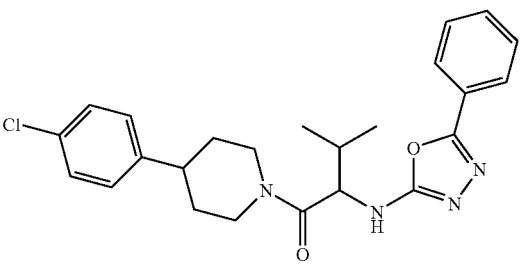

Step 1: Ethyl 2-(2-benzoylhydrazinecarboxamido)-3-methylbutanoate

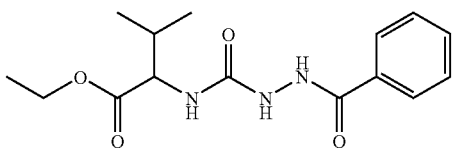

To a solution of benzyolhydrazide (489 mg, 5.0 mmol) in DCM (10 ml) was added dropwise a solution of ethyl-2-cyanato-3-methyl butyrate (0.856 g, 5.0 mmol) in DCM (5 mL). The reaction was stirred at rt for 3 h and the solvent was removed in vacuo to give ethyl 2-(2-benzoylhydrazinecarboxamido)-3-methylbutanoate in greater than >90% purity as judged by LCMS. MS found: 308 (M+H).

Step 2: ethyl 3-methyl-2-(5-phenyl-1,3,4-oxadiazol-2-ylamino)butanoate

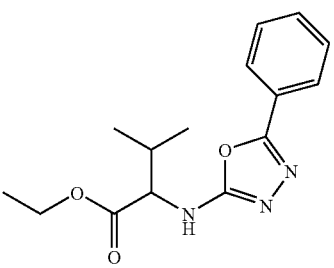

To a solution of crude ethyl 2-(2-benzoylhydrazinecarboxamido)-3-methylbutanoate (assumed 5 mmol) in DCE (10 ml) was added $POCl_3$ (1.5 g, 10 mmol). Upon completion of addition, the reaction was heated at 75-80° C. overnight. After this time, the excess solvent and $POCl_3$ were removed in vacuo. The resulting remains were dissolved in EtOAc (75 ml) and washed sequentially with sat. aqueous $NaHCO_3$ (2×25 mL) solution and sat. aqueous NaCl (25 mL) solution and dried over $MgSO_4$. The solvent was removed in vacuo to give ethyl 3-methyl-2-(5-phenyl-1,3,4-oxadiazol-2-ylamino)butanoate in greater than 90% purity by LCMS; m/z (290, M+1).

Step 3: 3-methyl-2-(5-phenyl-1,3,4-oxadiazol-2-ylamino)butanoic acid

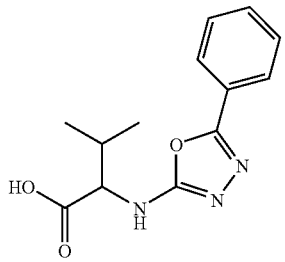

Crude ethyl 3-methyl-2-(5-phenyl-1,3,4-oxadiazol-2-ylamino)butanoate (assumed 5 mmol) was dissolved in a mixture of THF (10 ml) and MeOH (2 ml) and then treated dropwise (exothermic) with aqueous 1 N NaOH (6 mL) solution. The reaction was stirred for 1 h, diluted with $H_2O$ (50 mL) and then extracted with $Et_2O$ (1×50 mL). The aqueous layer was acidified to pH 3 with aqueous 1N HCl solution and then extracted with EtOAc (3×35 mL). The EtOAc extracts were combined, washed with sat. aqueous NaCl solution, dried ($MgSO_4$) and the solvent was removed in vacuo to give 3-methyl-2-(5-phenyl-1,3,4-oxadiazol-2-ylamino)butanoic acid in 50-75% yield over 3 steps in purity >90% as judged by LCMS. MS found: 262 (M+H).

Step 4: 1-(4-(4-Chlorophenyl)piperidin-1-yl)-3-methyl-2-(5-phenyl-1,3,4-oxadiazol-2-ylamino)butan-1-one 3-Methyl-2-(5-phenyl-1,3,4-oxadiazol-2-ylamino)butanoic acid (80 mg, 0.3 mmol), EDCI (65 mg, 0.33 mmol), 4-(4-chlorophenyl)-piperidine hydrochloride (78 mg, 0.33 mmol) and HOBt (40 mg, 0.3 mmol) were combined and suspended in DMF (2 mL). Diisopropylethylamine (210 μL, 1.2 mmol) was added and the reaction was stirred at rt. overnight. After this time, methanol (2 mL) was added to the reaction and the mixture was purified directly by preparative HPLC to give 1-(4-(4-chlorophenyl)piperidin-1-yl)-3-methyl-2-(5-phenyl-1,3,4-oxadiazol-2-ylamino)butan-1-one (60 mg, 30%). MS found: 439 (M+H).

Examples 280 to 287

Examples 280 to 287, as described in Table 12, were prepared in a similar manner as described for the preparation of Example 279. Typical yields ranged from 20-55%.

TABLE 12

| Example | Structure | m/z (M + 1) |
|---|---|---|
| 280 | 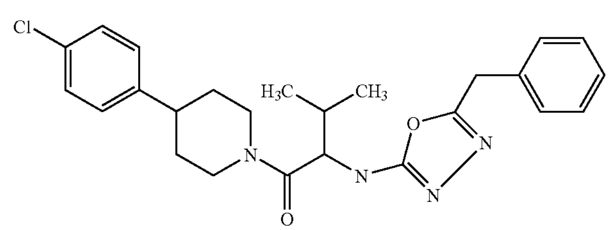 | 453 |

TABLE 12-continued

| Example | Structure | m/z (M + 1) |
|---|---|---|
| 281 | 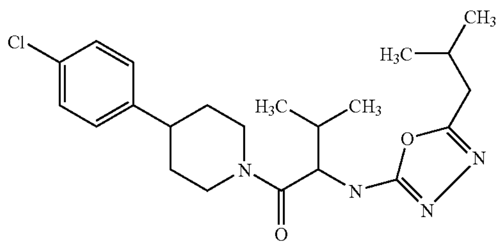 | 419 |
| 282 | 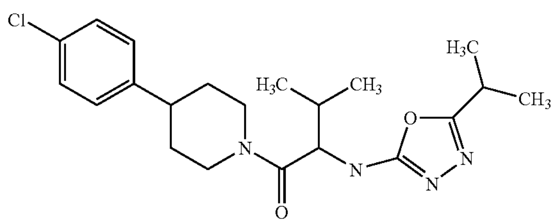 | 405 |
| 283 | 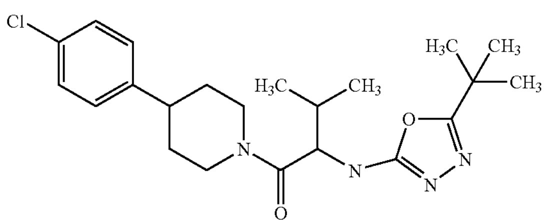 | 419 |
| 284 | 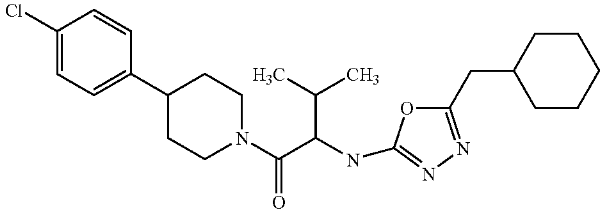 | 459 |
| 285 | 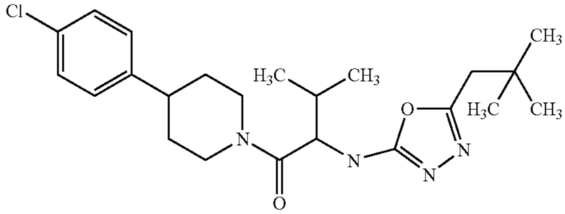 | 433 |
| 286 | 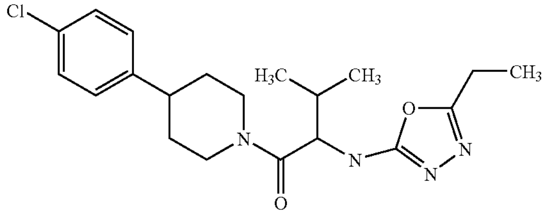 | 391 |

TABLE 12-continued

| Example | Structure | m/z (M + 1) |
|---|---|---|
| 287 | [Structure: 4-(4-chlorophenyl)piperidine coupled via N to C(=O)-CH(iPr)-NH-(5-cyclopropyl-1,3,4-oxadiazol-2-yl)] | 403 |

Example 288

N-(1-(4-(4-chlorophenyl)piperidin-1-yl)-3-methyl-1-oxobut-2-en-2-yl)benzamide

Step 1: 2-benzamido-3-methylbut-2-enoic acid

To a suspension of 3-fluoro-DL-valine (165 mg, 1 mmol) in ethyl acetate (10 mL) was added NaHCO$_3$ (sat. aq., 5 mL) followed by benzoyl chloride (1 mmol). The solution was stirred for 4 h, acidified with 1N HCl, and then extracted into ethyl acetate. The organic extracts were dried over MgSO$_4$, filtered and concentrated to provide the crude 2-benzamido-3-methylbut-2-enoic acid.

Step 2: N-(1-(4-(4-chlorophenyl)piperidin-1-yl)-3-methyl-1-oxobut-2-en-2-yl)benzamide The crude 2-benzamido-3-methylbut-2-enoic acid from Step 1 was coupled with 4-(4-chlorophenyl)piperidine hydrochloride in a similar manner as described for the preparation of Example 75 to provide Example 288, N-(1-(4-(4-chlorophenyl)piperidin-1-yl)-3-methyl-1-oxobut-2-en-2-yl)benzamide. MS found: 397 (M+H).

Example 289

Sodium (R)-(3-(1-(4-(4-chlorophenyl)piperidin-1-yl)-3-methyl-1-oxobutan-2-ylcarbamoyl)phenyl)methanesulfonate

Step 1: (R)-3-(chloromethyl)-N-(1-(4-(4-chlorophenyl)piperidin-1-yl)-3-methyl-1-oxobutan-2-yl)benzamide To a solution of (R)-2-Amino-1-(4-(4-chlorophenyl)piperidin-1-yl)-3-methylbutan-1-one hydrochloride (30.5 mg, 0.092 mmol) in DCM (1 mL) cooled to 0° C. was added DIEA (17.4 µL, 0.1 mmol) followed by 3-chloromethyl benzoyl-chloride (14.2 µL, 0.1 mmol). Upon completion of addition, the reaction mixture was allowed to warm slowly to rt. where it stirred overnight. After this time, the solution was diluted with dichloromethane and quenched by the addition of aqueous NaHCO$_3$. The layers were separated and the organic layer was dried over Na$_2$SO$_4$, filtered, and concentrated to yield a residue. The residue was purified via SiO$_2$ chromatography to give the (R)-3-(chloromethyl)-N-(1-(4-(4-chlorophenyl)piperidin-1-yl)-3-methyl-1-oxobutan-2-yl)benzamide as a clear glassy solid (23.7 mg, 58% yield). MS found: 447.3 (M+), 449.3 (M+2).

Step 2: (R)-3-(chloromethyl)-N-(1-(4-(4-chlorophenyl)piperidin-1-yl)-3-methyl-1-oxobutan-2-yl)benzamide To (R)-3-(chloromethyl)-N-(1-(4-(4-chlorophenyl)piperidin-1-yl)-3-methyl-1-oxobutan-2-yl)benzamide (23.7 mg, 0.053 mmol) was added Na$_2$SO$_3$ (34 mg, 0.27 mmol), water (0.25 mL), and ethanol (0.25 mL). The resulting solution was heated at 100° C. for 3 h. After this time, the solution was cooled to rt. and then concentrated to a residue. The residue was loaded onto a pre-washed C18 cartridge in water (1-2 mL) and the column was then eluted with water followed by 20% acetonitrile/water to provide Example 289, (R)-3-(chloromethyl)-N-(1-(4-(4-chlorophenyl)piperidin-1-yl)-3-methyl-1-oxobutan-2-yl)benzamide (19.2 mg, 70% yield), as a white solid. MS found: 493.3 (M+), 495.3 (M+2).

Example 290

(R)—N-(1-(4-(4-chlorophenyl)piperidin-1-yl)-3-methyl-1-oxobutan-2-yl)-2-(1H-pyrazol-1-yl)acetamide

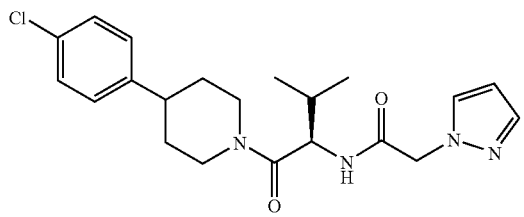

Step 1: (R)-2-chloro-N-(1-(4-(4-chlorophenyl)piperidin-1-yl)-3-methyl-1-oxobutan-2-yl)acetamide

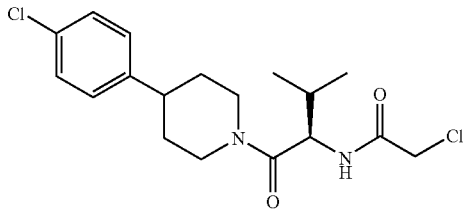

To a solution of (R)-2-amino-1-(4-(4-chlorophenyl)piperidin-1-yl)-3-methylbutan-1-one hydrochloride (340 mg, 1.03 mmol) in DCM (10 mL) cooled to 0° C. was added TEA (144 µL, 1.03 mmol) followed by chloroacetylchloride (82 µL, 1.03 mmol). Upon completion of addition, the reaction mixture was held at 0° C. for 4 h. After this time, an additional aliquot of chloroacetyl chloride (60 µL) was added followed by additional TEA (150 µL). The resulting solution was diluted with dichloromethane (40 mL) and quenched by the addition of aqueous NaHCO$_3$ (25 mL). The layers were separated. The organic layer was dried over Na$_2$SO$_4$, filtered, and concentrated to yield a residue. The residue was purified via SiO$_2$ chromatography (20% to 50% EtOac/heptane) to give (R)-2-chloro-N-(1-(4-(4-chlorophenyl)piperidin-1-yl)-3-methyl-1-oxobutan-2-yl)acetamide as a clear glassy solid (349 mg, 92% yield). MS found: 371.3 (M+), 373.3 (M+2).

Step 2: (R)—N-(1-(4-(4-chlorophenyl)piperidin-1-yl)-3-methyl-1-oxobutan-2-yl)-2-(1H-pyrazol-1-yl)acetamide In a sealed vial were added consecutively (R)-2-chloro-N-(1-(4-(4-chlorophenyl)piperidin-1-yl)-3-methyl-1-oxobutan-2-yl)acetamide (31.4 mg, 0.085 mmol), pyrazole (11.5 mg, 0.17 mmol), K$_2$CO$_3$ (35.2 mg, 0.26 mmol) and acetonitrile (0.4 mL). The reaction mixture was then heated at 75° C. for 36 h, cooled to rt., and the solids were filtered. The filtrate was concentrated and purified by preparative HPLC to provide Example 290, (R)—N-(1-(4-(4-chlorophenyl)piperidin-1-yl)-3-methyl-1-oxobutan-2-yl)-2-(1H-pyrazol-1-yl)acetamide (32 mg, 94% yield) as a white solid. MS found: 403.3 (M+H).

Example 291

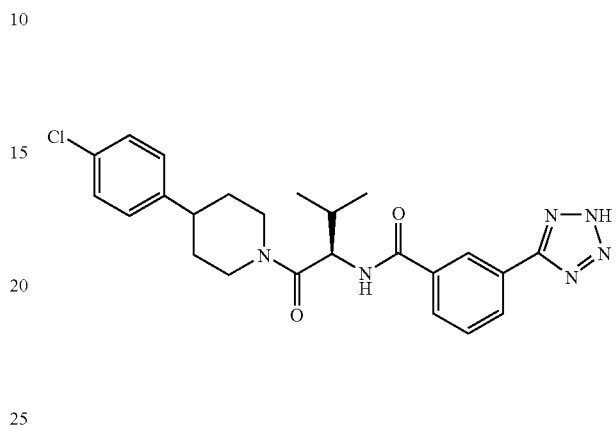

Example 291 was prepared from Example 122 in a similar manner as described by Sharpless and Demko (J. Org. Chem. 2001, 66, 7945-7950). A 5 mL microwave reaction tube was charged with Example 122 (115 mg, 0.27 mmol, 1.0 eq.), zinc bromide (92 mg, 0.41 mmol, 1.5 eq.), sodium azide (53 mg, 0.81 mmol, 3.0 eq.), water (2 mL) and isopropanol (1 mL). The tube was sealed and then heated via microwave at 175° C. for 5 h. After this time, the reaction mixture was partitioned between methylene chloride (5 mL) and 1 N aqueous HCl (5 mL), the layers were separated, and the organic layer was washed with 1 N HCl (2 times), water, and then brine. The combined aqueous phases were extracted with methylene chloride. The combined organic phases were dried over sodium sulfate and then concentrated in-vacuo to yield a residue. The residue was purified over silica gel, eluting with 5%-10%-15%-20% methanol/methylene chloride, to provide Example 291 (33 mg) as a colorless glass. MS (APCI) found: 467.2 (M+H)$^+$.

Example 292

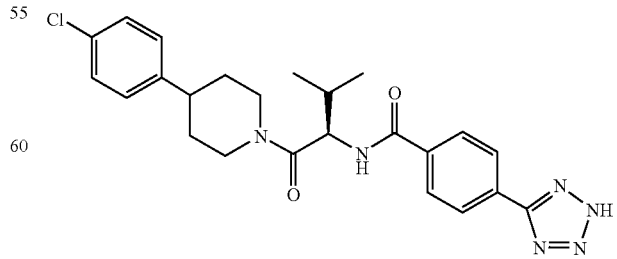

Example 292 was prepared in a similar manner as described for the preparation of Example 291 starting from Example 123. MS found: 467.3 (M+H)+.

Example 293

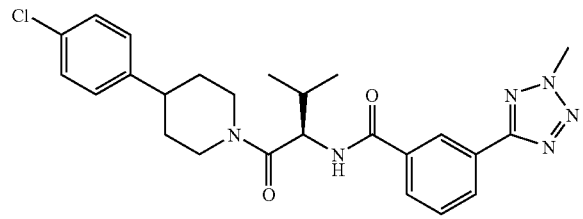

A 20 ml scintillation vial was charged with Example 291 (47 mg, 0.10 mmol, 1.0 eq.), trimethyloxonium fluoroborate (20 mg, 0.13 mmol, 1.3 eq.), proton sponge (60 mg, 0.25 mmol, 2.5 eq.), 4 Å molecular sieves (200 mg), and DCM (2 mL). The vial was filled with argon gas and sealed. The mixture was allowed to stir overnight at room temperature. After this time, the reaction mixture was diluted with ethyl acetate (50 mL), washed 3× with water (20 mL) followed by brine. The organic phase was dried over sodium sulfate and concentrated in-vacuo to yield a residue. The residue was purified over silica gel, eluting with 30%-50% ethyl acetate/hexanes-100% ethyl acetate, to yield crude product (38 mg) as a colorless glass contaminated with proton sponge. The crude product was purified by prep HPLC, using a Phenomenex Luna 5μ, C18 (2), 250×21.2 mm column, under the following conditions: 100% water (5 min) then 0% to 90% acetonitrile in water (0.05% TFA in each solvent) over 15 minutes. Lyopholization of the fractions containing the major peak yielded Example 293 (11 mg) as a colorless powder. MS (ESI) found: 481.3 (M+H)+.

Example 294

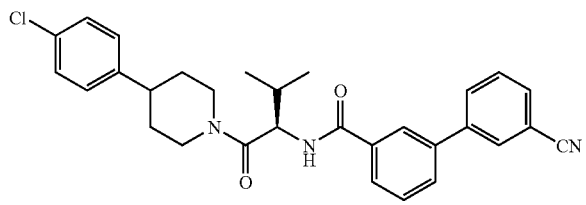

A 5 mL microwave reaction tube was charged with Example 130 (298 mg, 0.62 mmol, 1.0 eq.), 3-cyanophenylboronic acid (101 mg, 0.69 mmol, 1.1 eq.), 2 M aqueous potassium phosphate solution (0.93 mL, 1.86 mmol, 3.0 eq.), and DMF (3 mL). The resulting solution was degassed under vacuum and then backfilled with argon. Tetrakis(triphenylphosphine)palladium(0) (50 mg) was added and the resulting mixture was again degassed as described above. The tube was sealed, and the reaction mixture was heated via microwave at 150° C. for 30 minutes. After this time, the reaction mixture was cooled to rt. The reaction mixture was filtered to remove some solids, and the filter cake was rinsed with ethyl acetate. The combined filtrates were concentrated in-vacuo to yield a residue. The residue was purified over silica gel, eluting with 25%-50% ethyl acetate/hexanes, to yield Example 294 (202 mg) as a colorless foam. MS (ESI) found: 500.3 (M+H)+.

Example 295

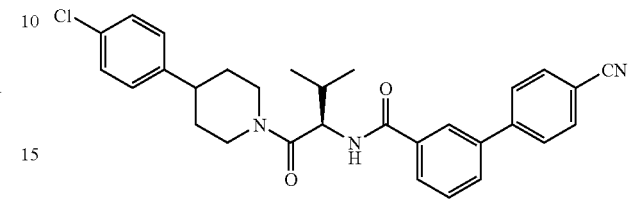

Example 295 was prepared in a similar manner as described for the preparation of Example 294 using 4-cyanophenylboronic acid. MS found: 500.3 (M+H)+.

Example 296

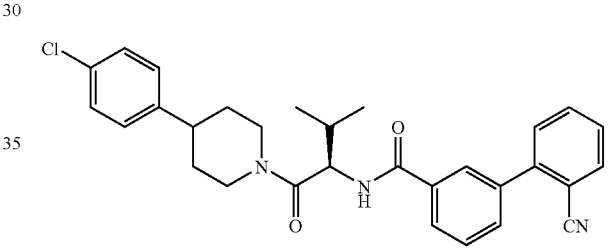

Example 296 was prepared in a similar manner as described for the preparation of Example 294 using 2-cyanophenylboronic acid. MS found: 500.3 (M+H)+.

Example 297

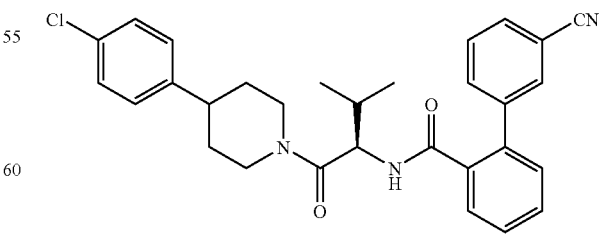

Example 297 was prepared in a similar manner as described for the preparation of Example 294 using 3-cyanophenylboronic acid and (R)-2-bromo-N-(1-(4-(4-chlorophenyl)piperidin-1-yl)-3-methyl-1-oxobutan-2-yl)benzamide. MS found: 500.4 (M+H)+.

Example 298

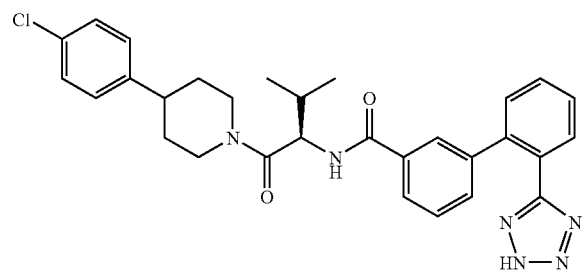

Example 298 was prepared in a similar manner as described for the preparation of Example 291 using Example 296. MS found: 543 (M+H).

Example 299

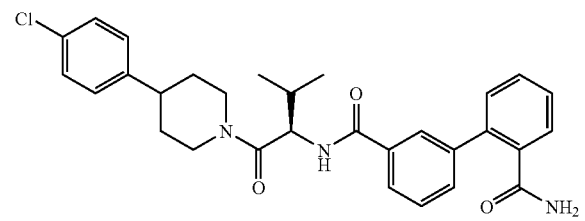

Example 299 was isolated as a by-product of the conversion of Example 296 to Example 298. MS found: 518 (M+H).

Example 300

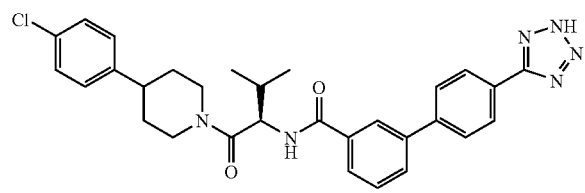

Example 300 was prepared in a similar manner as described for the preparation of Example 291 using Example 295. MS found: 543.4 (M+H).

Example 301

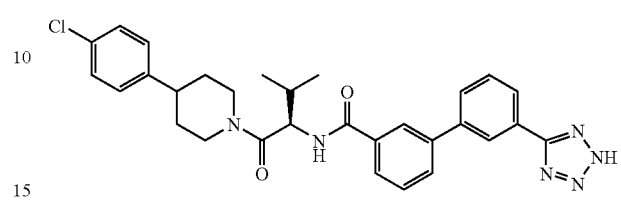

Example 301 was prepared in a similar manner as described for the preparation of Example 291 using Example 294. MS found: 543.5 (M+H).

Example 302

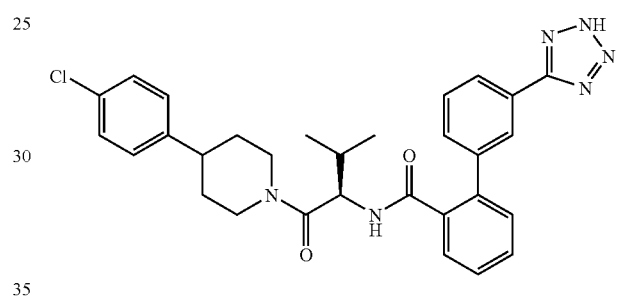

Example 302 was prepared in a similar manner as described for the preparation of Example 291 using Example 297. MS found: 543.5 (M+H).

Example 303

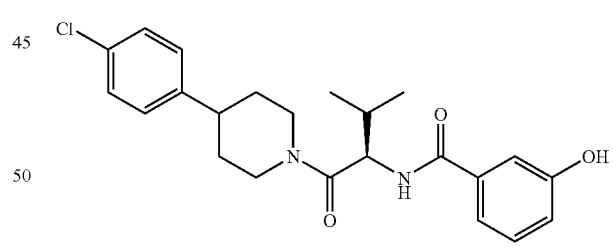

Step 1: (R)-3-((1-(4-(4-chlorophenyl)piperidin-1-yl)-3-methyl-1-oxobutan-2-yl)carbamoyl)phenyl acetate (R)-2-Amino-1-(4-(4-chlorophenyl)piperidin-1-yl)-3-methylbutan-1-one hydrochloride was coupled with 3-acetoxy benzoic acid in a similar manner as described for the preparation of Example 75 to give (R)-3-((1-(4-(4-chlorophenyl)piperidin-1-yl)-3-methyl-1-oxobutan-2-yl)carbamoyl)phenyl acetate (115 mg, 50% yield). MS found: 457.3 (M+).

Step 2: Example 303

To a solution of (R)-3-((1-(4-(4-chlorophenyl)piperidin-1-yl)-3-methyl-1-oxobutan-2-yl)carbamoyl)phenyl acetate (115 mg, 0.25 mmol) in methanol (2 mL) was added a solution of sodium methoxide (0.5 M, 0.5 mL) in methanol. The mixture was stirred at room temperature for one hour. After this time, the mixture was concentrated and then neutralized to pH=5 with 1 N HCl. The resulting precipitated solid was collected by filtration, rinsed with water, and dried under vacuum to give Example 303 (90 mg, 86.7% yield) as an off-white solid. MS found: 415.2 (M+H).

Example 304

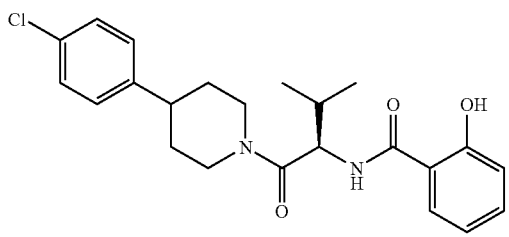

Example 304 was prepared in a similar manner as described for the preparation of Example 303 using 2-acetoxy benzoic acid. MS found 415.2 (M+H).

Example 305

TFA Salt of (R)-3-amino-N-(1-(4-(4-chlorophenyl) piperidin-1-yl)-3-methyl-1-oxobutan-2-yl)benzamide

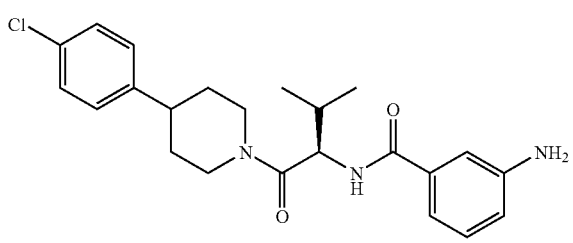

Example 128 (120 mg, 0.27 mmol) was dissolved in a mixture of methanol (5 mL) and ethyl acetate (5 mL). 5% Pd on carbon (8 mg) was added. The reaction system was degassed and charged with hydrogen three times and then allowed to stir at rt for one hour with a hydrogen balloon. The mixture was filtered and washed with ethyl acetate. The combined filtration was concentrated and purified by prep-HPLC.

The product containing fraction was concentrated and lyophilized to give Example 305 (89 mg, 62%). MS found: 414.2 (M+H).

Example 306

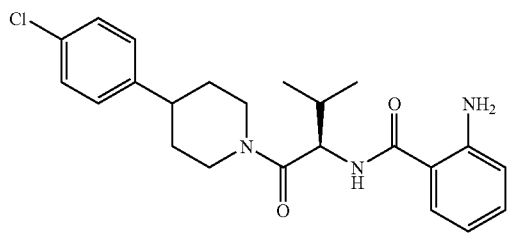

Example 306 was prepared in a similar manner as described for the preparation of Example 305 using Example 129. MS found: 414.2 (M+H).

Example 307

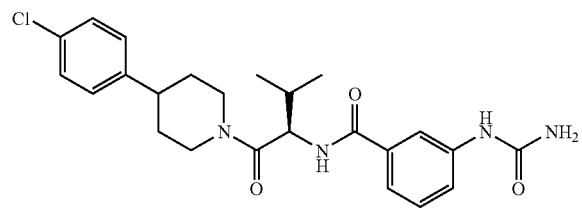

Sodium cyanate (2 mg, 0.031 mmol) was added into a solution of Example 305 (10 mg, 0.024 mmol) in acetic acid (1 mL). The mixture was stirred at rt for two hours and then concentrated to yield a residue. The residue was purified by prep-HPLC. The product containing fraction was concentrated and lyophilized to give Example 307 as a yellow solid (10 mg, 91.2% yield). MS found: 457.3 (M+H).

Example 308

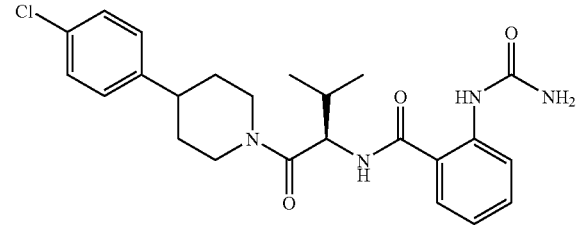

Example 308 was prepared in a similar manner as described for the preparation of Example 307 using Example 306. MS found: 457.3 (M+H).

Example 309

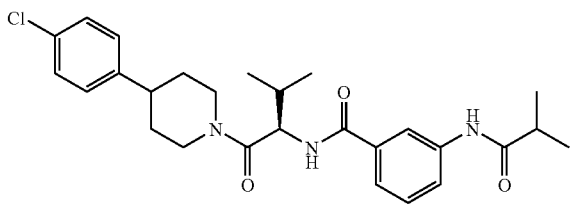

To a solution of Example 305 (15 mg, 0.036 mmol) in DCM (2 mL) was added isobutyryl chloride (4.2 µL, 0.04 mmol) and pyridine (4.5 µL, 004 mmol). The reaction was stirred at rt for 30 min and then concentrated to provide a residue. The residue was purified by preparative HPLC. The product containing fraction was concentrated and lyophilized to give Example 309 as a yellow powder (10 mg, 57.4%). MS found: 484.3 (M+H).

Example 310

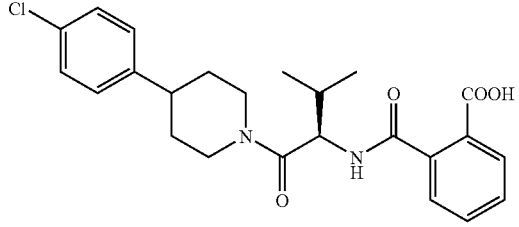

A solution of (R)-2-amino-1-(4-(4-chlorophenyl)piperidine-1-yl)-3-methylbutan-1-one hydrochloride (40 mg, 0.136 mmol, 1 eq) and phthalic anhydride (20 mg, 0.136 mmol, 1 eq) were stirred at 25° C. in 3 mL of chloroform for 20 hours. After this time, the reaction was concentrated and purified by preparative HPLC to afford Example 310, yield=55%. MS found: 443.30 (M+H)$^+$.

Example 311

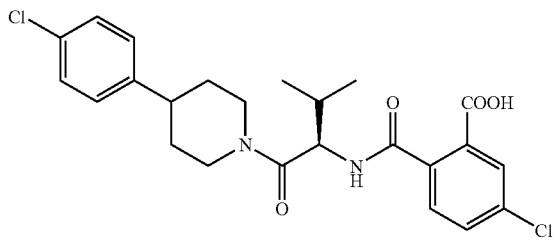

Example 311 was prepared in a similar manner as described for the preparation of Example 310. MS found: 477.3 (M+H)$^+$.

Example 312

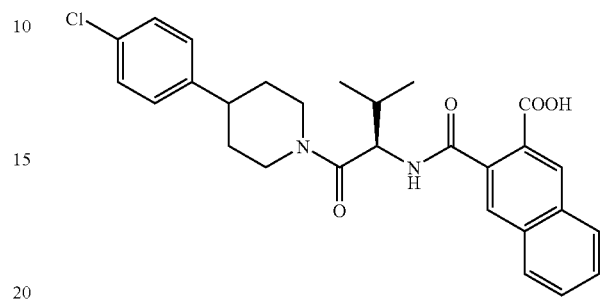

Example 312 was prepared in a similar manner as described for the preparation of Example 310. MS found: 493.2 (M+H)

Example 313

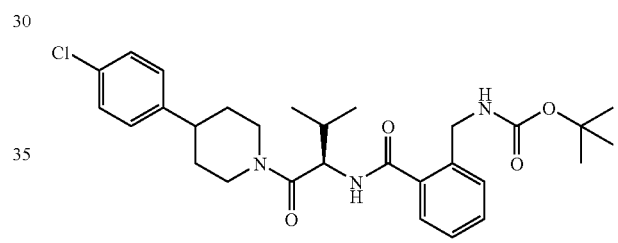

Step 1: Methyl 2-((tert-butoxycarbonyl)aminomethyl)benzoate

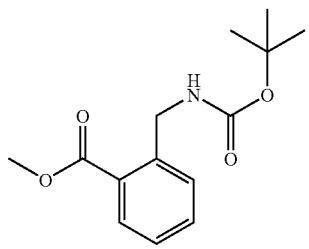

Methyl 2-(aminomethyl)benzoate-hydrochloride (500 mg, 2.48 mmol, 1 eq) was dissolved in 10 mL of THF at 25° C. under nitrogen. Triethylamine (0.35 mL, 4.96 mmol, 2 eq) was added followed by BOC anhydride (541 mg, 2.48 mmol, 1 eq). The reaction was stirred for 20 hours. After this time, saturated NH$_4$Cl (10 mL) was added and the product was extracted 3 times with methylene chloride. The organic extracts were combined, dried over sodium sulfate and stripped to give methyl 2-((tert-butoxycarbonyl)aminomethyl)benzoate (650 mg) as a light-colored oil.

Step 2: 2-((Tert-butoxycarbonyl)aminomethyl)benzoic acid

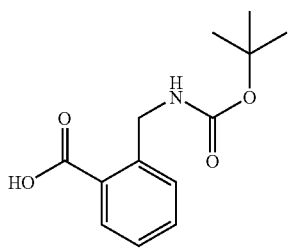

Methyl 2-((tert-butoxycarbonyl)aminomethyl)benzoate (600 mg, 1.99 mmol, 1 eq) was dissolved in 5 mL of THF at 25° C. 1 N NaOH (5.96 mL, 5.96 mmol, 3 eq) was added and the reaction stirred for 20 hours. After this time, 1.0 N HCl (5.86 mL) was added and the product was extracted 3 times with chloroform. The organic extracts were combined, dried over sodium sulfate and stripped to give 2-((tert-butoxycarbonyl)aminomethyl)benzoic acid (560 mg, 98% yield). MS (M+H—BOC)$^+$ found: 152.3.

Step 3: Example 313

Example 313 was prepared in a similar manner as described for the preparation of Example 75. MS found: 429.3 (M-Boc)

Example 314

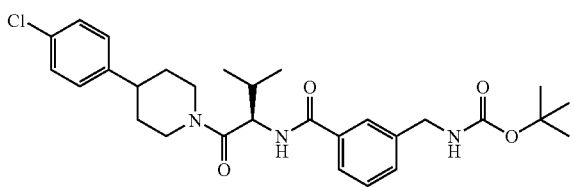

Example 314 was prepared in a similar manner as described for the preparation of Example 313 using methyl 3-(aminomethyl)benzoate-hydrochloride. MS found: 528.4 (M+H).

Example 315

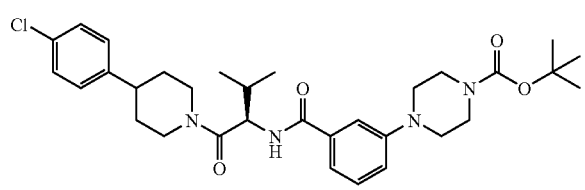

Example 315 was prepared in a similar manner as described for the preparation of Steps 1 and 2 of Example 313 using 3-(piperazin-1-yl)benzoic acid. MS Found: 583.5 (M+H).

Example 316

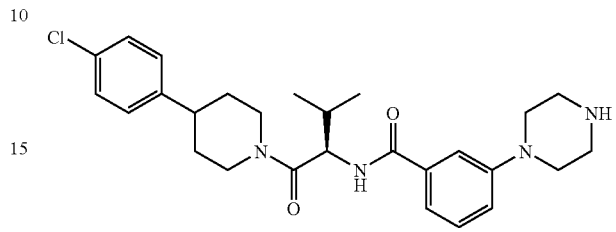

Example 315 was deprotected utilizing either TFA in dichlormethane or HCl in dioxane to provide Example 316 after preparative HPLC. MS Found: 483.4 (M+H).

Example 317

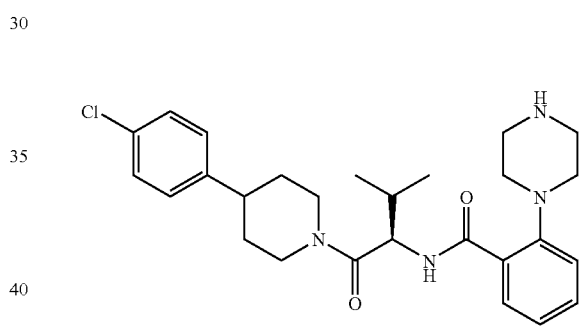

Example 317 was prepared in a similar manner as described for the preparation of Example 316 using 2-(piperazin-1-yl)benzoic acid. MS found 483.4 (M+H).

Example 318

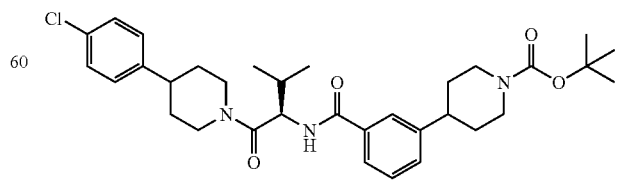

215

Example 318 was prepared in a similar manner as described for the preparation of Steps 1 and 2 of Example 314 using 3-(piperidin-1-yl)benzoic acid. MS found: 582.5 (M+H).

Example 319

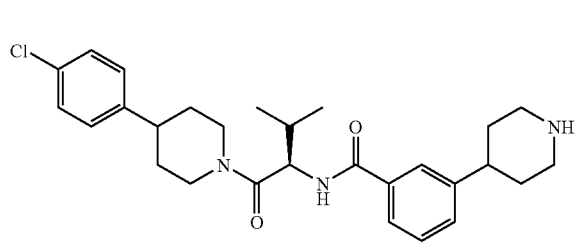

Example 318 was deprotected utilizing either TFA in dichlormethane or HCl in dioxane to provide Example 319 after preparative HPLC. MS found: 482.1 (M+H).

Example 320

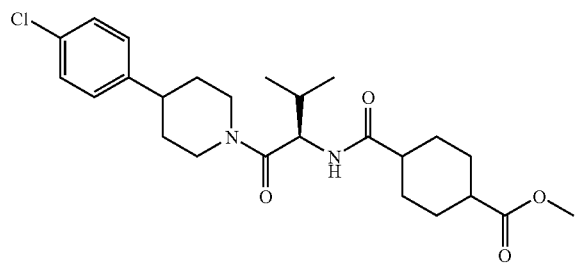

Example 320 was prepared in a similar manner as described for the preparation of Example 75 using trans-1,4-Cyclohexanedicarboxylic acid monomethyl ester. MS found: 463.4 (M+H).

Example 321

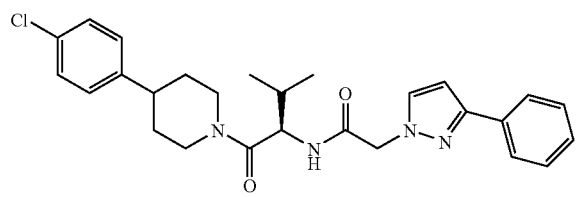

216

Example 321 was prepared in a similar manner as described for the preparation of Example 290 using 3-phenylpyrazole. MS found: 479.4 (M+).

Example 322

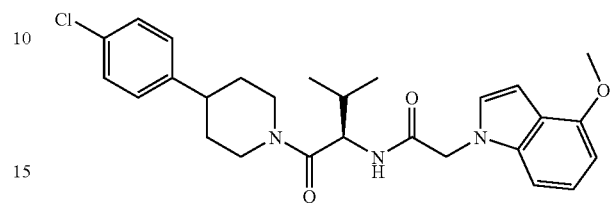

Example 322 was prepared in a similar manner as described for the preparation of Example 290 using 4-methoxy indole. MS found: 482.3 (M+).

Example 323

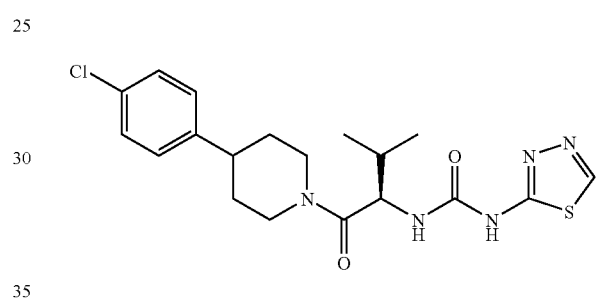

To a solution of (R)-2-amino-1-(4-(4-chlorophenyl)piperidin-1-yl)-3-methylbutan-1-one hydrochloride (59 mg, 0.195 mmol) in THF (2 mL) was added phenyl 1,3,4-thiadiazol-2-ylcarbamate (45 mg, 0.2 mmol) and DIPEA (35 µL, 0.2 mmol), the mixture was stirred at 50° C. overnight and then concentrated to provide a residue. The residue was purified by prep-HPLC. The product containing fraction was concentrated and lyophilized to give Example 323 as a white powder (52 mg, 55%). MS found: 422.3 (M+H).

Example 324

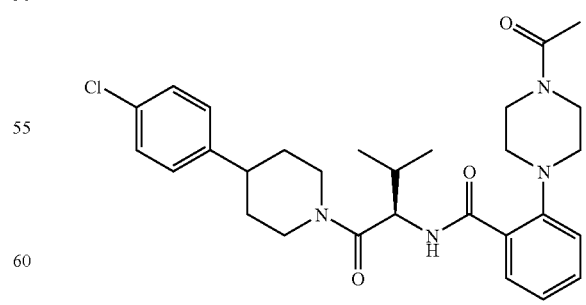

To a solution of Example 317 (15 mg, 0.025 mmol) in pyridine (2 mL) was added acetic anhydride (7 µL, 0.075 mmol) and the reaction allowed to stir overnight. After this time, the mixture was purified by preparative HPLC and the product isolated by extracting NaOH neutralized product fractions to give Example 324 (17 mg) as a colorless film. MS found: 525.5 (M+).

Example 325

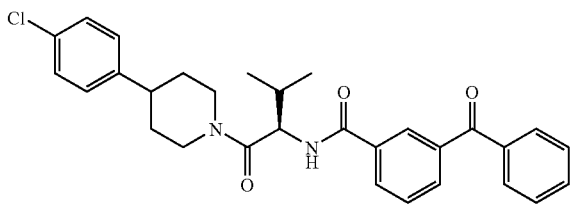

Example 325 was prepared in a similar manner as described for the preparation of Example 75 using 3-benzoylbenzoic acid. MS found: 503.2 (M+H).

Example 326

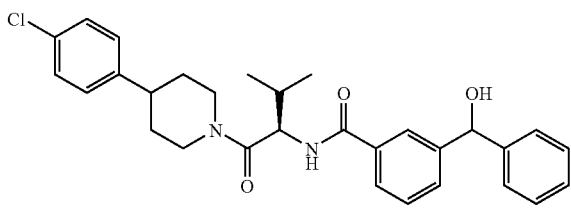

Example 326 was prepared by reacting a solution of Example 325 (50 mg, 0.1 mmol) in methanol (3 mL) with NaBH$_4$ (4 mg, 0.1 mmol) for 24 h. Aqueous workup followed by purification via silica gel provided Example 326 (40 mg, 80% yield) as an off-white solid. MS found: 505.3 (M+H).

Example 327

N—((R)-1-((S)-4-(4-chlorophenyl)-4-hydroxy-3,3-dimethylpiperidin-1-yl)-3-methyl-1-oxobutan-2-yl)benzamide

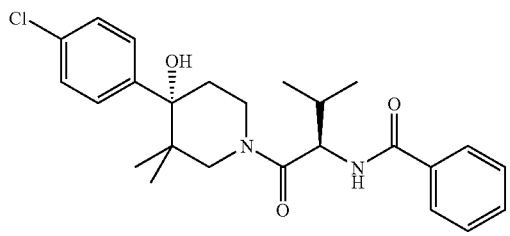

Step 1: (R)-2-amino-1-((S)-4-(4-chlorophenyl)-4-hydroxy-3,3-dimethylpiperidin-1-yl)-3-methylbutan-1-one hydrochloride

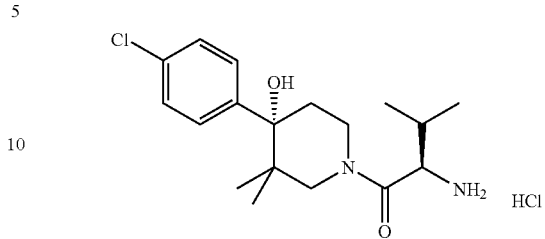

(R)-2-amino-1-((S)-4-(4-chlorophenyl)-4-hydroxy-3,3-dimethylpiperidin-1-yl)-3-methylbutan-1-one hydrochloride was prepared in a similar manner as described in Preparation C with the exception that (S)-4-(4-chlorophenyl)-3,3-dimethylpiperidin-4-ol (WO 04/043965) was used instead of 4(4-chlorophenyl)piperidine Step 2: N—((R)-1-((S)-4-(4-chlorophenyl)-4-hydroxy-3,3-dimethylpiperidin-1-yl)-3-methyl-1-oxobutan-2-yl)benzamide Example 327 was prepared in a similar manner as described in Example 75 from (R)-2-amino-1-((S)-4-(4-chlorophenyl)-4-hydroxy-3,3-dimethylpiperidin-1-yl)-3-methylbutan-1-one hydrochloride and benzoic acid.

Example 328

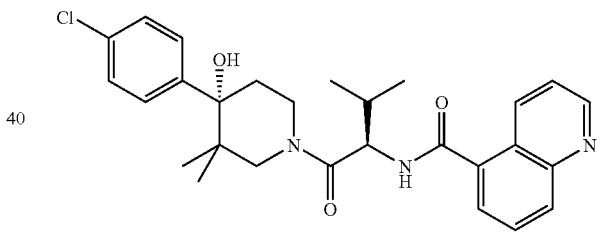

Example 328 was prepared in a similar manner as described for the preparation of Example 75 using (R)-2-amino-1-((S)-4-(4-chlorophenyl)-4-hydroxy-3,3-dimethylpiperidin-1-yl)-3-methylbutan-1-one hydrochloride and quinoline-5-carboxylic acid. MS found: 443.3 (M+).

Example 329

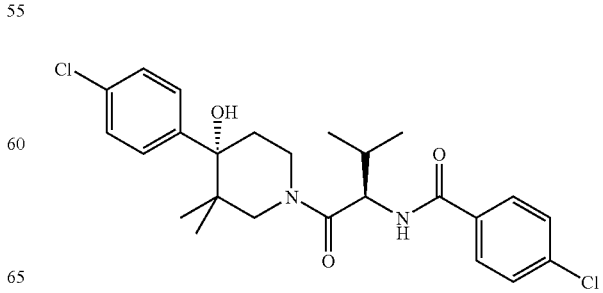

Example 329 was prepared in a similar manner as described for the preparation of Example 328 with the exception that 4-chlorobenzoic acid was used instead of benzoic acid. MS found 477.2 (M+).

Example 330

(R)—N-(1-(4-(4-chlorophenyl)piperidin-1-yl)-3-methyl-1-oxobutan-2-yl)-2'-nitrobiphenyl-3-carboxamide

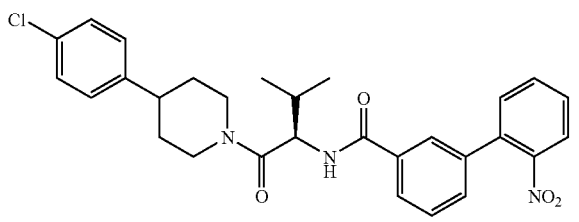

Step 1: (R)-3-(1-(4-(4-chlorophenyl)piperidin-1-yl)-3-methyl-1-oxobutan-2-ylcarbamoyl)phenylboronic acid

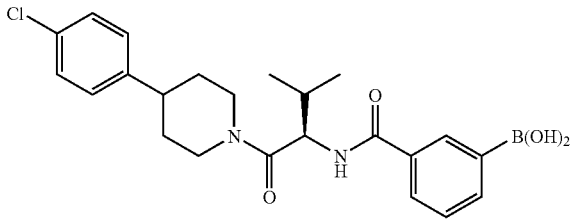

(R)-3-(1-(4-(4-chlorophenyl)piperidin-1-yl)-3-methyl-1-oxobutan-2-ylcarbamoyl)phenylboronic acid was prepared in a similar manner as Example 75 using 3-carboxybenzeneboronic acid.

Step 2: (R)-3-(1-(4-(4-chlorophenyl)piperidin-1-yl)-3-methyl-1-oxobutan-2-ylcarbamoyl)phenylboronic acid A solution of (R)-3-(1-(4-(4-chlorophenyl)piperidin-1-yl)-3-methyl-1-oxobutan-2-ylcarbamoyl)phenylboronic acid (100 mg, 2.26 mmol), 1-bromo-2-nitrobenzene (46 mg 2.26 mmol), Na$_2$CO$_3$ (72 mg, 6.7 mmol) and Pd(Ph$_3$P)$_4$ (13 mg) in toluene (5 mL) water (3 mL) and ethanol (3 mL) was heated at 100° C. for 30 min. After this time, the reaction mixture was cooled, filtered and then concentrated. Water was added and the resulting solution was extracted with ethyl acetate. The combined organic extracts were dried and concentrated to provide crude material. The crude material was purified via column chromatography (25% EtOAc/hexane to 50% EtOAc/hexane) to provide Example 330 as an off-white glass. MS found: 520.2 (M+H).

Example 331

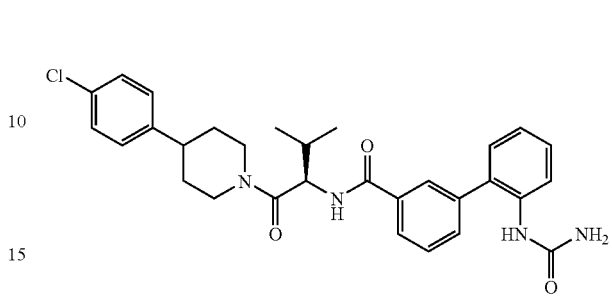

Step 1:

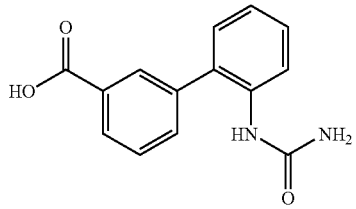

3-Carboxyphenyl boronic acid (100 mg, 0.60 mmol), 2-bromophenyl urea (130 mg, 0.60 mmol), tetrakis(triphenylphosphine)palladium(0) (35 mg, 0.030 mmol), sodium carbonate (192 mg, 1.81 mmol), toluene (5 mL), water (3 mL), and ethanol (3 mL) were mixed at 25° C. under nitrogen then heated in a microwave reactor for 30 minutes at 100° C. Water (5 mL) was added followed by removal of the EtOH in vacuo. The aqueous layer was washed with diethyl ether (2×) and the pH was adjusted to 3 with 1N HCl. The aqueous layer was extracted with ethyl acetate (2×) and the combined were dried over sodium sulfate and then concentrated in vacuo to give 2'-ureidobiphenyl-3-carboxylic acid (150 mg, 0.58 mmol, 97% yield) as a tan glass. MS found: (M+H)$^+$=257.29

Step 2: Example 331

Example 331 was prepared in a similar manner as described for the preparation of Example 75 using 2'-ureidobiphenyl-3-carboxylic acid. MS found 533.4 (M+H).

Example 332

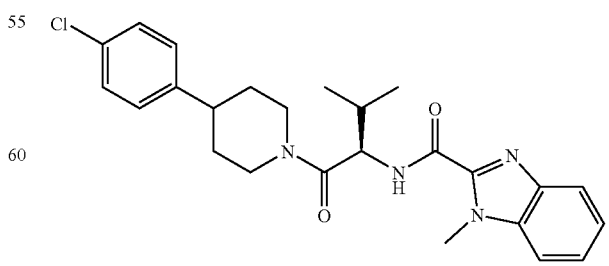

TFA Salt

To a solution of Example 142 (30 mg, 0.05 mmol) in acetone was added KOH (6 mg 0.1 mmol) and iodomethane (10 μL, 0.16 mmol). The resulting mixture was stirred at room temperature for 48 h. After this time, EtOAc was added to the solution, and the resulting mixture was washed with water and brine. The organic layer was dried and concentrated to an oil. The oil was purified by preparative HPLC to provide Example 332 (18 mg). MS found: 453.4 (M+H).

Example 333

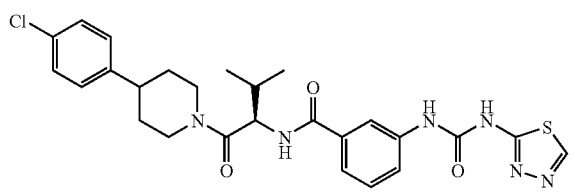

Example 333 was prepared in a similar manner as described for the preparation of Example 323 with the exception that Example 305 was used in place of (R)-2-amino-1-(4-(4-chlorophenyl)piperidin-1-yl)-3-methylbutan-1-one hydrochloride. MS found: 541.3 (M+).

Example 334

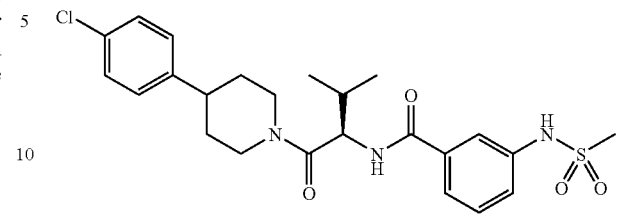

To a solution of Example 305 (31 mg, 0.075 mmol) in DCM (1 mL) was added methanesulfonyl chloride (6 μL, 0.075 mmol) and pyridine (8 μL, 075 mmol). The reaction was stirred at rt for 30 min and additional aliquots (1 equiv each) of pyridine and methanesulfonyl chloride was added. The reaction was stirred and then concentrated to yield a residue. The residue was purified by preparative HPLC. The product containing fraction was concentrated and lyophilized to give Example 334 as a white solid powder (21 mg). MS found: 492.2 (M+).

Examples 335 to 404

Examples 335 to 404, as described in Table 13, were prepared in a similar manner as described for the preparation of Example 75. In the synthesis of Examples 344 to 404, the appropriate acid needed to produce the product listed was used in place of the benzoic acid used in Example 75. Examples 404, 398, 399, 401 and 403 were prepared from the corresponding esters of Examples 395, 396, 397, 400 and 402, respectively, via standard hydrolysis.

TABLE 13

| Example | Structure | | MS (M+) |
|---|---|---|---|
| 335 | 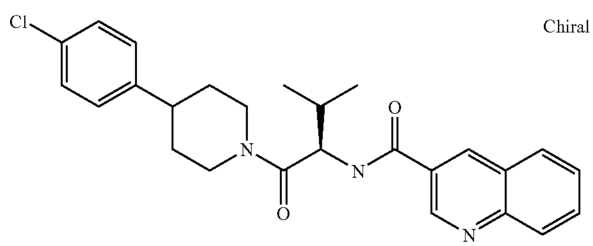 | Chiral | 450.3 |
| 336 | 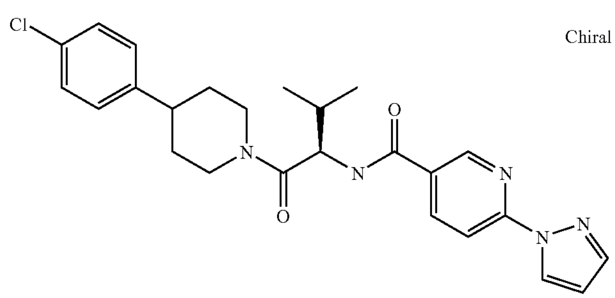 | Chiral | 466.3 |

TABLE 13-continued
| Example | Structure | | MS (M+) |
|---|---|---|---|
| 337 | 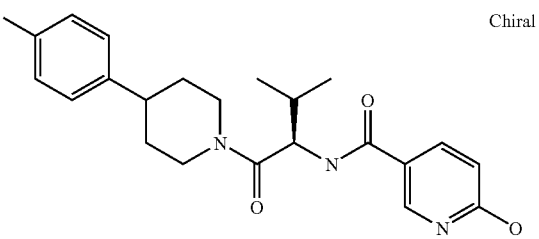 | Chiral | 416.3 |
| 338 | 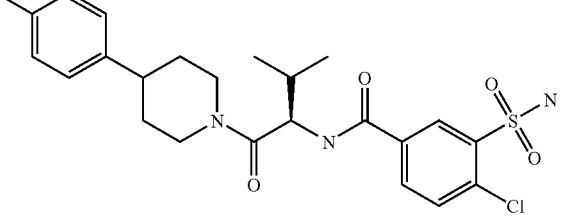 | Chiral | 512.2 |
| 339 | 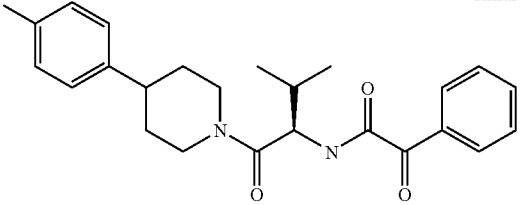 | Chiral | 427.3 |
| 340 | 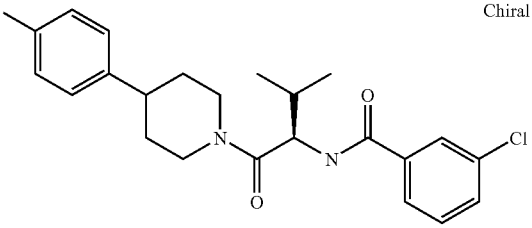 | Chiral | 433.4 |
| 341 | 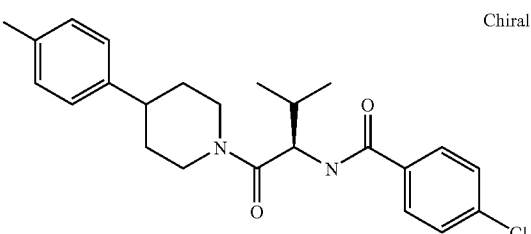 | Chiral | 433.3 |
| 342 | 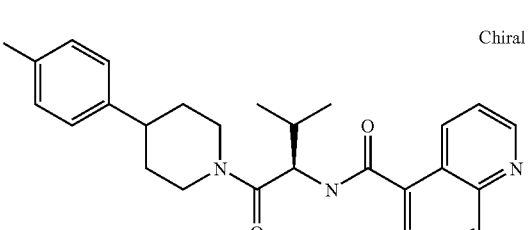 | Chiral | 450.3 |

TABLE 13-continued
| Example | Structure | | MS (M+) |
|---|---|---|---|
| 343 | 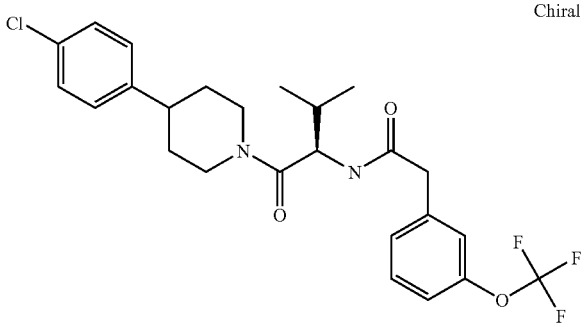 | Chiral | 497.2 |
| 344 | 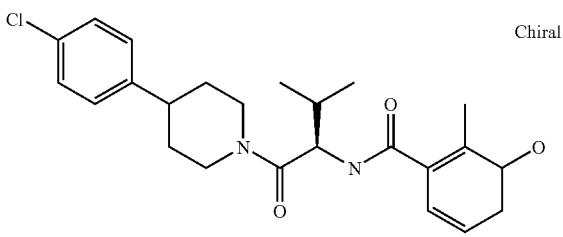 | Chiral | 429.2 |
| 345 | 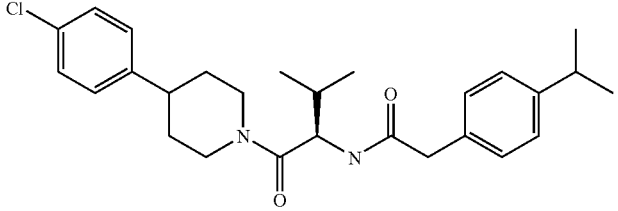 | Chiral | 455.3 |
| 346 | 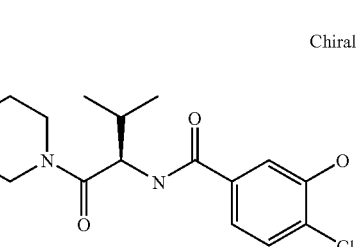 | Chiral | 449.2 |
| 347 | 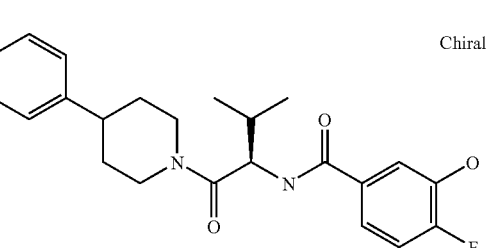 | Chiral | 433.2 |

TABLE 13-continued

| Example | Structure | MS (M+) |
|---|---|---|
| 348 | 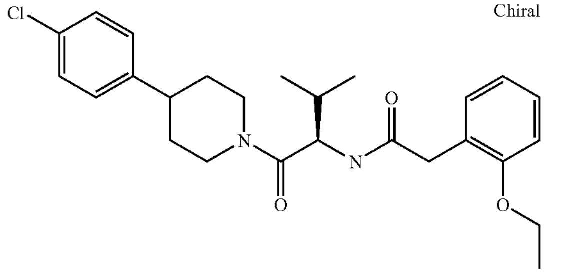 | 457.3 |
| 349 | 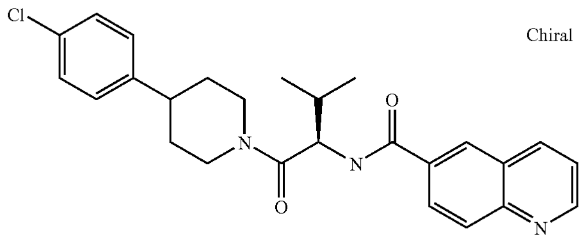 | 450.3 |
| 350 | 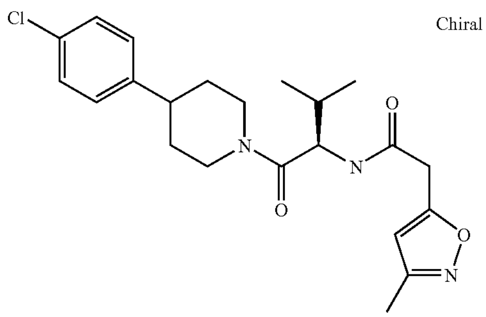 | 418.3 |
| 351 | 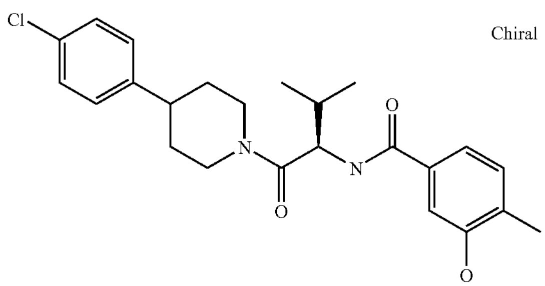 | 429.2 |
| 352 | 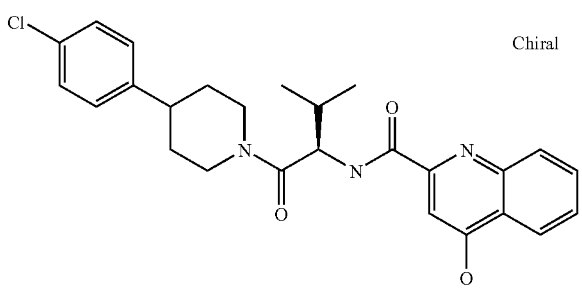 | 466.2 |

TABLE 13-continued
| Example | Structure | MS (M+) |
|---------|-----------|---------|
| 353 | 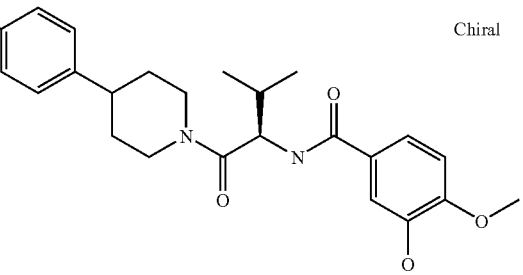 Chiral | 445.2 |
| 354 | 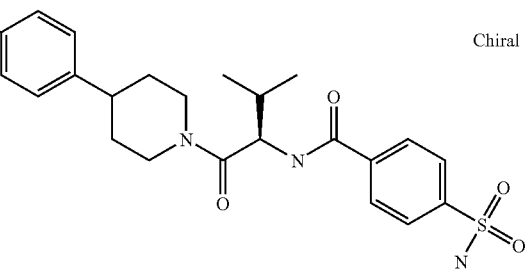 Chiral | 478.2 |
| 355 | 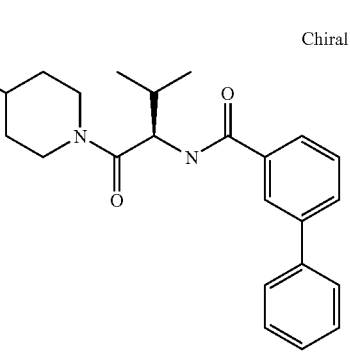 Chiral | 475.3 |
| 356 | 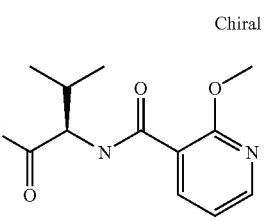 Chiral | 430.2 |
| 357 | 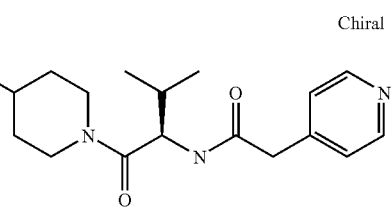 Chiral | 414.3 |

TABLE 13-continued
| Example | Structure | | MS (M+) |
|---|---|---|---|
| 358 | 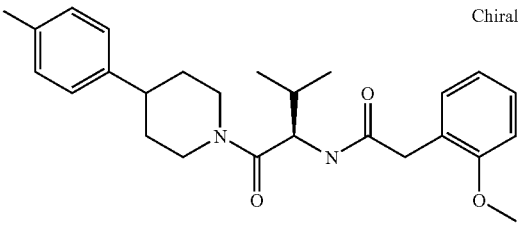 | Chiral | 443.3 |
| 359 | 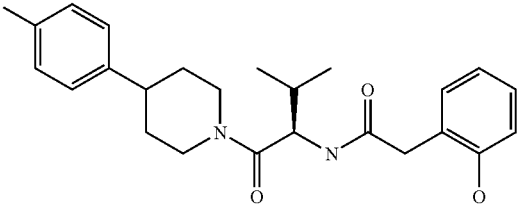 | Chiral | 429.3 |
| 360 | 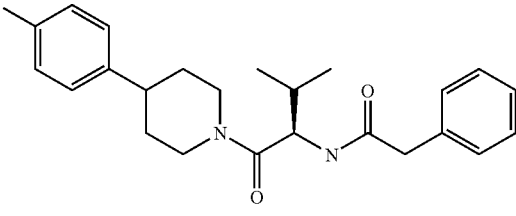 | Chiral | 443.3 |
| 361 | 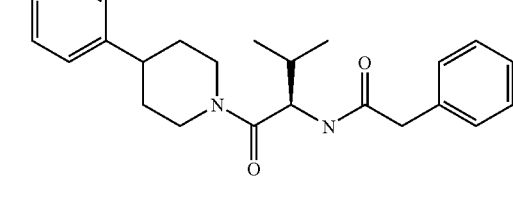 | Chiral | 429.3 |
| 362 | 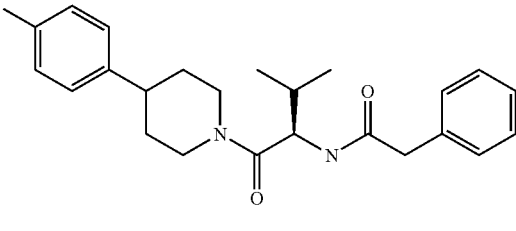 | Chiral | 481.2 |
| 363 | 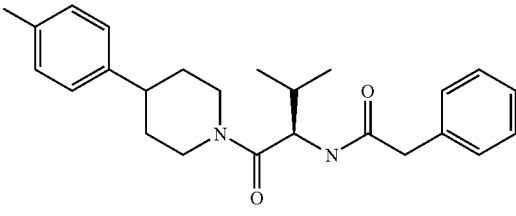 | Chiral | 427.3 |

TABLE 13-continued
| Example | Structure | | MS (M+) |
|---|---|---|---|
| 364 | 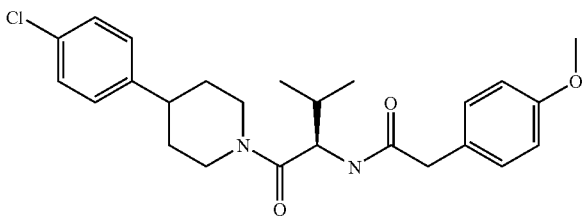 | Chiral | 443.3 |
| 365 | 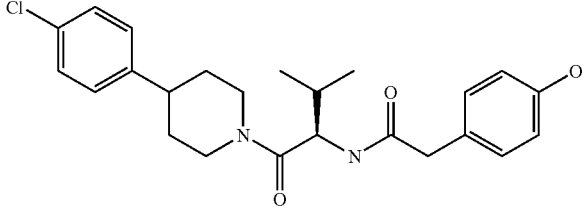 | Chiral | 429.3 |
| 366 | 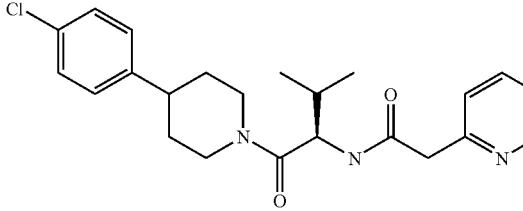 | Chiral | 414.3 |
| 367 | 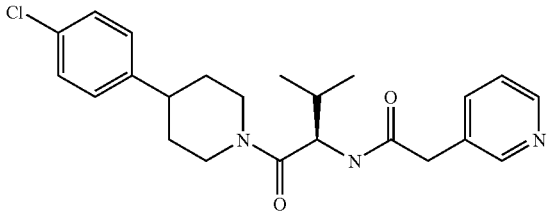 | Chiral | 414.3 |
| 368 | 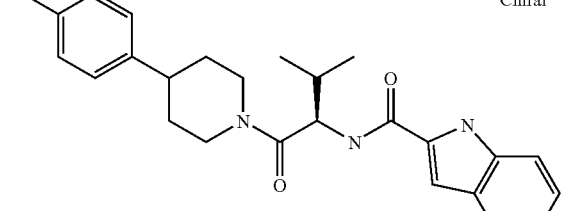 | Chiral | 438.2 |

TABLE 13-continued
| Example | Structure | | MS (M+) |
|---|---|---|---|
| 369 | 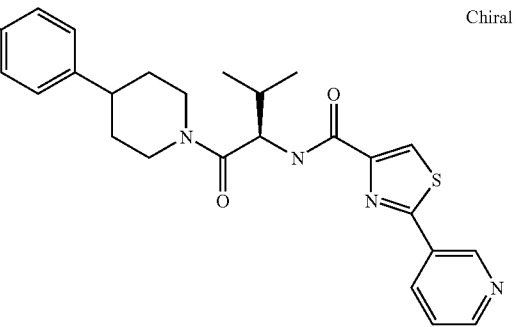 | Chiral | 483.2 |
| 370 | 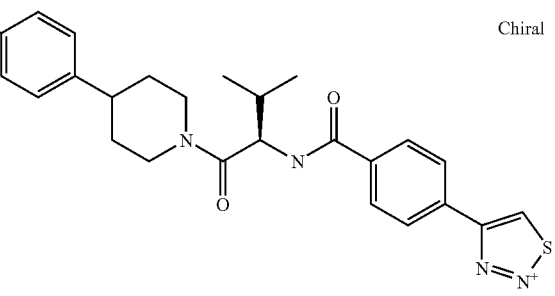 | Chiral | 483.2 |
| 371 | 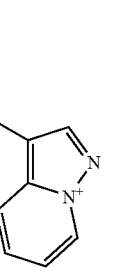 | Chiral | 439.3 |
| 372 | 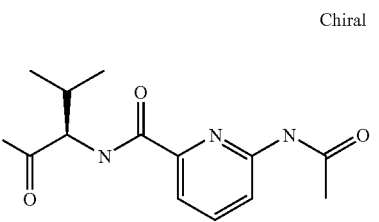 | Chiral | 457.3 |
| 373 | 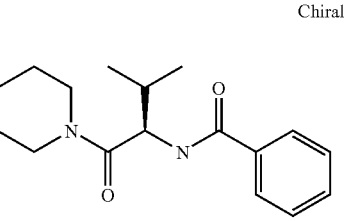 | Chiral | 433.2 |

TABLE 13-continued
| Example | Structure | | MS (M+) |
|---|---|---|---|
| 374 | 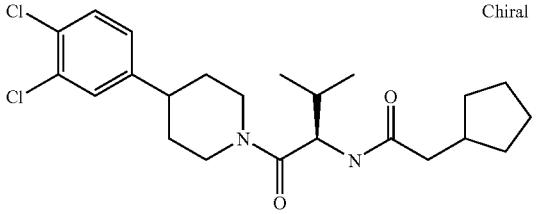 | Chiral | 439.3 |
| 375 | 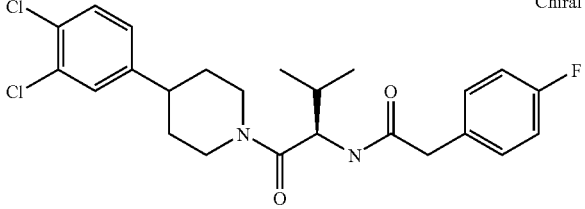 | Chiral | 465.3 |
| 376 | 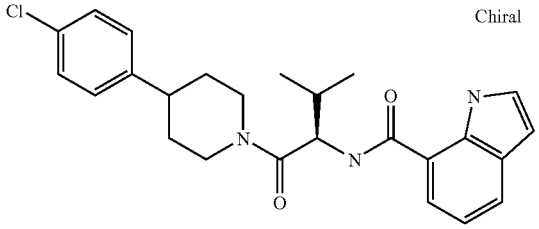 | Chiral | 438.4 |
| 377 | 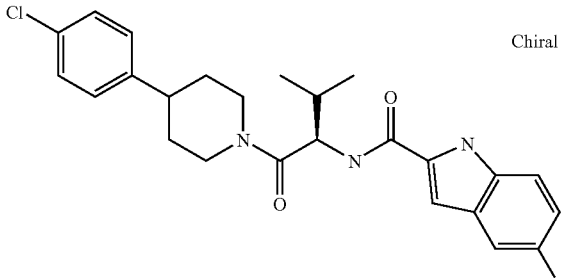 | Chiral | 456.4 |
| 378 | 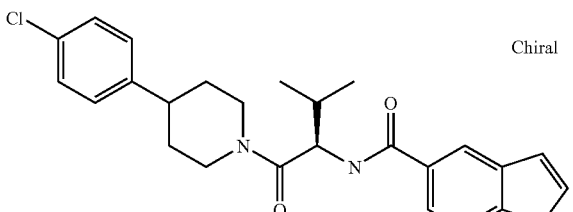 | Chiral | 438.4 |
| 379 | 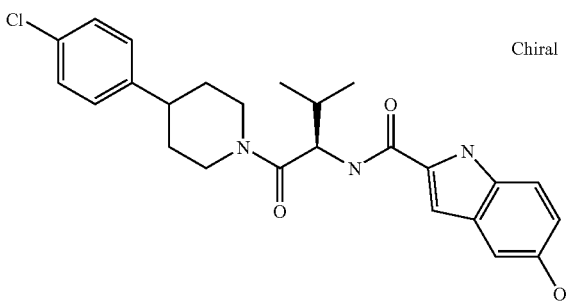 | Chiral | 454.4 |

TABLE 13-continued
| Example | Structure | MS (M+) |
|---|---|---|
| 380 | 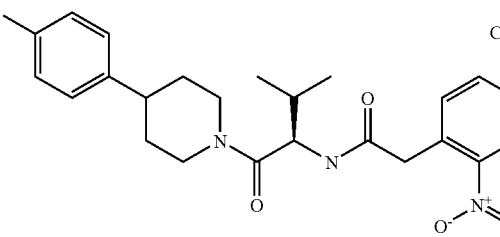 Chiral | 458.1 |
| 381 | 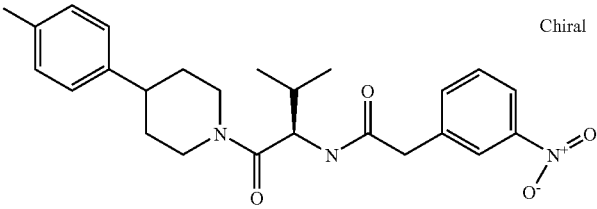 Chiral | 458.2 |
| 382 | 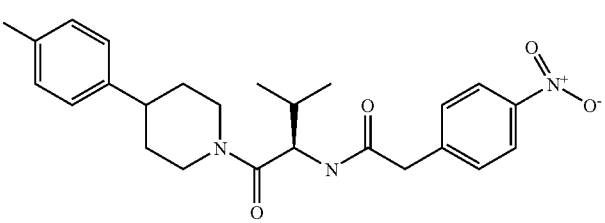 Chiral | 458.0 |
| 383 | 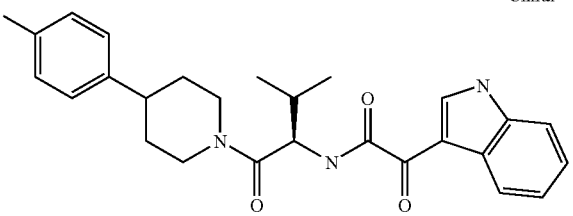 Chiral | 466.3 |
| 384 | 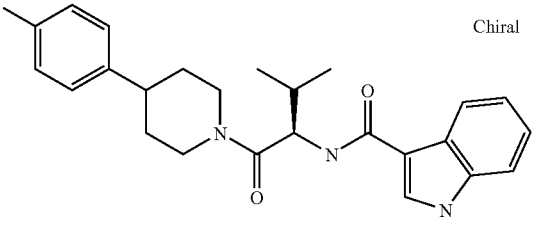 Chiral | 438.3 |
| 385 | 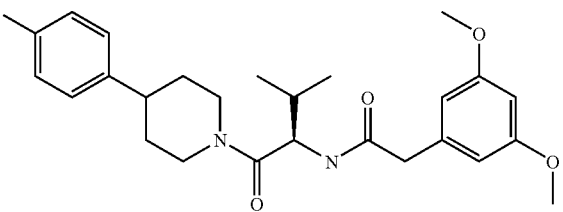 Chiral | 473.3 |

TABLE 13-continued

| Example | Structure | MS (M+) |
|---|---|---|
| 386 | Chiral, 4-Cl-phenyl-piperidine-N-CO-CH(iPr)-NH-CO-CH(OH)-phenyl | 429.3 |
| 387 | Chiral, 4-Cl-phenyl-piperidine-N-CO-CH(iPr)-NH-CO-CH(OH)-(4-F-phenyl) | 447.3 |
| 388 | Chiral, 4-Cl-phenyl-piperidine-N-CO-CH(iPr)-NH-CO-(3-NHSO2Me-phenyl) | 492.2 |
| 389 | Chiral, 4-Cl-phenyl-piperidine-N-CO-CH(iPr)-NH-CO-(2-Br-5-Cl-phenyl) | 513.2 |
| 390 | Chiral, 4-Cl-phenyl-piperidine-N-CO-CH(iPr)-NH-CO-(3-CO2Me-phenyl) | 457.3 |
| 391 | Chiral, 4-Cl-phenyl-piperidine-N-CO-CH(iPr)-NH-CO-(3-CO2H-phenyl) | 443.1 |

TABLE 13-continued

| Example | Structure | | MS (M+) |
|---|---|---|---|
| 392 | 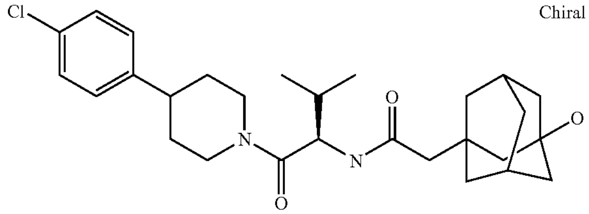 | Chiral | 487.3 |
| 393 | 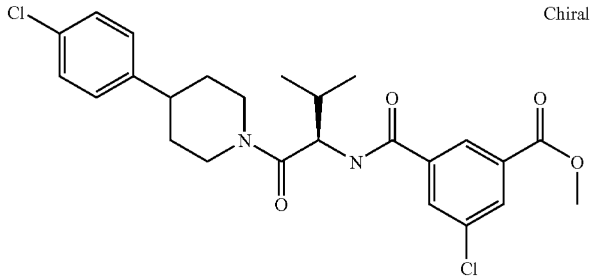 | Chiral | 491.2 |
| 394 | 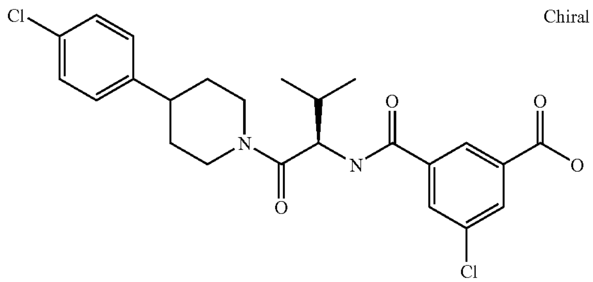 | Chiral | 477.0 |
| 395 | 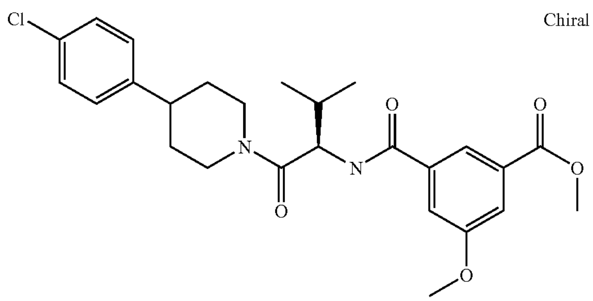 | Chiral | 487.1 |
| 396 | 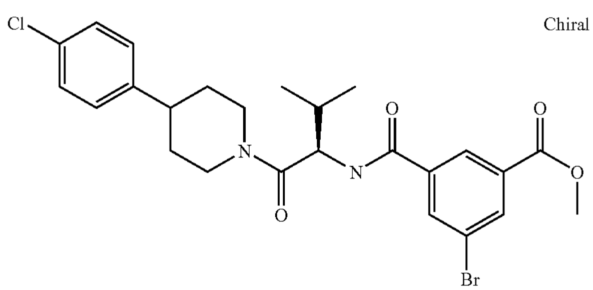 | Chiral | 535.1 |

TABLE 13-continued
| Example | Structure | MS (M+) |
|---|---|---|
| 397 | 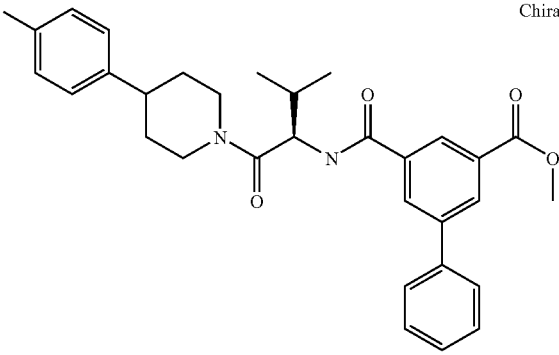 Chiral | 533.2 |
| 398 | 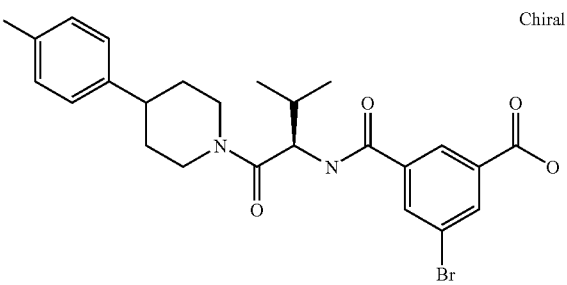 Chiral | 521.0 |
| 399 | 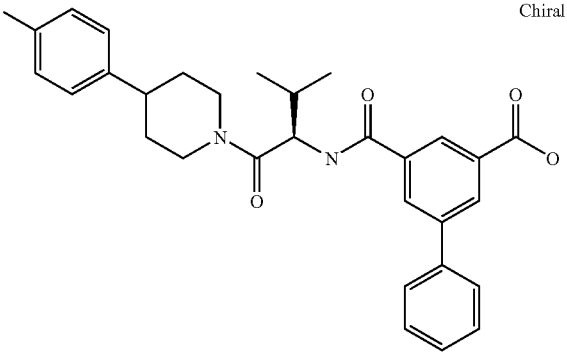 Chiral | 519.2 |
| 400 | 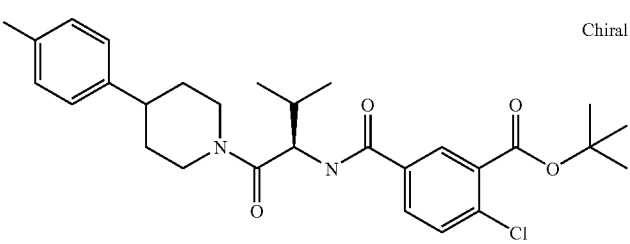 Chiral | 533.2 |
| 401 | 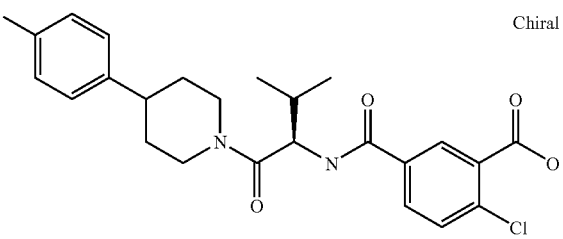 Chiral | 477.1 |

TABLE 13-continued

| Example | Structure | MS (M+) |
|---------|-----------|---------|
| 402 | Chiral | 472.2 |
| 403 | Chiral | 444.1 |
| 404 | Chiral | 473.0 |

Examples 405 to 438

Examples 405 to 438, as described in Table 14, were prepared in a similar manner as described for the preparation of Example 294. In the synthesis of Examples 404 to 438, the boronic acid needed to produce the product listed was used in place of the 3-cyanophenylboronic acid used in Example 294.

TABLE 14

| Example | Structure | MS (M+) |
|---------|-----------|---------|
| 405 | Chiral | 509.3 |

TABLE 14-continued
| Example | Structure | | MS (M+) |
|---|---|---|---|
| 406 | 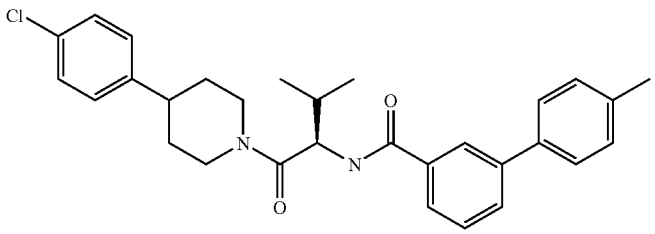 | Chiral | 489.4 |
| 407 | 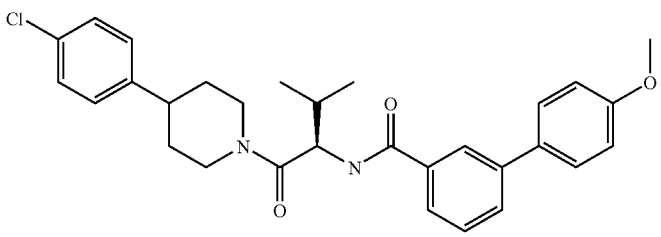 | Chiral | 505.4 |
| 408 | 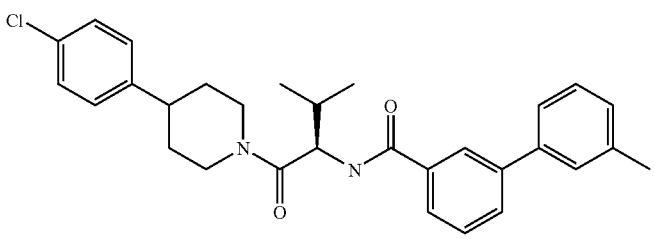 | Chiral | 489.4 |
| 409 | 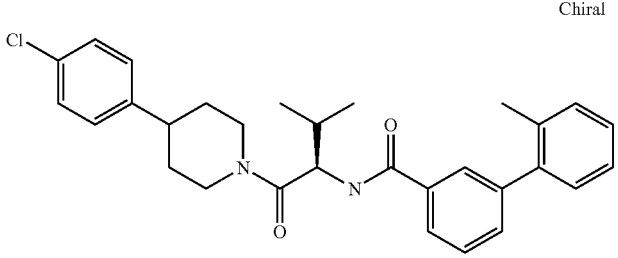 | Chiral | 489.4 |
| 410 | 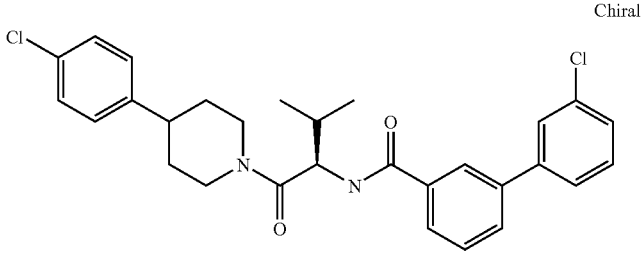 | Chiral | 509.3 |

TABLE 14-continued

| Example | Structure | | MS (M+) |
|---|---|---|---|
| 411 | 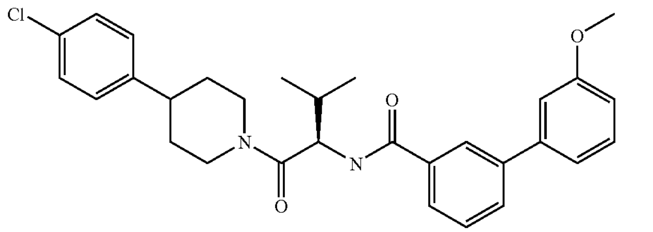 | Chiral | 505.4 |
| 412 | 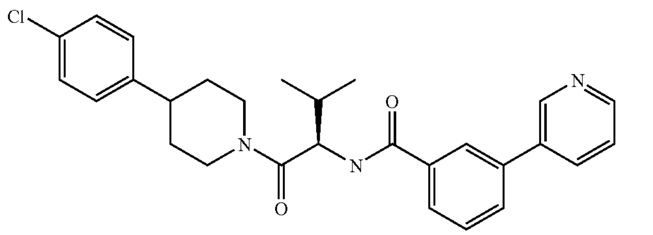 | Chiral | 476.3 |
| 413 | 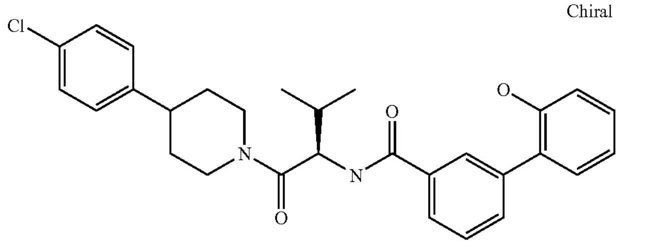 | Chiral | 491.3 |
| 414 | 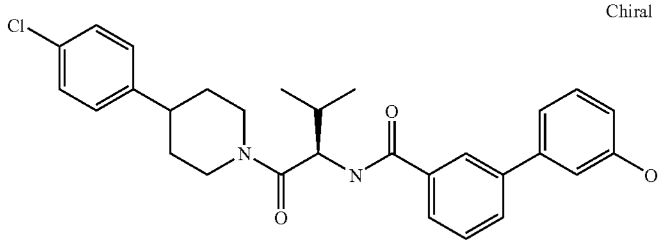 | Chiral | 491.3 |
| 415 | 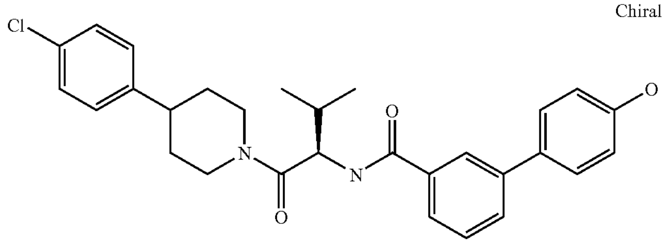 | Chiral | 491.3 |
| 416 | 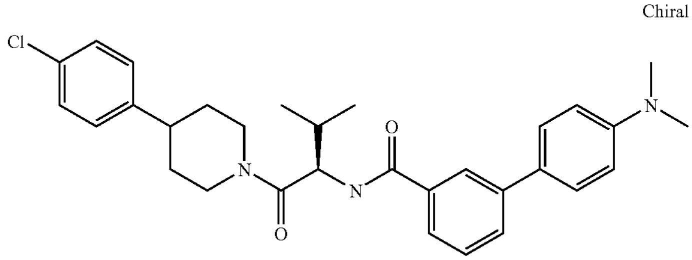 | Chiral | 518.4 |

TABLE 14-continued
| Example | Structure | | MS (M+) |
|---|---|---|---|
| 417 | 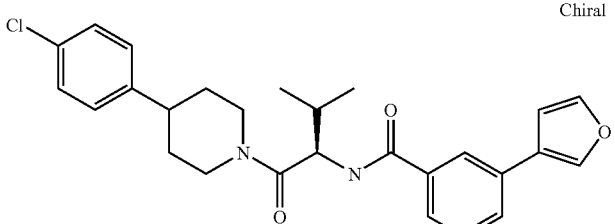 | Chiral | 465.3 |
| 418 | 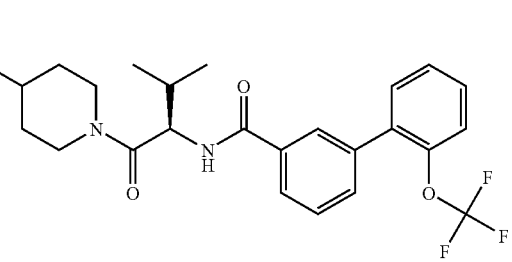 | | 559.3 |
| 419 | 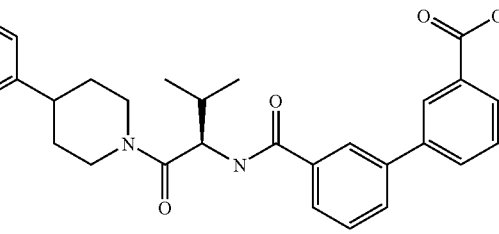 | Chiral | 519.3 |
| 420 | 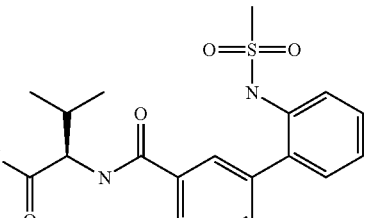 | Chiral | 568.3 |
| 421 | 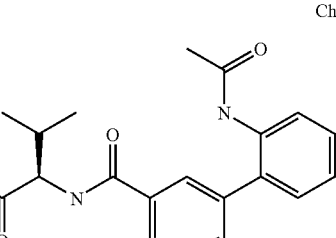 | Chiral | 532.3 |

TABLE 14-continued

| Example | Structure | | MS (M+) |
|---|---|---|---|
| 422 | 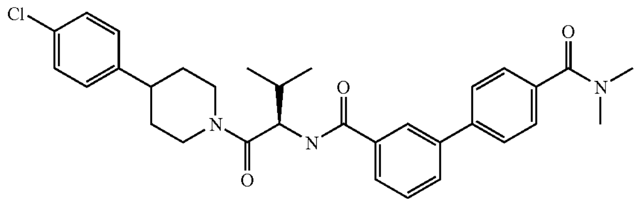 | Chiral | 546.3 |
| 423 | 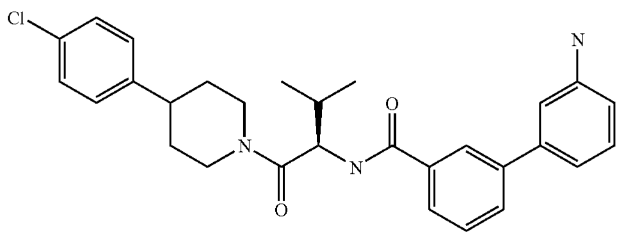 | Chiral | 490.3 |
| 424 | 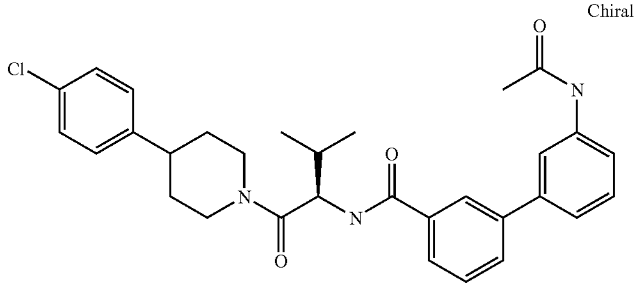 | Chiral | 532.3 |
| 425 | 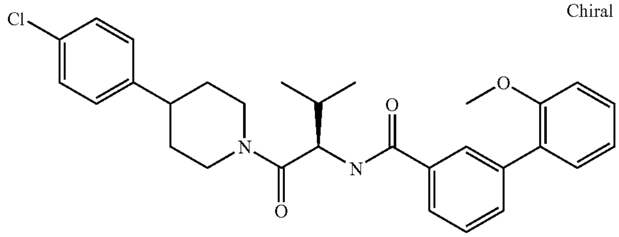 | Chiral | 505.3 |
| 426 | 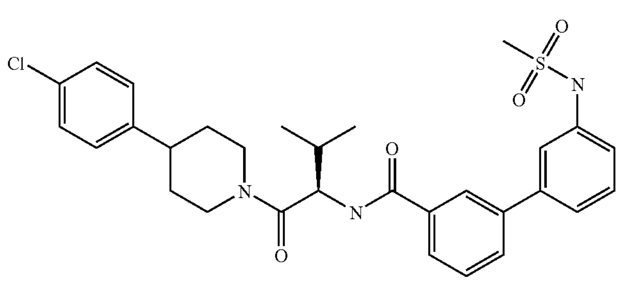 | Chiral | 568.3 |

TABLE 14-continued

| Example | Structure | | MS (M+) |
|---------|-----------|---|---------|
| 427 | 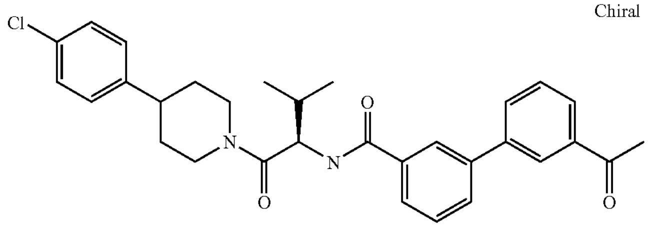 | Chiral | 517.3 |
| 428 | 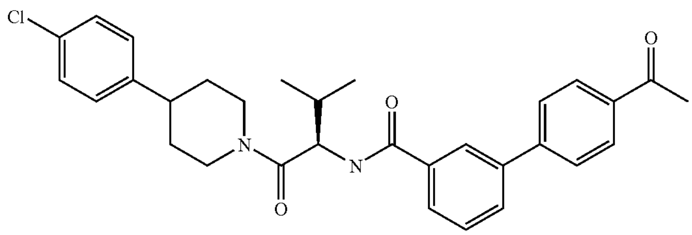 | Chiral | 517.3 |
| 429 | 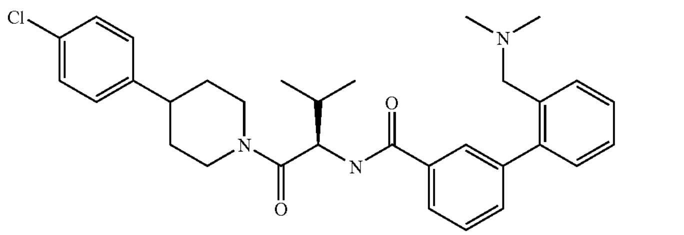 | Chiral | 532.3 |
| 430 | 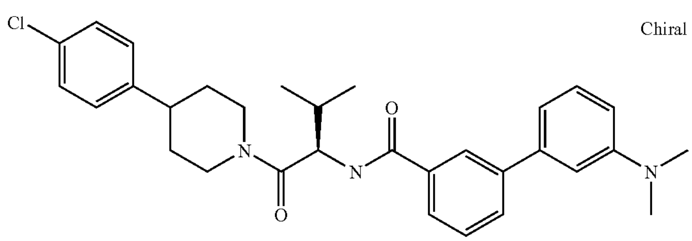 | Chiral | 518.3 |
| 431 | 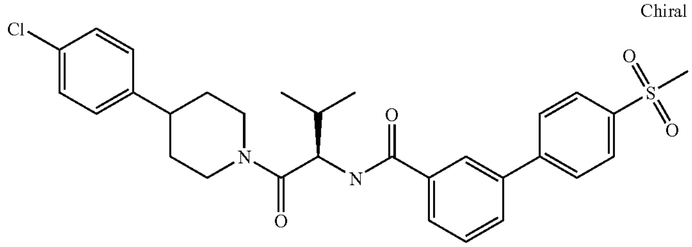 | Chiral | 553.3 |

TABLE 14-continued
| Example | Structure | | MS (M+) |
|---|---|---|---|
| 432 | 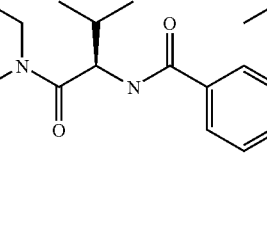 | Chiral | 517.3 |
| 433 | 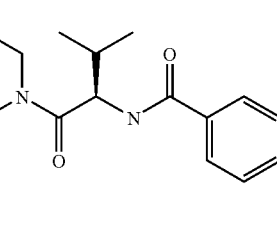 | Chiral | 481.2 |
| 434 | 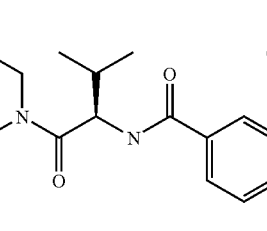 | Chiral | 509.2 |
| 435 | 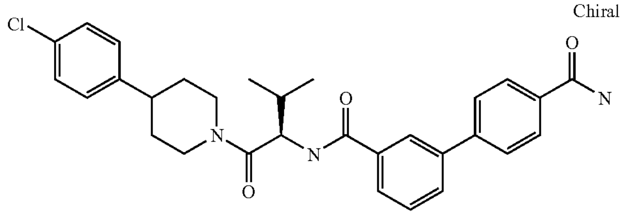 | Chiral | 518.3 |
| 436 | 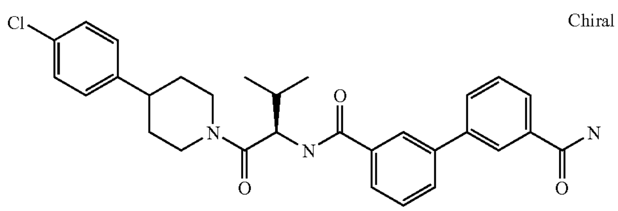 | Chiral | 518.3 |
| 437 | 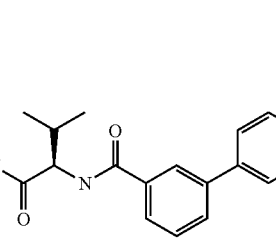 | Chiral | 553.2 |

TABLE 14-continued

| Example | Structure | | MS (M+) |
|---|---|---|---|
| 438 | 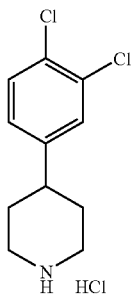 | Chiral | 490.3 |

Example 439

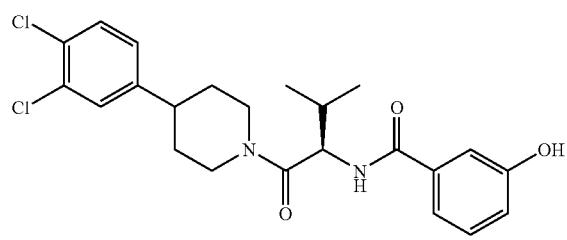

Step 1: Tert-butyl 4-(3,4-dichlorophenyl)-4-hydroxypiperidine-1-carboxylate

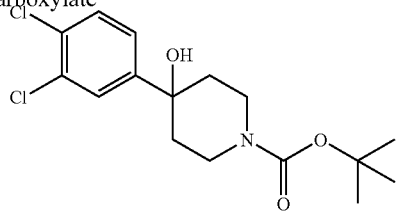

n-BuLi (2.5 M, 2 mL, 5.21 mmol) was added into a solution of 4-bromo-1,2-dichlorobenzene (1.07 g, 4.74 mmol) in dry THF (10 mL) at −78° C. The mixture was stirred for 20 mins and then a solution of tert-butyl 4-oxopiperidine-1-carboxylate (0.95 g, 4.74 mmol) in THF (5 mL) was added. The mixture was further stirred at −78° C. for 1 h. After this time, the reaction was quenched with NH$_4$Cl (aq., 15 mL), extracted with ethyl acetate (50 mL×3), dried over Na$_2$SO$_4$ and concentrated to yield a residue. The residue was purified by flash chromatography using 10-30% ethyl acetate in hexanes as an eluent to provide tert-butyl 4-(3,4-dichlorophenyl)-4-hydroxypiperidine-1-carboxylate (1.6 g, 90% purity, 88% yield) as a colorless oil. MS found: 346.3 (M$^+$).

Step 2: 4-(3,4-Dichlorophenyl)-1,2,3,6-tetrahydropyridine hydrochloride

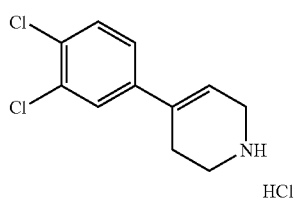

HCl (conc., 1.5 mL) was slowly added to a flask containing tert-butyl 4-(3,4-dichlorophenyl)-4-hydroxypiperidine-1-carboxylate (200 mg, 0.58 mmol). The mixture was stirred at rt for 30 mins, heated to 90° C. for 5 h and then cooled overnight. The resulting precipitate was collected by filtration to give 4-(3,4-dichlorophenyl)-1,2,3,6-tetrahydropyridine hydrochloride (107 mg, 70% yield). MS found: 215.6 (M$^+$).

Step 3: 4-(3,4-Dichlorophenyl)piperidine hydrochloride

A balloon filled with hydrogen was charged into a solution of 4-(3,4-dichlorophenyl)-1,2,3,6-tetrahydropyridine hydrochloride (107 mg, 0.41 mmol) in the presence of 5% Pd/C (5% mmol) after the system was degassed. The reaction was stirred at rt for 2 h, filtered, rinsed with MeOH and then concentrated to give 4-(3,4-Dichlorophenyl)piperidine hydrochloride (79 mg, 72% yield) as an oil. MS found: 266.4 (M$^+$).

Step 4: Example 439

Example 439 was prepared in a similar manner as described for the preparation of Example 75 by reacting 4-(3,4-dichlorophenyl)piperidine hydrochloride with N-Boc-D-valine, followed by Boc group removal and coupling with 3-hydroxy benzoic acid. MS found 449.2 (M$^+$).

Examples 440 to 458

Examples 440 to 458, as described in Table 15, were prepared in a similar manner as described for the preparation of Example 439. In the synthesis of Examples 449 to 458, the appropriate acid and piperidine needed to produce the product listed was used in place of the benzoic acid used in Example 439.

TABLE 15
| Example | Structure | MS (M+) |
|---|---|---|
| 440 | 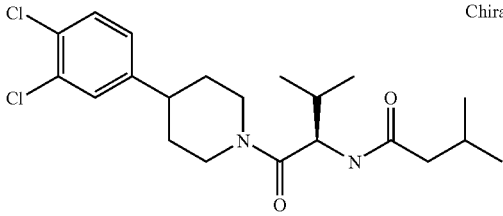 Chiral | 413.2 |
| 441 | 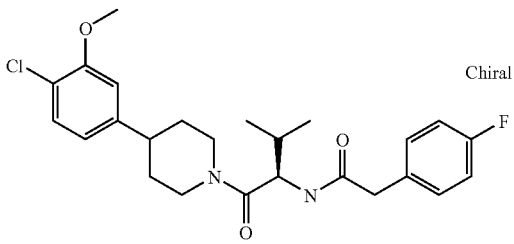 Chiral | 461.3 |
| 442 | 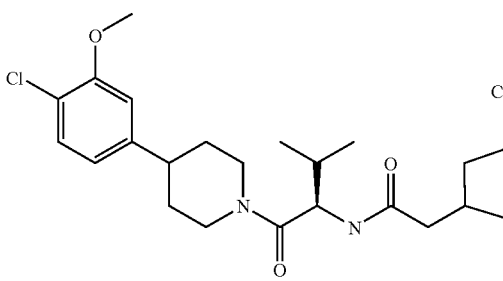 Chiral | 435.3 |
| 443 | 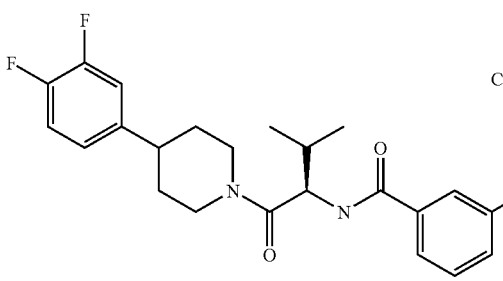 Chiral | 417.3 |
| 444 | 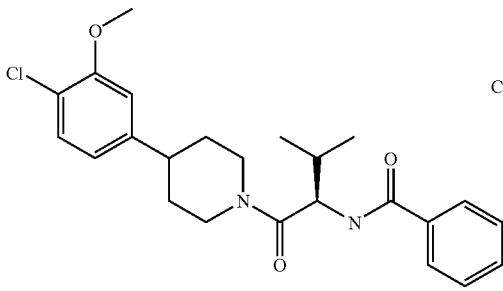 Chiral | 445.3 |

TABLE 15-continued
| Example | Structure | MS (M+) |
|---|---|---|
| 445 | 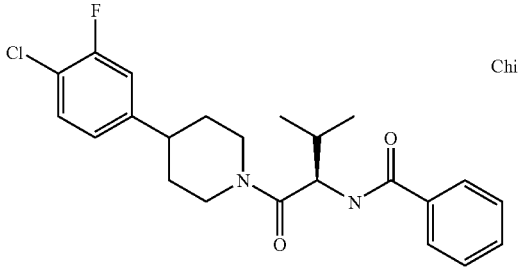 Chiral | 417.3 |
| 446 | 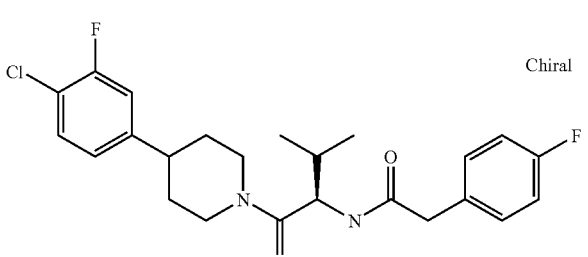 Chiral | 449 |
| 447 | 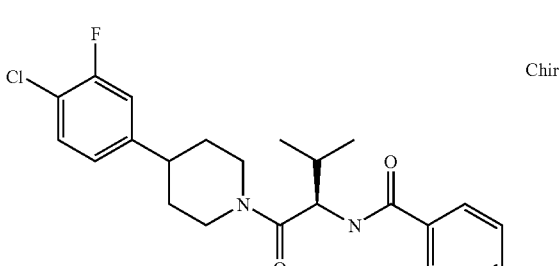 Chiral | 451.3 |
| 448 | 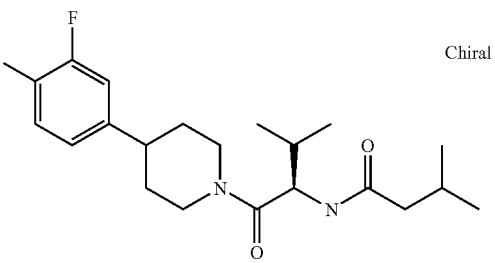 Chiral | 397.3 |
| 449 | 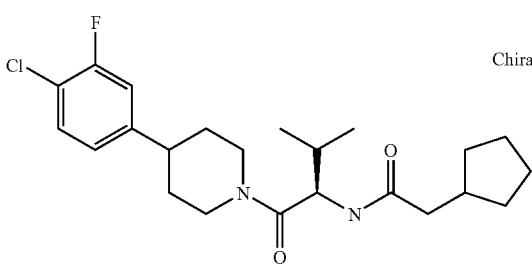 Chiral | 423.3 |

TABLE 15-continued
| Example | Structure | MS (M+) |
|---|---|---|
| 450 | 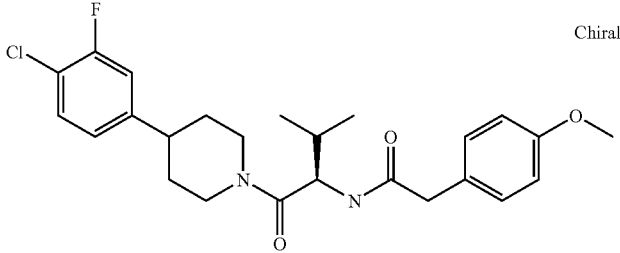 Chiral | 461.3 |
| 451 | 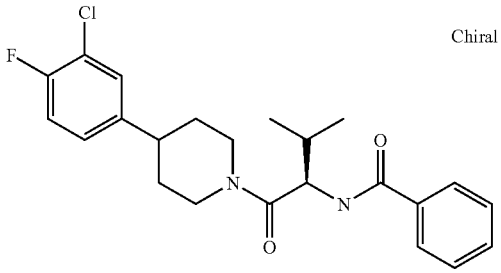 Chiral | 417.3 |
| 452 | 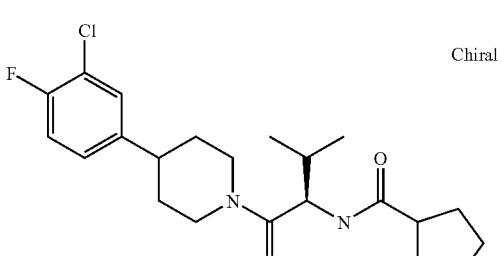 Chiral | 409.3 |
| 453 | 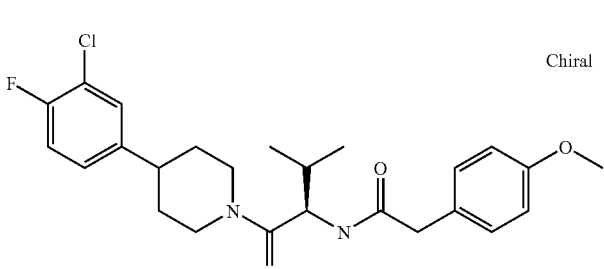 Chiral | 461.3 |
| 454 | 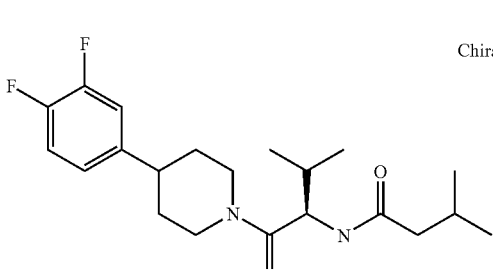 Chiral | 381.4 (M + H) |

TABLE 15-continued

| Example | Structure | MS (M+) |
|---|---|---|
| 455 | Chiral | 407.4 (M + H) |
| 456 | Chiral | 503.2 |
| 457 | Chiral | 415 |
| 458 | Chiral | 390.2 (M + H) |

Examples 459 to 497

Examples 459 to 497, as described in Table 16, were prepared in a similar manner as described for the preparation of Example 328. In the synthesis of Examples 459 to 496, the appropriate acid and piperidine needed to produce the product listed was used in place of the benzoic acid used in Example 328. Examples 463, 496 and 497 were prepared from the corresponding esters Examples 462, 494 and 495, respectively, via standard hydrolysis.

TABLE 16

| Example | Structure | MS (M+) |
|---|---|---|
| 459 | Chiral | 477.2 |

TABLE 16-continued

| Example | Structure | MS (M+) |
|---|---|---|
| 460 | Chiral | 436.3 (M + H) |
| 461 | Chiral | 461.2 |
| 462 | Chiral | 501.3 |
| 463 | Chiral | 487.3 |
| 464 | Chiral | 477.2 |
| 465 | Chiral | 459.2 |

TABLE 16-continued
| Example | Structure | MS (M+) |
|---|---|---|
| 466 | 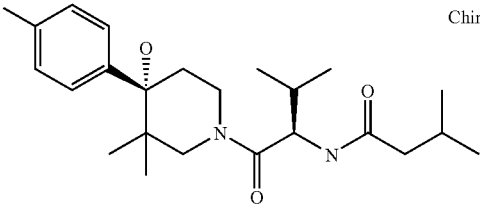 Chiral | 423.3 |
| 467 | 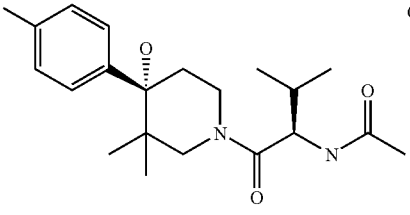 Chiral | 381.3 |
| 468 | 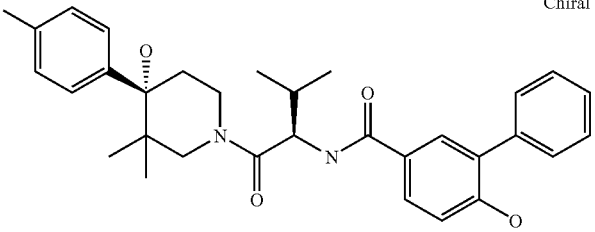 Chiral | 535.3 |
| 469 | 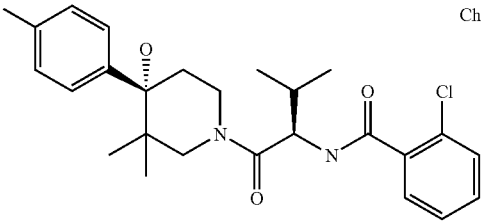 Chiral | 477.2 |
| 470 | 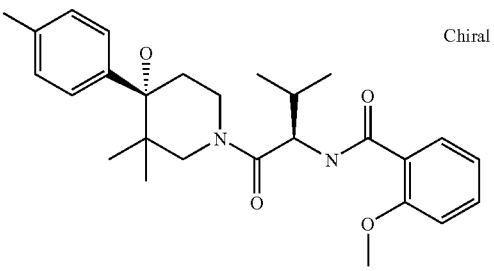 Chiral | 473.3 |
| 471 | 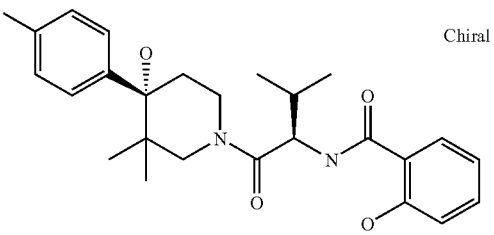 Chiral | 459.3 |

TABLE 16-continued
| Example | Structure | MS (M+) |
|---|---|---|
| 472 | 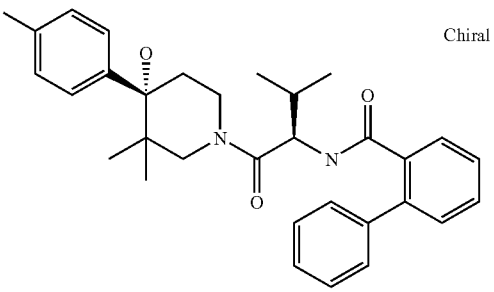 Chiral | 519.3 |
| 473 | 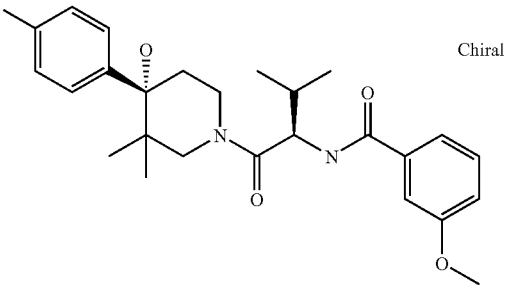 Chiral | 473.3 |
| 474 | 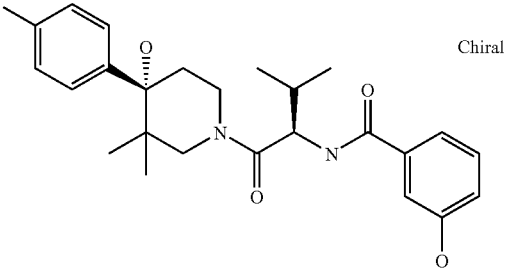 Chiral | 459.2 |
| 475 | 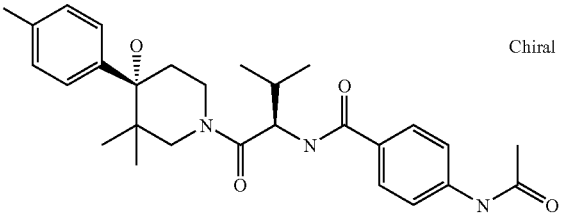 Chiral | 500.3 |
| 476 | 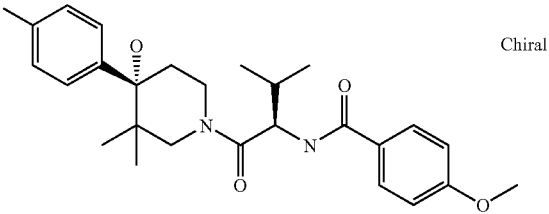 Chiral | 473.3 |

TABLE 16-continued
| Example | Structure | | MS (M+) |
|---|---|---|---|
| 477 | 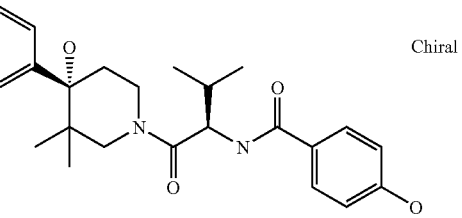 | Chiral | 459.3 |
| 478 | 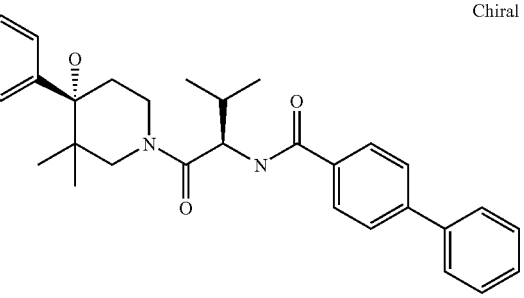 | Chiral | 519.4 |
| 479 | 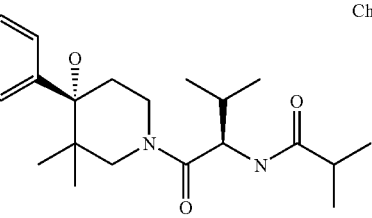 | Chiral | 409.4 |
| 480 | 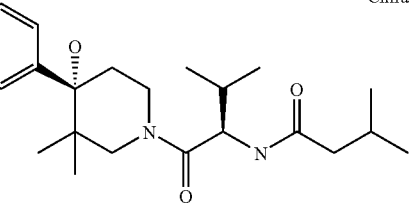 | Chiral | 423.3 |
| 481 | 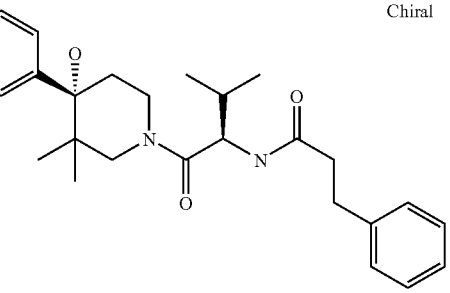 | Chiral | 471.3 |
| 482 | 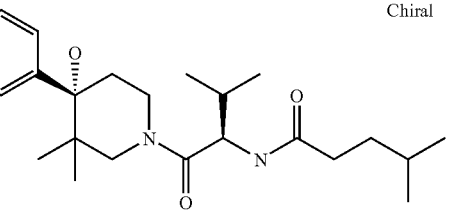 | Chiral | 437.4 |

TABLE 16-continued
| Example | Structure | | MS (M+) |
|---|---|---|---|
| 483 | 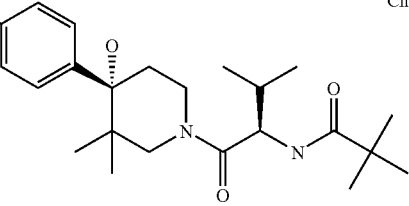 | Chiral | 423.4 |
| 484 | 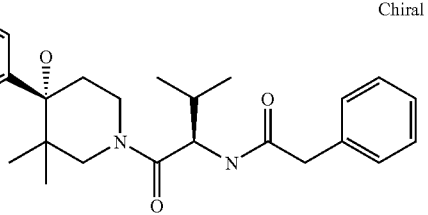 | Chiral | 457.3 |
| 485 | 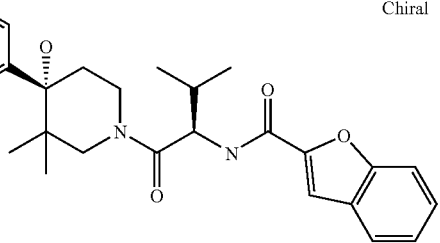 | Chiral | 483.3 |
| 486 | 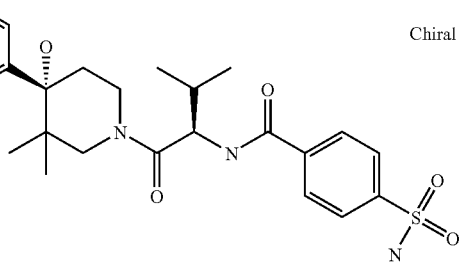 | Chiral | 522.3 |
| 487 | 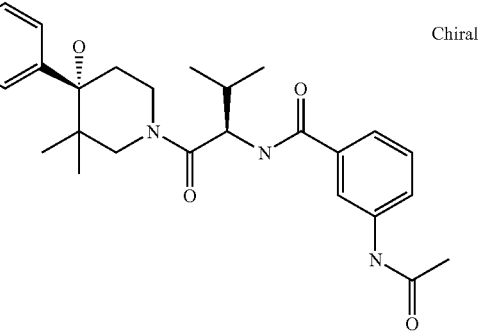 | Chiral | 500.3 |

TABLE 16-continued

| Example | Structure | | MS (M+) |
|---------|-----------|---|---------|
| 488 | 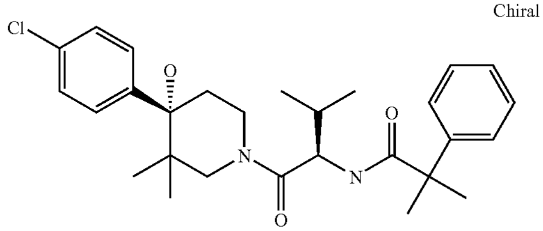 | Chiral | 485.2 |
| 489 | 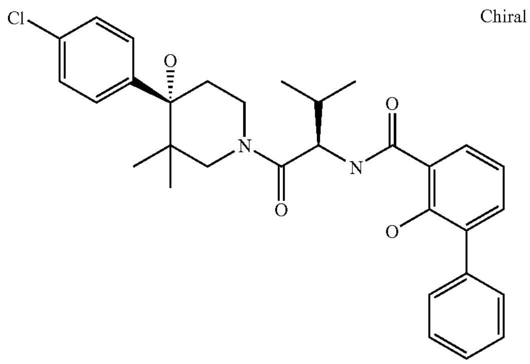 | Chiral | 535.3 |
| 490 | 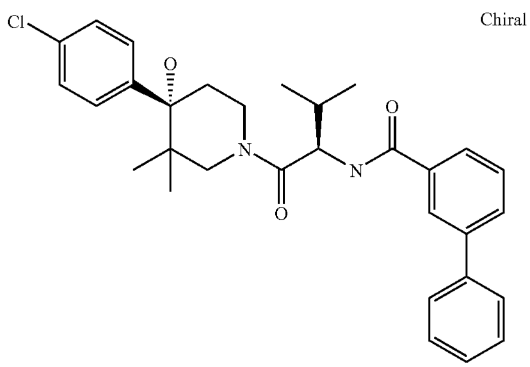 | Chiral | 519.3 |
| 491 | 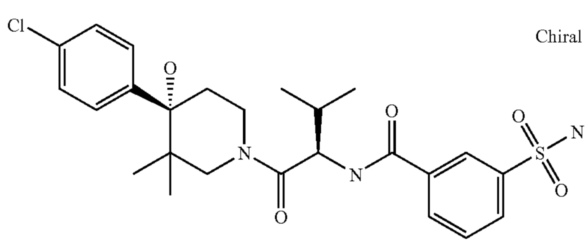 | Chiral | 522.3 |
| 492 | 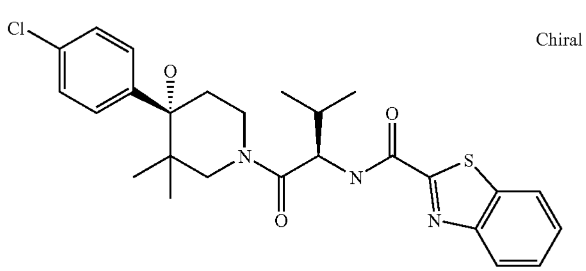 | Chiral | 500.3 |

TABLE 16-continued
| Example | Structure | | MS (M+) |
|---|---|---|---|
| 493 | 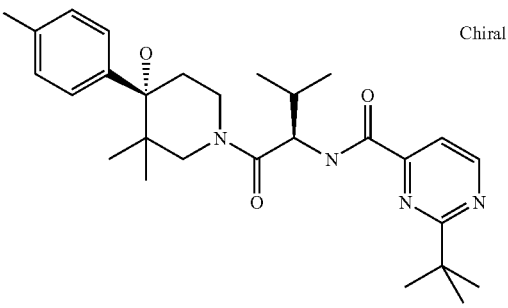 | Chiral | 501.3 |
| 494 | 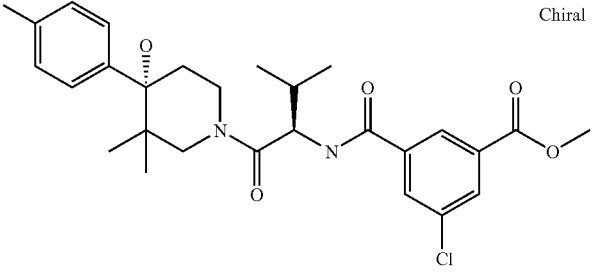 | Chiral | 535.2 |
| 495 | 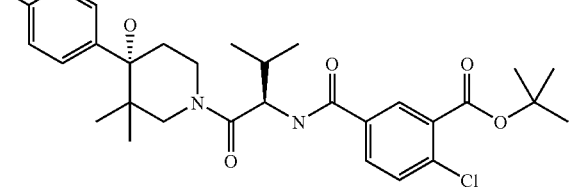 | Chiral | 577.2 |
| 496 | 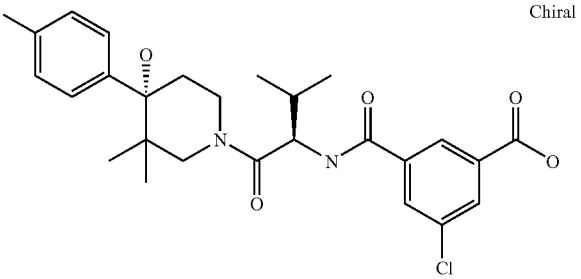 | Chiral | 521.1 |
| 497 | 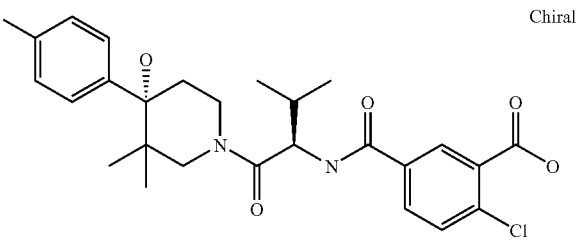 | Chiral | 521.1 |

Example 498

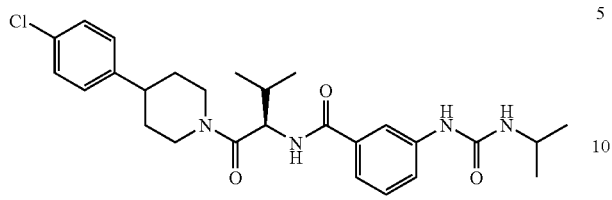

Example 498 was prepared in a similar manner as described for the preparation of Example 309 with the exception that isopropyl isocyanate was used in place of isobutyryl chloride. MS found: 499.3 (M+).

Example 499

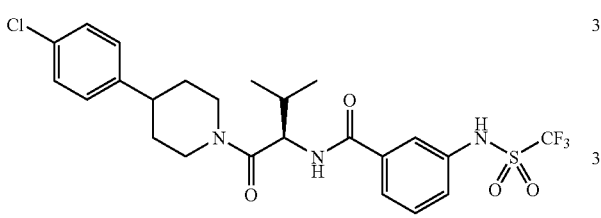

Example 499 was prepared in a similar manner as described for the preparation of Example 309 with the exception that trifluoromethanesulfonic anhydride was used in place of isobutyryl chloride. MS found: 545.9 (M+).

Example 500

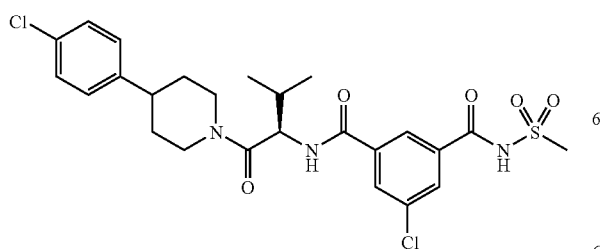

Example 500 was prepared by reacting with methyl sulfonamide and Example 394 in a similar manner as described for the preparation of Example 1. MS found: 553.9 (M+).

Example 501

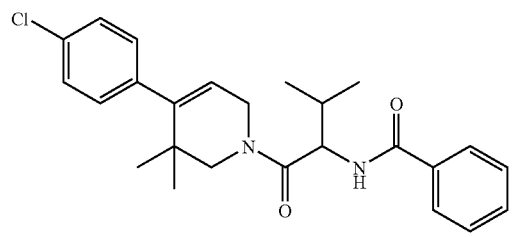

Step 1: 4-(4-Chlorophenyl)-3,3-dimethyl-1,2,3,6-tetrahydropyridine (S)-4-(4-chlorophenyl)-3,3-dimethylpiperidin-4-ol was dehydrated under acidic conditions in a similar manner as described for the preparation of Example 439 to give 4-(4-chlorophenyl)-3,3-dimethyl-1,2,3,6-tetrahydropyridine.

Step 2: Example 501

4-(4-Chlorophenyl)-3,3-dimethyl-1,2,3,6-tetrahydropyridine was coupled with racemic N-benzoyl valine in a similar manner as described for the preparation of Example 1 to give Example 501. MS found: 426.3 (M+).

Example 502

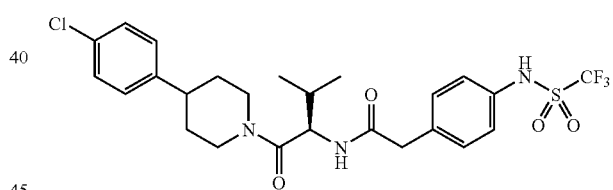

Step 1: (R)-2-(4-aminophenyl)-N-(1-(4-(4-chlorophenyl)piperidin-1-yl)-3-methyl-1-oxobutan-2-yl)acetamide

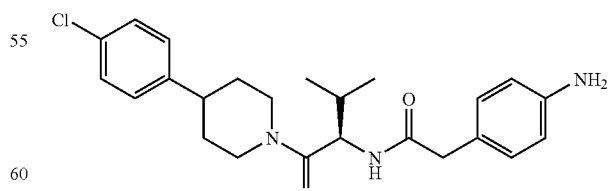

Example 382 was reduced under hydrogen balloon in a similar manner as described for the preparation of Example 305 to furnish the above amine.

Step 2: Example 502

The amine from Step 1 was treated with trifluoromethanesulfonic anhydride to furnish Example 502. MS found: 560.1 (M+).

Example 503

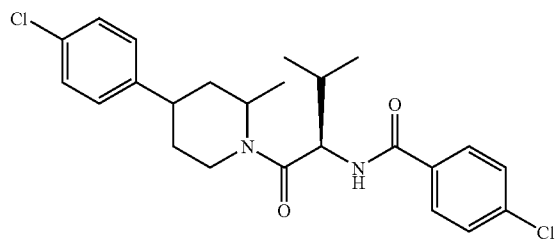

Step 1: Tert-butyl 4-(4-chlorophenyl)-2-methylpiperidine-1-carboxylate

A solution of N-Boc-4-chlorophenylpiperidine (6.0 g, 20.3 mmol) in ether (50 mL) was cooled to −78° C. and TMEDA (6.73 mL, 44.6 mmoL) was added followed by sec-butyl lithium (17.4 mL, 24.3 mmol) while maintaining the temperature below −60° C. After stirring for 5 h, iodomethane (1 eq) was added and the reaction was allowed to warm to rt. Once at the prescribed temperature, the reaction was quenched with water (50 mL) and the layers were separated. The aqueous layer was extracted with ether (50 mL) and the combined organic extracts were dried over $Na_2SO_4$, filtered and concentrated to an oil. The oil was purified by HPLC to give tert-butyl 4-(4-chlorophenyl)-2-methylpiperidine-1-carboxylate (1.35 g, 22% yield) as an oil. MS found: 310.3 (M+H).

Step 2: 4-(4-Chlorophenyl)-2-methylpiperidine hydrochloride 4-(4-Chlorophenyl)-2-methylpiperidine hydrochloride was prepared from tert-butyl 4-(4-chlorophenyl)-2-methylpiperidine-1-carboxylate in a similar manner as described for the preparation of Step 2, Example 439.

Step 3: Example 503

4-(4-Chlorophenyl)-2-methylpiperidine hydrochloride was converted to Example 503 in a similar manner as described for the preparation of the 3-step sequence outlined in Preparation C and Example 75 (EDC/HOBt coupling with Boc-D-valine, Boc removal with HCl in dioxane, and finally EDC/HOBt coupling with 4-chloro benzoic acid). MS found: 447.2 (M+)

Example 504

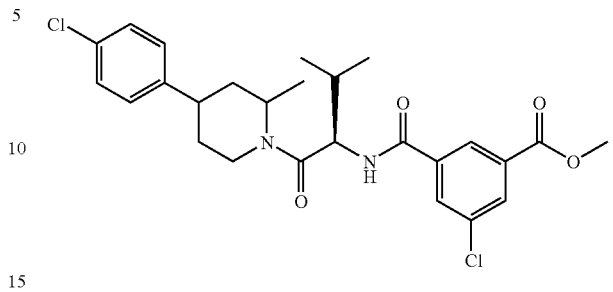

Example 504 was prepared in a similar manner as described for the preparation of Example 503 using (2R)-2-amino-1-(4-(4-chlorophenyl)-2-methylpiperidin-1-yl)-3-methylbutan-1-one hydrochloride with the exception that 3-chloro-5-(methoxycarbonyl)benzoic acid was used in place of 4-chloro benzoic acid in Step 3. MS found: 505.1 (M+).

Example 505

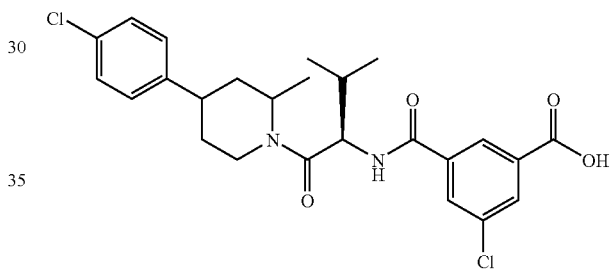

Example 505 was prepared from 504 under standard ester hydrolysis (1 N NaOH, methanol) conditions. MS found: 491.2 (M+).

Example 506

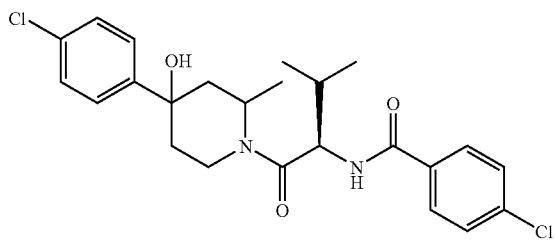

Step 1: (2R)-2-amino-1-(4-(4-chlorophenyl)-4-hydroxy-2-methylpiperidin-1-yl)-3-methylbutan-1-one hydrochloride (2R)-2-amino-1-(4-(4-chlorophenyl)-4-hydroxy-2-methylpiperidin-1-yl)-3-methylbutan-1-one hydrochloride was prepared from tert-Butyl 2-methyl-4-oxopiperidine-1-carboxylate in a similar manner as described for the preparation of Example 439. MS found: 463.2.

Step 2: Example 506

4-Chlorobenzoic acid was coupled to (2R)-2-amino-1-(4-(4-chlorophenyl)-4-hydroxy-2-methylpiperidin-1-yl)-3-methylbutan-1-one hydrochloride in a similar manner as described for the preparation of Example 75. MS found: 463.2 (M+).

Example 507

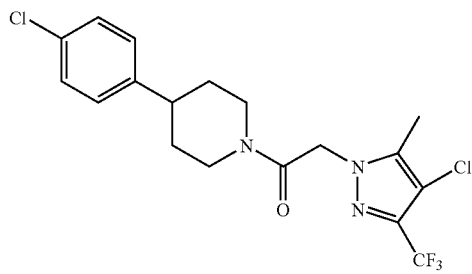

To a stirred solution of 2-(4-chloro-5-methyl-3-(trifluoromethyl)-1H-pyrazol-1-yl)acetic acid (see US 2004/0162282, 36.5 mg, 0.15 mmol), EDCi (32 mg, 0.17 mmol) and HOBt (22 mg, 0.17 mmol) in DMF (0.3 mL) was added 4-chlorophenylpiperidine hydrochloride (42 mg, 0.18 mmol) and DIPEA (66 μL). Upon completion of addition, the reaction mixture was stirred for 18 h and then purified directly by HPLC to provide Example 507 (46.5 mg, 74%) as a white solid. MS found: 420.1 (M+).

Example 508

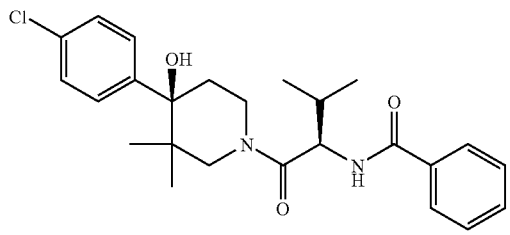

Example 508 was prepared in a similar manner as described for the preparation of Example 328 using (R)-4-(4-chlorophenyl)-3,3-dimethylpiperidin-4-ol. MS found: 443.3 (M+).

Example 509

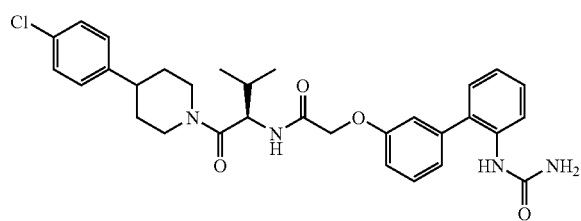

Step 1: 1-(3'-hydroxybiphenyl-2-yl)urea

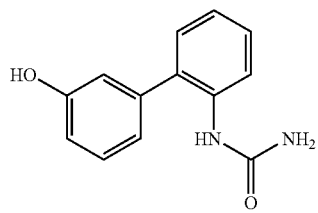

3-Hydroxy phenol and 2-bromophenyl urea were reacted under Suzuki cross coupling conditions in a similar manner as described for the preparation of Example 294 to provide 1-(3'-hydroxybiphenyl-2-yl)urea.

Step 2: Example 509

To a stirred solution of (R)-2-chloro-N-(1-(4-(4-chlorophenyl)piperidin-1-yl)-3-methyl-1-oxobutan-2-yl)acetamide (40 mg, 0.14 mmol) and $K_2CO_3$ (39 mg, 0.28 mmol) in DMSO (2 mL) was added 1-(3'-hydroxybiphenyl-2-yl)urea (32 mg, 0.14 mmol). Upon completion of addition, the reaction mixture was stirred or 18 h. After this time, the reaction mixture was purified via preparative HPLC to provide Example 509 (36% yield). MS found: 563.2 (M+).

Example 510

1-((R)-1-((S)-4-(4-chlorophenyl)-4-hydroxy-3,3-dimethylpiperidin-1-yl)-3-methyl-1-oxobutan-2-yl)-3-methylurea

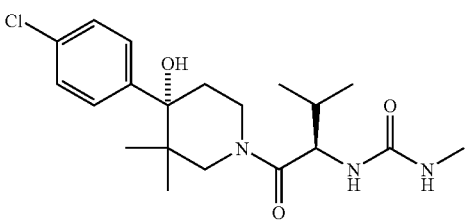

A reaction tube was charged with methyl isocyanate (3 μL), (R)-2-amino-1-((S)-4-(4-chlorophenyl)-4-hydroxy-3,3-dimethylpiperidin-1-yl)-3-methylbutan-1-one hydrochloride (20 mg) and THF (2 mL). Triethylamine (7.4 μL) was added and the reaction mixture was shaken overnight at rt. After this time, the resulting solution concentrated and purified by preparative silica gel chromatography (100% EtOAc to 20% MeOH/$CH_2Cl_2$) to provide Example 510. MS found: $(M+H)^+= 396.3$.

Example 511

1-((R)-1-((S)-4-(4-chlorophenyl)-4-hydroxy-3,3-dimethylpiperidin-1-yl)-3-methyl-1-oxobutan-2-yl)-3-cyclopentylurea

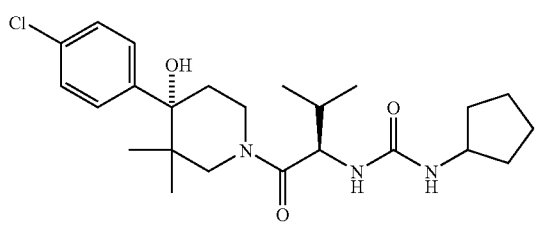

A reaction tube was charged with cyclopentyl isocyanate (9 μL), (R)-2-amino-1-((S)-4-(4-chlorophenyl)-4-hydroxy-3,3-dimethylpiperidin-1-yl)-3-methylbutan-1-one hydrochloride (30 mg) and THF (2 mL). Triethylamine (11 μL) was added and the reaction mixture was shaken overnight at rt. After this time, the resulting solution concentrated and purified by preparative silica gel chromatography (100% EtOAc to 20% MeOH/CH$_2$Cl$_2$) to provide Example 511. MS found: (M+H)$^+$=450.2.

Example 512

(R)—N-(1-(4-(4-chlorophenyl)-4-hydroxypiperidin-1-yl)-3-methyl-1-oxobutan-2-yl)cyclopentanecarboxamide

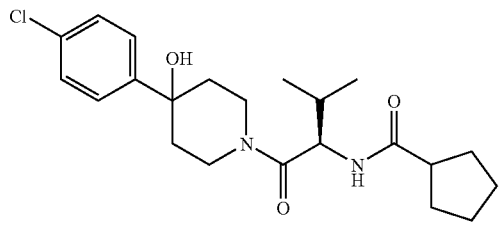

Step 1: (R)-tert-butyl 1-(4-(4-chlorophenyl)-4-hydroxypiperidin-1-yl)-3-methyl-1-oxobutan-2-ylcarbamate

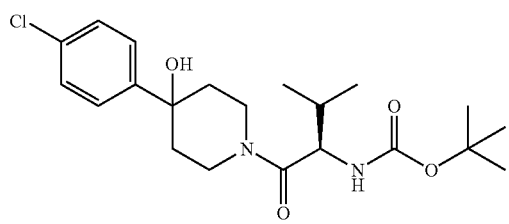

N-Boc-D-valine (2.22 g, 10.2 mmol), EDC (1.96 g, 10.2 mmol), HOBt (1.38 g, 10.2 mmol) was dissolved in dichloromethane (40 mL). DIPEA (4.0 mL, 23.3 mmol) and 4-hydroxy-(4-chlorophenyl)piperidine (1.98 g, 9.34 mmol) was added and the solution was stirred at rt for 2 h. The reaction was concentrated and the resulting oily residue partitioned between EtOAc (150 mL) and water (50 mL), shaken and then separated. The organic layer was then washed with aq NaHCO$_3$ (50 mL) and brine and the combined organic fractions were dried over solid sodium sulfate. The solution was filtered and concentrated by to give (R)-tert-butyl 1-(4-(4-chlorophenyl)-4-hydroxypiperidin-1-yl)-3-methyl-1-oxobutan-2-ylcarbamate (3.9 g) as a white foam. MS found: (M+)$^+$=411.1.

Step 2: (R)-2-amino-1-(4-(4-chlorophenyl)-4-hydroxypiperidin-1-yl)-3-methylbutan-1-one hydrochloride

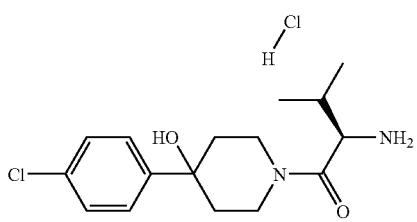

A 4M solution of HCl in dioxane (10 mL) was added to (R)-tert-butyl 1-(4-(4-chlorophenyl)-4-hydroxypiperidin-1-yl)-3-methyl-1-oxobutan-2-ylcarbamate (2.0 g) and the resulting solution was allowed to stir at rt. for 1 h. After this time, the solvent was removed by rotary evaporation to provide an oil. The oil was dried overnight in vacuo to provide (R)-2-amino-1-(4-(4-chlorophenyl)-4-hydroxypiperidin-1-yl)-3-methylbutan-1-one hydrochloride as a white foam.

Step 3: Example 512

To a solution of (R)-2-amino-1-(4-(4-chlorophenyl)-4-hydroxypiperidin-1-yl)-3-methylbutan-1-one hydrochloride (31.1 mg, 0.09 mmol) and cyclopentane carbonyl chloride (12 μL, 0.09 mmoL) in dichloromethane (0.5 mL) was added DIPEA (34.3 μL, 0.2 mmol) and the reaction solution was allowed to stir at rt for 1 h. The solvents were removed and the residue was partitioned between EtOAc (3 mL) and water (1.5 mL). the layers were separated, dried over sodium sulfate, filtered and concentrated in vacuo. The crude product was purified via column chromatography (33% EtOAc/heptane) to afford Example 512 (29.1 mg, 80% yield) as a white solid. MS found 407.04 (M+)+; HPLC rt 3.66 min.

Example 513

(N-((2R)-1-(4-(4-chloro-3-methoxyphenyl)-4-hydroxy-3,3-dimethylpiperidin-1-yl)-3-methyl-1-oxobutan-2-yl)cyclopentanecarboxamide

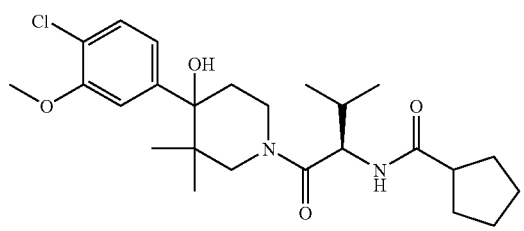

Step 1: tert-butyl 4-(4-chloro-3-methoxyphenyl)-4-hydroxy-3,3-dimethylpiperidine-1-carboxylate

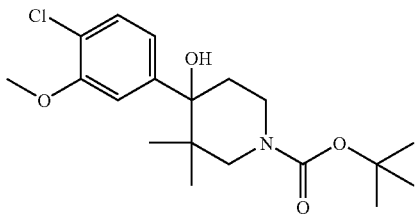

To a solution of 5-bromo-2-chloro-anisole (1.613 g, 7.3 mmol) in THF (15 mL) at −78° C. was added n-butyl lithium (4.75 mL, 7.6 mmol, 1.6 M) dropwise over 15 min and the resulting solution was allowed to stir at −78° C. for 1 h. A solution of tert-butyl 3,3-dimethyl-4-oxopiperidine-1-carboxylate (prepared in the manner described in International Patent Application WO 04/043965, 754 mg, 3.32 mmol) in THF (5 mL) was added dropwise via canula. The reaction was stirred for 2 h at −78° C. then allowed to warm to rt slowly over 30 min at which time the mixture was heated at 50° C. for 30 min. The reaction was cooled to rt, quenched by the addition of aq NH$_4$Cl, diluted with water and extracted into EtOAc. The combined organic extracts were dried over magnesium sulfate, filtered and concentrated. The residue was purified via column chromatography (15% to 33% to 50% EtOAc/heptane to afford tert-butyl 4-(4-chloro-3-methoxyphenyl)-4-hydroxy-3,3-dimethylpiperidine-1-carboxylate (728 mg, 60% yield).

Step 2: 4-(4-chloro-3-methoxyphenyl)-3,3-dimethylpiperidin-4-ol hydrochloride

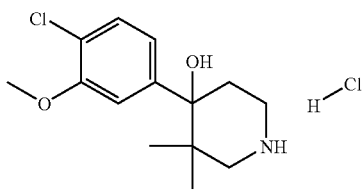

tert-Butyl 4-(4-chloro-3-methoxyphenyl)-4-hydroxy-3,3-dimethylpiperidine-1-carboxylate (1.36 g, 2.39 mmol) was added 4N HCl in dioxane (10 mL) and stirred for 30 min. The solvents were removed in vacuo and the resulting solids were dried azeotropically with toluene and then further dried under high vacuum to afford 4-(4-chloro-3-methoxyphenyl)-3,3-dimethylpiperidin-4-ol hydrochloride as a white solid.

Step 3: tert-butyl (2R)-1-(4-(4-chloro-3-methoxyphenyl)-4-hydroxy-3,3-dimethylpiperidin-1-yl)-3-methyl-1-oxobutan-2-ylcarbamate

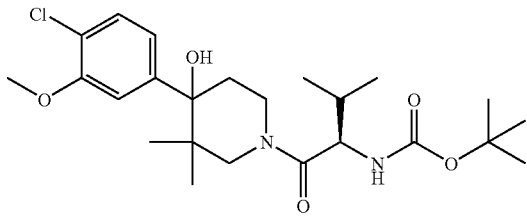

N-Boc-D-valine (85 mg, 0.39 mmol), EDC (75 mg, 0.39 mmol), HOBt (53 mg, 0.39 mmol) was dissolved in dichloromethane (2 mL). 4-(4-Chloro-3-methoxyphenyl)-3,3-dimethylpiperidin-4-ol hydrochloride (100 mg, 0.33 mmol) was added followed by DIPEA (136 μL, 0.78 mmol) and the solution was stirred at rt for 10 min. The reaction was concentrated and the resulting oily residue was purified via column chromatography (10% to 50% EtOAc/heptane) to furnish tert-butyl (2R)-1-(4-(4-chloro-3-methoxyphenyl)-4-hydroxy-3,3-dimethylpiperidin-1-yl)-3-methyl-1-oxobutan-2-ylcarbamate (153 mg, 99% yield) MS found: (M-Boc)$^+$ =396.3.

Step 4: (2R)-2-amino-1-(4-(4-chloro-3-methoxyphenyl)-4-hydroxy-3,3-dimethylpiperidin-1-yl)-3-methylbutan-1-one hydrochloride

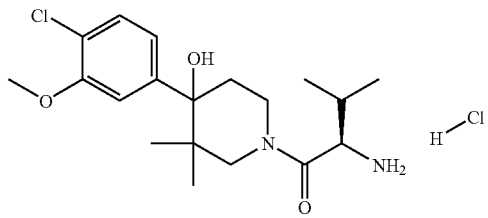

tert-Butyl (2R)-1-(4-(4-chloro-3-methoxyphenyl)-4-hydroxy-3,3-dimethylpiperidin-1-yl)-3-methyl-1-oxobutan-2-ylcarbamate (153 mg, 0.33 mmol) was added 4N HCl in dioxane (2 mL) and stirred for 60 min. The solvents were removed in vacuo and the resulting solids were dried azeotropically with toluene and then further dried under high vacuum to afford (2R)-2-amino-1-(4-(4-chloro-3-methoxyphenyl)-4-hydroxy-3,3-dimethylpiperidin-1-yl)-3-methylbutan-1-one hydrochloride as a white solid.

Step 5: Example 513

To a solution of (2R)-2-amino-1-(4-(4-chloro-3-methoxyphenyl)-4-hydroxy-3,3-dimethylpiperidin-1-yl)-3-methylbutan-1-one hydrochloride (20 mg, 0.05 mmol) and cyclopentane carbonyl chloride (7.4 μL, 0.06 mmoL) in dichloromethane (0.3 mL) was added DIPEA (22 μL, 0.13 mmol) and the reaction solution was allowed to stir at rt for 16 h. The solvents were removed and the residue was purified preparative HPLC to afford Example 513 (14.5 mg, 60% yield) as a white solid. MS found 465.3 (M+)$^+$; HPLC rt 3.89 min.

Example 514

N—((R)-1-((S)-4-(4-chlorophenyl)-4-hydroxy-3,3-dimethylpiperidin-1-yl)-5-guanidino-1-oxopentan-2-yl)cyclopentanecarboxamide

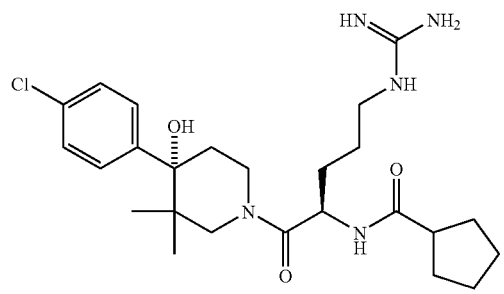

Step 1:

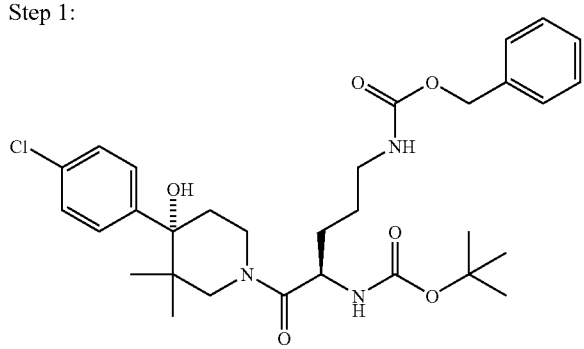

To a solution of Boc-D-ORN(Cbz)-OH (336 mg, 0.92 mmol), EDC (176 mg, 0.92 mmol) and HOBt (124 mg, 0.92 mmol) in dichloromethane (5 mL) was added (S)-4(4-chlorphenyl)-3,3-dimethylpiperdin-4-ol (200 mg, 0.83 mmol) followed by DIPEA (0.16 mL, 0.92 mmol). The solution was stirred for 2 h then poured into EtOAc and washed successively with water, aq. NaHCO₃, and brine. The organic layer was dried over magnesium sulfate, concentrated and dried under high vacuum to afford the crude solid which was used without further purification. MS found 588.4 (M+)$^+$.

Step 2: Benzyl (R)-4-amino-5-((S)-4-(4-chlorophenyl)-4-hydroxy-3,3-dimethylpiperidin-1-yl)-5-oxopentylcarbamate hydrochloride

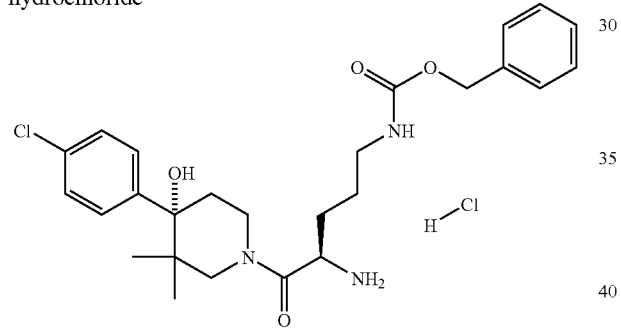

The product of step 1, above was deprotected in 4N HCl in dioxane (5 mL) to furnish benzyl (R)-4-amino-5-((S)-4-(4-chlorophenyl)-4-hydroxy-3,3-dimethylpiperidin-1-yl)-5-oxopentylcarbamate hydrochloride (463 mg, crude product).

Step 3: benzyl (R)-5-((S)-4-(4-chlorophenyl)-4-hydroxy-3,3-dimethylpiperidin-1-yl)-4-(cyclopentanecarboxamido)-5-oxopentylcarbamate

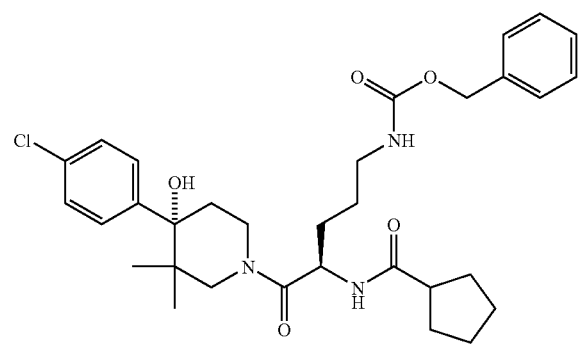

Benzyl (R)-4-amino-5-((S)-4-(4-chlorophenyl)-4-hydroxy-3,3-dimethylpiperidin-1-yl)-5-oxopentylcarbamate hydrochloride (50.5 mg, 0.096 mmol) was dissolved in dichloromethane (0.5 mL) and added cyclopentane carbonylchloride (14 µL, 0.12 mmol) followed by DIPEA (42 µL, 0.24 mmol). The solution was stirred for 2 h, concentrated, and partitioned between EtOAc (2 mL) and aq NaHCO₃ (0.5 mL). The EtOAc layer was separated, dried over magnesium sulfate, and concentrated to give benzyl (R)-5-((S)-4-(4-chlorophenyl)-4-hydroxy-3,3-dimethylpiperidin-1-yl)-4-(cyclopentanecarboxamido)-5-oxopentylcarbamate which was used without further purification.

Step 4: N—((R)-5-amino-1-((S)-4-(4-chlorophenyl)-4-hydroxy-3,3-dimethylpiperidin-1-yl)-1-oxopentan-2-yl)cyclopentanecarboxamide 2,2,2-trifluoroacetate

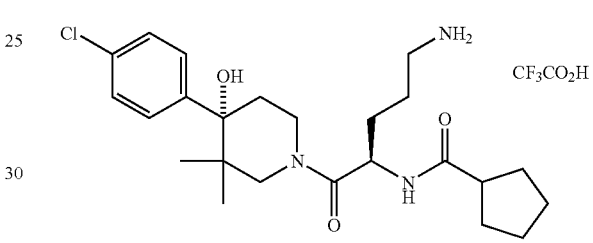

Benzyl (R)-5-((S)-4-(4-chlorophenyl)-4-hydroxy-3,3-dimethylpiperidin-1-yl)-4-(cyclopentanecarboxamido)-5-oxopentylcarbamate (0.096 mmol from step 3) was added HBr in acetic acid (0.5 mL) and the resulting solution was stirred for 1 h. Ether (15 mL) was added and stirring continued for an additional hour. The ether was removed via pipette and the gummy solids were washed again with ether. The residue was dissolved in MeOH, added solid potassium carbonate then filtered. The crude solution was purified via preparative HPLC to afford N—((R)-5-amino-1-((S)-4-(4-chlorophenyl)-4-hydroxy-3,3-dimethylpiperidin-1-yl)-1-oxopentan-2-yl)cyclopentanecarboxamide 2,2,2-trifluoroacetate (20.6 mg, 38% yield). MS found 450.29 (M+)$^+$.

Step 5: Example 514

To a mixture of afford N—((R)-5-amino-1-((S)-4-(4-chlorophenyl)-4-hydroxy-3,3-dimethylpiperidin-1-yl)-1-oxopentan-2-yl)cyclopentanecarboxamide 2,2,2-trifluoroacetate (10.6 mg, 0.019 mmol) and 1H-pyrazole-1-carboxamidine hydrochloride (3.03 mg, 0.021 mmol) in DMF was added DIPEA (13.1 µl, 0.075 mmol). The reaction mixture was stirred for 3 h at room temperature. The crude reaction mixture was diluted with MeOH and purified directly by preparative HPLC to give Example 514 (8.1 mg, 60% yield) as a white solid. MS found: 492.23 (M+)$^+$.

Example 515

2-(3-(3-((R)-1-((S)-4-(4-chlorophenyl)-4-hydroxy-3,3-dimethylpiperidin-1-yl)-3-methyl-1-oxobutan-2-ylcarbamoyl)phenyl)ureido)acetic acid

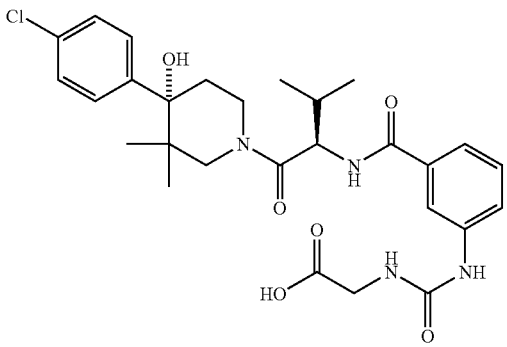

Step 1: 3-(3-(2-ethoxy-2-oxoethyl)ureido)benzoic acid

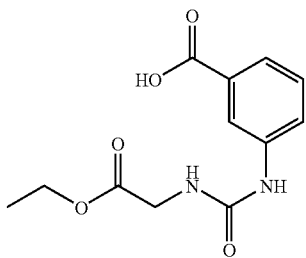

To a solution of 3-aminobenzoic acid (140 mg, 1 mmol) in THF (5 mL) at 0° C. was added ethyl isocyanato acetate (150 µL, 1.3 mmol). The reaction solution was allowed to warm to room temperature and stir for 18 h. The mixture was then poured into EtOAc (40 mL) and washed successively with water (15 mL) and brine (15 mL). The organic layer was dried over Na$_2$SO$_3$, filtered and concentrated to an oil which was used without further purification. MS found 267.17 (M+)$^+$.

Step 2: ethyl 2-(3-(3-((R)-1-((S)-4-(4-chlorophenyl)-4-hydroxy-3,3-dimethylpiperidin-1-yl)-3-methyl-1-oxobutan-2-ylcarbamoyl)phenyl)ureido)acetate

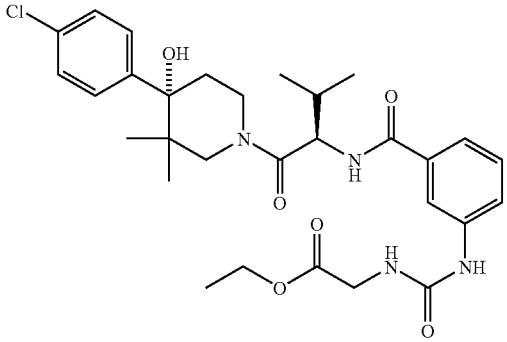

To a resealable vial was added (R)-2-amino-1-((S)-4-(4-chlorophenyl)-4-hydroxy-3,3-dimethylpiperidin-1-yl)-3-methylbutan-1-one, HCl, (24.1 mg, 0.064 mmol), 3-(3-(2-ethoxy-2-oxoethyl)ureido)benzoic acid (17.10 mg, 0.064 mmol), and benzotriazol-1-yloxytris(dimethylamino)-phosphonium hexafluorophosphate(BOP) (28.4 mg, 0.064 mmol). The solids were then added DMF (0.25 ml) followed by DIPEA (0.022 mL, 0.126 mmol). After stirring for 1 h, water (1.25 mL) was added to the reaction mixture and the precipitated solids stirred rapidly for several hours. The solids were collected by filtration and washed with water (2×0.5 mL) to give ethyl 2-(3-(3-((R)-1-((S)-4-(4-chlorophenyl)-4-hydroxy-3,3-dimethylpiperidin-1-yl)-3-methyl-1-oxobutan-2-ylcarbamoyl)phenyl)ureido)acetate (34.8 mg, 90% yield) a white solid. MS found: 587.26 (M+)$^+$.

Step 3: Example 515

To a solution of ethyl 2-(3-(3-((R)-1-((S)-4-(4-chlorophenyl)-4-hydroxy-3,3-dimethylpiperidin-1-yl)-3-methyl-1-oxobutan-2-ylcarbamoyl)phenyl)ureido)acetate, (34 mg, 0.058 mmol) in THF (0.2 mL) and methanol (0.2 mL) was added aqueous NaOH (1N) (60 µL, 0.058 mmol). HPLC/LCMS at 1 h indicates complete consumption of starting material and conversion to product (559.26, M+). The reaction was then neutralized with 1 N HCl (0.06 mL), diluted with water (0.2 mL) and concentrated to remove organic solvents. The resulting oily suspension was dissolved in methanol and purified directly by preparative HPLC. The product containing fraction was concentrated and the solids dried under high vacuum to give Example 515 (27.7 mg, 71% yield) as a white solid. MS found: 559.27 (M+)$^+$.

Example 516

Sodium (3-((R)-1-((S)-4-(4-chlorophenyl)-4-hydroxy-3,3-dimethylpiperidin-1-yl)-3-methyl-1-oxobutan-2-ylcarbamoyl)phenyl)methanesulfonate

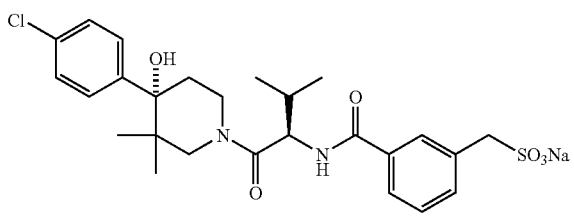

Step 1: 3-(Chloromethyl)-N—((R)-1-((S)-4-(4-chlorophenyl)-4-hydroxy-3,3-dimethylpiperidin-1-yl)-3-methyl-1-oxobutan-2-yl)benzamide

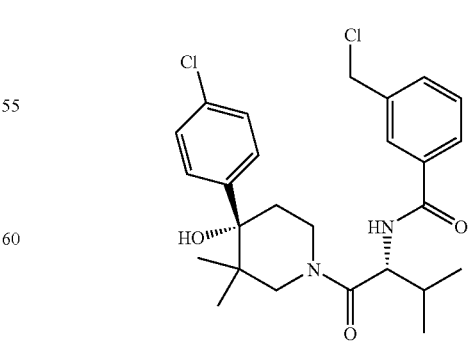

To an ice cooled solution of R)-2-amino-1-((S)-4-(4-chlorophenyl)-4-hydroxy-3,3-dimethylpiperidin-1-yl)-3-methylbutan-1-one, HCl, (30.3 mg, 0.089 mmol), in CH₂Cl₂ (0.8 mL) was added 3-(chloromethyl)benzoyl chloride (14 μL, 0.098 mmol) followed by DIPEA (34.4 μL, 0.197 mmol). The reaction was stirred overnight then partitioned between EtOAc and dilute aq. NaHCO₃. The aqueous layer was further extracted with EtOAc then dried over Na₂SO₄. Filter, strip, and flash to purify (20% EtOAc/heptane to 60% EtOAc/heptane) to afford 3-(chloromethyl)-N—((R)-1-((S)-4-(4-chlorophenyl)-4-hydroxy-3,3-dimethylpiperidin-1-yl)-3-methyl-1-oxobutan-2-yl)benzamide (33 mg, 75% yield). MS found: 491.20 (M+)⁺.

Step 2: Example 516

To a solution of 3-(chloromethyl)-N—((R)-1-((S)-4-(4-chlorophenyl)-4-hydroxy-3,3-dimethylpiperidin-1-yl)-3-methyl-1-oxobutan-2-yl)benzamide, (33 mg, 0.067 mmol) in Ethanol (0.25 mL)/Water (0.25 mL) was added Sodium Sulfite (0.016 mL, 0.336 mmol) and the reaction vessel heated at reflux overnight. The reaction was cooled to room temperature then concentrated on a rotovap. The remaining suspension was loaded onto a 1 gram C18 cartridge (pre-wetted with water) and eluted sequentially with water, 10% MeCN/water, 20% MeCN/water then 50% MeCN/water. The product containing fractions were combined, concentrated, and lyophilized to give Example 516 (27.0 mg, 72% yield), which was isolated as a white solid. MS found: 537.22 (M+)⁺.

Example 517

(R)-2-(benzo[d]oxazol-2-ylamino)-1-((S)-4-(4-chlorophenyl)-4-hydroxy-3,3-dimethylpiperidin-1-yl)-3-methylbutan-1-one

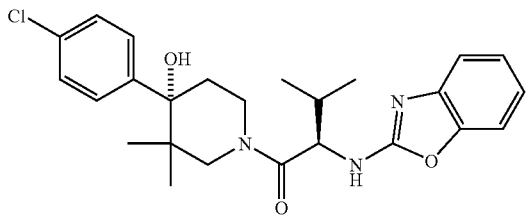

To an solution of (R)-2-amino-1-((S)-4-(4-chlorophenyl)-4-hydroxy-3,3-dimethylpiperidin-1-yl)-3-methylbutan-1-one, HCl, (23.7 mg, 0.07 mmol),) in EtOH (300 μL) was added 2-chlorobenzoxazole (8 μL, 0.070 mmol) and TEA (19.50 μL, 0.140 mmol). The reaction solution was heated at 150° C. for 45 min. The reaction was purified directly by preparative HPLC to furnish Example 517 (21 mg, 53% yield). MS found: 456.3 (M+)⁺.

Example 518

3-acetyl-N—((R)-1-((S)-4-(4-chlorophenyl)-4-hydroxy-3,3-dimethylpiperidin-1-yl)-3-methyl-1-oxobutan-2-yl)benzamide

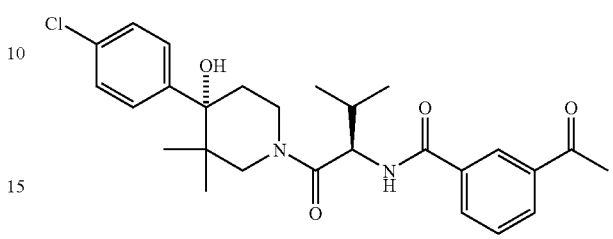

To a solution of 3-acetylbenzoic acid (10.4 mg, 0.063 mmol), (R)-2-amino-1-((S)-4-(4-chlorophenyl)-4-hydroxy-3,3-dimethylpiperidin-1-yl)-3-methylbutan-1-one (21.6 mg, 0.058 mmol), EDC (12.14 mg, 0.063 mmol), and HOBt (9.69 mg, 0.063 mmol) in DMF (250 μL) was added DIPEA (11.06 μL, 0.063 mmol) after stirring for ~20 min. The reaction mixture was stirred for 30 min then added water (1 mL). The precipitated solids were stirred for 45 min, filtered, and rinsed with water to afford Example 518 (24 mg, 86% yield) as a white solid. HPLC purity: >95%, rt 3.85 min; MS found 485.19 (M+)⁺.

Example 519

N—((R)-1-((S)-4-(4-chlorophenyl)-4-hydroxy-3,3-dimethylpiperidin-1-yl)-3-methyl-1-oxobutan-2-yl)-3-(1H-pyrazol-5-yl)benzamide, TFA

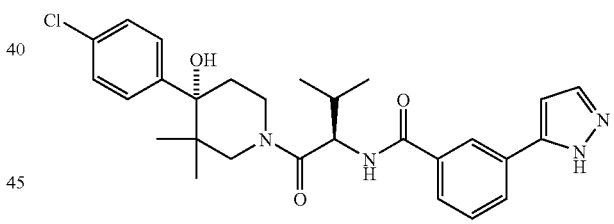

Step 1: N—((R)-1-((S)-4-(4-chlorophenyl)-4-hydroxy-3,3-dimethylpiperidin-1-yl)-3-methyl-1-oxobutan-2-yl)-3-((E)-3-(dimethylamino)acryloyl)benzamide

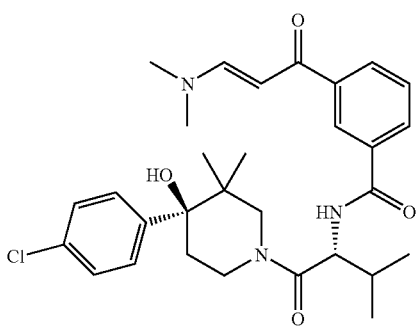

3-Acetyl-N—((R)-1-((S)-4-(4-chlorophenyl)-4-hydroxy-3,3-dimethylpiperidin-1-yl)-3-methyl-1-oxobutan-2-yl)benzamide was added DMF-DMA (0.3 mL) and the reaction mixture heated at 105° C. for ~5 h. The residual DMF-DMA was removed on a rotovap and the crude product was dried on house high vac for ~3 h to afford N—((R)-1-((S)-4-(4-chlorophenyl)-4-hydroxy-3,3-dimethylpiperidin-1-yl)-3-methyl-1-oxobutan-2-yl)-3-((E)-3-(dimethylamino)acryloyl)benzamide.

Step 2: Example 519

To a solution of N—((R)-1-((S)-4-(4-chlorophenyl)-4-hydroxy-3,3-dimethylpiperidin-1-yl)-3-methyl-1-oxobutan-2-yl)-3-((E)-3(dimethylamino)acryloyl)benzamide, (11 mg, 0.020 mmol) in ethanol (0.3 mL) was added hydrazine hydrate (20 μL, 0.411 mmol). The reaction was stirred overnight and the crude reaction purified directly via preparative HPLC to give Example 519 (10.0 mg, 0.016 mmol, 79% yield), as a white solid. HPLC purity >99%, rt 3.92 min; MS found: 509.30 (M+)+.

Example 520

Methyl 2-(2-((R)-1-((S)-4-(4-chlorophenyl)-4-hydroxy-3,3-dimethylpiperidin-1-yl)-3-methyl-1-oxobutan-2-ylamino)thiazol-4-yl)acetate

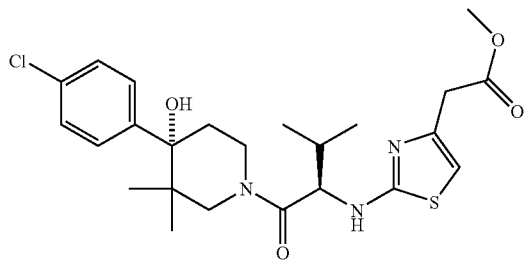

Step 1: 1-((R)-1-((S)-4-(4-chlorophenyl)-4-hydroxy-3,3-dimethylpiperidin-1-yl)-3-methyl-1-oxobutan-2-yl)thiourea

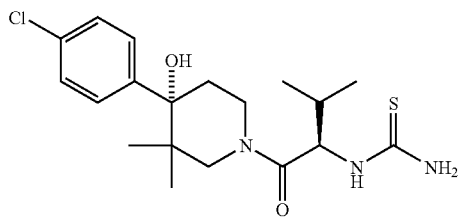

To a solution of (R)-2-amino-1-((S)-4-(4-chlorophenyl)-4-hydroxy-3,3-dimethylpiperidin-1-yl)-3-methylbutan-1-one, HCl (141.6 mg, 0.377 mmol) in CHCl₃ (2 mL) at 0° C. was added DIPEA (0.066 mL, 0.377 mmol) followed by the dropwise addition of benzoyl isothiocyanate (0.051 mL, 0.377 mmol). The reaction was stirred for 1 h then concentrated on a rotovap and added MeOH (2 mL). 5 N NaOH (0.080 mL) was added and the resulting mixture was stirred for 1 h then at 65° C. for 1 h. Cool to rt and concentrate. Add water (1 mL) and stir rapidly over the weekend. Extract into EtOAc (3×25 mL), dry over Na₂SO₄, filter, strip. Purify via column chromatography (50% EA/heptane to 75% EA/heptane) to afford 1-((R)-1-((S)-4-(4-chlorophenyl)-4-hydroxy-3,3-dimethylpiperidin-1-yl)-3-methyl-1-oxobutan-2-yl)thiourea (135 mg, 90% yield) as a white solid. HPLC purity: 98.6%, rt 3.64 min; MS found: 420.24 (M+Na)+.

Step 2: Example 520

To a solution of 1-((R)-1-((S)-4-(4-chlorophenyl)-4-hydroxy-3,3-dimethylpiperidin-1-yl)-3-methyl-1-oxobutan-2-yl)thiourea (21.4 mg, 0.054 mmol) in EtOH (0.3 mL) was added methyl 4-chloroacetoacetate (7.4 μL, 0.065 mmol) and the reaction mixture heated at 80° C. overnight. The reaction mixture was concentrated and purified via column chromatography (33% EA/heptane to 50% EA/heptane) to afford Example 520 (13.7 mg, 51.6% yield) as a clear glass. HPLC purity: 96.7%, rt 3.41 min; MS found: 494.25 (M+)+.

Example 521

N—((R)-1-((S)-4-(4-chlorophenyl)-4-hydroxy-3,3-dimethylpiperidin-1-yl)-3-methyl-1-oxobutan-2-yl)-3-(sulfamoylmethyl)benzamide

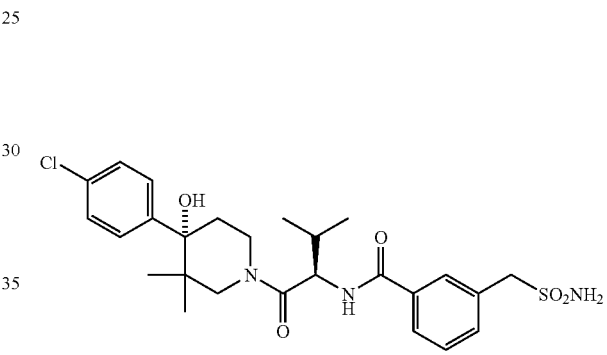

To a suspension of sodium (3-((R)-1-((S)-4-(4-chlorophenyl)-4-hydroxy-3,3-dimethylpiperidin-1-yl)-3-methyl-1-oxobutan-2-ylcarbamoyl)phenyl)methanesulfonate (19.9 mg, 0.036 mmol) in CH₂Cl₂ (1 mL) was added phosphorus pentachloride (0.012 mL, 0.089 mmol) in one portion. The reaction mixture was stirred for 2 h then quenched with water (1 mL) and stirred rapidly for 30 min. The layers were separated and the aqueous layer was extracted with CH₂Cl₂ (2×10 mL). The combined organics were washed with brine, dried over Na₂SO₄, filtered, and concentrated. CH₂Cl₂ (0.6 mL) was added and the solution cooled to 0° C. upon which aq. NH₄OH (0.5 mL) was added drop wise with rapid stirring. The mixture was stirred rapidly while gradually reaching room temperature. The reaction was diluted with CH₂Cl₂ (~15 mL) and water (3 mL), the layers separated and the aq. layer further extracted with CH₂Cl₂ (15 mL). The combined organic layers were dried (Na₂SO₄), filtered, and concentrated. The crude product was purified via column chromatography (50% EA/heptane to 100% EA) to furnish Example 521 (14.1 mg, 74% yield) which was lyophilized to a white powder overnight. HPLC purity: >99%, rt 3.59 min; LCMS: 536.18 (M+)+.

Example 522

(R)-1-((S)-4-(4-chlorophenyl)-4-hydroxy-3,3-dimethylpiperidin-1-yl)-2-(4-(hydroxymethyl)thiazol-2-ylamino)-3-methylbutan-1-one, TFA Salt

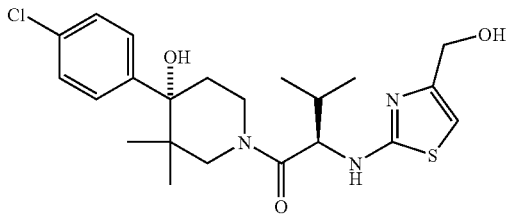

Step 1: (R)-2-(4-(chloromethyl)thiazol-2-ylamino)-1-((S)-4-(4-chlorophenyl)-4-hydroxy-3,3-dimethylpiperidin-1-yl)-3-methylbutan-1-one

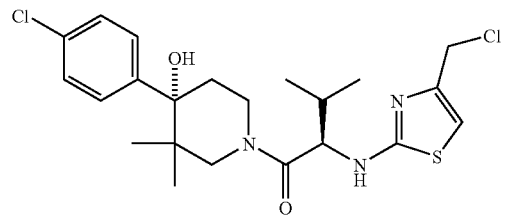

To a suspension of 1-((R)-1-((S)-4-(4-chlorophenyl)-4-hydroxy-3,3-dimethylpiperidin-1-yl)-3-methyl-1-oxobutan-2-yl)thiourea (29 mg, 0.073 mmol) in acetone (300 μL) was added 1,3-dichloropropan-2-one (14 mg, 0.105 mmol) and the reaction mixture was stirred overnight at rt. The solvents were removed and the residue purified via column chromatography (SiO2, 25% EtOAc/hep then 50% EtOAc/hep then 10% EtOAc with 0.06% DIPEA). (R)-2-(4-(chloromethyl)thiazol-2-ylamino)-1-((S)-4-(4-chlorophenyl)-4-hydroxy-3,3-dimethylpiperidin-1-yl)-3-methylbutan-1-one (35 mg, >95% yield) was isolated as a clear glass. HPLC purity: >99%, rt 3.87 min; MS found: 470.22 (M+)$^+$.

Step 2: Example 522

A solution of (R)-2-(4-(chloromethyl)thiazol-2-ylamino)-1-((S)-4-(4-chlorophenyl)-4-hydroxy-3,3-dimethylpiperidin-1-yl)-3-methylbutan-1-one (30 mg, 0.064 mmol) and Sodium Sulfite (40.2 mg, 0.319 mmol) in EtOH (0.6 mL)/Water (0.3 mL) was stirred at 80° C. The mixture was heated for 2 h, cooled and purified directly via preparative HPLC to give Example 522 (4.8 mg, 13.3% yield). HPLC purity >97, tr 3.12 min; MS found 452.31 (M+)$^+$.

Example 523

((R)-1-((S)-4-(4-chlorophenyl)-4-hydroxy-3,3-dimethylpiperidin-1-yl)-2-(4-(ethoxymethyl)thiazol-2-ylamino)-3-methylbutan-1-one, HCl

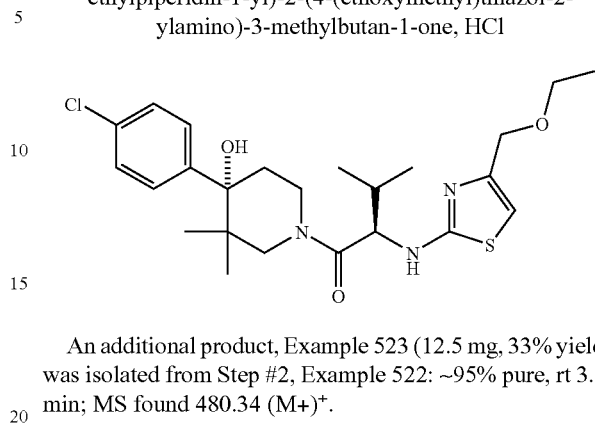

An additional product, Example 523 (12.5 mg, 33% yield), was isolated from Step #2, Example 522: ~95% pure, rt 3.55 min; MS found 480.34 (M+)$^+$.

Example 524

Ethyl 2-((R)-1-((S)-4-(4-chlorophenyl)-4-hydroxy-3,3-dimethylpiperidin-1-yl)-3-methyl-1-oxobutan-2-ylamino)thiazole-4-carboxylate

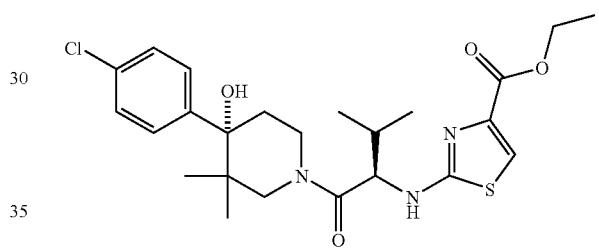

1-((R)-1-((S)-4-(4-chlorophenyl)-4-hydroxy-3,3-dimethylpiperidin-1-yl)-3-methyl-1-oxobutan-2-yl)thiourea (67.5 mg, 0.170 mmol) and ethyl bromopyruvate (0.026 mL, 0.187 mmol) in EtOH (0.6 mL) were heated at 65° C. overnight. The reaction was neutralized with 2 equiv TEA in CH$_2$Cl$_2$, concentrated, and purified via column chromatography (20% to 40% EtOAc/heptane) to afford Example 524 (74.9 mg, 89% yield) as a clear glass. HPLC purity: 99.5%, 4.00 min; LCMS: 494.28 (M+)$^+$.

Example 525

2-((R)-1-((S)-4-(4-chlorophenyl)-4-hydroxy-3,3-dimethylpiperidin-1-yl)-3-methyl-1-oxobutan-2-ylamino)thiazole-4-carboxylic acid

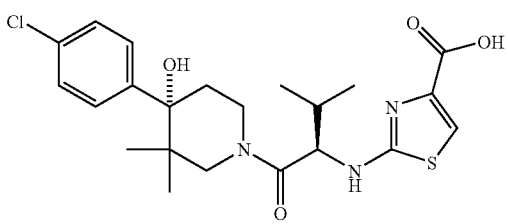

To a solution of ethyl 2-((R)-1-((S)-4-(4-chlorophenyl)-4-hydroxy-3,3-dimethylpiperidin-1-yl)-3-methyl-1-oxobutan-2-ylamino)thiazole-4-carboxylate (69 mg, 0.140 mmol) in MeOH (0.28 ml)/THF (0.280 ml) was added NaOH, 1N (0.140 ml, 0.140 mmol) and the reaction stirred at room temperature. The reaction was stirred for 8 h and then neutralized with 1 N HCL. The solvents were removed and water (~1 mL) was added. The resulting solids were stirred and sonicated briefly, filtered and rinsed with water. HPLC purity of crude solids, ~90%; MS found: 466.26 (M+)⁺.

Example 526

(R)-1-((S)-4-(4-chlorophenyl)-4-hydroxy-3,3-dimethylpiperidin-1-yl)-3-methyl-2-(4-(morpholine-4-carbonyl)thiazol-2-ylamino)butan-1-one, TFA

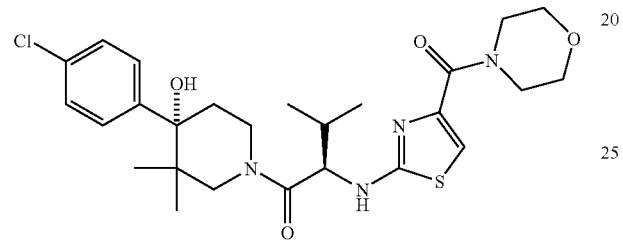

To a vial containing 2-((R)-1-((S)-4-(4-chlorophenyl)-4-hydroxy-3,3-dimethylpiperidin-1-yl)-3-methyl-1-oxobutan-2-ylamino)thiazole-4-carboxylic acid (14.4 mg, 0.031 mmol), HOBT (5.68 mg, 0.037 mmol), and EDC (7.11 mg, 0.037 mmol) was added DMF (0.2 mL). The reaction mixture was stirred for ~30 min followed by addition of morpholine (8.08 µL, 0.093 mmol). The reaction was stirred overnight and the product was purified directly by preparative HPLC and lyophilized to a solid. HPLC purity: 97.8%, T_r 3.70 min; LCMS: 535.31 (M+)⁺.

Example 527

(S)-2-amino-N—((R)-1-((S)-4-(4-chlorophenyl)-4-hydroxy-3,3-dimethylpiperidin-1-yl)-3-methyl-1-oxobutan-2-yl)propanamide 2,2,2-trifluoroacetate

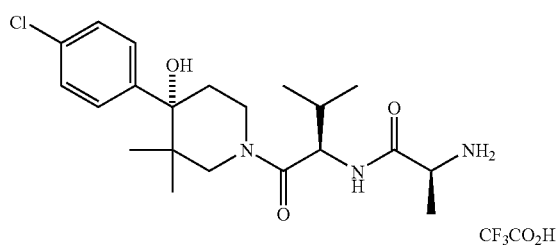

To a solution of (R)-2-amino-1-((S)-4-(4-chlorophenyl)-4-hydroxy-3,3-dimethylpiperidin-1-yl)-3-methylbutan-1-one hydrochloride (30.1 mg, 0.080 mmol), (R)-2-(tert-butoxycarbonylamino)propanoic acid (16.69 mg, 0.088 mmol), HOBt (13.51 mg, 0.088 mmol), and EDC (16.91 mg, 0.088 mmol) in DMF was added DIPEA (0.031 mL, 0.176 mmol). The reaction mixture was stirred for 2 h then added water (1 mL) slowly. The precipitated solids were stirred for 2 h, filtered and dried under high vacuum. The dried white solids were dissolved in CH₂Cl₂ (0.25 mL), added TFA (0.1 mL) and stirred for 4 h. The solvents were removed via N₂ sweep and the product purified by preparative HPLC to afford Example 527 (25.2 mg, 0.048 mmol, 60.0% yield) as a white solid. HPLC purity: >99.5%, 3.12 min; LCMS: 410.28 (M+).

Example 528

(R)-1-((S)-4-(4-chlorophenyl)-4-hydroxy-3,3-dimethylpiperidin-1-yl)-3-methyl-2-(phenylamino)butan-1-one, TFA

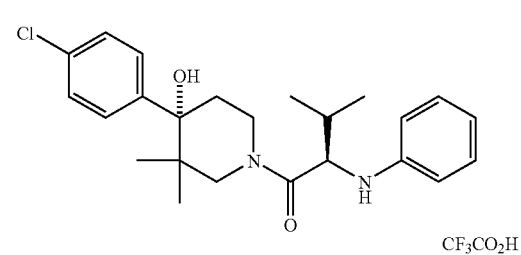

A solution of (R)-3-methyl-2-(phenylamino)butanoic acid (20 mg, 0.103 mmol), EDC (21.8 mg, 0.114 mmol), and HOBT (17.4 mg, 0.114 mmol) in dichloromethane (414 µL) was added (S)-4-(4-chlorophenyl)-3,3-dimethylpiperidin-4-ol (24.8 mg, 0.103 mmol) then DIPEA (19.89 µL, 0.114 mmol). The reaction was stirred for 30 min, the solvents removed and the residue purified directly by preparative HPLC to afford Example 528 (24.8 mg, 45% yield) as a white solid. HPLC purity: >98%, Tr 4.03 min; MS found: 415.20 (M+)⁺.

Example 529

(R)-2-acetamido-N—((R)-1-((S)-4-(4-chlorophenyl)-4-hydroxy-3,3-dimethylpiperidin-1-yl)-3-methyl-1-oxobutan-2-yl)-2-phenylacetamide

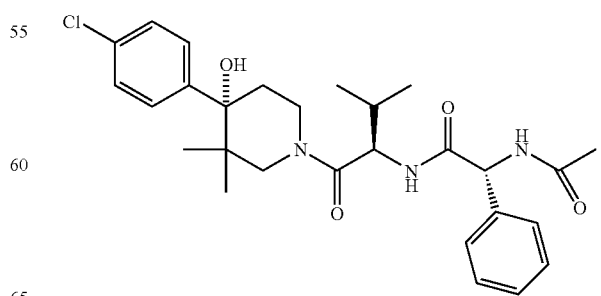

Step 1: (R)-2-amino-N—((R)-1-((S)-4-(4-chlorophenyl)-4-hydroxy-3,3-dimethylpiperidin-1-yl)-3-methyl-1-oxobutan-2-yl)-2-phenylacetamide

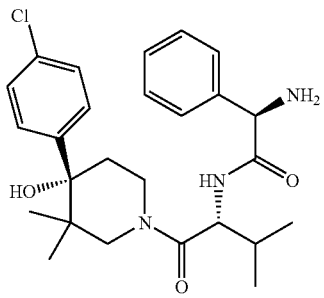

To a solution of (R)-2-amino-1-((S)-4-(4-chlorophenyl)-4-hydroxy-3,3-dimethylpiperidin-1-yl)-3-methylbutan-1-one hydrochloride (30.0 mg, 0.080 mmol), Boc-D-phenyl glycine (22.1 mg, 0.088 mmol), HOBt (13.5 mg, 0.088 mmol), and EDC (16.9 mg, 0.088 mmol) in DMF was added DIPEA (0.031 mL, 0.176 mmol The reaction mixture was stirred for 2 h then added water (1 mL) slowly. The precipitated solids were stirred for 2 h, filtered and dried under high vacuum. The dried white solids were dissolved in $CH_2Cl_2$ (0.25 mL), added TFA (0.1 mL) and stirred for 4 h. The solvents were removed via $N_2$ sweep and the product purified by preparative HPLC to afford (R)-2-amino-N—((R)-1-((S)-4-(4-chlorophenyl)-4-hydroxy-3,3-dimethylpiperidin-1-yl)-3-methyl-1-oxobutan-2-yl)-2-phenylacetamide, TFA (21.7 mg, 46% yield) as a white solid. HPLC purity: 95.2%, 3.14 min; MS found: 410.27 (M+)$^+$.

Step 2: Example 529

To a solution of (R)-2-amino-N—((R)-1-((S)-4-(4-chlorophenyl)-4-hydroxy-3,3-dimethylpiperidin-1-yl)-3-methyl-1-oxobutan-2-yl)-2-phenylacetamide, TFA, (6.9 mg, 0.012 mmol) in $CH_2Cl_2$ (0.2 mL) was added $Ac_2O$ (1.3 μL, 0.014 mmol) followed by DIPEA (4.1 μL, 0.024 mmol). The reaction was concentrated and purified via prep TLC to afford Example 529 (4 mg, 66.1% yield) after drying. HPLC purity: >99%, tr 3.67 min; MS found: 514.21 (M+)$^+$.

Example 530

Methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-2-carboxylate

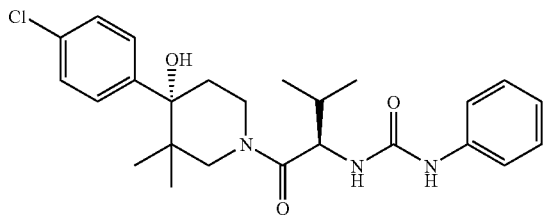

(R)-2-Amino-1-((S)-4-(4-chlorophenyl)-4-hydroxy-3,3-dimethylpiperidin-1-yl)-3-methylbutan-1-one, HCl (25 mg, 0.067 mmol) was stirred in THF (2 mL) and methylene chloride (2 mL) at 25° C. then triethylamine (0.019 mL, 0.13 mmol) was added followed by phenyl isocyanate (0.015 mL, 0.13 mmol). The reaction was stirred overnight then purified over silica gel (3:1 to 1:1 hexanes/EtOAc to 100% THF) to obtain Example 530 (9.0 mg, 0.020 mmol, 29.5% yield). MS found: (M+H)$^+$=458.28.

Example 531

3'-((R)-1-((S)-4-(4-chlorophenyl)-4-hydroxy-3,3-dimethylpiperidin-1-yl)-3-methyl-1-oxobutan-2-ylcarbamoyl)biphenyl-2-carboxylic acid

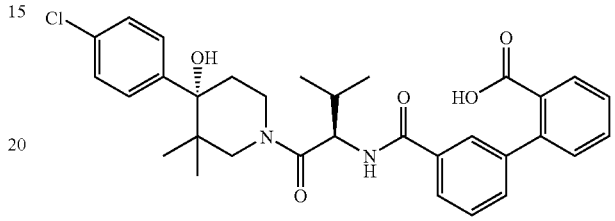

Step 1: Methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-2-carboxylate

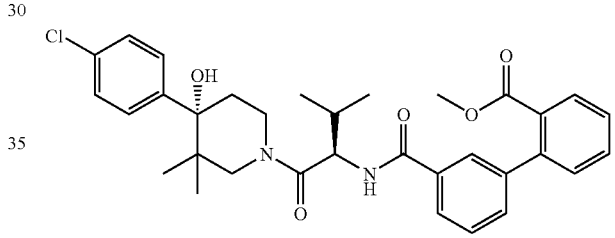

(R)-2-Amino-1-((S)-4-(4-chlorophenyl)-4-hydroxy-3,3-dimethylpiperidin-1-yl)-3-methylbutan-1-one (40 mg, 0.107 mmol), 2'-(methoxycarbonyl)biphenyl-3-carboxylic acid (33 mg, 0.128 mmol), HOBT (20 mg, 0.128 mmol), EDC (25 mg, 0.128 mmol) and triethylamine (0.030 mL, 0.213 mmol) were mixed in methylene chloride (3 mL) at 25° C. with stirring. The reaction was stirred for 20 hours then worked up by adding methylene chloride and washing with sat'd sodium bicarbonate. The methylene chloride layer was dried over sodium sulfate and concentrated in vacuo to give a white glass which was purified over silica gel (3:1 to 1:1 Hexanes/EtOAc) to obtain methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-2-carboxylate (40 mg, 0.069 mmol, 65.0% yield) as a white glass. MS found: (M+H)$^+$=577.31.

Step 2: Example 531

Methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-2-carboxylate (35 mg, 0.061 mmol) was dissolved in MeOH (3 mL) and added 1N NaOH (0.12 mL, 0.12 mmoL and stirred at 25° C. overnight. The MeOH was removed in vacuo and the aqueous was washed 2 times with diethyl ether. The basic aqueous was acidified to pH=3 with 1N HCl, then extracted 2 times with methylene chloride to give Example 531 (30 mg, 0.053 mmol, 88.0% yield) as a white glass product. MS found: (M+H)+=563.30.

Example 532

N—((R)-1-((S)-4-(4-chlorophenyl)-4-hydroxy-3,3-dimethylpiperidin-1-yl)-3-methyl-1-oxobutan-2-yl)-N-methylcyclopentanecarboxamide

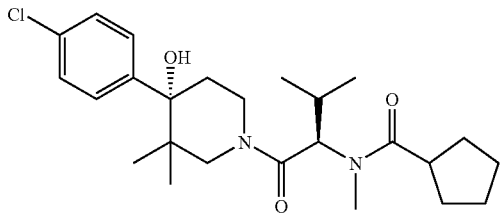

Step 1: tert-butyl (R)-1-((S)-4-(4-chlorophenyl)-4-hydroxy-3,3-dimethylpiperidin-1-yl)-3-methyl-1-oxobutan-2-yl(methyl)carbamate

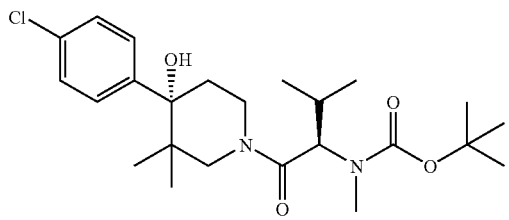

(S)-4-(4-chlorophenyl)-3,3-dimethylpiperidin-4-ol (100 mg, 0.417 mmol), (R)-2-(tert-butoxycarbonyl(methyl)amino)-3-methylbutanoic acid (116 mg, 0.501 mmol), HOBT (77 mg, 0.501 mmol), EDC (96 mg, 0.501 mmol) and triethylamine (0.116 mL, 0.834 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (9:1 to 3:1 to 1:1 Hexanes/EtOAc) to obtain tert-butyl (R)-1-((S)-4-(4-chlorophenyl)-4-hydroxy-3,3-dimethylpiperidin-1-yl)-3-methyl-1-oxobutan-2-yl(methyl)carbamate (190 mg, 0.417 mmol, 100% yield) as a white glass. MS found: (M+H)+=453.15.

Step 2: (R)-1-((S)-4-(4-chlorophenyl)-4-hydroxy-3,3-dimethylpiperidin-1-yl)-3-methyl-2-(methylamino)butan-1-one

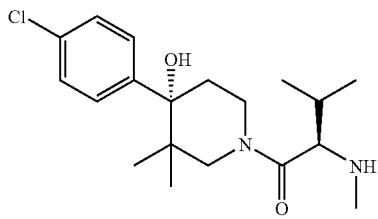

tert-Butyl (R)-1-((S)-4-(4-chlorophenyl)-4-hydroxy-3,3-dimethylpiperidin-1-yl)-3-methyl-1-oxobutan-2-yl(methyl)carbamate (190 mg, 0.42 mmol) was dissolved in dioxane (3 mL) at 25° C. with stirring then 4N HCl in dioxane (0.524 mL, 2.10 mmol) was added. The reaction was stirred for 20 then concentrated to obtain (R)-1-((S)-4-(4-chlorophenyl)-4-hydroxy-3,3-dimethylpiperidin-1-yl)-3-methyl-2-(methylamino)butan-1-one, HCl (150 mg, 0.39 mmol, 92% yield) as a white solid. MS found: (M+H)+=353.22.

Step 3: Example 532

(R)-1-((S)-4-(4-Chlorophenyl)-4-hydroxy-3,3-dimethylpiperidin-1-yl)-3-methyl-2-(methylamino)butan-1-one, HCl (30 mg, 0.077 mmol), cyclopentanecarboxylic acid (11 mg, 0.092 mmol), HOBT (15 mg, 0.092 mmol), EDC (18 mg, 0.092 mmol) and triethylamine (0.021 mL, 0.154 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (3:1 to 1:1 Hexanes/EtOAc) to obtain Example 532 (25 mg, 0.056 mmol, 72.3% yield) as a white glass. MS found: (M+H)+=449.20.

Examples 533A and 533B (1R,3S)—N—((R)-1-((S)-4-(4-chlorophenyl)-4-hydroxy-3,3-dimethylpiperidin-1-yl)-3-methyl-1-oxobutan-2-yl)-3-(1-methyl-1H-tetrazol-5-yl)cyclohexanecarboxamide and (1S,3R)—N—((R)-1-((S)-4-(4-chlorophenyl)-4-hydroxy-3,3-dimethylpiperidin-1-yl)-3-methyl-1-oxobutan-2-yl)-3-(1-methyl-1H-tetrazol-5-yl)cyclohexanecarboxamide

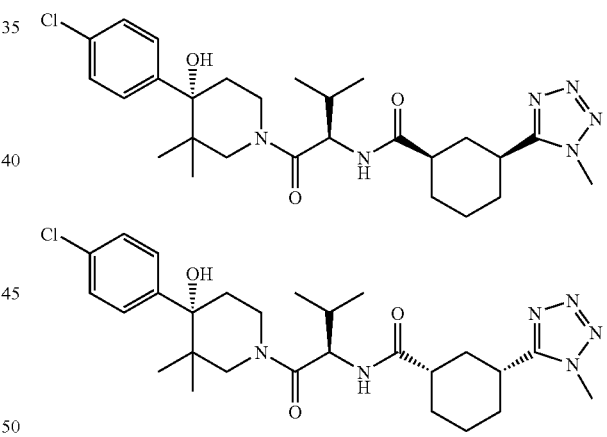

Step 1: (±)-cis-methyl 3-(methylcarbamoyl)cyclohexanecarboxylate

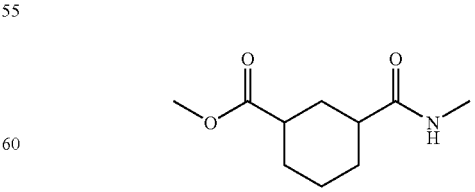

(±)-cis-3-(Methoxycarbonyl)cyclohexanecarboxylic acid (500 mg, 2.69 mmol), methylamine, HCl (218 mg, 3.22 mmol), HOBT (493 mg, 3.22 mmol), EDC (618 mg, 3.22 mmol) and triethylamine (0.75 mL, 5.37 mmol) were mixed and stirred in methylene chloride (10 mL) at 25° C. The reaction was stirred overnight then washed with 1N HCl, sat'd sodium bicarbonate, and brine. The organic layer was dried over sodium sulfate and concentrated in vacuo to give (±)-cis-3-(methyl 3-(methylcarbamoyl)cyclohexanecarboxylate (460 mg, 2.309 mmol, 86% yield) as a white glass. MS found: (M+H)⁺=200.10.

Step 2: (±)-cis-Methyl 3-(1-methyl-1H-tetrazol-5-yl)cyclohexanecarboxylate

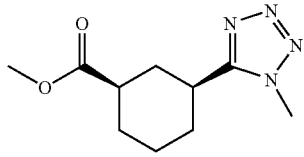

(±)-cis-Methyl 3-(methylcarbamoyl)cyclohexanecarboxylate (460 mg, 2.309 mmol) was dissolved in Acetonitrile (5 mL) at 25° C. under nitrogen with stirring, then sodium azide (150 mg, 2.309 mmol) was added. Cooled to 0° C. then added trifluoromethanesulfonic anhydride (0.390 mL, 2.309 mmol) dropwise over 2 minutes. The reaction was a colorless solution. Stirred for 20 hours then added sat'd sodium bicarbonate and stirred for 15 minutes, then added a little EtOAc and concentrated in vacuo the acetonitrile. Added more EtOAc and separated the layers. The EtOAc layer was rinsed again with sat'd sodium bicarbonate then 1 time with brine. The EtOAc layer was dried over sodium sulfate and stripped to give of a colorless oil. Obtained (±)-cis-methyl 3-(1-methyl-1H-tetrazol-5-yl)cyclohexanecarboxylate (350 mg, 1.561 mmol, 68% yield) as a colorless oil for product. MS found: (M+H)⁺=225.00.

Step 3: (±)-cis-3-(1-methyl-1H-tetrazol-5-yl)cyclohexanecarboxylic acid

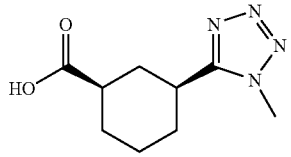

(±)-cis-Methyl 3-(1-methyl-1H-tetrazol-5-yl)cyclohexanecarboxylate (350 mg, 1.56 mmol) was dissolved in MeOH (3 mL) at 25° C. with stirring then 1.000 N NaOH (3.12 mL, 3.12 mmol) was added. Stirred for 3 hours then worked up by adding a little water then concentrating in vacuo the methanol. The pH was adjusted to =3 with conc. HCl. No solids formed. The acidic aqueous was extracted 3 times with methylene chloride. The methylene chloride extracts were combined, dried (sodium sulfate) and concentrated in vacuo to give (±)-cis-3-(1-methyl-1H-tetrazol-5-yl)cyclohexanecarboxylic (230 mg, 1.094 mmol, 70% yield) of a white solid as product. MS found: (M+H)⁺=211.10.

Step 4: (±)-cis-(±)-cis-3-(1-methyl-1H-tetrazol-5-yl)cyclohexanecarboxylic

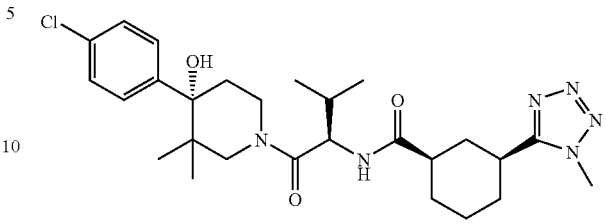

(R)-2-Amino-1-((S)-4-(4-chlorophenyl)-4-hydroxy-3,3-dimethylpiperidin-1-yl)-3-methylbutan-1-one (25 mg, 0.067 mmol), (±)-cis-3-(1-methyl-1H-tetrazol-5-yl)cyclohexanecarboxylic acid (17 mg, 0.080 mmol), HOBT (12 mg, 0.080 mmol), EDC (15 mg, 0.080 mmol) and triethylamine (0.019 mL, 0.133 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride) to obtain (±)-cis-N—((R)-1-((S)-4-(4-chlorophenyl)-4-hydroxy-3,3-dimethylpiperidin-1-yl)-3-methyl-1-oxobutan-2-yl)-3-(1-methyl-1H-tetrazol-5-yl) cyclohexanecarboxamide (35 mg, 0.066 mmol, 99% yield) as a white glass. MS found: (M+H)⁺=531.46.

Step 5: Examples 533A and 533B (±)-cis-N—((R)-1-((S)-4-(4-chlorophenyl)-4-hydroxy-3,3-dimethylpiperidin-1-yl)-3-methyl-1-oxobutan-2-yl)-3-(1-methyl-1H-tetrazol-5-yl)cyclohexanecarboxamide was separated by SFC HPLC to give Example 533A (4.0 mg, 7.53 mol), white solids for product, MS found: (M+H)⁺=531.43 and Example 533B (4.0 mg, 7.53 μmol), white solids for product. MS found: (M+H)⁺=531.43.

Example 534

2-(2-((R)-1-((S)-4-(4-chlorophenyl)-4-hydroxy-3,3-dimethylpiperidin-1-yl)-3-methyl-1-oxobutan-2-ylamino)-2-oxoethoxy)benzoic acid

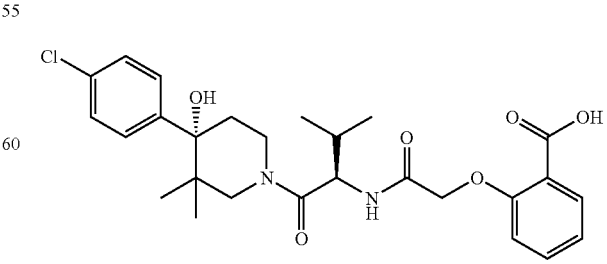

Step 1: 2-chloro-N—((R)-1-((S)-4-(4-chlorophenyl)-4-hydroxy-3,3-dimethylpiperidin-1-yl)-3-methyl-1-oxobutan-2-yl)acetamide

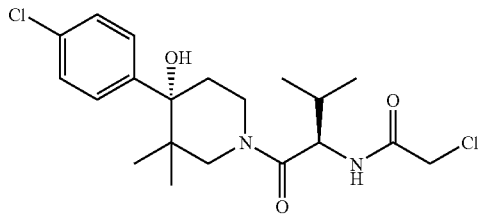

(R)-2-Amino-1-((S)-4-(4-chlorophenyl)-4-hydroxy-3,3-dimethylpiperidin-1-yl)-3-methylbutan-1-one, HCl (100 mg, 0.266 mmol), triethylamine (0.074 mL, 0.533 mmol) and methylene chloride (5 mL) were mixed and stirred at 25° C. then 2-chloroacetyl chloride (0.021 mL, 0.266 mmol) in 1 mL of methylene chloride was added dropwise. The reaction was stirred for 1 hour then concentrated in vacuo to give 2-chloro-N—((R)-1-((S)-4-(4-chlorophenyl)-4-hydroxy-3,3-dimethylpiperidin-1-yl)-3-methyl-1-oxobutan-2-yl)acetamide (90 mg, 0.218 mmol, 82% yield) as a tan solid. MS found: (M+H)$^+$=415.46. The product was used without further purification.

Step 2: methyl 2-(2-((R)-1-((S)-4-(4-chlorophenyl)-4-hydroxy-3,3-dimethylpiperidin-1-yl)-3-methyl-1-oxobutan-2-ylamino)-2-oxoethoxy)benzoate

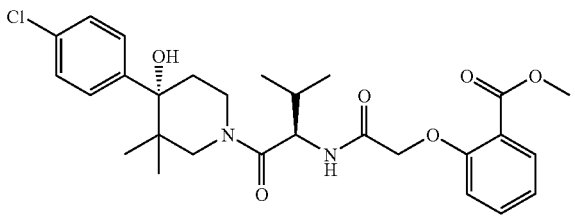

2-Chloro-N—((R)-1-((S)-4-(4-chlorophenyl)-4-hydroxy-3,3-dimethylpiperidin-1-yl)-3-methyl-1-oxobutan-2-yl)acetamide (35 mg, 0.084 mmol), potassium carbonate (35 mg, 0.253 mmol), methyl 2-hydroxybenzoate (13 mg, 0.084 mmol) and DMSO (3 mL) were mixed with stirring at 25° C. The reaction was stirred for 20 hours, diluted with EtOAc, and then rinsed 4 times with water. The organic layer was dried over sodium sulfate and concentrated in vacuo to give an amber oil which was purified over silica gel in (3:1 to 1:1 hexanes/EtOAc to 100% EtOAc) to obtain methyl 2-(2-((R)-1-((S)-4-(4-chlorophenyl)-4-hydroxy-3,3-dimethylpiperidin-1-yl)-3-methyl-1-oxobutan-2-ylamino)-2-oxoethoxy)benzoate (18 mg, 0.034 mmol, 40% yield) as a white glass. MS found: (M+H)$^+$=531.21.

Step 3: Example 534

Methyl 2-(2-((R)-1-((S)-4-(4-chlorophenyl)-4-hydroxy-3,3-dimethylpiperidin-1-yl)-3-methyl-1-oxobutan-2-ylamino)-2-oxoethoxy)benzoate (18 mg, 0.034 mmol) was dissolved in Methanol (2 mL) at 25° C. with stirring then 1.0 N NaOH (0.068 mL, 0.068 mmol) was added. The reaction was stirred 20 hours, added water, then concentrated to remove the MeOH. The basic aqueous was acidified to pH=3 with 1N HCl, then extracted with methylene chloride. The organic layers were combined, dried over sodium sulfate and concentrated in vacuo to give Example 534 (11 mg, 0.021 mmol, 62% yield) as a white solid. MS found: (M+H)$^+$=517.35.

Example 535

(R)-1-(4-amino-4-oxobutanoyl)-N—((R)-1-((S)-4-(4-chlorophenyl)-4-hydroxy-3,3-dimethylpiperidin-1-yl)-3-methyl-1'-oxobutan-2-yl)piperidine-3-carboxamide

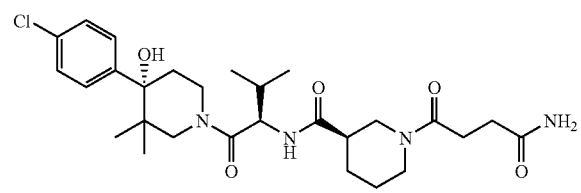

Step 1: (R)-tert-butyl 3-((R)-1-((S)-4-(4-chlorophenyl)-4-hydroxy-3,3-dimethylpiperidin-1-yl)-3-methyl-1-oxobutan-2-ylcarbamoyl)piperidine-1-carboxylate

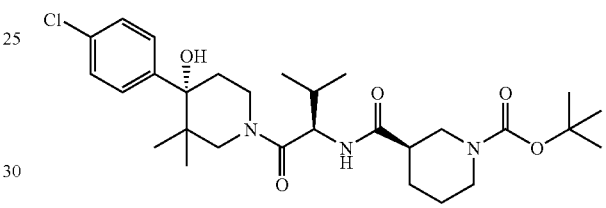

(R)-2-amino-1-((S)-4-(4-chlorophenyl)-4-hydroxy-3,3-dimethylpiperidin-1-yl)-3-methylbutan-1-one, HCl (100 mg, 0.266 mmol), (R)-1-(tert-butoxycarbonyl)piperidine-3-carboxylic acid (73 mg, 0.320 mmol), HOBT (49 mg, 0.320 mmol), EDC (61 mg, 0.320 mmol) and triethylamine (0.074 mL, 0.533 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride/MeOH) to obtain (R)-tert-butyl 3-((R)-1-((S)-4-(4-chlorophenyl)-4-hydroxy-3,3-dimethylpiperidin-1-yl)-3-methyl-1-oxobutan-2-ylcarbamoyl)piperidine-1-carboxylate (125 mg, 227 mmol, 85% yield) as a white solid. MS found: (M+H)$^+$=550.52.

Step 2: (R)—N—((R)-1-((S)-4-(4-chlorophenyl)-4-hydroxy-3,3-dimethylpiperidin-1-yl)-3-methyl-1-oxobutan-2-yl)piperidine-3-carboxamide, HCl

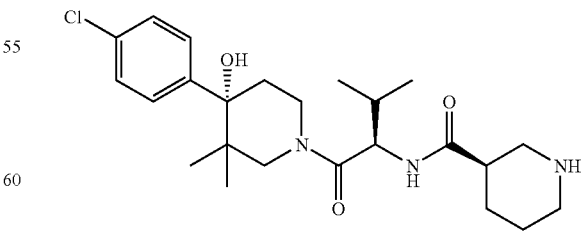

(R)-tert-butyl 3-((R)-1-((S)-4-(4-chlorophenyl)-4-hydroxy-3,3-dimethylpiperidin-1-yl)-3-methyl-1-oxobutan-2-ylcarbamoyl)piperidine-1-carboxylate (125 mg, 0.23 mmol) was stirred in Dioxane (2) at 25° C. under nitrogen then 4N HCl in dioxane (0.284 mL, 1.14 mmol) added. The reaction was stirred for 3 hours then concentrated to obtain (R)—N—((R)-1-((S)-4-(4-chlorophenyl)-4-hydroxy-3,3-dimethylpiperidin-1-yl)-3-methyl-1-oxobutan-2-yl)piperidine-3-carboxamide, HCl (100 mg, 0.206 mmol, 90% yield) as a white glass. MS found: (M+H)$^+$=450.23.

Step 3: Example 535

(R)—N—((R)-1-((S)-4-(4-chlorophenyl)-4-hydroxy-3,3-dimethylpiperidin-1-yl)-3-methyl-1-oxobutan-2-yl)piperidine-3-carboxamide, HCl (30 mg, 0.062 mmol), 4-amino-4-oxobutanoic acid (9 mg, 0.074 mmol), HOBT (11 mg, 0.074 mmol), EDC (14 mg, 0.074 mmol) and triethylamine (0.017 mL, 0.124 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (100% EtOAc to 4:1 methylene chloride) to obtain Example 535 (24 mg, 0.044 mmol, 70% yield) as a white glass. MS found: (M+H)$^+$=549.48.

Example 536

1-((R)-1-((S)-4-(4-chlorophenyl)-4-hydroxy-3,3-dimethylpiperidin-1-yl)-3-methyl-1-oxobutan-2-yl)-3-((1S,3S)-3-hydroxycyclopentyl)urea

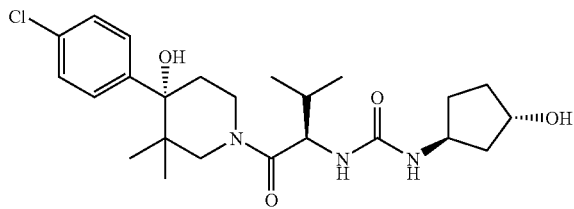

Step 1: Phenyl (R)-1-((S)-4-(4-chlorophenyl)-4-hydroxy-3,3-dimethylpiperidin-1-yl)-3-methyl-1-oxobutan-2-ylcarbamate

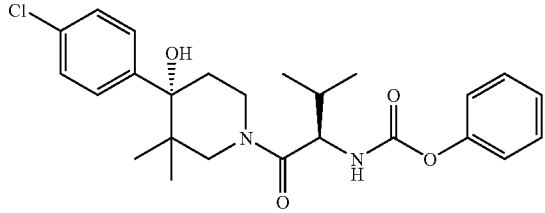

(R)-2-amino-1-((S)-4-(4-chlorophenyl)-4-hydroxy-3,3-dimethylpiperidin-1-yl)-3-methylbutan-1-one (500 mg, 1.33 mmol), triethylamine (0.371 mL, 2.66 mmol) and methylene chloride (10 mL) were mixed at 0° C. under nitrogen then a methylene chloride solution of phenyl carbonochloridate (209 mg, 1.33 mmol) was added dropwise via an addition funnel. The reaction was stirred for 1 hour, diluted with EtOAc, and washed consecutively with 1N HCl and sat'd sodium bicarbonate. The organic layer was dried over sodium sulfate and concentrated in vacuo to give a white glass which was purified over silica gel (3:1 to 1:1 hexanes/EtOAc) to obtain phenyl (R)-1-((S)-4-(4-chlorophenyl)-4-hydroxy-3,3-dimethylpiperidin-1-yl)-3-methyl-1-oxobutan-2-ylcarbamate (365 mg, 0.795 mmol, 59% yield) as a white glass. MS found: (M+H)$^+$=459.32.

Step 2: Example 536

Phenyl (R)-1-((S)-4-(4-chlorophenyl)-4-hydroxy-3,3-dimethylpiperidin-1-yl)-3-methyl-1-oxobutan-2-ylcarbamate (30 mg, 0.065 mmol), (1S,3S)-3-aminocyclopentanol (7 mg, 0.065 mmol) and triethylamine (0.018 mL, 0.131 mmol) were mixed in acetonitrile (3 mL) at 25° C. then heated in a microwave reactor at 150° C. for 30 minutes. The solvent was concentrated in vacuo then the residue purified over silica gel (1:1 hexanes/EtOAc to 100% EtOAc to 1:1 methylene chloride/MeOH) to obtain Example 536 (20 mg, 0.043 mmol, 65% yield) as a white glass. MS found: (M+H)$^+$=466.37.

Example 537

N1-((R)-1-((S)-4-(4-chlorophenyl)-4-hydroxy-3,3-dimethylpiperidin-1-yl)-3-methyl-1-oxobutan-2-yl)-4,4-dimethylpentanediamide

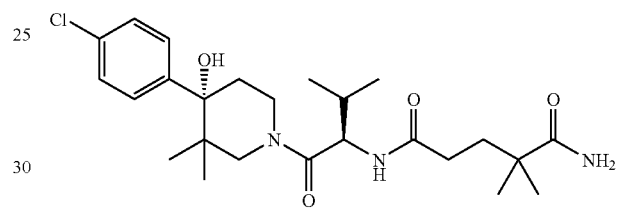

Step 1: 5-((R)-1-((S)-4-(4-chlorophenyl)-4-hydroxy-3,3-dimethylpiperidin-1-yl)-3-methyl-1-oxobutan-2-ylamino)-2,2-dimethyl-5-oxopentanoic acid

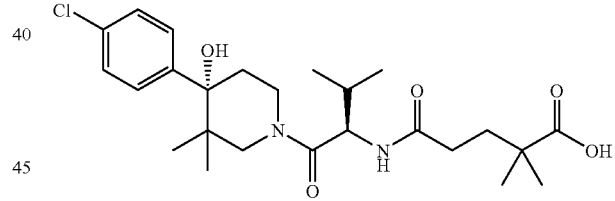

(R)-2-amino-1-((S)-4-(4-chlorophenyl)-4-hydroxy-3,3-dimethylpiperidin-1-yl)-3-methylbutan-1-one, HCl (50 mg, 0.133 mmol), 3,3-dimethyldihydro-2H-pyran-2,6(3H)-dione (19 mg, 0.133 mmol) and triethylamine (0.037 mL, 0.266 mmol) were mixed in methylene chloride (3 mL) at 25° C. with stirring. The reaction was stirred for 20 hours, concentrated in vacuo, and purified over silica gel (1:1 hexanes/EtOAc to 100% EtOAc to 4:1 methylene chloride/MeOH) to obtain 5-((R)-1-((S)-4-(4-chlorophenyl)-4-hydroxy-3,3-dimethylpiperidin-1-yl)-3-methyl-1-oxobutan-2-ylamino)-2,2-dimethyl-5-oxopentanoic acid (50 mg, 0.104 mmol, 78% yield) as a white glass. MS found: (M+H)$^+$=481.34.

Step 2: Example 537

5-((R)-1-((S)-4-(4-chlorophenyl)-4-hydroxy-3,3-dimethylpiperidin-1-yl)-3-methyl-1-oxobutan-2-ylamino)-2,2-dimethyl-5-oxopentanoic acid (25 mg, 0.052 mmol), ammonium chloride (14 mg, 0.260 mmol), HOBT (10 mg, 0.062 mmol), EDC (12 mg, 0.062 mmol) and triethylamine (7.24 µl, 0.052 mmol) were mixed in acetonitrile (2 mL) at 25° C. with stirring. The reaction was stirred for 20 hours, concentrated, and then methylene chloride was added. The methylene chloride layer was washed with sat'd sodium bicarbonate, dried over sodium sulfate, and concentrated in vacuo to give a white glass which was purified over silica gel (1:1 Hexanes/EtOAc to 100% EtOAc to 4:1 methylene chloride/MeOH) to obtain Example 537 (22 mg, 0.046 mmol, 88% yield) as a white glass. MS found: (M+H)$^+$=480.29.

Example 538

(R)—N3-((R)-1-((S)-4-(4-chlorophenyl)-4-hydroxy-3,3-dimethylpiperidin-1-yl)-3-methyl-1-oxobutan-2-yl)pyrrolidine-1,3-dicarboxamide

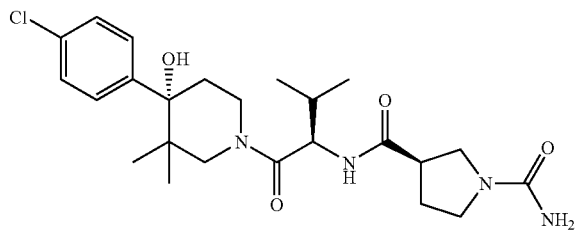

Step 1: (R)-tert-butyl 3-((R)-1-((S)-4-(4-chlorophenyl)-4-hydroxy-3,3-dimethylpiperidin-1-yl)-3-methyl-1-oxobutan-2-ylcarbamoyl)pyrrolidine-1-carboxylate

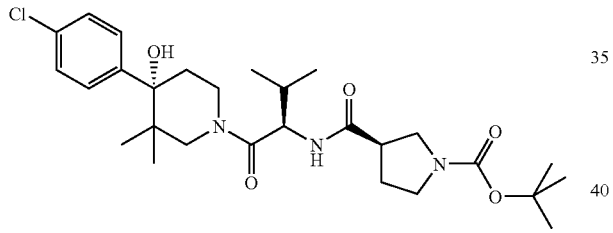

Followed the procedure of Example 535, Step 1, using (R)-1-(tert-butoxycarbonyl)pyrrolidine-3-carboxylic acid (0.69 g, 3.20 mmol), (R)-tert-butyl 3-((R)-1-((S)-4-(4-chlorophenyl)-4-hydroxy-3,3-dimethylpiperidin-1-yl)-3-methyl-1-oxobutan-2-ylcarbamoyl)pyrrolidine-1-carboxylate (1.1 g, 2.05 mmol, 77% yield) was obtained as a white glass. MS found: (M+H)$^+$=436.43.

Step 2: (R)—N—((R)-1-((S)-4-(4-chlorophenyl)-4-hydroxy-3,3-dimethylpiperidin-1-yl)-3-methyl-1-oxobutan-2-yl)pyrrolidine-3-carboxamide, HCl

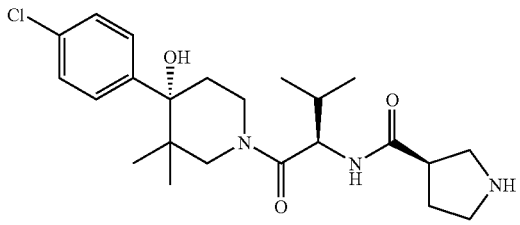

Followed the procedure of Example 535, Step 2, using (R)-tert-butyl 3-((R)-1-((S)-4-(4-chlorophenyl)-4-hydroxy-3,3-dimethylpiperidin-1-yl)-3-methyl-1-oxobutan-2-ylcarbamoyl)pyrrolidine-1-carboxylate (1.1 g, 2.052 mmol), (R)—N—((R)-1-((S)-4-(4-chlorophenyl)-4-hydroxy-3,3-dimethylpiperidin-1-yl)-3-methyl-1-oxobutan-2-yl)pyrrolidine-3-carboxamide, HCl (1.0 g, 2.12 mmol, 100% yield) was obtained as a white solid. MS found: (M+H)$^+$=436.28.

Step 3: Example 538

(R)—N—((R)-1-((S)-4-(4-chlorophenyl)-4-hydroxy-3,3-dimethylpiperidin-1-yl)-3-methyl-1-oxobutan-2-yl)pyrrolidine-3-carboxamide, HCl (40 mg, 0.085 mmol) was stirred in acetic acid (3 mL) at 25° C. then sodium cyanate (6.60 mg, 0.102 mmol) was added. After stirring for 2 hours, the reaction was heated at 50° C. for 20 hours. The pH was adjusted to pH=7-8 with 1N NaOH and the aqueous was then extracted with EtOAc. The EtOAc layers were combined, washed with sat'd sodium bicarbonate, dried (sodium sulfate) and concentrated in vacuo to give a tan glass which was purified over silica gel (1:1 hexanes/EtOAc to 100% EtOAc to 4:1 methylene chloride/MeOH) to obtain Example 538 (10 mg, 0.021 mmol, 24% yield) as a white solid. MS found: (M+H)$^+$=479.37.

Example 539

1,4-Diacetyl-N—((R)-1-((S)-4-(4-chlorophenyl)-4-hydroxy-3,3-dimethylpiperidin-1-yl)-3-methyl-1-oxobutan-2-yl)piperazine-2-carboxamide

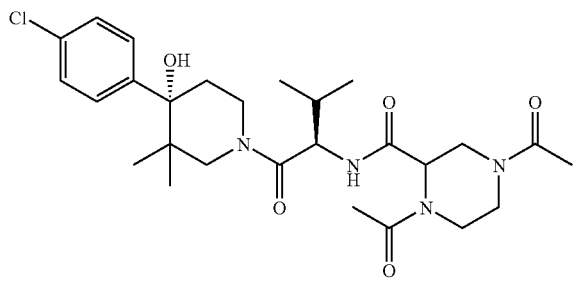

Step 1: 1,4-Diacetylpiperazine-2-carboxylic acid

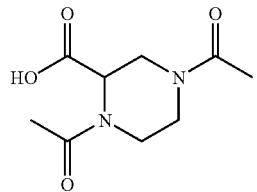

Piperazine-2-carboxylic acid, 2HCl (200 mg, 0.985 mmol), triethylamine (0.137 mL, 0.985 mmol) and acetic anhydride (0.093 mL, 0.985 mmol) were mixed in methylene chloride (3 mL) at 25° C. with stirring. Added 1 mL of 4N HCl in dioxane, then concentrated in vacuo 3 times from methylene chloride/MeOH to give of white solids. MS found: (M+H)$^+$=215.24. The product was used without further purification.

Step 2: Example 539

(R)-2-Amino-1-((S)-4-(4-chlorophenyl)-4-hydroxy-3,3-dimethylpiperidin-1-yl)-3-methylbutan-1-one (30 mg, 0.080 mmol), 1,4-diacetylpiperazine-2-carboxylic acid (21 mg, 0.096 mmol), HOBT (15 mg, 0.096 mmol), EDC (18 mg, 0.096 mmol) and triethylamine (0.022 mL, 0.160 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride/MeOH) to obtain Example 539 (40 mg, 0.075 mmol, 94% yield) as a white solid. MS found: (M+H)$^+$=535.45.

Example 540

2-(4-acetylpiperazin-1-yl)-N—((R)-1-((S)-4-(4-chlorophenyl)-4-hydroxy-3,3-dimethylpiperidin-1-yl)-3-methyl-1-oxobutan-2-yl)acetamide

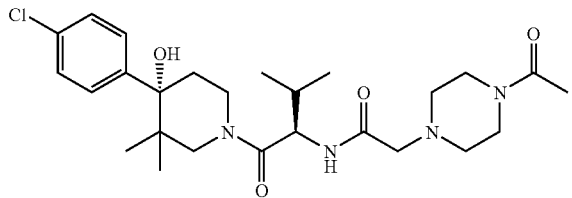

Step 1: Tert-butyl 4-(2-((R)-1-((S)-4-(4-chlorophenyl)-4-hydroxy-3,3-dimethylpiperidin-1-yl)-3-methyl-1-oxobutan-2-ylamino)-2-oxoethyl)piperazine-1-carboxylate

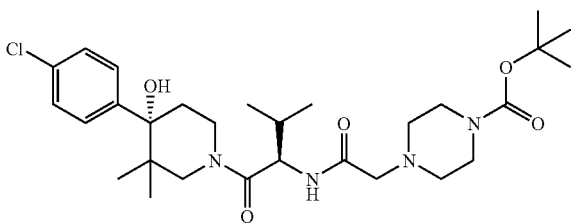

Following the procedure of Example 535, Step 1, using 2-(4-(tert-butoxycarbonyl)piperazin-1-yl)acetic acid (47 mg, 0.192 mmol), tert-butyl 4-(2-((R)-1-((S)-4-(4-chlorophenyl)-4-hydroxy-3,3-dimethylpiperidin-1-yl)-3-methyl-1-oxobutan-2-ylamino)-2-oxoethyl)piperazine-1-carboxylate (47 mg, 0.083 mmol, 52% yield) was obtained as a white glass. MS found: (M+H)$^+$=565.38.

Step 2: N—((R)-1-((S)-4-(4-chlorophenyl)-4-hydroxy-3,3-dimethylpiperidin-1-yl)-3-methyl-1-oxobutan-2-yl)-2-(piperazin-1-yl)acetamide, HCl

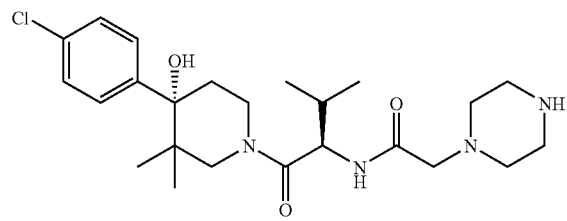

Following the procedure of Example 535, Step 2, using tert-butyl 4-(2-((R)-1-((S)-4-(4-chlorophenyl)-4-hydroxy-3,3-dimethylpiperidin-1-yl)-3-methyl-1-oxobutan-2-ylamino)-2-oxoethyl)piperazine-1-carboxylate (70 mg, 0.124 mmol), N—((R)-1-((S)-4-(4-chlorophenyl)-4-hydroxy-3,3-dimethylpiperidin-1-yl)-3-methyl-1-oxobutan-2-yl)-2-(piperazin-1-yl)acetamide, HCl (60 mg, 0.120 mmol, 97% yield) was obtained as a white solid. MS found: (M+H)$^+$=465.44.

Step 3: Example 540

N—((R)-1-((S)-4-(4-chlorophenyl)-4-hydroxy-3,3-dimethylpiperidin-1-yl)-3-methyl-1-oxobutan-2-yl)-2-(piperazin-1-yl)acetamide, HCl (30 mg, 0.060 mmol), triethylamine (0.042 mL, 0.299 mmol), and acetic anhydride (0.028 ml, 0.299 mmol) were mixed in methylene chloride (3 mL) at 25° C. with stirring. The reaction was stirred for 3 hours, concentrated in vacuo, and the residue purified over silica gel (1:1 hexanes/EtOAc to 100% EtOAc to 4:1 methylene chloride/MeOH) to afford Example 540 (21 mg, 0.041 mmol, 69% yield) as a colorless oil. MS found: (M+H)$^+$=507.46.

Example 541

N5-((R)-1-((S)-4-(4-chlorophenyl)-4-hydroxy-3,3-dimethylpiperidin-1-yl)-3-methyl-1-oxobutan-2-yl)-N1,2,2-trimethylpentanediamide

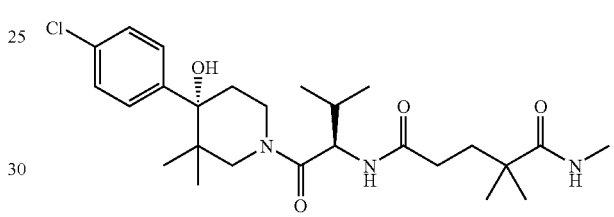

5-((R)-1-((S)-4-(4-chlorophenyl)-4-hydroxy-3,3-dimethylpiperidin-1-yl)-3-methyl-1-oxobutan-2-ylamino)-2,2-dimethyl-5-oxopentanoic acid (from Example 537, Step 1) (25 mg, 0.052 mmol), methylamine hydrochloride (4 mg, 0.062 mmol), HOBT (10 mg, 0.062 mmol), EDC (12 mg, 0.062 mmol) and triethylamine (0.014 mL, 0.104 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride) to obtain Example 541 (25 mg, 0.051 mmol, 97% yield) as a white glass. MS found: (M+H)$^+$=494.47.

Example 542

N5-((R)-1-((S)-4-(4-chlorophenyl)-4-hydroxy-3,3-dimethylpiperidin-1-yl)-3-methyl-1-oxobutan-2-yl)-N1,N1,2,2-tetramethylpentanediamide

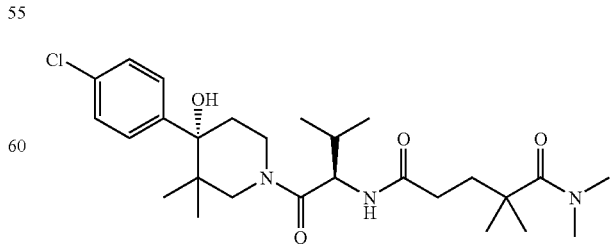

5-((R)-1-((S)-4-(4-chlorophenyl)-4-hydroxy-3,3-dimethylpiperidin-1-yl)-3-methyl-1-oxobutan-2-ylamino)-2,2- dimethyl-5-oxopentanoic acid (from Example 537, Step 1) (25 mg, 0.052 mmol), 2.0 M dimethylamine in THF (0.031 mL, 0.062 mmol), HOBT (10 mg, 0.062 mmol), EDC (12 mg, 0.062 mmol) and triethylamine (0.014 mL, 0.104 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride) to obtain Example 542 (10 mg, 0.020 mmol, 38%) as a white glass. MS found: (M+H)$^+$=508.49.

Example 543

N1-((R)-1-((S)-4-(4-chlorophenyl)-4-hydroxy-3,3-dimethylpiperidin-1-yl)-3-methyl-1-oxobutan-2-yl)-N-5-methylglutaramide

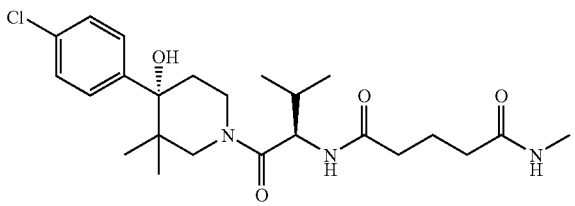

Step 1: 5-((R)-1-((S)-4-(4-chlorophenyl)-4-hydroxy-3,3-dimethylpiperidin-1-yl)-3-methyl-1-oxobutan-2-ylamino)-5-oxopentanoic acid

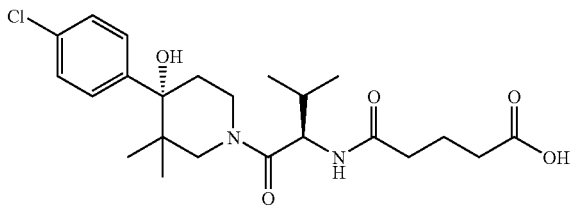

Following the procedure of Example 537, Step 1, using dihydro-2H-pyran-2,6(3H)-dione (18 mg, 0.160 mmol). The solvent was evaporated then the residue purified over silica gel (1:1 hexanes/EtOAc to 100% EtOAc to 4:1 methylene chloride/MeOH) to obtain 5-((R)-1-((S)-4-(4-chlorophenyl)-4-hydroxy-3,3-dimethylpiperidin-1-yl)-3-methyl-1-oxobutan-2-ylamino)-5-oxopentanoic acid (56 mg, 0.124 mmol, 77% yield) as a white glass. MS found: (M+H)$^+$=453.35.

Step 2: Example 543

5-((R)-1-((S)-4-(4-chlorophenyl)-4-hydroxy-3,3-dimethylpiperidin-1-yl)-3-methyl-1-oxobutan-2-ylamino)-5-oxopentanoic acid (25 mg, 0.055 mmol), methylamine hydrochloride (5 mg, 0.066 mmol), HOBT (10 mg, 0.066 mmol), EDC (13 mg, 0.066 mmol) and triethylamine (0.015 mL, 0.110 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride) to obtain Example 543 (23 mg, 0.049 mmol, 89% yield) as a white glass. MS found: (M+H)$^+$=466.41.

Example 544

N1-((R)-1-((S)-4-(4-chlorophenyl)-4-hydroxy-3,3-dimethylpiperidin-1-yl)-3-methyl-1-oxobutan-2-yl)-N5,N5-dimethylglutaramide

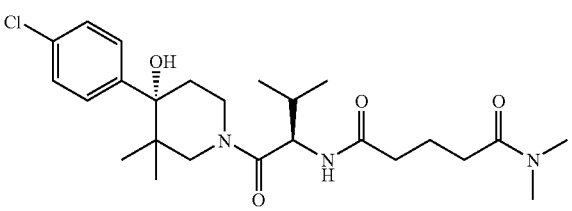

5-((R)-1-((S)-4-(4-chlorophenyl)-4-hydroxy-3,3-dimethylpiperidin-1-yl)-3-methyl-1-oxobutan-2-ylamino)-5-oxopentanoic acid (from Example 543, Step 1) (25 mg, 0.055 mmol), 2.0 M dimethylamine in THF (0.033 mL, 0.066 mmol), HOBT (10 mg, 0.066 mmol), EDC (13 mg, 0.066 mmol) and triethylamine (0.015 mL, 0.110 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride) to obtain Example 544 (16 mg, 0.033 mmol, 60% yield) as a white glass. MS found: (M+H)=480.44.

Example 545

6-((R)-1-((S)-4-(4-chlorophenyl)-4-hydroxy-3,3-dimethylpiperidin-1-yl)-3-methyl-1-oxobutan-2-ylamino)-6-oxohexanoic acid

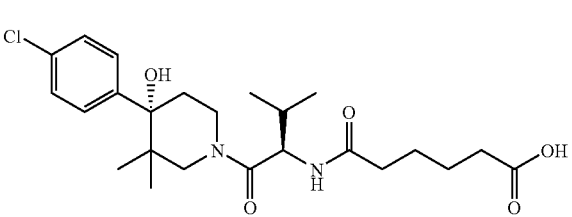

(R)-2-amino-1-((S)-4-(4-chlorophenyl)-4-hydroxy-3,3-dimethylpiperidin-1-yl)-3-methylbutan-1-one (50 mg, 0.133 mmol), oxepane-2,7-dione (20 mg, 0.160 mmol), HOBT (24 mg, 0.160 mmol), EDC (31 mg, 0.160 mmol) and triethylamine (0.037 mL, 0.266 mmol) were mixed in methylene chloride (3 mL) at 25° C. with stirring. The reaction was stirred for 20 hours and then the solvent was evaporated. The resulting residue was purified over silica gel (100% EtOAc to 4:1 methylene chloride/MeOH) to obtain Example 545 (50 mg, 0.107 mmol, 80% yield) as a white glass. MS found: (M+H)$^+$=467.38.

Example 546

1-acetyl-N—((R)-1-((S)-4-(4-chlorophenyl)-4-hydroxy-3,3-dimethylpiperidin-1-yl)-3-methyl-1-oxobutan-2-yl)azetidine-3-carboxamide, TFA

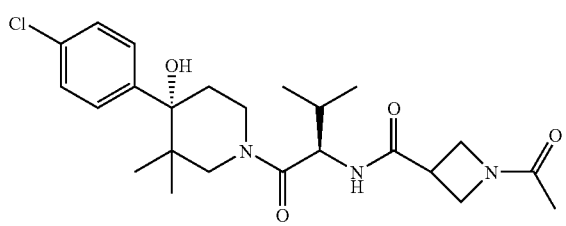

Step 1: Tert-butyl 3-((R)-1-((S)-4-(4-chlorophenyl)-4-hydroxy-3,3-dimethylpiperidin-1-yl)-3-methyl-1-oxobutan-2-ylcarbamoyl)azetidine-1-carboxylate

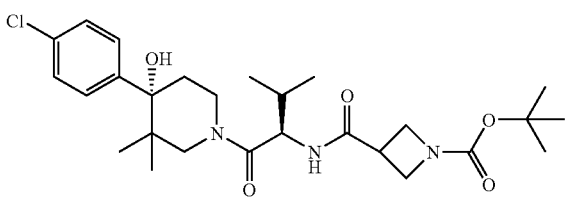

Following the procedure of Example 535, Step 1, using 1-(tert-butoxycarbonyl)azetidine-3-carboxylic acid (32 mg, 0.160 mmol), tert-butyl 3-((R)-1-((S)-4-(4-chlorophenyl)-4-hydroxy-3,3-dimethylpiperidin-1-yl)-3-methyl-1-oxobutan-2-ylcarbamoyl)azetidine-1-carboxylate (50 mg, 0.096 mmol, 71% yield) was obtained as a white glass. MS found: $(M+H)^+= 522.39$.

Step 2: N—((R)-1-((S)-4-(4-chlorophenyl)-4-hydroxy-3,3-dimethylpiperidin-1-yl)-3-methyl-1-oxobutan-2-yl)azetidine-3-carboxamide, HCl

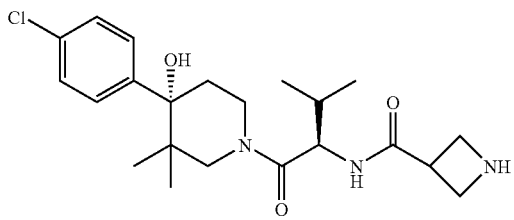

Following the procedure of Example 535, Step 2, using tert-butyl 3-((R)-1-((S)-4-(4-chlorophenyl)-4-hydroxy-3,3-dimethylpiperidin-1-yl)-3-methyl-1-oxobutan-2-ylcarbamoyl)azetidine-1-carboxylate (45 mg, 0.086 mmol), N—((R)-1-((S)-4-(4-chlorophenyl)-4-hydroxy-3,3-dimethylpiperidin-1-yl)-3-methyl-1-oxobutan-2-yl)azetidine-3-carboxamide, HCl (39 mg, 0.085 mmol, 99% yield) was obtained as a white glass. MS found: $(M+H)^+= 422.32$.

Step 3: Example 546

Following the procedure of Example 539, Step 1 using acetic anhydride (0.036 mL, 0.382 mmol), Example 546 (6.0 mg, 10.38 μmol, 13% yield) was obtained as a white solid after purification by LCMS HPLC. MS found: $(M+H)^+= 464.29$.

Example 547

3-(N-acetylsulfamoyl)-N—((R)-1-((S)-4-(4-chlorophenyl)-4-hydroxy-3,3-dimethylpiperidin-1-yl)-3-methyl-1-oxobutan-2-yl)benzamide

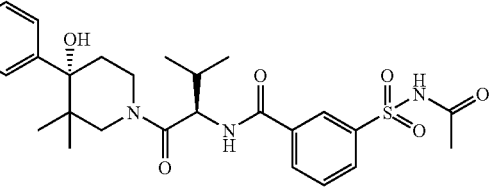

Step 1: N—((R)-1-((S)-4-(4-chlorophenyl)-4-hydroxy-3,3-dimethylpiperidin-1-yl)-3-methyl-1-oxobutan-2-yl)-3-sulfamoylbenzamide

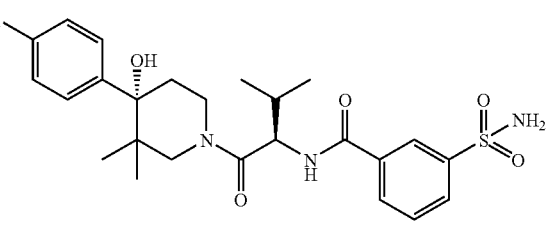

(R)-2-Amino-1-((S)-4-(4-chlorophenyl)-4-hydroxy-3,3-dimethylpiperidin-1-yl)-3-methylbutan-1-one (200 mg, 0.533 mmol), 3-sulfamoylbenzoic acid (129 mg, 0.639 mmol), HOBT (98 mg, 0.639 mmol), EDC (123 mg, 0.639 mmol) and triethylamine (0.149 mL, 1.066 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc) to obtain N—((R)-1-((S)-4-(4-chlorophenyl)-4-hydroxy-3,3-dimethylpiperidin-1-yl)-3-methyl-1-oxobutan-2-yl)-3-sulfamoylbenzamide (197 mg, 0.377 mmol, 70% yield) as a white glass. MS found: $(M+H)^+=522.32$.

Step 2: Example 547

N—((R)-1-((S)-4-(4-chlorophenyl)-4-hydroxy-3,3-dimethylpiperidin-1-yl)-3-methyl-1-oxobutan-2-yl)-3-sulfamoylbenzamide (40 mg, 0.077 mmol), acetic acid (5.70 μl, 0.100 mmol), DMAP (12 mg, 0.100 mmol), EDC (19 mg, 0.100 mmol) and triethylamine (0.021 mL, 0.153 mmol) were mixed and stirred in methylene chloride (3 mL). The reaction was stirred for 20 hours then washed with 1N HCl (2×) and brine. The organic layer was dried over sodium sulfate and concentrated in vacuo and purified over silica gel (1:1 hexanes/EtOAc to 100% EtOAc) to obtain Example 547 (27 mg, 0.048 mmol, 62% yield) as a white glass. MS found: $(M+H)^+= 564.36$.

Example 548

N—((R)-1-((S)-4-(4-chlorophenyl)-4-hydroxy-3,3-dimethylpiperidin-1-yl)-3-methyl-1-oxobutan-2-yl)-3-(N-propionylsulfamoyl)benzamide

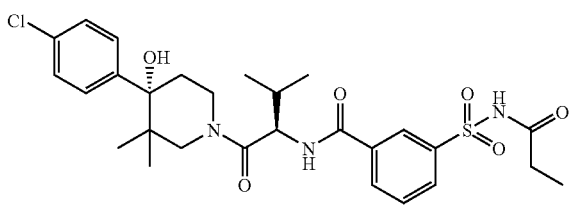

Following the procedure of Example 547, Step 2, using propionic acid (7.38 mg, 0.100 mmol), Example 548 (25 mg, 0.043 mmol, 56% yield) was obtained as a white glass. MS found: (M+H)$^+$=578.38.

Example 549

3-(N-benzoylsulfamoyl)-N—((R)-1-((S)-4-(4-chlorophenyl)-4-hydroxy-3,3-dimethylpiperidin-1-yl)-3-methyl-1-oxobutan-2-yl)benzamide

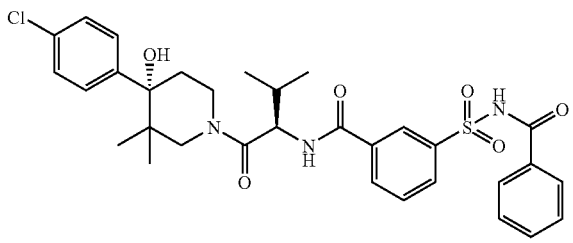

Following the procedure of Example 547, Step 2, using benzoic acid (12 mg, 0.100 mmol), Example 549 (35 mg, 0.056 mmol, 73.0% yield) was obtained as a white glass. MS found: (M+H)$^+$=626.40.

Example 550

2-((S)-1-acetylpyrrolidin-3-yl)-N—((R)-1-((S)-4-(4-chlorophenyl)-4-hydroxy-3,3-dimethylpiperidin-1-yl)-3-methyl-1-oxobutan-2-yl)acetamide

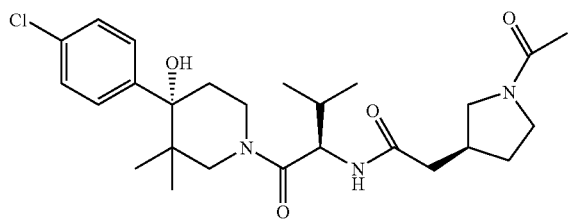

Step 1: (S)-tert-butyl 3-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate

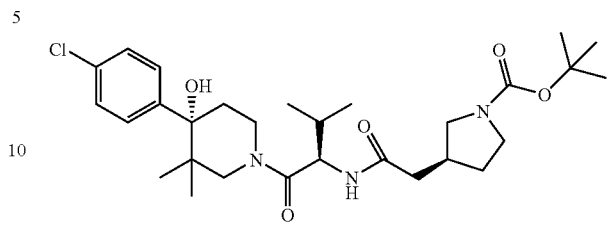

Following the procedure of Example 535, Step 1, using (S)-2-(1-(tert-butoxycarbonyl)pyrrolidin-3-yl)acetic acid (37 mg, 0.160 mmol), (S)-tert-butyl 3-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate (60 mg, 0.109 mmol, 82% yield) was obtained as a white glass. MS found: (M+H)$^+$=550.48.

Step 2: N—((R)-1-((S)-4-(4-chlorophenyl)-4-hydroxy-3,3-dimethylpiperidin-1-yl)-3-methyl-1-oxobutan-2-yl)-2-((S)-pyrrolidin-3-yl)acetamide, HCl

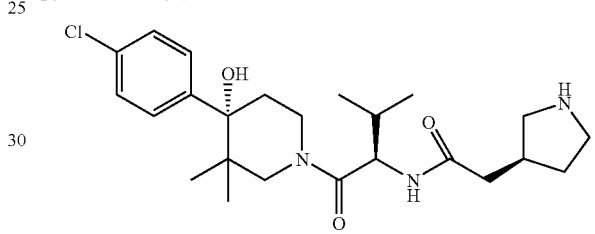

Following the procedure of Example 535, Step 2, using (S)-tert-butyl 3-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate (55 mg, 0.100 mmol), N—((R)-1-((S)-4-(4-chlorophenyl)-4-hydroxy-3,3-dimethylpiperidin-1-yl)-3-methyl-1-oxobutan-2-yl)-2-((S)-pyrrolidin-3-yl)acetamide, HCl (45 mg, 0.093 mmol, 93% yield) was obtained as a white solid. MS found: (M+H)$^+$=450.35.

Step 3: Example 550

Following the procedure of Example 537, Step 1 using acetic anhydride (0.039 ml, 0.411 mmol), Example 550 (40 mg, 0.081 mmol, 99% yield) was obtained as a white glass. MS found: (M+H)$^+$=492.39.

Example 551

2-((R)-1-acetylpyrrolidin-3-yl)-N—((R)-1-((S)-4-(4-chlorophenyl)-4-hydroxy-3,3-dimethylpiperidin-1-yl)-3-methyl-1-oxobutan-2-yl)acetamide

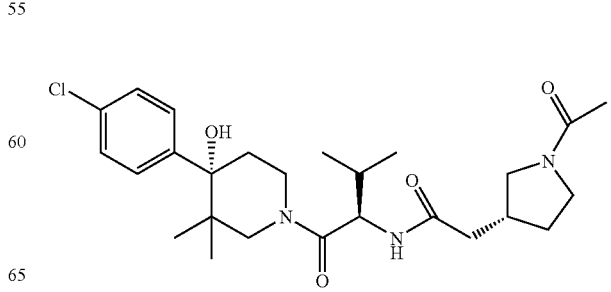

Step 1: (R)-tert-butyl 3-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate

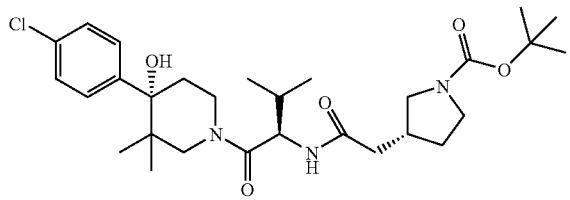

Following the procedure of Example 535, Step 1, using (R)-2-(1-(tert-butoxycarbonyl)pyrrolidin-3-yl)acetic acid (37 mg, 0.160 mmol), (R)-tert-butyl 3-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate (60 mg, 0.109 mmol, 82% yield) was obtained as a white glass. MS found: $(M+H)^+=550.42$.

Step 2: N—((R)-1-((S)-4-(4-chlorophenyl)-4-hydroxy-3,3-dimethylpiperidin-1-yl)-3-methyl-1-oxobutan-2-yl)-2-((R)-pyrrolidin-3-yl)acetamide, HCl

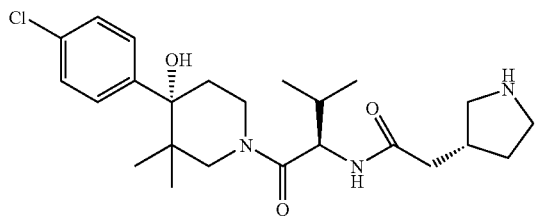

Following the procedure of Example 535, Step 2, using (R)-tert-butyl 3-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate (55 mg, 0.100 mmol), N—((R)-1-((S)-4-(4-chlorophenyl)-4-hydroxy-3,3-dimethylpiperidin-1-yl)-3-methyl-1-oxobutan-2-yl)-2-((R)-pyrrolidin-3-yl)acetamide, HCl (45 mg, 0.093 mmol, 93% yield) was obtained as a white solid. MS found: $(M+H)^+=450.37$.

Step 3: Example 551

Following the procedure of Example 537, Step 1 using acetic anhydride (0.039 ml, 0.411 mmol), Example 551 (40 mg, 0.081 mmol, 99% yield) was obtained as a white glass. MS found: $(M+H)^+=492.39$.

Example 552

2-((S)-1-acetylpyrrolidin-2-yl)-N—((R)-1-((S)-4-(4-chlorophenyl)-4-hydroxy-3,3-dimethylpiperidin-1-yl)-3-methyl-1-oxobutan-2-yl)acetamide

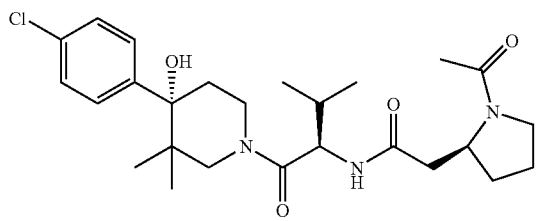

Step 1: (S)-tert-butyl 2-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate

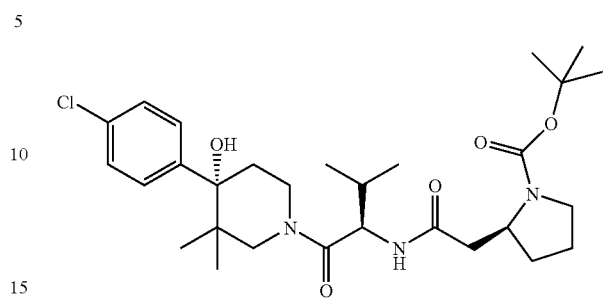

Following the procedure of Example 535, Step 1, using (S)-2-(1-(tert-butoxycarbonyl)pyrrolidin-2-yl)acetic acid (37 mg, 0.160 mmol), (S)-tert-butyl 2-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate (60 mg, 0.109 mmol, 82% yield) was obtained as a white glass. MS found: $(M+H)^+=550.42$.

Step 2: N—((R)-1-((S)-4-(4-chlorophenyl)-4-hydroxy-3,3-dimethylpiperidin-1-yl)-3-methyl-1-oxobutan-2-yl)-2-((S)-pyrrolidin-2-yl)acetamide, HCl

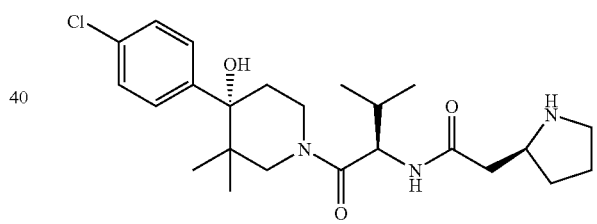

Following the procedure of Example 535, Step 2, using (S)-tert-butyl 2-(2-((R)-1-((S)-4-(4-chlorophenyl)-4-hydroxy-3,3-dimethylpiperidin-1-yl)-3-methyl-1-oxobutan-2-ylamino)-2-oxoethyl)pyrrolidine-1-carboxylate (55 mg, 0.100 mmol), N—((R)-1-((S)-4-(4-chlorophenyl)-4-hydroxy-3,3-dimethylpiperidin-1-yl)-3-methyl-1-oxobutan-2-yl)-2-((S)-pyrrolidin-2-yl)acetamide, HCl (48 mg, 0.099 mmol, 99% yield) was obtained as a white glass. MS found: $(M+H)^+=450.39$.

Step 3: Example 552

Following the procedure of Example 537, Step 1 using acetic anhydride (0.024 ml, 0.257 mmol), Example 552 (20 mg, 0.041 mmol, 79% yield) was obtained as a white glass. MS found: $(M+H)^+=492.40$.

Example 553

N—((R)-1-((S)-4-(4-chlorophenyl)-4-hydroxy-3,3-dimethylpiperidin-1-yl)-3-methyl-1-oxobutan-2-yl)-2'-ureidobiphenyl-3-carboxamide

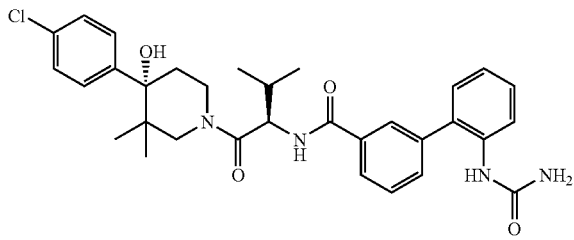

(R)-2-amino-1-((S)-4-(4-chlorophenyl)-4-hydroxy-3,3-dimethylpiperidin-1-yl)-3-methylbutan-1-one, HCl (30 mg, 0.080 mmol), 2'-ureidobiphenyl-3-carboxylic acid (25 mg, 0.096 mmol), HOBT (15 mg, 0.096 mmol), EDC (18 mg, 0.096 mmol) and triethylamine (0.022 mL, 0.160 mmol) were mixed in methylene chloride (3 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (1:1 Hexanes/EtOAc to 100% EtOAc to 4:1 methylene chloride/MeOH) to obtain Example 553 (40 mg, 0.069 mmol, 87% yield) as a tan solid. MS found: (M+H)$^+$=577.39.

Example 554

3-((R)-1-((S)-4-(4-chlorophenyl)-4-hydroxy-3,3-dimethylpiperidin-1-yl)-3-methyl-1-oxobutan-2-ylcarbamoyl)-5-(pyridin-2-yl)benzoic acid

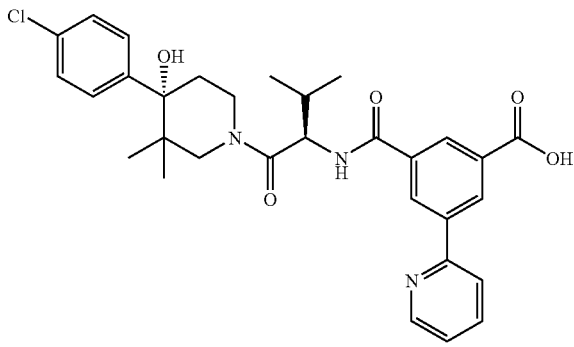

Step 1: Methyl 3-bromo-5-((R)-1-((S)-4-(4-chlorophenyl)-4-hydroxy-3,3-dimethylpiperidin-1-yl)-3-methyl-1-oxobutan-2-ylcarbamoyl)benzoate

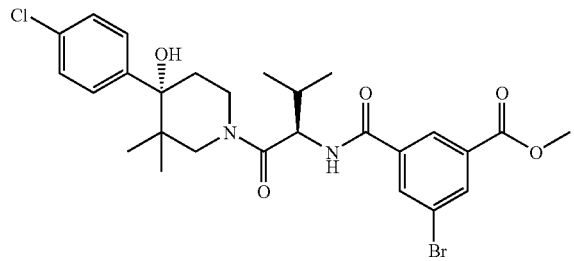

(R)-2-Amino-1-((S)-4-(4-chlorophenyl)-4-hydroxy-3,3-dimethylpiperidin-1-yl)-3-methylbutan-1-one, HCl (100 mg, 0.266 mmol), 3-bromo-5-(methoxycarbonyl)benzoic acid (83 mg, 0.320 mmol), HOBT (49 mg, 0.320 mmol), EDC (61 mg, 0.320 mmol) and triethylamine (0.074 mL, 0.533 mmol) were mixed in methylene chloride (5 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (3:1 to 1:1 Hexanes/EtOAc to 100% EtOAc) to obtain methyl 3-bromo-5-((R)-1-((S)-4-(4-chlorophenyl)-4-hydroxy-3,3-dimethylpiperidin-1-yl)-3-methyl-1-oxobutan-2-ylcarbamoyl)benzoate (120 mg, 0.207 mmol, 78% yield) as a white glass. MS found: (M+H)$^+$=579.10/581.13.

Step 2: Methyl 3-((R)-1-((S)-4-(4-chlorophenyl)-4-hydroxy-3,3-dimethylpiperidin-1-yl)-3-methyl-1-oxobutan-2-ylcarbamoyl)-5-(pyridin-2-yl)benzoate

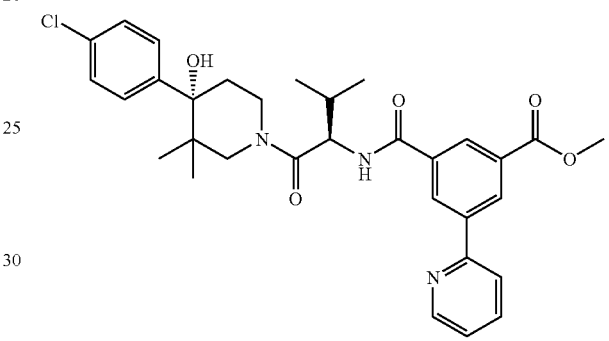

Methyl 3-bromo-5-((R)-1-((S)-4-(4-chlorophenyl)-4-hydroxy-3,3-dimethylpiperidin-1-yl)-3-methyl-1-oxobutan-2-ylcarbamoyl)benzoate (40 mg, 0.069 mmol) was dissolved in toluene (3 mL) at 25° C. then 2-(tributylstannyl)pyridine (76 mg, 0.207 mmol) was added. The reaction was degassed then placed under nitrogen. Tetrakis(triphenylphosphine)palladium(0) (4 mg, 3.45 μmol) was added and the reaction heated at reflux for 2 hours. The reaction was concentrated in vacuo to give a dark residue which was then dissolved in MeOH, filtered to remove insoluble material, then purified by LCMS HPLC. The obtained colorless oil was dissolved in EtOAc, dried over sodium sulfate and concentrated in vacuo to give methyl 3-((R)-1-((S)-4-(4-chlorophenyl)-4-hydroxy-3,3-dimethylpiperidin-1-yl)-3-methyl-1-oxobutan-2-ylcarbamoyl)-5-(pyridin-2-yl)benzoate (30 mg, 0.052 mmol, 75% yield) as a white glass. MS found: (M+H)$^+$=578.34.

Step 3: Example 554

Methyl 3-((R)-1-((S)-4-(4-chlorophenyl)-4-hydroxy-3,3-dimethylpiperidin-1-yl)-3-methyl-1-oxobutan-2-ylcarbamoyl)-5-(pyridin-2-yl)benzoate (25 mg, 0.043 mmol) was dissolved in MeOH (2 mL) at 25° C. then 1N NaOH (0.086 mL, 0.086 mmol) added with stirring. The reaction was stirred for 2 hours, diluted with water and concentrated to remove MeOH. The aqueous was acidified to pH=3 with 1N HCl and the formed solids were extracted into methylene chloride. The organic layers were combined, dried (sodium sulfate) and concentrated in vacuo to give Example 554 (12 mg, 0.021 mmol, 49% yield) as a white solid. MS found: (M+H)$^+$=564.33.

Example 555 tert-butyl 2-(3-((R)-1-((S)-4-(4-chlorophenyl)-4-hydroxy-3,3-dimethylpiperidin-1-yl)-3-methyl-1-oxobutan-2-yl)ureido)-2-methylpropanoate

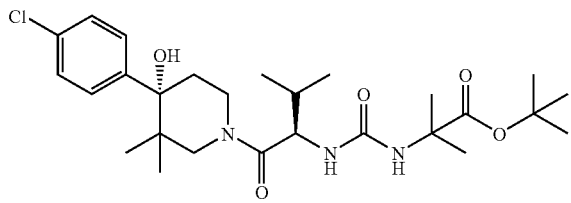

Step 1: tert-Butyl 2-methyl-2-(phenoxycarbonylamino)propanoate

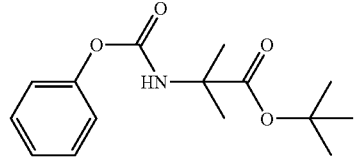

tert-Butyl 2-amino-2-methylpropanoate, HCl (66 mg, 0.337 mmol) and triethylamine (0.047 mL, 0.337 mmol) were mixed and stirred in THF (10 mL) at 25° C. then cooled to 0° C. and added a THF solution of phenyl carbonochloridate (53 mg, 0.337 mmol). The reaction was stirred for 20 hours, diluted with EtOAc, and washed with 1N HCl and brine. The organic layer was dried (sodium sulfate) and concentrated in vacuo to give tert-butyl 2-methyl-2-(phenoxycarbonylamino)propanoate (90 mg, 0.322 mmol, 96% yield) of a white glass as product. MS found: (M+H)$^+$=280.30.

Step 2: Example 555

(R)-2-amino-1-((S)-4-(4-chlorophenyl)-4-hydroxy-3,3-dimethylpiperidin-1-yl)-3-methylbutan-1-one, HCl (40 mg, 0.107 mmol), tert-butyl 2-methyl-2-(phenoxycarbonylamino)propanoate (30 mg, 0.107 mmol) and triethylamine (0.030 mL, 0.213 mmol) were mixed in acetonitrile (3 mL) at 25° C. then heated at 150° C. for 60 minutes in a microwave reactor. The reaction was concentrated in vacuo then purified over silica gel (3:1 to 1:1 hexanes/EtOAc to 100% EtOAc) to obtain Example 555 (40 mg, 0.076 mmol, 72% yield) as a white glass. MS found: (M+H)$^+$=524.35.

Example 556

3'-((R)-1-((S)-4-(4-chlorophenyl)-4-hydroxy-3,3-dimethylpiperidin-1-yl)-3-methyl-1-oxobutan-2-ylcarbamoyl)biphenyl-4-carboxylic acid

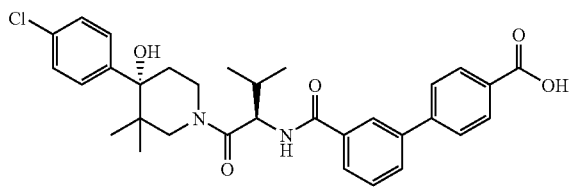

Step 1: 3-Bromo-N—((R)-1-((S)-4-(4-chlorophenyl)-4-hydroxy-3,3-dimethylpiperidin-1-yl)-3-methyl-1-oxobutan-2-yl)benzamide

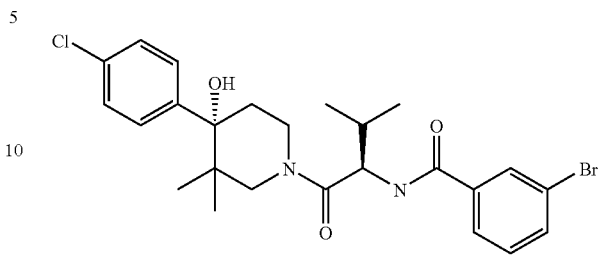

(R)-2-amino-1-((S)-4-(4-chlorophenyl)-4-hydroxy-3,3-dimethylpiperidin-1-yl)-3-methylbutan-1-one, HCl (100 mg, 0.266 mmol), 3-bromobenzoic acid (64 mg, 0.320 mmol), HOBT (49 mg, 0.320 mmol), EDC (61 mg, 0.320 mmol) and triethylamine (0.074 mL, 0.533 mmol) were mixed in methylene chloride (5 mL) at 25° C. with stirring. The reaction was stirred for 20 hours then washed with sat'd sodium bicarbonate. The methylene chloride layer was dried over sodium sulfate and concentrated in vacuo to give a white glass which was purified over silica gel (3:1 to 1:1 Hexanes/EtOAc to 100% EtOAc) to obtain 3-bromo-N—((R)-1-((S)-4-(4-chlorophenyl)-4-hydroxy-3,3-dimethylpiperidin-1-yl)-3-methyl-1-oxobutan-2-yl)benzamide (100 mg, 0.192 mmol, 72% yield) as a white solid. MS found: (M+H)$^+$=521.1/523.1.

Step 2: Methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-4-carboxylate

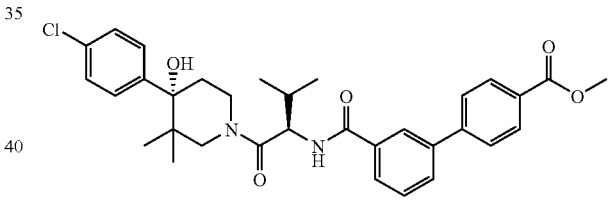

3-Bromo-N—((R)-1-((S)-4-(4-chlorophenyl)-4-hydroxy-3,3-dimethylpiperidin-1-yl)-3-methyl-1-oxobutan-2-yl)benzamide (50 mg, 0.096 mmol), 4-(methoxycarbonyl)phenylboronic acid (17 mg, 0.096 mmol), 1.5M cesium carbonate (0.192 ml, 0.287 mmol) and palladium(II) acetate (1.08 mg, 4.79 µmol) were dissolved in DMF (3 mL) in a microwave tube at 25° C. then heated at 60° C. for 30 minutes. The reaction was diluted with EtOAc then washed with water (4×). The organic layer was dried (sodium sulfate) and concentrated in vacuo to give methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-4-carboxylate (44 mg, 0.076 mmol, 80% yield) as a white solid. MS found: (M+H)$^+$=577.32.

Step 3: Example 556

Methyl 3'-((R)-1-((S)-4-(4-chlorophenyl)-4-hydroxy-3,3-dimethylpiperidin-1-yl)-3-methyl-1-oxobutan-2-ylcarbamoyl)biphenyl-4-carboxylate (40 mg, 0.069 mmol) was dissolved in MeOH (3 ml) and added 1N NaOH (0.14 mL, 0.14 mmol) at 25° C. and stirred over the weekend. The MeOH was removed in vacuo and the aqueous was acidified to pH=3 with 1N HCl. The formed solids were extracted 2 times with methylene chloride. The organic layers were combined, dried (so-

Example 557

3-((R)-1-((S)-4-(4-chlorophenyl)-4-hydroxy-3,3-dimethylpiperidin-1-yl)-3-methyl-1-oxobutan-2-yl)-1-methyl-1-phenylurea

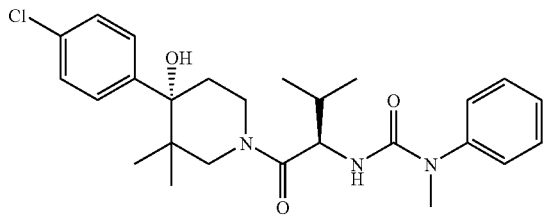

(R)-2-Amino-1-((S)-4-(4-chlorophenyl)-4-hydroxy-3,3-dimethylpiperidin-1-yl)-3-methylbutan-1-one, HCl (25 mg, 0.067 mmol) and methyl(phenyl)carbamic chloride (11 mg, 0.067 mmol) were stirred in acetonitrile (2 ml) at 25° C., then heated for 20 hours at 60° C. The reaction was cooled to rt, concentrated and purified over silica gel (3:1 hexanes/EtOAc to 1:1 hexanes/EtOAc to 100% EtOAc) to obtain Example 557 (30 mg, 0.064 mmol, 95% yield) as a white solid. MS found: (M+H)$^+$=472.28.

Example 558

N1-((R)-1-((S)-4-(4-chlorophenyl)-4-hydroxy-3,3-dimethylpiperidin-1-yl)-3-methyl-1-oxobutan-2-yl)-N3-(methylsulfonyl)isophthalamide

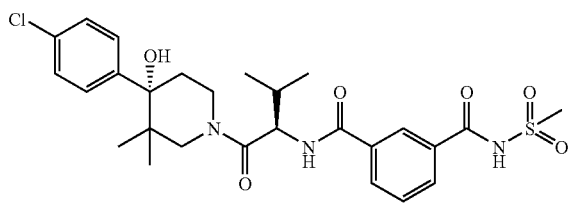

Step 1: Methyl 3-(methylsulfonylcarbamoyl)benzoate

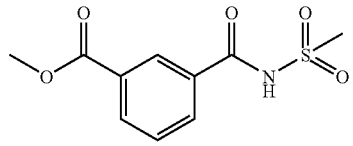

3-(Methoxycarbonyl)benzoic acid (500 mg, 2.78 mmol), methyl sulfonamide (264 mg, 2.78 mmol), HATU (1.06 g, 2.78 mmol), and diisopropylethylamine (1.45 mL, 8.33 mmol) were mixed in methylene chloride (20 mL) with stirring. The reaction was stirred for 20 hours, added sat'd ammonium chloride, and extracted with methylene chloride. The organic extracts were combined, dried over sodium sulfate and concentrated to give an amber oil which was purified over silica gel (1:1 hexanes/ethyl acetate to 100% ethyl acetate to 4:1 methylene chloride/methanol) to obtain methyl 3-(methylsulfonylcarbamoyl)benzoate (700 mg, 2.72 mmol, 97% yield). MS found: (M+H)$^+$=258.07.

Step 2: 3-(Methylsulfonylcarbamoyl)benzoic acid

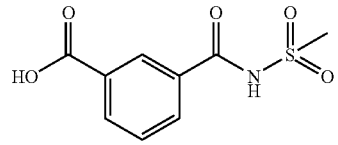

Methyl 3-(methylsulfonylcarbamoyl)benzoate (700 mg, 2.72 mmol) was dissolved in methanol at 25° C. with stirring then 1.0 N NaOH (5.56 mL, 5.56 mmol) was added. The reaction mixture was stirred for 20 hours, diluted with water, and the methanol removed in vacuo. The aqueous was washed with diethyl ether (2×) then acidified to pH=3 with 1N HCl. The resulting solution was extracted with ethyl acetate to give 3-(methylsulfonylcarbamoyl)benzoic acid (285 mg, 1.12 mmol, 42% yield). MS found: (M+H)$^+$=244.00.

Step 3: N1-((R)-1-((S)-4-(4-chlorophenyl)-4-hydroxy-3,3-dimethylpiperidin-1-yl)-3-methyl-1-oxobutan-2-yl)-N3-(methylsulfonyl)isophthalamide (R)-2-amino-1-((S)-4-(4-chlorophenyl)-4-hydroxy-3,3-dimethylpiperidin-1-yl)-3-methylbutan-1-one, HCl (20 mg, 0.053 mmol), 3-(methylsulfonylcarbamoyl)benzoic acid (17 mg, 0.069 mmol), DMAP (8 mg, 0.069 mmol), EDC (13 mg, 0.069 mmol) and triethylamine (8 µL, 0.053 mmol) were mixed in methylene chloride (3 mL) with stirring. The reaction was stirred for 20 hours, diluted with methylene chloride (10 mL) then washed with 1N HCl (2×5 mL). The organic layer was dried over sodium sulfate then concentrated in vacuo to give a solid which was purified over silica gel (100% ethylacetate to 4:1 methylene chloride/methanol) to obtain Example 558 (15 mg, 2.66 mmol, 50% yield) as a white solids. MS found: (M+H)=564.26.

Example 559

N-(1-(4-(4-chlorophenyl)-4-hydroxy-3,3-dimethylpiperidin-1-yl)-3-methyl-1-oxobutan-2-yl)benzamide, TFA

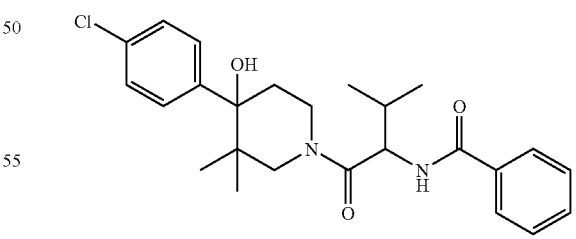

1-Bromo-4-chlorobenzene (17 mg, 0.091 mmol) and N-(1-(3,3-dimethyl-4-oxopiperidin-1-yl)-3-methyl-1-oxobutan-2-yl)benzamide (0.11 mL, 0.18 mmol) were dissolved in THF (5 mL) at 25° C. under nitrogen then the reaction was cooled to −70° C. with stirring, then 1.6 M n-butyllithium in hexanes was added dropwise via an addition funnel. The reaction was stirred at −70° C. for 2 hours then quenched with sat'd ammonium chloride (5 mL). The reaction was extracted 3 times with ethyl acetate and the combined organic extracts were dried over sodium sulfate then concentrated in vacuo to give a colorless oil which was purified by LCMS HPLC to give Example 559 (7 mg, 1.58 mmol, 17% yield). MS found: (M+H)$^+$=443.20.

Example 560

(S)-4-(4-chlorophenyl)-3,3-dimethyl-1-((R)-3-methyl-2-(3-methylureido)butanoyl)piperidin-4-yl acetate, TFA

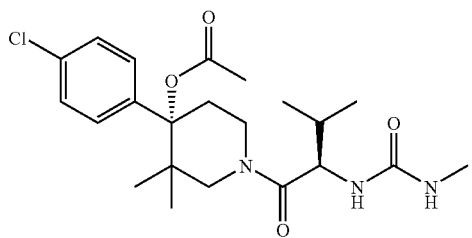

Step 1: 1-((R)-1-((S)-4-(4-chlorophenyl)-4-hydroxy-3,3-dimethylpiperidin-1-yl)-3-methyl-1-oxobutan-2-yl)-3-methylurea

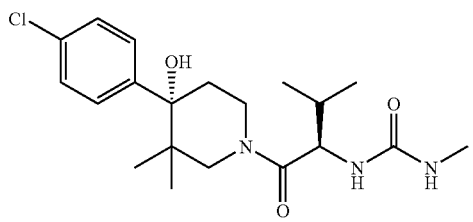

(R)-2-Amino-1-((S)-4-(4-chlorophenyl)-4-hydroxy-3,3-dimethylpiperidin-1-yl)-3-methylbutan-1-one, HCl (20 mg, 0.053 mmol) and triethylamine (7.4 μL, 0.053 mmol) were mixed in THF (2 mL) at 25° C. with stirring. Methyl isocyanate (6 μg, 0.11 mmol) was added. After 1 hour, additional methyl isocyanate (30 μg, 0.55 mmol) was added and the reaction heated at 100° C. for 30 minutes in a microwave reactor. The reaction was cooled, diluted with methylene chloride and washed with water (5 mL). The organic layer was dried over sodium sulfate and concentrated in vacuo to give an oil which was purified over silica gel (100% ethyl acetate to 4:1 methylene chloride/methanol) to give 1-((R)-1-((S)-4-(4-chlorophenyl)-4-hydroxy-3,3-dimethylpiperidin-1-yl)-3-methyl-1-oxobutan-2-yl)-3-methylurea (18 mg, 45 mmol, 86% yield) as an off-white solid. MS found: (M+H)$^+$=396.19.

Step 2: Example 560

1-((R)-1-((S)-4-(4-chlorophenyl)-4-hydroxy-3,3-dimethylpiperidin-1-yl)-3-methyl-1-oxobutan-2-yl)-3-methylurea (18 mg, 45 mmol) and triethylamine (6 μL) were mixed in THF (2 mL) at 25° C. with stirring then acetyl chloride (3 μL, 45 mmol) was added. Stirred for 20 hours then added additional acetyl chloride (15 μL, 225 mmol). Stirred stirring was continued for 6 hours and then the reaction mixture was filtered, diluted with water (3 mL) and extracted into methylene chloride. The organic extracts were combined, dried over sodium sulfate and concentrated in vacuo to give a colorless oil which was purified by HPLC to give Example 560 (3 mg, 5.4 mmol, 12% yield) as a white solid. MS found: (M+H)$^+$=438.37.

Example 561

(R)-1-(4-(4-chlorophenyl)piperidin-1-yl)-2-(7-chloroquinazolin-4-ylamino)-3-methylbutan-1-one

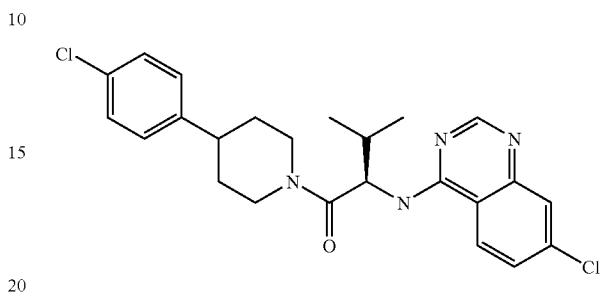

(R)-2-amino-1-(4-(4-chlorophenyl)piperidin-1-yl)-3-methylbutan-1-one, HCl (25 mg, 0.085 mmol), 4,7-dichloroquinazoline (20 mg, 0.10 mmol) and triethylamine (47 μL) were mixed in isopropanol (2 mL) at 25° C. then heated at 100° C. for 30 minutes in a microwave reactor. The reaction was concentrated in vacuo and purified over silica gel (9:1 to 1:1 hexanes/ethyl acetate) to obtain Example 561 (31 mg, 68 mmol, 80% yield) as a white solid. MS found: (M+H)$^+$=457.03.

Examples 562 and 563

(R)-1-((S)-4-(4-Chlorophenyl)-4-hydroxy-3,3-dimethylpiperidin-1-yl)-2-(2-chloropyrimidin-4-ylamino)-3-methylbutan-1-one and (R)-1-((S)-4-(4-Chlorophenyl)-4-hydroxy-3,3-dimethylpiperidin-1-yl)-2-(4-chloropyrimidin-2-ylamino)-3-methylbutan-1-one

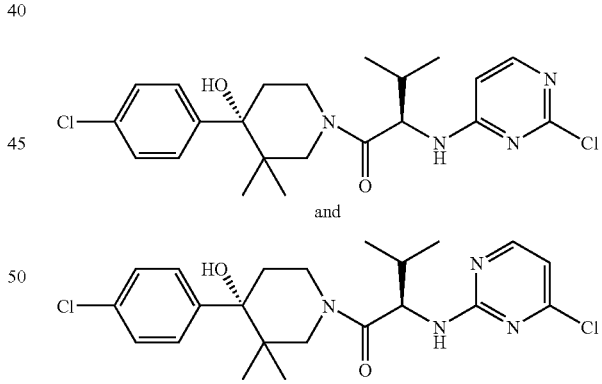

A reaction vessel was charged with 2,4-dichloropyrimidine (21.5 mg, 0.144 mmoles, 1 eq), (R)-2-amino-1-((S)-4-(4-chlorophenyl)-4-hydroxy-3,3-dimethylpiperidin-1-yl)-3-methylbutan-1-one (54.0 mg, 0.144 mmol, 1 eq), triethylamine (0.024 mL, 0.144 mmol, 1 eq) and DMF (2 mL) The reaction mixture was stirred overnight at rt. At the conclusion of this period, the resulting solution was evaporated, diluted with MeOH and purified by preparative LC-MS. The resulting fractions were lyophilized to provide 35.5 mg of Example 562 and 8.4 mg of Example 563. Example 562, MS found: (M+H)$^+$=451.37. Example 563, MS found: (M+H)$^+$=451.27.

Example 564

N-(1-(4-(2,4-dichlorophenyl)-4-hydroxypiperidin-1-yl)-3-methyl-1-oxobutan-2-yl)benzamide

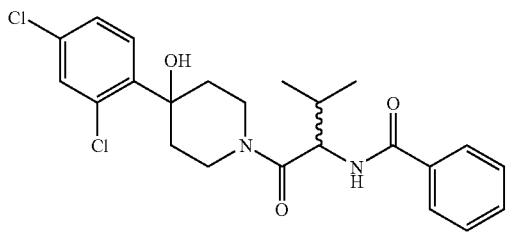

A reaction vessel was charged with N-(3-methyl-1-oxo-1-(4-oxopiperidin-1-yl)butan-2-yl)benzamide (68.4 mg, 0.23 mmoles, 1.0 eq), 1-bromo-2,4-dichlorobenzene (112.4 mg, 0.50 mmol, 2.2 eq), and THF (20 mL). The stirred reaction mixture was cooled to −78° C. 1.6 M n-BuLi in hexanes (0.31 mL, 0.50 mmoles, 1.0 eq) was added dropwise thereto via syringe (Caution: exotherm). The mixture was allowed to warm to rt in 2 hours. The mixture was quenched with water. Ethyl acetate was added thereto and the layers were separated. The organic layer was consecutively washed with 1N NaOH (3×) and 1N HCl (1×). The organic layer was dried (MgSO$_4$) and the solvent removed in vacuo. The residue was dissolved in MeOH and purified by preparative LC-MS. The collected fractions were evaporated and the residue dissolved in methylene chloride, dried (MgSO$_4$) and the solvent removed in vacuo to provide 30 mg of Example 564 as a white solid. MS found: (M+H)$^+$=449.03.

Example 565

(1R,3R)—N—((R)-1-(8-(4-chlorophenyl)-8-hydroxy-5-azaspiro[2.5]octan-5-yl)-3-methyl-1-oxobutan-2-yl)-3-hydroxycyclopentanecarboxamide

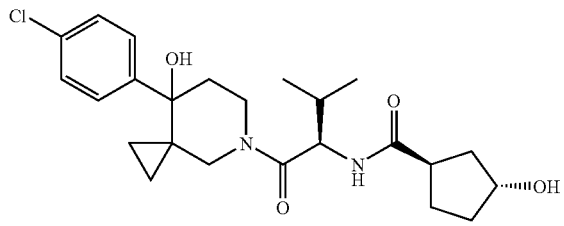

Step 1: (2-Chloroethyl)dimethylsulfonium iodide

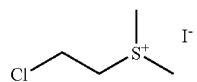

A mixture of (2-chloroethyl)(methyl)sulfane (24.73 g, 224 mmol) and iodomethane (100 mL, 1600 mmol) was stirred for two days at room temperature, during which time a solid precipitated. The reaction was diluted with 300 mL diethyl ether, and the suspension was stirred for 2 h. The solids were collected by filtration, rinsed with diethyl ether, and dried under vacuum to yield 27.2 g of a dark amber, sticky solid. This was stirred in 100 mL of 9:1 diethyl ether/methanol. The solids were collected by filtration, rinsed with diethyl ether, and dried under vacuum to yield the title compound (23.7 g, 94 mmol, 42.0% yield) as a pale yellow powder. Used as-is in the next step.

Step 2: tert-Butyl 8-oxo-5-azaspiro[2.5]octane-5-carboxylate

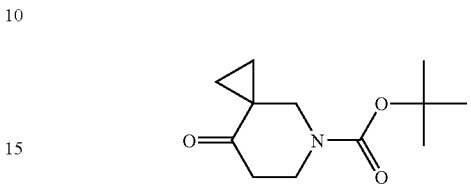

A solution of potassium tert-butoxide (3.26 g, 27.6 mmol) in tert-butanol (40 mL) was treated with tert-butyl 4-oxopiperidine-1-carboxylate (5 g, 25.09 mmol), causing the reaction to turn bright orange. The mixture was stirred for 1 h, then treated with (2-chloroethyl)dimethylsulfonium iodide (5.70 g, 22.59 mmol), added in three portions at 10 minute intervals. This addition caused the color of the reaction to gradually fade to pale yellow. The mixture was stirred for 2 hours, then diluted with tert-butanol (10 mL), treated with potassium tert-butoxide (2.96 g, 25.09 mmol), and stirred overnight at room temperature. The reaction was poured into water (100 mL) and extracted 3× with 100 mL ethyl acetate. The combined organic phases were washed with water and brine, then dried over sodium sulfate and concentrated in-vacuo. The residue was purified over a 5×15 cm silica gel column, eluting with ethyl acetate/hexanes (10%-15%-20%-25% EtOAc, 1 L at each concentration), to yield the title compound (1.15 g, 5.10 mmol, 20.34% yield) as a colorless oil.

Step 3: tert-Butyl 8-(4-chlorophenyl)-8-hydroxy-5-azaspiro[2.5]octane-5-carboxylate

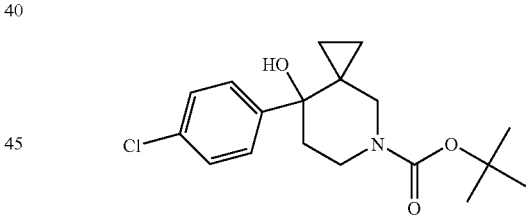

In a flame-dried 100 mL three necked flask, a solution of 1-bromo-4-chlorobenzene (3.51 g, 18.36 mmol) in THF (20 mL) was cooled to −78° C. and treated with the dropwise addition of 1.6 M BuLi in hexanes (12.00 mL, 19.19 mmol) at a rate which did not allow the temperature to exceed −60° C. The mixture was stirred at −78° C. for 1 h, during which time a white precipitate was observed. The mixture was treated with the dropwise addition of a solution of tert-butyl 8-oxo-5-azaspiro[2.5]octane-5-carboxylate (1.88 g, 8.35 mmol) in THF (5 mL), at a rate which did not allow the temperature to exceed −60° C. The mixture was stirred for 3 h, then allowed to warm to −20° C. and quenched with saturated ammonium chloride solution. The mixture was extracted 3× with ethyl acetate, the combined organic phases were washed with water followed by brine, then dried over sodium sulfate and concentrated in-vacuo. The residue was purified over a 5×15 cm silica gel column, eluting with ethyl acetate/hexanes (5%-10%-15%-20% ethyl acetate, to yield the title compound Step 4: 8-(4-Chlorophenyl)-5-azaspiro[2.5]octan-8-ol

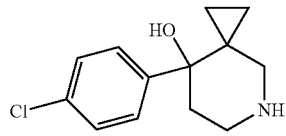

A solution of tert-butyl 8-(4-chlorophenyl)-8-hydroxy-5-azaspiro[2.5]octane-5-carboxylate (1.81 g, 5.36 mmol) in dioxane (2 mL) was treated with 4.0 M HCl in dioxane (7 mL, 28.0 mmol), and the reaction was stirred for 30 minutes at room temperature. The mixture was concentrated in-vacuo then concentrated 2× from methylene chloride to remove residual HCl. The residue was dissolved in water and washed 2× with diethyl ether. The aqueous phase was treated with sodium bicarbonate until the mixture was basic, then washed 2× with 10 mL diethyl ether. The aqueous phase was treated with solid sodium hydroxide until the pH was >13, and the mixture was extracted 5× with ethyl acetate. The combined ethyl acetate extracts were dried over sodium sulfate and concentrated in vacuo to yield (±)-8-(4-chlorophenyl)-5-azaspiro[2.5]octan-8-ol as a colorless powder (1.1 g, 87% yield). MS (ESI+)=238.1, (M+H)+. The isomers were separated via chiral super critical fluid chromatography to yield 463 mg of isomer A and 522 mg of isomer B.

Step 5: (R)-3-methyl-2-((2-(trimethylsilyl)ethoxy)carbonylamino)butanoic acid

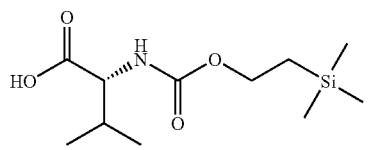

A mixture of (R)-2-amino-3-methylbutanoic acid (2.01 g, 17.16 mmol) and 2,5-dioxopyrrolidin-1-yl 2-(trimethylsilyl)ethyl carbonate (4.89 g, 18.87 mmol) in 1:1 dioxane/water (40 mL) was treated with triethylamine (3.59 mL, 25.7 mmol), and the mixture was stirred for two days at room temperature. The mixture was acidified with saturated sodium hydrogen sulfate and extracted 3× with ethyl acetate. The combined organic phases were washed with saturated sodium hydrogen sulfate, water, and brine, then dried over sodium sulfate and concentrated in-vacuo to yield the title compound (4.17 g, 15.96 mmol, 93% yield) as an amber oil.

Step 6: (2R)-1-(8-(4-chlorophenyl)-8-hydroxy-5-azaspiro[2.5]octan-5-yl)-3-methyl-1-oxobutan-2-ylcarbamate A solution of 8-(4-chlorophenyl)-5-azaspiro[2.5]octan-8-ol, isomer A (463 mg, 1.948 mmol), (R)-3-methyl-2-((2-(trimethylsilyl)ethoxy)carbonylamino)butanoic acid (560 mg, 2.142 mmol), EDC (821 mg, 4.28 mmol), and HOBT (656 mg, 4.28 mmol) in methylene chloride (10 mL) was stirred at room temperature for 30 minutes, the mixture was treated with triethylamine (1.086 mL, 7.79 mmol), and the reaction was stirred for an additional 30 minutes at room temperature. The reaction was concentrated in vacuo, and the residue was taken up in ethyl acetate. The organic phase was washed 3× with 1 N NaOH, 3× with 1 N HCl, and once with brine, then dried over sodium sulfate and concentrated in-vacuo. The residue was purified over silica gel eluting with ethyl acetate/hexanes (25-50% EtOAc) to yield the title compound (754 mg, 1.567 mmol, 80% yield) as a colorless, viscous oil.

Step 7: (2R)-2-amino-1-(8-(4-chlorophenyl)-8-hydroxy-5-azaspiro[2.5]octan-5-yl)-3-methylbutan-1-one

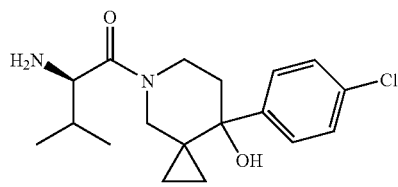

A solution of 2-(trimethylsilyl)ethyl (2R)-1-(8-(4-chlorophenyl)-8-hydroxy-5-azaspiro[2.5]octan-5-yl)-3-methyl-1-oxobutan-2-ylcarbamate (754 mg, 1.567 mmol) in THF (10 mL) was treated with TBAF (1.0 M in THF) (6.27 mL, 6.27 mmol), and the mixture was stirred overnight at room temperature. The reaction mixture was concentrated in-vacuo, and the residue was partitioned between EtOAc and saturated sodium bicarbonate. The layers were separated, and the organic phase was washed 2× with saturate sodium bicarbonate, once with water, and once with brine. The combined aqueous phases were extracted once with ethyl acetate, and the combined organic phases were washed with water and brine, then dried over sodium sulfate and concentrated in-vacuo. The residue was taken up in acetonitrile (100 mL), and washed 3× with 20 mL of hexanes. The acetonitrile phase was concentrated in-vacuo to yield the title compound (420 mg, 1.247 mmol, 80% yield) as a colorless glass. MS (ESI+)=337.4, (M+H)+.

Step 8: Example 565

A mixture of (R)-2-amino-1-(8-(4-chlorophenyl)-8-hydroxy-5-azaspiro[2.5]octan-5-yl)-3-methylbutan-1-one, HCl (41.7 mg, 0.112 mmol), (1R,3R)-3-hydroxycyclopentanecarboxylic acid (16 mg, 0.123 mmol), HOBT (37.7 mg, 0.246 mmol), and triethylamine (78 µL, 0.559 mmol) in methylene chloride was treated with EDC (47.1 mg, 0.246 mmol), and the reaction was allowed to stir overnight at room temperature. The mixture was concentrated in-vacuo, and the residue was taken up in ethyl acetate. The organic phase was washed 3× with saturated sodium carbonate, 3× with 1M HCl, and once with brine, dried over sodium sulfate, and concentrated in-vacuo. The residue was purified over a 12 g silica gel column via ISCO, eluting at 30 mL/min with a 0-10% MeOH/EtOAc gradient over 35 minutes to yield Example 565 (33 mg, 0.073 mmol, 65.8% yield) as a colorless glass. MS (ESI+)=431.13, (M+H—H₂O)+.

The following examples in Table 17 were prepared using the procedures described in Example 565, substituting the appropriate carboxylic acid for (1R,3R)-3-hydroxycyclopentanecarboxylic acid in Step 8.

TABLE 17
| Example | Carboxylic Acid | Structure | MS (ESI+) |
|---|---|---|---|
| 566 | 4-Chlorobenzoic acid | 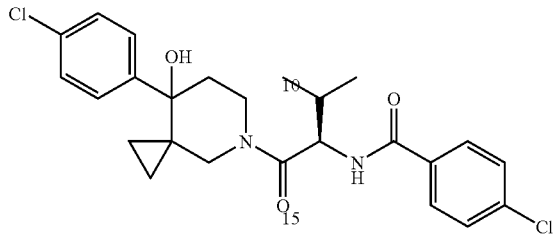 | 475.3 |
| 567 | Nicotinic acid | 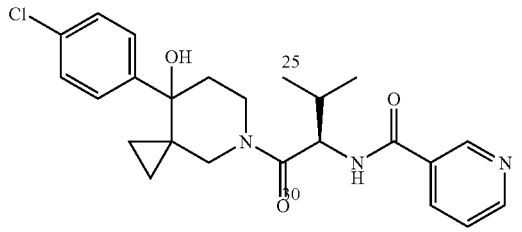 | 442.4 |
| 568 | 3-Sulfamoylbenzoic acid | 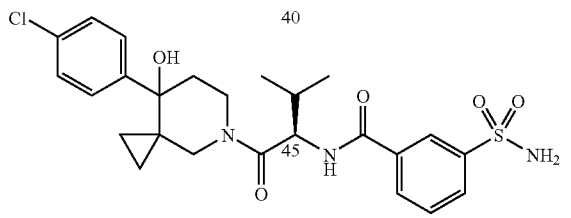 | 502.3 |
| 569 | Cyclopentanoic acid | 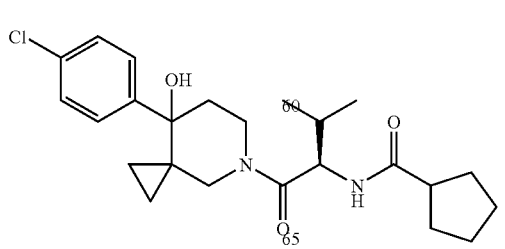 | 433.3 |

Example 571

3-((2R)-1-(8-(4-chlorophenyl)-8-hydroxy-5-azaspiro[2.5]octan-5-yl)-3-methyl-1-oxobutan-2-ylcarbamoyl)benzoic acid

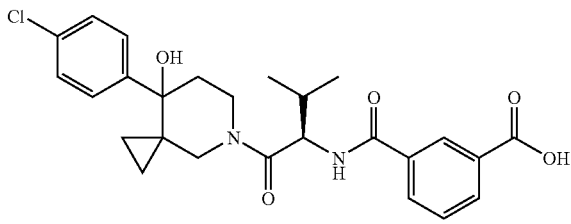

A mixture of (2R)-2-amino-1-(8-(4-chlorophenyl)-8-hydroxy-5-azaspiro[2.5]octan-5-yl)-3-methylbutan-1-one (21 mg, 0.062 mmol), 3-(methoxycarbonyl)benzoic acid (12.35 mg, 0.069 mmol), HOBT (21.00 mg, 0.137 mmol), and triethylamine (35 µl, 0.251 mmol) in CH$_2$Cl$_2$ (2 mL) was treated with EDC (26.3 mg, 0.137 mmol), and the mixture was stirred for three days at room temperature. The mixture was concentrated in-vacuo, and the residue was taken up in ethyl acetate. The organic phase was washed 3× with saturated sodium carbonate, 3× with 1M HCl, and once with saturated sodium chloride, dried over sodium sulfate, and concentrated in-vacuo. The residue was taken up in THF (1 mL), treated with 0.5 M LiOH (aq) (187 µl, 0.094 mmol), and the mixture was stirred overnight at room temperature. The reaction mixture was diluted with 1:1 acetonitrile/water, and injected directly onto the prep HPLC for purification to yield Example 571 (9.2 mg, 0.019 mmol, 30.4% yield). MS (ESI+)=485.29, (M+H)$^+$.

Example 572

(1R,3R)—N—((R)-1-((S)-4-(4-chlorophenyl)-4-hydroxy-3,3-dimethylpiperidin-1-yl)-3-methyl-1-oxobutan-2-yl)-3-hydroxycyclopentanecarboxamide

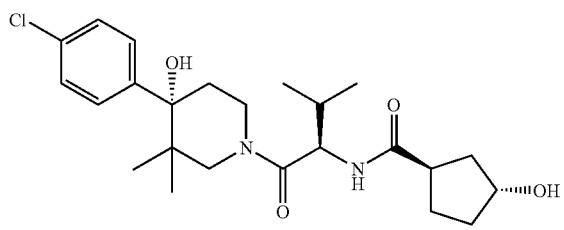

Step 1. tert-Butyl (R)-1-((S)-4-(4-chlorophenyl)-4-hydroxy-3,3-dimethylpiperidin-1-yl)-3-methyl-1-oxobutan-2-ylcarbamate

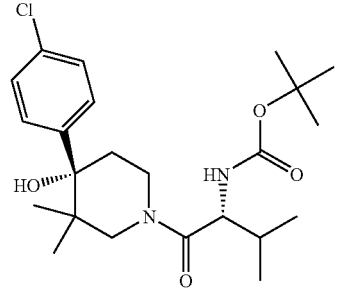

A solution of (S)-4-(4-chlorophenyl)-3,3-dimethylpiperidin-4-ol (6.3 g, 26.3 mmol), Boc-D-Val-OH (6.28 g, 28.9 mmol), EDC (11.08 g, 57.8 mmol), and HOBT (8.85 g, 57.8 mmol) in methylene chloride (250 mL) was stirred at room temperature for 30 minutes, treated with triethylamine (14.65 mL, 105 mmol), and stirred at room temperature for 3 hours. The solution was washed 3× with saturated sodium carbonate, 3× with 1M HCl, once with water, and once with brine, dried over sodium sulfate, and concentrated in-vacuo. The residue was purified over a 330 g silica gel column via ISCO, eluting at 100 mL/min with a 0-100% ethyl acetate/hexanes gradient over 40 minutes to yield the title compound (11.0 g, 25.06 mmol, 95% yield) as a colorless glass. MS (ESI+)=439.18, (M+H)$^+$.

Step 2. (R)-2-amino-1-((S)-4-(4-chlorophenyl)-4-hydroxy-3,3-dimethylpiperidin-1-yl)-3-methylbutan-1-one, HCl

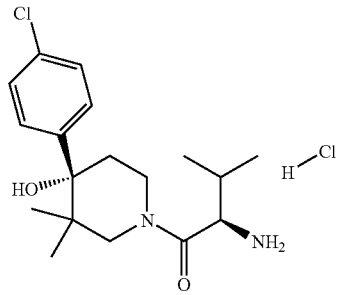

A solution of tert-butyl (R)-1-((S)-4-(4-chlorophenyl)-4-hydroxy-3,3-dimethylpiperidin-1-yl)-3-methyl-1-oxobutan-2-ylcarbamate (11 g, 25.06 mmol) in 4 M HCl in dioxane (100 mL, 400 mmol) was stirred at room temperature for 2 h. The mixture was concentrated in-vacuo, then concentrated 3× from methanol and 3× from methylene chloride to remove residual HCl, to yield the title compound (9.3 g, 24.78 mmol, 99% yield) as a colorless powder. MS (ESI+)=339, (M+H)$^+$.

Step 3: Example 572

A mixture of (R)-2-amino-1-((S)-4-(4-chlorophenyl)-4-hydroxy-3,3-dimethylpiperidin-1-yl)-3-methylbutan-1-one, HCl (5.77 g, 15.37 mmol), (1R,3R)-3-hydroxycyclopentanecarboxylic acid (2 g, 15.37 mmol), HOBT (5.18 g, 33.8 mmol), and triethylamine (10.71 mL, 77 mmol) in methylene chloride (100 mL) was treated with EDC (6.48 g, 33.8 mmol), and the reaction was allowed to stir overnight at room temperature. The mixture was concentrated in-vacuo, and the residue was taken up in ethyl acetate. The organic phase was washed 3× with saturated sodium carbonate, 3× with 1M HCl, and once with brine, dried over sodium sulfate, and concentrated in-vacuo. The residue was purified over a 330 g silica gel column via ISCO, eluting at 100 mL/min with ethyl acetate for 10 minutes followed by a 0-10% methanol/ethyl acetate gradient over 35 minutes to yield 3.2 g of (1R,3R)—N—((R)-1-((S)-4-(4-chlorophenyl)-4-hydroxy-3,3-dimethylpiperidin-1-yl)-3-methyl-1-oxobutan-2-yl)-3-hydroxycyclopentanecarboxamide as a colorless solid. Another 1.7 g of desired product which contained a small amount of impurity was also isolated. This material was subjected to the chromatography conditions described above, substituting an 80 g silica column and a 60 mL/minute flow rate, to yield an additional 800 mg of (1R,3R)—N—((R)-1-((S)-4-(4-chlorophenyl)-4-hydroxy-3,3-dimethylpiperidin-1-yl)-3-methyl-1-oxobutan-2-yl)-3-hydroxycyclopentanecarboxamide as a colorless solid, and 700 mg of material which was 88.6% pure by HPLC. The three lots of material were combined and purified by chiral super-critical fluid chromatography to yield Example 572 (3.7 g, 53% yield). An analytical sample was crystallized by dissolving 400 mg in 2 mL of acetone, adding water until the solution became hazy (3 mL), heating the mixture until a clear solution was observed, and allowing the mixture to stand uncovered at room temperature overnight. The resulting solids were collected by filtration and dried under vacuum at 60° C. to yield 265 mg of crystalline powder.

Examples 572A and 572B (1R,3S,4S)—N—((R)-1-((S)-4-(4-chlorophenyl)-4-hydroxy-3,3-dimethylpiperidin-1-yl)-3-methyl-1-oxobutan-2-yl)-3-hydroxy-4-methylcyclopentanecarboxamide, and (1S,3R,4R)—N—((R)-1-((S)-4-(4-chlorophenyl)-4-hydroxy-3,3-dimethylpiperidin-1-yl)-3-methyl-1-oxobutan-2-yl)-3-hydroxy-4-methylcyclopentanecarboxamide

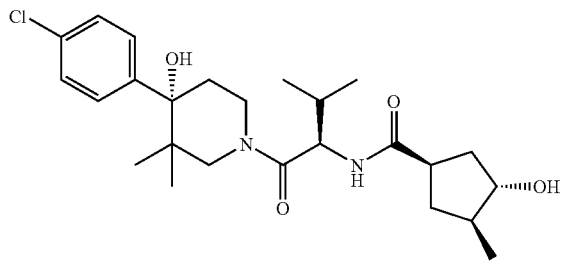

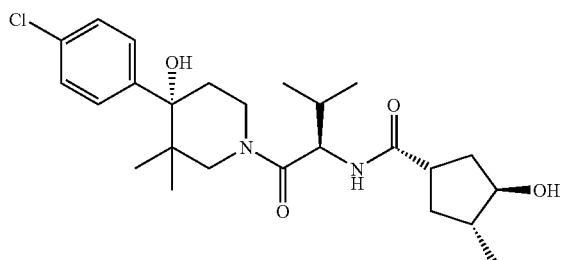

Step 1. Benzyl cyclopent-3-enecarboxylate

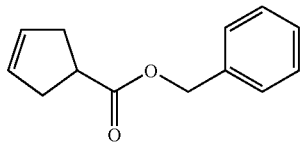

In a round bottom flask equipped with a reflux condenser and a Dean-Stark trap, a solution of cyclopent-3-enecarboxylic acid (5.2 g, 46.4 mmol) and benzyl alcohol (6.03 mL, 58.0 mmol) in benzene (100 mL) was treated with sulfuric acid (0.3 mL, 5.63 mmol), and the mixture was heated to revlux. Over the course of 2.5 hours, ~0.9 mL of water was collected in the Dean-Stark trap. The mixture was cooled to room temperature and treated with saturated aqueous sodium carbonate solution (25 mL). The layers were separated, and the organic phase was washed 3× with 25 mL saturated sodium carbonate, once with water, and once with brine, then dried over sodium sulfate and concentrated in-vacuo. The residue was purified over a 8×10 cm silica gel column, eluting with ethyl acetate/hexanes (5%-10%-15%-20% ethyl acetate), to yield the title compound (4.54 g, 22.45 mmol, 48.4% yield) as a colorless oil.

Step 2. Trans-benzyl 6-oxabicyclo[3.1.0]hexane-3-carboxylate and cis-benzyl 6-oxabicyclo[3.1.0]hexane-3-carboxylate

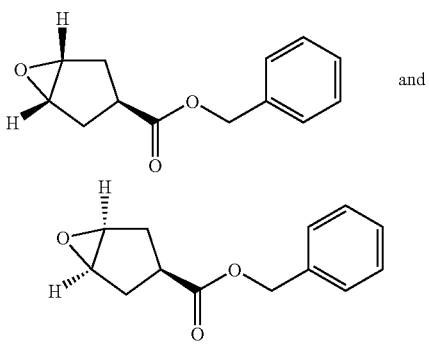

The titled compounds were prepared via the method of Lizotte, et. al.; *J. Org. Chem.*; 1983; 48(20); 3594-3597. A solution of benzyl cyclopent-3-enecarboxylate (4.54 g, 22.45 mmol) in methylene chloride (50 mL) was cooled to 0° C. and treated with the dropwise addition of a solution of m-CPBA (7.04 g, 31.4 mmol) in methylene chloride (50.0 mL) over 40 minutes. The resulting suspension was allowed to come to room temperature and stirred overnight. The mixture was treated with 20 mL of saturated sodium sulfite and stirred for 20 minutes. The solids were removed by filtration, rinsed with methylene chloride, and the layers of the filtrate were separated. The organic phase was washed with saturated sodium sulfite, 3× with saturated sodium bicarbonate, once with water, and once with brine, then dried over sodium sulfate and concentrated in-vacuo to 3.6 g of an amber oil. The residue was purified over a 5×15 cm silica gel column, eluting with ethyl acetate/hexanes (15% EtOAc), to yield trans-benzyl 6-oxabicyclo[3.10]hexane-3-carboxylate (3.4 g, 64% yield) and cis-benzyl 6-oxabicyclo[3.1.0]hexane-3-carboxylate (1.2 g, 24.5% yield) as colorless oils.

Step 3. Racemic mixture of (1R,3R,4R)-benzyl 3-hydroxy-4-methylcyclopentanecarboxylate and (1S,3S,4S)-benzyl 3-hydroxy-4-methylcyclopentanecarboxylate

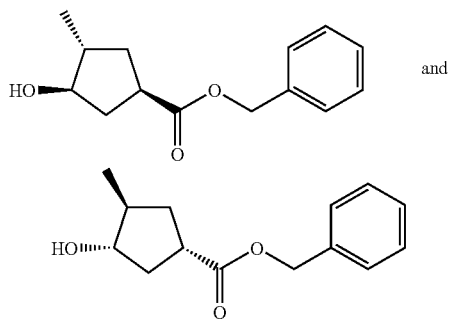

and

A 50 mL three neck round bottom flask equipped with a magnetic stirrer and two addition funnels, which had been flame dried under argon, charged with COPPER(I) CYANIDE (226 mg, 2.52 mmol), and evacuated under high vacuum overnight, was charged with THF (5 mL), and the suspension was cooled to −78° C. The mixture was treated with the dropwise addition of methyllithium (1.6 M in diethylether) (3.15 mL, 5.04 mmol). When the addition was complete, the cooling bath was removed, and the suspension was allowed to slowly warm, until a homogeneous solution was observed. The solution was cooled to −78° C., then treated with the slow dropwise addition of a solution of trans-benzyl 6-oxabicyclo[3.1.0]hexane-3-carboxylate (250 mg, 1.145 mmol) in THF (5 mL) followed by boron trifluoride etherate (0.581 mL, 4.58 mmol) in one portion. The mixture was stirred at −78° C. for 2 h, at which point a precipitate was observed, and the color quickly changed to bright yellow. The reaction was allowed to slowly come to room temperature, during which the color began to turn grey. The reaction was quenched with 30 mL of a 9:1 aqueous solution of saturated NH$_4$Cl and 10% NH$_4$OH, and the mixture was stirred for 30 minutes. The resulting deep blue mixture was filtered to remove a small amount of precipitate, and extracted 3× with ethyl acetate. The combined organic phases were washed with water followed by brine, then dried over sodium sulfate and concentrated in-vacuo. The residue was purified over a 2×15 cm silica gel column, eluting with ethyl acetate/hexanes (25%-50% EtOAc), to yield a racemic mixture of (1R,3R,4R)-benzyl 3-hydroxy-4-methylcyclopentanecarboxylate and (1S,3S,4S)-benzyl 3-hydroxy-4-methylcyclopentanecarboxylate (225 mg, 0.480 mmol, 84% yield) as a colorless oil.

Step 4. Racemic mixture of (1R,3R,4R)-3-hydroxy-4-methylcyclopentanecarboxylic acid and (1S,3S,4S)-3-hydroxy-4-methylcyclopentanecarboxylic acid

A racemic mixture of (1R,3R,4R)-benzyl 3-hydroxy-4-methylcyclopentanecarboxylate and (1S,3S,4S)-benzyl 3-hydroxy-4-methylcyclopentanecarboxylate (217 mg, 0.463 mmol) and palladium hydroxide on carbon (65.0 mg, 0.463 mmol) in methanol (10 mL) was degassed under vacuum/nitrogen, and the mixture was hydrogenated overnight at 50 psi. The catalyst was removed by filtration and rinsed with methanol. The filtrates were combined and concentrated in-vacuo to yield a racemic mixture of (1R,3R,4R)-3-hydroxy-4-methylcyclopentanecarboxylic acid and (1S,3S,4S)-3-hydroxy-4-methylcyclopentanecarboxylic acid (131 mg, 0.454 mmol, 98% yield) as a colorless oil which solidified upon standing overnight.

Step 5: Examples 572A and 572B

A mixture of (R)-2-amino-1-((S)-4-(4-chlorophenyl)-4-hydroxy-3,3-dimethylpiperidin-1-yl)-3-methylbutan-1-one, HCl (56.0 mg, 0.149 mmol), (±)-[(1R,3R,4R)-3-hydroxy-4-methylcyclopentanecarboxylic acid, (1S,3S,4S)-3-hydroxy-4-methylcyclopentanecarboxylic acid (47.3 mg, 0.164 mmol)], HOBT (50.2 mg, 0.328 mmol), and triethylamine (0.104 mL, 0.745 mmol) in methylene chloride (2 mL) was treated with EDC (62.9 mg, 0.328 mmol), and the reaction was allowed to stir overnight at room temperature. The mixture was concentrated in-vacuo, and the residue was taken up in ethyl acetate. The organic phase was washed 3× with 1M NaOH, 3× with 1M HCl, and once with brine, dried over sodium sulfate, and concentrated in-vacuo. The residue was purified over a 2×10 cm silica gel column, eluting with 50-100% EtOAc/Hexanes then 5% MeOH/EtOAc to yield 47 mg of a mixture of the two titled compounds. The two diastereomers were separated via chiral super-critical fluid chromatography to yield 20.0 mg of Example 572A, and 15.2 mg of Example 572B. MS (ESI+)=465.2, M$^+$ for both isomers.

Examples 572C and 572D (1R,3S,4S)—N—((R)-1-((S)-4-(4-chlorophenyl)-4-hydroxy-3,3-dimethylpiperidin-1-yl)-3-methyl-1-oxobutan-2-yl)-3-hydroxy-4-methylcyclopentanecarboxamide and (1R,3S,4S)—N—((R)-1-((S)-4-(4-chlorophenyl)-4-hydroxy-3,3-dimethylpiperidin-1-yl)-3-methyl-1-oxobutan-2-yl)-3-hydroxy-4-methylcyclopentanecarboxamide

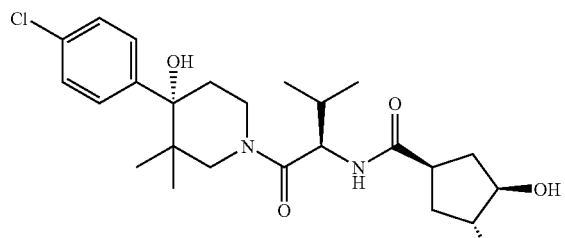

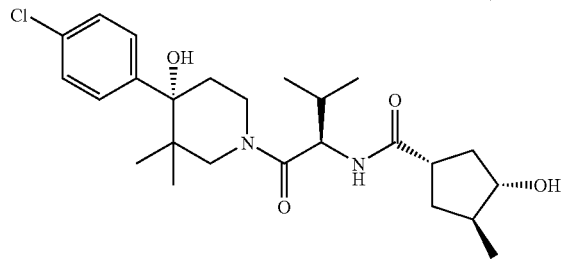

Examples 572C and 572D were prepared using the procedures described in Examples 572A and 572B, substituting cis-benzyl 6-oxabicyclo[3.1.0]hexane-3-carboxylate for

349 trans-benzyl 6-oxabicyclo[3.1.0]hexane-3-carboxylate in Step 3. MS (ESI+)=465.2, M⁺ for both isomers.

Example 573

N—((R)-1-((4R,5S)-4-(4-chlorophenyl)-4,5-dihydroxy-3,3-dimethylpiperidin-1-yl)-3-methyl-1-oxobutan-2-yl)cyclopentanecarboxamide

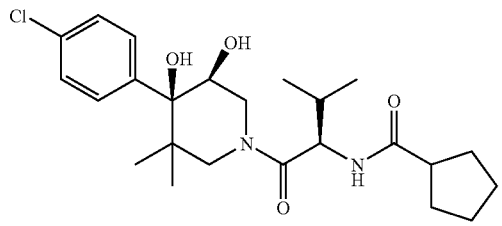

Step 1: 4-(4-Chlorophenyl)-3,3-dimethyl-1,2,3,6-tetrahydropyridine

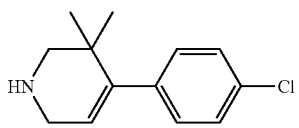

A suspension of (R)-4-(4-chlorophenyl)-3,3-dimethylpiperidin-4-ol, D-(−)-Tartaric Acid (6.2 g, 15.90 mmol) in concentrated hydrochloric acid (150 mL) was refluxed for 27 hours, during which time a clear solution was observed. The solution was cooled to 0° C., which caused a white solid to precipitate, and the pH was adjusted to ~13 with the slow, careful addition of solid sodium hydroxide. The aqueous was extracted with EtOAc (3×300 mL), the combined organic layers were washed with 1N NaOH (3×100 mL), once with brine (100 mL), then dried over sodium sulfate and concentrated in-vacuo to yield the title compound (3.46 g, 15.60 mmol, 98% yield) as a pale yellow oil. MS (ESI+)=222/224, (M+H)⁺.

Step 2. tert-Butyl 4-(4-chlorophenyl)-5,5-dimethyl-5,6-dihydropyridine-1(2H)-carboxylate

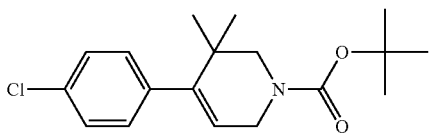

A solution of 4-(4-chlorophenyl)-3,3-dimethyl-1,2,3,6-tetrahydropyridine (3.46 g, 15.60 mmol) in THF (50 mL) was treated di-tert-butyl dicarbonate (3.99 mL, 17.17 mmol), causing a color change to amber, and the mixture was stirred overnight at room temperature. The solution was concentrated in-vacuo, and the residue was purified by flushing through silica gel, eluting with hexanes/ethyl acetate (10%-15% EtOAc), to yield the title compound (5.0 g, 15.54 mmol, 100% yield) as a colorless oil. MS (ESI+)=266, (M+H-t-Bu)⁺.

350

Step 3. (4R,5S)-tert-butyl 4-(4-chlorophenyl)-4,5-dihydroxy-3,3-dimethylpiperidine-1-carboxylate

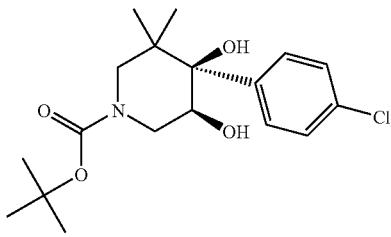

The title compound was prepared via the method of Sharpless, et. al., J. Org. Chem. 57, 1992, 2768. A stirring suspension of AD-MIX-alpha (2.3 g, 1.554 mmol) and methanesulfonamide (148 mg, 1.554 mmol) in 1:1 tert-butanol/water (16 mL) was cooled to 0° C., then treated with tert-butyl 4-(4-chlorophenyl)-5,5-dimethyl-5,6-dihydropyridine-1 (2H)-carboxylate (500 mg, 1.554 mmol). The mixture was allowed to come to room temperature, and stirred for 8 days. The reaction was treated with sodium sulfite (3 g), stirred for 30 minutes, then extracted 3× with ethyl acetate. The combined organic phases were washed 3× with 1M NaOH, once with water, and once with brine, dried over sodium sulfate, and concentrated in-vacuo. The residue was purified over silica gel, eluting with ethyl acetate/hexanes (10%-20%-50% EtOAc) to yield the title compound (196 mg, 0.551 mmol, 35.5% yield) as a colorless foam. MS (ESI+)=378.26, (M+Na)⁺.

Step 4. (3S,4R)-4-(4-chlorophenyl)-5,5-dimethylpiperidine-3,4-diol, HCl

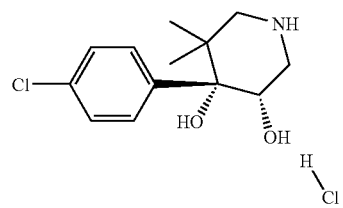

A solution of (4R,5S)-tert-butyl 4-(4-chlorophenyl)-4,5-dihydroxy-3,3-dimethylpiperidine-1-carboxylate (196 mg, 0.551 mmol) in dioxane (3 mL) was treated with 4N HCl in Dioxane (5 mL, 20.00 mmol), and the mixture was stirred for 1 h, upon which a precipitate was observed. The mixture was diluted with dichloromethane (5 mL) to facilitate stirring, and the reaction was stirred for an additional 2 h. The mixture was concentrated in-vacuo, then concentrated 3× from dichloromethane to remove residual HCl and dioxane. The residue was used as-is in the next step. MS (ESI+)=256.29, (M+H)⁺.

Step 5. tert-Butyl (R)-1-((4R,5S)-4-(4-chlorophenyl)-4,5-dihydroxy-3,3-dimethylpiperidin-1-yl)-3-methyl-1-oxobutan-2-ylcarbamate Step 6. (R)-2-amino-1-((4R,5S)-4-(4-chlorophenyl)-4,5-dihydroxy-3,3-dimethylpiperidin-1-yl)-3-methylbutan-1-one, HCl

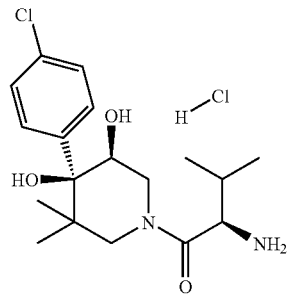

A solution of tert-butyl (R)-1-((4R,5S)-4-(4-chlorophenyl)-4,5-dihydroxy-3,3-dimethylpiperidin-1-yl)-3-methyl-1-oxobutan-2-ylcarbamate (200 mg, 0.440 mmol) in dioxane (3 mL) was treated with 4N HCl in dioxane (3 mL, 12.00 mmol), and the mixture was allowed to stir at room temperature for 6 hours. The mixture was concentrated in-vacuo and concentrated 3× from methylene chloride to remove residual dioxane and HCl. The residue was used as-is in the next step. MS (ESI+)=355.34, (M+H)+.

Step 7: Example 573

A mixture of (R)-2-amino-1-((4R,5S)-4-(4-chlorophenyl)-4,5-dihydroxy-3,3-dimethylpiperidin-1-yl)-3-methylbutan-1-one (22 mg, 0.056 mmol), cyclopentanecarboxylic acid (6.70 µl, 0.062 mmol), HOBT (18.94 mg, 0.124 mmol), and TEA (39 µl, 0.280 mmol) in dichloromethane (2 mL) was treated with EDC (23.71 mg, 0.124 mmol), and the mixture was stirred overnight at room temperature. The solvent was blown off with a stream of nitrogen, and the residue was taken up in 1:1 acetonitrile/water and purified via prep HPLC to yield Example 573 (16.5 mg, 0.029 mmol, 51.9% yield) as a colorless powder. MS (ESI+)=452.4, (M+H)+.

The following examples in Table 18 were prepared using the procedures described in Example 573, substituting AD-Mix-beta for AD-Mix-alpha in Step 3, and the appropriate carboxylic acid in Step 7.

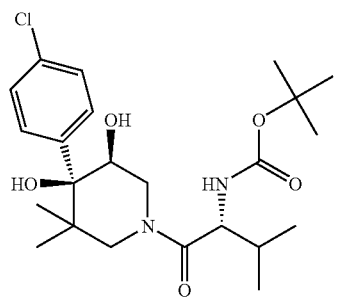

A mixture of 4-(4-chlorophenyl)-5,5-dimethylpiperidine-3,4-diol, HCl (155 mg, 0.530 mmol), Boc-D-Val-OH (127 mg, 0.584 mmol), HOBT (179 mg, 1.167 mmol), and triethylamine (0.296 mL, 2.122 mmol) in dichloromethane (5 mL) was treated with EDC (224 mg, 1.167 mmol), and the mixture was stirred overnight at room temperature. The mixture was concentrated in-vacuo, and the residue was taken up in ethyl acetate. The organic phase was washed 3× with 1M NaOH, 3× with 1M HCl, and once with brine, dried over sodium sulfate, and concentrated in-vacuo. The residue was purified over silica gel, eluting with ethyl acetate/methylene chloride (0%-10%-50% EtOAc) to yield the title compound as a colorless foam. 455.4 (M+H)+.

TABLE 18

| Example | Carboxylic Acid | Structure | MS (ESI+) |
|---|---|---|---|
| 574 | Mono-Methyl isophthalate | 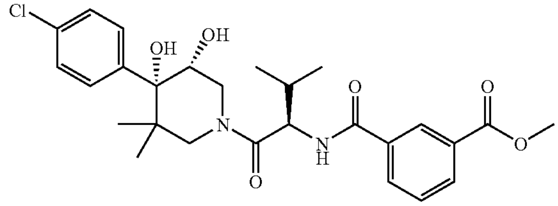 | 517.4 |

TABLE 18-continued

| Example | Carboxylic Acid | Structure | MS (ESI+) |
|---|---|---|---|
| 575 | cyclopentanecarboxylic acid | 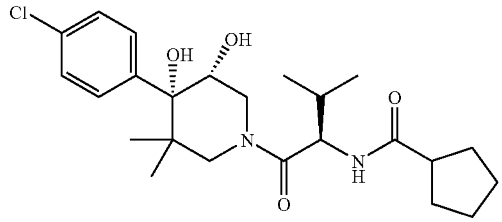 | 452.4 |

Example 576

3-((R)-1-((4S,5R)-4-(4-chlorophenyl)-4,5-dihydroxy-3,3-dimethylpiperidin-1-yl)-3-methyl-1-oxobutan-2-ylcarbamoyl)benzoic acid

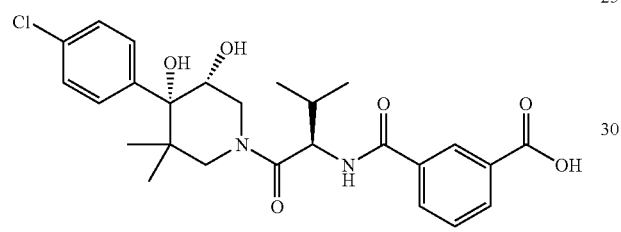

A solution of methyl 3-((R)-1-((4S,5R)-4-(4-chlorophenyl)-4,5-dihydroxy-3,3-dimethylpiperidin-1-yl)-3-methyl-1-oxobutan-2-ylcarbamoyl)benzoate (30 mg, 0.058 mmol) in methanol (2 mL) was treated with 1 M NaOH (aq) (1 mL, 1.000 mmol), and the mixture was stirred overnight. The reaction mixture was acidified with 1 N HCl (1.1 mL), diluted with 1:1 acetonitrile/water, and injected directly onto the prep HPLC for purification to yield Example 576 (17 mg, 0.028 mmol, 47.5% yield) as a colorless powder. MS (ESI+)=503.3 (M+H)+.

Example 577

(R)—N-(1-(4-amino-4-(4-chlorophenyl)-3,3-dimethylpiperidin-1-yl)-3-methyl-1-oxobutan-2-yl)-4-chlorobenzamide

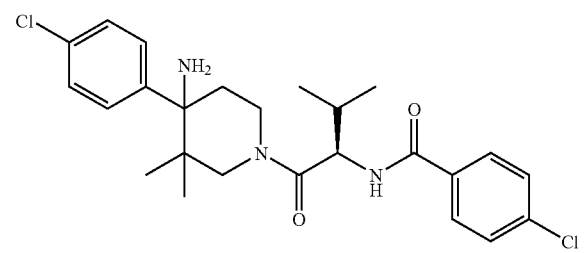

Step 1: (R)-ethyl 4-(4-chlorophenyl)-4-hydroxy-3,3-dimethylpiperidine-1-carboxylate

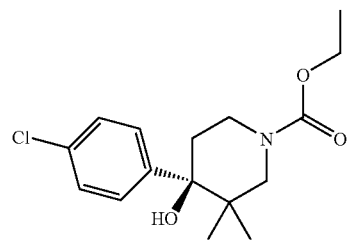

A solution of (R)-4-(4-chlorophenyl)-3,3-dimethylpiperidin-4-ol (1.96 g, 8.18 mmol) in Pyridine (20 mL) was cooled to 0° C., then treated with the dropwise addition of ethyl chloroformate (0.942 mL, 9.81 mmol), causing a color change to orange. The mixture was allowed to come to room temperature and stirred over night. The reaction was concentrated in-vacuo, and the residue was taken up in ethyl acetate, washed 3× with 1M NaOH, 3× with 1M HCl, once with brine, dried over sodium sulfate, and concentrated in-vacuo to yield the title compound (2.4 g, 7.70 mmol, 94% yield). The residue was used as-is in the next step. MS (ESI+)=334, (M+Na)+.

Step 2. Ethyl 4-acetamido-4-(4-chlorophenyl)-3,3-dimethylpiperidine-1-carboxylate

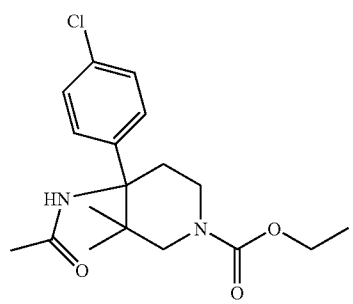

A suspension of (R)-ethyl 4-(4-chlorophenyl)-4-hydroxy-3,3-dimethylpiperidine-1-carboxylate (322 mg, 1.033 mmol) in acetonitrile (3 mL) was treated with sulfuric acid (0.275 mL, 5.16 mmol), and the resulting clear solution was stirred overnight at room temperature. The reaction was quenched with saturated sodium carbonate, and then extracted 3× with ethyl acetate. The combined organic phases were washed with brine, dried over sodium sulfate, and concentrated in-vacuo. The residue was purified over silica gel, eluting with ethyl acetate/hexanes (10%-25%-100% EtOAc) to yield the title compound (245 mg, 0.694 mmol, 67.2% yield) as a colorless foam.

Step 3: 4-(4-Chlorophenyl)-3,3-dimethylpiperidin-4-amine

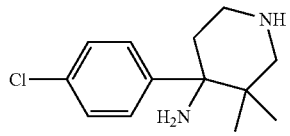

A solution of ethyl 4-acetamido-4-(4-chlorophenyl)-3,3-dimethylpiperidine-1-carboxylate (2.04 g, 5.78 mmol) in ethanol (25 mL) was treated with 5 N NaOH (aq) (23.13 mL, 116 mmol), and the mixture was heated at reflux for two days. During the reflux, a colorless, soapy solid predipitated. Water was added until a clear solution was observed. The ethanol was removed under reduced pressure, and the aqueous mixture was extracted 4× with ethyl acetate. The combined organic layers were dried over sodium sulfate and concentrated in-vacuo to yield the title compound (1.28 g, 5.36 mmol, 93% yield) as a colorless powder. MS (ESI+)=239, (M+H)+.

Step 4: (R)-tert-butyl 1-(4-amino-4-(4-chlorophenyl)-3,3-dimethylpiperidin-1-yl)-3-methyl-1-oxobutan-2-ylcarbamate

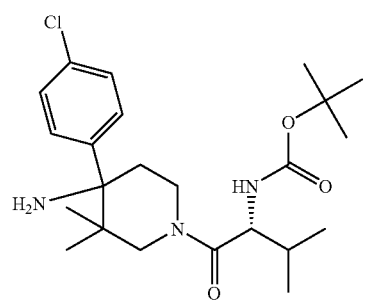

A mixture of 4-(4-chlorophenyl)-3,3-dimethylpiperidin-4-amine (488 mg, 2.044 mmol), Boc-D-Val-OH (444 mg, 2.044 mmol), HOBT (626 mg, 4.09 mmol), and triethylamine (1.140 mL, 8.18 mmol) in dichloromethane (5 mL) was treated with EDC (784 mg, 4.09 mmol), and the mixture was stirred overnight at room temperature. The mixture was concentrated in-vacuo, and the residue was taken up in ethyl acetate. The organic phase was washed 3× with WATER, 3× with sat. sodium carbonate, and 1× with sat sodium chloride, dried over sodium sulfate, and concentrated in-vacuo. The residue was purified over silica gel, eluting with ethyl acetate/hexanes (25%-50%-100% EtOAc) to yield the title compound (845 mg, 1.929 mmol, 94% yield) as a colorless glass. MS (ESI+)=438.36, M+.

Step 5: (R)-2-amino-1-(4-amino-4-(4-chlorophenyl)-3,3-dimethylpiperidin-1-yl)-3-methylbutan-1-one, 2HCl

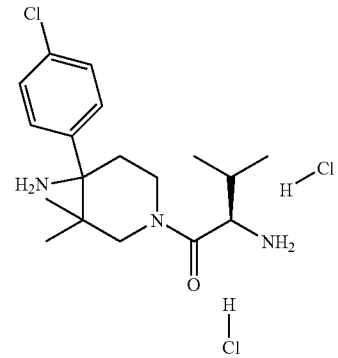

The title compound was prepared from (R)-tert-butyl 1-(4-amino-4-(4-chlorophenyl)-3,3-dimethylpiperidin-1-yl)-3-methyl-1-oxobutan-2-ylcarbamate using the procedure described in Example 571, Step 2. MS (ESI+)=338.5, (M+H)+.

Step 6: Example 577

A mixture of (R)-2-amino-1-(4-amino-4-(4-chlorophenyl)-3,3-dimethylpiperidin-1-yl)-3-methylbutan-1-one, 2HCl (330 mg, 0.803 mmol), 4-chlorobenzoic acid (126 mg, 0.803 mmol), HOBT (246 mg, 1.607 mmol), and triethylamine (0.672 mL, 4.82 mmol) in methylene chloride (3 mL) was treated with EDC (308 mg, 1.607 mmol), and the mixture was stirred overnight at room temperature. The mixture was concentrated in-vacuo, and the residue was taken up in ethyl acetate. The organic phase was washed 3× with saturated sodium carbonate, 3× with 1N HCl, and once with brine, dried over sodium sulfate, and concentrated in-vacuo. The residue was purified over silica gel, eluting with ethyl acetate/methylene chloride (10%-25%-50%-100% EtOAc) to yield Example 577 (255 mg, 0.535 mmol, 66.6% yield) as a colorless powder. MS (ESI+)=476.4, M+. The isomers were separated via chiral super-critical fluid chromatography to yield 69 mg of isomer A, and 16 mg of isomer B.

The following examples in Table 19 were prepared using the procedure described in Example 577, Step 6, substituting the appropriate carboxylic acid for 4-chlorobenzoic acid. The following examples were tested as diastereomeric mixtures.

TABLE 19

| Example | Carboxylic Acid | Structure | MS (ESI+) |
|---|---|---|---|
| 578 | Mono-Methyl isophthalate | 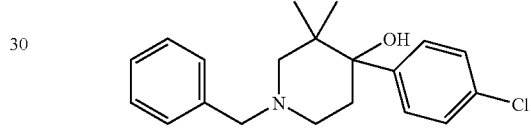 | 500.4 |
| 579 | cyclopentanecarboxylic acid | 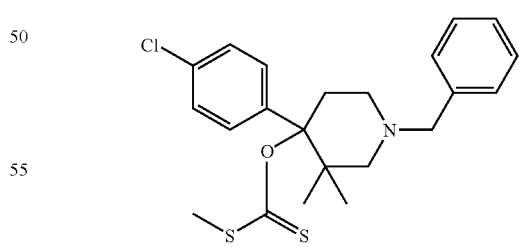 | 435.4 |

Example 580

(R)-3-(1-(4-amino-4-(4-chlorophenyl)-3,3-dimethylpiperidin-1-yl)-3-methyl-1-oxobutan-2-ylcarbamoyl)benzoic acid

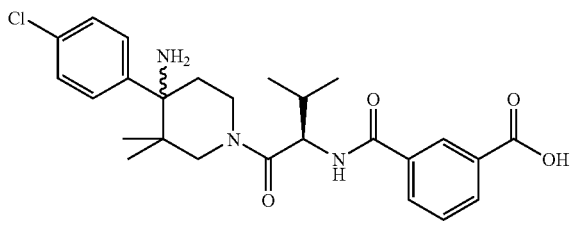

Example 580 was prepared from (R)-methyl 3-(1-(4-amino-4-(4-chlorophenyl)-3,3-dimethylpiperidin-1-yl)-3-methyl-1-oxobutan-2-ylcarbamoyl)benzoate using the procedure described in Example 576. MS (ESI+)=486.3, (M+H)+.

Example 581

N-((2R)-1-(4-(4-chlorophenyl)-3,3-dimethylpiperidin-1-yl)-3-methyl-1-oxobutan-2-yl)-3-sulfamoylbenzamide

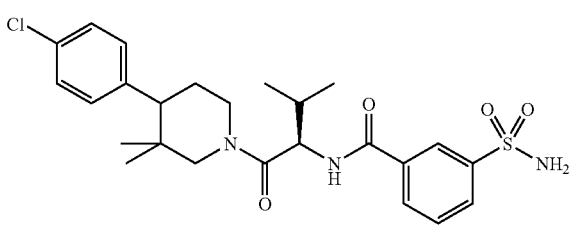

Step 1: 1-Benzyl-4-(4-chlorophenyl)-3,3-dimethylpiperidin-4-ol

A suspension of 4-(4-chlorophenyl)-3,3-dimethylpiperidin-4-ol (540 mg, 2.252 mmol) and benzaldehyde (0.274 mL, 2.70 mmol) in methylene chloride (15 mL) was treated with sodium triacetoxyborohydride (716 mg, 3.38 mmol), and the mixture was stirred overnight at room temperature. The mixture was concentrated in-vacuo. The residue was taken up in ethyl acetate, washed 3× with 1 N NaOH, once with brine, dried over sodium sulfate, and concentrated in-vacuo to yield the title compound (696 mg, 2.110 mmol, 94% yield) as a colorless oil. MS (ESI+)=330.14, (M+H)+.

Step 2: O-1-benzyl-4-(4-chlorophenyl)-3,3-dimethylpiperidin-4-yl S-methyl carbonodithioate A solution of 1-benzyl-4-(4-chlorophenyl)-3,3-dimethylpiperidin-4-ol (6.9 g, 20.92 mmol) and imidazole (0.214 g, 3.14 mmol) in THF (175 mL) was treated with sodium hydride (2.510 g, 62.8 mmol) in two portions. The mixture was heated at reflux overnight. Vigorous gas evolution was observed 20 minutes after heat was applied, before the reaction reached reflux temperature. The mixture was cooled to room temperature, and treated with carbon disulfide (23.96 mL, 397 mmol), causing the color to change to a burnt amber. The reaction was returned to reflux temperature for 2 hours. The mixture was cooled to room temperature, treated with iodomethane (1.570 mL, 25.1 mmol), and stirred at room temperature for 1.5 hours. The reaction was quenched with brine, and the mixture was extracted 3× with ethyl acetate. The combined organic phases were washed with brine, dried over sodium sulfate, and concentrated in-vacuo. The residue was purified over a 8×10 cm silica gel column, eluting with ethyl acetate/hexanes (5%-10%-15%-20% ethyl acetate), to yield the title compound (7.3 g, 17.38 mmol, 83% yield) as an amber oil. MS (ESI+)=421, (M+H)+.

Step 3: 1-Benzyl-4-(4-chlorophenyl)-3,3-dimethylpiperidine

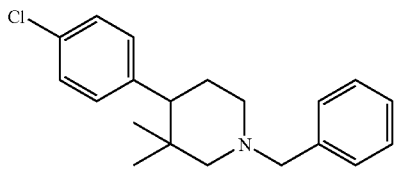

A solution of O-1-benzyl-4-(4-chlorophenyl)-3,3-dimethylpiperidin-4-yl S-methyl carbonodithioate (7.3 g, 17.38 mmol), tributyltin hydride (4.68 mL, 17.38 mmol), and AIBN (0.856 g, 5.21 mmol) in benzene (150 mL) was degassed with argon, then refluxed overnight. The mixture was concentrated in-vacuo. The residue was adsorbed onto a small amount of silica gel and purified over a 8×15 cm silica gel column, eluting with ethyl acetate/hexanes (0%-5%-20% EtOAc), to yield in two fractions 6.2 g of a strong smelling amber oil. The oil was adsorbed onto a small amount of silica gel and purified over a 5×15 cm silica gel column, eluting with ethyl acetate/hexanes (0-5% EtOAc), to yield the title compound (4.8 g, 14.38 mmol, 83% yield) as a colorless oil.

Step 4: 4-(4-Chlorophenyl)-3,3-dimethylpiperidine

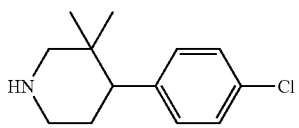

A solution of 1-benzyl-4-(4-chlorophenyl)-3,3-dimethylpiperidine (4.8 g, 15.29 mmol) and 1-chloroethyl chloroformate (1.667 mL, 15.45 mmol) in dichloroethane (40 mL) was stirred overnight at room temperature, then refluxed for 3 hours. The solution was concentrated in-vacuo. The residue was taken up in methanol (50 mL), the mixture was refluxed overnight The mixture was diluted with 75 mL of 1 N HCl, and the methanol was removed under vacuum. The aqueous solution was washed 3× with diethyl ether (20 mL), and the mixture was treated with the careful addition of saturated sodium bicarbonate to reach pH 8. The aqueous solution was washed 3× with diethyl ether (25 mL), and the mixture was treated with the careful addition of solid sodium hydroxide to reach pH>13. The aqueous phase was extracted 3× with ethyl acetate (50 mL), and the combined organic phases were dried over sodium sulfate and concentrated in vacuo to yield (±)-4-(4-chlorophenyl)-3,3-dimethylpiperidine (2.44 g, 10.91 mmol, 71.3% yield) as a pale yellow oil which solidified upon standing. MS: (ESI+)=224.3, (M+H)+. The enantiomers were separated via chiral super-critical fluid chromatography to yield 1.09 g of isomer A, and 1.05 g of isomer B.

Step 5: tert-Butyl (2R)-1-(4-(4-chlorophenyl)-3,3-dimethylpiperidin-1-yl)-3-methyl-1-oxobutan-2-ylcarbamate

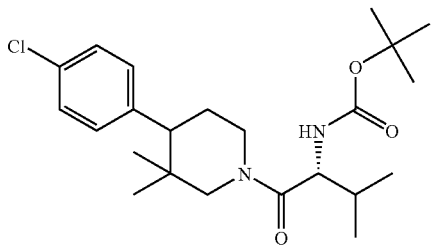

A mixture of 4-(4-chlorophenyl)-3,3-dimethylpiperidine, isomer A (1.1 g, 4.92 mmol), Boc-D-Val-OH (1.068 g, 4.92 mmol), HOBT (1.656 g, 10.82 mmol), and triethylamine (3.43 mL, 24.58 mmol) in methylene chloride (20 mL) was treated with EDC (2.073 g, 10.82 mmol), and the reaction was allowed to stir overnight at room temperature. The mixture was concentrated in-vacuo, and the residue was taken up in ethyl acetate. The organic phase was washed 3× with 1M NaOH, 3× with 1M HCl, and once with brine, dried over sodium sulfate, and concentrated in-vacuo to yield the title compound (2.25 g). MS (ESI+)=423.5, (M+H)+.

Step 6: (2R)-2-amino-1-(4-(4-chlorophenyl)-3,3-dimethylpiperidin-1-yl)-3-methylbutan-1-one, HCl

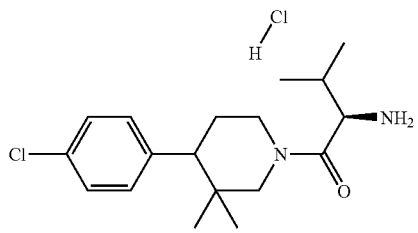

The title compound was prepared from tert-butyl (2R)-1-(4-(4-chlorophenyl)-3,3-dimethylpiperidin-1-yl)-3-methyl-1-oxobutan-2-ylcarbamate using the conditions described in Example 572, step 2. MS (ESI+)=323.39, (M+H)+.

Step 7: Example 581

A mixture of (2R)-2-amino-1-(4-(4-chlorophenyl)-3,3-dimethylpiperidin-1-yl)-3-methylbutan-1-one, HCl (32 mg, 0.089 mmol), 3-sulfamoylbenzoic acid (19.71 mg, 0.098 mmol), HOBT (30.0 mg, 0.196 mmol), and triethylamine (62.1 µL, 0.445 mmol) in methylene chloride was treated with EDC (37.6 mg, 0.196 mmol), and the reaction was allowed to stir for two days at room temperature. The mixture was concentrated in-vacuo, and the residue was taken up in ethyl acetate. The organic phase was washed 3× with 1M NaOH, 3× with 1M HCl, and 1× with brine, dried over sodium sulfate, and concentrated in-vacuo. The residue was purified via prep HPLC to yield Example 581 (27 mg, 0.053 mmol, 59.9% yield) as a colorless powder. MS (ESI+)=506.2, M+.

Example 582a

N-((2R)-1-(4-(4-chlorophenyl)-3,3-dimethylpiperidin-1-yl)-3-methyl-1-oxobutan-2-yl)nicotinamide

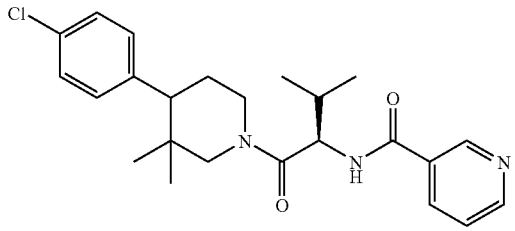

A mixture of (2R)-2-amino-1-(4-(4-chlorophenyl)-3,3-dimethylpiperidin-1-yl)-3-methylbutan-1-one, HCl (30 mg, 0.083 mmol), nicotinic acid (11.31 mg, 0.092 mmol), HOBT (28.1 mg, 0.184 mmol), and triethylamine (58.2 μL, 0.417 mmol) in methylene chloride was treated with EDC (35.2 mg, 0.184 mmol), and the reaction was allowed to stir overnight at room temperature. The mixture was concentrated in-vacuo, and the residue was taken up in ethyl acetate. The organic phase was washed 3× with water, 3× with 1M NaOH, and once with brine, dried over sodium sulfate, and concentrated in-vacuo. The residue was purified via prep HPLC. Fractions containing the desired product were combined and freeze-dried to yield a colorless powder. NMR indicates that this material contained a 15% impurity. The material was stirred in 1 N NaOH and extracted 3× with ethyl acetate. The combined organic phases were dried over sodium sulfate and concentrated in-vacuo. The residue was purified via 1 MM silica prep plate, eluting with 1:1 EtOAc/Hexanes to yield Example 582a (13 mg, 0.030 mmol, 36.4% yield) as a colorless film. MS (ESI+)=428.5, (M+H)+.

Example 582b

N-((2R)-1-(4-(4-chlorophenyl)-3,3-dimethylpiperidin-1-yl)-3-methyl-1-oxobutan-2-yl)nicotinamide The diastereomeric analog of Example 582a was prepared using isomer B of 4-(4-chlorophenyl)-3,3-dimethylpiperidine prepared in Example 581, step 4.

The following examples in Table 20 were prepared using the procedures described in Example 581, substituting (±)-4-(4-chlorophenyl)-3,3-dimethylpiperidine for 4-(4-chlorophenyl)-3,3-dimethylpiperidine, isomer A in Step 5, and the appropriate carboxylic acid in Step 7. Examples 583 and 584 were contaminated with a 15% impurity, in which the (±)-4-(4-chlorophenyl)-3,3-dimethylpiperidine moiety of the examples was replaced with a 4-(4-chlorophenyl)-3,3-dimethyl-1,2,3,6-tetrahydropyridine moiety, as seen in Example 586.

TABLE 20

| Example | Carboxylic Acid | Structure | MS (ESI+) |
|---|---|---|---|
| 583 | Nicotinic Acid | diastereomeric mixture | 428.4 |
| 584 | cyclopentanecarboxylic acid | diastereomeric mixture | 420.5 |

Examples 585 and 586

3-((2R)-1-(4-(4-chlorophenyl)-3,3-dimethylpiperidin-1-yl)-3-methyl-1-oxobutan-2-ylcarbamoyl)benzoate and (R)-methyl 3-(1-(4-(4-chlorophenyl)-5,5-dimethyl-5,6-dihydropyridin-1(2H)-yl)-3-methyl-1-oxobutan-2-ylcarbamoyl)benzoate

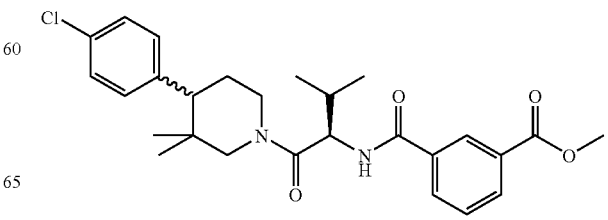

-continued

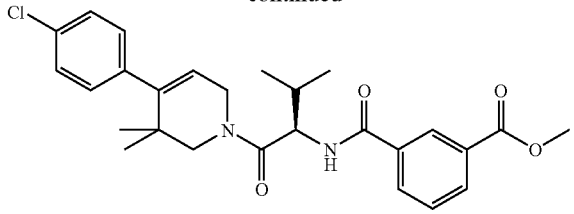

A mixture of (2R)-2-amino-1-(4-(4-chlorophenyl)-3,3-dimethylpiperidin-1-yl)-3-methylbutan-1-one, HCl (60 mg, 0.167 mmol), 3-(methoxycarbonyl)benzoic acid (33.1 mg, 0.184 mmol), HOBT (56.3 mg, 0.367 mmol), and triethylamine (116 µL, 0.835 mmol) in methylene chloride was treated with EDC (70.4 mg, 0.367 mmol), and the reaction was allowed to stir overnight at room temperature. The mixture was concentrated in-vacuo, and the residue was taken up in ethyl acetate. The organic phase was washed 3× with saturated sodium carbonate, 3× with 1M HCl, and once with brine, dried over sodium sulfate, and concentrated in-vacuo. The residue was taken up in methanol and purified via prep HPLC to yield two products: Example 585 (9 mg, 0.019 mmol, 11.1% yield), MS (ESI+)=485.4, M+, and Example 586 (1.7 mg, 3.52 µmol, 2.1% yield), MS=483.4, M+, as colorless powders.

Example 587

(R)—N-(1-(5-chloro-3H-spiro[isobenzofuran-1,4'-piperidine]-1'-yl)-3-methyl-1-oxobutan-2-yl)nicotinamide, TFA

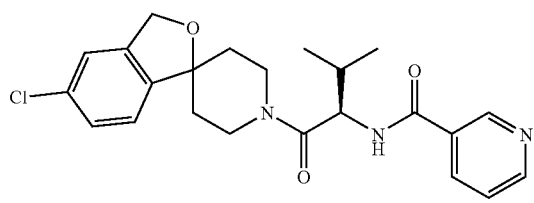

Step 1: (2-Bromo-5-chlorophenyl)methanol

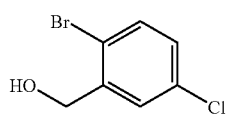

A solution of methyl 2-bromo-5-chlorobenzoate (4.9 g, 19.64 mmol) in THF (50 mL) was cooled to 0° C. and treated with the dropwise addition of LAH (1.0M in THF) (20.62 mL, 20.62 mmol), causing a mild exotherm and gas evolution. The mixture was allowed to warm to room temperature and stirred for 3 hours. The reaction was quenched using the Steinhardt procedure (see Fieser & Fieser, *Reagents for Organic Synthesis*, p. 584). The resulting precipitate was removed by filtration and washed with ethyl acetate. The combined filtrates were concentrated in-vacuo to yield a colorless oil which solidified upon standing. The residue was purified over a 330 g silica gel column via ISCO, eluting with a 10-100% EtOAc/Hexanes gradient over 30 minutes, to yield the title compound (2.04 g, 47% yield) as a colorless powder.

Step 2: tert-Butyl 4-(4-chloro-2-(hydroxymethyl)phenyl)-4-hydroxypiperidine-1-carboxylate

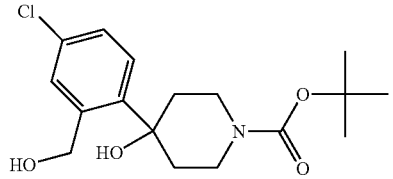

A solution of (2-bromo-5-chlorophenyl)methanol (1.48 g, 6.68 mmol) in anhydrous THF (30 mL) was cooled to −78° C. and treated with the dropwise addition of n-BuLi (1.6 M in hexanes) (8.77 mL, 14.03 mmol), and the mixture was stirred for 30 minutes at −78° C., during which a thick white precipitate was observed. The dianion was treated with the dropwise addition of a solution of tert-butyl 4-oxopiperidine-1-carboxylate (1.465 g, 7.35 mmol) in THF (10 mL), and the mixture was stirred for 1 hour at −78° C., during which a yellow homogeneous solution was observed, then allowed to warm to room temperature and stirred overnight. The reaction was quenched with saturated ammonium chloride and the mixture was extracted 3× with ethyl acetate. The combined organic phases were washed with water and brine, then dried over sodium sulfate and concentrated in-vacuo. The residue was split into two equal fractions, and each was purified over a 40 g silica gel column via ISCO, eluting with a 10-100% EtOAc/Hexanes gradient over 15 minutes. The fractions from each run which contained the desired product were combined to yield the title compound (1.4 g, 4.10 mmol, 61.3% yield) as a colorless foam. MS (ESI+)=268, (M+H-tBuOH)+.

Step 3: tert-Butyl 5-chloro-3H-spiro[isobenzofuran-1,4'-piperidine]-1'-carboxylate

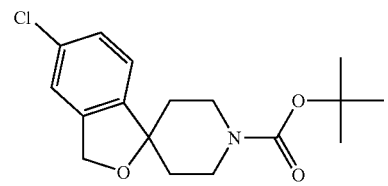

A solution of tert-butyl 4-(4-chloro-2-(hydroxymethyl)phenyl)-4-hydroxypiperidine-1-carboxylate (1.3 g, 3.80 mmol) and triphenylphosphine (1.496 g, 5.70 mmol) in THF (20 mL) was treated with DEAD (0.903 mL, 5.70 mmol), and the mixture was stirred overnight at room temperature. The mixture was concentrated in-vacuo, and the residue was purified over silica gel, eluting with ethyl acetate/hexanes (5%-25% ethyl acetate), to yield the title compound (1.19 g, 3.67 mmol, 97% yield) as a colorless oil.

Step 4: 5-Chloro-3H-spiro[isobenzofuran-1,4'-piperidine], HCl

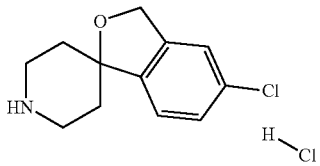

The title compound was prepared from tert-butyl 5-chloro-3H-spiro[isobenzofuran-1,4'-piperidine]-1'-carboxylate using the procedure described in Example 571, Step 2.

Step 5: (R)-tert-butyl 1-(5-chloro-3H-spiro[isobenzofuran-1,4'-piperidine]-1'-yl)-3-methyl-1-oxobutan-2-ylcarbamate

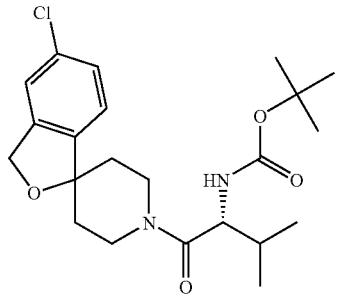

The title compound was prepared from 5-chloro-3H-spiro[isobenzofuran-1,4'-piperidine], HCl and Boc-D-Val-OH using the procedure described in Example 565, Step 6.

Step 6: (R)-2-amino-1-(5-chloro-3H-spiro [isobenzofuran-1,4'-piperidine]-1'-yl)-3-methylbutan-1-one, 2HCl

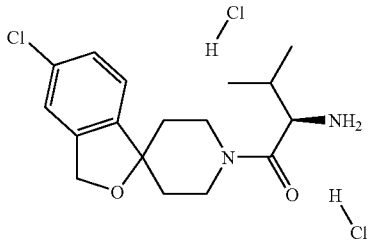

The title compound was prepared from (R)-tert-butyl 1-(5-chloro-3H-spiro[isobenzofuran-1,4'-piperidine]-1'-yl)-3-methyl-1-oxobutan-2-ylcarbamate using the procedure described in Example 571, Step 2. MS (ESI+)=323.2, (M+H)+.

Step 7: Example 587

A mixture of (R)-2-amino-1-(5-chloro-3H-spiro[isobenzofuran-1,4'-piperidine]-1'-yl)-3-methylbutan-1-one, HCl (28 mg, 0.078 mmol), nicotinic acid (10.55 mg, 0.086 mmol), HOBT (26.3 mg, 0.171 mmol), and triethylamine (54.3 µL, 0.390 mmol) in methylene chloride was treated with EDC (32.9 mg, 0.171 mmol), and the reaction was allowed to stir overnight at room temperature. The mixture was concentrated in-vacuo, and the residue was taken up in ethyl acetate. The organic phase was washed 3× with water, 3× with 1M NaOH, and 1× with brine, dried over sodium sulfate, and concentrated in-vacuo. The residue was purified via prep HPLC to yield Example 587 (21 mg, 0.039 mmol, 49.7% yield) as a colorless powder. MS (ESI+)=428.1, (M+H)+.

Example 588

(1R,3R)-3-((R)-1-((S)-4-(4-chlorophenyl)-4-hydroxy-3,3-dimethylpiperidin-1-yl)-3-methyl-1-oxobutan-2-ylcarbamoyl)cyclopentyl acetate

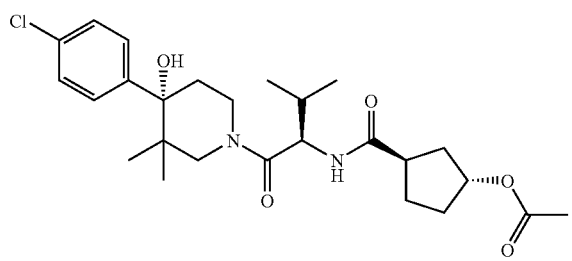

A solution of (1R,3R)—N—((R)-1-((S)-4-(4-chlorophenyl)-4-hydroxy-3,3-dimethylpiperidin-1-yl)-3-methyl-1-oxobutan-2-yl)-3-hydroxycyclopentanecarboxamide (20 mg, 0.044 mmol) in pyridine (0.5 mL) was treated with acetic anhydride (5.02 µl, 0.053 mmol), and the mixture was stirred overnight at room temperature. Analysis by LC/MS indicated only 50% conversion, so the mixture was treated with acetic anhydride (5.02 µl, 0.053 mmol), and stirred for two days at room temperature. The reaction was concentrated in-vacuo, and the residue was purified via prep HPLC to yield Example 588 (11.6 mg, 0.024 mmol, 53.1% yield) as a colorless powder. MS (ESI+)=493.2, M+.

Example 589

(1R,3R)-3-((R)-1-((S)-4-(4-chlorophenyl)-4-hydroxy-3,3-dimethylpiperidin-1-yl)-3-methyl-1-oxobutan-2-ylcarbamoyl)cyclopentyl 3-methylbutanoate

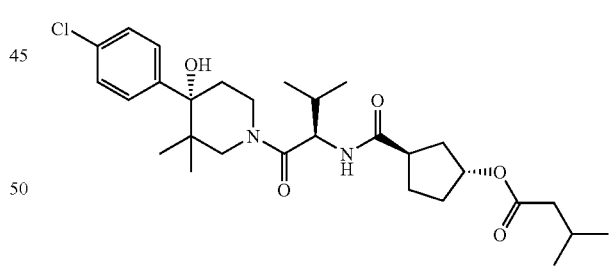

A solution of (1R,3R)—N—((R)-1-((S)-4-(4-chlorophenyl)-4-hydroxy-3,3-dimethylpiperidin-1-yl)-3-methyl-1-oxobutan-2-yl)-3-hydroxycyclopentanecarboxamide (20 mg, 0.044 mmol) and triethylamine (12 µl, 0.086 mmol) in methylene chloride (0.5 mL) was treated with isovaleryl chloride (5.41 µl, 0.044 mmol), and the mixture was stirred overnight at room temperature. Analysis by LC/MS indicated only ~50% conversion, so the mixture was treated with isovaleryl chloride (5.41 µl, 0.044 mmol), and stirred for four days at room temperature. The reaction was concentrated in-vacuo, and the residue was purified via prep HPLC to yield Example 589 (14 mg, 0.026 mmol, 59.0% yield) as a colorless powder. MS (ESI+)=535.2, M+.

Example 590

(R)—N-(1-(4-(4-fluorophenyl)-4-hydroxy-3,3-dimethylpiperidin-1-yl)-3-methyl-1-oxobutan-2-yl)cyclopentanecarboxamide

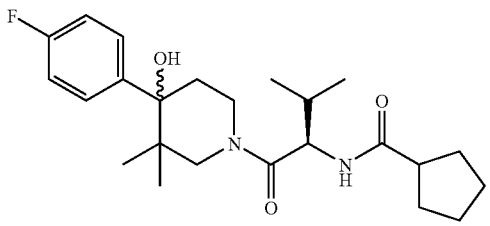

Step 1: tert-Butyl 4-(4-fluorophenyl)-4-hydroxy-3,3-dimethylpiperidine-1-carboxylate

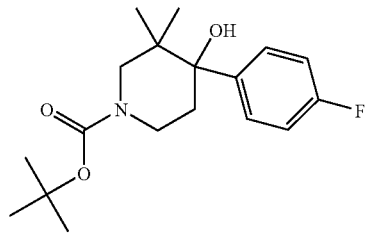

A solution of 1-Bromo-4-fluorobenzene (5.32 mL, 48.4 mmol) in THF (100 mL) was cooled to −78° C., and treated with the dropwise addition of 1.6 M BuLi in hexane (30.2 mL, 48.4 mmol), at a rate which did not allow the temperature of the reaction to exceed −60° C. The mixture was stirred at −78° C. for 30 minutes, then treated with the dropwise addition of a solution of tert-butyl 3,3-dimethyl-4-oxopiperidine-1-carboxylate (5 g, 22.00 mmol) in THF (50 mL) at a rate which did not allow the temperature to exceed −60° C. The mixture was stirred at −78° C. for 1.5H, then allowed to warm to 10° C. and quenched with saturated NH$_4$Cl (50 mL). The layers were separated, and the organic phase was concentrated in-vacuo. The aqueous was extracted with ethyl acetate (100 mL), and the organic phase was combined with the residue from the original organic phase. This solution was washed 3× with water, 1× with brine, dried over sodium sulfate, and concentrated in-vacuo. The residue was digested with hexanes (70 mL), and the resulting white powder was collected by filtration, rinsed with hot hexanes, and dried under vacuum to yield the title compound (3.3 g, 10.20 mmol, 46.4% yield). MS (ESI+)=324.4, (M+H)$^+$, 250.3, (M-tBuOH)$^+$.

Step 2: 4-(4-Fluorophenyl)-3,3-dimethylpiperidin-4-ol, HCl

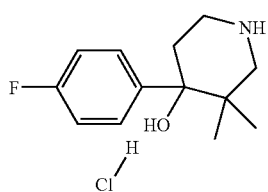

The title compound was prepared from tert-butyl 4-(4-fluorophenyl)-4-hydroxy-3,3-dimethylpiperidine-1-carboxylate using the procedure described in Example 571, Step 2. MS (ESI+)=224.32, (M+H)$^+$.

Step 3: (R)-tert-butyl 1-(4-(4-fluorophenyl)-4-hydroxy-3,3-dimethylpiperidin-1-yl)-3-methyl-1-oxobutan-2-ylcarbamate

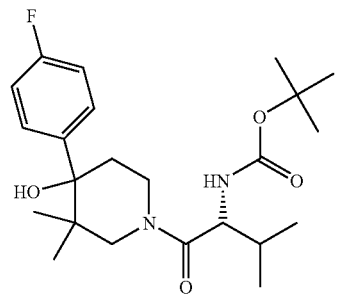

The title compound was prepared from of 4-(4-fluorophenyl)-3,3-dimethylpiperidin-4-ol, HCl and Boc-D-Val-OH using the procedure described in Example 565, Step 6. MS (ESI+)=424.4, (M+H)$^+$.

Step 4: (R)-2-amino-1-(4-(4-fluorophenyl)-4-hydroxy-3,3-dimethylpiperidin-1-yl)-3-methylbutan-1-one, HCl

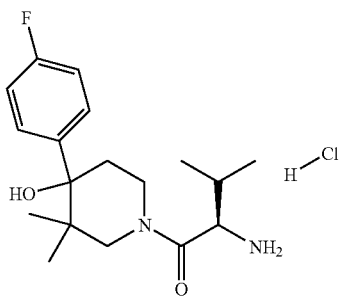

The title compound was prepared from (R)-tert-butyl 1-(4-(4-fluorophenyl)-4-hydroxy-3,3-dimethylpiperidin-1-yl)-3-methyl-1-oxobutan-2-ylcarbamate using the procedure described in Example 571, Step 2. MS (ESI+)=323.4, (M+H)$^+$.

Step 5: Example 590

Example 590 was prepared from (R)-2-amino-1-(4-(4-fluorophenyl)-4-hydroxy-3,3-dimethylpiperidin-1-yl)-3-methylbutan-1-one, HCl and cyclopentanecarboxylic acid using the procedure described in Example 573, Step 7. MS (ESI+)=420.4, M$^+$.

Example 591

(R)—N-(1-(4-(4-fluorophenyl)-3,3-dimethylpiperidin-1-yl)-3-methyl-1-oxobutan-2-yl)cyclopentanecarboxamide

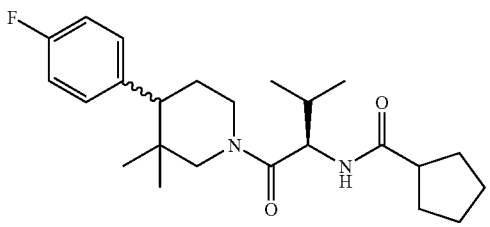

Step 1: 4-(4-Fluorophenyl)-3,3-dimethyl-1,2,3,6-tetrahydropyridine

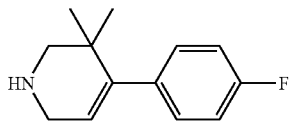

The title compound was prepared from 4-(4-fluorophenyl)-3,3-dimethylpiperidin-4-ol, HCl using the procedure described in Example 573, Step 1. MS (ESI+)=206.3, M+.

Step 2: 4-(4-Fluorophenyl)-3,3-dimethylpiperidine

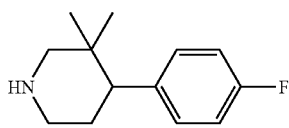

A mixture of 4-(4-fluorophenyl)-3,3-dimethyl-1,2,3,6-tetrahydropyridine (450 mg, 2.192 mmol), palladium hydroxide on carbon (308 mg, 2.192 mmol), and acetic acid (1.5 mL, 26.2 mmol) in methanol (10 mL) was degassed under nitrogen/vacuum, then hydrogenated at 50 psi for two days. The catalyst was removed by filtration and rinsed with methanol, and the filtrate was concentrated in vacuo to yield the title compound (442 mg, 2.132 mmol, 97% yield) as a pale yellow oil. MS (ESI+)=208.29, (M+H)+.

Step 3: (R)-tert-butyl 1-(4-(4-fluorophenyl)-3,3-dimethylpiperidin-1-yl)-3-methyl-1-oxobutan-2-ylcarbamate

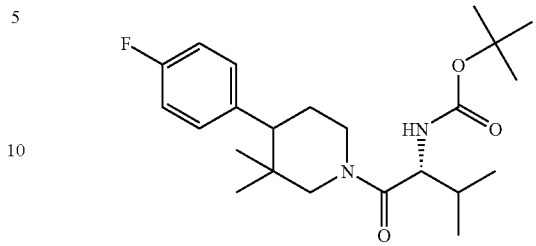

The title compound was prepared from 4-(4-fluorophenyl)-3,3-dimethylpiperidine and Boc-D-Val-OH using the procedure described in Example 581, Step 5. MS (ESI+)= 351.40, (M-tert-Bu)+.

Step 4: (R)-2-amino-1-(4-(4-fluorophenyl)-3,3-dimethylpiperidin-1-yl)-3-methylbutan-1-one, HCl

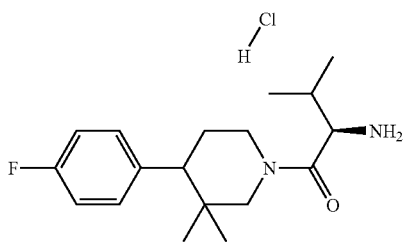

The title compound was prepared from (R)-tert-butyl 1-(4-(4-fluorophenyl)-3,3-dimethylpiperidin-1-yl)-3-methyl-1-oxobutan-2-ylcarbamate using the conditions described in Example 571, Step 2. MS (ESI+)=307.4, (M+H)+.

Step 5: Example 591

The title compound was prepared from of (R)-2-amino-1-(4-(4-fluorophenyl)-3,3-dimethylpiperidin-1-yl)-3-methylbutan-1-one, HCl and cyclopentanecarboxylic acid using the conditions described in Example 573, Step 7. MS (ESI+)= 404.4, M+.

Example 592

3-(2-(benzyloxymethyl)-2H-tetrazol-5-yl)-N—((R)-1-((S)-4-(4-chlorophenyl)-4-hydroxy-3,3-dimethylpiperidin-1-yl)-3-methyl-1-oxobutan-2-yl)benzamide

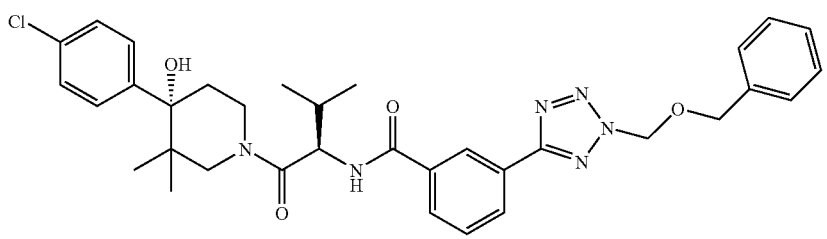

Step 1: 2-(Benzyloxymethyl)-2H-tetrazole

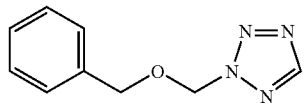

A suspension of 1-H-tetrazole (2.0 g, 28.5 mmol) and potassium carbonate (5.9 g, 42.7 mmol) in DMF (30 mL) was treated with benzyl chloromethyl ether (5.36 g, 34.2 mmol), and the mixture was stirred for 4 hours. Analysis by LC/MS indicated that the reaction was not complete, so the reaction was treated with benzyl chloromethyl ether (0.5 g, 3.19 mmol) and stirred overnight. The mixture was filtered, and the filtrate was concentrated in-vacuo. The residue was diluted with diethyl ether (200 mL), washed 5× with water (50 mL), once with brine, dried over sodium sulfate, and concentrated in-vacuo. The residue was purified over a 6×20 mm silica gel column, eluting with 20% then 30% ethyl acetate/hexanes to yield the title compound (2.39 g, 44% yield), and 1-(benzyloxymethyl)-2H-tetrazole (2.56 g, 47% yield).

Step 2: 2-(Benzyloxymethyl)-5-(tributylstannyl)-2H-tetrazole

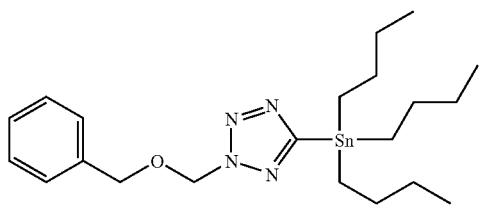

In a flame-dried three-neck flask, a solution of 2-(benzyloxymethyl)-2H-tetrazole (2.01 g, 10.57 mmol) and tetramethylethylenediamine (3.16 mL, 21.4 mmol) in diethyl ether (30 mL) was cooled to −78° C. and treated with the dropwise addition of n-butyllithium (1.6 M in hexanes, 7.3 mL, 11.62 mmol), causing the color of the solution to turn dark red. The mixture was stirred for 10 minutes, then transferred via canulus to a solution of tributyltin chloride (2.9 mL, 10.57 mmol) in diethyl ether (20 mL) which had been pre-cooled to −78° C. The reaction was stirred for 45 minutes, then quenched with saturated ammonium chloride solution. The mixture was allowed to come to room temperature, and the layers were separated. The aqueous phase was extracted 3× with ethyl acetate, and the combined organic phases were washed with brine, dried over sodium sulfate, and concentrated in-vacuo. The residue was purified over silica gel, eluting with 1% then 5% then 10% ethyl acetate/hexanes to yield the title compound (3.0 g, 60% yield) as a colorless oil.

Step 3: Ethyl 3-(2-(benzyloxymethyl)-2H-tetrazol-5-yl)benzoate

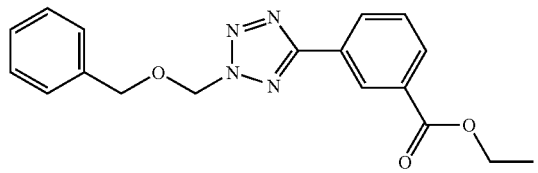

A solution of ethyl-3-bromobenzoate (0.47 g, 2.05 mmol) and 2-(benzyloxymethyl)-5-(tributylstannyl)-2H-tetrazole in toluene (20 mL) was degassed under vacuum and argon. To this solution was added copper (I) iodide (20 mg, 0.20 mmol) and tetrakis(triphenylphosphine)palladium(0) (115 mg, 0.10 mmol), and the mixture was again degassed under vacuum and argon. The flask and condenser were covered in foil to exclude light, and the reaction was heated at reflux temperature for 3 hours. After cooling to room temperature, the mixture was filtered and the filtrate was concentrated in-vacuo. The residue was purified over a 3.5×12 cm silica gel column, eluting with 5% then 10% then 15% ethyl acetate/hexanes to yield the title compound as a colorless oil which contained 5% of a tributyltin impurity. MS (ESI+)=339.22, (M+H)⁺. The oil was used as-is in the next step.

Step 4: 3-(2-(Benzyloxymethyl)-2H-tetrazol-5-yl)benzoic acid

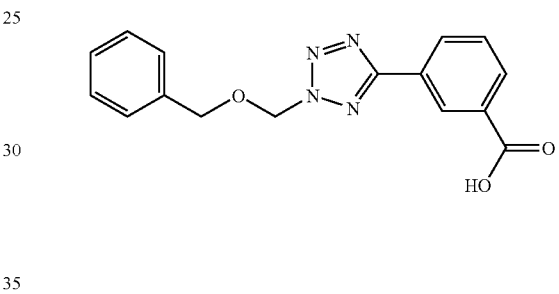

A solution of ethyl 3-(2-(benzyloxymethyl)-2H-tetrazol-5-yl)benzoate (653 mg, 1.93 mmol) in THF (10 mL) was treated with a 0.5 M aqueous lithium hydroxide solution (5.8 mL, 2.9 mmol), and the reaction was stirred overnight. Analysis by LC/MS indicated that the reaction had not gone to completion, so the mixture was treated with a 0.5 M aqueous lithium hydroxide solution (1 mL, 0.5 mmol), and the reaction was stirred for an additional 6 hours. The THF was removed under reduced pressure, and the aqueous solution was treated with 1 N HCl (3.5 mL, 3.5 mmol). The mixture was extracted 3× with ethyl acetate, and the combined organic phases were dried over sodium sulfate and concentrated in-vacuo to yield the title compound as a colorless powder which was used as-is in the next step.

Step 5: Example 592

A mixture of (R)-2-amino-1-((S)-4-(4-chlorophenyl)-4-hydroxy-3,3-dimethylpiperidin-1-yl)-3-methylbutan-1-one, HCl (35 mg, 0.09 mmol), 3-(2-(benzyloxymethyl)-2H-tetrazol-5-yl)benzoic acid (29 mg, 0.09 mmol), HOBT (25 mg, 0.19 mmol), and triethylamine (0.052 mL, 0.37 mmol) in methylene chloride (2 mL) was treated with EDC (36 mg, 0.19 mmol), and the reaction was allowed to stir overnight at room temperature. The reaction mixture was applied directly to a 2×10 cm silica gel column, and the product was eluted with methylene chloride then 10% to 20% ethyl acetate/methylene chloride to yield Example 592 (45 mg, 80% yield) as a colorless glass. MS (ESI+)=631.3, M⁺.

Example 593

N—((R)-1-((S)-4-(4-chlorophenyl)-4-hydroxy-3,3-dimethylpiperidin-1-yl)-3-methyl-1-oxobutan-2-yl)-3-(2H-tetrazol-5-yl)benzamide

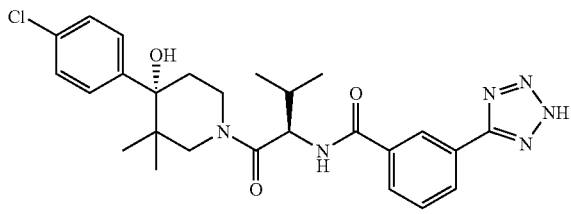

A solution of 3-(2-(benzyloxymethyl)-2H-tetrazol-5-yl)-N—((R)-1-((S)-4-(4-chlorophenyl)-4-hydroxy-3,3-dimethylpiperidin-1-yl)-3-methyl-1-oxobutan-2-yl)benzamide (34 mg, 0.05 mmol) in methanol (1 mL) was treated with 6 M HCl (0.2 mL, 1.2 mmol), and the mixture was heated to 50° C., at which point the starting material precipitated. The mixture was diluted with methanol (3 mL) and 6 M HCl (0.2 mL, 1.2 mmol), and the reaction was heated at 50° C. for 10 hours. The mixture was concentrated in-vacuo, and the residue was purified over silica gel, eluting with 25% to 50% ethyl acetate/hexanes, then 100% ethyl acetate, then 5% to 10% to 15% methanol/ethyl acetate to yield Example 593 (19 mg, 75% yield) as a colorless glass. MS (ESI+)=511.2, M+. Analysis by LC/MS indicates 88% purity.

Example 594

2-((R)-1-((S)-4-(4-chlorophenyl)-4-hydroxy-3,3-dimethylpiperidin-1-yl)-3-methyl-1-oxobutan-2-ylcarbamoyl)benzoic acid

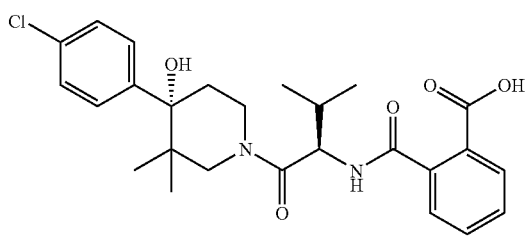

A solution of (R)-2-amino-1-((S)-4-(4-chlorophenyl)-4-hydroxy-3,3-dimethylpiperidin-1-yl)-3-methylbutan-1-one, HCl (32 mg, 0.09 mmol) and phthalic anhydride (14 mg, 0.09 mmol) in methylene chloride (1 mL) was stirred overnight at room temperature. The mixture was concentrated in-vacuo, and the residue was purified via prep HPLC to yield Example 594 (25 mg, 57% yield) as a colorless powder. MS (ESI+)=487.18, M+.

Example 595

N—((R)-1-((S)-4-(4-chlorophenyl)-4-hydroxy-3,3-dimethylpiperidin-1-yl)-3-methyl-1-oxobutan-2-yl)-3-(hydroxymethyl)benzamide

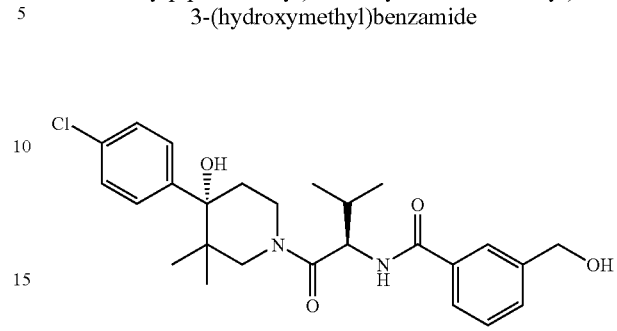

Step 1: Methyl 3-(hydroxymethyl)benzoate

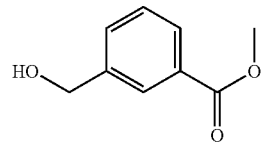

A solution of 3-(methoxycarbonyl)benzoic acid (1.05 g, 5.83 mmol) in THF (25 mL) was cooled to 0° C., and treated with the dropwise addition of 2.0 M borane-methylsulfide complex in THF (14.57 mL, 29.1 mmol) at a rate which did not allow the temperature to exceed 5° C. The mixture was stirred at 0° C. for 15 minutes, then allowed to warm to room temperature and stirred for 4 hours. The reaction was cooled to 0° C. and quenched with the addition of small pieces of ice, causing vigorous gas evolution. When gas evolution had ceased, the mixture was diluted with brine and extracted 3× with ethyl acetate. The combined organic phases were washed 3× with dilute bleach to remove residual methyl sulfide, 3× with saturated sodium carbonate to remove any unreacted acid, 1× with water, and 1× with brine, then dried over sodium sulfate and concentrated in vacuo to yield the title compound (845 mg, 5.09 mmol, 87% yield) as a colorless oil.

Step 2: 3-(Hydroxymethyl)benzoic acid

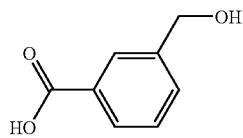

A solution of methyl 3-(hydroxymethyl)benzoate (845 mg, 5.09 mmol) in methanol (15 mL) was treated with 1 M NaOH (aq) (15.300 mL, 15.30 mmol), and the reaction was stirred overnight at room temperature. The methanol was removed under reduced pressure, and the remaining aqueous solution was washed 3× with 10 mL of diethyl ether. The aqueous phase was acidified to pH 1 with concentrated HCl, then extracted 3× with 20 mL of ethyl acetate. The combined organic phases were washed with brine, dried over sodium sulfate, and concentrated in-vacuo to yield the title compound (680 mg, 4.47 mmol, 88% yield) as a colorless powder. MS (ESI+)=153.10, (M+H)+.

Step 3: Example 595

Example 595 was prepared from (R)-2-amino-1-((S)-4-(4-chlorophenyl)-4-hydroxy-3,3-dimethylpiperidin-1-yl)-3-methylbutan-1-one, HCl and 3-(hydroxymethyl)benzoic acid using the procedure described in Example 573, Step 7. MS (ESI+)=473.4, (M+H)+.

Example 596

3-((R)-1-((S)-4-(4-chlorophenyl)-4-hydroxy-3,3-dimethylpiperidin-1-yl)-3-methyl-1-oxobutan-2-ylcarbamoyl)benzyl acetate

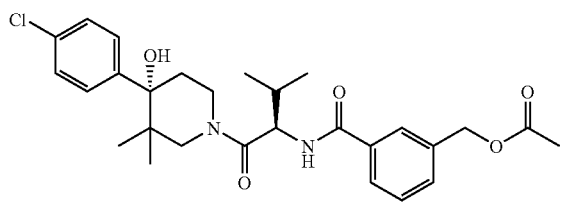

A solution of N—((R)-1-((S)-4-(4-chlorophenyl)-4-hydroxy-3,3-dimethylpiperidin-1-yl)-3-methyl-1-oxobutan-2-yl)-3-(hydroxymethyl)benzamide (37 mg, 0.078 mmol) in Pyridine (0.6 mL) was treated with acetic anhydride (0.015 mL, 0.156 mmol), and the mixture was stirred overnight at room temperature. The reaction was concentrated in-vacuo, and the residue was purified via prep HPLC to yield Example 596 (25 mg, 0.049 mmol, 62.1% yield) as a colorless powder. MS (ESI+)=515.4, M+.

Example 597

2-(3-((R)-1-((S)-4-(4-chlorophenyl)-4-hydroxy-3,3-dimethylpiperidin-1-yl)-3-methyl-1-oxobutan-2-ylcarbamoyl)phenyl)-2-methylpropanoic acid

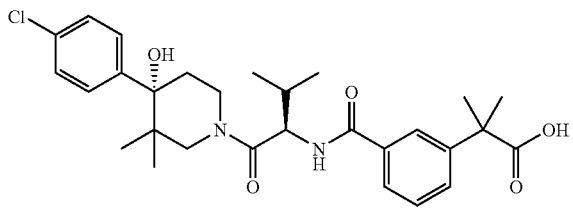

Step 1: Methyl 2-(3-bromophenyl)acetate

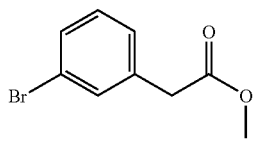

A solution of 2-(3-bromophenyl)acetic acid (2.64 g, 12.28 mmol) in 8:2 benzene/methanol (50 mL) was cooled to 0° C., then treated with the dropwise addition of 2.0 M TMS-diazomethane in hexanes (6.14 mL, 12.28 mmol) over 10 minutes. The mixture was allowed to come to room temperature and stirred for 7 days. The mixture was concentrated in-vacuo, and the residue was purified over silica gel, eluting with 10% ethyl acetate/hexanes to yield the title compound (1.96 g, 8.56 mmol, 69.7% yield) as a colorless oil.

Step 2: Methyl 2-(3-bromophenyl)-2-methylpropanoate

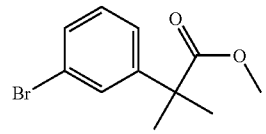

A solution of methyl 2-(3-bromophenyl)acetate (502 mg, 2.191 mmol) in THF (10 mL) was cooled to −78° C., and 0.5 M potassium hexamethyldisilazide in toluene (4.82 mL, 2.411 mmol) was added dropwise at a rate which did not allow the temperature to exceed −60° C. The mixture was allowed to stir at −78° C. for 20 minutes, allowed to warm to −30° C., stirred for 20 minutes, recooled to −78° C., and quenched with iodomethane (0.206 mL, 3.29 mmol). The reaction was allowed to come to room temperature and stirred for 1 h. The mixture was recooled to −78° C., and the additions described above were repeated a second time. The mixture was allowed to come to room temperature and stirred overnight. The reaction was quenched with water, then extracted 3× with ethyl acetate. The combined organic phases were washed with brine, dried over sodium sulfate, and concentrated in-vacuo. The residue was purified over silica gel, eluting with 10% ethyl acetate/hexanes to yield the title compound (513 mg, 1.995 mmol, 91% yield) as a colorless oil.

Step 3: Methyl 3-(1-methoxy-2-methyl-1-oxopropan-2-yl)benzoate

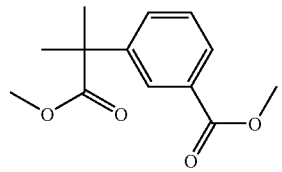

A mixture of methyl 2-(3-bromophenyl)-2-methylpropanoate (260 mg, 1.011 mmol), bis(triphenylphosphine)palladium(II) chloride (71.0 mg, 0.101 mmol), and Hunig's Base (0.353 mL, 2.022 mmol) in methanol (5 mL) in a 50 mL sealable reaction bottle was treated with carbon monoxide (28.3 mg, 1.011 mmol) via a gas dispersion tube for two minutes, the bottle was sealed, and the mixture was heated overnight at 80° C. The reaction was cooled to room temperature, and the catalyst was removed by filtration and rinsed with methanol. The filtrate was concentrated in-vacuo, and the residue was purified over a 2×15 cm silica gel column, eluting with ethyl acetate/hexanes (5%-10%-15%-20% ethyl acetate), to yield the title compound (54 mg, 0.229 mmol, 22.60% yield) as a colorless oil.

Step 4: 3-(2-Carboxypropan-2-yl)benzoic acid

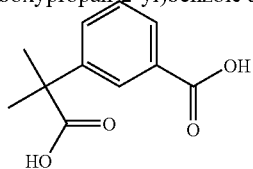

A solution of methyl 3-(1-methoxy-2-methyl-1-oxopropan-2-yl)benzoate (54 mg, 0.229 mmol) in methanol (2 mL) was treated with 1 M NaOH (aq) (1 mL, 1.000 mmol), and the mixture was stirred overnight at room temperature. The mixture was treated with 1.0 N HCl (aq) (1.2 mL), and the methanol was removed in-vacuo. The remaining aqueous mixture was freeze dried to yield a mixture of the title compound and sodium chloride as colorless powder, which was used as-is in the next step.

Step 5: Example 597

A mixture of (R)-2-amino-1-((S)-4-(4-chlorophenyl)-4-hydroxy-3,3-dimethylpiperidin-1-yl)-3-methylbutan-1-one, HCl (78 mg, 0.208 mmol), 3-(2-carboxypropan-2-yl)benzoic acid (47.7 mg, 0.229 mmol), HOBT (70.1 mg, 0.458 mmol), and triethylamine (0.145 mL, 1.040 mmol) in methylene chloride (1 mL) was treated with EDC (88 mg, 0.458 mmol), and the mixture was stirred overnight at room temperature. The mixture was concentrated in-vacuo, and the residue was taken up in ethyl acetate. The organic phase was washed 3× with water, 3× with 1M HCl, and once with brine, dried over sodium sulfate, and concentrated in-vacuo. The residue was purified via prep HPLC. Fractions containing the mono-coupled product were combined and freeze-dried to yield a colorless powder which was a 2:1 mixture of two regioisomers. Fractions containing the bis-coupled product were combined and freeze dried to yield N—((R)-1-((S)-4-(4-chlorophenyl)-4-hydroxy-3,3-dimethylpiperidin-1-yl)-3-methyl-1-oxobutan-2-yl)-3-(1-((R)-1-((S)-4-(4-chlorophenyl)-4-hydroxy-3,3-dimethylpiperidin-1-yl)-3-methyl-1-oxobutan-2-ylamino)-2-methyl-1-oxopropan-2-yl)benzamide (13 mg, 0.015 mmol, 7.35% yield) as a colorless powder. The 2:1 mixture of mono-coupled products was purified via a 1 mm silica prep plate, eluting 3× with 5% MeOH/CH$_2$Cl$_2$, to yield Example 597 (16 mg, 0.027 mmol, 13.09% yield) as an amber solid. MS (ESI+)=529.5, M$^+$. This material was contaminated with 10% of 3-(1-((R)-1-((S)-4-(4-chlorophenyl)-4-hydroxy-3,3-dimethylpiperidin-1-yl)-3-methyl-1-oxobutan-2-ylamino)-2-methyl-1-oxopropan-2-yl)benzoic acid.

Example 598

(R)-2-(6-tert-butylpyrimido[5,4-d]pyrimidin-4-ylamino)-1-((S)-4-(4-chlorophenyl)-4-hydroxy-3,3-dimethylpiperidin-1-yl)-3-methylbutan-1-one

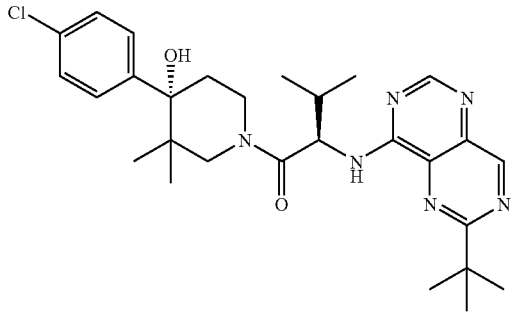

Step 1. 5-Bromo-2-tert-butyl-pyrimidine-4-carboxylic acid

A 22% solution of sodium ethoxide in ethanol (53 mL, 165 mmol) was added dropwise to a magnetically stirred suspension of tert-butylcarbamadine hydrochloride (20.0 g, 146 mmol) in ethanol (100 mL). When the addition was complete, the yellow suspension was warmed to 50° C., the heating mantle was removed, and a solution of mucobromic acid (15.7 g, 61 mmol) in ethanol (50 mL) was added dropwise at a rate which did not allow the temperature to exceed 55° C. When this addition was complete, a 22% solution of sodium ethoxide in ethanol (32 mL, 98 mmol) was added dropwise, then the mixture was allowed to cool to room temperature. The suspension was filtered, the solids were rinsed with ethanol (2×20 mL), and the combined filtrates were concentrated in-vacuo. The residue thus obtained was stirred in 2 N aqueous HCl (30 mL). The resulting solids were collected by filtration, rinsed with ice-cold water (2×20 mL), and air dried to yield 12.1 g of a beige powder as product. MS (ESI+)=259, 261, (M+H)$^+$. Yield=76%.

Step 2. 5-Bromo-2-tert-butyl-pyrimidine-4-carboxylic acid methyl ester

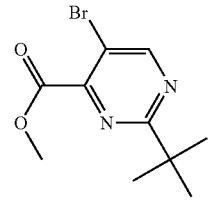

A 2.0 M hexanes solution of trimethylsilyldiazomethane (11.8 mL, 23.62 mmol) was added dropwise to a stirring solution of 5-bromo-2-tert-butyl-pyrimidine-4-carboxylic acid (6.12 g, 23.62 mmol) in 9:1 benzene/methanol (100 mL), and the reaction was stirred for 2 days. TLC analysis showed that the reaction was complete, so the mixture was concentrated in-vacuo. The residue was dissolved in ethyl acetate (100 mL), washed with water (3×20 mL), dried over sodium sulfate, then concentrated in-vacuo. Purified over silica gel, eluting with 10% ethyl acetate/hexanes, to yield 5.2 g of a colorless oil as product. MS (ESI+)=273/275, (M+H)$^+$. Yield=81%.

Step 3. 5-tert-Butoxycarbonylamino-2-tert-butyl-pyrimidine-4-carboxylic acid methyl ester

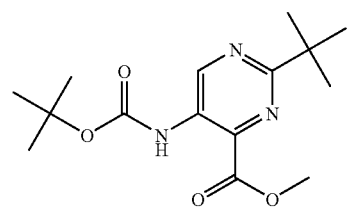

A flame dried reaction tube charged with tert-butylcarbamate (140 mg, 1.2 mmol), cesium carbonate (456 mg, 1.4 mmol), 4,5-bis(diphenylphosphino)-9,9-dimethylxanthane (18 mg, 0.03 mmol), and tris(dibenzylidineacetone)dipalladium(0) (19 mg, 0.02 mmol) was evacuated under vacuum, then backfilled with argon. Dioxane (2 mL) and 5-bromo-2-tert-butyl-pyrimidine-4-carboxylic acid methyl ester (273 mg, 1.0 mmol) were added, and the mixture was degassed under vacuum. The tube was then backfilled with argon, sealed, and heated at 100° C. for 2 hours. Analysis by LC/MS showed complete consumption of starting bromide. The mixture was diluted with methylene chloride (20 mL), filtered to remove solids, and concentrated in-vacuo. The residue was purified over silica gel, eluting with 10% ethyl acetate/heptane, to yield 152 mg of white solids as product. MS (ESI+) =310, (M+H)⁺. Yield=50%.

Step 4. 5-Amino-2-tert-butyl-pyrimidine-4-carboxylic acid methyl ester, HCl salt

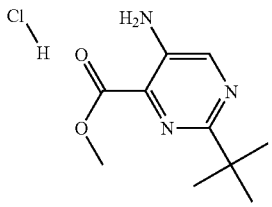

5-tert-Butoxycarbonylamino-2-tert-butyl-pyrimidine-4-carboxylic acid methyl ester (2.4 g, 7.75 mmol) was dissolved in a 4 M solution of HCl in dioxane (30 mL). After 10 minutes of stirring, a thick white solid precipitated. The reaction was allowed to stir overnight, during which time the mixture became a homogenous, amber solution. Concentrated in-vacuo, and the residue was concentrated from toluene (2×50 mL) followed by methylene chloride (3×50 mL) to remove excess HCl. The resulting 1.85 g of yellow solids was used without further purification in the next step. MS (ESI+) =210, (M+H)⁺.

Step 5. 6-tert-Butyl-pyrimido[5,4-d]pyrimidin-4-ol

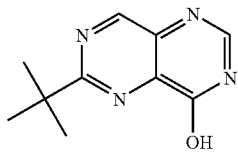

A mixture of 5-amino-2-tert-butyl-pyrimidine-4-carboxylic acid methyl ester, HCl salt (1.1 g, 4.48 mmol) and formamidine acetate (1.86 g, 17.90 mmol) in 2-ethoxyethanol (20 mL) was heated at reflux for 5 hours. LC/MS analysis showed the reaction to be essentially complete, so the mixture was cooled to room temperature, then concentrated in-vacuo. The residue was purified over silica gel, eluting with ethyl acetate, 1% methanol/ethyl acetate, then 2% methanol/ethyl acetate to yield 1.06 g of a beige solid as product. MS (ESI+)=205, (M+H)⁺. Yield=94%.

Step 6. 2-tert-Butyl-8-chloro-pyrimido[5,4-d]pyrimidine

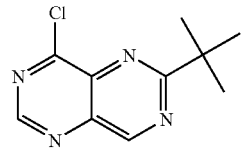

6-tert-Butyl-pyrimido[5,4-d]pyrimidin-4-ol (210 mg, 1.03 mmol) was dissolved in phosphorous oxychloride (10 mL), and the mixture was heated at reflux for 4 hours. The solution was concentrated in-vacuo, then concentrated from methylene chloride (3×50 mL) to remove excess phosphorous oxychloride. The residue was stirred for 10 minutes in saturated sodium bicarbonate (50 mL), then extracted with ethyl acetate (3×30 mL). The combined organic phases were washed with water (30 mL), followed by brine (30 mL), dried over sodium sulfate, then concentrated in-vacuo. The residue was purified over silica gel, eluting with 50% ethyl acetate/heptane, to yield 150 mg of a white solid as product. NMR (500 MHz, CDCl3) δ 9.61 (s, 1H), 9.15 (S, 1H), 1.52 (s, 9H).

Step 7: Example 598

A solution of (R)-2-amino-1-((S)-4-(4-chlorophenyl)-4-hydroxy-3,3-dimethylpiperidin-1-yl)-3-methylbutan-1-one, HCl (17 mg, 0.04 mmol), 2-tert-Butyl-8-chloro-pyrimido[5,4-d]pyrimidine (10 mg, 0.04 mmol), and triethylamine (0.016 mL, 0.11 mmol) in isopropanol (1 mL) was stirred overnight at room temperature. The solution was diluted with 1:1 acetonitrile/water (2 mL), and the mixture was purified via prep HPLC to yield Example 598 as a pale yellow powder. MS (ESI+)=526.3, M⁺.

Example 599

(R)-2-(8-bromoquinazolin-4-ylamino)-1-((S)-4-(4-chlorophenyl)-4-hydroxy-3,3-dimethylpiperidin-1-yl)-3-methylbutan-1-one, TFA

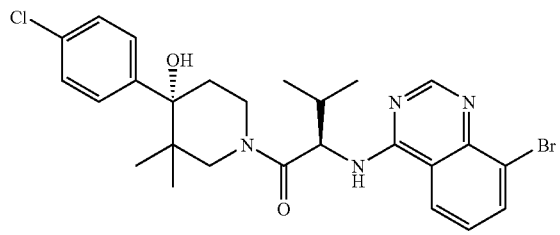

Step 1: 8-Bromoquinazolin-4-ol

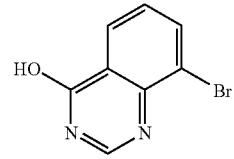

A solution of formamadine acetate (836 mg, 8.03 mmol) and 2-amino-3-bromobenzoic acid (578 mg, 2.68 mmol) in 2-ethoxyethanol (15 mL) was heated at reflux for 18 h. Cooled to room temperature, upon which a precipitate was observed. Diluted with diethyl ether (15 mL), and stirred for 20 minutes. The solids were collected by vacuum filtration, rinsed with 2-ethoxyethanol (5 mL), followed by diethyl ether, then air dried to yield the title compound (445 mg, 1.977 mmol, 73.9% yield) as a tan powder. MS (ESI+) =225.1/227.1, (M+H)$^+$.

Step 2: 8-Bromo-4-chloroquinazoline

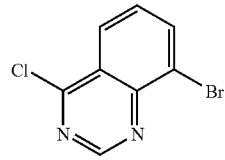

A suspension of 8-bromoquinazolin-4-ol (410 mg, 1.822 mmol) in phosphorous oxychloride (15.000 mL, 161 mmol) was heated to reflux. After refluxing 45 min, a clear, amber solution was observed. Refluxed an additional 30 min, concentrated in-vacuo, and concentrated 2× from methylene chloride to remove residual phosphorous oxychloride. The residue was taken up in ethyl acetate (50 mL), treated with the careful addition of saturated sodium bicarbonate, and this mixture was stirred for 5 minutes, until gas evolution had ceased. The layers were separated, the and the aqueous phase was extracted with ethyl acetate (20 mL). The combined organic phases were washed with saturated sodium bicarbonate, water, and saturated sodium chloride, dried over sodium sulfate, and concentrated in-vacuo to yield the title compound (442 mg, 1.815 mmol, 100% yield) as a tan powder which was used as-is in the next step.

Step 3: Example 599

A solution of (R)-2-amino-1-((S)-4-(4-chlorophenyl)-4-hydroxy-3,3-dimethylpiperidin-1-yl)-3-methylbutan-1-one, HCl (35 mg, 0.093 mmol) and N,N-Diisopropylethylamine (0.049 mL, 0.280 mmol) in 2-Propanol (1 mL) was treated with 8-bromo-4-chloroquinazoline (24.9 mg, 0.103 mmol), and the mixture was stirred overnight at room temperature. The reaction mixture was diluted with 1:1 acetonitrile/water, and injected directly onto the prep HPLC for purification. Fractions containing the desired product were freeze dried to yield 38 mg of colorless powder which was ~80% pure by NMR/LCMS. The powder was repurified via HPLC to yield Example 599 (24 mg, 0.036 mmol, 39.0% yield). MS (ESI+) =545.13/547.24, M$^+$.

Example 600

N—((R)-1-((S)-4-(4-chlorophenyl)-4-hydroxy-3,3-dimethylpiperidin-1-yl)-3-methyl-1-oxobutan-2-yl)-3-(N,N-dimethylsulfamoyl)benzamide

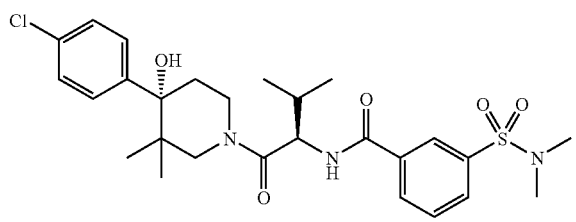

Step 1 3-(N,N-dimethylsulfamoyl)benzoic acid

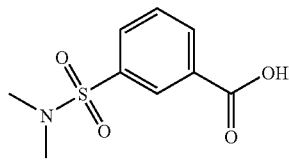

A solution of 3-(chlorosulfonyl)benzoic acid (152 mg, 0.689 mmol) in methylene chloride (2 mL) was treated with 2.0 M dimethylamine in THF (1.137 mL, 2.274 mmol), and the mixture was stirred overnight at room temperature. The reaction was quenched with 1 N HCl, and extracted 3× with EtOAc. The combined organic phases were washed with 1 N HCl followed by brine, then dried over sodium sulfate and concentrated in-vacuo to yield the title compound (138 mg, 0.602 mmol, 87% yield). MS (ESI+)=230.18, (M+H)$^+$.

Step 2: Example 600

Example 600 was prepared from (R)-2-amino-1-((S)-4-(4-chlorophenyl)-4-hydroxy-3,3-dimethylpiperidin-1-yl)-3-methylbutan-1-one, HCl and 3-(N,N-dimethylsulfamoyl)benzoic acid using the procedure described in Example 573, Step 7. MS (ESI+)=550.38, M$^+$.

Example 601

3-((R)-1-((S)-4-(4-chlorophenyl)-4-hydroxy-3,3-dimethylpiperidin-1-yl)-1-oxopropan-2-ylcarbamoyl)benzoic acid

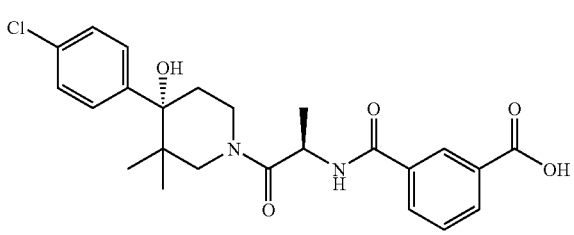

Step 1 (R)-2-amino-1-((S)-4-(4-chlorophenyl)-4-hydroxy-3,3-dimethylpiperidin-1-yl)propan-1-one, HCl

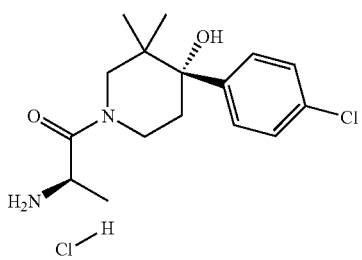

A mixture of (S)-4-(4-chlorophenyl)-3,3-dimethylpiperidin-4-ol (107 mg, 0.45 mmol), Boc-D-Ala-OH (93 mg, 0.49 mmol), HOBT (133 mg, 0.98 mmol), and triethylamine (0.25 mL, 1.78 mmol) in methylene chloride (2 mL) was treated with EDC (187 mg, 0.98 mmol), and the reaction was allowed to stir overnight at room temperature. The solvent was evaporated with a stream of nitrogen, and the residue was taken up in ethyl acetate. The organic phase was washed 3× with 1M NaOH, 3× ×with 1M HCl, and once with brine, dried over sodium sulfate, and concentrated in-vacuo. The residue was dissolved in dioxane (2 mL) and treated with 4 N HCl in dioxane (2 mL, 8 mmol). The mixture was stirred for 4 hours, then concentrated in-vacuo. Twice, the residue was taken up in methylene chloride (10 mL) and the mixture was concentrated in-vacuo, to remove residual HCl, to yield the title compound. MS (ESI+)=311.3, (M+H)$^+$.

Step 2 Methyl 3-((R)-1-((S)-4-(4-chlorophenyl)-4-hydroxy-3,3-dimethylpiperidin-1-yl)-1-oxopropan-2-ylcarbamoyl)benzoate

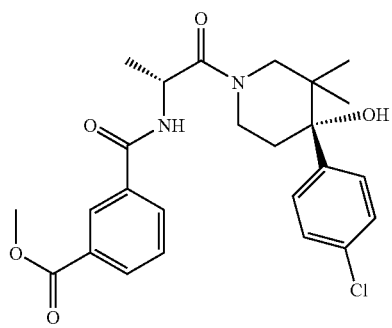

The title compound was prepared from (R)-2-amino-1-((S)-4-(4-chlorophenyl)-4-hydroxy-3,3-dimethylpiperidin-1-yl)propan-1-one, HCl (47 mg, 0.14 mmol) and mono-methyl isophthalate (27 mg, 0.16 mmol) using the conditions described in Example 572, Step 5. MS (ESI+)=473.3, M$^+$.

Step 3: Example 601

A solution of methyl 3-((R)-1-((S)-4-(4-chlorophenyl)-4-hydroxy-3,3-dimethylpiperidin-1-yl)-1-oxopropan-2-ylcarbamoyl)benzoate (33 mg, 0.07 mmol) in THF (1 mL) was treated with 0.5 M aqueous lithium hydroxide, and the mixture was stirred overnight at room temperature. The reaction mixture was purified via prep HPLC to yield Example 601 (24 mg, 75% yield) as a colorless powder. MS (ESI+)=459.3, M$^+$.

Example 602

(R)—N—((R)-1-((S)-4-(4-chlorophenyl)-4-hydroxy-3,3-dimethylpiperidin-1-yl)-3-methyl-1-oxobutan-2-yl)-3-oxocyclopentanecarboxamide

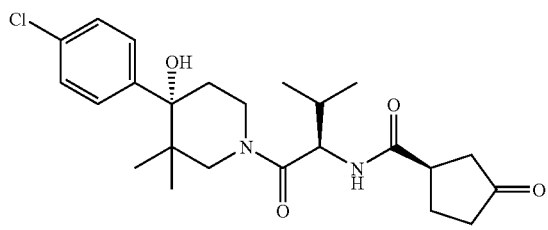

Example 602 was prepared from (R)-3-oxocyclopentanecarboxylic acid, prepared via the method of Curry, et. al. J. Med. Chem. 1988, 31, 861. (304 mg, 2.37 mmol) and (R)-2-amino-1-((S)-4-(4-chlorophenyl)-4-hydroxy-3,3-dimethylpiperidin-1-yl)-3-methylbutan-1-one, HCl (810 mg, 2.16 mmol) using the procedures described in Examples 572A and 572B, Step 5. MS (ESI+)=449.5, M$^+$.

Example 603

(1R)—N—((R)-1-((S)-4-(4-chlorophenyl)-4-hydroxy-3,3-dimethylpiperidin-1-yl)-3-methyl-1-oxobutan-2-yl)-3-hydroxy-3-methylcyclopentanecarboxamide

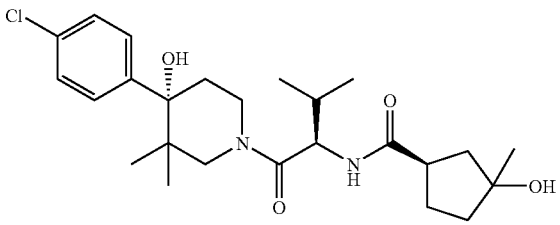

Step 1. (1R)-3-hydroxy-3-methylcyclopentanecarboxylic acid

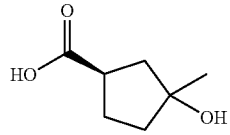

A solution of (R)-3-oxocyclopentanecarboxylic acid, prepared via the method of Curry, et. al. J. Med. Chem. 1988, 31, 861. (215 mg, 1.678 mmol) in THF (10 mL) was cooled to −78° C., then treated with the dropwise addition of 1.6 M methyllithium in diethyl ether (2.927 mL, 4.68 mmol) at a rate which did not allow the temperature to rise above −60° C. The mixture was allowed to stir at −78° C. for 2 h, then allowed to warm to 0° C. and quenched with 1 N HCl. The layers were separated, and the aqueous phase was extracted 3× with ethyl acetate. The aqueous phase was concentrated in-vacuo, then concentrated 3× from isopropanol to remove all water. NMR of the residue indicated a complex mixture of materials. The material was used as-is in the next step.

Step 2: Example 603

Example 603 was prepared from (R)-2-amino-1-((S)-4-(4-chlorophenyl)-4-hydroxy-3,3-dimethylpiperidin-1-yl)-3-methylbutan-1-one, HCl and mixture of materials prepared in Step A., which contained (1R)-3-hydroxy-3-methylcyclopentanecarboxylic acid, using the procedure described in Example 573, Step 7. MS (ESI+)=465.5, M$^+$.

Example 604

N—((R)-1-((S)-4-(4-chlorophenyl)-4-hydroxy-3,3-dimethylpiperidin-1-yl)-3-methyl-1-oxobutan-2-yl)-6-(trifluoromethyl)pyrido[3,2-d]pyrimidine-4-carboxamide

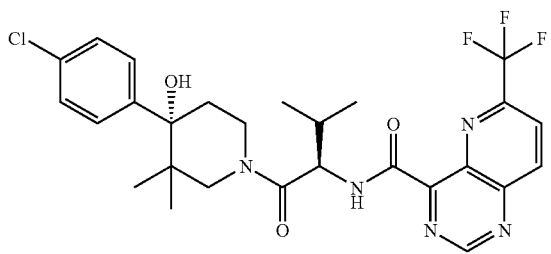

Step-1: 5-amino-6-iodo-2-(trifluoromethyl)pyridine

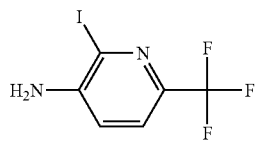

To a solution of 8 g (0.0494 mol, 1 eq) of 5-amino-2-(trifluoromethyl)pyridine in 160 mL of water and 160 mL of methanol was added 8 mL of conc. HCl followed by 8.2 g (0.0494 mol, 1 eq) of potassium iodide and 5.2 g (0.0243 mol, 0.5 eq) of potassium iodate and stirred at RT for 48 h. The reaction mixture was basified with 10% NaOH solution and extracted with ethyl acetate. The organic layer was washed with brine and concentrated. The crude product obtained was purified by 60-120 silica gel using 10% of ethyl acetated in pet ether to get 12.5 g (87.9%) of off white solid. Results: $^1$H NMR (CDCl$_3$, 400 MHz): 6.94 (1H, d), 7.42 (1H, d), 4.0-5.0 (2H, bs). MS 289 (M+H)$^+$.

Step-2: 5-Amino-6-cyano-2-(trifluoromethyl)pyridine

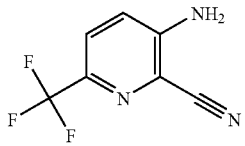

12.5 g (0.434 mol, 1 eq) of 5-amino-6-iodo-2-(trifluoromethyl)pyridine was dissolved in 125 mL of dry DMF and degasified with nitrogen for 5 min. 6.1 g (0.519 mol, 1.2 eq) of zinc cyanide and 5 g (0.1 eq) of Pd(PPh$_3$)$_4$ were added and heated at 100° C. for over night. The reaction mixture was quenched with water and extracted with ethyl acetate. The organic layer was washed with brine and concentrated. The crude product obtained was purified by 60-120 silica gel using 15% of ethyl acetate in pet ether to get 7 g (86.31%) of pale yellow solid. $^1$H NMR (CDCl$_3$, 400 MHz): 4.85 (2H, bs), 7.25 (1H, d), 7.62 (1H, d). MS 188 (M+H)$^+$.

Step-3: 3-Amino-6-trifluoromethyl-pyridine-2-carboxylic acid amide

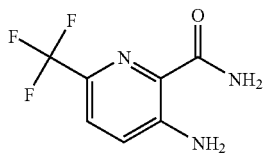

7 g (0.0374 mol, 1 eq) of 5-amino-6-cyano-2-(trifluoromethyl)pyridine dissolved in 106 ml of 90% sulfuric acid was and heated at 70° C. for 3 h. The reaction mixture was cooled to RT and quenched with ice water and extracted with ethyl acetate. The organic layer was washed with brine and concentrated. The solid product obtained was washed with to get 6.8 g (89.47%) of off white solid. $^1$H NMR (CDCl$_3$, 400 MHz) 5.5 (1H, bs), 7.1 (1H, d), 7.53 (1H, d), 7.80 (1H, bs). MS 206 (M+H)$^+$.

Step-4: 6-Trifluoromethyl-3H-pyrido[3,2-d]pyrimidin-4-one

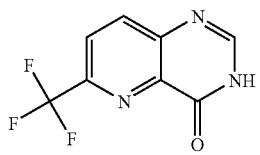

6.8 g (0.0332 mol, 1 eq) of 3-amino-6-trifluoromethyl-pyridine-2-carboxylic acid amide in 170 ml of triethylorthoformate under nitrogen was heated at 145° C. for 8 h. Excess triethylorthoformate was removed under reduced pressure and the solid product obtained was washed with pet-ether and dried under vacuum to get 6.8 g (95.37%) of white solid. $^1$H NMR (CDCl$_3$, 400 MHz): 8.11 (1H, d), 8.35 (1H, d), 12.28 (1H, bs). MS 216 (M+H)$^+$.

Step-5: 4-Chloro-6-(trifluoromethyl)pyrido[3,2-d]pyrimidine

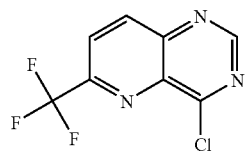

The title compound was prepared from trifluoromethyl-3H-pyrido[3,2-d]pyrimidin-4-one using the procedure described in Example 599, Step 2. A POCl$_3$ (9.3 ml) suspension of 6-Trifluoromethyl-3H-pyrido[3,2-d]pyrimidin-4-one (1.0 g, 4.7 mmol) was heated at reflux for 4 hours, over which time the amber suspension became a clear, deep blue solution. The reaction was cooled to room temperature and concentrated under reduced pressure. The residue concentrated from dichloromethane 3× to remove residual POCl$_3$. The residue was partitioned between 1:1 EtOAc and saturated sodium bicarbonate (28 ml). The mixture was stirred until visible gas evolution ceased. The suspension was filtered through a plug of celite. The layers of the filtrate were separated, and the organic phase was washed successively with saturated sodium bicarbonate and saturated sodium chloride, dried with magnesium sulfate and concentrated under reduced pressure to yield the semi-pure product as a purple solid. No further purification was carried out. The crude product was greater than 90% pure (as determined by analytical HPLC). MS: ES+ 234.11 (M+H, 100%

Step 6: Example 604

Example 604 was prepared from (R)-2-amino-1-((S)-4-(4-chlorophenyl)-4-hydroxy-3,3-dimethylpiperidin-1-yl)-3-methylbutan-1-one, HCl and 4-chloro-6-(trifluoromethyl)pyrido[3,2-d]pyrimidine using the procedure described in Example 598, Step 7. MS (ESI+)=536.3, M$^+$.

Example 605

Ethyl-3-((R)-1-((S)-4-(4-chlorophenyl)-4-hydroxy-3,3-dimethylpiperidin-1-yl)-3-methyl-1-oxobutan-2-ylamino)benzoate

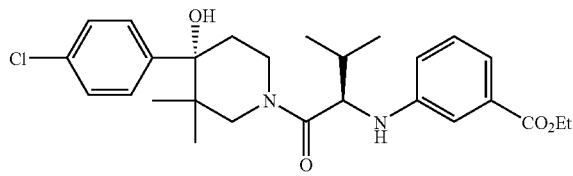

Step 1: (R)-2-(3-(Ethoxycarbonyl)phenylamino)-3-methylbutanoic acid

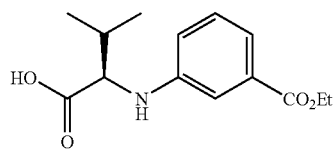

Ethyl 3-iodobenzoate (857 mg, 3.10 mmol), DMF (5 mL), copper(I) iodide (65 mg, 0.34 mmol), N1,N2-dimethylaminoethylene (62.9 mg, 0.714 mmol), D-valine (400 mg, 3.41 mmol) and potassium carbonate (429 mg, 3.10 mmol) were charged into a flask. The flask was evacuated, then filled with nitrogen over several cycles to remove oxygen, then the reaction was heated to 140° C. under nitrogen for 4 hrs. The reaction was cooled, the DMF removed by evaporation, and 1 N HCl added. The reaction mixture was partitioned between EtOAc and water, and the organic layer was dried over sodium sulfate, filtered, and concentrated to yield a brown oil. This was used in next step without further purification.

Step 2: Example 605

(S)-4-(4-Chlorophenyl)-3,3-dimethylpiperidin-4-ol (106 mg, 0.44 mmol), (R)-2-(3-(ethoxycarbonyl)phenylamino)-3-methylbutanoic acid (167 mg, 0.44 mmol), DIPEA (228 mg, 1.76 mmol), HOBT (59.5 mg, 0.44 mmol), EDC (101 mg, 0.53 mmol), and DMF (2 mL) were stirred overnight at rt. The reaction was partitioned between EtOAc and water, the organics were dried over sodium sulfate, filtered, concentrated, and the residue was purified by preparative reverse phase HPLC (MeOH/water/TFA) yielding Example 605 as a white solid (109 mg, 50.7% yield) M+H=487.19.

Example 606

3-((R)-1-((S)-4-(4-Chlorophenyl)-4-hydroxy-3,3-dimethylpiperidin-1-yl)-3-methyl-1-oxobutan-2-ylamino)benzoic acid

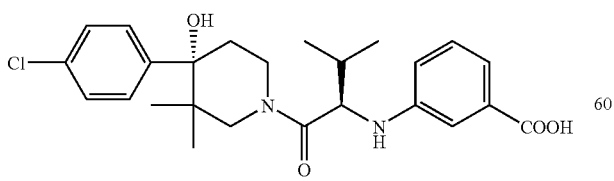

Ethyl-3-(R)-1-(S)-4-(4-chlorophenyl)-4-hydroxy-3,3-dimethylpiperidine-1-yl)-3-methyl-1-oxobutan-2-ylamino)benzoate (92 mg), MeOH, and 1N sodium hydroxide was stirred overnight at rt. The reaction was concentrated and the residue was purified by preparative reverse-phase HPLC (MeOH/water/TFA) to give Example 606 as a white solid (83.3 mg 95.7% yield).

Example 607

(R)-1-((S)-4-(4-chlorophenyl)-4-hydroxy-3,3-dimethylpiperidin-1-yl)-3-methyl-2-(pyridine-3-ylamino)butan-1-one

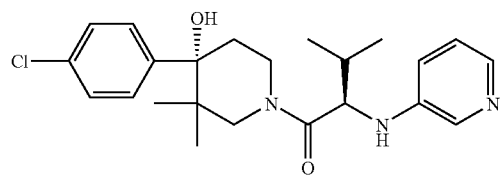

Step 1: (R)-3-Methyl-2-(pyridine-3-ylamino)butanoic acid

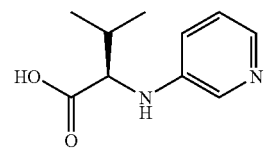

3-Iodopyridine (525 mg, 2.58 mmol), D-valine (250 mg, 2.13 mmol), copper(I) iodide (40.6 mg, 0.213 mmol), dimethylaminoethanol (400 mg, 4.49 mmol), potassium phosphate tribasic (1359 mg, 6.40 mmol), and water (2 mL) was stirred at 80° C. overnight. The reaction was washed with EtOAc, then the aqueous portion was concentrated. The residue was slurried with MeOH and the MeOH portion was concentrated. The product was isolated using preparative reverse phase HPLC (MeOH/water/TFA) and used in next step without further purification.

Step 2: Example 607

(R)-3-Methyl-2-(pyridine-3-ylamino)butanoic acid (162 mg, 0.83 mmol), (S)-4-(4-chlorophenyl)-3,3-dimethylpiperidin-4-ol (200 mg, 0.83 mmol), EDC (320 mg, 1.67 mmol), HOBT (113 mg, 0.83 mmol), DIPEA (431 mg, 3.34 mmol), and DMF (4 mL) was stirred overnight at rt. Example 607 was isolated as a greenish solid using preparative reverse phase HPLC (22.5 mg, 6.5% yield). M+H=416.18.

Example 608

(R)-1-((S)-4-(4-chlorophenyl)-4-hydroxy-3,3-dimethylpiperidin-1-yl)-3-methyl-2-(pyrimidin-5-ylamino)butan-1-one

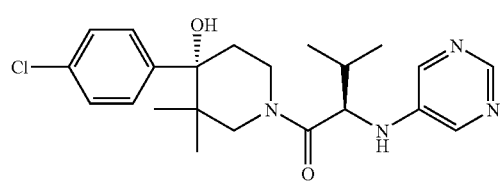

Step 1: (R)-3-Methyl-2-(pyrimidin-5-ylamino)butanoic acid

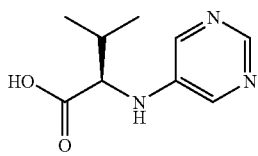

5-Bromopyrimidine (407 mg, 2.56 mmol), D-valine (250 mg, 2.13 mmol), copper(I) iodide (40.6 mg, 0.213 mmol), dimethylaminoethanol (400 mg, 4.49 mmol), potassium phosphate tribasic (1359 mg, 6.40 mmol), and water (2 mL) was stirred at 80° C. for several hours. 1 N hydrochloric acid (3 mL) was added to the reaction mixture followed by TFA (3 mL) and the reaction was extracted with EtOAc. The organic portion was dried over sodium sulfate, filtered, concentrated, and the product was isolated as a brown solid using preparative reverse-phase HPLC and used in next step without further purification.

Example 608

(R)-3-Methyl-2-(pyridine-3-ylamino)butanoic (64 mg, 0.207 mmol), (S)-4-(4-chlorophenyl)-3,3-dimethylpiperidin-4-ol (59.4 mg, 0.248 mmol), EDC (47.5 mg, 0.248 mmol), HOBT (27.9 mg, 0.207 mmol), DIPEA (107 mg, 0.826 mmol), and DMF (2 mL) was stirred overnight at rt. Example 608 was isolated as a light tan solid using preparative reverse phase HPLC. (6.6 mg, 7.7% yield). M+H=417.15.

Example 609

Methyl-5-((R)-1-((S)-4-(4-chlorophenyl)-4-hydroxy-3,3-dimethylpiperidin-1-yl)-3-methyl-1-oxobutan-2-ylcarbamoyl)-2-isopropylbenzoate

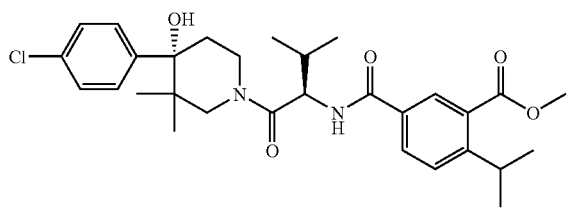

Step 1: 3-Iodo-4-isopropylbenzoic acid

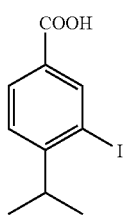

4-Isopropylbenzoic acid (4.26 g, 25.9 mmol), sulfuric acid (25 mL), and water (2 mL) was heated to 95° C. and iodine (14.42 g, 56.8 mmol) was slowly added portionwise. The reaction was maintained at this temperature for 48 h. The reaction was cooled, poured into ice and extracted with methylene chloride. The organic extracts were dried over sodium sulfate, filtered, concentrated and then purified by reverse phase HPLC (MeOH/water/TFA) to yield 3-iodo-4-isopropylbenzoic acid (60 mg).

Step 2: 4-Isopropyl-3-(methoxycarbonyl)benzoic acid

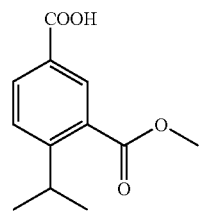

A parr reactor was charged with 3-iodo-4-isopropylbenzoic acid (60 mg, 0.207 mmol), palladium acetate, MeOH (25 mL), 1,3-bis(diphenylphosphino)propane (4.31 mg, 0.021 mmol), and potassium carbonate (57 mg, 0.414 mmol) and pressurized with 80 psi of carbon monoxide gas. The reaction was heated at 75° C. overnight. The reaction was cooled, concentrated, and partitioned between 15 mL water/15 mL methylene chloride. The aqueous portion was acidified with 1 N HCl and extracted with methylene chloride. The organics were dried over sodium sulfate, filtered, and concentrated to yield a yellowish solid (40 mg).

Step 3: Example 609

4-Isopropyl-3-(methoxycarbonyl)benzoic acid (40 mg, 0.180 mmol), HOBT (20 mg, 0.15 mmol), EDC (56.3 mg, 015 mmol), DIPEA (58.2 mg, 0.58 mmol), and DMF (2 mL) was stirred briefly at rt, then (R)-2-amino-1-((S)-4-(4-chlorophenyl)-4-hydroxy-3,3-dimethylpiperidin-1-yl)-3-methylbutan-1-one hydrochloride was added. The reaction was stirred overnight at rt then purified by reverse phase HPLC to yield Example 609 as a white solid (47 mg, 58% yield), M+H=543.31.

Example 610

5-((R)-1-((S)-4-(4-chlorophenyl)-4-hydroxy-3,3-dimethylpiperidin-1-yl)-3-methyl-1-oxobutan-2-ylcarbamoyl)-2-isopropylbenzoic acid

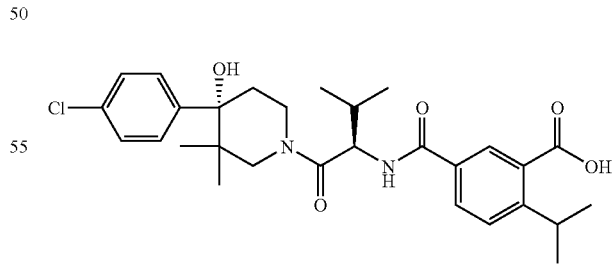

Methyl-5-((R)-1-((S)-4-(4-chlorophenyl)-4-hydroxy-3,3-dimethylpiperidin-1-yl)-3-methyl-1-oxobutan-2-ylcarbamoyl)-2-isopropylbenzoate (Example 609, 45 mg) was stirred overnight at rt in MeOH (5 mL) and 1 N sodium hydroxide (5 mL). The reaction was acidified with 1 N HCl (10 mL) and extracted into methylene chloride. The organic layer was

Example 611

Methyl-3-(R)-1-((S)-4-(4-chlorophenyl)-4-hydroxy-3,3-dimethylpiperidin-1-yl)-3-methyl-1-oxobutan-2-ylcarbamoyl)-5-(trifluoromethyl)benzoate

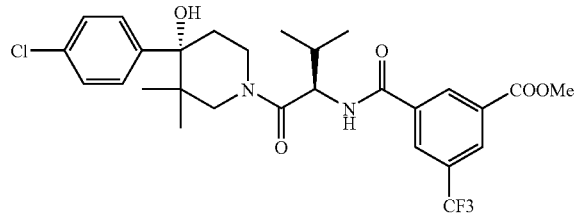

Step 1: 3,5-Diiodobenzotrifluoride

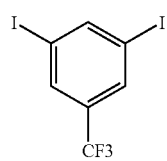

To a stirred solution of isopentylnitrite (365 mg, 3.12 mmol) in DMF (8 mL) at 65° C. was added 2,6-diiodo-4-(trifluoromethyl)aniline (685 mg, 1.66 mmol). The reaction was stirred overnight at rt then poured into 1 N HCl (10 mL) and extracted with methylene chloride. The organic layer was dried over sodium sulfate, filtered, concentrated and the residue was purified on silica (hexanes) to afford a pink solid.

Step 2: 3-(Methoxycarbonyl)-5-(trifluoromethyl)benzoic acid

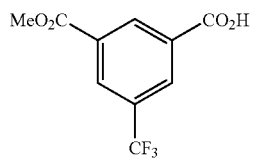

A Parr reactor was charged with 3,5-diiodobenzotrifluoride (450 mg, 1.13 mmol), 1,3-bis(diphenylphosphino)propane (46.6 mg, 0.11 mmol), MeOH (30 mL), and potassium carbonate (313 mg, 2.3 mmol). The reactor was then charged with 80 psi carbon monoxide gas and heated to 100° C. overnight with stirring. The crude reaction mixture was filtered through Celite and concentrated to a purple solid which was redissolved into methylene chloride and washed with water. The aqueous portion was acidified and extracted with methylene chloride, dried over sodium sulfate, and concentrated to afford 3-(methoxycarbonyl)-5-(trifluoromethyl)benzoic acid as a crude solid which was used without further purification.

Step 3: Example 611

3-(Methoxycarbonyl)-5-(trifluoromethyl)benzoic acid (58 mg, 0.234 mmol) HOBT (78 mg, 0.58 mmol), EDC (74 mg, 0.38 mmol), DIPEA (75 mg, 0.58 mmol), and DMF (1 mL) was stirred for 30 min at rt, then (R)-2-amino-1-((S)-4-(4-chlorophenyl)-4-hydroxy-3,3-dimethylpiperidin-1-yl)-3-methylbutan-1-one hydrochloride was added. The reaction was stirred overnight at rt and Example 611 was isolated as a white solid using preparative reverse phase HPLC (36 mg, 11% yield), M+H=569.18.

Example 612

3-((R)-1-((S)-4-(4-Chlorophenyl)-4-hydroxy-3,3-dimethylpiperidin-1-yl)-3-methyl-1-oxobutan-2-ylcarbamoyl)-5-(trifluoromethyl)benzoic acid

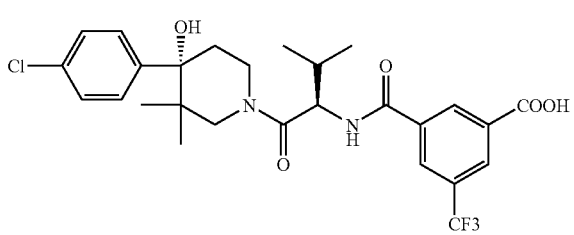

Example 612 was prepared in a similar manner as Example 610. M+H=555.2

Example 613

Methyl-5-((R)-1-((S)-4-(4-chlorophenyl)-4-hydroxy-3,3-dimethylpiperidin-1-yl)-3-methyl-1-oxobutan-2-ylcarbamoyl)-2-methylbenzoate

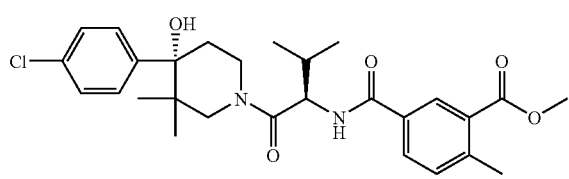

Step 1: 3-(Methoxycarbonyl)-4-methylbenzoic acid

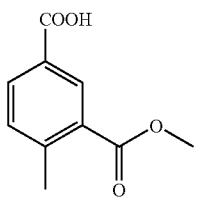

A parr reactor was charged with 3-bromo-4-methylbenzoic acid, MeOH (50 mL), palladium acetate (0.44 g, 1.95 mmol), bis(1,3-diphenylphosphino)propane, and potassium carbonate (4.0 g, 29.3 mmol) was pressurized to 80 psi with carbon monoxide gas. The reaction was maintained at this temperature for 48 h. The reaction was cooled, acidified with 1 N HCl, and extracted with methylene chloride. The organic extracts were dried over sodium sulfate, filtered, concentrated and then purified by reverse phase HPLC to yield the title compound.

Step 2: Example 613

4-Methyl 1-3-(methoxycarbonyl)benzoic acid (32 mg, 0.165 mmol), HOBT (22 mg, 0.165 mmol), EDC (39 mg, 0.25 mmol), DIPEA (50 mg, 0.38 mmol), and DMF (1 mL) was stirred briefly at rt, then (R)-2-amino-1-((S)-4-(4-chlorophenyl)-4-hydroxy-3,3-dimethylpiperidin-1-yl)-3-methylbutan-1-one hydrochloride was added. The reaction was stirred overnight at rt then purified by reverse phase HPLC to yield Example 613 (44.6 mg, 68% yield), M+H=515.35

Example 614

5-((R)-1-((S)-4-(4-Chlorophenyl)-4-hydroxy-3,3-dimethylpiperidin-1-yl)-3-methyl-1-oxobutan-2-ylcarbamoyl)-2-methylbenzoic acid

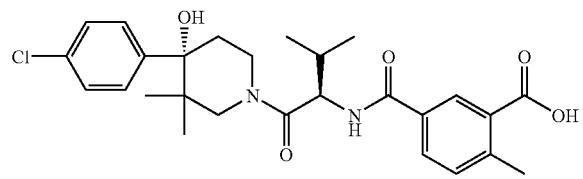

Example 614 was prepared in a similar manner as Example 610 (28.1 mg, 87.5% yield) M+H=501.34.

Example 615

3-((R)-1-((S)-4-(4-Chlorophenyl)-4-hydroxy-3,3-dimethylpiperidin-1-yl)-3-methyl-1-oxobutan-2-ylcarbamoyl)-5-methylbenzoic acid

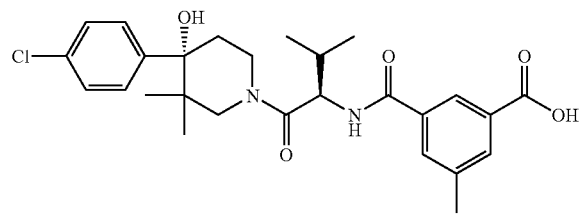

Step 1: 3-(Methoxycarbonyl)-5-methylbenzoic acid

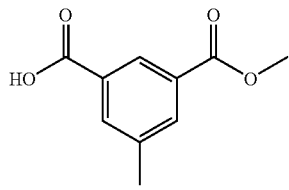

5-Methylisophthalic acid (1.21 g, 6.5 mmol), dichloroethane (20 mL), DMF (3 drops), and thionyl chloride (2.42 g, 20 mmol) was heated to 80° C. for 4 hrs. The reaction was concentrated to dryness and a solution of MeOH (208 mg, 6.5 mmol) was added slowly and the reaction was stirred overnight at rt. 1 N Hydrochloric acid (10 mL) was added and reaction stirred for 1 hr. The pH was adjusted with sat'd sodium bicarbonate (50 mL) and the aqueous solution was extracted with methylene chloride to remove the diester. The aqueous portion was then acidified with 1 N HCl and extracted with methylene chloride/MeOH 95:5. The organic extracts were dried over sodium sulfate, filtered, concentrated, and the product was isolated via preparative reverse-phase HPLC.

Step 2: Methyl-3-((R)-1-((S)-4-(chlorophenyl)-4-hydroxy-3,3-dimethylpiperidin-1-yl)-3-methyl-1-oxobutan-2-ylcarbamoyl)-5-methylbenzoate

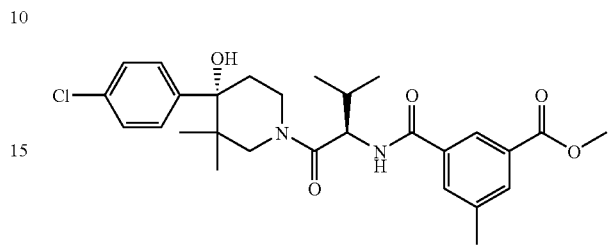

5-Methyl 1-3-(methoxycarbonyl)benzoic acid (35 mg, 0.180 mmol), HOBT (21 mg, 0.156 mmol), EDC (48 mg, 0.31 mmol), DIPEA (81 mg, 0.63 mmol), and chloroform (2 mL) was stirred briefly at rt, then (R)-2-amino-1-((S)-4-(4-chlorophenyl)-4-hydroxy-3,3-dimethylpiperidin-1-yl)-3-methylbutan-1-one hydrochloride was added. Reaction stirred overnight at rt, concentrated and purified via reverse phase HPLC to yield methyl-3-((R)-1-((S)-4-(chlorophenyl)-4-hydroxy-3,3-dimethylpiperidin-1-yl)-3-methyl-1-oxobutan-2-ylcarbamoyl)-5-methylbenzoate.

Step 3: Example 615

Methyl-3-((R)-1-((S)-4-(chlorophenyl)-4-hydroxy-3,3-dimethylpiperidin-1-yl)-3-methyl-1-oxobutan-2-ylcarbamoyl)-5-methylbenzoate (21 mg) was stirred overnight in THF (0.5 mL), MeOH (0.5 mL) and 1 N NaOH (0.5 mL). The reaction acidified with 1 N hydrochloric acid then partitioned between water (10 mL) and methylene chloride (10 mL). The layers were separated and the organic layer was dried over sodium sulfate, filtered, then concentrated to yield Example 615 (18 mg, 90% yield), M+H=501.29.

Example 616

N—((R)-1-((S)-4-(4-Chlorophenyl)-4-fluoro-3,3-dimethylpiperidin-1-yl)-3-methyl-1-oxobutan-2-yl)cyclopentanecarboxamide

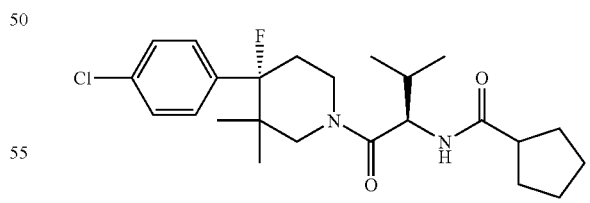

N—((R)-1-((S)-4-(4-Chlorophenyl)-4-hydroxy-3,3-dimethylpiperidin-1-yl)-3-methyl-1-oxobutan-2-yl)cyclopentanecarboxamide (30 mg, 0.069 mmol) was dissolved into methylene chloride (2 mL) then cooled to −78° C. and DAST (13.3 mg, 0.083 mmol) was added. The reaction was stirred overnight at rt. HPLC showed some starting material present and 2 additional drops of DAST was added at rt. Some starting material was still present and 2 additional drops DAST was added and HPLC then showed the reaction was complete.

The reaction was concentrated and Example 616 was isolated as a white solid by preparative reverse-phase HPLC (15.3 mg, 51% yield), M+H=437.38.

Example 617

(R)—N-(1-(4-(4-Chlorophenyl)-4-flouropiperidin-1-yl)-3-methyl-1-oxobutan-2-yl)cyclopentanecarboxamide

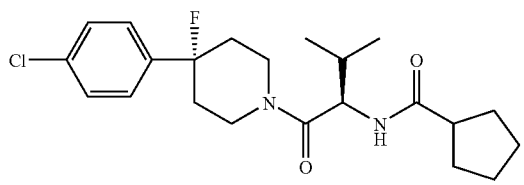

(R)—N-(1-(4-(4-chlorophenyl)-4-hydroxypiperidin-1-yl)-3-methyl-1-oxobutan-2-yl)cyclopentanecarboxamide was converted to Example 617 using the methods outlined for Example 616. (23.2 mg, 42% yield), M+23=431.36.

Example 618

2-(2-((R)-1-((S)-4-(4-Chlorophenyl)-4-hydroxy-3,3-dimethylpiperidin-1-yl)-3-methyl-1-oxobutan-2-ylamino)thiazol-4-yl)-N-isopropylacetamide

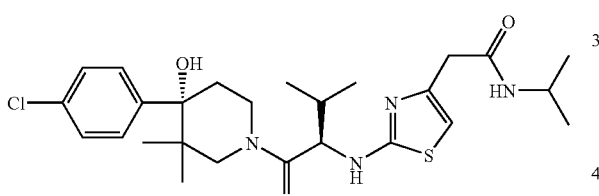

Step 1: 2-(2-((R)-1-((S)-4-(4-Chlorophenyl)-4-hydroxy-3,3-dimethylpiperidin-1-yl)-3-methyl-1-oxobutan-2-ylamino)thiazol-4-yl)acetic acid

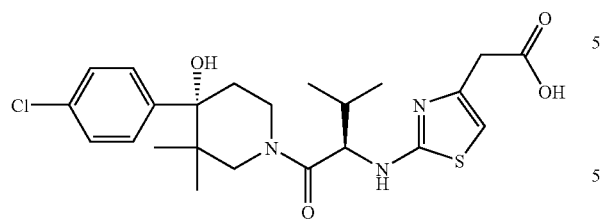

Methyl 2-(2-((R)-1-((S)-4-(4-chlorophenyl)-4-hydroxy-3,3-dimethylpiperidin-1-yl)-3-methyl-1-oxobutan-2-ylamino)thiazol-4-yl)acetate (Example 520, 356 mg, 0.895 mmol) was stirred overnight in 1 N sodium hydroxide (2 mL) and ethanol (15 mL). The reaction was neutralized to pH 7 with 0.1N hydrochloric acid and the product was extracted with EtOAc:MeOH 95:5. The organic extracts were dried over sodium sulfate, filtered, and concentrated to yield the title compound (180 mg) which was used without further purification.

Step 2: Example 618

2-(2-((R)-1-((S)-4-(4-chlorophenyl)-4-hydroxy-3,3-dimethylpiperidin-1-yl)-3-methyl-1-oxobutan-2-ylamino)thiazol-4-yl)acidic acid (30 mg, 0.062 mmol), DMF (1 mL), HOBT (8.4 mg, 0.06 mmol), EDC (18 mg, 0.094 mmol), isopropylamine hydrochloride (10 mg, 0.125 mmol), and DIPEA (32 mg, 0.25 mmol) was stirred 72 hrs at rt. Example 618 was isolated directly by reverse phase HPLC (3.4 mg, 10.4% yield), M+H=521.29.

Example 619

2-(2-((R)-1-((S)-4-(4-Chlorophenyl)-4-hydroxy-3,3-dimethylpiperidin-1-yl)-3-methyl-1-oxobutan-2-ylamino)thiazol-4-yl)-N-cyclopentylacetamide

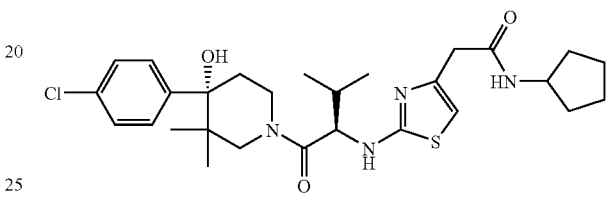

Example 619 was prepared in a similar fashion as Example 618 (2.9 mg, 8.5% yield), M+H=547.34.

Example 620

(R)-1-((S)-4-(4-Chlorophenyl)-4-hydroxy-3,3-dimethylpiperidin-1-yl)-3-methyl-2-(4-(2-morpholino-2-oxoethyl)thiazol-2-ylamino)butan-1-one

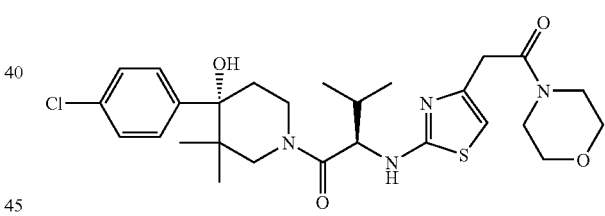

Example 620 was prepared in a similar fashion as Example 618 (36.3 mg, 62% yield), M+H=549.

Example 621

(R)-1-((S)-4-(4-chlorophenyl)-4-hydroxy-3,3-dimethylpiperidin-1-yl)-3-methyl-2-(4-methylthiazol-2-ylamino)butan-1-one

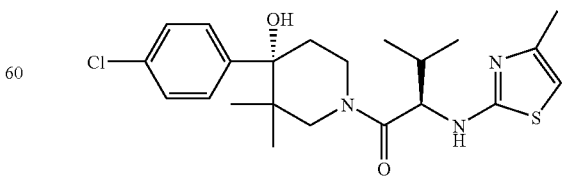

1-((R)-1-((S)-4-(4-chlorophenyl)-4-hydroxy-3,3-dimethylpiperidin-1-yl)-3-methyl-1-oxobutan-2-)thiourea (50 mg, 0.126 mmol), ethanol (5 mL), and 1-chloropropan-2-one was heated at 80° C. for 4 hrs. The reaction was cooled and the product isolated by reverse phase preparative HPLC to afford Example 621 as a white solid (36.5 mg, 66.6% yield) M+H=436.2.

Example 622

(R)-1-((S)-4-(4-Chlorophenyl)-4-hydroxy-3,3-dimethylpiperidin-1-yl)-3-methyl-2-(4-(trifluoromethyl)thiazol-2-ylamino)butan-1-one

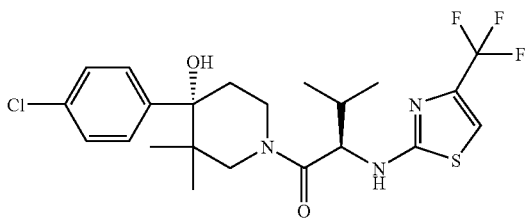

1-((R)-1-((S)-4-(4-chlorophenyl)-4-hydroxy-3,3-dimethylpiperidin-1-yl)-3-methyl-1-oxobutan-2-)thiourea (55 mg, 0.138 mmol), ethanol (6 mL), and 3-chloro-1,1,1-trifluoropropan-2-one (24.3 mg, 0.166 mmol) was stirred at 80° C. for 3 days. The reaction was cooled and the product isolated by reverse phase preparative HPLC to afford Example 622 as a white solid (14.3 mg, 21% yield) M+H=490.12.

Example 623

N—((R)-1-((S)-4-(4-Chlorophenyl)-4-hydroxy-3,3-dimethylpiperidin-1-yl)-3-methyl-1-oxobutan-2-yl)-6-isopropoxynicotinamide

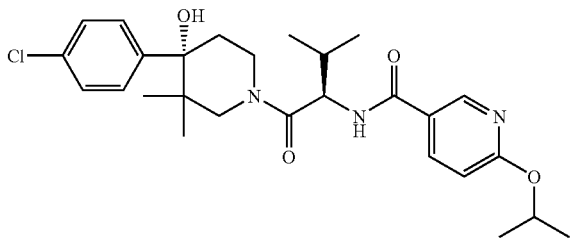

Step 1: 6-Chloro-N—((R)-1-((S)-4-(chlorophenyl)-4-hydroxy-3,3-dimethylpiperidin-1-yl)-3-methyl-1-oxobutan-2-yl)nicotinamide

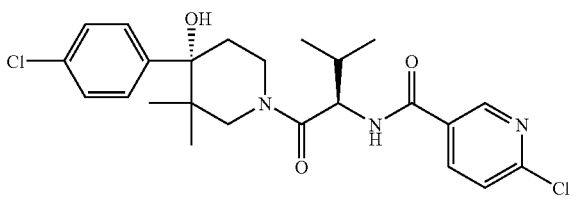

(R)-2-amino-1-((S)-4-(4-chlorophenyl)-4-hydroxy-3,3-dimethylpiperidin-1-yl)-3-methylbutan-1-one hydrochloride (338 mg, 0.90 mmol), THF (5 mL), and 6-chloronicotinoyl chloride (132 mg, 0.75 mmol) was cooled to 0° C. and DIPEA (233 mg, 1.80 mmol) was added dropwise. The reaction was allowed to warm to rt and stir overnight. The solvent was then removed and residue was partitioned between methylene chloride and saturated sodium bicarbonate. The layers were separated and the organic extracts were dried, filtered, and concentrated to yield 6-chloro-N—((R)-1-((S)-4-(chlorophenyl)-4-hydroxy-3,3-dimethylpiperidin-1-yl)-3-methyl-1-oxobutan-2-yl)nicotinamide as a white solid.

Step 2: Example 623

A microwave vial was charged with 6-chloro-N—((R)-1-((S)-4-(chlorophenyl)-4-hydroxy-3,3-dimethylpiperidin-1-yl)-3-methyl-1-oxobutan-2-yl)nicotinamide (18 mg, 0.038 mmol), 2-propanol (1 mL), and freshly prepared sodium propan-2-olate (0.5 mL, 0.083 mmol). The vial was sealed and heated for 30 minutes at 150° C. The product was isolated visa preparative reverse phase HPLC to give Example 623 (13.2 mg, 69.9% yield) as a white solid. M+H=502.41

Example 624

5-Chloro-N—((R)-1-((S)-4-(4-chlorophenyl)-4-hydroxy-3,3-dimethylpiperidin-1-yl)-3-methyl-1-oxobutan-2-yl)-6-phenoxynicotinamide

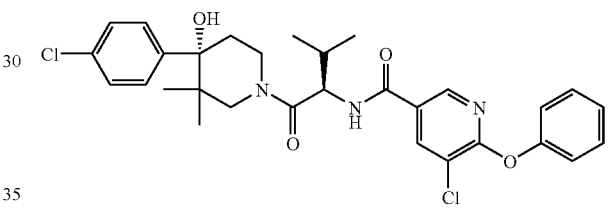

Step 1: 5,6-Dichloro-N—((R)-1-((S)-4-(4-chlorophenyl)-4-hydroxy-3,3-dimethylpiperidin-1-yl)-3-methyl-1-oxobutan-2-yl)nicotinamide

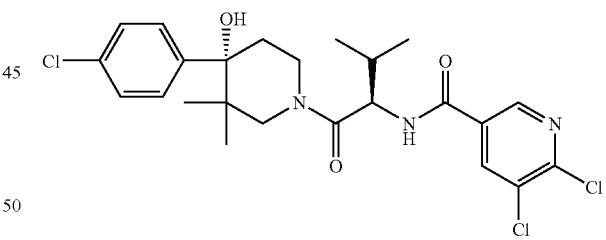

(R)-1-((S)-4-(4-Chlorophenyl)-4-hydroxy-3,3-dimethylpiperidin-1-yl)-3-methyl-1-oxobutan-2-aminium chloride (150 mg, 0.40 mmol), THF (10 mL), and 5,6-dichloronicotinoyl chloride (101 mg, 0.48 mmol) was stirred together at rt then DIPEA (114 mg, 0.88 mmol) was added dropwise. The reaction was stirred overnight, then the solvent was removed and residue was partitioned between EtOAc and 1N sodium hydroxide. The organic extracts were dried, filtered, and concentrated to yield 5,6-dichloro-N—((R)-1-((S)-4-(4-chlorophenyl)-4-hydroxy-3,3-dimethylpiperidin-1-yl)-3-methyl-1-oxobutan-2-yl)nicotinamide as a white solid.

Step 2: Example 624

5,6-Dichloro-N—((R)-1-((S)-4-(4-chlorophenyl)-4-hydroxy-3,3-dimethylpiperidin-1-yl)-3-methyl-1-oxobutan-2- yl)nicotinamide (35 mg, 0.068 mmol), 0.5 mL DMF, and sodium phenolate (9.51 mg, 0.08 mmol) was heated for 1 hr at 120° C. Example 624 was isolated as a white solid by preparative reverse phase HPLC (13.7 mg, 35.2% yield), M+H=570.07.

Example 625

5-Chloro-N—((R)-1-((S)-4-(4-chlorophenyl)-4-hydroxy-3,3-dimethylpiperidin-1-yl)-3-methyl-1-oxobutan-2-yl)-6-methoxynicotinamide

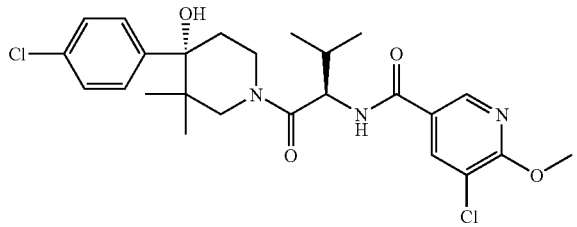

Example 625 was prepared in a similar manner as Example 624. (25.6 mg, 51.6% yield), M+H=508.05.

Example 626

N—((R)-1-((S)-4-(4-Chlorophenyl)-4-hydroxy-3,3-dimethylpiperidin-1-yl)-3-methyl-1-oxobutan-2-yl)-6-(methylamino)nicotinamide

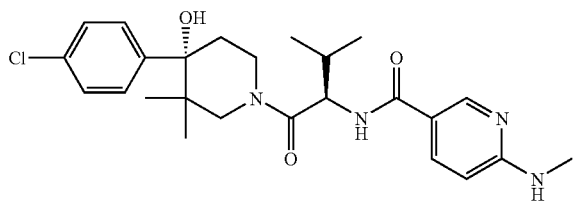

A microwave vial was charged with 6-chloro-N—((R)-1-((S)-4-(chlorophenyl)-4-hydroxy-3,3-dimethylpiperidin-1-yl)-3-methyl-1-oxobutan-2-yl)nicotinamide (25 mg, 0.05 mmol), ethanol (1 mL), methylamine hydrochloride (7.06 mg, 0.105 mmol), and DIPEA (40.5 mg, 0.31 mmol). The vial was sealed and heated in a microwave reactor for 6 hrs at 150° C. Example 626 was isolated as a white solid by preparative reverse phase HPLC (15.1 mg, 61.1% yield), M+H=473.33.

Example 627

N—((R)-1-((S)-4-(4-Chlorophenyl)-4-hydroxy-3,3-dimethylpiperidin-1-yl)-1-oxobutan-2-yl)cyclopentanecarboxamide

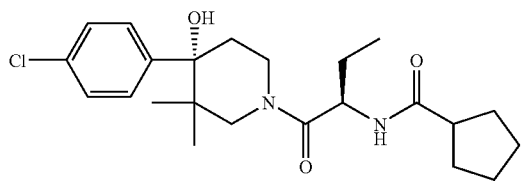

Step 1: tert-Butyl (R)-1-((S)-4-(4-Chlorophenyl)-4-hydroxy-3,3-dimethylpiperidin-1-yl)-1-oxobutan-2-ylcarbamate

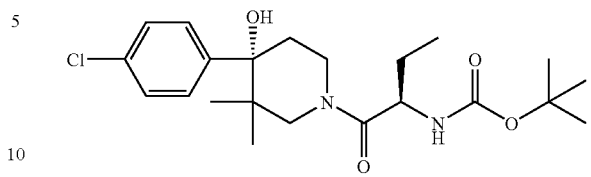

(S)-4-(4-chlorophenyl)-3,3-dimethylpiperidin-4-ol (100 mg, 0.42 mmol), (R)-2-(tert-butoxycarbonylamino)butanoic acid (102 mg, 0.50 mmol), HOBT (68 mg, 0.5 mmol), EDC (155 mg, 1 mmol), DIPEA (129 mg, 1 mmol), and chloroform (2 mL) was stirred overnight at rt. The reaction mixture was then partitioned between methylene chloride and saturated sodium bicarbonate solution, the layers were separated and the organic extracts were dried over magnesium sulfate, filtered, and concentrated to yield the product, which was used in next step without further purification.

Step 2: (R)-1-((S)-4-(4-chlorophenyl)-4-hydroxy-3,3-dimethylpiperidin-1-yl)-1-oxobutan-2-aminium chloride

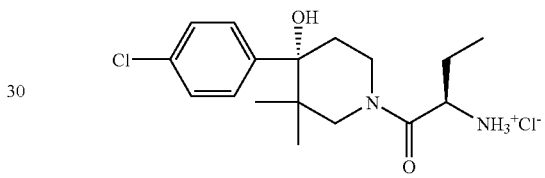

tert-Butyl (R)-1-((S)-4-(4-chlorophenyl)-4-hydroxy-3,3-dimethylpiperidin-1-yl)-1-oxobutan-2-ylcarbamate (200 mg, 0.46 mmol) and 4 N Hydrochloric acid in dioxane (8 mL) was stirred at rt for 2 hrs. The reaction mixture was then concentrated and dried under high vacuum to yield the product, which was used in next step without further purification.

Step 3: Example 627

(R)-1-((S)-4-(4-chlorophenyl)-4-hydroxy-3,3-dimethylpiperidin-1-yl)-1-oxobutan-2-aminium chloride (52.4 mg, 0.14 mmol), cyclopentane carbonylchloride (20 mg, 0.17 mmol), THF (5 mL), and DIPEA (135 mg, 1.1 mmol) were stirred overnight at rt. The reaction was concentrated, and Example 627 was isolated as a white solid using preparative reverse-phase HPLC (30.75 mg, 52.3% yield), M+H=421.31.

Example 628

3-((R)-1-((S)-4-(4-Chlorophenyl)-4-hydroxy-3,3-dimethylpiperidin-1-yl)-1-oxobutan-2-ylcarbamoyl)benzoic acid

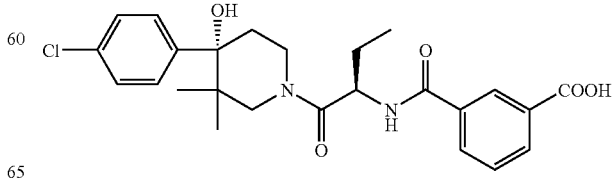

Step 1: Methyl 3-((R)-1-((S)-4-(4-chlorophenyl)-4-hydroxy-3,3-dimethylpiperidin-1-yl)-1-oxobutan-2-ylcarbamoyl)benzoate

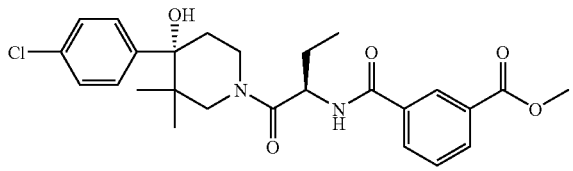

(R)-1-((S)-4-(4-chlorophenyl)-4-hydroxy-3,3-dimethylpiperidin-1-yl)-1-oxobutan-2-aminium chloride (52.4 mg, 0.14 mmol), methyl 3-(chlorocarbonyl)benzoate (33 mg, 0.17 mmol), THF (5 mL), and diisopropylethylamine (135 mg, 1.1 mmol) were stirred overnight at rt. The reaction was concentrated and the product isolated as a white solid using preparative reverse-phase HPLC.

Step 2: Example 628

Methyl 3-((R)-1-((S)-4-(4-chlorophenyl)-4-hydroxy-3,3-dimethylpiperidin-1-yl)-1-oxobutan-2-ylcarbamoyl)benzoate (49 mg, 0.10 mmol), MeOH (1 mL), and 1 N sodium hydroxide (0.6 mL) were stirred for 4 at rt for 4 h, then acidified with 1N hydrochloric acid (1 mL). The product was extracted into methylene chloride. The organic layer was dried over magnesium sulfate, filtered, and concentrated to yield Example 628 as a white solid. (34.0 mg, 72.0% yield), M+H=473.27.

Example 629

N1-((R)-1-((S)-4-(4-Chlorophenyl)-4-hydroxy-3,3-dimethylpiperidin-1-yl)-3-methyl-1-oxobutan-2-yl)isophthalamide

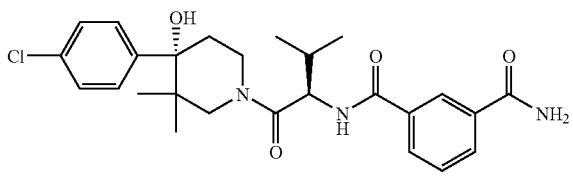

(R)-3-(1-(4-(4-chlorophenyl)-4-hydroxypiperidin-1-yl)-3-methyl-1-oxobutan-2-ylcarbamoyl)benzoic acid (170 mg, 0.35 mmol), DMF (5 mL), HOBT (52 mg, 0.38 mmol), EDC (108 mg, 0.70 mmol), and DIPEA (136 mg, 1.0 mmol) was stirred at rt. Ammonium chloride (8 mg, 0.13 mmol) was added and the reaction stirred overnight. The product was isolated directly via preparative reverse-phase HPLC to give Example 629 (19.0 mg, 73.3% yield) as a white solid, M+H=486.25.

Example 630

2-(3-((R)-1-((S)-4-(4-Chlorophenyl)-4-hydroxy-3,3-dimethylpiperidin-1-yl)-3-methyl-1-oxobutan-2-ylcarbamoyl)benzamido)acetic acid

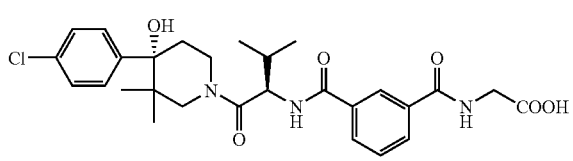

Step 1: Ethyl 2-(3-((R)-1-((S)-4-(4-Chlorophenyl)-4-hydroxy-3,3-dimethylpiperidin-1-yl)-3-methyl-1-oxobutan-2-ylcarbamoyl)benzamido)acetate

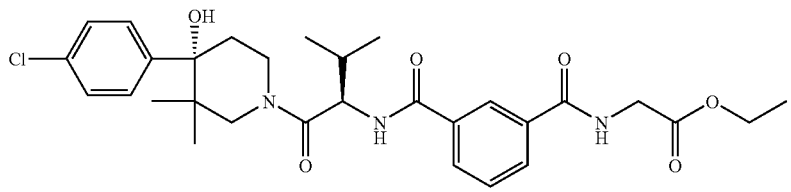

(R)-3-(1-(4-(4-Chlorophenyl)-4-hydroxypiperidin-1-yl)-3-methyl-1-oxobutan-2-ylcarbamoyl)benzoic acid (30.5 mg, 0.06 mmol)), chloroform (1 mL), HOBT (9 mg, 0.06 mmol), EDC (20 mg, 0.13 mmol), ethylamino acetate hydrochloride, and DIPEA (32 mg, 0.25 mmol) was stirred at rt for 18 h. The product was purified directly via preparative reverse-phase HPLC.

Step 2: Example 630

Ethyl 2-(3-((R)-1-((S)-4-(4-chlorophenyl)-4-hydroxy-3,3-dimethylpiperidin-1-yl)-3-methyl-1-oxobutan-2-ylcarbamoyl)benzamido)acetate was stirred overnight at rt in THF (0.5 mL), MeOH (0.50 mL), and 0.5 mL 1 N sodium hydroxide. The reaction was acidified with 1 N hydrochloric acid (1 mL) and product was extracted into methylene chloride. The organic extracts were dried over sodium sulfate, filtered, and concentrated. The product was purified via preparative reverse-phase HPLC to afford Example 630 (3.4 mg, 10.4% yield), as a white solid. M+H=544.24.

Example 631

3-Acetamido-N—((R)-1-((S)-4-(4-chlorophenyl)-4-hydroxy-3,3-dimethylpiperidin-1-yl)-3-methyl-1-oxobutan-2-yl)benzamide

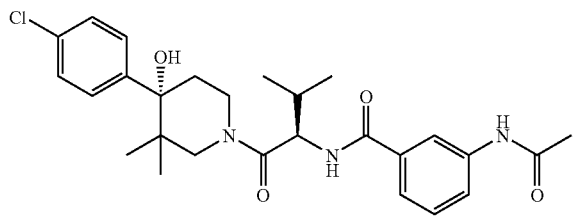

Step 1: N—((R)-1-((S)-4-(4-chlorophenyl)-4-hydroxy-3,3-dimethylpiperidin-1-yl)-3-methyl-1-oxobutan-2-yl)-3-nitrobenzamide

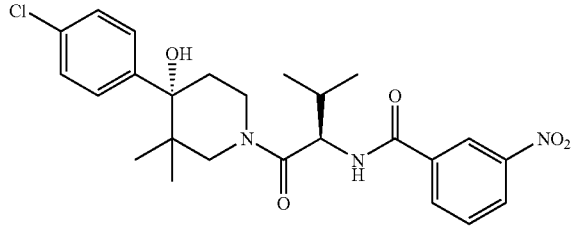

3-Nitrobenzoyl chloride (112 mg, 0.67 mmol) was added into a mixture of (R)-2-amino-1-((S)-4-(4-chlorophenyl)-4-hydroxy-3,3-dimethylpiperidin-1-yl)-3-methylbutan-1-one hydrochloride (250 mg, 0.668 mmol) and DIPEA (240 µL, 1.35 mmol) in dichloromethane (2 mL). The mixture was stirred at rt for 1 h. The reaction was quenched with aq NaHCO₃, extracted with dichloromethane, dried over Na₂SO₄, filtered and concentrated. The residue was purified by a flash column using 30% EtOAc in hexanes as an eluent to give N—((R)-1-((S)-4-(4-chlorophenyl)-4-hydroxy-3,3-dimethylpiperidin-1-yl)-3-methyl-1-oxobutan-2-yl)-2-nitrobenzamide (287 mg) as a yellow solid.

Step 2: 3-Amino-N—((R)-1-((S)-4-(4-chlorophenyl)-4-hydroxy-3,3-dimethylpiperidin-1-yl)-3-methyl-1-oxobutan-2-yl)benzamide

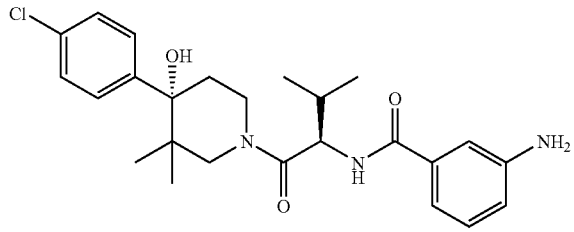

To a solution of N—((R)-1-((S)-4-(4-chlorophenyl)-4-hydroxy-3,3-dimethylpiperidin-1-yl)-3-methyl-1-oxobutan-2-yl)-2-nitrobenzamide (287 mg) in methanol (10 mL), was added Pd/C (5%, 10% mmol). The mixture was degassed and charged with hydrogen for 3 h. The reaction was filtered and rinsed with methanol then EtOAc. The filtrate was concentrated to give a mixture of 3-amino-N—((R)-1-((S)-4-(4-chlorophenyl)-4-hydroxy-3,3-dimethylpiperidin-1-yl)-3-methyl-1-oxobutan-2-yl)benzamide and 3-amino-N—((R)-1-((S)-4-hydroxy-3,3-dimethyl-4-phenylpiperidin-1-yl)-3-methyl-1-oxobutan-2-yl)benzamide (213 mg).

Step 3: Example 631

To a mixture of 3-amino-N—((R)-1-((S)-4-(4-chlorophenyl)-4-hydroxy-3,3-dimethylpiperidin-1-yl)-3-methyl-1-oxobutan-2-yl)benzamide from Step 2 (30 mg, 0.068 mmol) in dichloromethane (0.5 mL) was added acetyl chloride (15 µL) and DIPEA (15 µL). The mixture was stirred at rt for 1 h and concentrated. The residue was purified by Prep-HPLC to give Example 631 (12 mg) as a yellow solid. MS found 500.2 (M+).

Example 632

6-Acetamido-N—((R)-1-((S)-4-(4-chlorophenyl)-4-hydroxy-3,3-dimethylpiperidin-1-yl)-3-methyl-1-oxobutan-2-yl)picolinamide, TFA salt

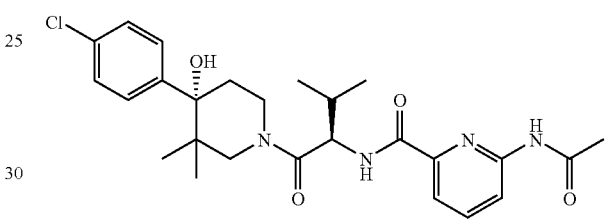

Step 1: 6-Amino-N—((R)-1-((S)-4-(4-chlorophenyl)-4-hydroxy-3,3-dimethylpiperidin-1-yl)-3-methyl-1-oxobutan-2-yl)picolinamide

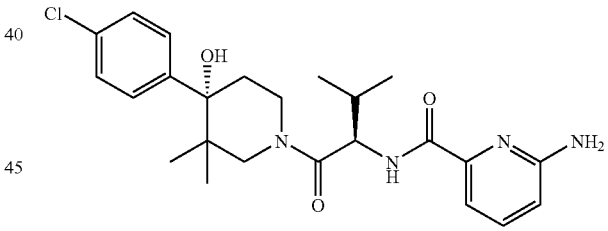

To a suspension of 6-aminopicolinic acid (33 mg, 0.24 mmol) in DMF (2 mL) was added EDC (45.9 mg, 0.24 mmol), HOBt (32.3 mg, 0.24 mmol). The mixture was stirred at rt for 0.5 h, then was added DIPEA (0.083 mL, 0.48 mmol) and (R)-2-amino-1-((S)-4-(4-chlorophenyl)-4-hydroxy-3,3-dimethylpiperidin-1-yl)-3-methylbutan-1-one hydrochloride (90 mg, 0.239 mmol). The mixture was stirred at rt overnight. The reaction was quenched with NaHCO₃ (aq) and stirred at rt for 1 h, extracted by EtOAc, washed with brine and dried over Na₂SO₄. After concentrating in vacuo, the residue was triturated with CH₂Cl₂ and filtered to give a yellow solid as 6-amino-N—((R)-1-((S)-4-(4-chlorophenyl)-4-hydroxy-3,3-dimethylpiperidin-1-yl)-3-methyl-1-oxobutan-2-yl)picolinamide (86 mg, 0.187 mmol, 78% yield).

Step 2: Example 632

To a mixture of 6-amino-N—((R)-1-((S)-4-(4-chlorophenyl)-4-hydroxy-3,3-dimethylpiperidin-1-yl)-3-methyl-1-oxobutan-2-yl)picolinamide (18 mg, 0.039 mmol) and DIPEA (7.50 μL, 0.043 mmol) in CH₂Cl₂ (1 mL), was added acetyl chloride (3.08 mg, 0.039 mmol). The mixture was stirred at rt for 1 h, concentrated and purified by Prep-HPLC. The product containing fraction was concentrated and lyophilyzed to give Example 632 (11 mg, 0.022 mmol, 56% yield) as a white TFA salt. MS found 501.2 (M+)

Example 633

4-Chloro-N-((2R,3S)-1-((S)-4-(4-chlorophenyl)-4-hydroxy-3,3-dimethylpiperidin-1-yl)-3-methyl-1-oxopentan-2-yl)benzamide

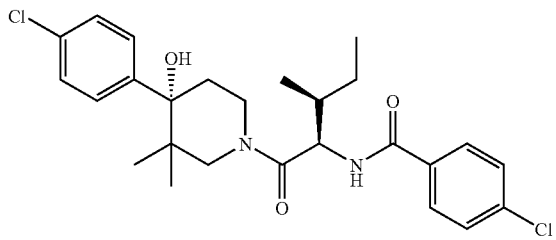

Step 1: tert-butyl (2R,3S)-1-((S)-4-(4-Chlorophenyl)-4-hydroxy-3,3-dimethylpiperidin-1-yl)-3-methyl-1-oxopentan-2-ylcarbamate

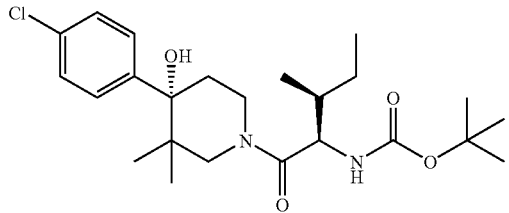

(2R,3S)-2-(tert-butoxycarbonylamino)-3-methylpentanoic acid (197 mg, 0.85 mmol), EDC (162 mg, 0.85 mmol), HOBt (115 mg, 0.85 mmol) was dissolved in chloroform (10 mL). DIPEA (0.15 mL, 0.85 mmol) and (S)-4-(4-chlorophenyl)-3,3-dimethylpiperidin-4-ol (200 mg, 0.834 mmol) were added. The mixture was stirred at rt for 2 h, diluted with dichloromethane and washed with aq NaHCO₃ and brine. The organic layer was dried over Na₂SO₄, filtered and concentrated to give tert-butyl (2R,3S)-1-((S)-4-(4-chlorophenyl)-4-hydroxy-3,3-dimethylpiperidin-1-yl)-3-methyl-1-oxopentan-2-ylcarbamate (327 mg) as a yellow solid.

Step 2: (2R,3S)-2-amino-1-((S)-4-(4-chlorophenyl)-4-hydroxy-3,3-dimethylpiperidin-1-yl)-3-methylpentan-1-one trifluoroacetic acid

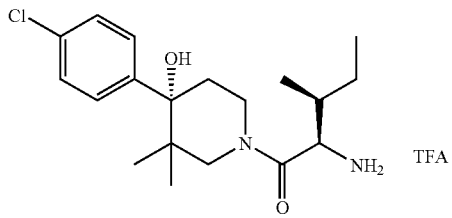

TFA (0.5 mL) was added into a solution of 4-(4-chlorophenyl)-4-hydroxy-3,3-dimethylpiperidin-1-yl)-3-methyl-1-oxopentan-2-ylcarbamate (327 mg) in dichloromethane (2 mL) and the mixture was allowed to stirred at rt for 1 h. The mixture was concentrated and the residue was dried overnight in vacuo to provide (2R,3S)-2-amino-1-((S)-4-(4-chlorophenyl)-4-hydroxy-3,3-dimethylpiperidin-1-yl)-3-methylpentan-1-one trifluoroacetic acid as a light brown oil.

Step 3: Example 633

To a solution of 2R,3S)-2-amino-1-((S)-4-(4-chlorophenyl)-4-hydroxy-3,3-dimethylpiperidin-1-yl)-3-methylpentan-1-one trifluoroacetic acid (35 mg, 0.1 mmol) in dichloromethane (0.5 mL) was added DIPEA (44 μL, 0.25 mmol) and 4-chlorobenzoyl chloride (26 mg, 0.15 mmol). The mixture was stirred at rt for 0.5 h and concentrated. The residue was purified by prep-HPLC to give Example 633 (14 mg, 29% yield). MS found 491.2 (M+H).

Example 634

4-Chloro-N—((R)-1-((S)-4-(4-chlorophenyl)-4-hydroxy-3,3-dimethylpiperidin-1-yl)-4-cyano-1-oxobutan-2-yl)benzamide

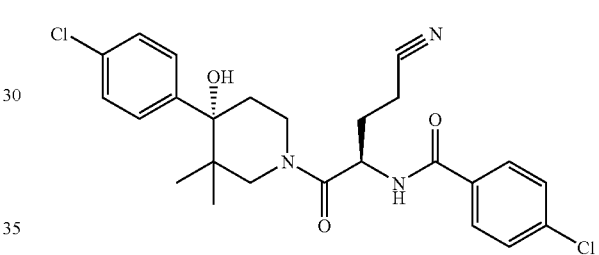

To a solution of (R)-4-amino-5-((S)-4-(4-chlorophenyl)-4-hydroxy-3,3-dimethylpiperidin-1-yl)-5-oxopentanamide (25 mg, 0.068 mmol) in dichloromethane (1 mL) was added DIPEA (30 μL, 0.17 mmoL) and 4-chlorobenzoyl chloride (17 mg, 0.1 mmol). The mixture was stirred at rt for 1 h and concentrated. The residue was purified by Prep-HPLC to give Example 634 (15 mg, 45% yield). MS found 488.2 (M+).

Example 635

N—((R)-1-((S)-4-(4-chlorophenyl)-4-hydroxy-3,3-dimethylpiperidin-1-yl)-3-methyl-1-oxobutan-2-yl)-3-(2-(dimethylamino)acetamido)benzamide

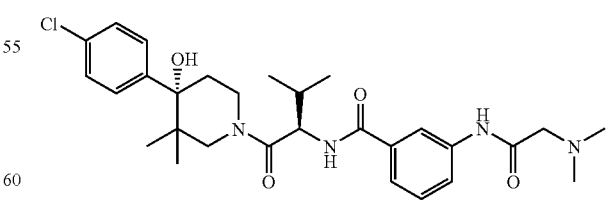

To a solution of 2-(dimethylamino)acetic acid (6.2 mg, 0.06 mmol) in DMF (0.5 mL), was added HOBt (8.1 mg, 0.06 mmol), EDC (12 mg, 0.06 mmol). The mixture was stirred at rt for 1 h, then was added 3-amino-N—((R)-1-((S)-4-(4-chlorophenyl)-4-hydroxy-3,3-dimethylpiperidin-1-yl)-3-methyl- 1-oxobutan-2-yl)benzamide (25 mg, 0.055 mmol). The mixture was then stirred at rt for 2 h and purified via preparative HPLC to give Example 635 (16 mg, 54% yield). MS found 543.3 (M+).

Examples 636A and 636B (S)-1-((R)-2-(3-aminobenzamido)-3-methylbutanoyl)-4-(4-chlorophenyl)-3,3-dimethylpiperidin-4-yl carbamate and N—((R)-1-((S)-4-(4-chlorophenyl)-4-hydroxy-3,3-dimethylpiperidin-1-yl)-3-methyl-1-oxobutan-2-yl)-3-ureidobenzamide

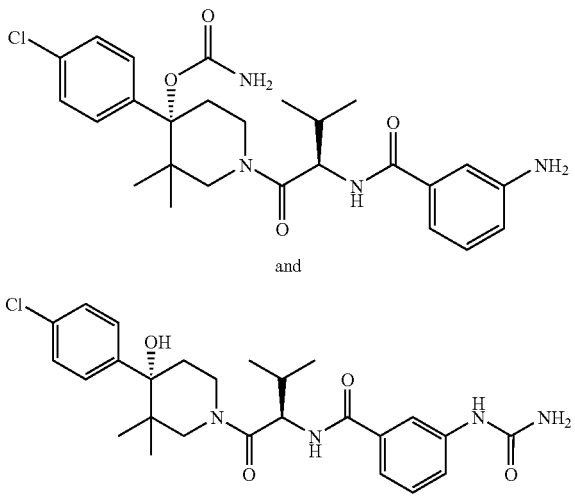

and

To a solution of 3-amino-N—((R)-1-((S)-4-(4-chlorophenyl)-4-hydroxy-3,3-dimethylpiperidin-1-yl)-3-methyl-1-oxobutan-2-yl)benzamide (23 mg, 0.05 mmol) in HOAc (0.5 mL), was added NaOCN (4 mg, 6 mmol). The mixture was stirred at rt for 3 h then concentrated. The residue was added aq NaHCO₃ and extracted into EtOAc. The organic extracts were dried over Na₂SO₄, filtered and concentrated. The residue was purified via HPLC to give Example 636A (6 mg), MS found 501.2 (M+H) and Example 636B (4 mg) MS found 500.3 (M+).

Example 637

(R)—N-(1-(4-(4-chlorophenyl)-4-cyanopiperidin-1-yl)-3-methyl-1-oxobutan-2-yl)benzamide

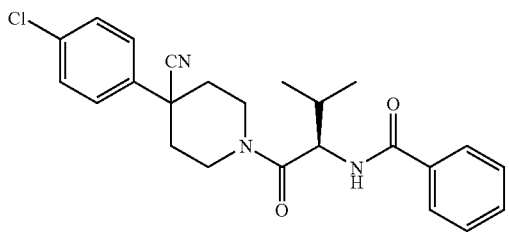

Step 1: (R)-methyl 1-(2-amino-3-methylbutanoyl)-4-(4-chlorophenyl)piperidine-4-carboxylate, TFA salt

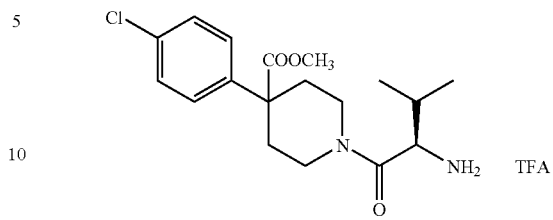

To a solution of (S)-3-(tert-butoxycarbonylamino)-4-methylpentanoic acid (279 mg, 1.21 mmol) in CHCl₃ (5 mL) was added EDC (231 mg, 1.205 mmol), HOBt (0.219 mL, 1.21 mmol) and methyl 4-(4-chlorophenyl)piperidine-4-carboxylate (279 mg). The mixture was stirred at rt overnight. The reaction was then quenched with aq NaHCO₃ and extracted by CH₂Cl₂. The organic extracts were washed with 0.5N HCl, brine, then dried over Na₂SO₄ and concentrated to give a yellow oil. The oil was dissolved in CH₂Cl₂ (3 mL) and TFA (1 mL) was added. The mixture was stirred at rt for 3 h and concentrated to give (R)-methyl 1-(2-amino-3-methylbutanoyl)-4-(4-chlorophenyl)piperidine-4-carboxylate, TFA salt (432 mg, 0.960 mmol, 88% yield).

Step 2: (R)-methyl 1-(2-benzamido-3-methylbutanoyl)-4-(4-chlorophenyl)piperidine-4-carboxylate

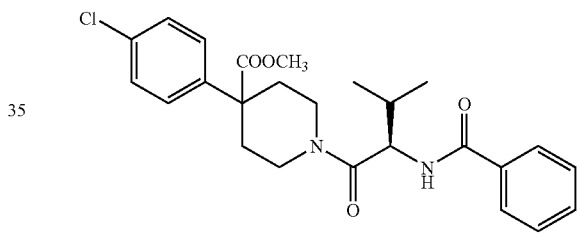

To a solution of (R)-methyl 1-(2-amino-3-methylbutanoyl)-4-(4-chlorophenyl)piperidine-4-carboxylate (396 mg, 1.123 mmol) and benzoyl chloride (0.139 ml, 1.2 mmol) in CH₂Cl₂ (5 mL) was added N-ethyl-N-isopropylpropan-2-amine (0.401 mL, 2.3 mmol). The mixture was stirred for 1 h at rt. The reaction was quenched with NaHCO₃ (aq), extracted with dichloromethane, dried over Na₂SO₄ and concentrated. The residue was purified via column chromatography (20% EtOAc/heptane) to give (R)-methyl 1-(2-benzamido-3-methylbutanoyl)-4-(4-chlorophenyl)piperidine-4-carboxylate (467 mg, 91% yield) as a yellow solid.

Step 3

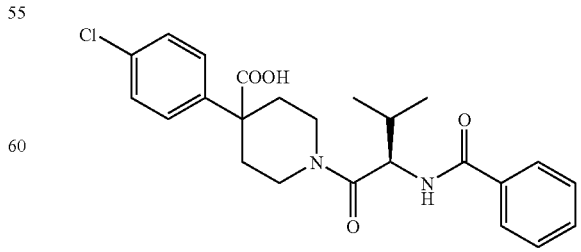

To a solution of (R)-methyl 1-(2-benzamido-3-methylbutanoyl)-4-(4-chlorophenyl)piperidine-4-carboxylate (467 mg, 0.99 mmol) in THF (5 mL) was added aq NaOH (625 mg, 2.5 mmol, 10%). The mixture was stirred at rt for 4 h. The reaction was quenched with HCl (2N) to pH=3, extracted into EtOAc then dried over $Na_2SO_4$ to give the desired product (451 mg, 96% yield) as a yellow solid.

Step 4

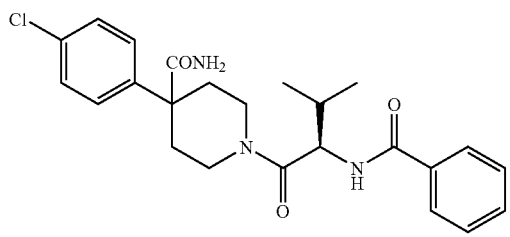

To a solution of the product of Step 3 (20 mg, 0.045 mmol) in DMF (200 μL), was added EDC (7.71 mg, 0.050 mmol) and HOBt (6.71 mg, 0.050 mmol). The reaction was stirred at rt for 0.5 h and aq. $NH_4OH$ (100 μL) was added. The mixture was stirred at rt for 0.5 h, quenched with water (2 mL), stirred at rt for 0.5 h and filtered and purified by Prep-HPLC to give the desired product (10 mg, 0.023 mmol, 50.1% yield).

Step 5: Example 637

To a solution of the product of Step 4 (30 mg, 0.068 mmol) and pyridine (11 μL, 0.136 mmol) in THF (4 mL) at 0, was added 2,2,2-trifluoroacetic anhydride (0.014 mL, 0.102 mmol). The mixture was stirred at 0° C. for 2 h, then at rt for 2 h. The reaction was quenched with $NaHCO_3$, extracted into EtOAc. The organic extracts were washed brine, concentrated, and the residue was purified by Prep-HPLC to give Example 637 (19 mg, 0.045 mmol, 66.0% yield). MS found 424.3 (M+).

Example 638

N—((R)-1-((S)-4-(4-chlorophenyl)-4-hydroxy-3,3-dimethylpiperidin-1-yl)-3-methyl-1-oxobutan-2-yl)-2-ethoxyacetamide

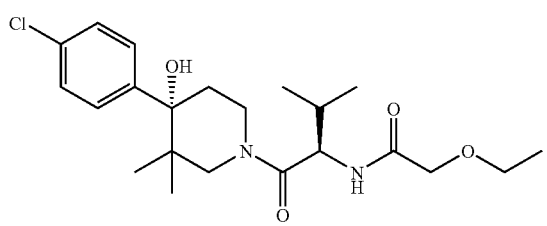

To ethanol (2 mL), was added sodium hydride (14.4 mg, 0.36 mmol). The mixture was stirred at rt for 15 min. The mixture was then added 2-chloro-N—((R)-1-((S)-4-(4-chlorophenyl)-4-hydroxy-3,3-dimethylpiperidin-1-yl)-3-methyl-1-oxobutan-2-yl)acetamide (30 mg, 0.072 mmol) and then heated at 120° C. for 30 min. The reaction was concentrated and purified by Prep-HPLC to give Example 638 (18 mg, 59% yield). MS found 425.2 (M+)

Example 639

N—((R)-1-((S)-4-(4-chlorophenyl)-4-hydroxy-3,3-dimethylpiperidin-1-yl)-3-methyl-1-oxobutan-2-yl)-2-(1H-pyrazol-1-yl)acetamide

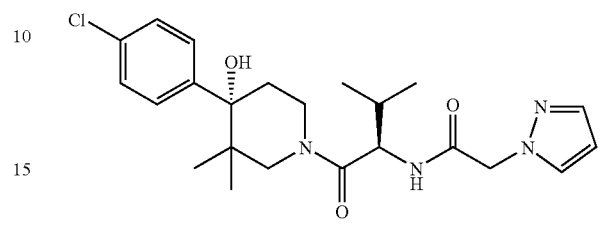

To a solution of 2-chloro-N—((R)-1-((S)-4-(4-chlorophenyl)-4-hydroxy-3,3-dimethylpiperidin-1-yl)-3-methyl-1-oxobutan-2-yl)acetamide (30 mg, 0.072 mmol) and 1H-pyrazole (50 μL) in acetonitrile (1 mL), was added $K_2CO_3$ (13.8 mg, 0.1 mmol). The reaction was heated at 120° C. for 1 h, filtered, and purified by prep-HPLC to give Example 639 (12 mg, 38% yield). MS found 447.2 (M+)

Example 640

2-Acetamido-N—((R)-1-((S)-4-(4-chlorophenyl)-4-hydroxy-3,3-dimethylpiperidin-1-yl)-3-methyl-1-oxobutan-2-yl)acetamide

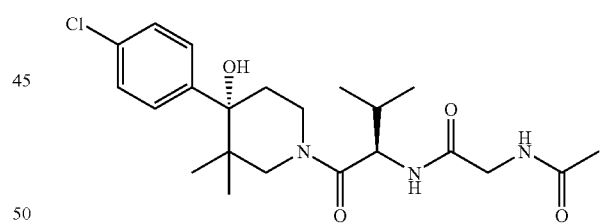

To a mixture of 2-acetamidoacetic acid (7.55 mg, 0.064 mmol) in DMF (500 μL), was added HOBt (8.71 mg, 0.064 mmol) and EDCI (12.38 mg, 0.064 mmol). The mixture was stirred at rt for 0.5 h, added (R)-2-amino-1-((S)-4-(4-chlorophenyl)-4-hydroxy-3,3-dimethylpiperidin-1-yl)-3-methylbutan-1-one hydrochloride (22 mg, 0.059 mmol) and DIPEA (11.21 μL, 0.064 mmol), then stirred at rt for 2 h. The reaction was purified by prep-HPLC to give Example 640 (19 mg, 0.043 mmol, 74.0% yield) as a white solid. MS found 438.3 (M+)

Example 641

Ethyl 5-((R)-1-((S)-4-(4-chlorophenyl)-4-hydroxy-3,3-dimethylpiperidin-1-yl)-3-methyl-1-oxobutan-2-ylamino)-1H-pyrazole-3-carboxylate

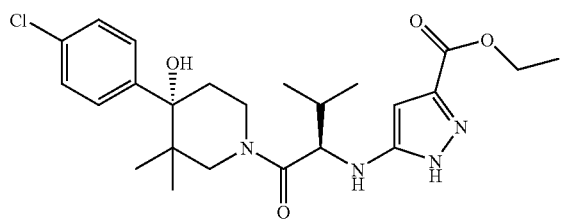

Step 1: N—((R)-1-((S)-4-(4-chlorophenyl)-4-hydroxy-3,3-dimethylpiperidin-1-yl)-3-methyl-1-oxobutan-2-yl)formamide

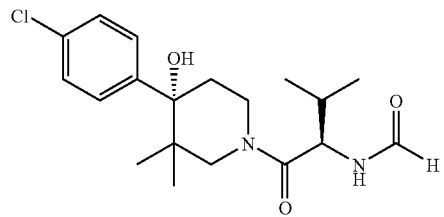

To a solution of (R)-2-amino-1-((S)-4-(4-chlorophenyl)-4-hydroxy-3,3-dimethylpiperidin-1-yl)-3-methylbutan-1-one hydrochloride (111 mg, 0.296 mmol), 2-chloro-4,6-dimethoxy-1,3,5-triazine (57.1 mg, 0.325 mmol), formic acid (0.012 mL, 0.325 mmol) and NMM (0.068 mL, 0.62 mmol) $CH_2Cl_2$ (10 mL), was added DMAP (3.61 mg, 0.03 mmol). The mixture was stirred at rt for 3 h. The reaction was filtered and the filtrate was washed with $Na_2CO_3$, 0.5N HCl, and brine. The organic layer was dried over $Na_2SO_4$ and Concentrated to give N—((R)-1-((S)-4-(4-chlorophenyl)-4-hydroxy-3,3-dimethylpiperidin-1-yl)-3-methyl-1-oxobutan-2-yl)formamide (76 mg, 0.207 mmol, 70.0% yield).

Step 2: (R)-1-((S)-4-(4-chlorophenyl)-4-hydroxy-3,3-dimethylpiperidin-1-yl)-2-isocyano-3-methylbutan-1-one

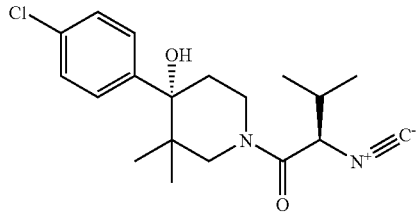

To a mixture of N-((2S)-1-((4R)-4-(4-chlorophenyl)-4-hydroxy-3,3-dimethylcyclohexyl)-3-methyl-1-oxobutan-2-yl)formamide (109 mg, 0.298 mmol) and TEA (0.208 mL, 1.490 mmol) in $CH_2Cl_2$ (5 mL) was added $POCl_3$ (0.027 mL, 0.298 mmol) at 0° C. for 3 h. The mixture was quenched with $NaHCO_3$(aq), extracted into $CH_2Cl_2$, and dried over $Na_2SO_4$. After concentrating, the crude residue was purified via column chromatography ($CH_2Cl_2$) to give (2S)-1-((4R)-4-(4-chlorophenyl)-4-hydroxy-3,3-dimethylcyclohexyl)-2-isocyano-3-methylbutan-1-one (85 mg, 0.244 mmol, 82% yield) as a light yellow oil.

Step 3: Example 641

To a mixture of (2S)-1-((4R)-4-(4-chlorophenyl)-4-hydroxy-3,3-dimethylcyclohexyl)-2-isocyano-3-methylbutan-1-one (90 mg, 0.26 mmol) and (Z)-tert-butyl 2-(3-bromo-1-ethoxy-1-oxopropan-2-ylidene)hydrazinecarboxylate (80 mg, 0.26 mmol) in $CH_2Cl_2$ (10 mL), was added sodium carbonate (137 mg, 1.29 mmol). The mixture was stirred at rt for 18 h. The reaction was quenched with water, extracted into $CH_2Cl_2$ and the combined organic extracts were dried over $Na_2SO_4$ and concentrated. The product dissolved in $CH_2Cl_2$ (2 mL) and then TFA (0.5 mL) was added. The mixture was stirred at rt for 2 h, concentrated and purified via prep-HPLC to give Example 641 (6 mg, 0.013 mmol, 4.87% yield) a yellow solid. MS found 477.2 (M+).

Example 642

(R)-2-(4-((1H-pyrazol-1-yl)methyl)thiazol-2-ylamino)-1-((S)-4-(4-chlorophenyl)-4-hydroxy-3,3-dimethylpiperidin-1-yl)-3-methylbutan-1-one

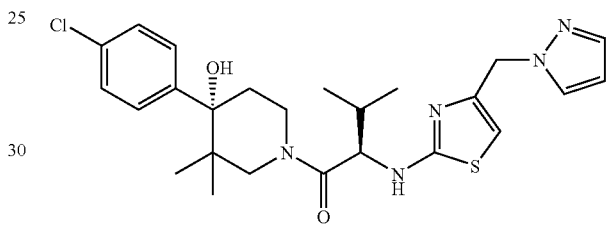

To a solution of (R)-2-(4-(chloromethyl)thiazol-2-ylamino)-1-((S)-4-(4-chlorophenyl)-4-hydroxy-3,3-dimethylpiperidin-1-yl)-3-methylbutan-1-one (18 mg, 0.04 mmol) in Acetonitrile (1 mL) was added 1H-pyrazole (5.21 mg, 0.08 mmol) and potassium carbonate (10.6 mg, 0.08 mmol). The mixture was heated at 80° C. for 1.5 h then cooled. The crude reaction was purified via Prep-HPLC to give Example 642 (9 mg, 0.018 mmol, 46.9% yield) as a yellow solid. MS found 502.2 (M+).

Example 643

2-((R)-1-((S)-4-(4-chlorophenyl)-4-hydroxy-3,3-dimethylpiperidin-1-yl)-3-methyl-1-oxobutan-2-ylamino)-2-oxoethanesulfonic acid

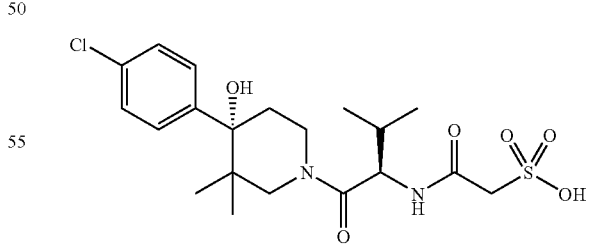

A mixture of 2-chloro-N—((R)-1-((S)-4-(4-chlorophenyl)-4-hydroxy-3,3-dimethylpiperidin-1-yl)-3-methyl-1-oxobutan-2-yl)acetamide (40 mg, 0.096 mmol) and sodium sulfite (60.7 mg, 0.482 mmol) in EtOH and water was heated at 120 c for 1 h. The mixture was filtered, concentrated. Purified via preparative HPLC to give Example 643 (26 mg, 0.056 mmol, 58.6% yield). MS found 461.2 (M+).

Example 644

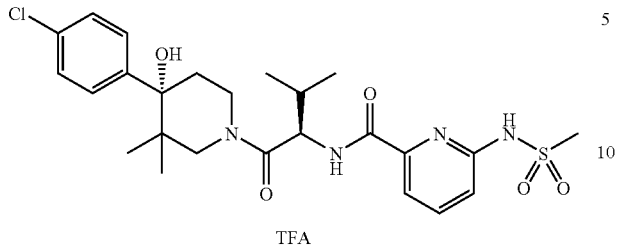

TFA

To a mixture of 6-amino-N—((R)-1-((S)-4-(4-chlorophenyl)-4-hydroxy-3,3-dimethylpiperidin-1-yl)-3-methyl-1-oxobutan-2-yl)picolinamide (18 mg, 0.039 mmol) and DIPEA (10.23 µL, 0.059 mmol) in CH$_2$Cl$_2$ (1 mL) was added methanesulfonic anhydride (10.25 mg, 0.059 mmol). The mixture was stirred at rt for 3 h. The mixture was concentrated and purified by Prep-HPLC to give Example 644 (6 mg, 0.011 mmol, 28.5% yield) as a TFA salt. MS found 537.2 (M+).

Example 645

Methyl 3-((R)-1-((S)-4-(4-chlorophenyl)-4-hydroxy-3,3-dimethylpiperidin-1-yl)-3-methyl-1-oxobutan-2-ylamino)-3-oxopropylcarbamate

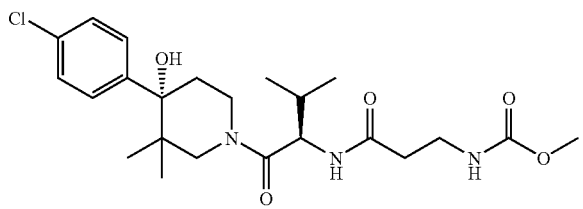

To a mixture of 3-amino-N—((R)-1-((S)-4-(4-chlorophenyl)-4-hydroxy-3,3-dimethylpiperidin-1-yl)-3-methyl-1-oxobutan-2-yl)propanamide (20 mg, 0.049 mmol) and DIPEA (0.021 mL, 0.122 mmol) in CH$_2$Cl$_2$ (1 mL), was added methyl carbonochloridate (6.9 mg, 0.073 mmol). The mixture was stirred at rt for 2 h, concentrated, and the residue was purified by Prep HPLC to give Example 645 (15 mg, 0.032 mmol, 65.7% yield) as a white solid. MS found 468.2 (M+H).

Example 646

N—((R)-1-((S)-4-(4-chlorophenyl)-4-hydroxy-3,3-dimethylpiperidin-1-yl)-3-methyl-1-oxobutan-2-yl)-3-(3-isopropylureido)propanamide

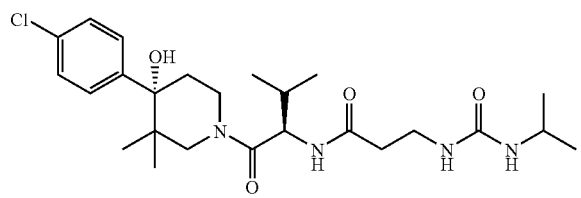

To a mixture of 3-amino-N—((R)-1-((S)-4-(4-chlorophenyl)-4-hydroxy-3,3-dimethylpiperidin-1-yl)-3-methyl-1-oxobutan-2-yl)propanamide (20 mg, 0.049 mmol) and DIPEA (0.021 ml, 0.122 mmol) in CH$_2$Cl$_2$ (1.5 ml), was added 2-isocyanatopropane (2.076 mg, 0.024 mmol). The mixture was stirred at rt for 2 h and then was concentrated. The residue was purified by Prep-HPLC to give Example 646 (21 mg, 0.042 mmol, 87% yield) as a white solid. MS found 495.3 (M+).

Example 647

2-(1H-benzo[d]imidazol-2-ylamino)-N—((R)-1-((S)-4-(4-chlorophenyl)-4-hydroxy-3,3-dimethylpiperidin-1-yl)-3-methyl-1-oxobutan-2-yl)acetamide, TFA

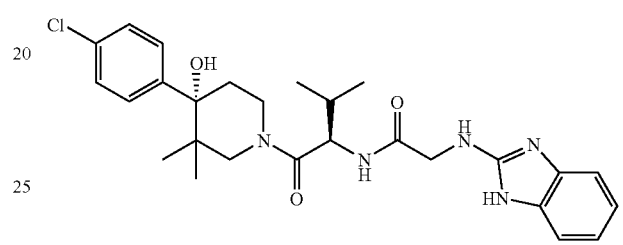

To a mixture of 2-amino-N—((R)-1-((S)-4-(4-chlorophenyl)-4-hydroxy-3,3-dimethylpiperidin-1-yl)-3-methyl-1-oxobutan-2-yl)acetamide, TFA (30 mg, 0.059 mmol) and 2-bromo-1H-benzo[d]imidazole (11.6 mg, 0.07 mmol) in MeOH (1 mL), was added DIPEA (0.011 mL, 0.07 mmol). The mixture was heated at 150° C. for 1 h, cooled and concentrated. The crude residue was purified via prep HPLC to give Example 647 (12 mg, 0.023 mmol, 39.8% yield) as an off-white solid. MS found 512.3 (M+).

Example 648

N-(2-((R)-1-((S)-4-(4-chlorophenyl)-4-hydroxy-3,3-dimethylpiperidin-1-yl)-3-methyl-1-oxobutan-2-ylamino)-2-oxoethyl)cyclopentanecarboxamide

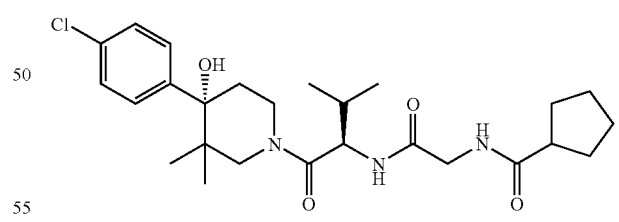

Cyclopentanecarboxylic acid (7.61 mg, 0.067 mmol), HOBt (9.01 mg, 0.067 mmol) and EDCI (12.80 mg, 0.067 mmol) were dissolved in DMF (0.3 ml). The mixture was stirred at rt for 0.5 h, then was added 2-amino-N—((R)-1-((S)-4-(4-chlorophenyl)-4-hydroxy-3,3-dimethylpiperidin-1-yl)-3-methyl-1-oxobutan-2-yl)acetamide, TFA (34 mg, 0.067 mmol) and DIPEA (0.014 ml, 0.080 mmol). The mixture was stirred for 2 h, concentrated, and purified via Prep-HPLC to give Example 648 (9 mg, 0.018 mmol, 27.4% yield). MS found 492.2 (M+).

Example 649

2-((R)-1-((S)-4-(4-chlorophenyl)-4-hydroxy-3,3-dimethylpiperidin-1-yl)-3-methyl-1-oxobutan-2-ylamino)thiazole-5-carboxylic acid

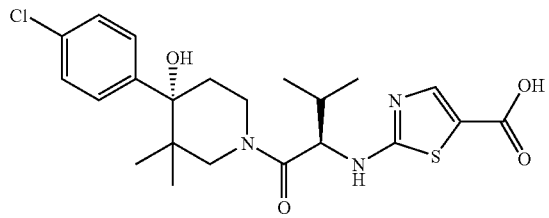

To a solution of methyl 2-((R)-1-((S)-4-(4-chlorophenyl)-4-hydroxy-3,3-dimethylpiperidin-1-yl)-3-methyl-1-oxobutan-2-ylamino)thiazole-5-carboxylate (65 mg, 0.135 mmol) in THF (1 mL) and MeOH (1 mL) was added sodium hydroxide (108 mg, 0.271 mmol). The mixture was stirred at rt for 18 h and then neutralized with 1 N HCl. The resulting solids were filtered and rinsed with water to give Example 649 (60 mg, 0.129 mmol, 95% yield). MS found 466.2 (M+).

Example 650

2-((R)-1-((S)-4-(4-chlorophenyl)-4-hydroxy-3,3-dimethylpiperidin-1-yl)-3-methyl-1-oxobutan-2-ylamino)-N-isopropylthiazole-5-carboxamide

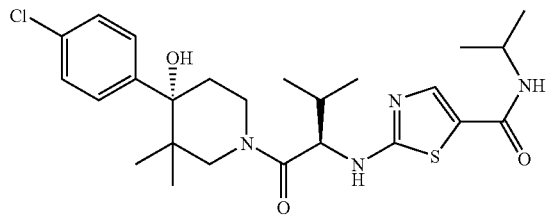

2-((R)-1-((S)-4-(4-chlorophenyl)-4-hydroxy-3,3-dimethylpiperidin-1-yl)-3-methyl-1-oxobutan-2-ylamino)thiazole-5-carboxylic acid (20 mg, 0.043 mmol), HOBt (5.80 mg, 0.043 mmol) and EDCI (10.71 mg, 0.056 mmol) were dissolved in CH$_2$Cl$_2$ (0.5 mL). The mixture was stirred at rt for 0.5 h and added iso-propylamine (3.04 mg, 0.052 mmol) and DIPEA (9.70 µL, 0.056 mmol). The mixture was stirred at rt for 1 h, concentrated, and the residue was purified by Prep-HPLC to give Example 650 (12 mg, 0.024 mmol, 55.1% yield) as an off-white solid. MS found 507.2 (M+).

Example 651

N—((R)-1-((S)-4-(4-chlorophenyl)-4-hydroxy-3,3-dimethylpiperidin-1-yl)-3-methyl-1-oxobutan-2-yl)-2-(cyclopentanecarboxamido)oxazole-4-carboxamide

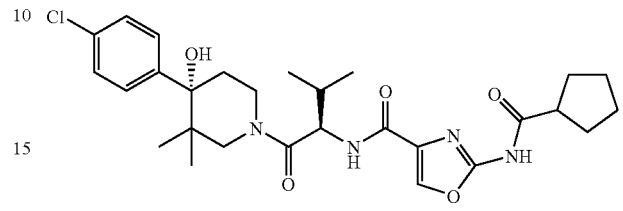

Step 1: Sodium 2-aminooxazole-4-carboxylate

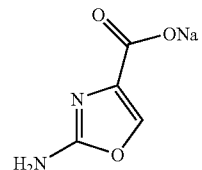

To a solution of ethyl 2-aminooxazole-4-carboxylate (1.56 g, 9.99 mmol) in THF (4 mL) and MeOH (4 mL), was added sodium hydroxide (8.0 g, 20 mmol, 10%) aq solution. The reaction was stirred at rt for 18 h then quenched with 4N HCl to pH=3. The aqueous solution was concentrated to give a yellow solid as a mixed acid and salts. The mixture was washed with EtOAc and MeOH, and the filtrate was collected and concentrated to give sodium 2-aminooxazole-4-carboxylate as a yellow solid.

Step 2: 2-Amino-N—((R)-1-((S)-4-(4-chlorophenyl)-4-hydroxy-3,3-dimethylpiperidin-1-yl)-3-methyl-1-oxobutan-2-yl)oxazole-4-carboxamide

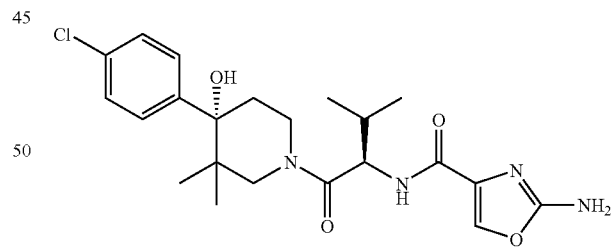

Sodium 2-aminooxazole-4-carboxylate (75 mg, 0.500 mmol), HOBt (67.5 mg, 0.500 mmol) and EDCI (96 mg, 0.500 mmol) were dissolved in DMF (0.5 mL). The mixture was stirred at rt for 0.5 h, then was added (R)-2-amino-1-((S)-4-(4-chlorophenyl)-4-hydroxy-3,3-dimethylpiperidin-1-yl)-3-methylbutan-1-one hydrochloride (188 mg, 0.500 mmol) and further stirred for 2 h. The reaction was quenched with water and stirred at rt for 2 h. The solids were filtered and rinsed with water to give 2-amino-N—((R)-1-((S)-4-(4-chlorophenyl)-4-hydroxy-3,3-dimethylpiperidin-1-yl)-3-methyl-1-oxobutan-2-yl)oxazole-4-carboxamide (169 mg, 0.376 mmol, 75% yield).

Step 3: Example 651

To a solution of 2-amino-N—((R)-1-((S)-4-(4-chlorophenyl)-4-hydroxy-3,3-dimethylpiperidin-1-yl)-3-methyl-1-oxobutan-2-yl)oxazole-4-carboxamide (20 mg, 0.045 mmol) and DIPEA (7.75 µL, 0.045 mmol) in CH$_2$Cl$_2$ (1 mL) was added cyclopentanecarbonyl chloride (11.8 mg, 0.09 mmol). The mixture was stirred at rt for 1 h and concentrated. The residue was purified by Prep-HPLC to give Example 651 (9 mg, 0.017 mmol, 37.1% yield). MS found 545.2 (M+).

The following examples, as described in Table 21, were prepared in similar manners as described for the preparation of the examples described above. Examples containing a carboxylic acid functional group were prepared for the corresponding esters following standard alkali base procedures known to one of ordinary skill in the art.

TABLE 21

| Example | Structure | LCMS (M⁺) or (M + H)⁺ | Example for general method of preparation |
|---------|-----------|------------------------|-------------------------------------------|
| 652 | Chiral | 434.9 | 512 |
| 653 | Chiral | 448.9 | 512 |
| 654 | Chiral | 458.9 | 512 |
| 655 | Chiral | 448.9 | 75 |

TABLE 21-continued
| Example | Structure | LCMS (M+) or (M + H)+ | Example for general method of preparation |
|---|---|---|---|
| 656 | 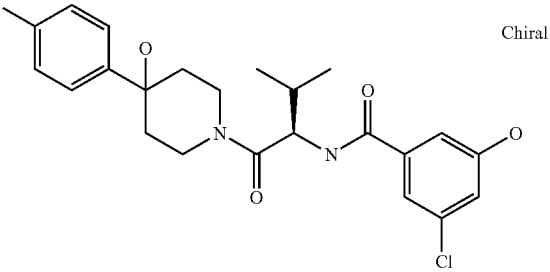 Chiral | 464.9 | 512 |
| 657 | 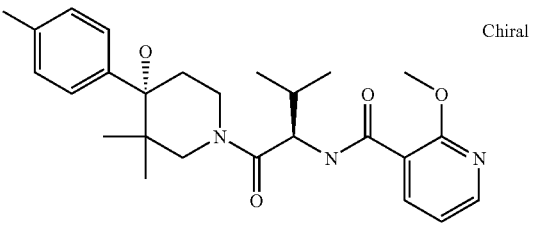 Chiral | 473.9 | 327 |
| 658 | 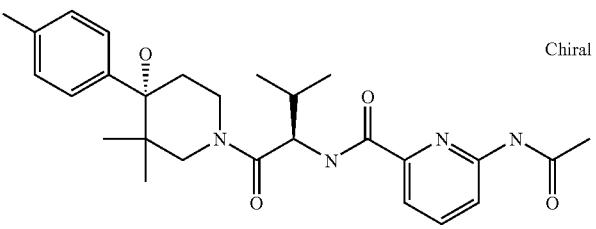 Chiral | 501.2 | 327 |
| 659 | 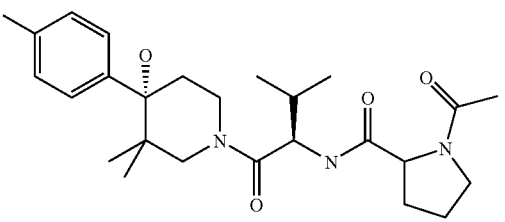 | 478.0 | 327 |
| 660 | 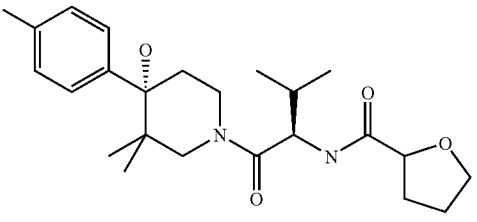 | 458.9 | 327 |
| 661 | 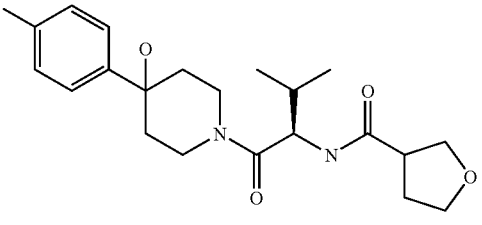 | 430.9 | 512 |

TABLE 21-continued
| Example | Structure | LCMS (M+) or (M + H)+ | Example for general method of preparation |
|---|---|---|---|
| 662 | 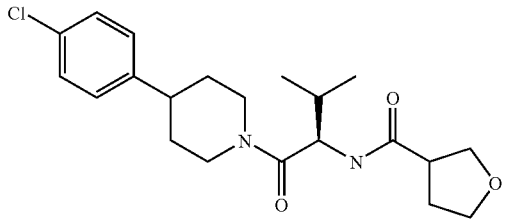 | 393.1 | 75 |
| 663 | 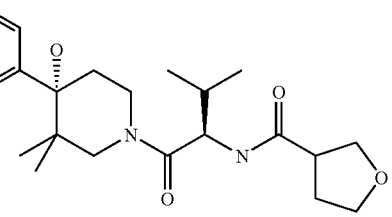 | 458.9 | 327 |
| 664 | 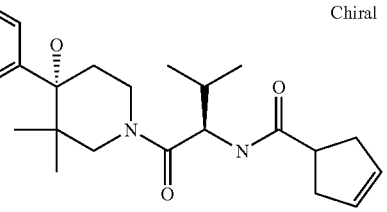 Chiral | 432.9 | 327 |
| 665 | 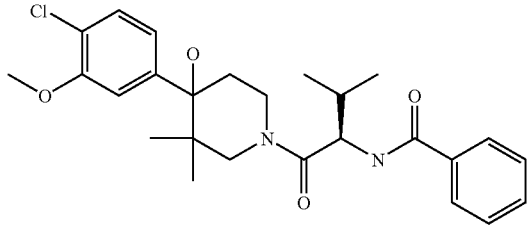 | 495.2 | 513 |
| 666 | 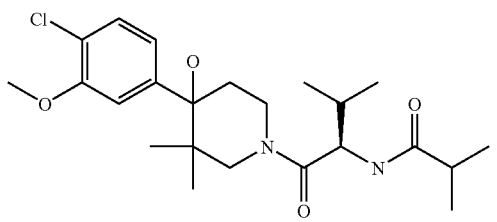 | 439.3 | 513 |
| 667 | 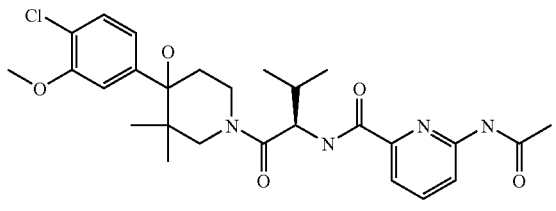 | 531.2 | 513 |

TABLE 21-continued

| Example | Structure | LCMS (M+) or (M + H)+ | Example for general method of preparation |
|---|---|---|---|
| 668 | Chiral | 515.3 | 327 |
| 669 | Chiral | 449.3 | 327 |
| 670 | Chiral | 491.2 | 327 |
| 671 | Chiral | 489.3 | 513 |
| 672 | Chiral | 501.2 | 327 |
| 673 | Chiral | 450.3 | 327 |

TABLE 21-continued

| Example | Structure | | LCMS (M+) or (M + H)+ | Example for general method of preparation |
|---|---|---|---|---|
| 674 | 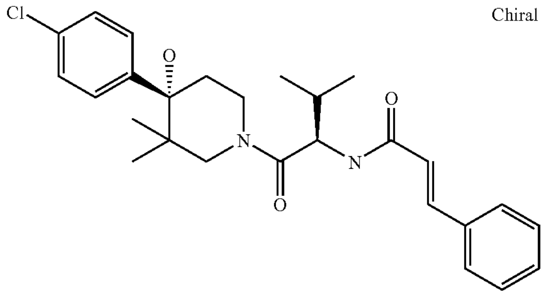 | Chiral | 469.2 | 327 |
| 675 | 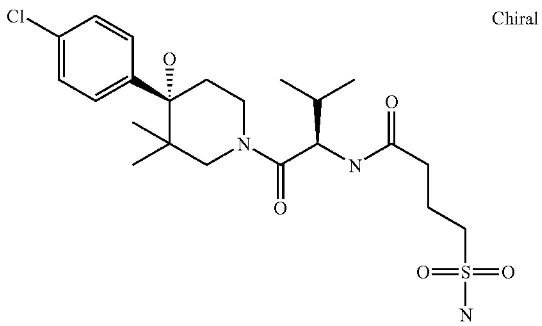 | Chiral | 470.2 | 327 |
| 676 | 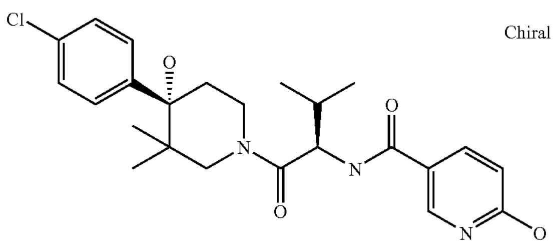 | Chiral | 460.2 | 327 |
| 677 | 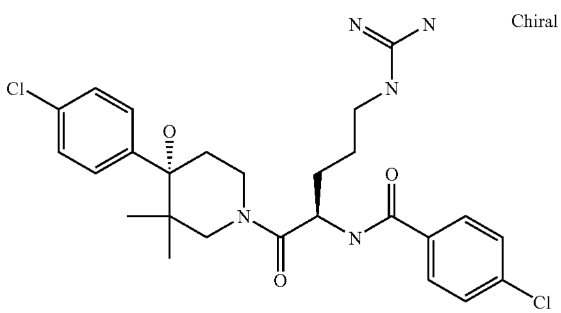 | Chiral | 534.1 | 514 |
| 678 | 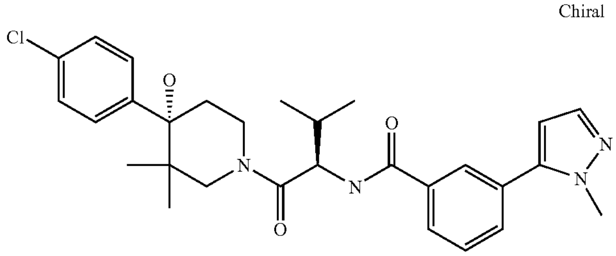 | Chiral | 523.4 | 519 |

TABLE 21-continued
| Example | Structure | | LCMS (M+) or (M + H)+ | Example for general method of preparation |
|---|---|---|---|---|
| 679 | 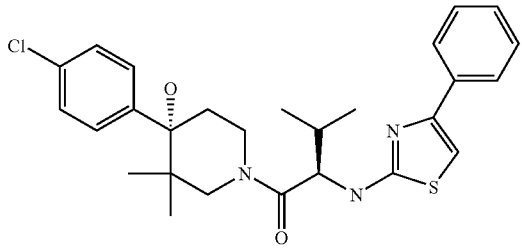 | Chiral | 498.3 | 520 |
| 680 | 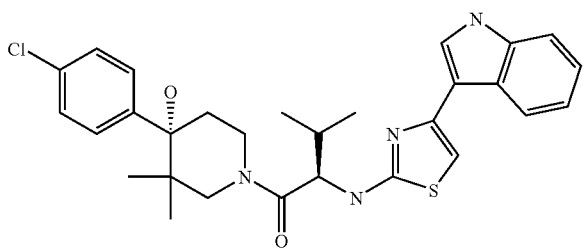 | Chiral | 537.2 | 520 |
| 681 | 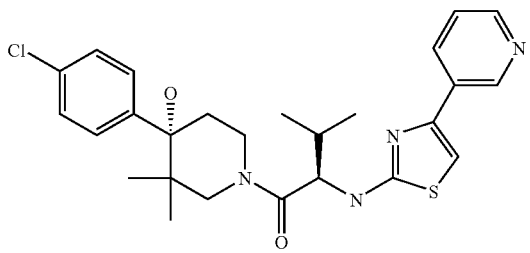 | Chiral | 499.2 | 520 |
| 682 | 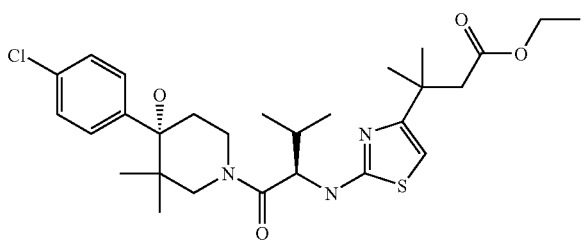 | Chiral | 550.3 | 520 |
| 683 | 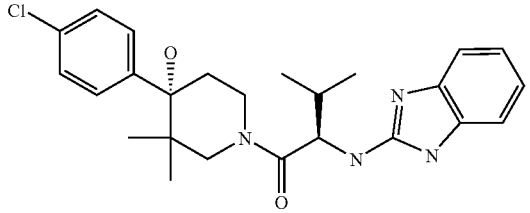 | Chiral | 455.3 | 517 |

TABLE 21-continued

| Example | Structure | LCMS (M+) or (M + H)+ | Example for general method of preparation |
|---|---|---|---|
| 684 | Chiral | 467.2 | 517 |
| 685 | Chiral | 501.2 | 517 |
| 686 | Chiral | 501.2 | 517 |
| 687 | Chiral | 485.2 | 517 |
| 688 | Chiral | 493.3 | 517 |
| 689 | Chiral | 417.2 | 517 |

TABLE 21-continued

| Example | Structure | LCMS (M+) or (M + H)+ | Example for general method of preparation |
|---|---|---|---|
| 690 | Chiral | 422.2 | 520 |
| 691 | Chiral | 410.3 | 527 |
| 692 | Chiral | 472.3 | 527 |
| 693 | Chiral | 410.3 | 527 |
| 694 | Chiral | 486.3 | 527 |

TABLE 21-continued

| Example | Structure | LCMS (M+) or (M + H)+ | Example for general method of preparation |
|---|---|---|---|
| 695 | Chiral | 486.2 | 527 |
| 696 | Chiral | 452.2 | 527 |
| 697 | Chiral | 452.3 | 527 |
| 698 | Chiral | 478.2 | 527 |
| 699 | Chiral | 492.2 | 527 |

TABLE 21-continued

| Example | Structure | LCMS (M+) or (M + H)+ | Example for general method of preparation |
|---|---|---|---|
| 700 | 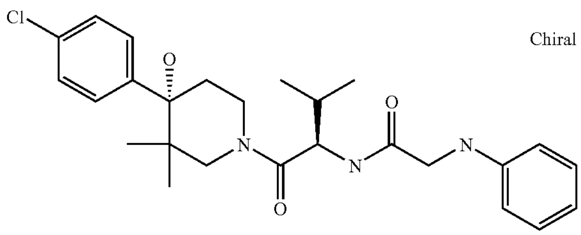 | 472.1 | 327 |
| 701 | 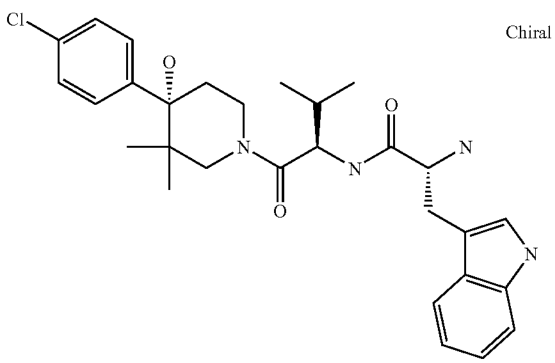 | 525.3 | 527 |
| 702 | 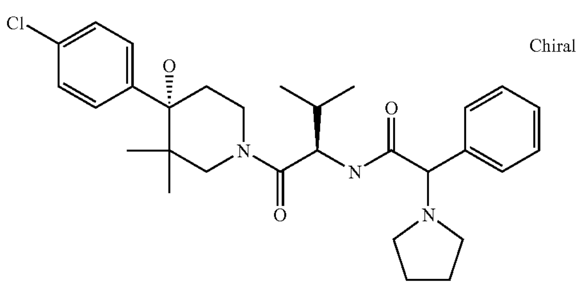 | 526.3 | 327 |
| 703 | 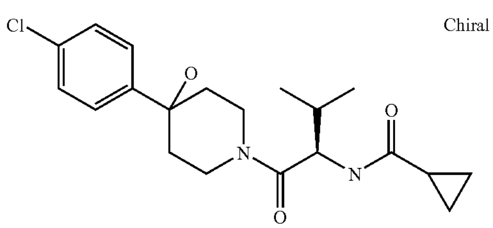 | 379.2 | 512 |
| 704 | 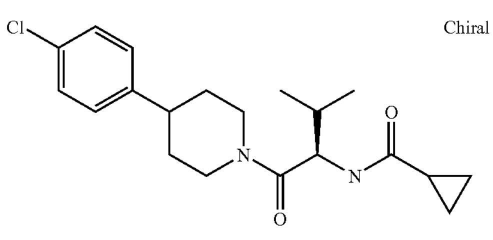 | 363.2 | 75 |

TABLE 21-continued

| Example | Structure | LCMS (M+) or (M + H)+ | Example for general method of preparation |
|---|---|---|---|
| 705 | Chiral | 482.2 | 631 |
| 706 | Chiral | 518.1 | 631 |
| 707 | Chiral | 518.1 | 631 |
| 708 | Chiral | 510.1 | 631 |
| 709 | Chiral | 448.1 | 631 |

TABLE 21-continued

| Example | Structure | LCMS (M+) or (M + H)+ | Example for general method of preparation |
|---|---|---|---|
| 710 | (Chiral) | 526 | 631 |
| 711 | (Chiral) | 490.1 | 631 |
| 712 | (Chiral) | 381.2 | 512 |
| 713 | (Chiral) | 433.1 | 512 |
| 714 | (Chiral) | 395.2 | 512 |

TABLE 21-continued
| Example | Structure | LCMS (M+) or (M + H)+ | Example for general method of preparation |
|---|---|---|---|
| 715 | 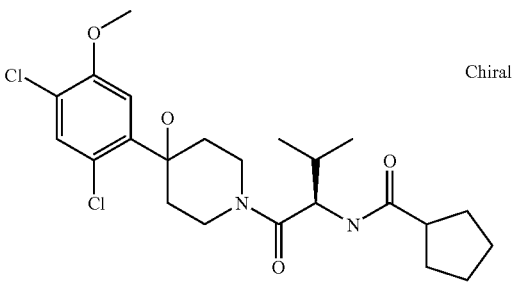 | 471.1 | 513 |
| 716 | 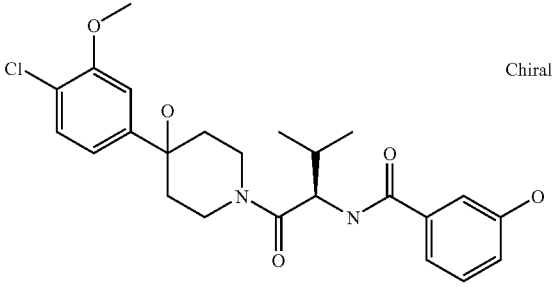 | 461.1 | 513 |
| 717 | 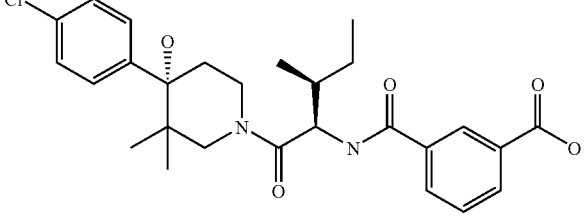 | 501.3 | 633 |
| 718 | 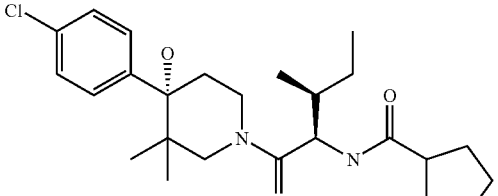 | 449.3 | 633 |
| 719 | 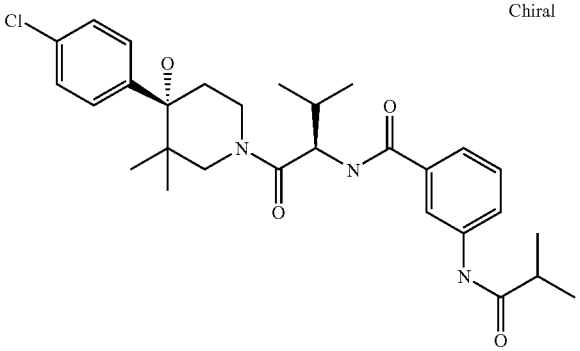 | 528.3 | 631 |

TABLE 21-continued

| Example | Structure | | LCMS (M+) or (M + H)+ | Example for general method of preparation |
|---|---|---|---|---|
| 720 | 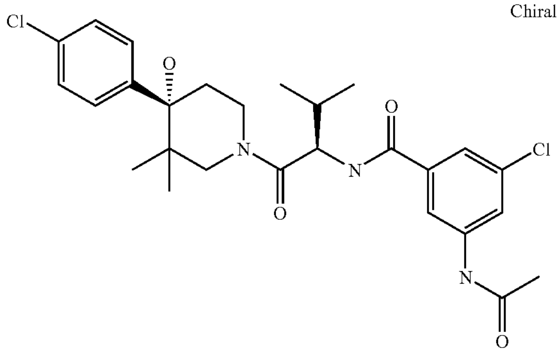 | Chiral | 534.3 | 631 |
| 721 | 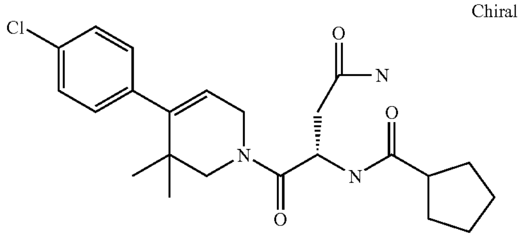 | Chiral | 432.3 | 632 |
| 722 | 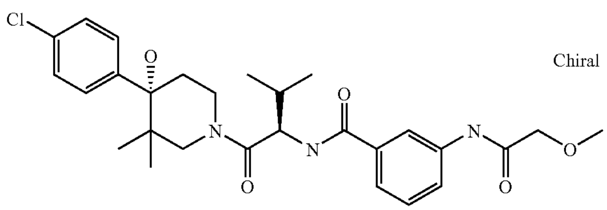 | Chiral | 530.3 | 631 |
| 723 | 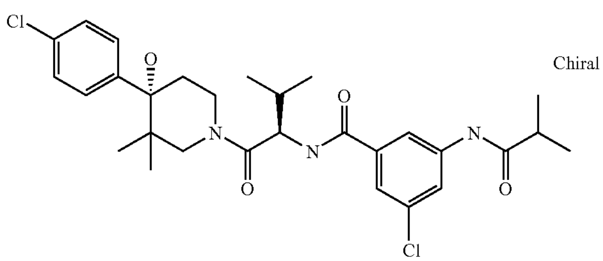 | Chiral | 562.3 | 631 |
| 724 | 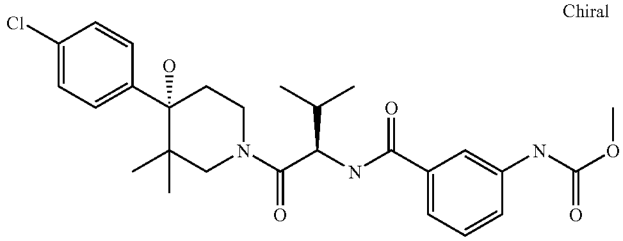 | Chiral | 516.3 | 631 |

TABLE 21-continued

| Example | Structure | LCMS (M+) or (M + H)+ | Example for general method of preparation |
|---|---|---|---|
| 725 | Chiral | 550.2 | 632 |
| 726 | Chiral | 536.3 | 631 |
| 727 | Chiral | 466.3 | 631 |
| 728 | Chiral | 500.3 | 631 |
| 729 | Chiral | 530.2 | 631 |

TABLE 21-continued

| Example | Structure | LCMS (M+) or (M + H)+ | Example for general method of preparation |
|---|---|---|---|
| 730 | Chiral | 482.3 | 631 |
| 731 | Chiral | 516.3 | 631 |
| 732 | Chiral | 496.3 | 631 |
| 733 | Chiral | 577.3 | 635 |
| 734 | Chiral | 590.1 | 631 |

TABLE 21-continued

| Example | Structure | | LCMS (M+) or (M + H)+ | Example for general method of preparation |
|---|---|---|---|---|
| 735 | [structure] | Chiral | 624.2 | 631 |
| 736 | [structure] | Chiral | 496.3 | 631 |
| 737 | [structure] | Chiral | 502.3 | 631 |
| 738 | [structure] | Chiral | 536.2 | 631 |
| 739 | [structure] | Chiral | 482.3 | 631 |

TABLE 21-continued

| Example | Structure | LCMS (M+) or (M + H)+ | Example for general method of preparation |
|---|---|---|---|
| 740 | Chiral | 472.2 | 517 |
| 741 | Chiral | 480.2 | 520 |
| 742 | Chiral | 439.2 | 638 |
| 743 | Chiral | 465.2 | 638 |
| 744 | Chiral | 452.3 | 640 |
| 745 | Chiral | 500.3 | 640 |

TABLE 21-continued

| Example | Structure | LCMS (M+) or (M + H)+ | Example for general method of preparation |
|---|---|---|---|
| 746 | Chiral | 514.3 | 640 |
| 747 | Chiral | 514.3 | 640 |
| 748 | Chiral | 517.3 | 632 |
| 749 | Chiral | 505.3 | 642 |
| 750 | Chiral | 466.3 | 645 |

TABLE 21-continued

| Example | Structure | LCMS (M+) or (M + H)+ | Example for general method of preparation |
|---|---|---|---|
| 751 | Chiral | 481.3 | 646 |
| 752 | Chiral | 526.3 | 647 |
| 753 | Chiral | 474.3 | 647 |
| 754 | Chiral | 506.2 | 648 |
| 755 | Chiral | 454.2 | 645 |
| 756 | Chiral | 535.3 | 650 |

TABLE 21-continued
| Example | Structure | LCMS (M+) or (M + H)+ | Example for general method of preparation |
|---|---|---|---|
| 757 | 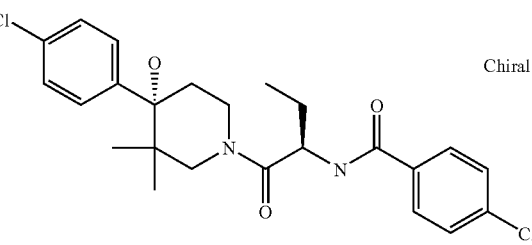 Chiral | 463.3 | 627 |
| 758 | 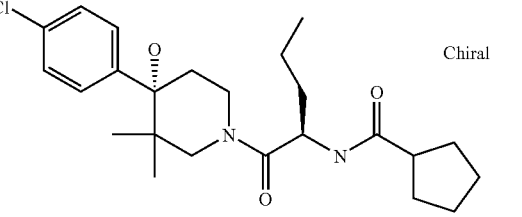 Chiral | 487.3 | 627 |
| 759 | 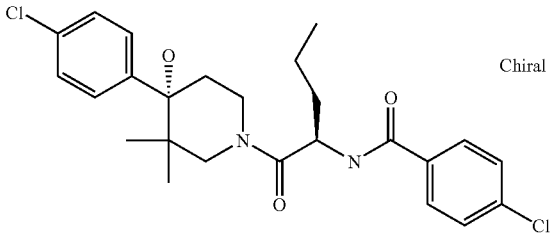 Chiral | 491.3 | 627 |
| 760 | 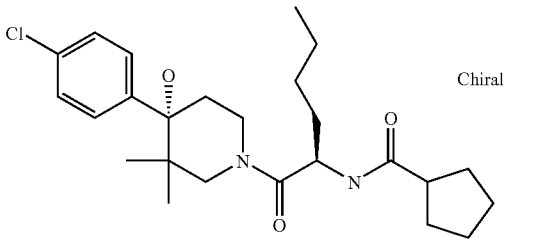 Chiral | 501.3 | 627 |
| 761 | 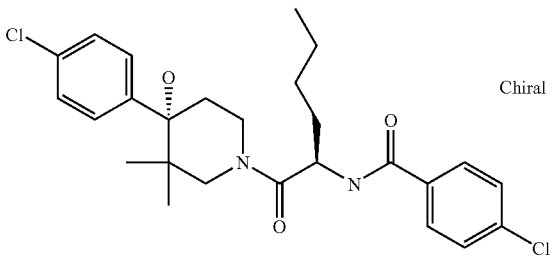 Chiral | 477.3 | 627 |
| 762 | 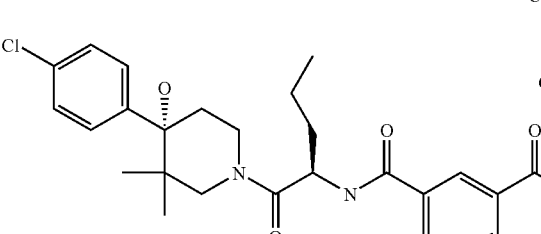 Chiral | 487.3 | 628 |

TABLE 21-continued
| Example | Structure | LCMS (M+) or (M + H)+ | Example for general method of preparation |
|---|---|---|---|
| 763 | 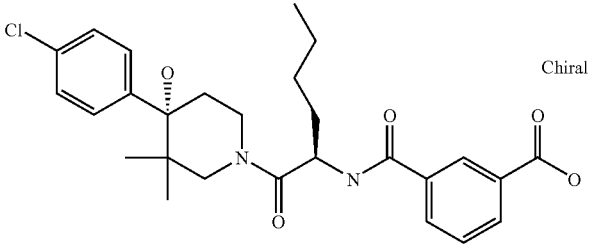 | 501.3 | 628 |
| 764 | 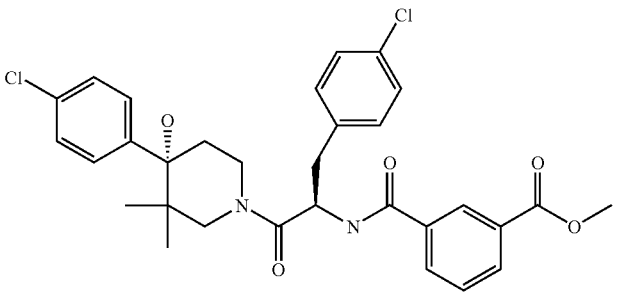 | 585.3 | 627 |
| 765 | 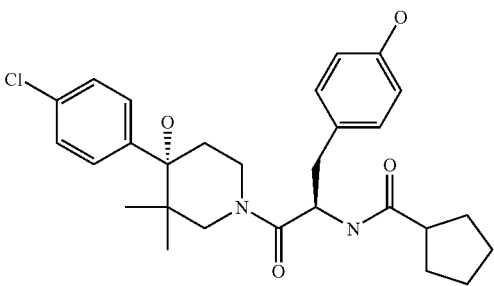 | 499.3 | 627 |
| 766 | 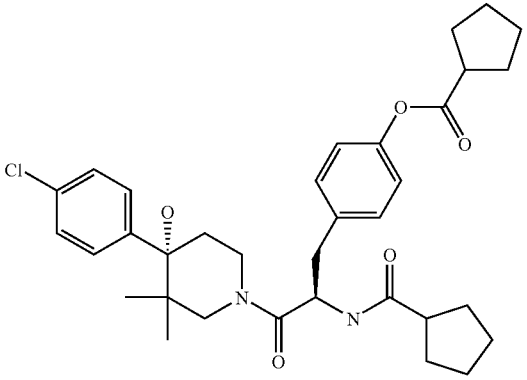 | 595.3 | 627 |

TABLE 21-continued

| Example | Structure | LCMS (M+) or (M + H)+ | Example for general method of preparation |
|---|---|---|---|
| 767 | Chiral | 551.2 | 628 |
| 768 | Chiral | 629.3 | 327 |
| 769 | Chiral | 513.2 | 327 |
| 770 | Chiral | 628.3 | 629 |
| 771 | Chiral | 514.3 | 629 |

TABLE 21-continued

| Example | Structure | | LCMS (M+) or (M + H)+ | Example for general method of preparation |
|---|---|---|---|---|
| 772 | 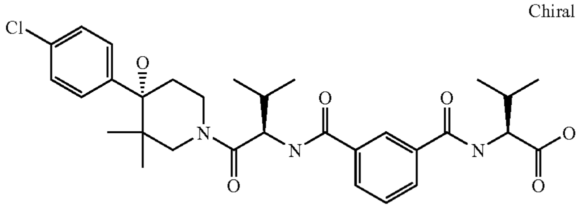 | Chiral | 586.3 | 630 |
| 773 | 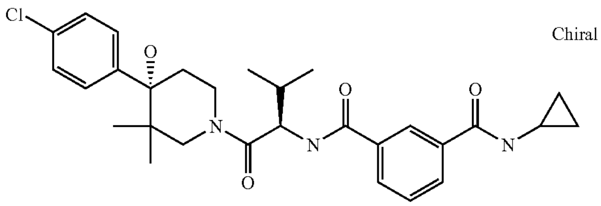 | Chiral | 526.7 | 629 |
| 774 | 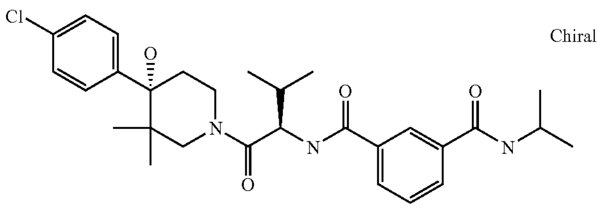 | Chiral | 528.3 | 629 |
| 775 | 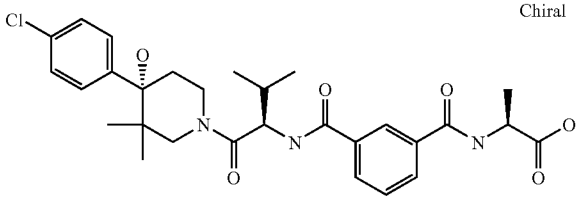 | Chiral | 558.26 | 630 |
| 776 | 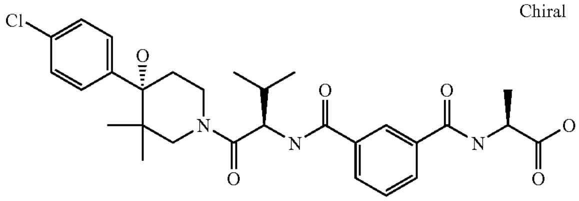 | Chiral | 558.3 | 630 |
| 777 | 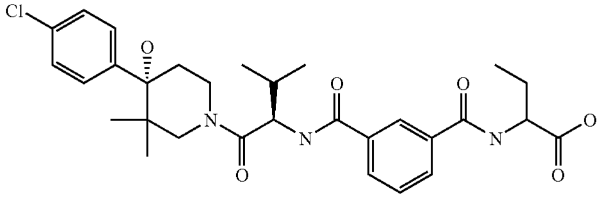 | | 572.3 | 630 |
| 778 | 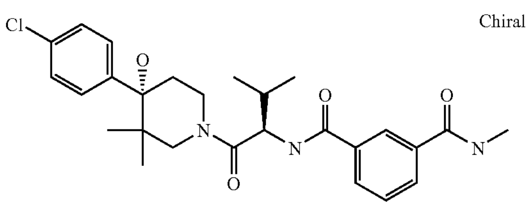 | Chiral | 500.3 | 629 |

TABLE 21-continued

| Example | Structure | LCMS (M+) or (M + H)+ | Example for general method of preparation |
|---|---|---|---|
| 779 | Chiral | 461.3 | 327 |
| 780 | Chiral | 529.4 | 626 |
| 781 | Chiral | 528.4 | 623 |
| 782 | Chiral | 501.5 | 626 |
| 783 | Chiral | 487.5 | 626 |

TABLE 21-continued

| Example | Structure | LCMS (M+) or (M + H)+ | Example for general method of preparation |
|---|---|---|---|
| 784 | Chiral | 487.4 | 626 |
| 785 | Chiral | 513.5 | 626 |
| 786 | Chiral | 501.4 | 626 |
| 787 | Chiral | 572.6 | 626 |
| 788 | 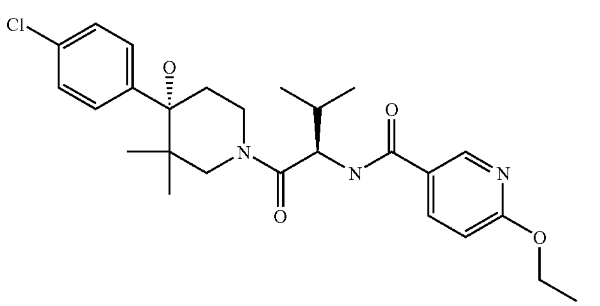 | 488.4 | 623 |

TABLE 21-continued
| Example | Structure | | LCMS (M+) or (M + H)+ | Example for general method of preparation |
|---|---|---|---|---|
| 789 | 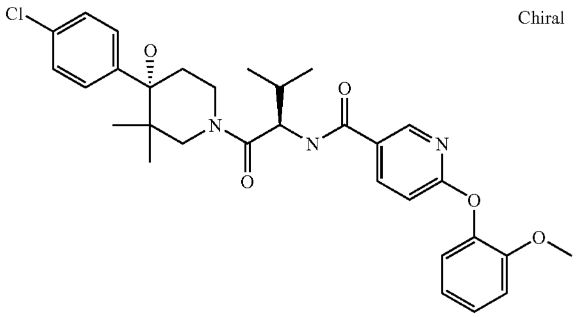 | Chiral | 566.6 | 623 |
| 790 | 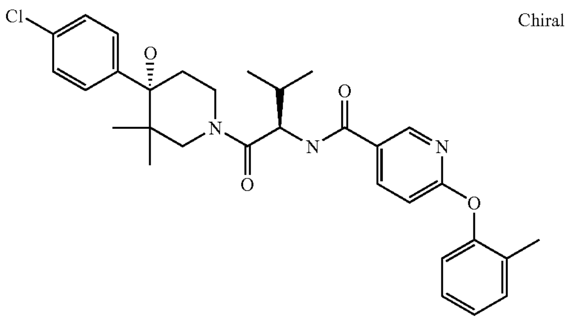 | Chiral | 550.2 | 623 |
| 791 | 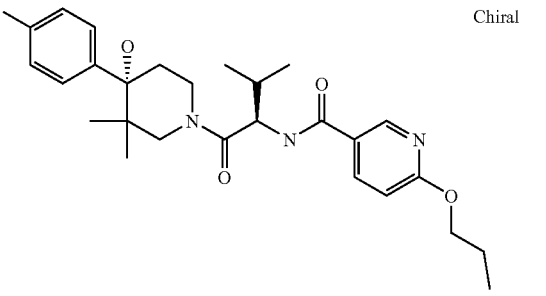 | Chiral | 502.4 | 623 |
| 792 | 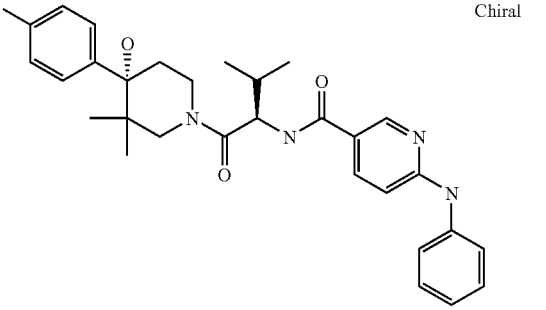 | Chiral | 535.1 | 626 |
| 793 | 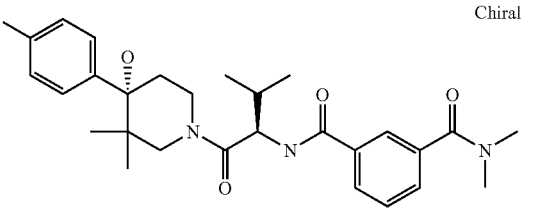 | Chiral | 514.2 | 629 |

TABLE 21-continued

| Example | Structure | LCMS (M+) or (M + H)+ | Example for general method of preparation |
|---|---|---|---|
| 794 | Chiral | 550.2 | 623 |
| 795 | Chiral | 435.2 | 327 |
| 796 | Chiral | 501.2 | 327 |
| 797 | Chiral | 521 | 327 |
| 798 | Chiral | ¹H NMR (400 MHz, CD3OD) d ppm: 7.47 (dd, J=11.97, 8.68 Hz, 2 H), 7.30 (dd, J=8.46, 4.72 Hz, 2 H), 4.92-4.83 (m, 1H + H₂O), 4.53 (d, J=13.18 Hz, 0.5 H), 4.26-4.19 (m, 1 H), 4.15-3.91 (m, 1 H), 3.73-3.49 (m, 1.5 H), 3.25-3.03 (m, 1 H), 2.78-2.49 (m | 327 |

TABLE 21-continued

| Example | Structure | LCMS (M+) or (M + H)+ | Example for general method of preparation |
|---|---|---|---|
| 799 | 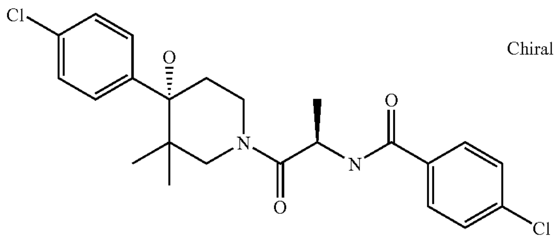 | 449.3 | 327 |
| 800 | 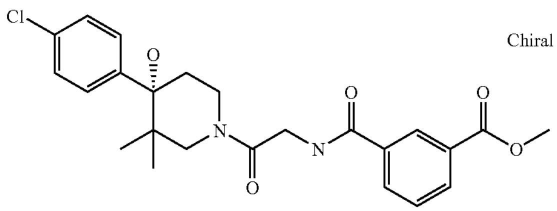 | 459.3 | 327 |
| 801 | 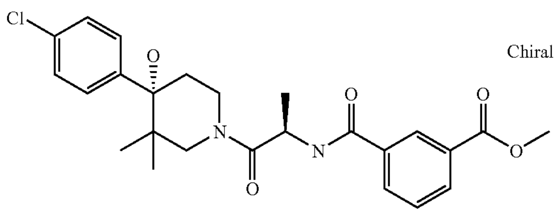 | 473.3 | 327 |
| 802 | 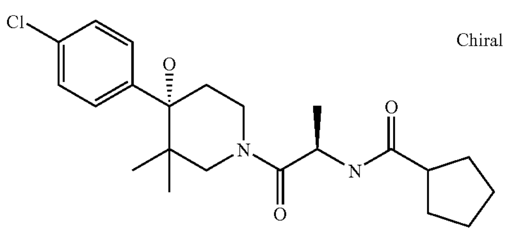 | 407.3 | 327 |
| 803 | 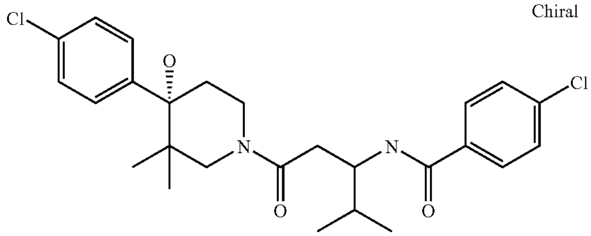 | 491.3 | 327 |
| 804 | 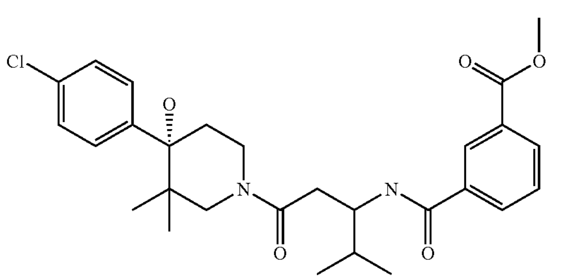 | 515.4 | 327 |

TABLE 21-continued

| Example | Structure | LCMS (M+) or (M + H)+ | Example for general method of preparation |
|---|---|---|---|
| 805 | Chiral | 451.3 | 327 |
| 806 | Chiral | 451.3 | 327 |
| 807 | Chiral | 451.3 | 327 |
| 808 | Chiral | 444.4 | 327 |
| 809 | Chiral | 536.3 | 517 |

TABLE 21-continued

| Example | Structure | LCMS (M+) or (M + H)+ | Example for general method of preparation |
|---|---|---|---|
| 810 | 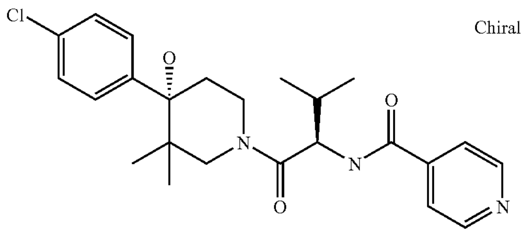 | 444.3 | 327 |
| 811 | 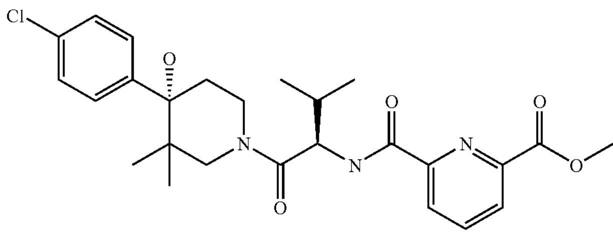 | 502.3 | 327 |
| 812 | 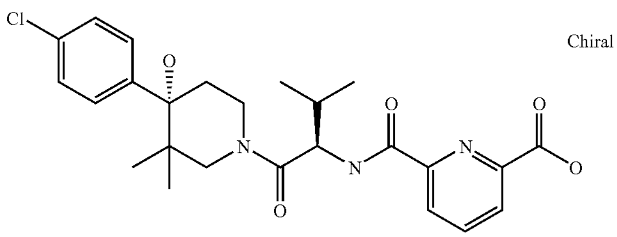 | 488.2 | 601 |
| 813 | 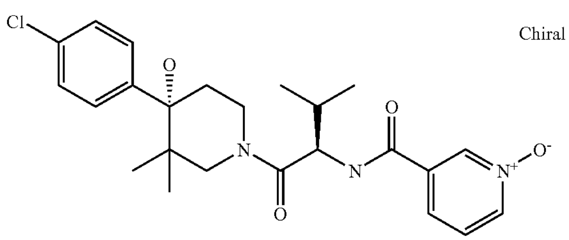 | 460.3 | 327 |
| 814 | 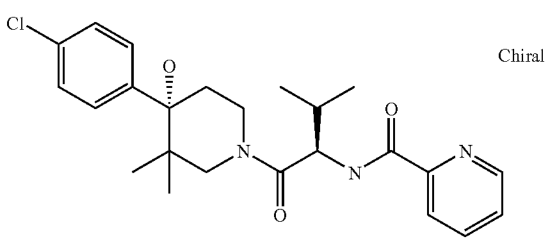 | 444.3 | 327 |
| 815 | 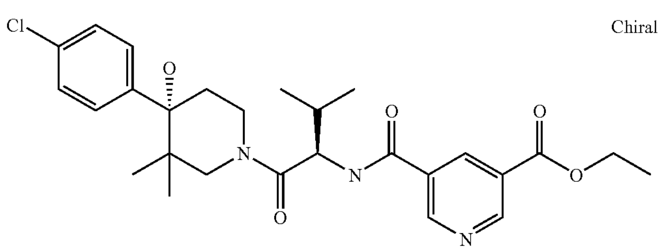 | 516.3 | 327 |

TABLE 21-continued

| Example | Structure | | LCMS (M+) or (M + H)+ | Example for general method of preparation |
|---|---|---|---|---|
| 816 | 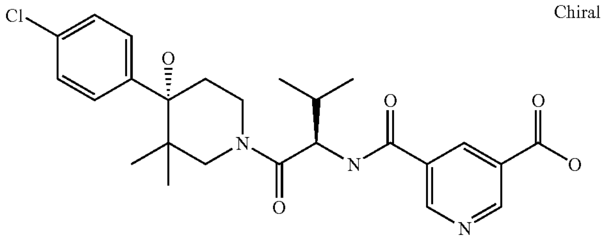 | Chiral | 488.3 | 327 |
| 817 | 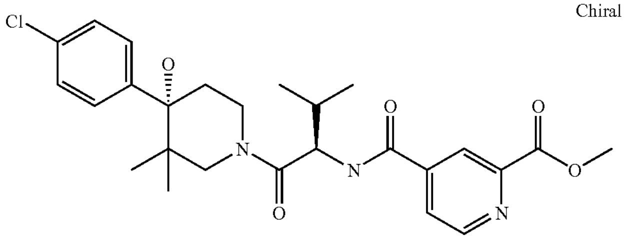 | Chiral | 502.4 | 327 |
| 818 | 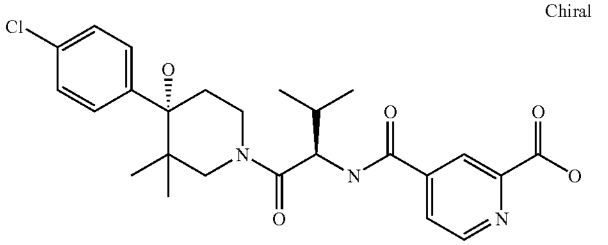 | Chiral | 488.3 | 327 |
| 819 | 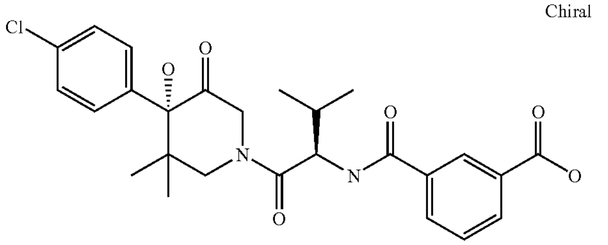 | Chiral | 503.3 | 327 |
| 820 | 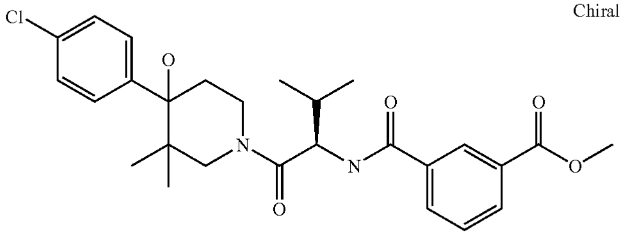 | Chiral | 485.4 | 590 |
| 821 | 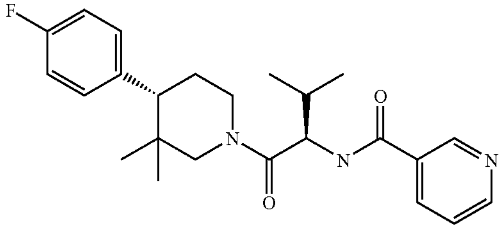 | | 412.5 | 591 |

TABLE 21-continued

| Example | Structure | LCMS (M+) or (M + H)+ | Example for general method of preparation |
|---|---|---|---|
| 822 | 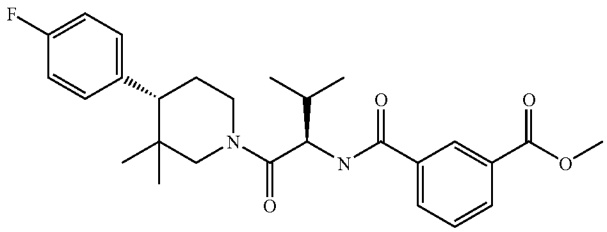 | 469.4 | 591 |
| 823 | 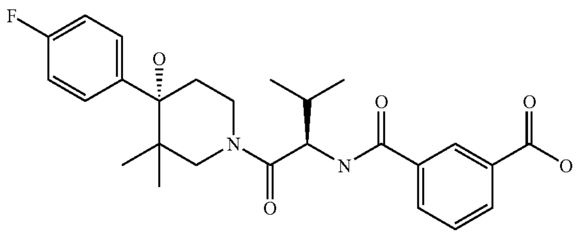 | 471.4 | 590 |
| 824 | 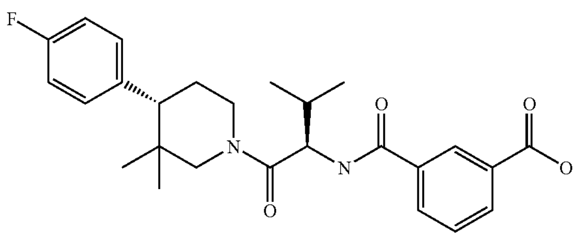 | 455.4 | 590 |
| 825 | Chiral | 537.4 | 600 |
| 826 | Chiral | 521.3 | 589 |
| 827 | Chiral | 508.2 | 589 |

TABLE 21-continued

| Example | Structure | LCMS (M+) or (M + H)+ | Example for general method of preparation |
|---|---|---|---|
| 828 | Chiral | 465.2 | 327 |
| 829 | Chiral | 416.1 | 512 |
| 830 | Chiral | 506.2 | 587 |
| 831 | Chiral | 485 | 587 |
| 832 | Chiral | 419.1 | 587 |
| 833 | Chiral | 471.1 | 587 |

TABLE 21-continued

| Example | Structure | LCMS (M+) or (M + H)+ | Example for general method of preparation |
|---|---|---|---|
| 833 | Chiral | 475.1 | 531, Step 2 |
| 834 | Chiral | 472.19 | 531, Step 1 |
| 835 | Chiral | 444.11 | 531, Step 2 |
| 836 | 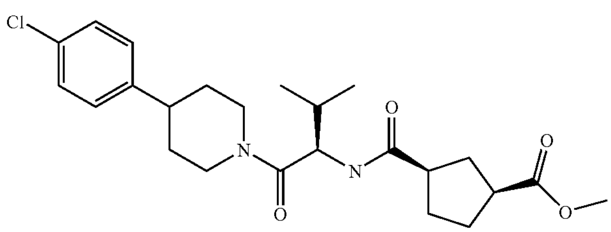 | 449.2 | 531, Step 1 |
| 837 | 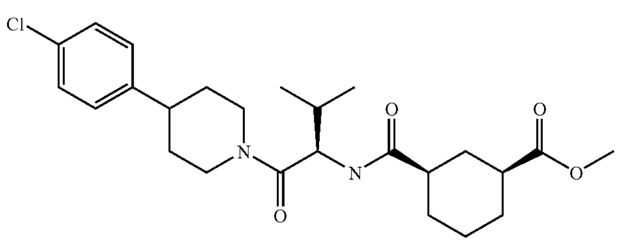 | 463.24 | 531, Step 1 |
| 838 | 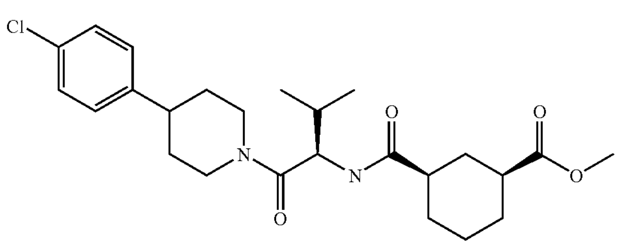 | 463.2 | 531, Step 1 |

TABLE 21-continued

| Example | Structure | LCMS (M⁺) or (M + H)⁺ | Example for general method of preparation |
|---|---|---|---|
| 839 | 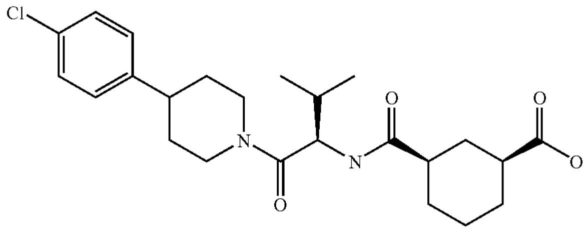 | 449.21 | 531, Step 2 |
| 840 | 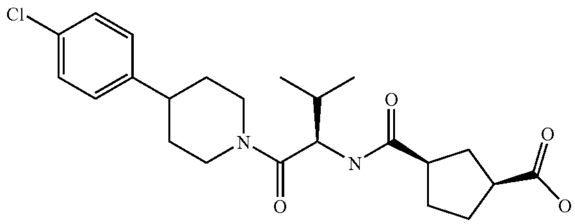 | 435.19 | 531, Step 2 |
| 841 | 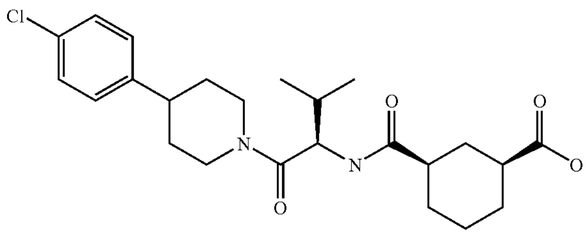 | 449.18 | 531, Step 2 |
| 842 | Chiral | 473.15 | 531, Step 1 |
| 843 | Chiral | 459.16 | 531, Step 2 |
| 844 | Chiral | 438.2 | 531, Step 1 |

TABLE 21-continued

| Example | Structure | LCMS (M+) or (M + H)+ | Example for general method of preparation |
|---|---|---|---|
| 845 | 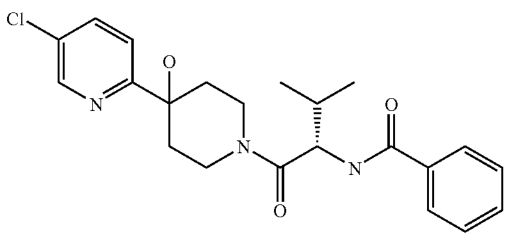 | 416.28 | 559 |
| 846 | Chiral | 457.23 | 531, Step 2 |
| 847 | 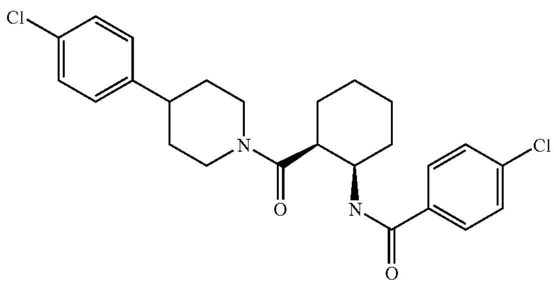 | 459.14 | 531, Step 1 |
| 848 | 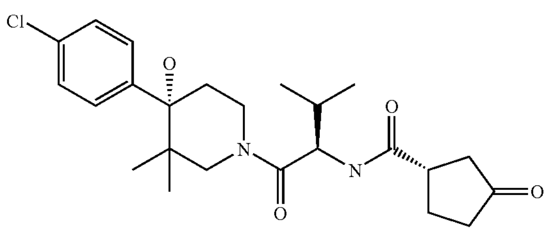 | 449.4 | 327 |
| 849 | 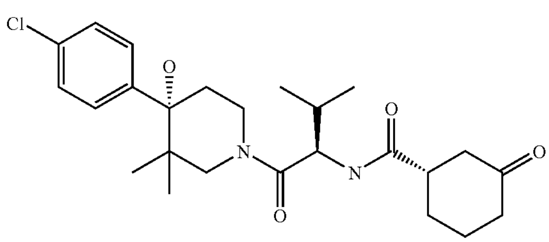 | 463.4 | 327 |
| 850 | Chiral | 424.4 | 530 |

TABLE 21-continued

| Example | Structure | LCMS (M+) or (M + H)+ | Example for general method of preparation |
|---|---|---|---|
| 851 | Chiral | 438.45 | 530 |
| 852 | Chiral | 486.23 | 530 |
| 853 | Chiral | 410 | 530 |
| 854 | Chiral | 472 | 530 |
| 855 | Chiral | 438 | 530 |
| 856 | 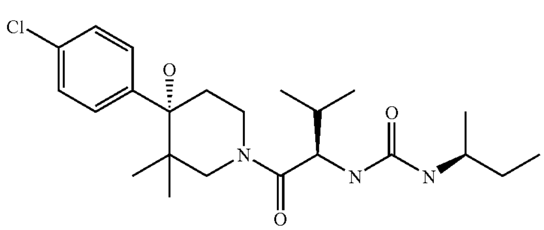 | 438.01 | 530 |

TABLE 21-continued
| Example | Structure | | LCMS (M+) or (M + H)+ | Example for general method of preparation |
|---|---|---|---|---|
| 857 | 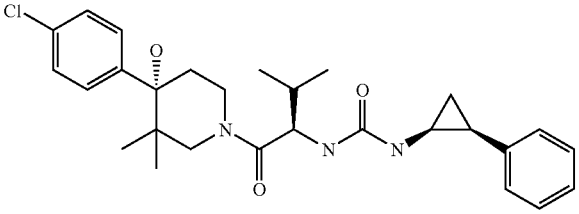 | | 477.37 | 530 |
| 858 | 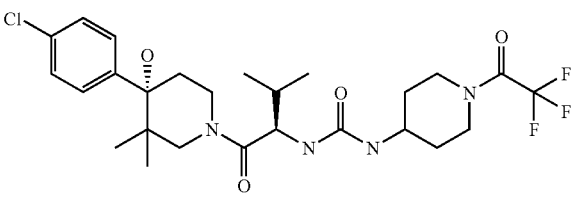 | Chiral | 561 | 530 |
| 859 | 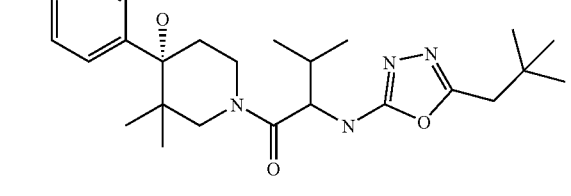 | Chiral | 477.4 | 327 |
| 860 | 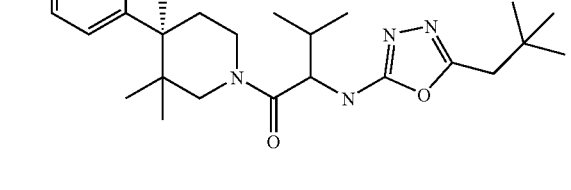 | Chiral | 477.39 | 327 |
| 861 | 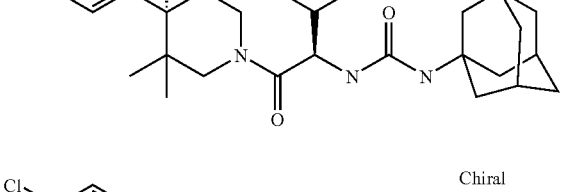 | Chiral | 516.33 | 530 |
| 862 | 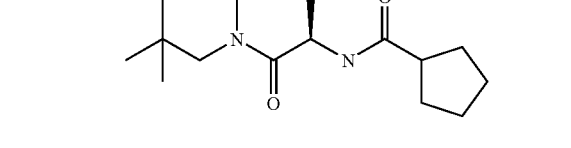 | Chiral | 449.43 | 327 |

TABLE 21-continued
| Example | Structure | LCMS (M+) or (M + H)+ | Example for general method of preparation |
|---|---|---|---|
| 863 | 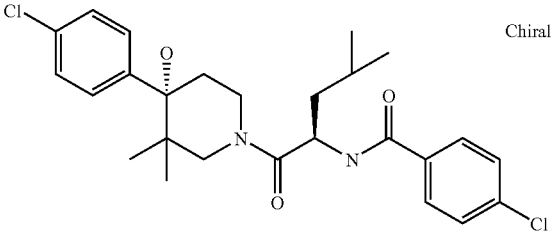 Chiral | 491.32 | 327 |
| 864 | 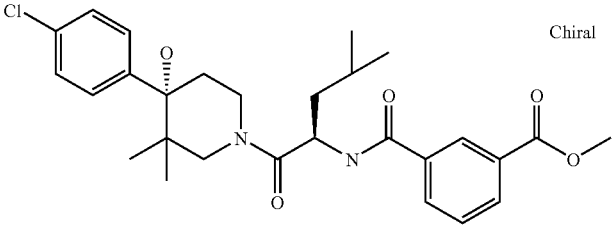 Chiral | 515.39 | 327 |
| 865 | 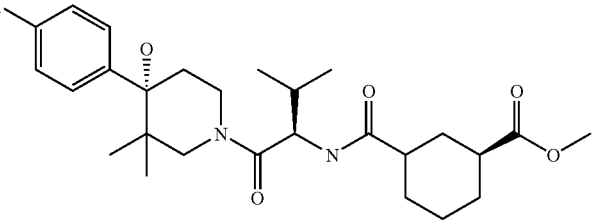 | 507.41 | 327 |
| 866 | 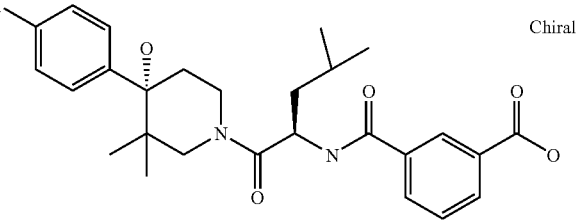 Chiral | 501.36 | 327 |
| 867 | 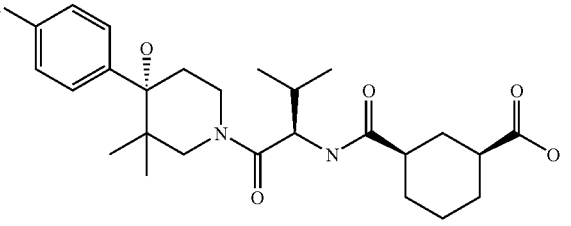 | 493.35 | 327 |
| 868 | 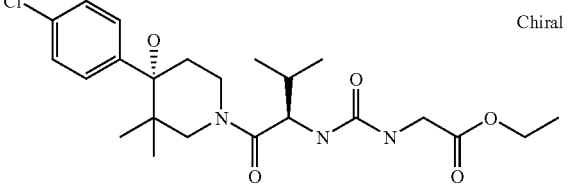 Chiral | 468.35 | 530 |

TABLE 21-continued

| Example | Structure | LCMS (M⁺) or (M + H)⁺ | Example for general method of preparation |
|---------|-----------|------------------------|-------------------------------------------|
| 869 | Chiral | 482.34 | 530 |
| 870 | Chiral | 440.34 | 530 |
| 871 | Chiral | 454.35 | 530 |
| 872 | Chiral | 423.36 | 327 |
| 873 | Chiral | 465.25 | 327 |
| 874 | Chiral | 489.28 | 327 |

TABLE 21-continued

| Example | Structure | LCMS (M+) or (M + H)+ | Example for general method of preparation |
|---|---|---|---|
| 875 | 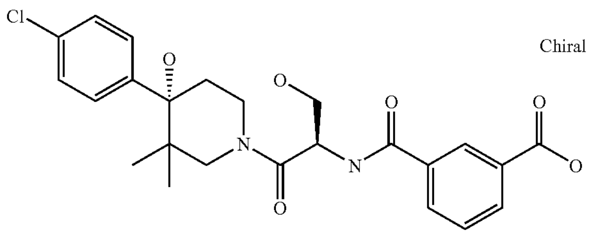 | 475.23 | 327 |
| 876 | 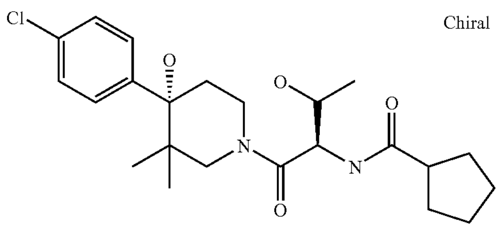 | 437.27 | 327 |
| 877 | 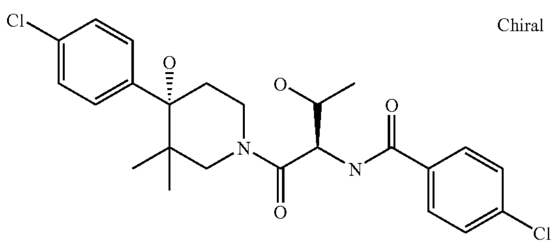 | 479.16 | 327 |
| 878 | 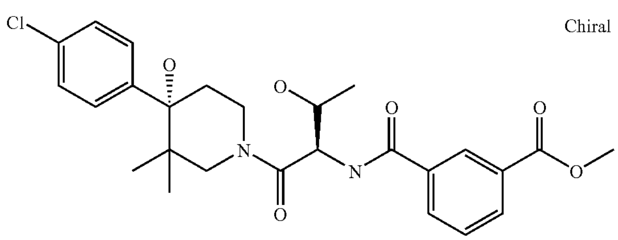 | 503.22 | 327 |
| 879 | 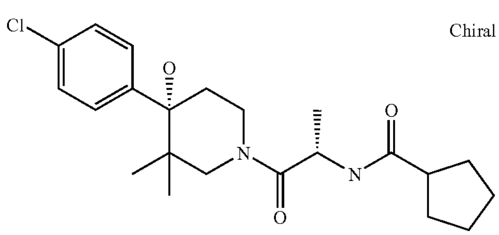 | 407.18 | 327 |
| 880 | 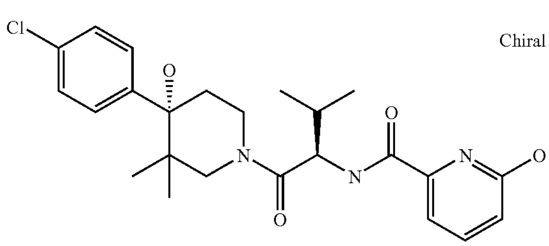 | 460.24 | 327 |

TABLE 21-continued

| Example | Structure | LCMS (M+) or (M + H)+ | Example for general method of preparation |
|---|---|---|---|
| 881 | 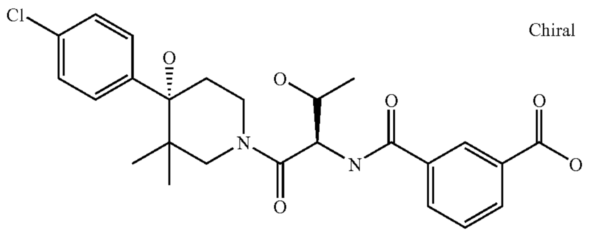 | 489.21 | 327 |
| 882 | 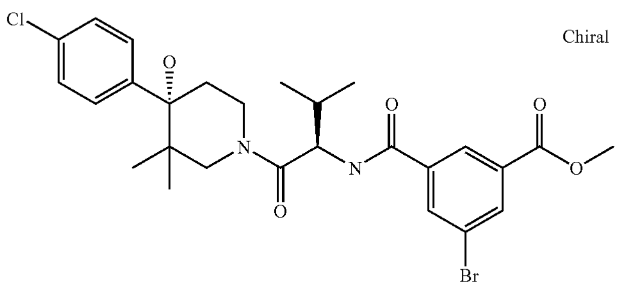 | 581.14 | 327 |
| 883 | 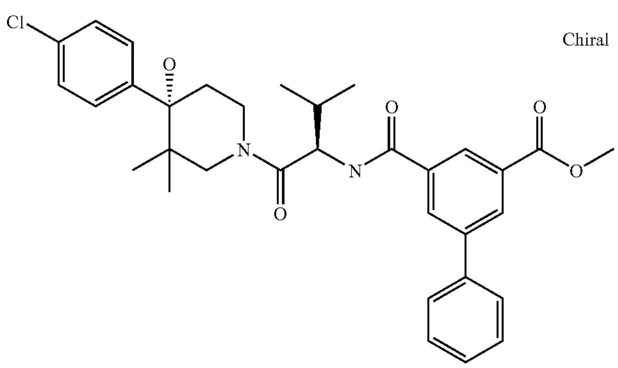 | 577.29 | 327 |
| 884 | 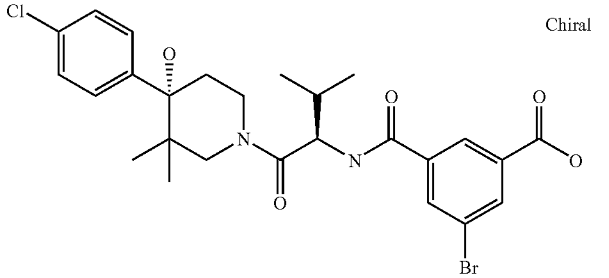 | 567.11 | 327 |

TABLE 21-continued

| Example | Structure | LCMS (M+) or (M + H)+ | Example for general method of preparation |
|---|---|---|---|
| 885 | (Chiral structure) | 563.21 | 327 |
| 886 | (Chiral structure) | 498.22 | 536, Step 2 |
| 887 | (Chiral structure) | 530.3 | 536, Step 2 |
| 888 | (Chiral structure) | 530.3 | 536, Step 2 0 |
| 889 | (Chiral structure) | 530.3 | 536, Step 2 |

TABLE 21-continued

| Example | Structure | LCMS (M+) or (M + H)+ | Example for general method of preparation |
|---|---|---|---|
| 890 | Chiral | 516.29 | 530 |
| 891 | Chiral | 516.29 | 530 |
| 892 | Chiral | 516.28 | 530 |
| 893 | Chiral | 598.21 | 558 |
| 894 | Chiral | 424.25 | 327 |
| 895 | Chiral | 506.36 | 536, Step 2 |

TABLE 21-continued

| Example | Structure | LCMS (M+) or (M + H)+ | Example for general method of preparation |
|---|---|---|---|
| 896 | Chiral | 468.31 | 536, Step 2 |
| 897 | Chiral | 438.33 | 536, Step 2 |
| 898 | Chiral | 438.34 | 536, Step 2 |
| 899 | Chiral | 531.34 | 327 |
| 900 | Chiral | 452.3 | 530 |
| 901 | Chiral | 627.42 | 535, Step 1 |

TABLE 21-continued

| Example | Structure | LCMS (M+) or (M + H)+ | Example for general method of preparation |
|---|---|---|---|
| 902 | Chiral | 527.34 | 535, Step 2 |
| 903 | Chiral | 453.29 | 327 |
| 904 | Chiral | 425.24 | 327 |
| 905 | Chiral | 545.36 | 327 |
| 906 | Chiral | 536.37 | 535, Step 1 |
| 907 | Chiral | 436.31 | 535, Step 2 |

TABLE 21-continued

| Example | Structure | LCMS (M+) or (M + H)+ | Example for general method of preparation |
|---|---|---|---|
| 908 | 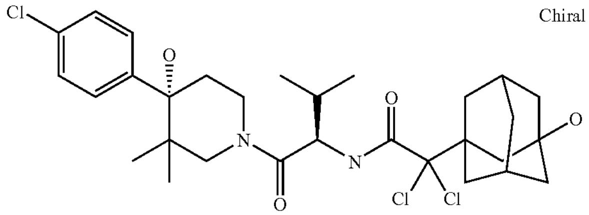 | 601.23 | 327 |
| 909 | 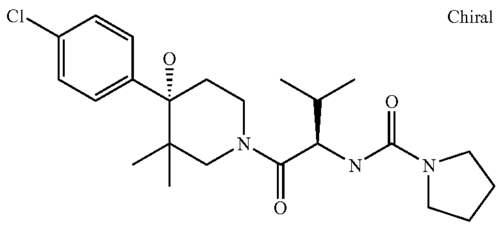 | 436.28 | 557 |
| 910 | 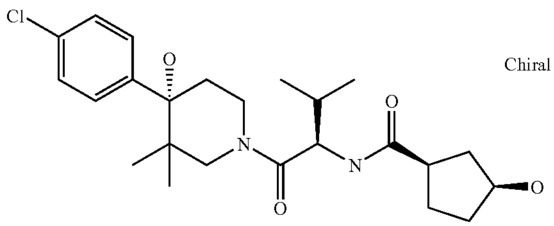 | 453.29 | 327 |
| 911 | 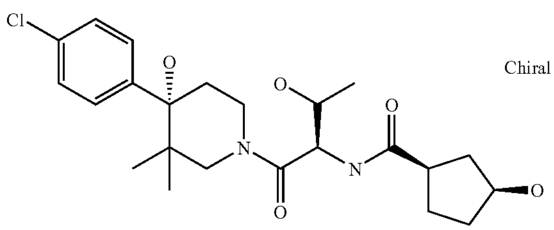 | 453.28 | 327 |
| 912 | 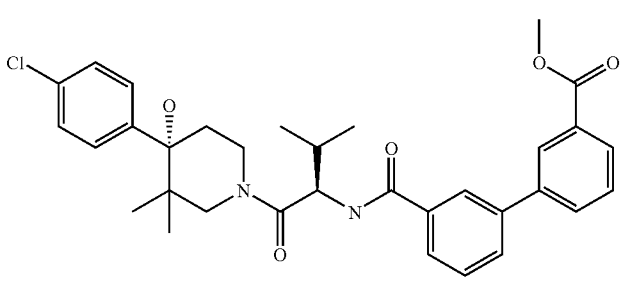 | 577.28 | 327 |

TABLE 21-continued
| Example | Structure | LCMS (M+) or (M + H)+ | Example for general method of preparation |
|---|---|---|---|
| 913 | 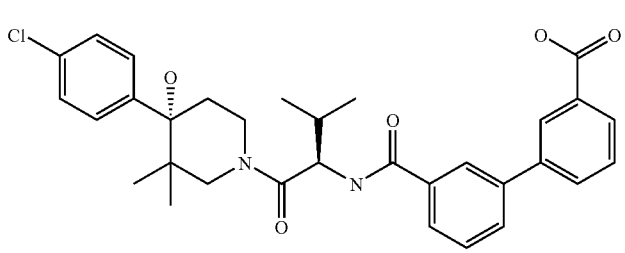 Chiral | 563.27 | 327 |
| 914 | 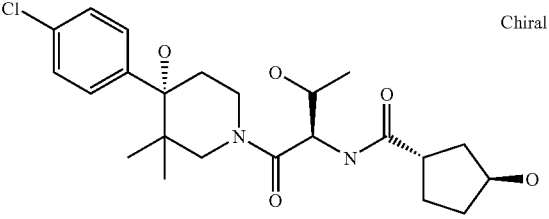 Chiral | 453.26 | 327 |
| 915 | 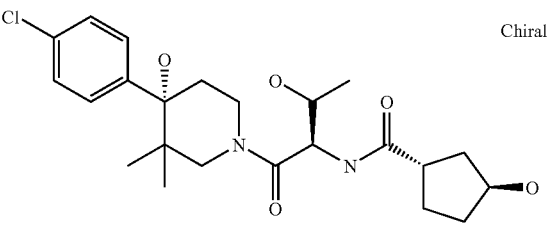 Chiral | 453.29 | 327 |
| 916 | 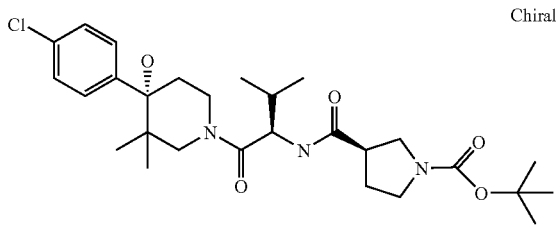 Chiral | 536.36 | 327 |
| 917 | 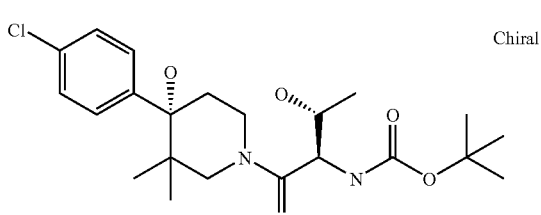 Chiral | 441.25 | Preparation C |

TABLE 21-continued

| Example | Structure | LCMS (M+) or (M + H)+ | Example for general method of preparation |
|---|---|---|---|
| 918 | Chiral | 646.39 | 327 |
| 919 | Chiral | 436.29 | 535, Step 2 |
| 920 | Chiral | 546.36 | 535, Step 2 |
| 921 | Chiral | 572.37 | 327 |
| 922 | Chiral | 433.27 | 327 |
| 923 | Chiral | 499.23 | 327 |

TABLE 21-continued

| Example | Structure | LCMS (M+) or (M + H)+ | Example for general method of preparation |
|---|---|---|---|
| 924 | Chiral | 437.28 | 327 |
| 925 | Chiral | 503.23 | 327 |
| 926 | Chiral | 485.26 | 327 |
| 927 | Chiral | 489.25 | 327 |
| 928 | Chiral | 482.29 | 555 |
| 929 | Chiral | 577.32 | 556, Step 2 |

TABLE 21-continued
| Example | Structure | LCMS (M+) or (M + H)+ | Example for general method of preparation |
|---|---|---|---|
| 930 | 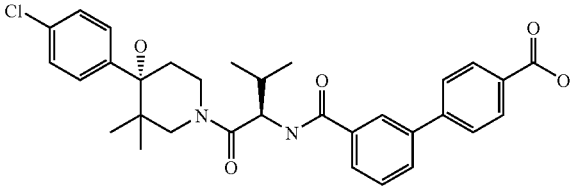 Chiral | 563.32 | 556, Step 3 |
| 931 | 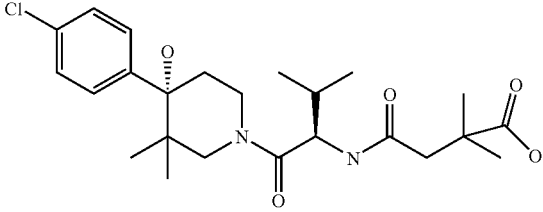 Chiral | 467.29 | 537, Step 1 |
| 932 | 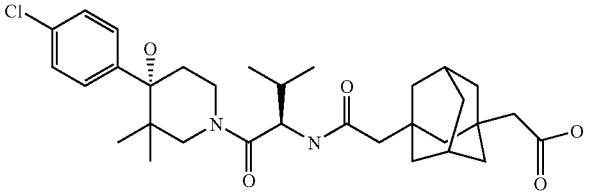 Chiral | 573.34 | 327 |
| 933 | 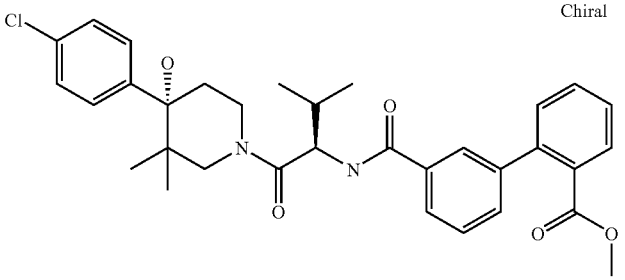 Chiral | 577.31 | 327 |
| 934 | 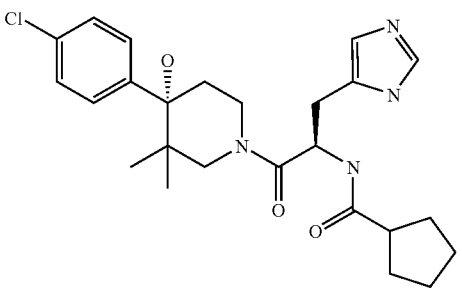 Chiral | 473.28 | 327 |

TABLE 21-continued

| Example | Structure | LCMS (M+) or (M + H)+ | Example for general method of preparation |
|---|---|---|---|
| 935 | Chiral | 563.3 | 327 |
| 936 | Chiral | 550.37 | 535, Step 1 |
| 937 | Chiral | 550.38 | 535, Step 1 |
| 938 | Chiral | 525.24 | 327 |
| 939 | Chiral | 450.26 | 535, Step 2 |

TABLE 21-continued

| Example | Structure | LCMS (M+) or (M + H)+ | Example for general method of preparation |
|---|---|---|---|
| 940 | Chiral | 515.28 | 537, Step 1 |
| 941 | Chiral | 550.37 | 535, Step 1 |
| 942 | Chiral | 550.39 | 535, Step 1 |
| 943 | Chiral | 492.31 | 537, Step 1 |
| 944 | Chiral | 492.32 | 537, Step 1 |
| 945 | Chiral | 450.29 | 535, Step 2 |

TABLE 21-continued

| Example | Structure | LCMS (M+) or (M + H)+ | Example for general method of preparation |
|---|---|---|---|
| 946 | (structure) Chiral | 492.29 | 537, Step 1 |
| 947 | (structure) Chiral | 492.28 | 537, Step 1 |
| 948 | (structure) Chiral | 578.34 | 554, Step 1 |
| 949 | (structure) Chiral | 564.33 | 554, Step 2 |
| 950 | (structure) Chiral | 517.33 | 327 |

TABLE 21-continued

| Example | Structure | LCMS (M+) or (M + H)+ | Example for general method of preparation |
|---|---|---|---|
| 951 | Chiral | 837.43 | 327 |
| 952 | Chiral | 597.32 | 327 |
| 953 | Chiral | 439.17 | 327 |
| 954 | Chiral | 464.25 | 327 |
| 955 | Chiral | 620.13 | 547 |
| 956 | Chiral | 568.12 | 547 |

TABLE 21-continued

| Example | Structure | | LCMS (M+) or (M + H)+ | Example for general method of preparation |
|---|---|---|---|---|
| 957 | 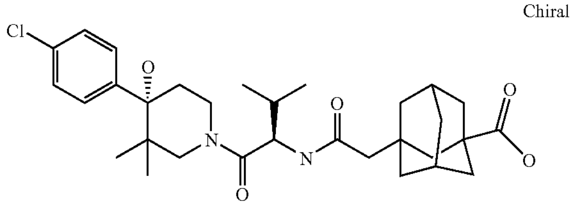 | Chiral | 559.32 | 327 |
| 958 | 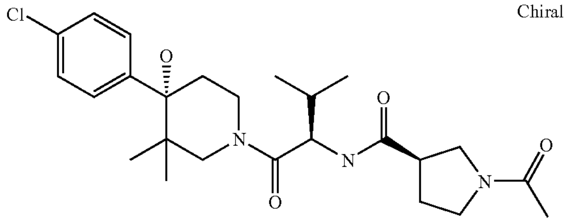 | Chiral | 460.31 | 537, Step 1 |
| 959 | 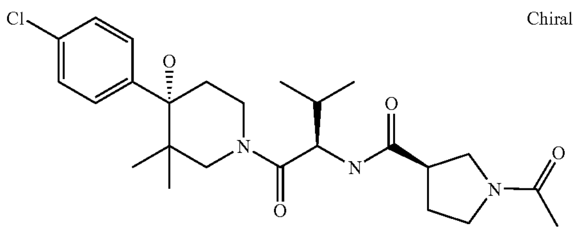 | Chiral | 460.31 | 537, Step 1 |
| 960 | 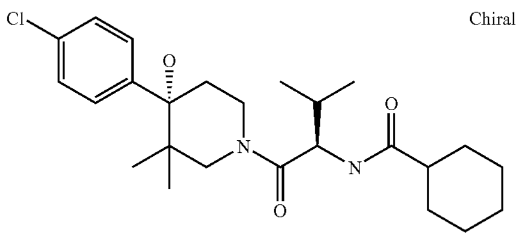 | Chiral | 449.32 | 327 |
| 961 | 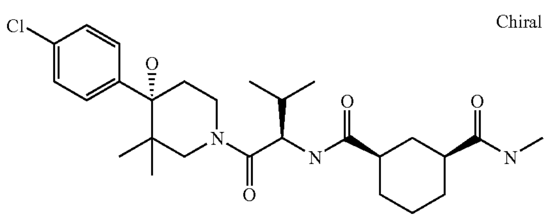 | Chiral | 506.36 | 327 |
| 962 | 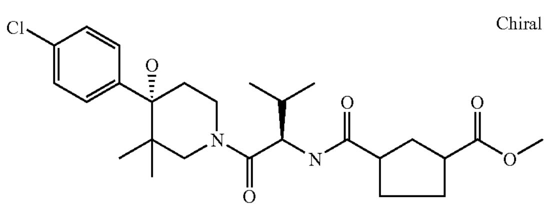 | Chiral | 493.34 | 327 |

TABLE 21-continued

| Example | Structure | LCMS (M+) or (M + H)+ | Example for general method of preparation |
|---|---|---|---|
| 963 | 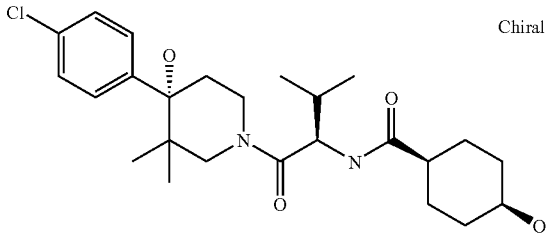 | 465.24 | 327 |
| 964 | 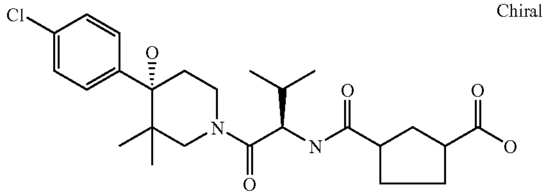 | 479.22 | 327 |
| 965 | 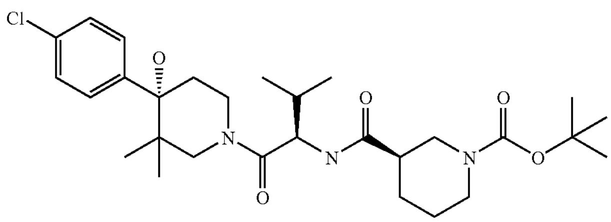 | 550.35 | 535, Step 1 |
| 966 | 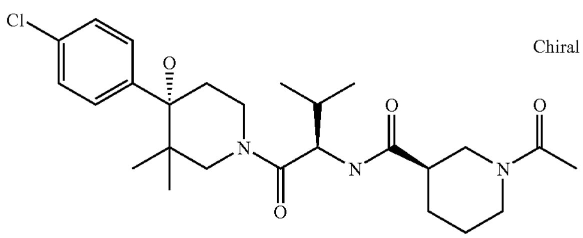 | 492.4 | 535, Step 3 |
| 967 | 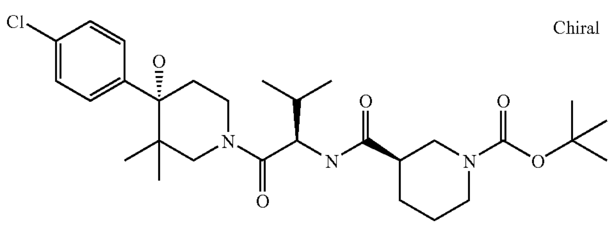 | 550.44 | 535, Step 1 |
| 968 | 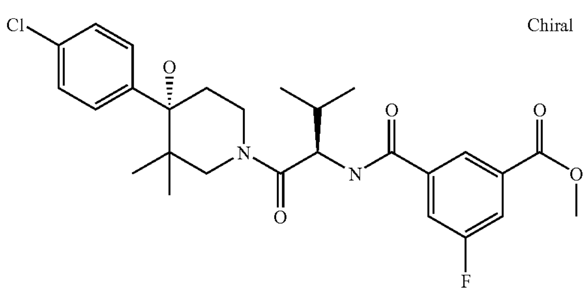 | 519.36 | 327 |

TABLE 21-continued

| Example | Structure | LCMS (M+) or (M + H)+ | Example for general method of preparation |
|---|---|---|---|
| 969 | 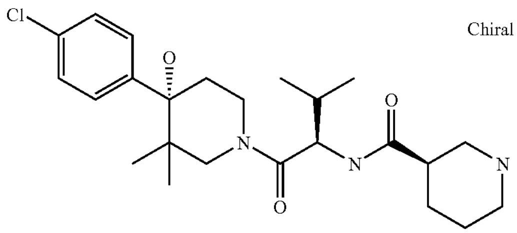 | 450.43 | 535, Step 2 |
| 970 | 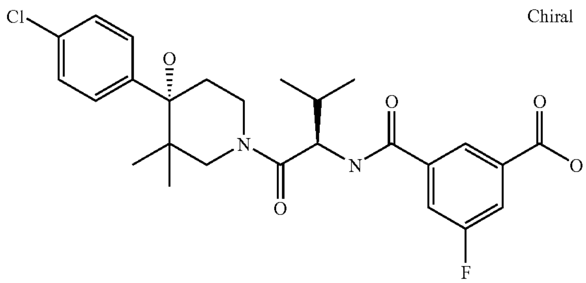 | 503.31 | 327 |
| 971 | 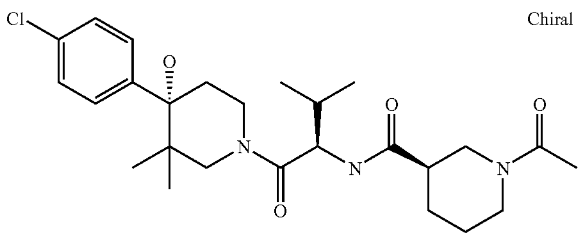 | 492.39 | 535, Step 3 |
| 972 | 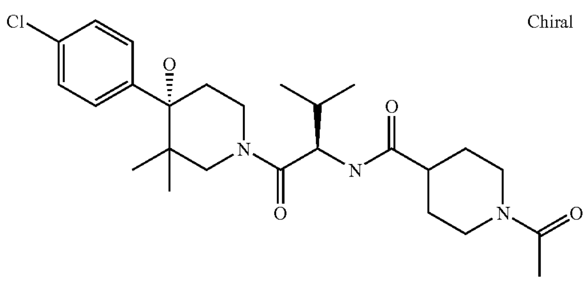 | 492.36 | 327 |
| 973 | 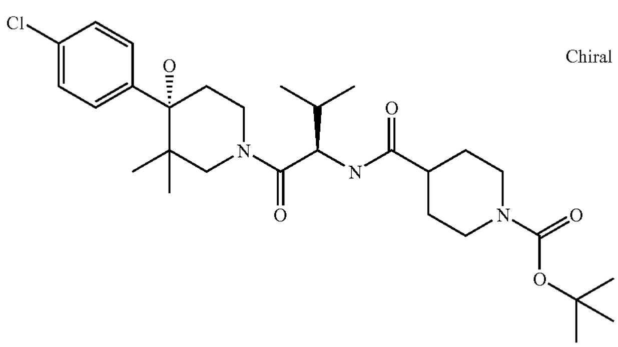 | 550.45 | 535, Step 1 |

TABLE 21-continued

| Example | Structure | LCMS (M+) or (M + H)+ | Example for general method of preparation |
|---|---|---|---|
| 974 | Chiral | 550.42 | 552 |
| 975 | Chiral | 522.39 | 546, Step 1 |
| 976 | Chiral | 450.39 | 552, Step 2 |
| 977 | Chiral | 422.32 | 546, Step 2 |
| 978 | Chiral | 465.38 | 327 |

TABLE 21-continued

| Example | Structure | LCMS (M+) or (M + H)+ | Example for general method of preparation |
|---------|-----------|----------------------|-------------------------------------------|
| 979 | Chiral | 492.4 | 552, Step 1 |
| 980 | Chiral | 550.49 | 551 |
| 981 | Chiral | 550.48 | 551 |
| 982 | Chiral | 481.33 | 537 |
| 983 | Chiral | 453.35 | 540 |

TABLE 21-continued

| Example | Structure | LCMS (M+) or (M + H)+ | Example for general method of preparation |
|---|---|---|---|
| 984 | (Chiral structure) | 450.37 | 551 |
| 985 | (Chiral structure) | 450.35 | 550 |
| 986 | (structure) | 531.45 | 533 |
| 987 | (Chiral structure) | 466.32 | 327 |
| 988 | (Chiral structure) | 565.38 | 540 |
| 989 | (Chiral structure) | 465.44 | 540 |

TABLE 21-continued

| Example | Structure | LCMS (M+) or (M + H)+ | Example for general method of preparation |
|---|---|---|---|
| 990 | Chiral | 480.38 | 536 |
| 991 | Chiral | 452.33 | 536 |
| 992 | Chiral | 452.34 | 536 |
| 993 | Chiral | 489.35 | 536 |
| 994 | Chiral | 480.44 | 536 |
| 995 | Chiral | 480.44 | 536 |

TABLE 21-continued

| Example | Structure | | LCMS (M+) or (M + H)+ | Example for general method of preparation |
|---|---|---|---|---|
| 996 | 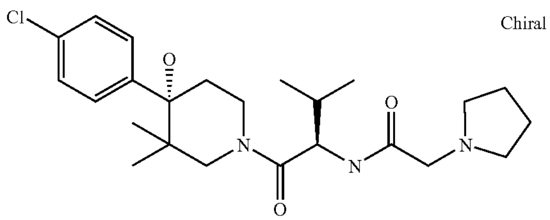 | Chiral | 450.47 | 327 |
| 997 | 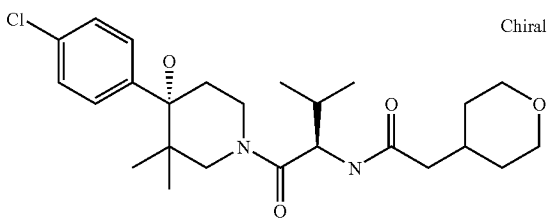 | Chiral | 465.44 | 327 |
| 998 | 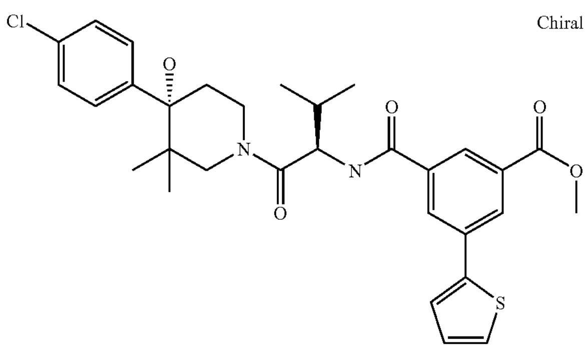 | Chiral | 583.3 | 327 |
| 999 | 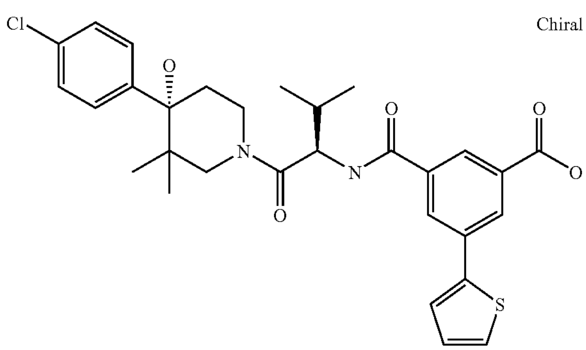 | Chiral | 569.36 | 327 |
| 1000 | 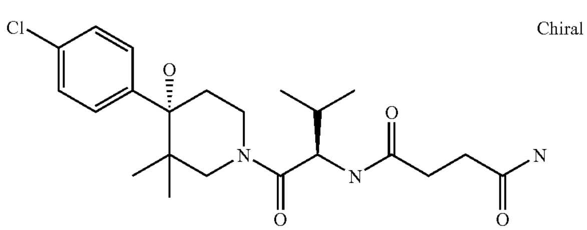 | Chiral | 438.41 | 327 |

TABLE 21-continued

| Example | Structure | LCMS (M+) or (M + H)+ | Example for general method of preparation |
|---|---|---|---|
| 1001 | Chiral | 450.41 | 327 |
| 1002 | Chiral | 464.47 | 327 |
| 1003 | Chiral | 494.42 | 327 |
| 1004 | Chiral | 397.37 | 327 |
| 1005 | Chiral | 447.26 | 327 |
| 1006 | Chiral | 449.25 | 327 |

TABLE 21-continued

| Example | Structure | LCMS (M+) or (M + H)+ | Example for general method of preparation |
|---|---|---|---|
| 1007 | (Chiral) | 466.25 | 536 |
| 1008 | (Chiral) | 466.41 | 536 |
| 1009 | (Chiral) | 466.26 | 536 |
| 1010 | (Chiral) | 480.29 | 536 |
| 1011 | (Chiral) | 474.21 | 327 |
| 1012 | (Chiral) | 513.35 | 327 |

TABLE 21-continued

| Example | Structure | LCMS (M+) or (M + H)+ | Example for general method of preparation |
|---|---|---|---|
| 1013 | Chiral | 507.31 | 327 |
| 1014 | Chiral | 447.18 | 327 |
| 1015 | Chiral | 461.17 | 327 |
| 1016 | Chiral | 496.12 | 327 |
| 1017 | Chiral | 510.24 | 327 |
| 1018 | Chiral | 448.24 | 327 |

TABLE 21-continued

| Example | Structure | LCMS (M+) or (M + H)+ | Example for general method of preparation |
|---|---|---|---|
| 1019 | Chiral | 549.48 | 535 |
| 1020 | Chiral | 549.49 | 552 |
| 1021 | Chiral | 549.48 | 552 |
| 1022 | Chiral | 531.21 | 534, Step 2 |
| 1023 | Chiral | 531.29 | 534, Step 2 |
| 1024 | Chiral | 531.3 | 534, Step 2 |

TABLE 21-continued

| Example | Structure | LCMS (M⁺) or (M + H)⁺ | Example for general method of preparation |
|---------|-----------|----------------------|-------------------------------------------|
| 1025 | Chiral | 517.43 | 534, Step 3 |
| 1026 | Chiral | 517.4 | 534, Step 3 |
| 1027 | Chiral | 524.13 | 327 |
| 1028 | Chiral | 509.15 | 327 |
| 1029 | Chiral | 425.22 | Preparation C |

TABLE 21-continued

| Example | Structure | LCMS (M+) or (M + H)+ | Example for general method of preparation |
|---|---|---|---|
| 1030 | Chiral | 437.2 | Preparation C |
| 1031 | Chiral | 499.18 | 327 |
| 1032 | Chiral | 421.09 | 327 |
| 1033 | Chiral | 455.16 | 327 |
| 1034 | Chiral | 681.37 | 327 |
| 1035 | Chiral | 437.11 | 327 |
| 1036 | Chiral | 437.12 | 327 |

TABLE 21-continued

| Example | Structure | LCMS (M+) or (M + H)+ | Example for general method of preparation |
|---|---|---|---|
| 1037 | 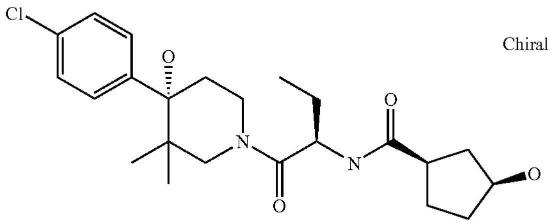 | 437.24 | 327 |
| 1038 | 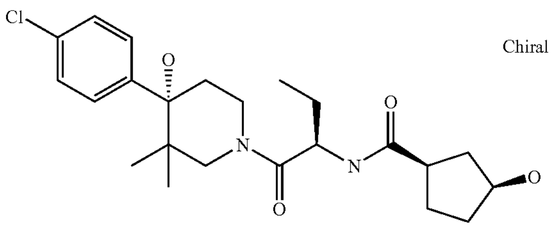 | 437.16 | 327 |
| 1039 | 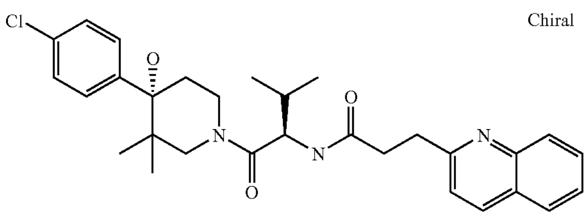 | 522.3 | 327 |
| 1040 | 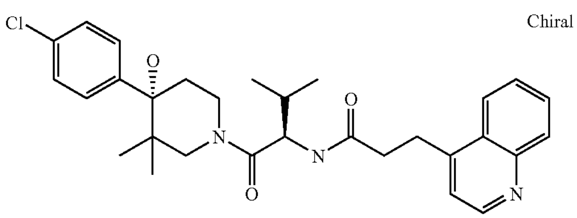 | 522.24 | 327 |
| 1041 | 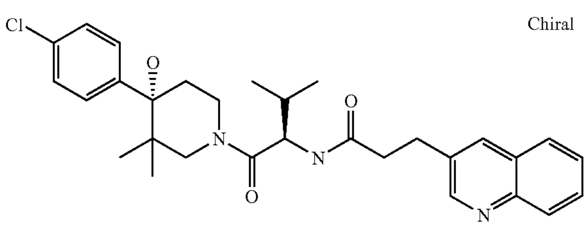 | 522.24 | 327 |
| 1042A | 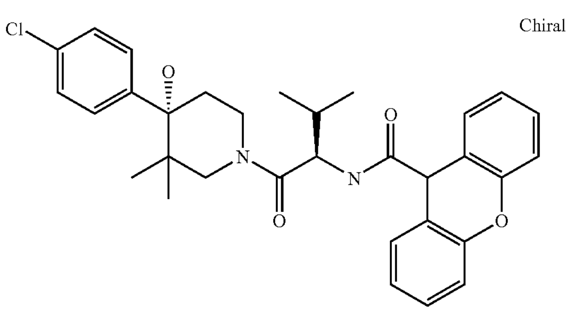 | 547.13 | 327 |

TABLE 21-continued

| Example | Structure | LCMS (M+) or (M + H)+ | Example for general method of preparation |
|---|---|---|---|
| 1042B | Chiral | 483.27 | 327 |
| 1043 | Chiral | 467.23 | 327 |
| 1044 | Chiral | 533.21 | 327 |
| 1045 | Chiral | 509.15 | 327 |

TABLE 21-continued

| Example | Structure | LCMS (M+) or (M + H)+ | Example for general method of preparation |
|---|---|---|---|
| 1046 | Chiral | 519.22 | 327 |
| 1047 | Chiral | 747.34 | 327 |
| 1048 | 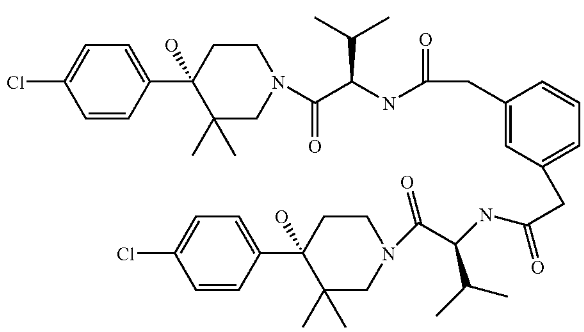 | 835.47 | 327 |
| 1049 | Chiral | 470.42 | 327 |
| 1050 | 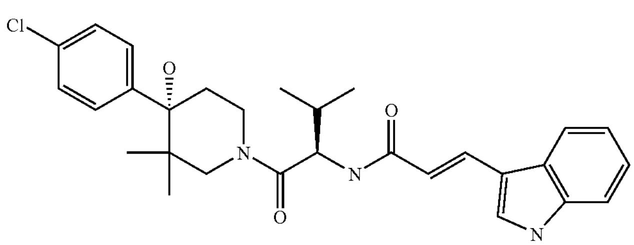 | 508.43 | 327 |

TABLE 21-continued

| Example | Structure | LCMS (M+) or (M + H)+ | Example for general method of preparation |
|---|---|---|---|
| 1051 | Chiral | 510.45 | 327 |
| 1052 | 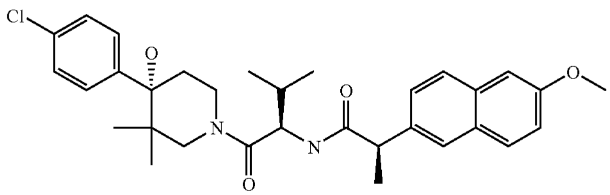 | 551.48 | 327 |
| 1053 | Chiral | 492.46 | 327 |
| 1054 | 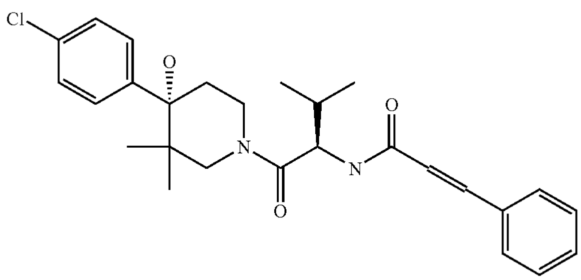 | 467.43 | 327 |
| 1055 | Chiral | 511.4 | 327 |
| 1056 | Chiral | 511.47 | 327 |

TABLE 21-continued

| Example | Structure | LCMS (M+) or (M + H)+ | Example for general method of preparation |
|---|---|---|---|
| 1057 | Chiral structure | 459.38 | 327 |
| 1058 | Chiral structure | 520.39 | 327 |
| 1059 | Chiral structure | 520.38 | 327 |
| 1060 | Chiral structure | 520.38 | 327 |
| 1061 | Chiral structure | 461.43 | 327 |
| 1062 | Chiral structure | 497.43 | 327 |

TABLE 21-continued

| Example | Structure | LCMS (M+) or (M + H)+ | Example for general method of preparation |
|---|---|---|---|
| 1063 | Chiral | 575.49 | 327 |
| 1064 | 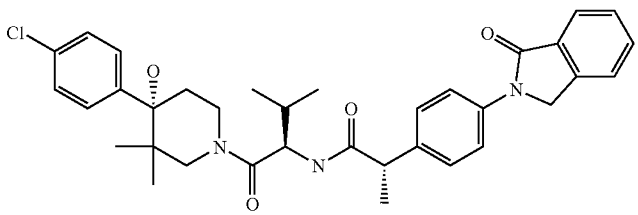 | 602/604.47 | 327 |
| 1065 | Chiral | 472.17 | 327 |
| 1066 | Chiral | 472.17 | 327 |
| 1067 | Chiral | 472.16 | 327 |
| 1068 | Chiral | 493.27 | |

TABLE 21-continued

| Example | Structure | LCMS (M+) or (M + H)+ | Example for general method of preparation |
|---|---|---|---|
| 1069 | (Chiral) | 507.28 | |
| 1070 | (Chiral) | 479.38 | |
| 1071 | (Chiral) | 417.46 | |
| 1072 | (Chiral) | 445.45 | |
| 1073 | (Chiral) | 431.42 | |

TABLE 21-continued
| Example | Structure | LCMS (M+) or (M + H)+ | Example for general method of preparation |
|---|---|---|---|
| 1074 | 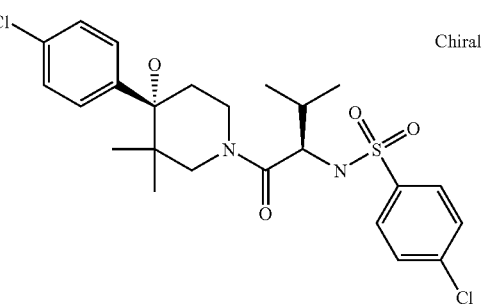 Chiral | 513.23 | |
| 1075 | 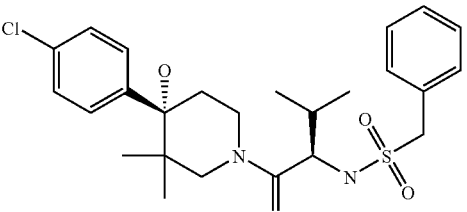 Chiral | 493.33 | |
| 1076 | 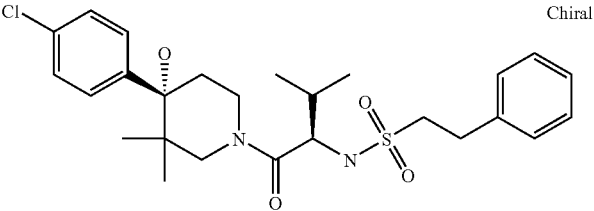 Chiral | 507.29 | |
| 1077 | 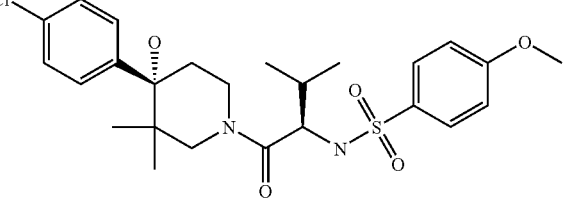 Chiral | 509.27 | |
| 1078 | 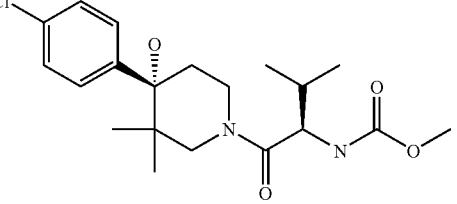 Chiral | 397.46 | |

TABLE 21-continued

| Example | Structure | LCMS (M+) or (M + H)+ | Example for general method of preparation |
|---------|-----------|------------------------|-------------------------------------------|
| 1079 | Chiral | 493.29 | |
| 1080 | Chiral | 489.34 | |
| 1081 | Chiral | 459.39 | |
| 1082 | Chiral | 473.38 | |
| 1083 | Chiral | 439.47 | |

TABLE 21-continued
| Example | Structure | | LCMS (M+) or (M + H)+ | Example for general method of preparation |
|---|---|---|---|---|
| 1084 | 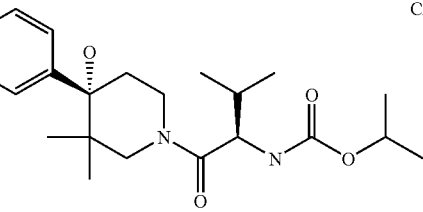 | Chiral | 425.48 | |
| 1085 | 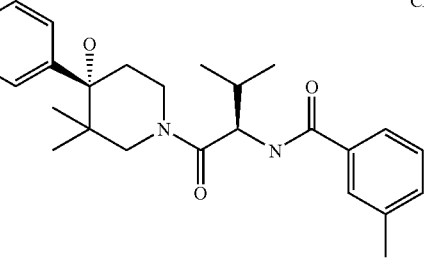 | Chiral | 457.45 | |
| 1086 | 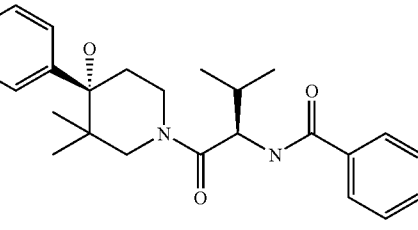 | Chiral | 461.43 | |
| 1087 | 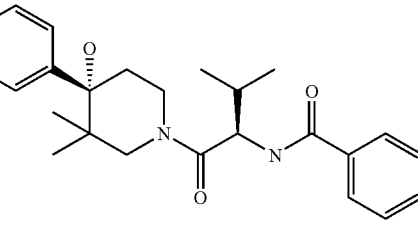 | Chiral | 457.45 | |
| 1088 | 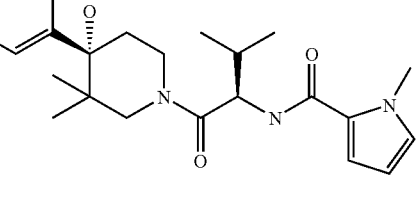 | Chiral | 446.46 | |
| 1089 | 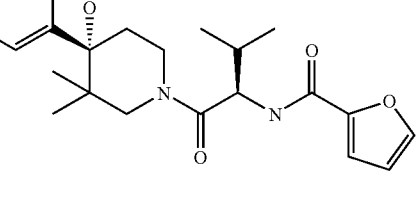 | Chiral | 433.47 | |

TABLE 21-continued

| Example | Structure | | LCMS (M+) or (M + H)+ | Example for general method of preparation |
|---|---|---|---|---|
| 1090 | 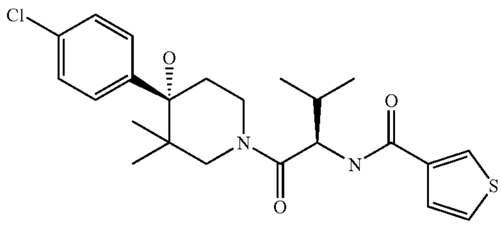 | Chiral | 449.41 | |
| 1091 | 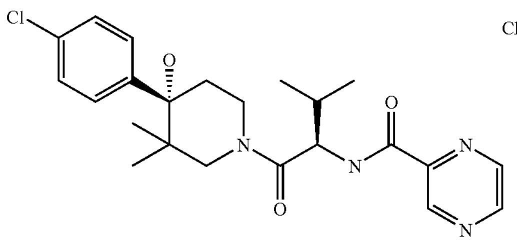 | Chiral | 445.46 | |
| 1092 | 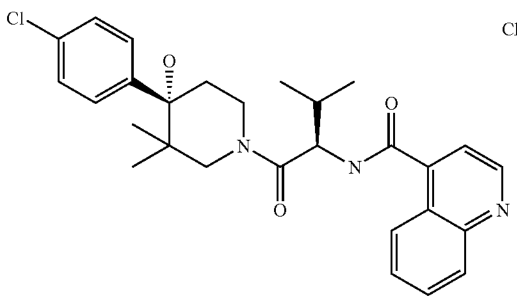 | Chiral | 494.37 | |
| 1093 | 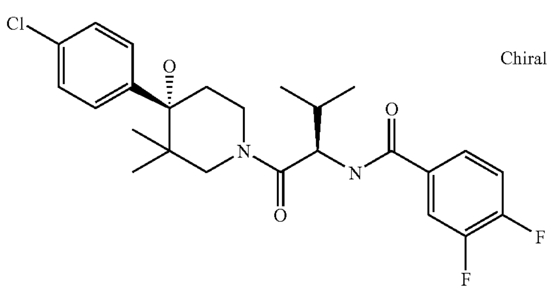 | Chiral | 479.37 | |
| 1094 | 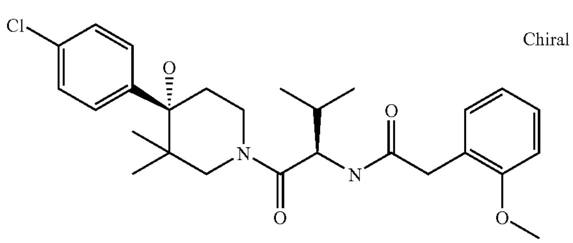 | Chiral | 487.39 | |

TABLE 21-continued

| Example | Structure | LCMS (M+) or (M + H)+ | Example for general method of preparation |
|---|---|---|---|
| 1095 | Chiral | 424.50 | |
| 1096 | Chiral | 395.51 | |
| 1097 | Chiral | 437.51 | |
| 1098 | Chiral | 449.50 | |
| 1099 | Chiral | 421.51 | |
| 1100 | Chiral | 407.50 | |

TABLE 21-continued

| Example | Structure | LCMS (M+) or (M + H)+ | Example for general method of preparation |
|---------|-----------|----------------------|-------------------------------------------|
| 1101 | Chiral | 457.45 | |
| 1102 | Chiral | 449.40 | |
| 1103 | Chiral | 499.34 | |
| 1104 | Chiral | 485.42 | |
| 1105 | Chiral | 471.43 | |
| 1106 | Chiral | 491.34 | |

TABLE 21-continued
| Example | Structure | LCMS (M+) or (M + H)+ | Example for general method of preparation |
|---|---|---|---|
| 1107 | 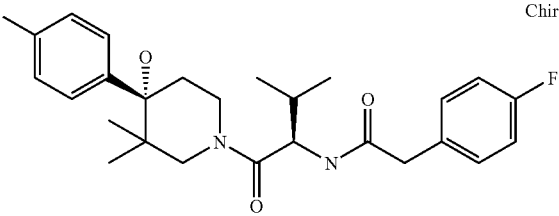 Chiral | 475.42 | |
| 1108 | 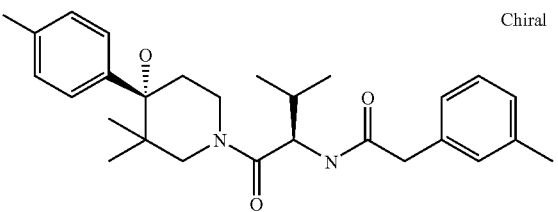 Chiral | 471.44 | |
| 1109 | 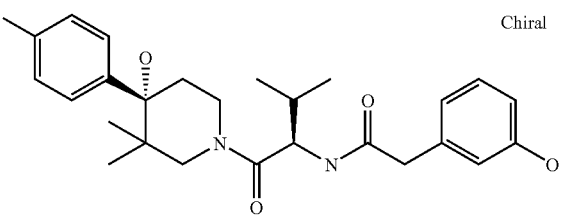 Chiral | 473.40 | |
| 1110 | 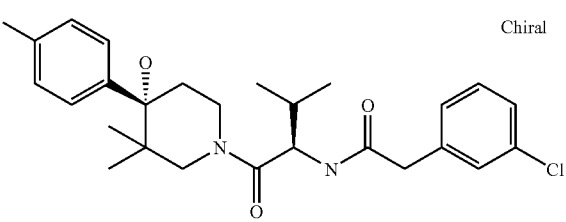 Chiral | 491.35 | |
| 1111 | 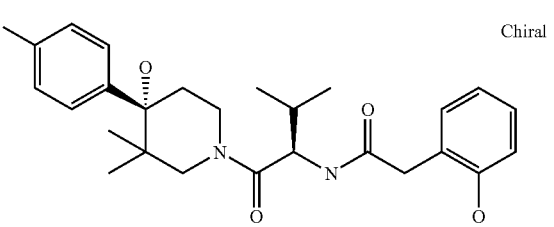 Chiral | 473.43 | |
| 1112 | 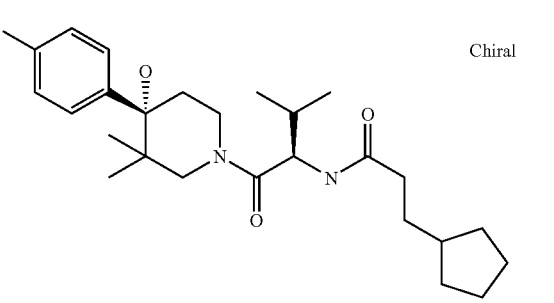 Chiral | 463.48 | |

TABLE 21-continued

| Example | Structure | | LCMS (M+) or (M + H)+ | Example for general method of preparation |
|---|---|---|---|---|
| 1113 | [Structure with 4-chlorophenyl, hydroxypiperidine, dimethyl, valine, methyl succinate] | Chiral | 453.45 | |
| 1114 | [Structure with 4-chlorophenyl, hydroxypiperidine, dimethyl, valine, phenoxyacetyl] | Chiral | 473.41 | |
| 1115 | [Structure with 4-chlorophenyl, hydroxypiperidine, dimethyl, valine, tetrazolylmethyl] | Chiral | 449.45 | |
| 1116 | [Structure with 4-chlorophenyl, hydroxypiperidine, dimethyl, valine, methoxypropanoyl] | Chiral | 425.48 | |
| 1117 | [Structure with 4-chlorophenyl, hydroxypiperidine, dimethyl, valine, cyclopropylacetyl] | Chiral | 421.48 | |
| 1118 | [Structure with 4-chlorophenyl, hydroxypiperidine, dimethyl, valine, pentanoyl] | Chiral | 423.52 | |

TABLE 21-continued

| Example | Structure | LCMS (M+) or (M + H)+ | Example for general method of preparation |
|---|---|---|---|
| 1119 | Chiral | 499.31 | |
| 1120 | Chiral | 483.43 | |
| 1121 | Chiral | 494.36 | |
| 1122 | Chiral | 485.42 | |
| 1123 | Chiral | 485.43 | |

TABLE 21-continued

| Example | Structure | LCMS (M+) or (M + H)+ | Example for general method of preparation |
|---|---|---|---|
| 1124 | Chiral | 463.50 | |
| 1125 | Chiral | 471.48 | |
| 1126 | Chiral | 468.44 | |
| 1127 | Chiral | 535.38 | |
| 1128 | Chiral | 482.45 | |

TABLE 21-continued

| Example | Structure | | LCMS (M+) or (M + H)+ | Example for general method of preparation |
|---|---|---|---|---|
| 1129 | [structure] | Chiral | 494.42 | |
| 1130 | [structure] | Chiral | 527.34 | |
| 1131 | [structure] | Chiral | 521.33 | |
| 1132 | [structure] | Chiral | 509.37 | |

TABLE 21-continued

| Example | Structure | LCMS (M⁺) or (M + H)⁺ | Example for general method of preparation |
|---------|-----------|-----------------------|-------------------------------------------|
| 1133 | Chiral | 526.31 | |
| 1134 | 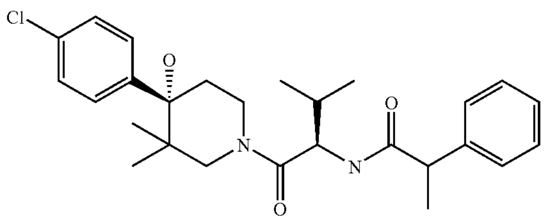 | 471.45 | |
| 1135 | Chiral | 547.35 | |
| 1136 | 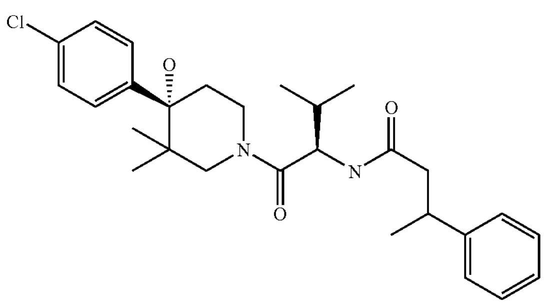 | 485.44 | |
| 1137 | Chiral | 475.40 | |

TABLE 21-continued
| Example | Structure | LCMS (M+) or (M + H)+ | Example for general method of preparation |
|---|---|---|---|
| 1138 | 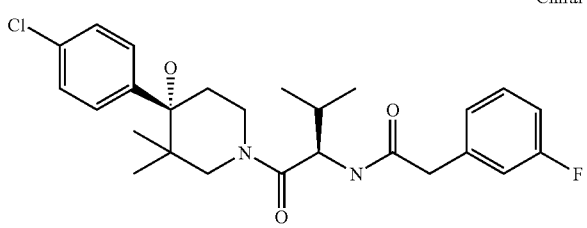 Chiral | 475.42 | |
| 1139 | 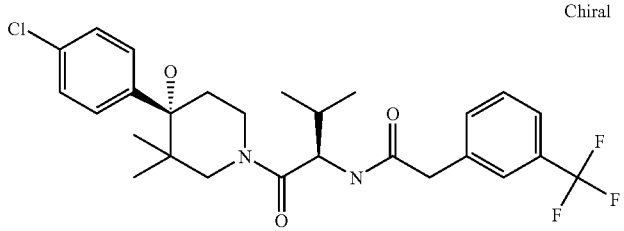 Chiral | 525.30 | |
| 1140 | 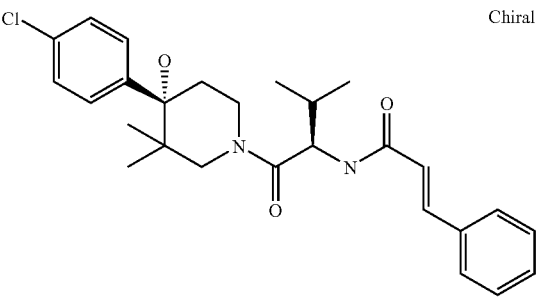 Chiral | 469.41 | |
| 1141 | 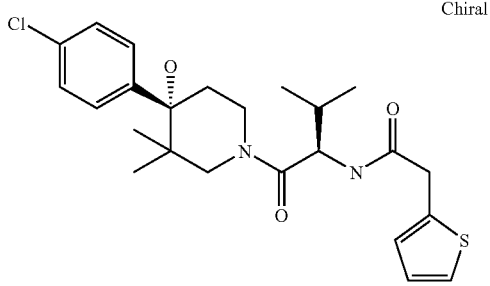 Chiral | 463.40 | |
| 1142 | 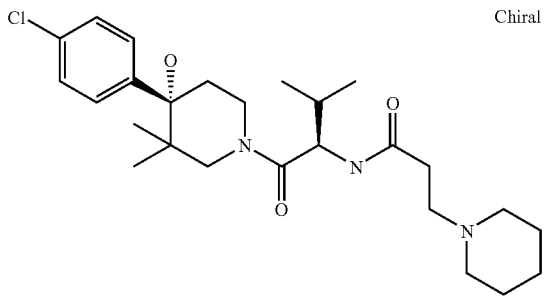 Chiral | 478.50 | |

TABLE 21-continued
| Example | Structure | LCMS (M+) or (M + H)+ | Example for general method of preparation |
|---|---|---|---|
| 1143 | 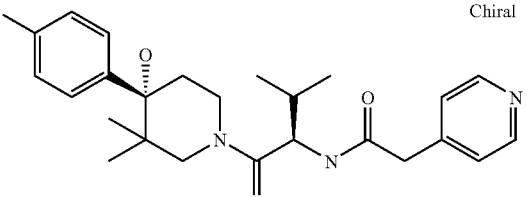 Chiral | 458.49 | |
| 1144 | 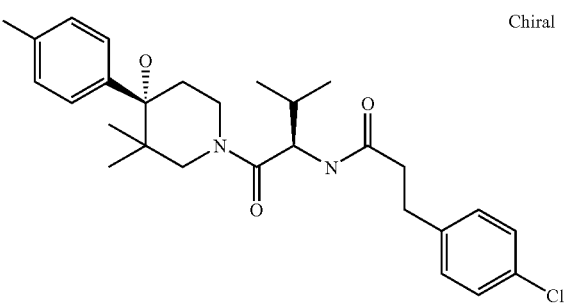 Chiral | 505.35 | |
| 1145 | 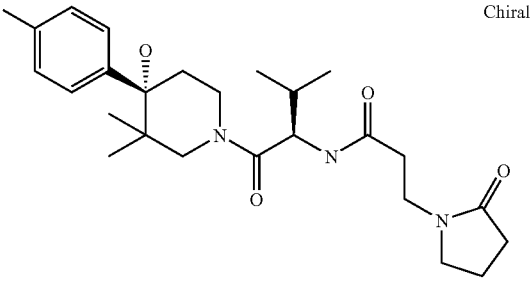 Chiral | 478.48 | |
| 1146 | 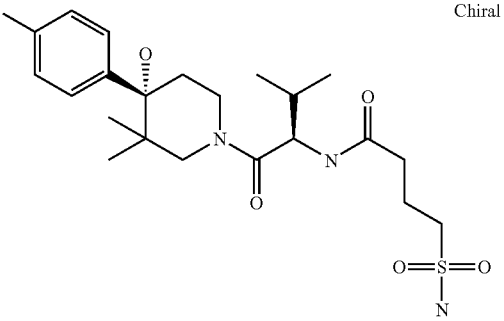 Chiral | 488.39 | |
| 1147 | 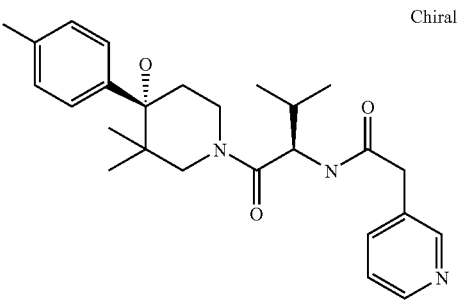 Chiral | 458.48 | |

TABLE 21-continued

| Example | Structure | | LCMS (M+) or (M + H)+ | Example for general method of preparation |
|---|---|---|---|---|
| 1148 | [Structure: 4-chlorophenyl, hydroxy, dimethyl piperidine with valine amide linked to diphenylacetamide] | Chiral | 533.34 | |
| 1149 | [Structure: 4-chlorophenyl, hydroxy, dimethyl piperidine with valine amide linked to 3-(4-methoxyphenyl)propanamide] | Chiral | 501.39 | |
| 1150 | [Structure: 4-chlorophenyl, hydroxy, dimethyl piperidine with valine amide linked to 1-methylcyclopropanecarboxamide] | Chiral | 421.50 | |
| 1151 | [Structure: 4-chlorophenyl, hydroxy, dimethyl piperidine with valine amide linked to 2-bromobenzamide] | Chiral | 523.23 | |
| 1152 | [Structure: 4-chlorophenyl, hydroxy, dimethyl piperidine with valine amide linked to 2-(cyclopent-2-enyl)acetamide] | | 447.49 | |

TABLE 21-continued

| Example | Structure | LCMS (M+) or (M + H)+ | Example for general method of preparation |
|---|---|---|---|
| 1153 | Chiral | 471.44 | |
| 1154 | Chiral | 471.45 | |
| 1155 | Chiral | 475.43 | |
| 1156 | Chiral | 489.43 | |
| 1157 | Chiral | 515.46 | |

TABLE 21-continued

| Example | Structure | LCMS (M+) or (M + H)+ | Example for general method of preparation |
|---|---|---|---|
| 1158 | 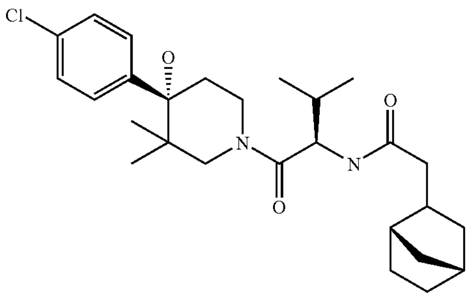 | 475.52 | |
| 1159 | Chiral | 547.34 | |
| 1160 | Chiral | 482.45 | |
| 1161 | Chiral | 473.46 | |
| 1162 | Chiral | 499.47 | |

TABLE 21-continued
| Example | Structure | LCMS (M+) or (M + H)+ | Example for general method of preparation |
|---------|-----------|------------------------|-------------------------------------------|
| 1163 | 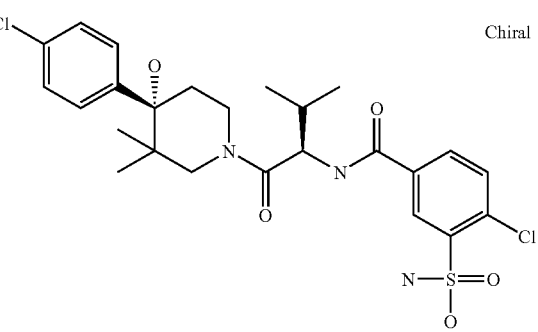 Chiral | 556.25 | |
| 1164 | 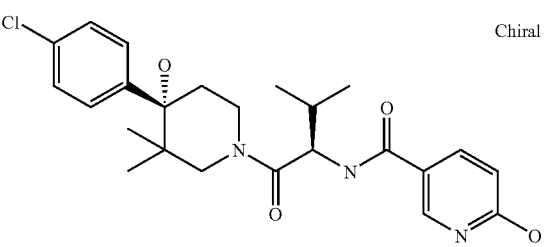 Chiral | 460.47 | |
| 1165 | 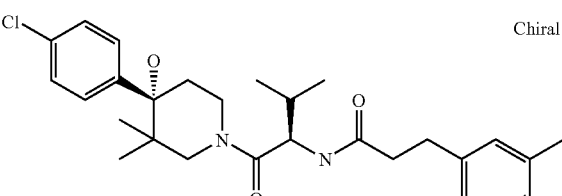 Chiral | 485.47 | |
| 1166 | 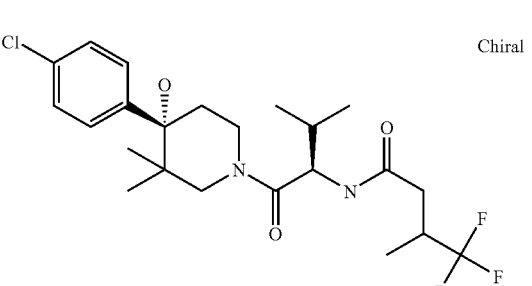 Chiral | 477.43 | |
| 1167 | 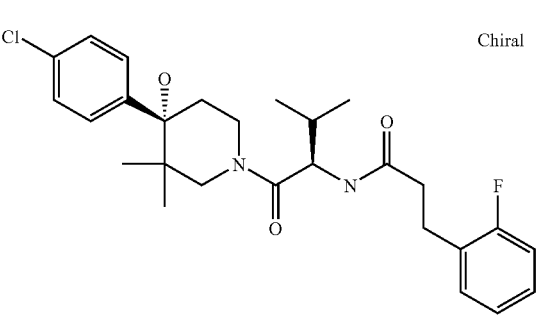 Chiral | 489.40 | |

TABLE 21-continued
| Example | Structure | LCMS (M+) or (M + H)+ | Example for general method of preparation |
|---|---|---|---|
| 1168 | 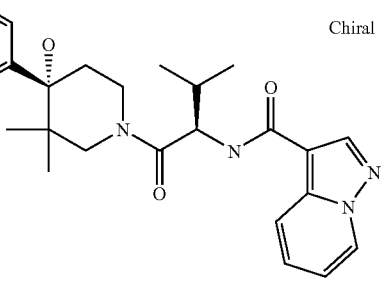 | 483.40 | |
| 1169 | 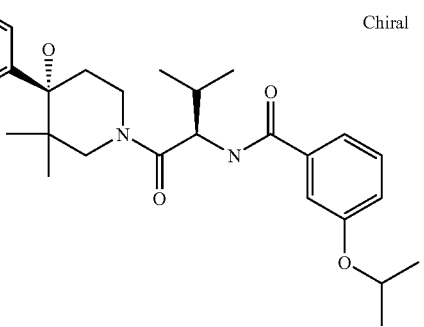 | 501.38 | |
| 1170 | 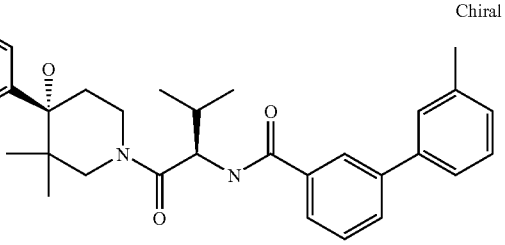 | 533.34 | |
| 1171 | 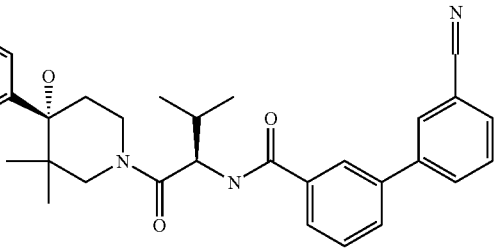 | 544.32 | |
| 1172 | 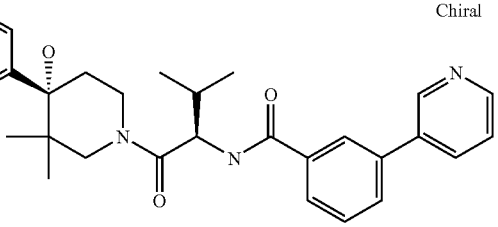 | 520.34 | |

TABLE 21-continued

| Example | Structure | LCMS (M+) or (M + H)+ | Example for general method of preparation |
|---|---|---|---|
| 1173 | Chiral | 468.39 | |
| 1174 | 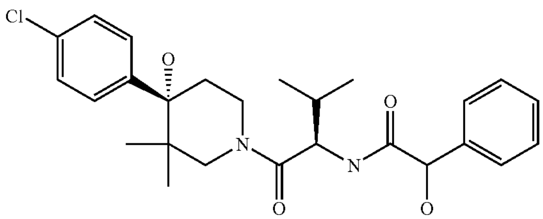 | 473.40 | |
| 1175 | Chiral | 493.31 | |
| 1176 | Chiral | 477.36 | |
| 1177 | Chiral | 458.43 | |
| 1178 | Chiral | 526.36 | |

TABLE 21-continued

| Example | Structure | | LCMS (M+) or (M + H)+ | Example for general method of preparation |
|---|---|---|---|---|
| 1179 | 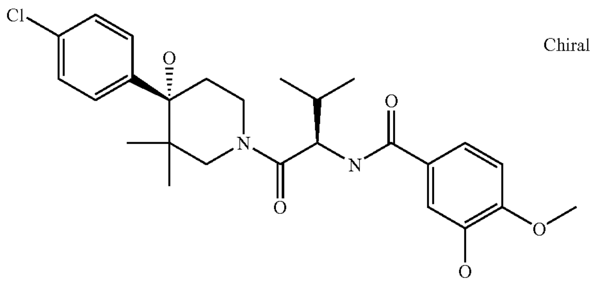 | Chiral | 489.36 | |
| 1180 | 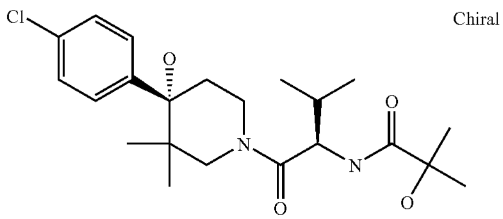 | Chiral | 425.47 | |
| 1181 | 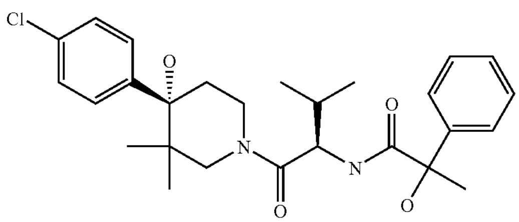 | | 487.41 | |
| 1182 | 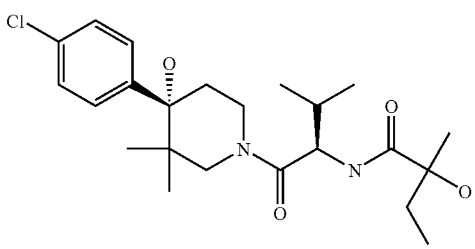 | | 439.48 | |
| 1183 | 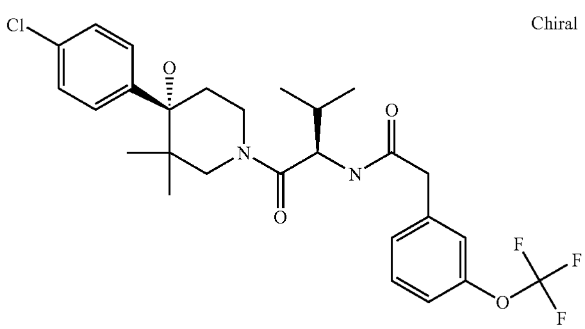 | Chiral | 541.25 | |

TABLE 21-continued

| Example | Structure | LCMS (M+) or (M + H)+ | Example for general method of preparation |
|---|---|---|---|
| 1184 | Chiral | 482.38 | |
| 1185 | 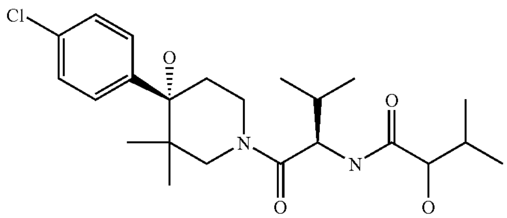 | 439.48 | |
| 1186 | Chiral | 462.41 | |
| 1187 | Chiral | 549.30 | |
| 1188 | Chiral | 533.33 | |

TABLE 21-continued

| Example | Structure | LCMS (M+) or (M + H)+ | Example for general method of preparation |
|---|---|---|---|
| 1189 | Chiral | 535.30 | |
| 1190 | Chiral | 549.29 | |
| 1191 | Chiral | 549.29 | |
| 1192 | Chiral | 485.41 | |
| 1193 | Chiral | 485.42 | |

TABLE 21-continued

| Example | Structure | LCMS (M+) or (M + H)+ | Example for general method of preparation |
|---|---|---|---|
| 1194 | 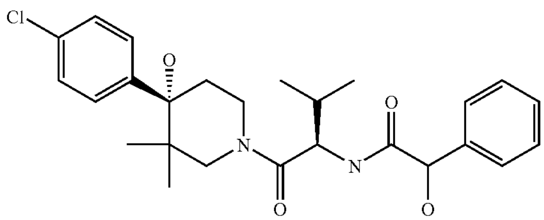 | 473.41 | |
| 1195 | 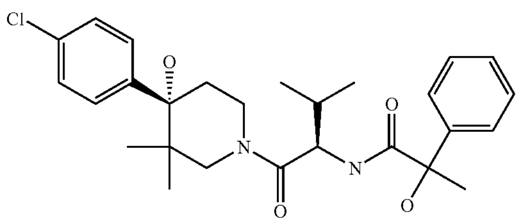 | 487.43 | |
| 1196 | 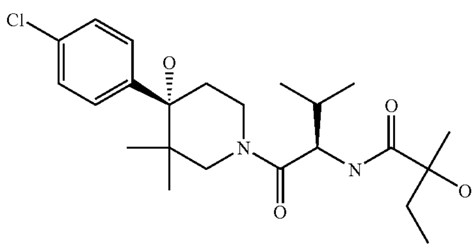 | 439.48 | |
| 1197 | 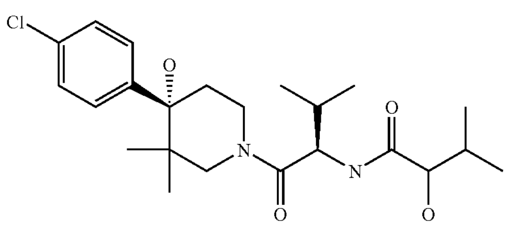 | 439.48 | |
| 1198 | 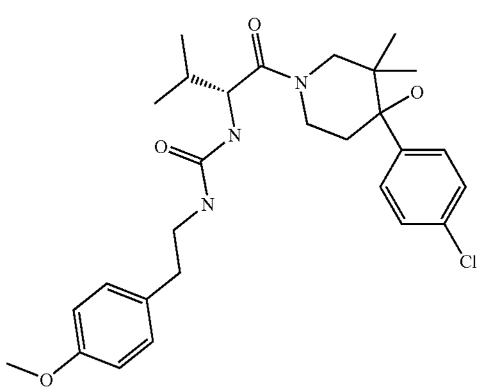 | 516.34 | |

TABLE 21-continued

| Example | Structure | LCMS (M⁺) or (M + H)⁺ | Example for general method of preparation |
|---|---|---|---|
| 1199 | 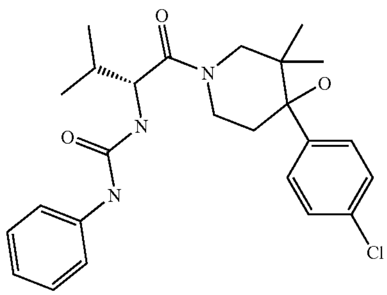 | 458.41 | |
| 1200 | 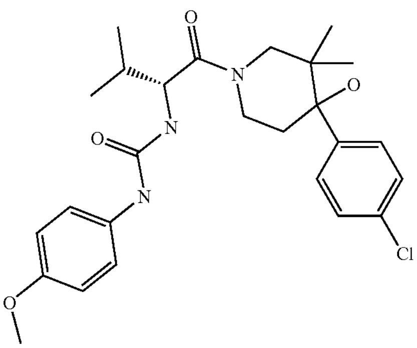 | 488.37 | |
| 1201 | 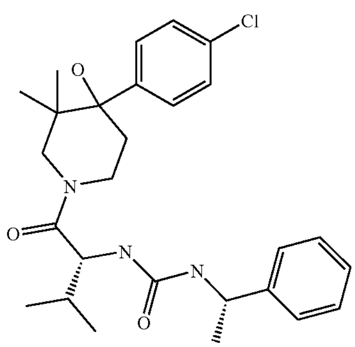 | 486.38 | |
| 1202 | 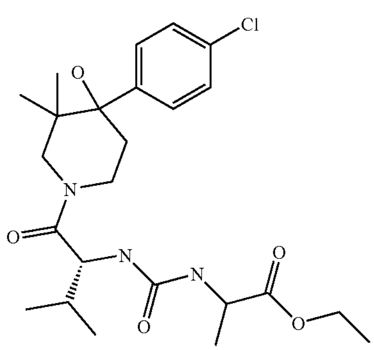 | 482.39 | |

TABLE 21-continued

| Example | Structure | LCMS (M+) or (M + H)+ | Example for general method of preparation |
|---|---|---|---|
| 1203 | 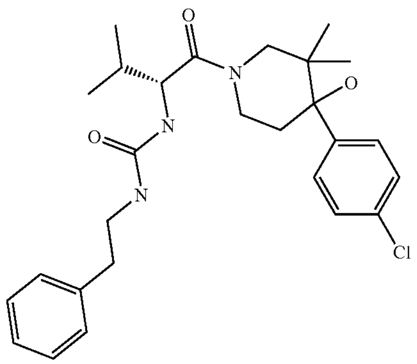 | 486.39 | |
| 1204 | 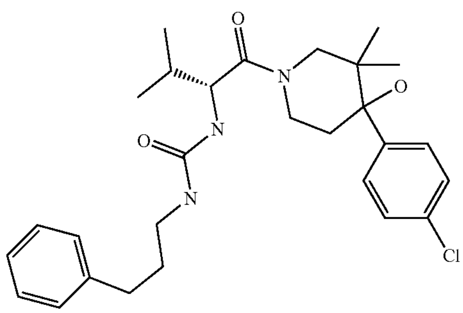 | 500.39 | |
| 1205 | 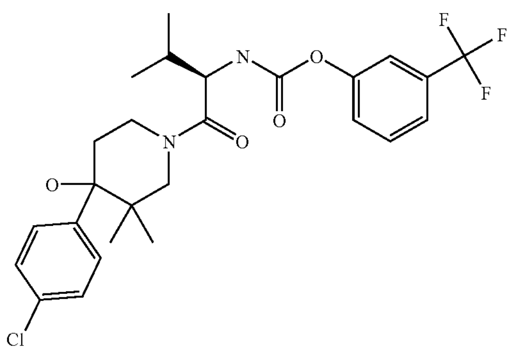 | 527.27 | |
| 1206 | 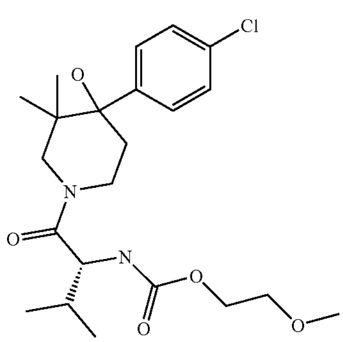 | 441.45 | |

TABLE 21-continued

| Example | Structure | LCMS (M+) or (M + H)+ | Example for general method of preparation |
|---------|-----------|----------------------|-------------------------------------------|
| 1207 | 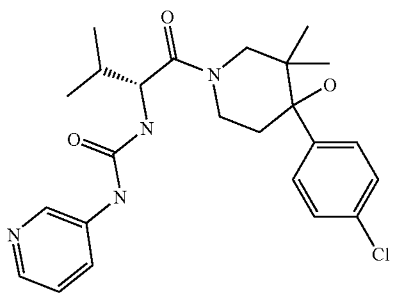 | 459.44 | |
| 1208 | 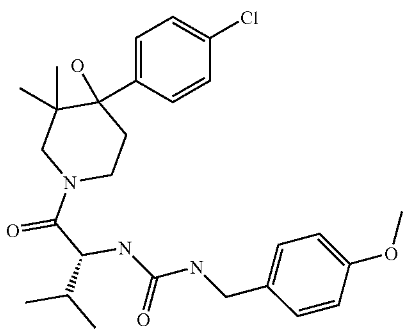 | 502.36 | |
| 1209 | 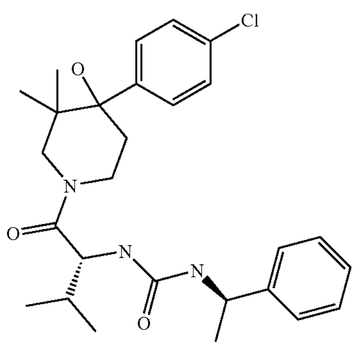 | 486.40 | |
| 1210 | 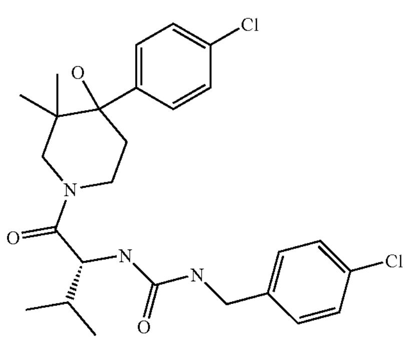 | 506.30 | |

TABLE 21-continued

| Example | Structure | LCMS (M+) or (M + H)+ | Example for general method of preparation |
|---------|-----------|------------------------|---------------------------------------------|
| 1211 | Chiral | 626.37 | |
| 1212 | Chiral | 578.34 | |
| 1213 | Chiral | 630.33 | |
| 1214 | Chiral | 618.29 | |
| 1215 | Chiral | 676.35 | |
| 1216 | Chiral | 534.46 | |

TABLE 21-continued

| Example | Structure | LCMS (M+) or (M + H)+ | Example for general method of preparation |
|---|---|---|---|
| 1217 | Chiral | 537.47 | |
| 1218 | Chiral | 553.44 | |
| 1219 | Chiral | 533.52 | |
| 1220 | Chiral | 553.43 | |
| 1221 | Chiral | 576.48 | |

TABLE 21-continued

| Example | Structure | LCMS (M+) or (M + H)+ | Example for general method of preparation |
|---------|-----------|------------------------|--------------------------------------------|
| 1222 | Chiral | 537.46 | |
| 1223 | Chiral | 553.43 | |
| 1224 | Chiral | 537.47 | |
| 1225 | Chiral | 535.47 | |
| 1226 | Chiral | 535.47 | |
| 1227 | Chiral | 562.49 | |

TABLE 21-continued

| Example | Structure | LCMS (M+) or (M + H)+ | Example for general method of preparation |
|---|---|---|---|
| 1228 | Chiral | 534.47 | |
| 1229 | Chiral | 603.43 | |
| 1230 | Chiral | 544.45 | |
| 1231 | Chiral | 603.41 | |
| 1232 | Chiral | 544.47 | |
| 1233 | Chiral | 576.45 | |

TABLE 21-continued

| Example | Structure | LCMS (M+) or (M + H)+ | Example for general method of preparation |
|---|---|---|---|
| 1234 | Chiral | 612.41 | |
| 1235 | Chiral | 612.41 | |
| 1236 | Chiral | 576.47 | |
| 1237 | Chiral | 612.42 | |
| 1238 | Chiral | 590.47 | |

TABLE 21-continued

| Example | Structure | | LCMS (M+) or (M + H)+ | Example for general method of preparation |
|---|---|---|---|---|
| 1239 | 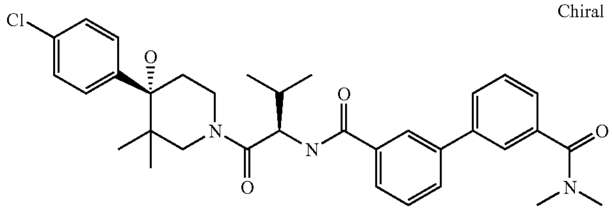 | Chiral | 590.46 | |
| 1240 | 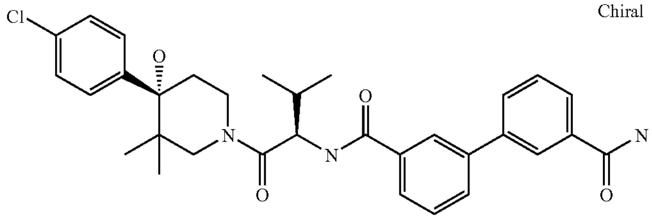 | Chiral | 562.43 | |
| 1241 | 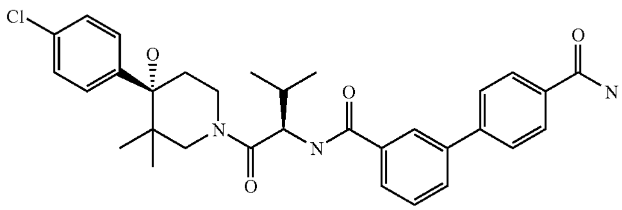 | Chiral | 562.44 | |
| 1242 | 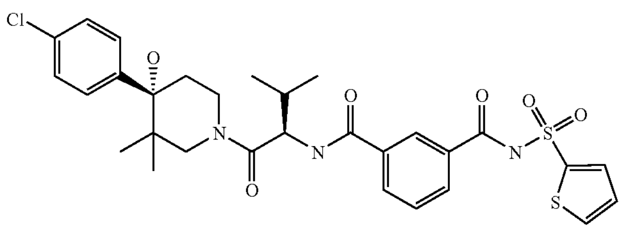 | Chiral | 632.37 | |
| 1243 | 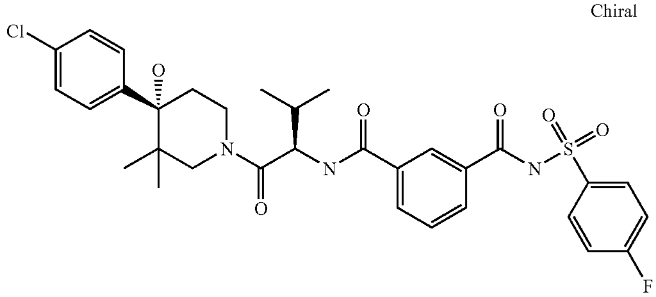 | Chiral | 644.39 | |

TABLE 21-continued

| Example | Structure | LCMS (M+) or (M + H)+ | Example for general method of preparation |
|---|---|---|---|
| 1244 | Chiral | 644.43 | |
| 1245 | Chiral | 641.42 | |
| 1246 | Chiral | 640.41 | |
| 1247 | Chiral | 678.38 | |
| 1248 | Chiral | 644.38 | |
| 1249 | Chiral | 660.36 | |

TABLE 21-continued
| Example | Structure | | LCMS (M+) or (M + H)+ | Example for general method of preparation |
|---|---|---|---|---|
| 1250 | 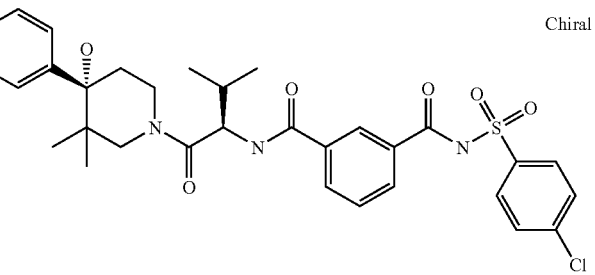 | Chiral | 660.45 | |
| 1251 | 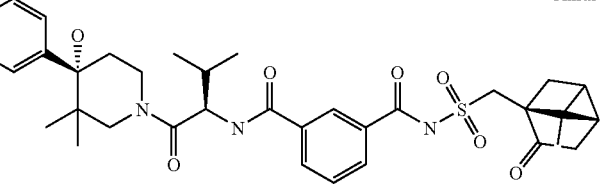 | Chiral | 700.46 | |
| 1252 | 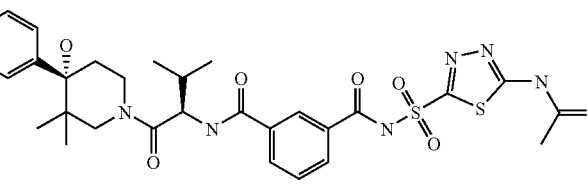 | Chiral | 691.37 | |
| 1253 | 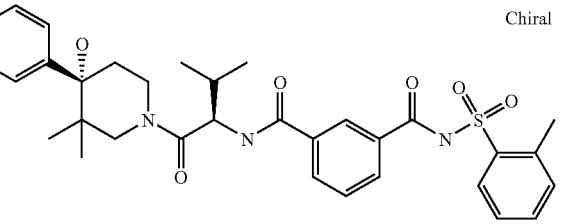 | Chiral | 640.43 | |
| 1254 | 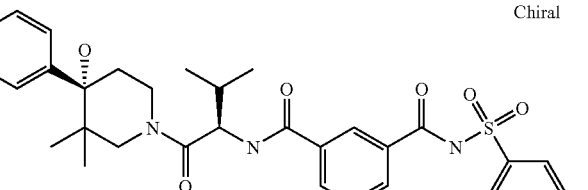 | Chiral | 640.44 | |
| 1255 | 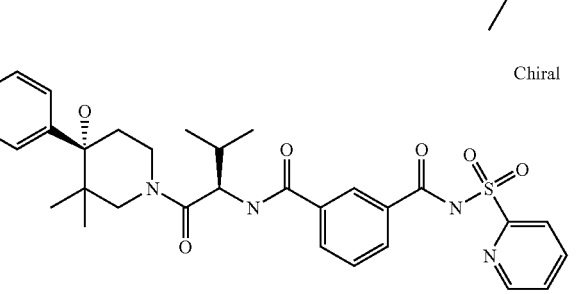 | Chiral | 627.41 | |

TABLE 21-continued

| Example | Structure | LCMS (M⁺) or (M + H)⁺ | Example for general method of preparation |
|---|---|---|---|
| 1256 | Chiral | 681.44 | |
| 1257 | 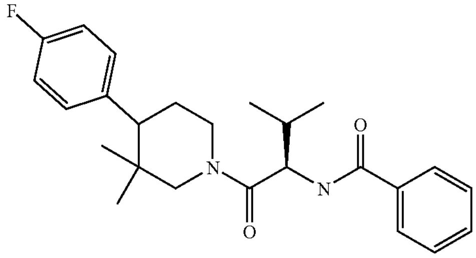 | 411.38 | |
| 1258 | 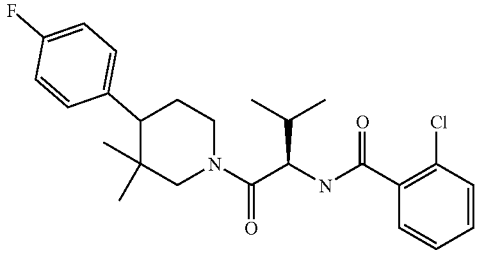 | 445.43 | |
| 1259 | 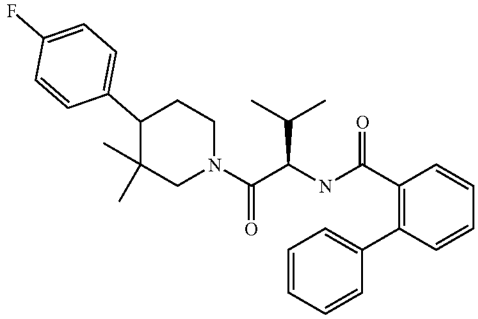 | 487.36 | |
| 1260 | 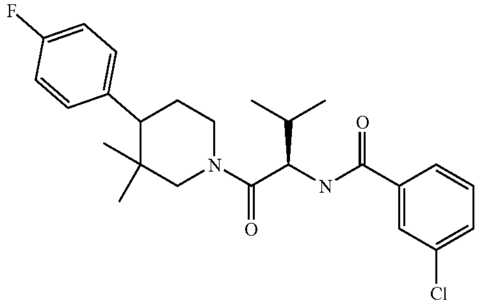 | 445.47 | |

TABLE 21-continued

| Example | Structure | LCMS (M+) or (M + H)+ | Example for general method of preparation |
|---|---|---|---|
| 1261 | 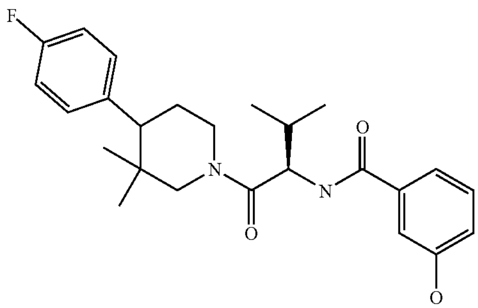 | 427.31 | |
| 1262 | 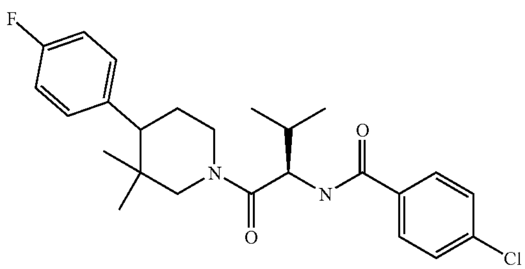 | 445.47 | |
| 1263 | 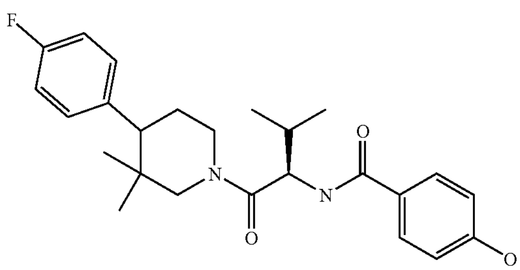 | 427.37 | |
| 1264 | 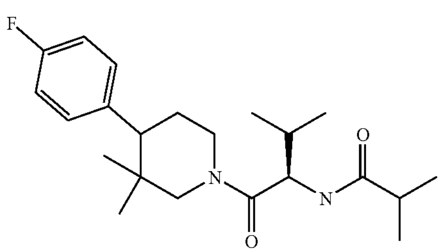 | 377.42 | |
| 1265 | 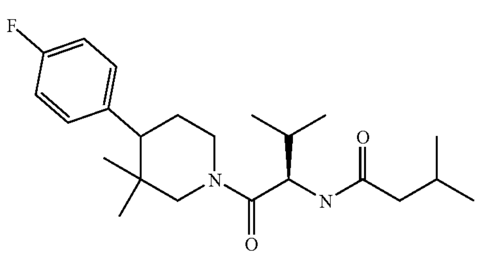 | 391.43 | |

TABLE 21-continued

| Example | Structure | LCMS (M+) or (M + H)+ | Example for general method of preparation |
|---------|-----------|------------------------|--------------------------------------------|
| 1266 | 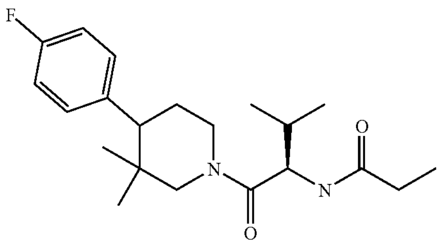 | 363.43 | |
| 1267 | 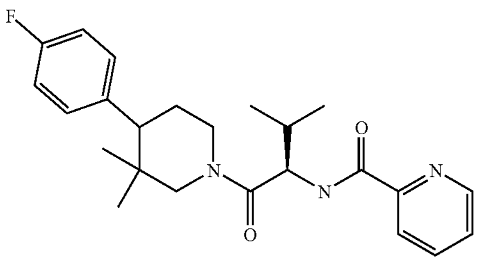 | 412.43 | |
| 1268 | 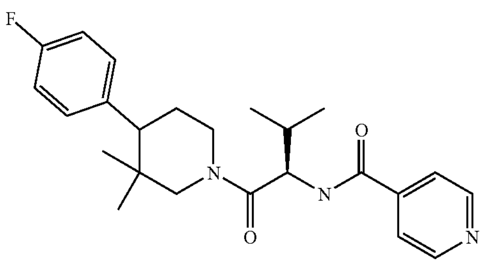 | 412.39 | |
| 1269 | 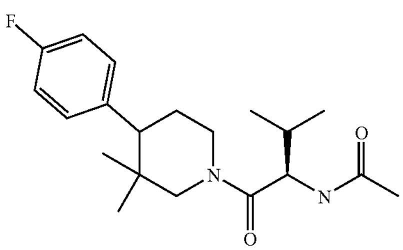 | 349.39 | |
| 1270 | 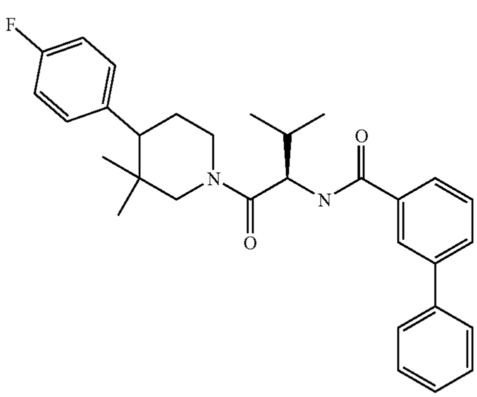 | 487.37 | |

TABLE 21-continued

| Example | Structure | LCMS (M+) or (M + H)+ | Example for general method of preparation |
|---|---|---|---|
| 1271 | 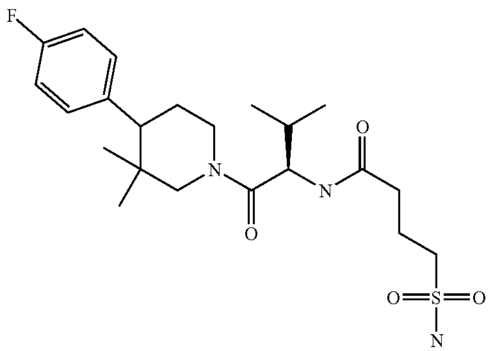 | 456.34 | |
| 1272 | Chiral | 459.47 | |
| 1273 | Chiral | 458.33 | |
| 1274 | Chiral | 536.47 | |
| 1275 | Chiral | 462.29 | |

TABLE 21-continued

| Example | Structure | LCMS (M+) or (M + H)+ | Example for general method of preparation |
|---|---|---|---|
| 1276 | Chiral | 504.44 | |
| 1277 | Chiral | 512.46 | |
| 1278 | Chiral | 542.42 | |
| 1279 | Chiral | 487.27 | |
| 1280 | Chiral | 488.48 | |

TABLE 21-continued
| Example | Structure | LCMS (M+) or (M + H)+ | Example for general method of preparation |
|---|---|---|---|
| 1281 | 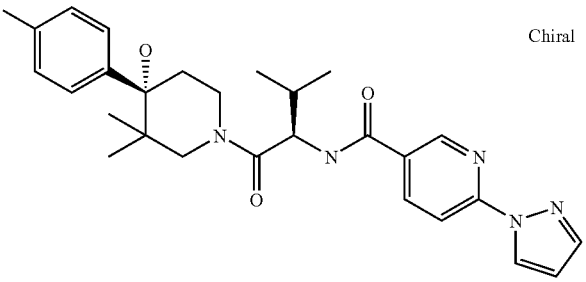 Chiral | 510.46 | |
| 1282 | 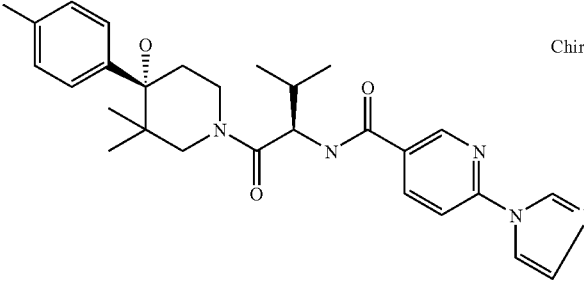 Chiral | 510.31 | |
| 1283 | 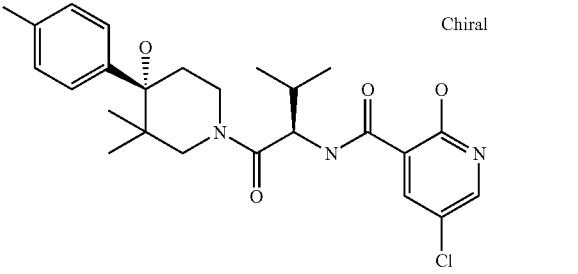 Chiral | 494.39 | |
| 1284 | 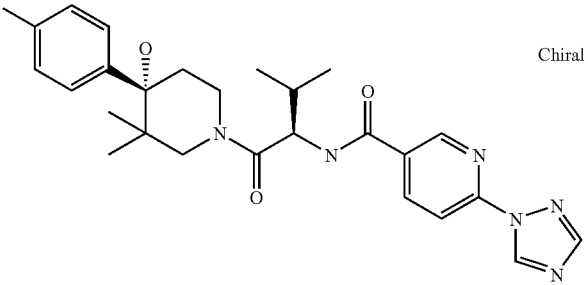 Chiral | 511.45 | |
| 1285 | 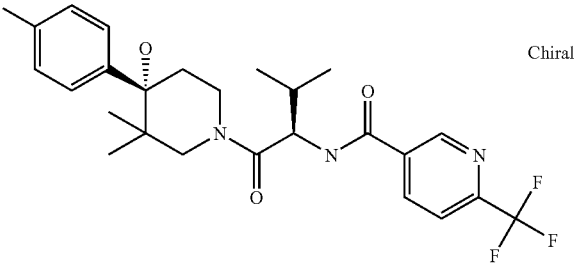 Chiral | 512.40 | |

TABLE 21-continued
| Example | Structure | LCMS (M+) or (M + H)+ | Example for general method of preparation |
|---|---|---|---|
| 1286 | 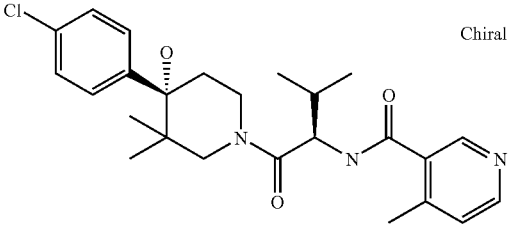 | 458.46 | |
| 1287 | 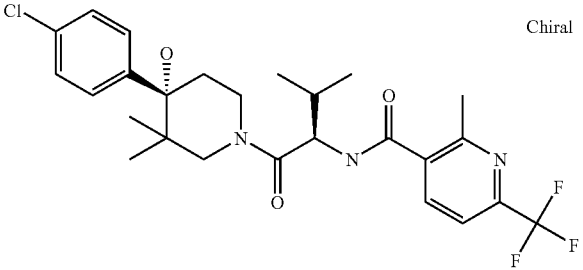 | 526.43 | |
| 1288 | 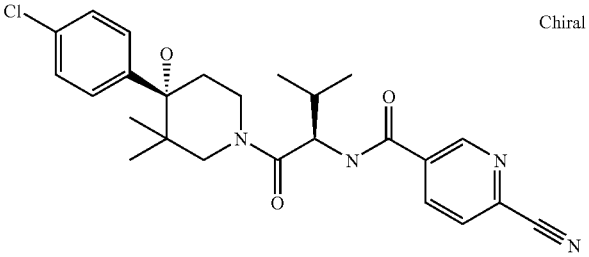 | 469.42 | |
| 1289 | 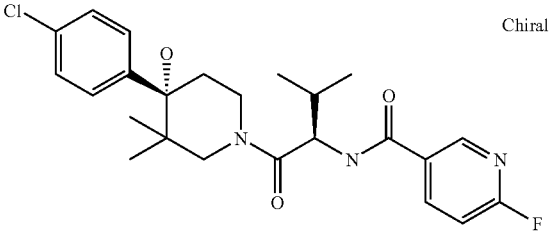 | 462.43 | |
| 1290 | 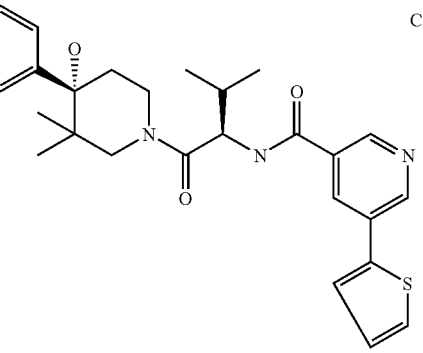 | 526.44 | |

TABLE 21-continued
| Example | Structure | LCMS (M+) or (M + H)+ | Example for general method of preparation |
|---|---|---|---|
| 1291 | 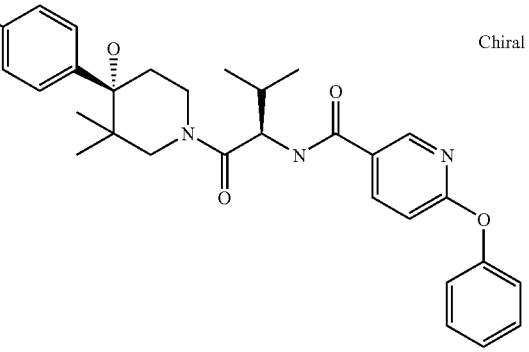 | 536.44 | |
| 1292 | 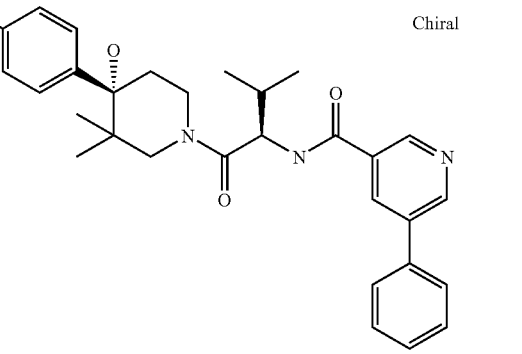 | 520.49 | |
| 1293 | 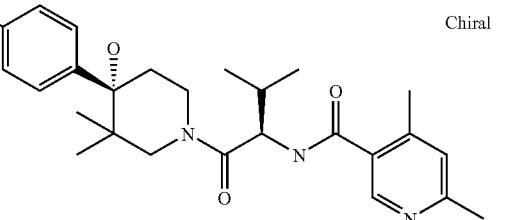 | 472.48 | |
| 1294 | 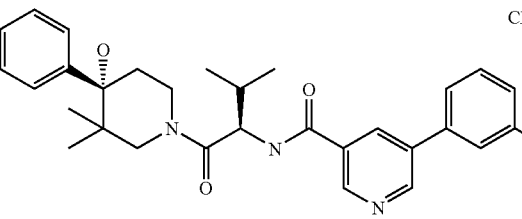 | 554.43 | |
| 1295 | 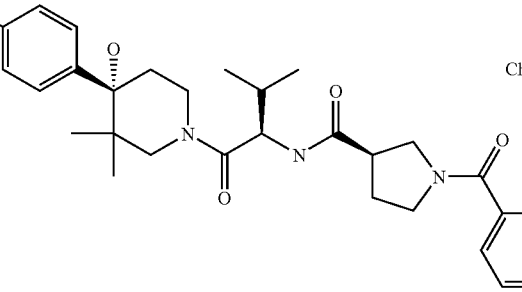 | 540.36 | |

TABLE 21-continued
| Example | Structure | LCMS (M+) or (M + H)+ | Example for general method of preparation |
|---|---|---|---|
| 1296 | 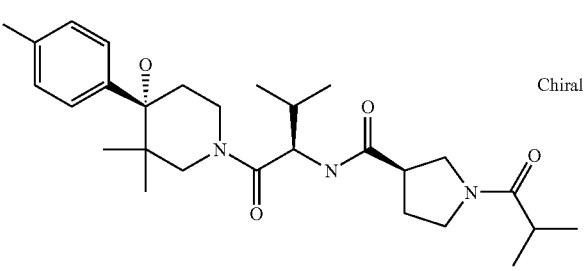 Chiral | 506.42 | |
| 1297 | 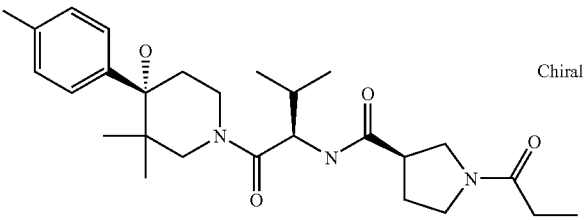 Chiral | 492.41 | |
| 1298 | 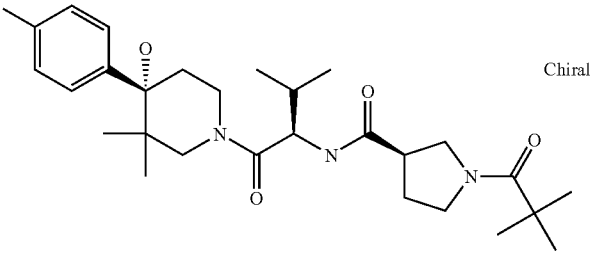 Chiral | 520.41 | |
| 1299 | 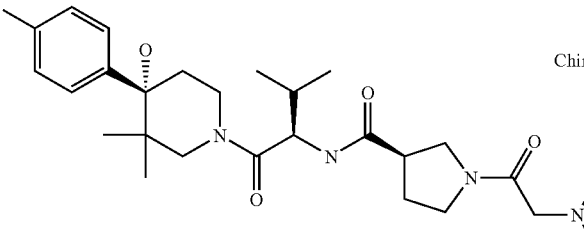 Chiral | 521.41 | |
| 1300 | 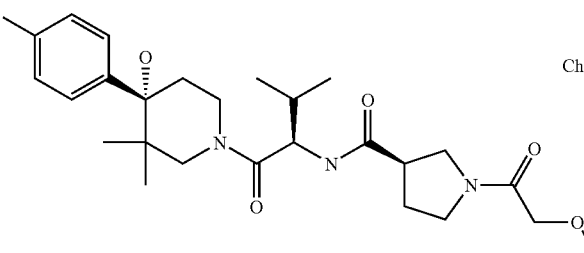 Chiral | 508.37 | |

US 7,601,844 B2
TABLE 21-continued
| Example | Structure | LCMS (M+) or (M + H)+ | Example for general method of preparation |
|---|---|---|---|
| 1301 | 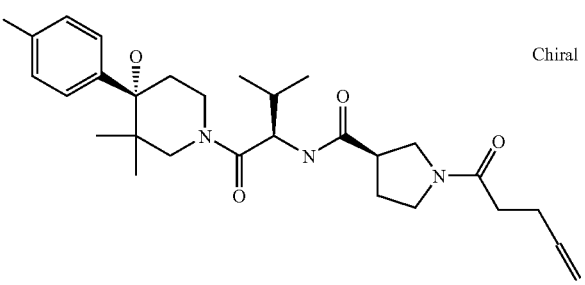 Chiral | 516.38 | |
| 1302 | 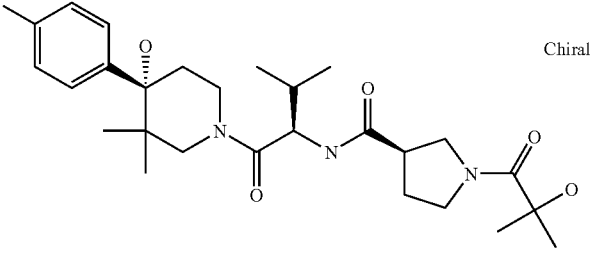 Chiral | 522.40 | |
| 1303 | 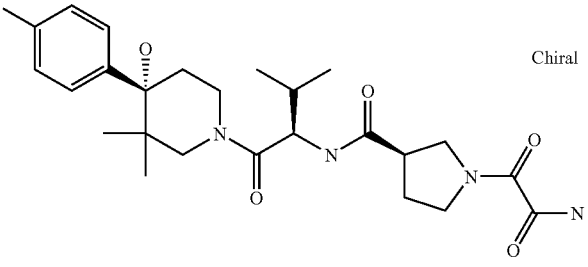 Chiral | 507.34 | |
| 1304 | 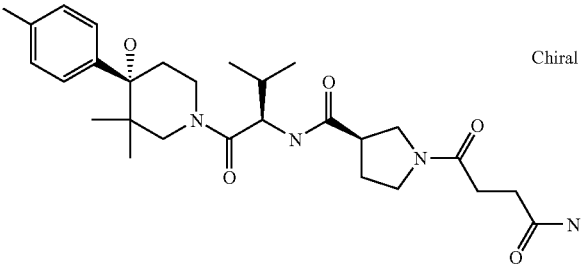 Chiral | 535.38 | |
| 1305 | 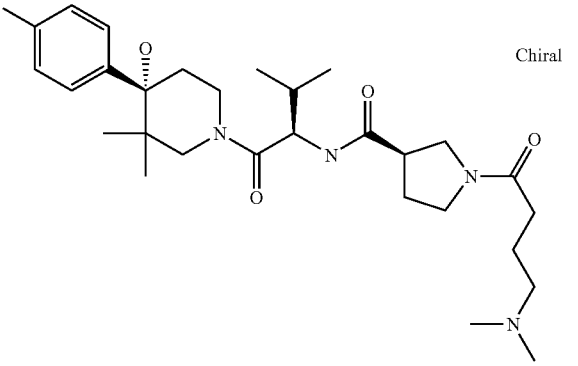 Chiral | 549.43 | |

TABLE 21-continued
| Example | Structure | LCMS (M+) or (M + H)+ | Example for general method of preparation |
|---|---|---|---|
| 1306 | 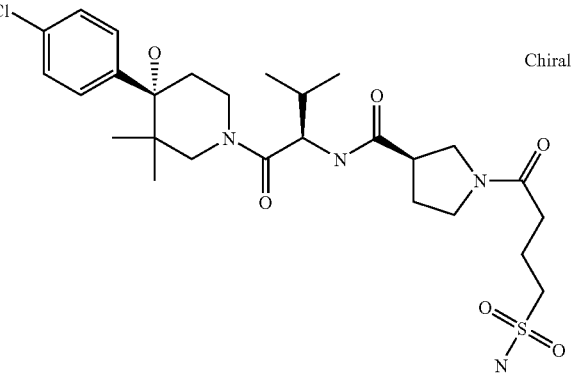 | 585.36 | |
| 1307 | 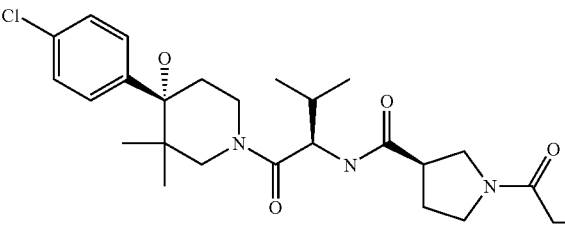 | 535.42 | |
| 1308 | 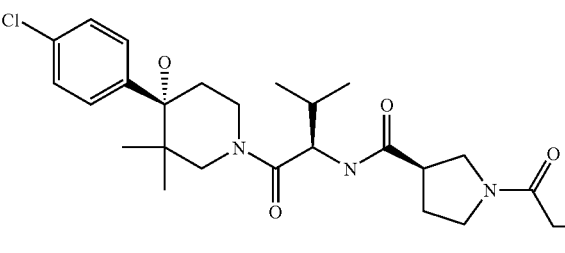 | 546.36 | |
| 1309 | 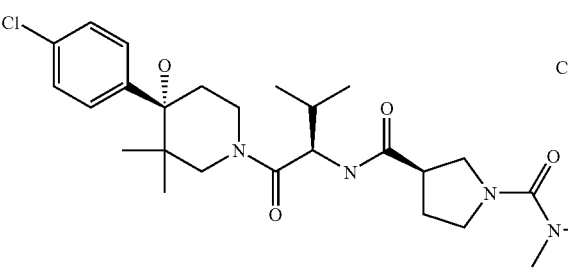 | 507.45 | |
| 1310 | 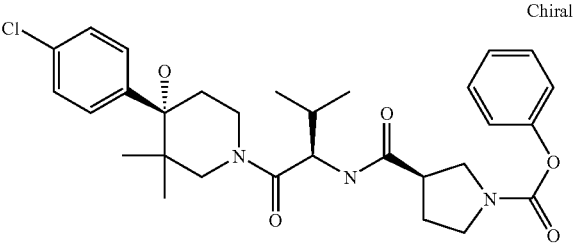 | 556.42 | |

TABLE 21-continued

| Example | Structure | LCMS (M+) or (M + H)+ | Example for general method of preparation |
|---|---|---|---|
| 1311 | 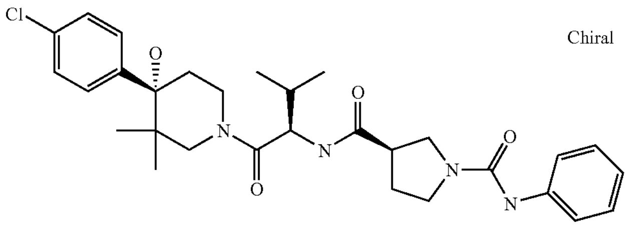 | 555.39 | |
| 1312 | 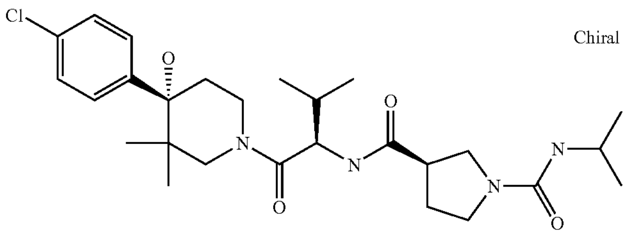 | 521.42 | |
| 1313 | 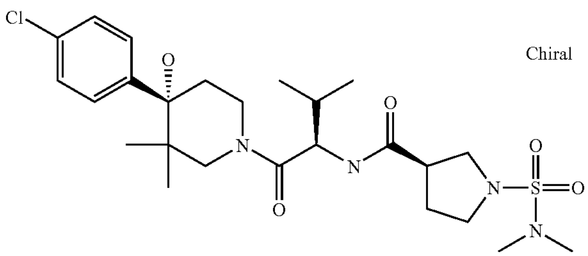 | 543.37 | |
| 1314 | 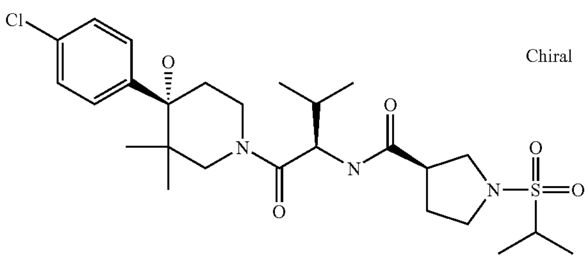 | 542.35 | |
| 1315 | 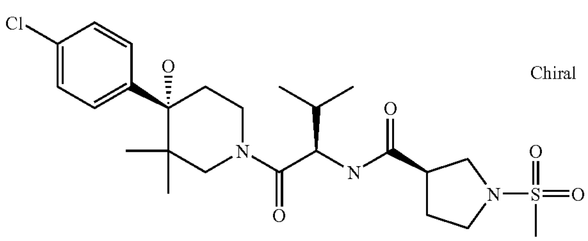 | 514.34 | |
| 1316 | 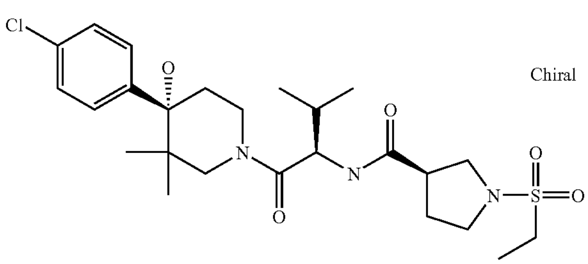 | 528.37 | |

TABLE 21-continued
| Example | Structure | LCMS (M+) or (M + H)+ | Example for general method of preparation |
|---------|-----------|----------------------|--------------------------------------------|
| 1317 | 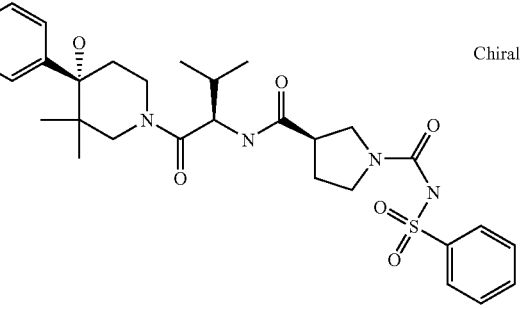 Chiral | 619.35 | |
| 1318 | 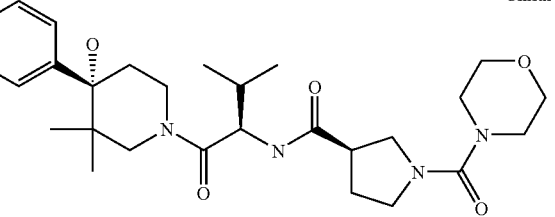 Chiral | 549.41 | |
| 1319 | 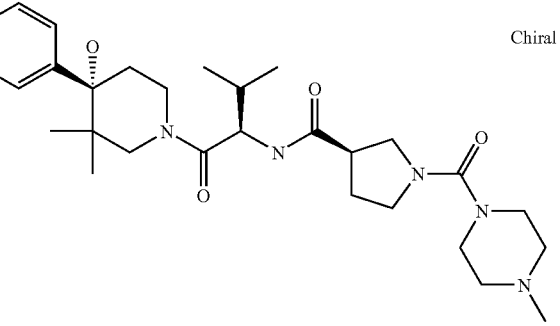 Chiral | 562.42 | |
| 1320 | 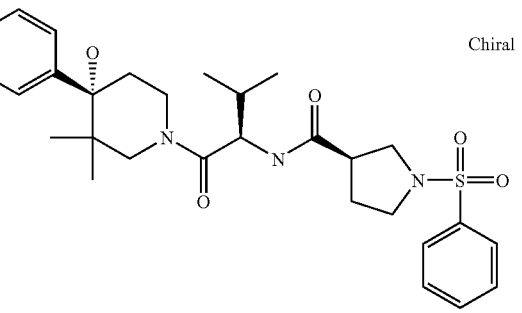 Chiral | 576.34 | |
| 1321 | 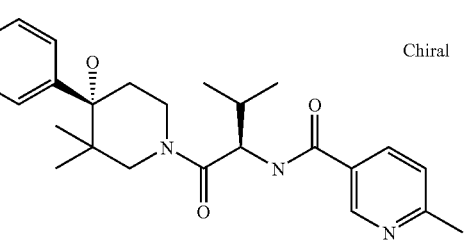 Chiral | 458.44 | |

TABLE 21-continued
| Example | Structure | LCMS (M+) or (M + H)+ | Example for general method of preparation |
|---|---|---|---|
| 1322 | 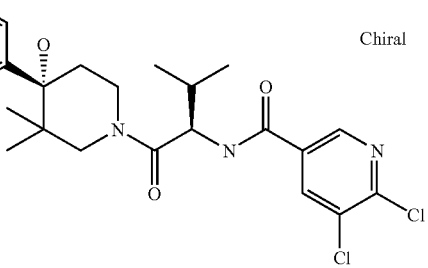 | 512.30 | |
| 1323 | 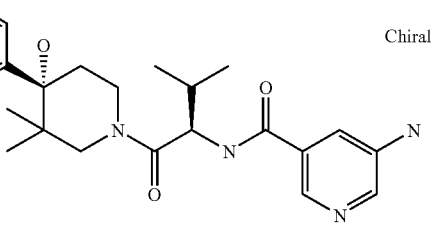 | 459.42 | |
| 1324 | 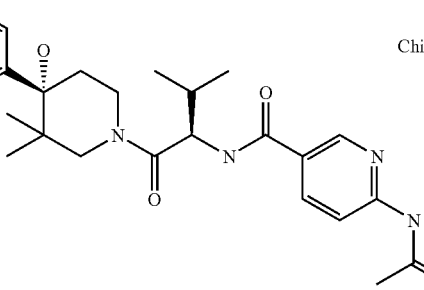 | 501.38 | |
| 1325 | 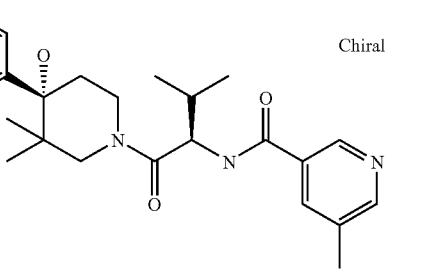 | 458.41 | |
| 1326 | 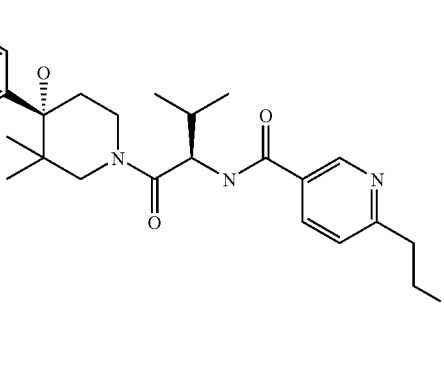 | 541.44 | |

TABLE 21-continued
| Example | Structure | LCMS (M+) or (M + H)+ | Example for general method of preparation |
|---|---|---|---|
| 1327 | Chiral 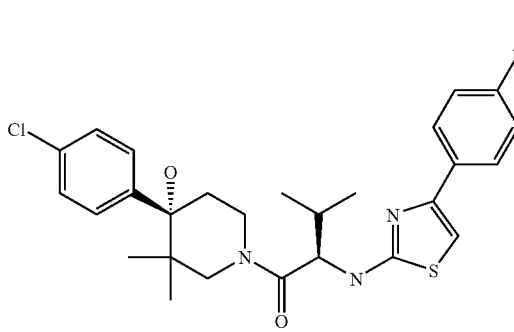 | 523.11 | |
| 1328 | Chiral 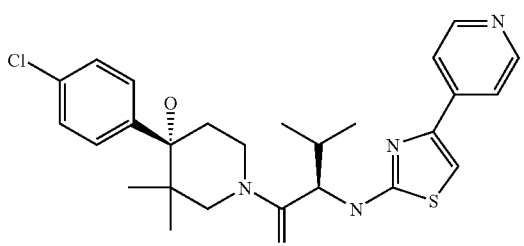 | 499.11 | |
| 1329 | Chiral 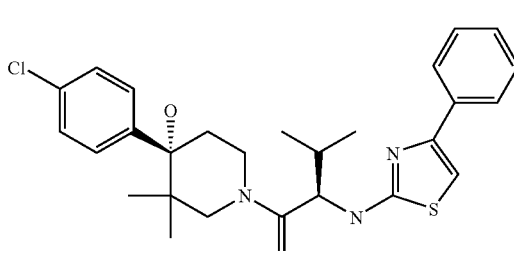 | 528.12 | |
| 1330 | Chiral 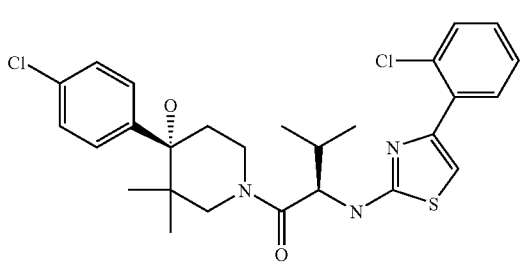 | 532.04 | |

TABLE 21-continued

| Example | Structure | LCMS (M+) or (M + H)+ | Example for general method of preparation |
|---|---|---|---|
| 1331 | Chiral | 528.11 | |
| 1332 | Chiral | 445.30 | |
| 1333 | Chiral | 483.30 | |
| 1334 | Chiral | 495.28 | |
| 1335 | Chiral | 495.28 | |

TABLE 21-continued
| Example | Structure | LCMS (M+) or (M + H)+ | Example for general method of preparation |
|---|---|---|---|
| 1336 | 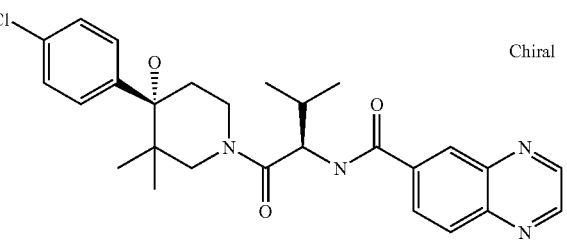 | 495.27 | |
| 1337 | 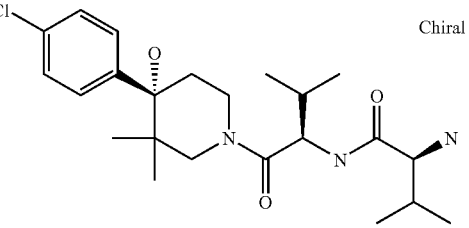 | 438.44 | |
| 1338 | 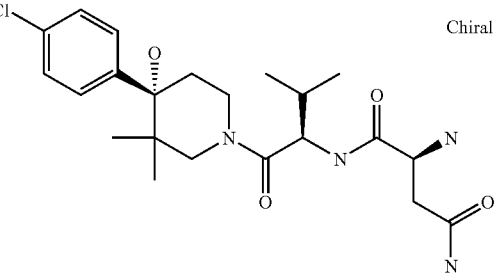 | 453.40 | |
| 1339 | 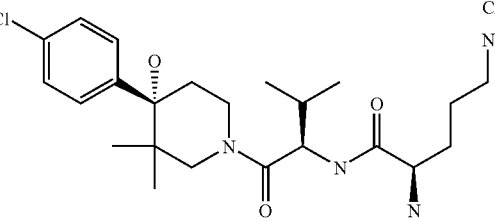 | 453.44 | |
| 1340 | 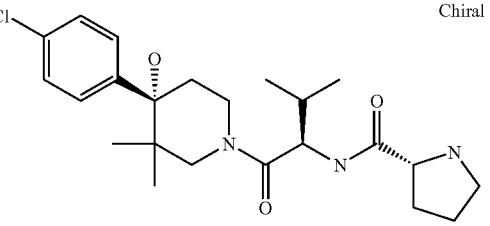 | 436.40 | |
| 1341 | 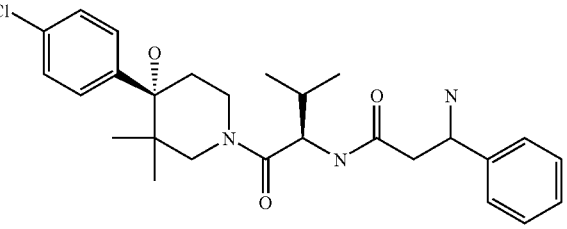 | 486.41 | |

TABLE 21-continued

| Example | Structure | LCMS (M+) or (M + H)+ | Example for general method of preparation |
|---|---|---|---|
| 1342 | (Chiral) | 450.42 | |
| 1343 | (Chiral) | 498.41 | |
| 1344 | (Chiral) | 454.34 | |
| 1345 | (Chiral) | 500.42 | |
| 1346 | (Chiral) | 452.42 | |

TABLE 21-continued

| Example | Structure | LCMS (M⁺) or (M + H)⁺ | Example for general method of preparation |
|---|---|---|---|
| 1347 | (structure, Chiral) | 452.43 | |
| 1348 | (structure, Chiral) | 438.42 | |
| 1349 | (structure, Chiral) | 493.35 | |
| 1350 | (structure, Chiral) | 502.40 | |
| 1351 | (structure, Chiral) | 440.38 | |

TABLE 21-continued

| Example | Structure | LCMS (M+) or (M + H)+ | Example for general method of preparation |
|---|---|---|---|
| 1352 | Chiral | 487.39 | |
| 1353 | Chiral | 410.36 | |
| 1354 | Chiral | 410.37 | |
| 1355 | Chiral | 452.37 | |
| 1356 | Chiral | 439.2 | |
| 1357 | Chiral | 429.3 | |

TABLE 21-continued

| Example | Structure | | LCMS (M+) or (M + H)+ | Example for general method of preparation |
|---|---|---|---|---|
| 1358 | 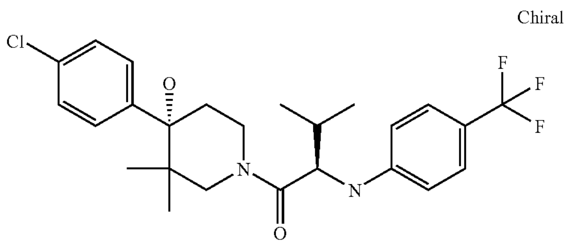 | Chiral | 488.3 | |
| 1359 | 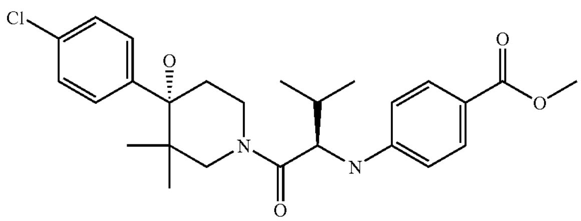 | | 473.2 | |
| 1360 | 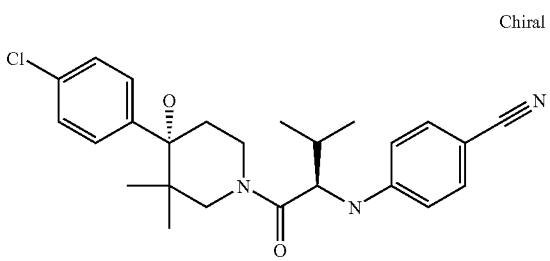 | Chiral | 440.2 | |
| 1361 | 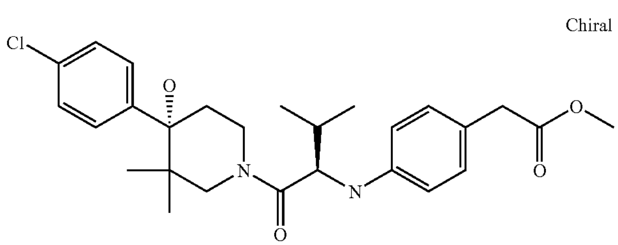 | Chiral | 487.3 | |
| 1362 | 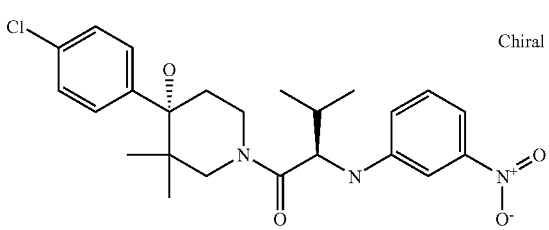 | Chiral | 460.2 | |

It is noted that the proceeding examples, while illustrative of the present invention, are not in sequential order and some example numbers may be missing.

Utility

In general, compounds of the present invention, such as particular compounds disclosed in the preceding examples, have been shown to be modulators of chemokine receptor activity at concentrations equivalent to, or more potently than, 20 μM, preferably 10 μM, more preferably 5 μM. By displaying activity at these concentrations, compounds of the present invention are expected to be useful in the treatment of human diseases associated with chemokines and their cognate receptors. Potencies can be calculated and expressed as either inhibition constants (Ki values) or as $IC_{50}$ values, and refer to activity measured employing the assay system(s) described below.

Antagonism of MIP-1α Binding to Human THP-1 Cells (Yoshimura et al., *J. Immunol.*, 1990, 145, 292)

Compounds of the present invention have activity in the antagonism of MIP-1α binding to human THP-1 cells described here.

Millipore filter plates (#MABVN1250) are treated with 100 μl of binding buffer (0.5% bovine serum albumin, 20 mM HEPES buffer and 5 mM magnesium chloride in RPMI 1640 media) for thirty minutes at room temperature. To measure binding, 50 μl of binding buffer, with or without a known concentration of compound, is combined with 50 μl of $^{125}$-I labeled human MIP-1α (to give a final concentration of 50 pM radioligand) and 50 μl of binding buffer containing $5 \times 10^5$ cells. Cells used for such binding assays can include the THP-1 cell line, which expresses the endogenous CCR1 receptor, or human peripheral blood mononuclear cells, isolated by Ficoll-Hypaque gradient centrifugation, or human monocytes (Weiner et al., *J. Immunol. Methods*, 1980, 36, 89). The mixture of compound, cells and radioligand is incubated at room temperature for thirty minutes. Plates are placed onto a vacuum manifold, vacuum applied, and the plates washed three times with binding buffer containing 0.5M NaCl. The plastic skirt is removed from the plate, the plate allowed to air dry, the wells punched out and counted. The percent inhibition of binding is calculated using the total counts obtained in the absence of any competing compound and the background binding determined by addition of 100 nM MIP-1α in place of the test compound.

Antagonism of MIP-1α-induced Calcium Influx (Sullivan et al., *Methods Mol. Biol.*, 114, 125-133 (1999)

Compounds of the present invention have activity in the antagonism of MIP-1α-induced calcium influx assay described here.

Calcium mobilization is measured using the fluorescent $Ca^{2+}$ indicator dye, fluo-3. Cells used can include cell lines that express the endogenous CCR1 receptor such as Mono-Mac-6 cells and THP-1 cells, or freshly obtained human monocytes isolated as described by Weiner et al., *J. Immunol. Methods*, 36, 89-97 (1980). The cells are incubated at $8 \times 10^5$ cells/mL in phosphate-buffered saline containing 0.1% bovine serum albumin, 20 mM HEPES buffer, 5 mM glucose, 1% fetal bovine serum, 4 μM fluo-3 AM and 2.5 mM probenecid for 60 minutes at 37° C. After washing three times in phosphate-buffered saline containing 0.1% bovine serum albumin, 20 mM HEPES, 5 mM glucose and 2.5 mM probenecid, the cells are resuspended in phosphate-buffered saline containing 0.5% bovine serum albumin, 20 mM HEPES and 2.5 mM probenecid at a final concentration of $2-4 \times 10^6$ cells/mL. Cells are plated into 96-well, black-wall microplates (100 μl/well) and the plates centrifuged at 200×g for 5 minutes. Various graded concentrations of compound are added to the wells (50 μl/well) and after 5 minutes, 50 μl/well of MIP-1α is added to give a final concentration of 10 nM. Calcium mobilization occurs immediately after addition of ligand and is detected using a fluorescent-imaging plate reader, utilizing an argon laser (488 nm). Cell-associated fluorescence is measured for 3 minutes (every second for the first 90 seconds and every 10 seconds for the next 90 seconds). Data are generated as arbitrary fluorescence units and the change in fluorescence for each well determined as the maximum-minimum differential. Compound-dependent inhibition is calculated relative to the response of MIP-1α alone.

Antagonism of MIP-1α-induced THP-1 Cells Chemotaxis

Compounds of the present invention have activity in the antagonism of MIP-1α-induced THP-1 cells chemotaxis assay described here.

BD Falcon HTX Fluoroblok 96-Multiwell Insert System plates (8 micron, catalog #351164) are warmed in a 37° C. incubator. After centrifugation, THP-1 cells ($1.5 \times 10^7$ cells per plate) are resuspended in 1 mL of RPMI 1640 medium (without phenol red). 5 μl of 1 mg/mL calcein-AM (Molecular Probes catalog#C-3100) are added to the cell suspension. After mixing gently, the cells are incubated at 37° C. for 30 minutes. 14 mL of RPMI 1640 (with 0.1% BSA) are added and the cells centrifuged at 1300 rpm for 5 minutes. The pellet is resuspended in 7.5 mL of pre-warmed RPMI 1640 (with 0.1% BSA). A 20 nM solution of human MIP-1α is also warmed at 37° C. Compounds are diluted in RPMI 1640 to give concentrations twice the final values. The THP-1 cell suspension and the 20 nM MIP-1α solution are mixed 1:1 in polypropylene tubes with pre-warmed RPMI with or without a dilution of the test compounds. These mixtures are warmed in a 37° C. tube warmer. 50 μl of the cell suspension+compound are added to each of the insert wells. 225 μl of MIP-1α+compound are added to the lower reservoirs of the BD-Falcon Fluoroblok. The Fluoroblok plate is placed in a 37° C. incubator, incubated for 60 minutes and read in a Cytofluor II Fluorescence Multi-Well Plate Reader (PerSeptive Biosystems, Inc.) under instrumental settings of excitation wavelength at 485 nm and detection wavelength at 530 nm. Data are generated as arbitrary fluorescence units and the change in fluorescence for each well determined as the maximum-background differential. Compound-dependent inhibition is calculated relative to the response of MIP-1α alone.

Mammalian chemokine receptors provide a target for interfering with or promoting immune cell function in a mammal, such as a human. Compounds that inhibit or promote chemokine receptor function are particularly useful for modulating immune cell function for therapeutic purposes.

Accordingly, the present invention is directed to compounds which are useful in the prevention and/or treatment of a wide variety of inflammatory, infectious, and immunoregulatory disorders and diseases, including asthma and allergic diseases, infection by pathogenic microbes (which, by definition, includes viruses), as well as autoimmune pathologies such as the rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation or infectious disease. As a result, one or more inflammatory process, such as leukocyte emigration, adhesion, chemotaxis, exocytosis (e.g., of enzymes, histamine) or inflammatory mediator release, is inhibited.

Similarly, an instant compound which promotes one or more functions of the mammalian chemokine receptor (e.g., a human chemokine) as administered to stimulate (induce or enhance) an immune or inflammatory response, such as leukocyte emigration, adhesion, chemotaxis, exocytosis (e.g., of enzymes, histamine) or inflammatory mediator release, resulting in the beneficial stimulation of inflammatory processes. For example, eosinophils can be recruited to combat parasitic infections. In addition, treatment of the aforementioned inflammatory, allergic and autoimmune diseases can also be contemplated for an instant compound which promotes one or more functions of the mammalian chemokine receptor if one contemplates the delivery of sufficient compound to cause the loss of receptor expression on cells through the induction of chemokine receptor internalization or the delivery of compound in a manner that results in the misdirection of the migration of cells.

In addition to primates, such as humans, a variety of other mammals can be treated according to the method of the present invention. For instance, mammals, including but not limited to, cows, sheep, goats, horses, dogs, cats, guinea pigs, rats or other bovine, ovine, equine, canine, feline, rodent or murine species can be treated. However, the method can also be practiced in other species, such as avian species. The subject treated in the methods above is a mammal, male or female, in whom modulation of chemokine receptor activity is desired. "Modulation" as used herein is intended to encompass antagonism, agonism, partial antagonism and/or partial agonism.

Diseases or conditions of human or other species which can be treated with inhibitors of chemokine receptor function, include, but are not limited to: inflammatory or allergic diseases and conditions, including respiratory allergic diseases such as asthma, allergic rhinitis, hypersensitivity lung diseases, hypersensitivity pneumonitis, eosinophilic cellulitis (e.g., Well's syndrome), eosinophilic pneumonias (e.g., Loeffler's syndrome, chronic eosinophilic pneumonia), eosinophilic fasciitis (e.g., Shulman's syndrome), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), eosinophilia-myalgia syndrome due to the ingestion of contaminated tryptophan, insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such as an dermatitis, eczema, atopic dermatitis, allergic contact dermatitis, urticaria; vasculitis (e.g., necrotizing, cutaneous, and hypersensitivity vasculitis); eosinophilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematological malignancies, cytokine-induced toxicity (e.g., septic shock, endotoxic shock), polymyositis, dermatomyositis.

Infectious diseases or conditions of human or other species which can be treated with inhibitors of chemokine receptor function, include, but are not limited to, HIV.

Diseases or conditions of humans or other species which can be treated with promoters of chemokine receptor function, include, but are not limited to: immunosuppression, such as that in individuals with immunodeficiency syndromes such as AIDS or other viral infections, individuals undergoing radiation therapy, chemotherapy, therapy for autoimmune disease or drug therapy (e.g., corticosteroid therapy), which causes immunosuppression; immunosuppression due to congenital deficiency in receptor function or other causes; and infections diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migraines (e.g., *Toxocara*), eosinophilic gastroenteritis (e.g., *Anisaki* sp., *Phocanema* sp.), cutaneous larva migraines (*Ancylostona braziliense, Ancylostoma caninum*). The compounds of the present invention are accordingly useful in the prevention and treatment of a wide variety of inflammatory, infectious and immunoregulatory disorders and diseases.

In addition, treatment of the aforementioned inflammatory, allergic and autoimmune diseases can also be contemplated for promoters of chemokine receptor function if one contemplates the delivery of sufficient compound to cause the loss of receptor expression on cells through the induction of chemokine receptor internalization or delivery of compound in a manner that results in the misdirection of the migration of cells.

In another aspect, the instant invention may be used to evaluate the putative specific agonists or antagonists of a G protein coupled receptor. The present invention is directed to the use of these compounds in the preparation and execution of screening assays for compounds that modulate the activity of chemokine receptors. Furthermore, the compounds of this invention are useful in establishing or determining the binding site of other compounds to chemokine receptors, e.g., by competitive inhibition or as a reference in an assay to compare its known activity to a compound with an unknown activity. When developing new assays or protocols, compounds according to the present invention could be used to test their effectiveness. Specifically, such compounds may be provided in a commercial kit, for example, for use in pharmaceutical research involving the aforementioned diseases.

The compounds of the instant invention are also useful for the evaluation of putative specific modulators of the chemokine receptors. In addition, one could utilize compounds of this invention to examine the specificity of G protein coupled receptors that are not thought to be chemokine receptors, either by serving as examples of compounds which do not bind or as structural variants of compounds active on these receptors which may help define specific sites of interaction.

The compounds of the present invention are used to treat or prevent disorders selected from rheumatoid arthritis, osteoarthritis, septic shock, atherosclerosis, aneurysm, fever, cardiovascular effects, haemodynamic shock, sepsis syndrome, post ischemic reperfusion injury, malaria, Crohn's disease, inflammatory bowel diseases, mycobacterial infection, meningitis, psoriasis, congestive heart failure, fibrotic diseases, cachexia, graft rejection, autoimmune diseases, skin inflammatory diseases, multiple sclerosis, radiation damage, hyperoxic alveolar injury, HIV, HIV dementia, non-insulin dependent diabetes mellitus, asthma, allergic rhinitis, atopic dermatitis, idiopathic pulmonary fibrosis, bullous pemphigoid, helminthic parasitic infections, allergic colitis, eczema, conjunctivitis, transplantation, familial eosinophilia, eosinophilic cellulitis, eosinophilic pneumonias, eosinophilic fasciitis, eosinophilic gastroenteritis, drug induced eosinophilia, cystic fibrosis, Churg-Strauss syndrome, lymphoma, Hodgkin's disease, colonic carcinoma, Felty's syndrome, sarcoidosis, uveitis, Alzheimer, Glomerulonephritis, and systemic lupus erythematosus.

In another aspect, the compounds are used to treat or prevent inflammatory disorders selected from rheumatoid arthritis, osteoarthritis, atherosclerosis, aneurysm, fever, cardiovascular effects, Crohn's disease, inflammatory bowel diseases, psoriasis, congestive heart failure, multiple sclerosis, autoimmune diseases, skin inflammatory diseases.

In another aspect, the compounds are used to treat or prevent inflammatory disorders selected from rheumatoid arthritis, osteoarthritis, atherosclerosis, Crohn's disease, inflammatory bowel diseases, and multiple sclerosis.

Combined therapy to prevent and treat inflammatory, infectious and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities. For example, in the treatment or prevention of inflammation, the present compounds may be used in conjunction with an anti-inflammatory or analgesic agent such as an opiate agonist, a lipoxygenase inhibitor, a cyclooxygenase-2 inhibitor, an interleukin inhibitor, such as an interleukin-1 inhibitor, a tumor necrosis factor inhibitor, an NMDA antagonist, an inhibitor or nitric oxide or an inhibitor of the synthesis of nitric oxide, a non-steroidal anti-inflammatory agent, a phosphodiesterase inhibitor, or a cytokine-suppressing anti-inflammatory agent, for example with a compound such as acetaminophen, aspirin, codeine, fentaynl, ibuprofen, indomethacin, ketorolac, morphine, naproxen, phenacetin, piroxicam, a steroidal analgesic, sufentanyl, sunlindac, interferon alpha and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levodesoxy-ephedrine; and antitussive such as codeine, hydrocodone, caramiphen, carbetapentane, or dextramethorphan; a diuretic; and a sedating or non-sedating antihistamine. Likewise, compounds of the present invention may be used in combination with other drugs that are used in the treatment/prevention/suppression or amelioration of the diseases or conditions for which compound of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention may be used. Accordingly, the pharmaceutical compositions of the present invention include those that also contain one or more other active ingredients, in addition to a compound of the present invention.

Examples of other active ingredients that may be combined with a compound of the present invention, either administered separately or in the same pharmaceutical compositions, include, but are not limited to: (a) integrin antagonists such as those for selectins, ICAMs and VLA-4; (b) steroids such as beclomethasone, methylprednisolone, betamethasone, prednisone, dexamethasone, and hydrocortisone; (c) immunosuppressants such as cyclosporine, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as b2-agonists (terbutaline, metaproterenol, fenoterol, isoetharine, albuteral, bitolterol, and pirbuterol), theophylline, cromolyn sodium, atropine, ipratropium bromide, leukotriene antagonists (zafirlukast, montelukast, pranlukast, iralukast, pobilukast, SKB-102, 203), leukotriene biosynthesis inhibitors (zileuton, BAY-1005); (f) non-steroidal anti-inflammatory agents (NSAIDs) such as propionic acid derivatives (alminoprofen, benxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (I) other antagonists of the chemokine receptors; (j) cholesterol lowering agents such as HMG-COA reductase inhibitors (lovastatin, simvastatin and pravastatin, fluvastatin, atorvsatatin, and other statins), sequestrants (cholestyramine and colestipol), nicotonic acid, fenofibric acid derivatives (gemfibrozil, clofibrat, fenofibrate and benzafibrate), and probucol; (k) anti-diabetic agents such as insulin, sulfonylureas, biguanides (metformin), a-glucosidase inhibitors (acarbose) and glitazones (troglitazone ad pioglitazone); (1) preparations of interferons (interferon alpha-2a, interferon-2B, interferon alpha-N3, interferon beta-1a, interferon beta-1b, interferon gamma-1b); (m) antiviral compounds such as efavirenz, nevirapine, indinavir, ganciclovir, lamivudine, famciclovir, and zalcitabine; (o) other compound such as 5-aminosalicylic acid an prodrugs thereof, anti-metabolites such as azathioprine and 6-mercaptopurine, and cytotoxic cancer chemotherapeutic agents. The weight ratio of the compound of the present invention to the second active ingredient may be varied and will depend upon the effective doses of each ingredient.

Generally, an effective dose of each will be used. Thus, for example, when a compound of the present invention is combined with an NSAID the weight ratio of the compound of the present invention to the NSAID will generally range from about 1000:1 to about 1:1000, or alternatively from about 200:1 to about 1:200. Combinations of a compound of the present invention and other active ingredients will generally also be within the aforementioned range, but in each case, an effective dose of each active ingredient should be used.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Intravenously, the doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination. Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

While the invention has been described in detail and with reference to specific embodiments thereof, it will be apparent to one skilled in the art that various changes and modifications can be made therein without departing from the spirit and scope thereof.

What is claimed is:

1. A compound of Formula (I):

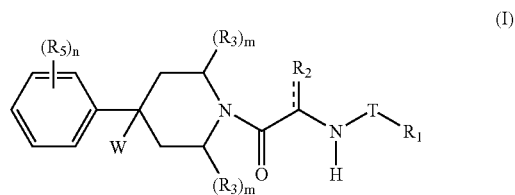

or stereoisomers or pharmaceutically acceptable salt forms thereof, wherein:

the dashed line represents an optional double bond;

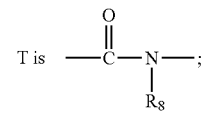

$R_1$ is alkyl, phenyl or cycloalkyl, all of which may be optionally substituted with 0-5 $R_{1a}$;

$R_{1a}$, at each occurrence, is independently selected from alkyl, haloalkyl, aryl, halo, —C(=O)OH, —C(=O)O$(CR_8R_8)_rR_{10}$—OH, wherein the aryl, may be optionally substituted with 0-3 $R_{1b}$;

$R_{1b}$, at each occurrence, is alkyl, or —OH;

$R_2$ is alkyl, wherein the alkyl may be optionally substituted with —OH;

$R_3$, at each occurrence, is alkyl;

W is F, —OH, —CN or —NH$_2$;

$R_5$ is halo, —CN or —Oalkyl;

$R_8$, at each occurrence, is independently hydrogen or alkyl;

$R_{10}$, is alkyl;

m, at each occurrence, is 0-2;

n is 1-3; and r is 0-5.

2. A compound of formula (Ia):

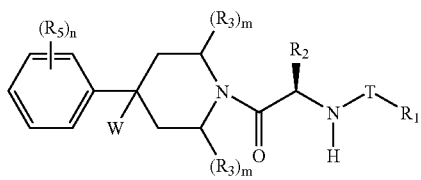

or pharmaceutically acceptable salt forms thereof, wherein:

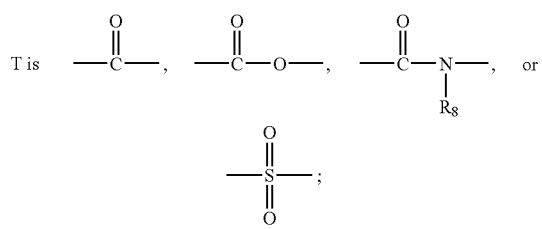

R₁ is alkyl, phenyl or cycloalkyl, all of which may be optionally substituted with 0-5 $R_{1a}$;
$R_{1a}$, at each occurrence, is independently selected from alkyl, haloalkyl, aryl, halo, —C(=O)OH, —C(=O)O(CR₈R₈)ᵣR₁₀—OH,
wherein the aryl, may be optionally substituted with 0-3 $R_{1b}$;
$R_{1b}$, at each occurrence, is alkyl, or —OH;
$R_2$ is alkyl, wherein the alkyl may be optionally substituted with —OH;
$R_3$, at each occurrence, is alkyl;
W is F, —OH, —CN or —NH₂;
$R_5$ is halo, —CN or —Oalkyl;
$R_8$, at each occurrence, is independently hydrogen or alkyl;
$R_9$, at each occurrence, is independently hydrogen or alkyl;
$R_{10}$, is alkyl;
m, at each occurrence, is 0-2;
n is 1-3; and
r is 0-5.

3. A compound of Formula (Ib):

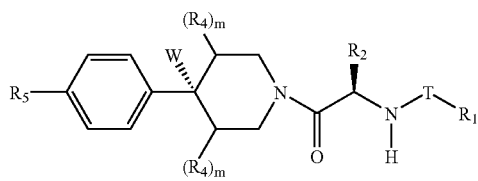

or stereoisomers or pharmaceutically acceptable salt forms thereof, wherein:

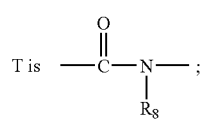

R₁ is alkyl, phenyl or cycloalkyl, all of which may be optionally substituted with 0-5 $R_{1a}$;

$R_{1a}$, at each occurrence, is independently selected from alkyly, haloalkyly, aryl halo, —C(=O)OH, —c(=O)O(CR₈R₈)ᵣR₁₀—OH, wherein the aryl, may be optionally substituted with 0-3 $R_{1b}$; —
$R_{1b}$, at each occurrence, is alkyl, or —OH
$R_2$ is alkyl, wherein the alkyl may be optionally substituted with —OH;
$R_4$, at each occurrence, is F, —OH or alkyl;
W is F, —OH, —CN, or —NH₂;
$R_5$ is halo, —CN or —Oalkyl;
$R_8$, at each occurrence, is independently hydrogen or alkyl;
$R_{10}$, is alkyl;
m, at each occurrence, is 0-2; and
r is 0-5.

4. A compound of formula (Ib'):

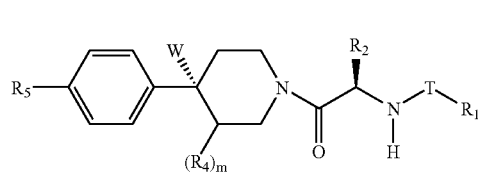

or pharmaceutically acceptable salt forms thereof, wherein:

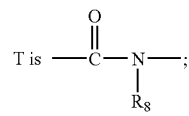

R₁ is alkyl phenyl or cycloalkyl, all of which may be optionally substituted with 0-5 $R_{1a}$;
$R_{1a}$, at each occurrence, is independently selected from alkyl, haloalkyl, aryl, halo, —C(=O)OH, —C(=O)O(CR₈R₈)ᵣR₁₀—OH, wherein the aryl, may be optionally substituted with 0-3 $R_b$;
$R_{1b}$, at each occurrence, is alkyl, or —OH,
$R_2$ is alkyl, wherein the alkyl may be optionally substituted with —OH;
$R_4$, at each occurrence, is F, —OH or alkyl;
W is —OH;
$R_5$ is halo, —CN or —Oalkyl;
$R_8$, at each occurrence, is independently hydrogen or alkyl;
$R_{10}$, is alkyl;
m, at each occurrence, is 0-2; and
r is 0-5.

5. The compound of claim 4, wherein $R_2$ is isopropyl or sec-butyl; $R_4$ is methyl; $R_5$ is Cl, F or Br; and $R_1$ is alkyl, phenyl or cycloalkyl, all of which may be optionally substituted with 0-5 $R_{1a}$.

6. A compound selected from the group consisting of:
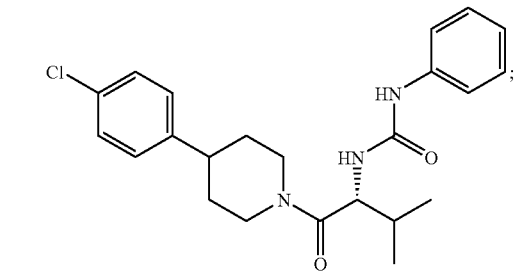
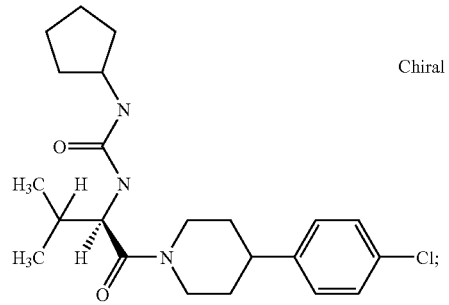
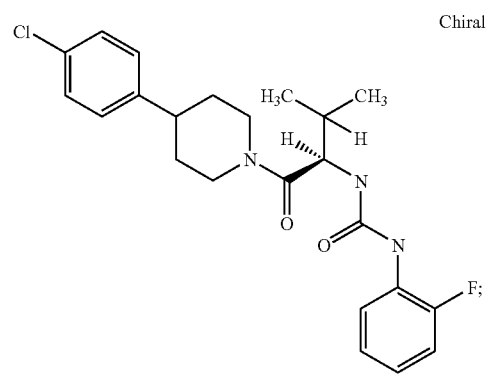
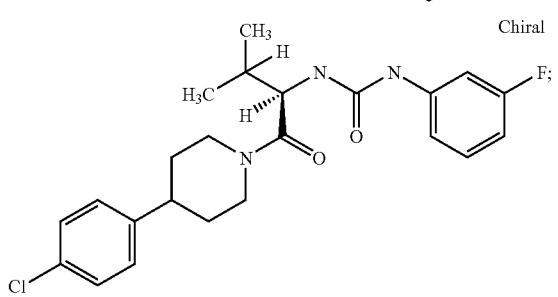
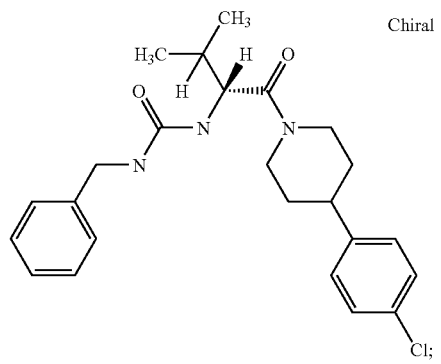
-continued
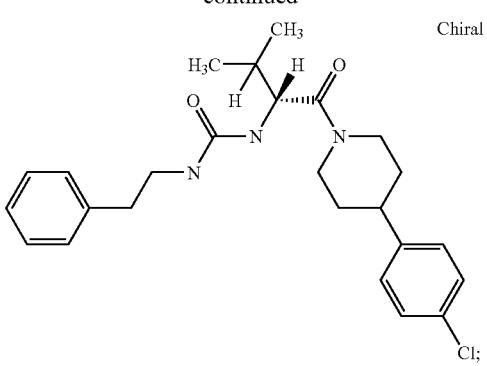
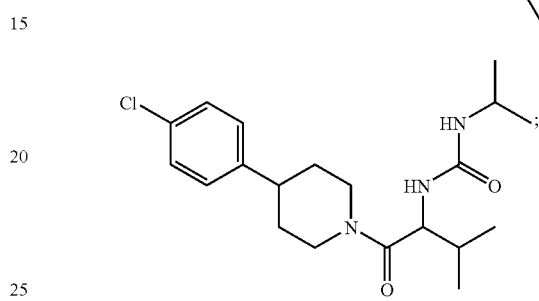
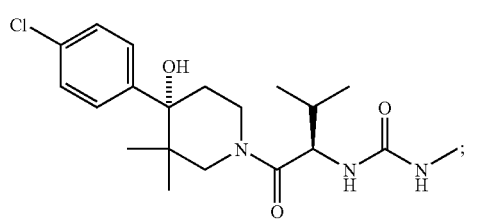
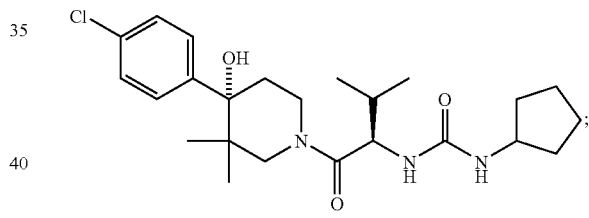
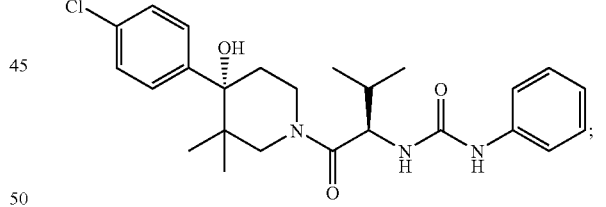
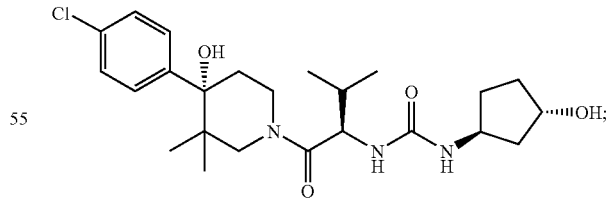
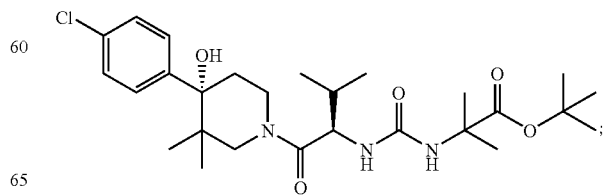

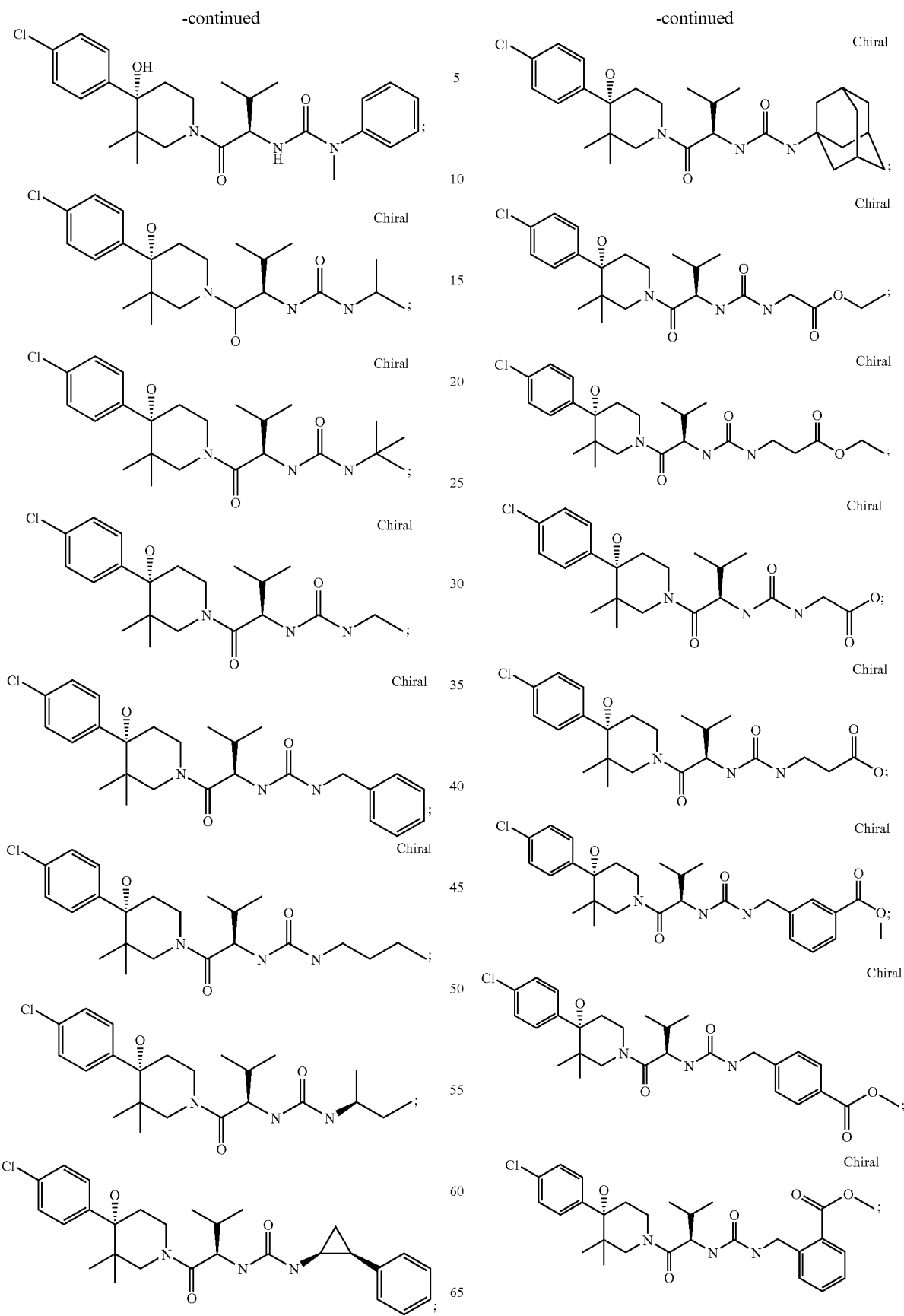

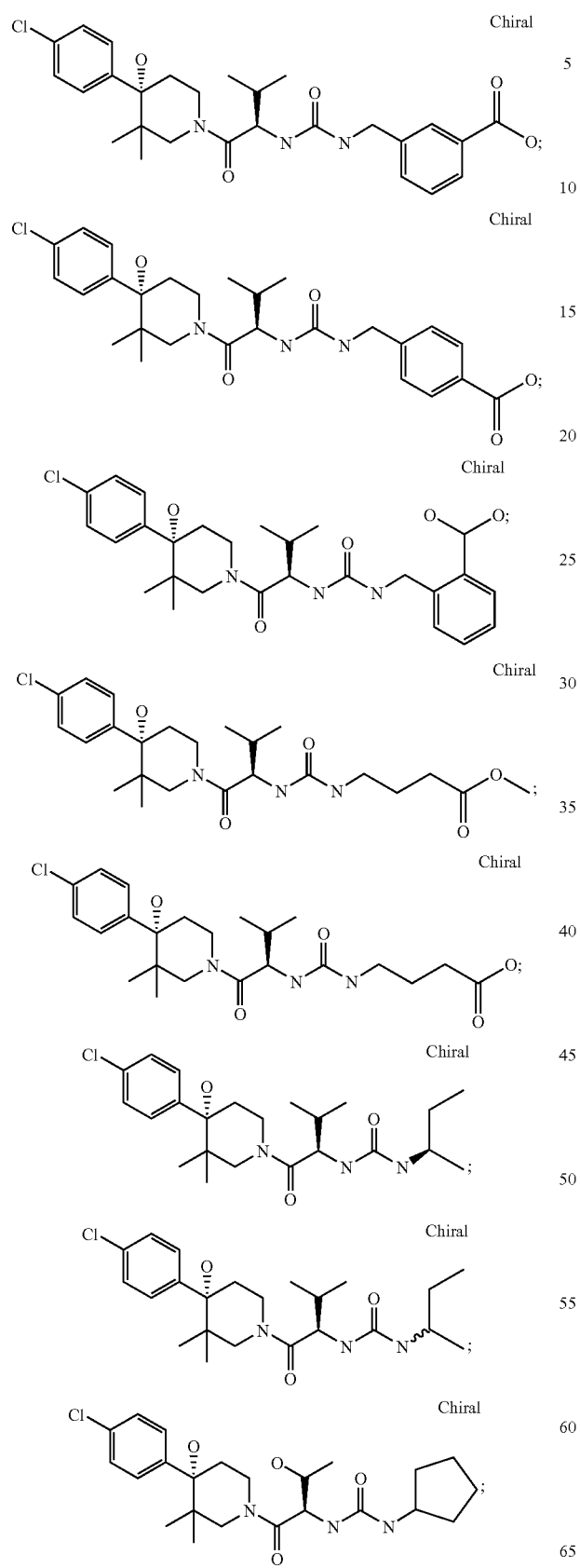
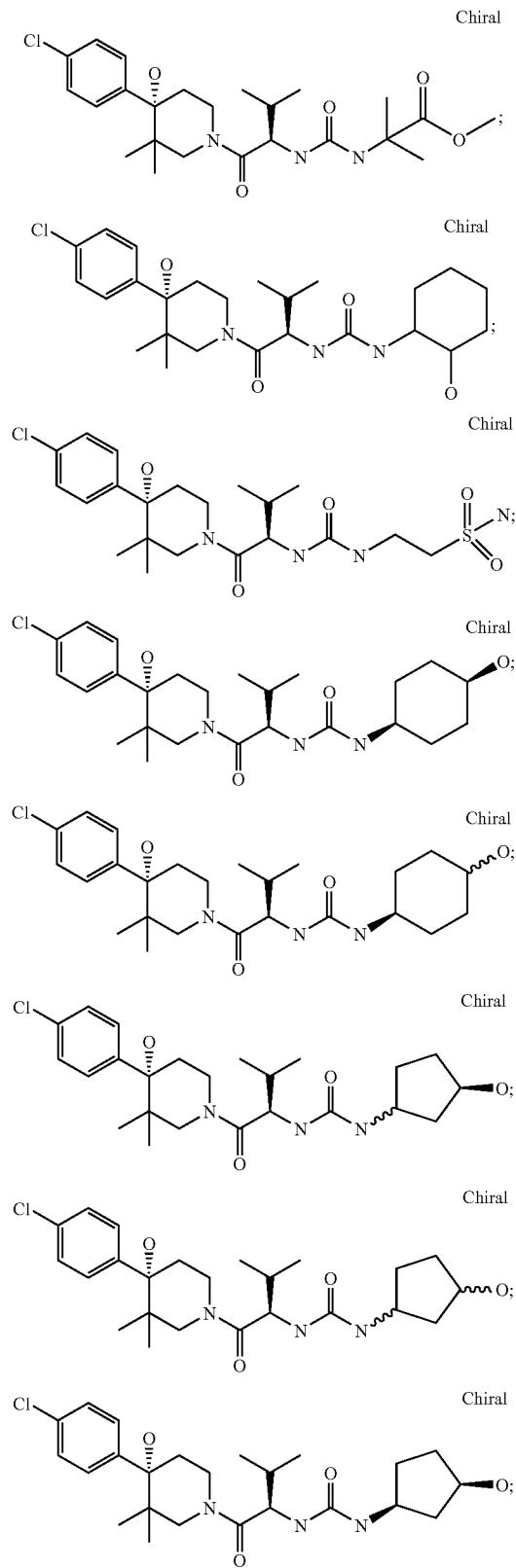

701
-continued
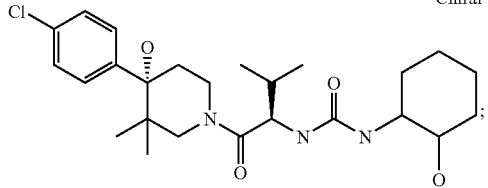
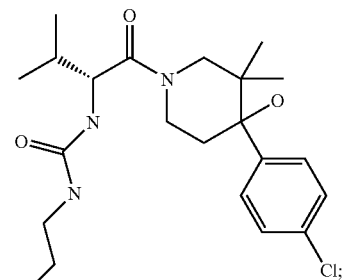
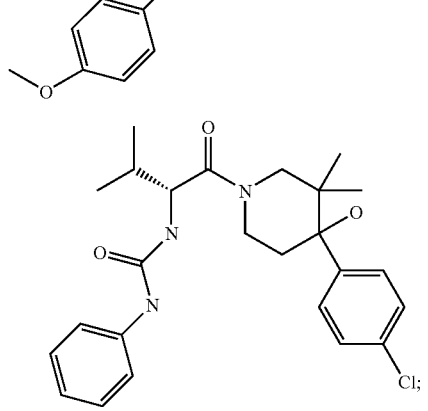
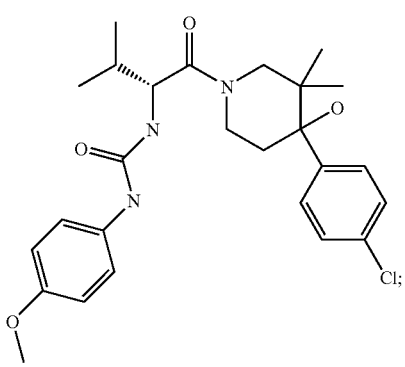
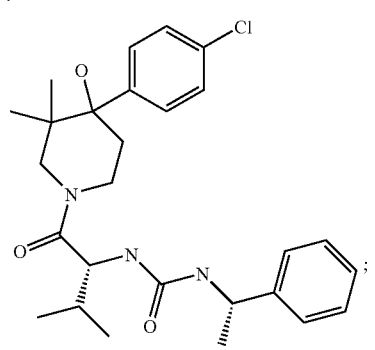
702
-continued
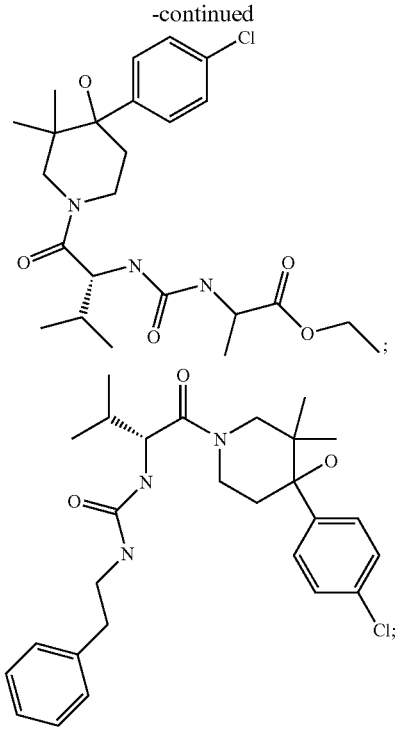
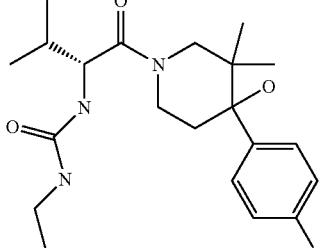
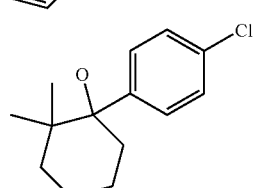
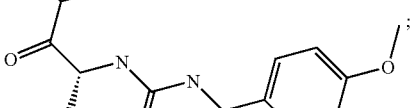
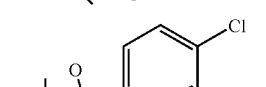
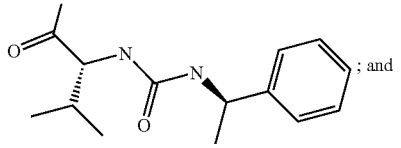

-continued
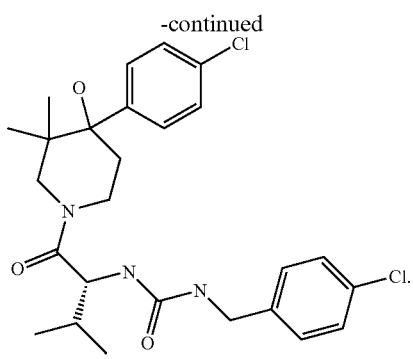
7. A pharmaceutical composition comprised of a pharmaceutically acceptable carrier and a therapeutically effective amount of at least one compound of claim 1.
8. A pharmaceutical composition comprised of a pharmaceutically acceptable carrier and a therapeutically effective amount of at least one compound of claim 4.
* * * * *

UNITED STATES PATENT AND TRADEMARK OFFICE
CERTIFICATE OF CORRECTION

PATENT NO.       : 7,601,844 B2
APPLICATION NO.  : 11/625874
DATED            : October 13, 2009
INVENTOR(S)      : Carter et al.

It is certified that error appears in the above-identified patent and that said Letters Patent is hereby corrected as shown below:

On the Title page, In Column 2, Under Other Publications, item (56) Line 5:
Delete "anagonist" and insert -- antagonist --

In Column 692, Line 53: Delete "$(CR_8R_8)_rR_{10}$" and insert -- $(CR_8R_8)_rR_{10}$, --

In Column 693, Line 15-20:

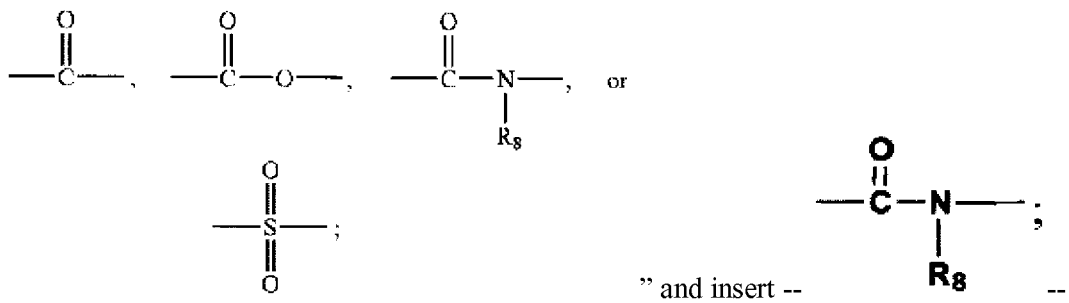

In Column 693, Line 30: Delete "$(CR_8R_8)_rR_{10}$" and insert -- $(CR_8R_8)_rR_{10}$, --

In Column 693, Line 33: Delete "alkyl," and insert -- alkyl --

In Column 693, Line 34: Delete "$R_2$is" and insert -- $R_2$ is --

In Column 694, Line 2: Delete "alkyly, haloalkyly, aryl" and insert -- alkyl, haloalkyl, aryl, --

In Column 694, Line 2-3:
Delete " 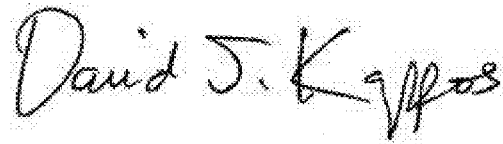 " and insert -- $-C(=O)O(CR_8R_8)_rR_{10}$, --

In Column 694, Line 4: After "$R_{1b}$;" delete "—"

In Column 694, Line 5: Delete "alkyl, or —OH" and insert -- alkyl or —OH; --

Signed and Sealed this
Fifth Day of April, 2011

David J. Kappos
*Director of the United States Patent and Trademark Office*

CERTIFICATE OF CORRECTION (continued)
U.S. Pat. No. 7,601,844 B2

In Column 694, Line 15: Delete "$R_{10}$," and insert -- $R_{10}$ --

In Column 694, Line 44: Delete "alkyl" and insert -- alkyl, --

In Column 694, Line 49: Delete "$(CR_8R_8)_rR_{10}$—OH," and insert -- $(CR_8R_8)_rR_{10}$, and —OH, --

In Column 694, Line 51: Delete "alkyl, or —OH," and insert -- alkyl or —OH; --

In Column 694, Line 52: Delete "$R_2$is" and insert -- $R_2$ is --

In Column 702, Line 45-50:

Delete " 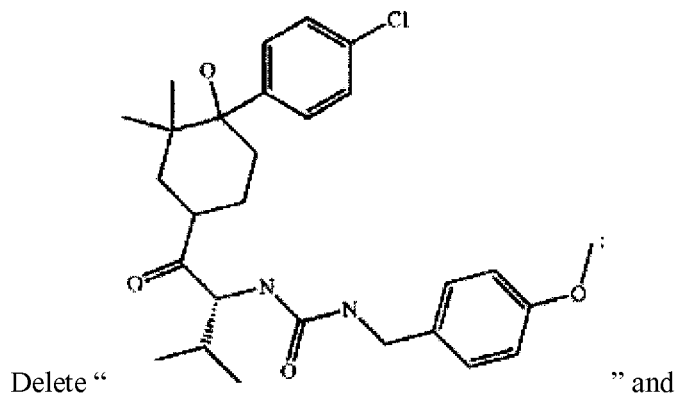 " and insert -- 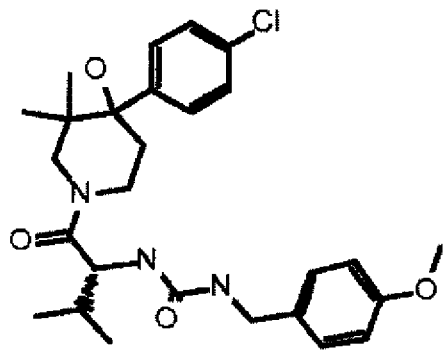 ; --